United States Patent
Wagner et al.

(10) Patent No.: US 9,029,544 B2
(45) Date of Patent: May 12, 2015

(54) TRICYCLIC PYRIDINE DERIVATIVES, MEDICAMENTS CONTAINING SUCH COMPOUNDS, THEIR USE AND PROCESS FOR THEIR PREPARATION

(75) Inventors: Holger Wagner, Mettenberg (DE); Daniela Berta, Milan (IT); Klaus Fuchs, Mittelbiberach (DE); Riccardo Giovannini, Verona (IT); Dieter Wolfgang Hamprecht, Pozzolengo (IT); Ingo Konetzki, Aachen-Oberforstbach (DE); Ruediger Streicher, Biberach (DE); Thomas Trieselmann, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 468 days.

(21) Appl. No.: 13/029,697

(22) Filed: Feb. 17, 2011

(65) Prior Publication Data

US 2012/0046304 A1 Feb. 23, 2012

(30) Foreign Application Priority Data

Feb. 19, 2010 (EP) .................................... 10154086

(51) Int. Cl.
| | | |
|---|---|---|
| *C07D 491/20* | (2006.01) | |
| *A61K 31/506* | (2006.01) | |
| *C07D 491/048* | (2006.01) | |
| *C07D 491/04* | (2006.01) | |
| *C07D 215/56* | (2006.01) | |

(52) U.S. Cl.
CPC ............ *C07D 491/04* (2013.01); *A61K 31/506* (2013.01); *C07D 491/20* (2013.01); *C07D 215/56* (2013.01)

(58) Field of Classification Search
CPC . C07D 491/20; C07D 491/048; A61K 31/506
USPC ............................................ 546/89; 514/291
See application file for complete search history.

(56) References Cited

U.S. PATENT DOCUMENTS

| | | | |
|---|---|---|---|
| 4,475,407 | A | 10/1984 | Kruncos |
| 4,798,619 | A | 1/1989 | Los |
| 5,932,587 | A | 8/1999 | Schmeck et al. |
| 5,977,136 | A | 11/1999 | Di Fabio et al. |
| 2002/0062024 | A1 | 5/2002 | Stoltefuss et al. |
| 2003/0191306 | A1 | 10/2003 | Sikorski et al. |
| 2005/0043341 | A1 | 2/2005 | Gielen et al. |
| 2008/0194609 | A1 | 8/2008 | Bischoff et al. |
| 2008/0255068 | A1 | 10/2008 | Bischoff et al. |
| 2011/0021550 | A1 | 1/2011 | Wagner et al. |
| 2012/0046304 | A1 | 2/2012 | Wagner et al. |
| 2012/0053197 | A1 | 3/2012 | Wagner et al. |
| 2013/0053404 | A1 | 2/2013 | Wagner et al. |
| 2013/0210850 | A1 | 8/2013 | Trieselmann et al. |
| 2013/0210851 | A1 | 8/2013 | Ostermeier et al. |

FOREIGN PATENT DOCUMENTS

| | | |
|---|---|---|
| CA | 2302350 A1 | 3/1999 |
| EP | 0818197 A1 | 1/1998 |
| JP | 2008201760 A | 9/2008 |
| WO | 9002129 A1 | 3/1990 |
| WO | 9712870 A1 | 4/1997 |
| WO | 9911629 A1 | 3/1999 |
| WO | 9914215 A1 | 3/1999 |
| WO | 03028727 A1 | 4/2003 |
| WO | 2006024517 A1 | 3/2006 |
| WO | 2006063828 A1 | 6/2006 |
| WO | 2006072362 A1 | 7/2006 |
| WO | 2009109549 A1 | 9/2009 |
| WO | 2011101424 A1 | 8/2011 |
| WO | 2012110599 A1 | 8/2012 |

OTHER PUBLICATIONS

International Search Report and Written Opinion for PCT/EP2011/052376 mailed May 11, 2011.
Rano, T.A. et al., "Design and synthesis of potent inhibitors of cholesteryl ester transfer protein (CETP) exploiting a 1,2,3,4-tetrahydroquinoline platform." Bioroganic and Medicinal Chemistry Letters, Vo. 19, No. 9, May 1, 2009, p. 2456-2460.
Tamura Y. et al., A Synthesis of 5-Amino- and 5-Hydroxy-1-ethyl-1,4-dihydro-4-oxo-3-quinolinecarboxylic acides and their derivatives:. Journal of Heterocyclic Chemistry, vol. 19, 1982, p. 289-296.
Torii, S. et al., "A Facile Synthesisof Polyfunctionally Substituted Phroidines from Ethoxycarbonylmalonaldehyde". Synthesis, Communications. May 1986, p. 400-402.
Vasil'ev, A.N. et al., "Reduction of Alkyl-2-amino-5,6-dialky1-3-cyanopyridine-4-carboxylates". Russian Journal of Organic Chemistry, vol. 41, No. 2, 2005, p. 288-291.
International Search Report and Written Opinion for PCT/EP2012/052687 mailed Mar. 26, 2012.
International Search Report and Written Opinion for PCT/EP2012/065989 mailed Oct. 8, 2012.

*Primary Examiner* — Rita Desai
(74) *Attorney, Agent, or Firm* — Michael P. Morris; David L. Kershner; Usha R. Patel

(57) ABSTRACT

The present invention relates to compounds defined by formula I

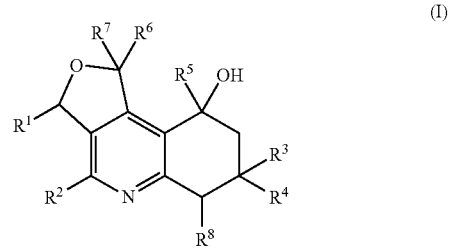

wherein the variables $R^1$-$R^8$ are defined as in the description, possessing valuable pharmacological activity. Particularly, the compounds are inhibitors of cholesterol ester transfer protein (CETP) and thus are suitable for treatment and prevention of diseases which can be influenced by inhibition of this enzyme.

15 Claims, No Drawings

US 9,029,544 B2

TRICYCLIC PYRIDINE DERIVATIVES, MEDICAMENTS CONTAINING SUCH COMPOUNDS, THEIR USE AND PROCESS FOR THEIR PREPARATION

FIELD OF INVENTION

The present invention relates to 1,3,6,7,8,9-hexahydro-furo[3,4-c]quinoline derivatives having the following chemical scaffold which is structurally defined by the formula I

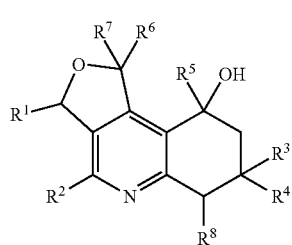

wherein the groups $R^1$ to $R^8$ are as defined hereinafter, including the tautomers, the stereoisomers, the mixtures thereof and the salts thereof. These compounds according to the invention have valuable pharmacological properties and can be used in the pharmaceutical industry for the production of pharmaceutical compositions for use in human and/or veterinary medicine. The invention further relates to pharmaceutical compositions containing one or more compounds according to the invention as well as the use of the compounds according to the invention as medicaments, particularly for preparing pharmaceutical compositions for the treatment and/or prevention of cardiometabolic or cardiovascular disorders. In addition, the invention relates to processes for preparing the compounds and pharmaceutical compositions according to the invention. Further, the invention relates to compounds and pharmaceutical compositions according to the invention for use in methods of inhibiting CETP as well as of treating and/or preventing cardiovascular or related disorders.

BACKGROUND OF THE INVENTION

In the literature, compounds which have an inhibitory effect on the enzyme cholesterol ester transfer protein (CETP) are proposed for the treatment of the cardiovascular disorders, in particular hypolipoproteinemia, dyslipidemia, hypertriglyceridemia, hyperlipidemia, hypercholesterolemia and atherosclerosis.

Compounds from various chemical classes are described in the literature as inhibitors of CETP (WO 98/35937, WO 00/017164, WO 05/100298, US2002120011, US2002177708, WO 00/18724). Also, substituted tetrahydroquinoline derivatives (WO 06/063828) have been described, however substituted 1,3,6,7,8,9-hexahydro-furo[3,4-c]quinoline derivatives defined by formula I have not yet been described for the inhibition of CETP.

The aim of the present invention is to find new compounds particularly those which have valuable pharmacological properties, especially those which are active with regard to the enzyme CETP, such as e.g. 1,3,6,7,8,9-hexahydro-furo[3,4-c]quinoline derivatives. A further aim of the present invention is to discover 1,3,6,7,8,9-hexahydro-furo[3,4-c]quinoline derivatives which have an inhibitory effect on the enzyme CETP in vitro and/or in vivo and possess suitable pharmacological and pharmacokinetic properties to use them as medicaments.

A further aim of the present invention is to provide new pharmaceutical compositions which are suitable for the prevention and/or treatment of cardiometabolic or cardiovascular disorders, particularly hypolipoproteinemia, dyslipidemia, hypertriglyceridemia, hyperlipidemia, hypercholesterolemia and atherosclerosis.

Other aims of the present invention will become apparent to the skilled man directly from the foregoing and following remarks.

SUMMARY OF THE INVENTION

In a first aspect the present invention relates to compounds which are structurally defined by the formula I

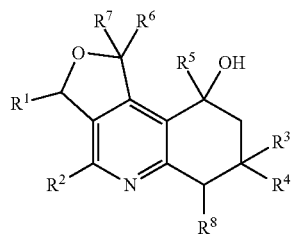

wherein
$R^1$ is a mono- or bicyclic 5- to 10-membered aryl or heteroaryl group, which heteroaryl contains 1 to 4 heteroatoms selected from the group consisting of N, O and S, and which aryl or heteroaryl may optionally be substituted by $R^9$, $R^{10}$ and/or $R^{11}$, in which
$R^9$ is hydrogen, halogen, cyano, 1-4C-alkyl, 2-4C-alkenyl, 3-6C-cycloalkyl, 1-4C-alkoxy, completely or partially fluorine-substituted 1-4C-alkyl, completely or partially fluorine-substituted 1-4C-alkoxy, pentafluorosulfanyl, cyano-1-4C-alkyl, 1-2C-alkyl-3-6C-cycloalkyl, cyano-3-6C-cycloalkyl, 1-2C-alkoxy-1-4C-alkyl, hydroxy-1-4C-alkyl, or 3-(1-2C-alkyl)-oxetan-3-yl,
$R^{10}$ is hydrogen, halogen, cyano, 1-4C-alkyl, 2-4C-alkenyl, 3-6C-cycloalkyl, 1-4C-alkoxy, completely or partially fluorine-substituted 1-4C-alkyl, completely or partially fluorine-substituted 1-4C-alkoxy, cyano-1-4C-alkyl, methyl-3-6C-cycloalkyl, cyano-3-6C-cycloalkyl, methoxy-1-4C-alkyl, hydroxy-1-4C-alkyl, or 3-(1-2C-alkyl)-oxetan-3-yl,
$R^{11}$ is hydrogen or halogen,
or $R^9$ and $R^{10}$ together and with inclusion of the carbon atoms, to which they are attached, form a 5-6C-cycloalkane ring wherein one methylene group may optionally be replaced by oxygen,
which ring, for the case of a 6-membered ring system, may optionally contain a double bond, and/or
which ring may optionally be mono- or disubstituted by methyl, wherein, for the case that both methyl groups are connected to the same carbon, the methyl groups together with the carbon to which they are connected, may optionally form a cyclopropyl ring,
$R^2$ is 1-6C-alkyl, 1-3C-perfluoroalkyl, 1-4C-alkoxy-1-4C-alkyl, or 4-7C-cycloalkyl, which 4-7C-cycloalkyl may optionally be mono- or disubstituted by fluorine, hydroxy, methoxy and/or 1-2C-alkyl and in which, for the case of 5-7C-cycloalkyl systems, one methylene group may optionally be replaced by oxygen, $R^3$ is hydrogen or 1-4C-alkyl, $R^4$ is hydrogen or 1-4C-alkyl, or $R^3$ and $R^4$ together and with inclusion of the carbon atom, to which they are attached, form a 3-7C-cycloalkane ring, $R^5$ is hydrogen or 1-4C-alkyl, $R^6$ is 1-4C-alkyl, $R^7$ is hydrogen or 1-4C-alkyl, or $R^6$ and $R^7$ together and with inclusion of the carbon atom, to which they are attached, form a 5-7C-cycloalkane ring wherein one methylene group may optionally be replaced by oxygen, which ring may optionally contain one double bond, and/or which ring may optionally be mono- or disubstituted by fluorine, hydroxyl, 1-2C-alkoxy and/or 1-2C-alkyl, $R^8$ is hydrogen, acetoxy, propionyloxy, methoxy or hydroxyl, the tautomers, the stereoisomers thereof, the mixtures thereof and the salts thereof.

The compounds of formula I according to the invention and the pharmaceutically acceptable salts thereof have valuable pharmacological properties, particularly an inhibitory effect on the enzyme cholesteryl ester transfer protein (CETP).

The present invention also relates to the pharmaceutically acceptable salts of the compounds of formula I according to the invention with inorganic or organic acids.

This invention also relates to pharmaceutical compositions, comprising at least one compound of formula I according to the invention or a pharmaceutically acceptable salt thereof, optionally together with one or more inert carriers and/or diluents.

This invention also relates to pharmaceutical compositions comprising or made of (e.g. by combining or mixing of) at least one compound according to the invention (including a pharmaceutically acceptable salt thereof), and one or more excipients, carriers and/or diluents.

This invention also relates to the use of at least one compound of formula I according to the invention or one of the pharmaceutically acceptable salts thereof for preparing a pharmaceutical composition which is suitable for the treatment and/or prevention of diseases, disorders or conditions which can be influenced by inhibiting the enzyme cholesteryl ester transfer protein (CETP), such as e.g. those cardiometabolic or cardiovascular disorders mentioned herein.

This invention also relates to the use of at least one compound of formula I according to the invention or one of the pharmaceutically acceptable salts thereof for preparing a pharmaceutical composition which is suitable for the treatment and/or prevention of cardiovascular and related disorders, such as e.g. hypolipoproteinemia, dyslipidemia, hypertriglyceridemia, hyperlipidemia, hypercholesterolemia or atherosclerosis.

This invention also relates to the use of at least one compound of formula I according to the invention or one of the pharmaceutically acceptable salts thereof for preparing a pharmaceutical composition for inhibiting the enzyme cholesteryl ester transfer protein (CETP).

This invention also relates to a compound according to the present invention which is suitable for use in therapy and/or prophylaxis, e.g. for the treatment and/or prevention of diseases or conditions which can be influenced by inhibiting the enzyme cholesteryl ester transfer protein (CETP), e.g. cardiovascular, cardiometabolic and related disorders, such as e.g. any of those diseases, disorders and conditions mentioned herein.

This invention also relates to a compound according to the present invention which is suitable for inhibiting the enzyme cholesteryl ester transfer protein (CETP).

The invention further relates to a process for preparing a pharmaceutical composition according to the invention, comprising incorporating a compound of formula I according to the invention or one of the pharmaceutically acceptable salts thereof in one or more inert carriers and/or diluents preferably by a non-chemical method.

The present invention also relates to a method for treating and/or preventing a disease or condition which can be influenced by inhibiting the enzyme cholesteryl ester transfer protein (CETP), e.g. a cardiovascular, cardiometabolic or related disorder, such as e.g. any of those diseases and conditions mentioned herein, in a mammalian (particularly human) patient in need thereof comprising administering to said patient a therapeutically effective amount of a compound of formula I according to the invention or one of the pharmaceutically acceptable salts thereof.

The present invention also relates to a pharmaceutical compound or composition according to this invention for use in a method of treating and/or preventing a condition which can be influenced by inhibiting the enzyme cholesteryl ester transfer protein (CETP), e.g. a cardiovascular, cardiometabolic or related disorder, such as e.g. any of those diseases and conditions mentioned herein, said method comprising administration of said compound or composition, optionally alone or in combination (such as e.g. separately, sequentially, simultaneously, concurrently or chronologically staggered) with one or more other therapeutic agents, such as e.g. selected from those mentioned herein.

The present invention also relates to a compound of formula I according to this invention or a pharmaceutically acceptable salt thereof for use in a method of treating and/or preventing a cardiovascular, cardiometabolic or related disorder selected from atherosclerosis, dyslipidemia (e.g. mixed dyslipidemia), hyperbeta-lipoproteinemia, hypoalpha-lipoproteinemia, hypercholesterolemia, hypertriglyceridemia, hyperlipidemia, hypolipoproteinemia, hyperlipoproteinemia, hypo-HDL cholesterolemia, hyper-LDL cholesterolemia, familial hypercholesterolemia, peripheral vascular disease, hypertension, endothelial dysfunction, angina, ischemia, cardiac ischemia, stroke, myocardial infarction, reperfusion injury, angioplastic restenosis, arteriosclerosis, coronary heart disease, coronary artery disease, coronary vascular disease or congestive heart failure, vascular complications of diabetes, insulin resistance, obesity, metabolic syndrome, diabetes (especially type 2 diabetes mellitus) or endotoxemia, said method comprising administration of said compound or pharmaceutically acceptable salt thereof, optionally in monotherapy or in combination therapy (such as e.g. separately, sequentially, simultaneously, concurrently or chronologically staggered) with one or more other therapeutic agents, such as e.g. selected from those mentioned herein, such as e.g. a HMG-CoA reductase inhibitor (e.g. a statin).

The present invention also relates to a compound of formula I according to this invention or a pharmaceutically acceptable salt thereof for use in a method of increasing patient's levels of HDL cholesterol and/or decreasing patient's levels of VLDL cholesterol and/or of LDL cholesterol, optionally in combination with one or more other therapeutic agents, such as e.g. selected from those mentioned herein, such as e.g. a HMG-CoA reductase inhibitor (e.g. a statin).

The present invention also relates to a compound of formula I according to this invention or a pharmaceutically acceptable salt thereof for use in a method of primary or secondary prevention of cardiovascular diseases, particularly major cardiovascular events, optionally in combination with one or more other therapeutic agents, such as e.g. selected from those mentioned herein, such as e.g. a HMG-CoA reductase inhibitor (e.g. a statin).

The present invention also relates to processes and intermediates for preparing the compounds of general formula I according to the invention (see processes a, b, c and d in general synthesis section).

Among the synthesis processes according to this invention, especially noteworthy is the process for the preparation of compounds of formula IV from compounds of formula II and III

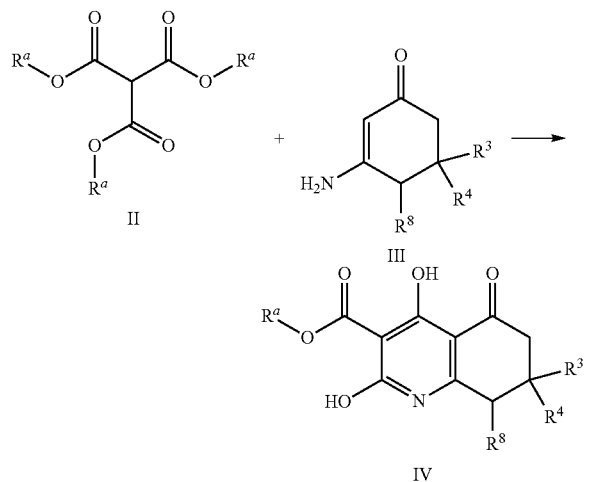

wherein the variables $R^3$ and $R^4$ are defined as hereinbefore and hereinafter, $R^a$ denotes independently methyl or ethyl and $R^8$ denotes hydrogen.

In this process compounds of formula II are reacted at temperatures between 150° C. and 250° C. with compounds of formula III to yield the bicyclic dihydroxypyridines of formula IV.

Other aspects of the present invention become apparent from the description hereinbefore and hereinafter (including the examples) as well as the claims.

DETAILED DESCRIPTION OF THE INVENTION

Unless otherwise stated, the groups, residues, and substituents, particularly $R^1$, $R^2$, $R^3$, $R^4$, $R^5$, $R^6$, $R^7$, $R^8$, $R^9$, $R^{10}$ and $R^{11}$ are defined as above and hereinafter. If residues, substituents, or groups occur several times in a compound they may have the same or different meanings. Some preferred meanings of groups and substituents of the compounds according to the invention will be given hereinafter.

Preferred embodiments of the invention are characterized by the following definitions:

a) Definitions ($a^i$) for $R^1$ in the order of preference, ascending from preferably ($a^1$) to more preferably ($a^2$) up to most preferably ($a^4$):

($a^1$): Preferably, $R^1$ denotes thiophenyl, thiazolyl, phenyl, pyridyl, pyrimidinyl, pyridazinyl or pyrazinyl, each of which substituted by $R^9$, $R^{10}$ and/or $R^{11}$, or 1,1-dimethyl-1,3-dihydroisobenzofuran-5-yl, 3'H-spiro[cyclopropane-1,1'-isobenzofuran]-5'-yl, 3,3-dimethyl-2,3-dihydrobenzofuran-6-yl or 2H-spiro[benzofuran-3,1'-cyclopropane]-6-yl, in which $R^9$ is hydrogen, halogen, cyano, 1-4C-alkyl, 2-4C-alkenyl, 3-4C-cycloalkyl, 1-3C-alkoxy, completely or predominantly fluorine-substituted 1-3C-alkyl, completely or predominantly fluorine-substituted 1-3C-alkoxy, pentafluorosulfanyl, cyano-1-3C-alkyl, 1-2C-alkyl-3-4C-cycloalkyl, cyano-3-4C-cycloalkyl, 1-2C-alkoxy-1-3C-alkyl, hydroxy-1-3C-alkyl, or 3-(1-2C-alkyl)-oxetan-3-yl, $R^{10}$ is hydrogen, halogen, cyano, 1-4C-alkyl, 1-3C-alkoxy, completely or predominantly fluorine-substituted 1-3C-alkyl, completely or predominantly fluorine-substituted 1-3C-alkoxy, cyano-1-3C-alkyl, or methoxy-1-3C-alkyl, $R^{11}$ is hydrogen or halogen.

($a^2$): More preferably, $R^1$ denotes 2-($R^9$)-3-($R^{10}$)-thiophen-5-yl, 5-($R^9$)-4-($R^{10}$)-thiazol-2-yl, 1-($R^{10}$)-2-($R^9$)-3-($R^{11}$)-benzene-5-yl, 5-($R^9$)-4-($R^{10}$)-pyridine-2-yl, 2-($R^9$)-3-($R^{10}$)-pyridine-5-yl, 5-($R^9$)-4-($R^{10}$)-pyrimidine-2-yl, 2-($R^9$)-pyrimidine-5-yl, 3-($R^9$)-4-($R^{10}$)-pyridazine-6-yl, 2-($R^9$)-3-($R^{10}$)-pyrazine-5-yl, 1,1-dimethyl-1,3-dihydroisobenzofuran-5-yl, 3'H-spiro[cyclopropane-1,1'-isobenzofuran]-5'-yl, 3,3-dimethyl-2,3-dihydrobenzofuran-6-yl or 2H-spiro[benzofuran-3,1'-cyclopropane]-6-yl, in which $R^9$ is hydrogen, halogen, cyano, isopropyl, isobutyl, tert.-butyl, isopropenyl, cyclopropyl, cyclobutyl, methoxy, ethoxy, trifluoromethyl, pentafluoroethyl, difluoromethyl, 1,1-difluorethan-1-yl, trifluoromethoxy, difluoromethoxy, pentafluorosulfanyl, 2-cyano-propan-2-yl, 1-methyl-cyclopropan-1-yl, 1-methyl-cyclobutan-1-yl, 1-cyano-cyclopropan-1-yl, 1-cyano-cyclobutan-1-yl, 1-methoxy-ethan-1-yl, 2-methoxy-propan-2-yl, 1-hydroxy-ethan-1-yl, 2-hydroxy-propan-2-yl, or 3-(1-2C-alkyl)-oxetan-3-yl, $R^{10}$ is hydrogen, halogen, cyano, methyl, ethyl, isopropyl, tert.-butyl, methoxy, trifluoromethyl, trifluoromethoxy, or methoxymethyl, $R^{11}$ is hydrogen, fluorine or chlorine.

($a^3$): Even more preferably, $R^1$ denotes 2-($R^9$)-thiophen-5-yl, 1-($R^9$)-2-($R^{10}$)-benzene-4-yl, 4-($R^9$)-benzene-1-yl, 3-tert.-butylphenyl, 3-trifluoromethylphenyl, 1,2,3-trifluoro-benzene-5-yl, 1,3-difluoro-benzene-5-yl, 5-($R^9$)-pyridine-2-yl, 2-($R^9$)-pyridine-5-yl, 2-($R^9$)-pyrimidine-5-yl, 1,1-dimethyl-1,3-dihydroisobenzofuran-5-yl or 3,3-dimethyl-2,3-dihydrobenzofuran-6-yl, in which $R^9$ is fluorine, chlorine, bromine, cyano, isopropyl, isobutyl, tert.-butyl, cyclopropyl, cyclobutyl, methoxy, ethoxy, trifluoromethyl, pentafluoroethyl, difluoromethyl, 1,1-difluorethan-1-yl, trifluoromethoxy, difluoromethoxy, pentafluorosulfanyl, 2-cyano-propan-2-yl, 1-methyl-cyclopropan-1-yl, 1-methyl-cyclobutan-1-yl, 1-cyano-cyclopropan-1-yl, 1-cyano-cyclobutan-1-yl, 2-methoxy-propan-2-yl, 2-hydroxy-propan-2-yl, or 3-methyl-oxetan-3-yl, $R^{10}$ is hydrogen, fluorine or chlorine.

($a^4$): Most preferably, $R^1$ denotes 4-trifluoromethylphenyl, 3-trifluoromethylphenyl, 4-(1,1-difluor-ethan-1-yl)-phenyl, 4-methylphenyl, 4-isopropylphenyl, 4-isobutylphenyl, 4-tert.-butylphenyl, 3-tert.-butylphenyl, 4-cyanophenyl, 4-fluorphenyl, 3,5-difluorphenyl, 4-chlorphenyl, 4-methoxyphenyl, 4-trifluormethoxyphenyl, 4-pentafluorosulfanylphenyl, 2-trifluoromethyl-pyridin-5-yl, 5-trifluormethyl-pyridin-2-yl, 3-fluor-4-trifluormethyl-phenyl, 4-(2-cyano-propan-2-yl)-phenyl, 4-(2-hydroxy-propan-2-yl)-phenyl, 4-cyclopropylphenyl, 4-(1-methylcyclopropyl-1-yl)-phenyl, 4-(1-cyanocyclopropyl-1-yl)-phenyl, 2-trifluormethyl-thiophen-5-yl, or 2-tert.-butyl-pyrimidin-5-yl.

b) Definitions (b') for $R^2$ in the order of preference, ascending from preferably ($b^1$) to more preferably ($b^2$) up to most preferably ($b^4$):

($b^1$): Preferably, $R^2$ denotes 1-5C-alkyl, trifluormethyl, pentafluorethyl, 1-3C-alkoxy-1-2C-alkyl, or 4-7C-cycloalkyl, which 4-7C-cycloalkyl may optionally be mono- or disubstituted by fluorine, hydroxy, methoxy and/or methyl and in which, for the case of 5-7C-cycloalkyl systems, one methylene group may optionally be replaced by oxygen.

($b^2$): More preferably, $R^2$ denotes 1-5C-alkyl, trifluormethyl, 1-3C-alkoxy-1-2C-alkyl, cyclobutyl, methylcyclobutyl, dimethylcyclobutyl, cyclopentyl, methylcyclopentyl, cyclohexyl, methylcyclohexyl, dimethylcyclohexyl, fluorcyclohexyl, difluorcyclohexyl, hydroxycyclohexyl, methoxycyclohexyl, tetrahydrofuranyl or tetrahydropyranyl.

($b^3$): Even more preferably, $R^2$ denotes ethyl, isopropyl, 2-butyl, isobutyl, 3-pentyl, cyclobutyl, cyclopentyl, cyclohexyl, tetrahydrofuran-2-yl, tetrahydrofuran-3-yl, tetrahydropyran-4-yl, tetrahydropyran-3-yl or tetrahydropyran-2-yl.

($b^4$): Most preferably, $R^2$ denotes ethyl, isopropyl, cyclobutyl, cyclopentyl or tetrahydropyran-4-yl.

c) Definitions (c') for $R^3$ and $R^4$ in the order of preference, ascending from preferably ($c^1$) to more preferably ($c^2$) up to most preferably ($c^3$):

($c^1$) Preferably, $R^3$ and $R^4$ are independently selected from hydrogen and 1-3C-alkyl, or
$R^3$ and $R^4$ together and with inclusion of the carbon atom, to which they are attached, form a 3-6C-cycloalkane ring.

($c^2$) More preferably, $R^3$ and $R^4$ are independently selected from methyl and ethyl, or
$R^3$ and $R^4$ together and with inclusion of the carbon atom, to which they are attached, form a cyclopropane, cyclobutane or cyclopentane ring.

($c^3$) Most preferably, $R^3$ is methyl and $R^4$ is methyl, or
$R^3$ and $R^4$ together and with inclusion of the carbon atom, to which they are attached, form a cyclobutane ring.

d) Definitions (d') for $R^5$ in the order of preference, ascending from preferably ($d^1$) to more preferably ($d^2$) up to most preferably ($d^3$):

($d^1$) Preferably, $R^5$ denotes hydrogen, methyl or ethyl.

($d^2$) More preferably, $R^5$ denotes hydrogen or methyl.

($d^3$) Most preferably, $R^5$ denotes hydrogen.

e) Definitions (e') for $R^6$ and $R^7$ in the order of preference, ascending from preferably ($e^1$) to more preferably ($e^2$) up to most preferably ($e^4$):

($e^1$) Preferably, $R^6$ denotes methyl, ethyl, propyl or isopropyl and $R^7$ denotes hydrogen, methyl or ethyl, or
$R^6$ and $R^7$ together and with inclusion of the carbon atom, to which they are attached, form a 5-6C-cycloalkane ring wherein one methylene group may optionally be replaced by oxygen, which ring may optionally contain one double bond, and/or which ring may optionally be mono- or disubstituted by fluorine, hydroxyl, 1-2C-alkoxy and/or 1-2C-alkyl.

($e^2$) More preferably, $R^6$ denotes methyl, ethyl, propyl or isopropyl and $R^7$ denotes hydrogen, methyl or ethyl, or
$R^6$ and $R^7$ together and with inclusion of the carbon atom, to which they are attached, form a cyclopentane ring, cyclopentene ring, cyclohexane ring or tetrahydropyrane ring.

($e^3$): Even more preferably, $R^6$ and $R^7$ independently denote methyl or ethyl, or
$R^6$ and $R^7$ together and with inclusion of the carbon atom, to which they are attached, form a cyclopentane ring, cyclopent-2-ene-1,1-diyl ring, cyclohexane ring or tetrahydropyrane-4,4-diyl ring.

($e^4$) Most preferably, $R^6$ denotes methyl and $R^7$ denotes methyl, or
$R^6$ and $R^7$ together and with inclusion of the carbon atom, to which they are attached, form a cyclopentane ring, cyclopent-2-ene-1,1-diyl ring, cyclohexane ring or tetrahydropyrane-4,4-diyl ring.

f) Definitions (f') for $R^8$ in the order of preference, ascending from preferably ($f^1$) to more preferably ($f^2$) up to most preferably ($f^3$):

($f^1$) Preferably, $R^8$ denotes hydrogen, acetoxy or hydroxy.

($f^2$) More preferably, $R^8$ denotes hydrogen or hydroxy.

($f^3$) Most preferably, $R^8$ denotes hydrogen.

Further preferred embodiments of the invention are characterized by the following definitions:

a') Definitions (a') for $R^1$ in the order of preference, ascending from preferably ($a^1$) to more preferably ($a^2$) up to most preferably ($a^4$):

($a^1$): Preferably, $R^1$ denotes thiophenyl, thiazolyl, phenyl, pyridyl, pyrimidinyl, pyridazinyl or pyrazinyl, each of which substituted by $R^9$, $R^{10}$ and/or $R^{11}$, or 1,1-dimethyl-1,3-dihydroisobenzofuran-5-yl, 3'H-spiro[cyclopropane-1,1'-isobenzofuran]-5'-yl, 3,3-dimethyl-2,3-dihydrobenzofuran-6-yl or 2H-spiro[benzofuran-3,1'-cyclopropane]-6-yl, in which
$R^9$ is hydrogen, halogen, cyano, 1-4C-alkyl, 2-4C-alkenyl, 3-4C-cycloalkyl, 1-3C-alkoxy, completely or predominantly fluorine-substituted 1-3C-alkyl, completely or predominantly fluorine-substituted 1-3C-alkoxy, pentafluorosulfanyl, cyano-1-3C-alkyl, 1-2C-alkyl-3-4C-cycloalkyl, cyano-3-4C-cycloalkyl, 1-2C-alkoxy-1-3C-alkyl, hydroxy-1-3C-alkyl, or 3-(1-2C-alkyl)-oxetan-3-yl,
$R^{10}$ is hydrogen, halogen, cyano, 1-4C-alkyl, 1-3C-alkoxy, completely or predominantly fluorine-substituted 1-3C-alkyl, completely or predominantly fluorine-substituted 1-3C-alkoxy, cyano-1-3C-alkyl, or methoxy-1-3C-alkyl,
$R^{11}$ is hydrogen or halogen.

($a^2$): More preferably, $R^1$ denotes 2-($R^9$)-3-($R^{10}$-thiophen-5-yl, 5-($R^9$)-4-($R^{10}$-thiazol-2-yl, 1-($R^{10}$)-2-($R^9$)-3-($R^{11}$)-benzene-5-yl, 1-($R^{10}$)-2-($R^9$)-4-($R^{11}$)-benzene-5-yl, 5-($R^9$)-4-($R^{10}$)-pyridine-2-yl, 2-($R^9$)-3-($R^{10}$)-pyridine-5-yl, 5-($R^9$)-3-($R^{10}$)-pyridine-2-yl, 5-($R^9$)-4-($R^{10}$)-pyrimidine-2-yl, 2-($R^9$)-pyrimidine-5-yl, 3-($R^9$)-4-($R^{10}$)-pyridazine-6-yl, 2-($R^9$)-3-($R^{10}$)-pyrazine-5-yl, 1,1-dimethyl-1,3-dihydroisobenzofuran-5-yl, 3'H-spiro[cyclopropane-1,1'-isobenzofuran]-5'-yl, 3,3-dimethyl-2,3-dihydrobenzofuran-6-yl or 2H-spiro[benzofuran-3,1'-cyclopropane]-6-yl, in which
$R^9$ is hydrogen, halogen, cyano, isopropyl, isobutyl, tert.-butyl, isopropenyl, cyclopropyl, cyclobutyl, methoxy, ethoxy, isopropoxy, tert.-butoxy, trifluoromethyl, pentafluoroethyl, difluoromethyl, 1,1-difluorethan-1-yl, trifluoromethoxy, difluoromethoxy, pentafluorosulfanyl, 2-cyano-propan-2-yl, 1-methyl-cyclopropan-1-yl, 1-methyl-cyclobutan-1-yl, 1-cyano-cyclopropan-1-yl, 1-cyano-cyclobutan-1-yl, 1-methoxy-ethan-1-yl, 2-methoxy-propan-2-yl, 1-hydroxy-ethan-1-yl, 2-hydroxy-propan-2-yl, or 3-(1-2C-alkyl)-oxetan-3-yl,
$R^{10}$ is hydrogen, halogen, cyano, methyl, ethyl, isopropyl, tert.-butyl, methoxy, trifluoromethyl, trifluoromethoxy, or methoxymethyl,
$R^{11}$ is hydrogen, fluorine or chlorine.

(a³'): Even more preferably, $R^1$ denotes 2-($R^9$)-thiophen-5-yl, 1-($R^9$)-2-($R^{10}$)-benzene-4-yl, 1-($R^9$)-3-($R^{10}$)-benzene-4-yl, 4-($R^9$)-benzene-1-yl, 3-tert.-butylphenyl, 3-trifluoromethylphenyl, 1,2,3-trifluoro-benzene-5-yl, 1,3-difluoro-benzene-5-yl, 5-($R^9$)-pyridine-2-yl, 2-($R^9$)-pyridine-5-yl, 5-($R^9$)-3-($R^{10}$)-pyridine-2-yl, 2-($R^9$)-pyrimidine-5-yl, 5-($R^9$)-4-($R^{10}$)-thiazol-2-yl, 1,1-dimethyl-1,3-dihydroisobenzofuran-5-yl or 3,3-dimethyl-2,3-dihydrobenzofuran-6-yl, in which $R^9$ is fluorine, chlorine, bromine, cyano, isopropyl, isobutyl, isopropenyl, tert.-butyl, cyclopropyl, cyclobutyl, methoxy, ethoxy, isopropoxy, tert.-butoxy, trifluoromethyl, pentafluoroethyl, difluoromethyl, 1,1-difluorethan-1-yl, trifluoromethoxy, difluoromethoxy, pentafluorosulfanyl, 2-cyano-propan-2-yl, 1-methyl-cyclopropan-1-yl, 1-methyl-cyclobutan-1-yl, 1-cyano-cyclopropan-1-yl, 1-cyano-cyclobutan-1-yl, 2-methoxy-propan-2-yl, 2-hydroxy-propan-2-yl, or 3-methyl-oxetan-3-yl, $R^{10}$ is hydrogen, methyl, cyano, fluorine or chlorine.

(a⁴'): Most preferably, $R^1$ denotes 4-trifluoromethylphenyl, 3-trifluoromethylphenyl, 4-(1,1-difluor-ethan-1-yl)-phenyl, 4-methylphenyl, 4-isopropylphenyl, 4-isobutylphenyl, 4-tert.-butylphenyl, 3-tert.-butylphenyl, 4-isopropenylphenyl, 4-cyanophenyl, 4-fluorophenyl, 3,5-difluorophenyl, 4-chlorophenyl, 4-methoxyphenyl, 4-isopropoxyphenyl, 4-tert.-butoxyphenyl, 4-trifluoromethoxyphenyl, 4-pentafluorosulfanylphenyl, 4-pentafluoroethylphenyl, 2-trifluoromethyl-pyridin-5-yl, 5-trifluoromethyl-pyridin-2-yl, 3-fluoro-4-trifluoromethylphenyl, 2-fluoro-4-trifluoromethylphenyl, 3-fluoro-5-trifluoromethyl-pyridin-2-yl, 3-cyano-4-trifluoromethylphenyl, 4-(2-cyano-propan-2-yl)-phenyl, 4-(2-hydroxy-propan-2-yl)-phenyl, 4-cyclopropylphenyl, 4-(1-methylcyclopropyl-1-yl)-phenyl, 4-(1-cyanocyclopropyl-1-yl)-phenyl, 2-trifluormethyl-thiophen-5-yl, 4-(3-methyl-oxetan-3-yl)-phenyl, 5-tert.-butyl-4-methyl-thiazol-2-yl or 2-tert.-butyl-pyrimidin-5-yl.

b') Definitions (bⁱ') for $R^2$ in the order of preference, ascending from preferably (b¹') to more preferably (b²') up to most preferably (b⁴'):

(b¹'): Preferably, $R^2$ denotes 1-5C-alkyl, trifluormethyl, pentafluorethyl, 1-3C-alkoxy-1-2C-alkyl, 1-3C-alkoxy-3C-alkyl or 4-7C-cycloalkyl, which 4-7C-cycloalkyl may optionally be mono- or disubstituted by fluorine, hydroxy, methoxy and/or methyl and in which, for the case of 5-7C-cycloalkyl systems, one methylene group may optionally be replaced by oxygen.

(b²'): More preferably, $R^2$ denotes 1-5C-alkyl, trifluormethyl, 1-3C-alkoxy-1-2C-alkyl, 1-3C-alkoxy-3C-alkyl, cyclobutyl, methylcyclobutyl, dimethylcyclobutyl, cyclopentyl, methylcyclopentyl, cyclohexyl, methylcyclohexyl, dimethylcyclohexyl, fluorcyclohexyl, difluorcyclohexyl, hydroxycyclohexyl, methoxycyclohexyl, tetrahydrofuranyl or tetrahydropyranyl.

(b³'): Even more preferably, $R^2$ denotes ethyl, isopropyl, 2-butyl, isobutyl, tert.-butyl, 3-pentyl, cyclobutyl, cyclopentyl, cyclohexyl, methoxymethyl, 1-methoxyethyl, 2-methoxy-propan-2-yl, tetrahydrofuran-2-yl, tetrahydrofuran-3-yl, tetrahydropyran-4-yl, tetrahydropyran-3-yl or tetrahydropyran-2-yl.

(b⁴'): Most preferably, $R^2$ denotes ethyl, isopropyl, tert.-butyl, methoxymethyl, 1-methoxyethyl, 2-methoxy-propan-2-yl, cyclobutyl, cyclopentyl or tetrahydropyran-4-yl.

c') Definitions (cⁱ') for $R^3$ and $R^4$ in the order of preference, ascending from preferably (c¹') to more preferably (c²') up to most preferably (c³'):

(c¹') Preferably, $R^3$ and $R^4$ are independently selected from hydrogen and 1-3C-alkyl, or
$R^3$ and $R^4$ together and with inclusion of the carbon atom, to which they are attached, form a 3-6C-cycloalkane ring.

(c²') More preferably, $R^3$ and $R^4$ are independently selected from methyl and ethyl, or
$R^3$ and $R^4$ together and with inclusion of the carbon atom, to which they are attached, form a cyclopropane, cyclobutane or cyclopentane ring.

(c³') Most preferably, $R^3$ is methyl and $R^4$ is methyl, or
$R^3$ and $R^4$ together and with inclusion of the carbon atom, to which they are attached, form a cyclobutane ring.

d') Definitions (dⁱ') for $R^5$ in the order of preference, ascending from preferably (d¹') to more preferably (d²') up to most preferably (d³'):

(d¹') Preferably, $R^5$ denotes hydrogen, methyl or ethyl.
(d²') More preferably, $R^5$ denotes hydrogen or methyl.
(d³') Most preferably, $R^5$ denotes hydrogen.

e') Definitions (eⁱ') for $R^6$ and $R^7$ in the order of preference, ascending from preferably (e¹') to more preferably (e²') up to most preferably (e⁴'):

(e¹') Preferably, $R^6$ denotes methyl, ethyl, propyl or isopropyl and $R^7$ denotes hydrogen, methyl or ethyl, or
$R^6$ and $R^7$ together and with inclusion of the carbon atom, to which they are attached, form a 5-6C-cycloalkane ring wherein one methylene group may optionally be replaced by oxygen, which ring may optionally contain one double bond, and/or which ring may optionally be mono- or disubstituted by fluorine, hydroxyl, 1-2C-alkoxy and/or 1-2C-alkyl.

(e²') More preferably, $R^6$ denotes methyl, ethyl, propyl or isopropyl and $R^7$ denotes hydrogen, methyl or ethyl, or
$R^6$ and $R^7$ together and with inclusion of the carbon atom, to which they are attached, form a cyclopentane ring, cyclopentene ring, cyclohexane ring or tetrahydropyrane ring.

(e³') Even more preferably, $R^6$ and $R^7$ independently denote methyl or ethyl, or
$R^6$ and $R^7$ together and with inclusion of the carbon atom, to which they are attached, form a cyclopentane ring, cyclopent-2-ene-1,1-diyl ring, cyclohexane ring, 4,4-difluorocyclohexane-1,1-diyl ring or tetrahydropyrane-4,4-diyl ring.

(e⁴') Most preferably, $R^6$ denotes methyl and $R^7$ denotes methyl, or
$R^6$ and $R^7$ together and with inclusion of the carbon atom, to which they are attached, form a cyclopentane ring, cyclopent-2-ene-1,1-diyl ring, cyclohexane ring or tetrahydropyrane-4,4-diyl ring.

f') Definitions (fⁱ') for $R^8$ in the order of preference, ascending from preferably (f¹') to more preferably (f²') up to most preferably (f³'):

(f¹') Preferably, $R^8$ denotes hydrogen, acetoxy or hydroxy.
(f²') More preferably, $R^8$ denotes hydrogen or hydroxy.
(f³') Most preferably, $R^8$ denotes hydrogen.

Any and each of the above definitions a) (a¹) to f) (f³) and/or a') (a¹') to f') (f³') may be combined with one another.

Each aⁱ, bⁱ, cⁱ, dⁱ, eⁱ, fⁱ of a) to f) or of a') to f') represents a characterized, individual embodiment of the corresponding substituent as described above. Thus given the above definitions, preferred individual embodiments of the compounds of formula I according to the invention (including the tautomers, the stereoisomers, the mixtures, and the salts thereof) are fully characterized by the term (aⁱbⁱcⁱdⁱeⁱfⁱ), wherein for each index i an individual figure is given and i ranges from 1 to the highest number given above; index 0 for each letter refers to the individual embodiment given at the outset of the part "Object of the invention". Indices i vary independently from each other. All individual embodiments described by the term in parentheses with full permutation of the indices i, including i equals 0, referring to the definitions above, shall be comprised by the present invention.

The following Table 1 shows, exemplarily and in the order of increasing preference from the first line to the last line, such embodiments E-1 to E-12 of the compounds according to the invention that are considered preferred. This means that embodiment E-12, represented by the entries in the last row of Table 1, is the most preferred embodiment.

TABLE 1

Preferred individual embodiments E-1 to E-12 of the invention

|   | $R^1$ | $R^2$ | $R^3/R^4$ | $R^5$ | $R^6/R^7$ | $R^8$ |
|---|---|---|---|---|---|---|
| E-1 | $a^1$ | $b^1$ | $c^1$ | $d^1$ | $e^1$ | $f^1$ |
| E-2 | $a^1$ | $b^1$ | $c^1$ | $d^2$ | $e^1$ | $f^1$ |
| E-3 | $a^2$ | $b^1$ | $c^1$ | $d^2$ | $e^1$ | $f^1$ |
| E-4 | $a^2$ | $b^2$ | $c^1$ | $d^2$ | $e^1$ | $f^2$ |
| E-5 | $a^2$ | $b^2$ | $c^1$ | $d^2$ | $e^2$ | $f^1$ |
| E-6 | $a^2$ | $b^3$ | $c^2$ | $d^3$ | $e^2$ | $f^1$ |
| E-7 | $a^3$ | $b^3$ | $c^2$ | $d^3$ | $e^2$ | $f^2$ |
| E-8 | $a^3$ | $b^3$ | $c^2$ | $d^3$ | $e^3$ | $f^2$ |
| E-9 | $a^3$ | $b^4$ | $c^2$ | $d^3$ | $e^3$ | $f^2$ |
| E-10 | $a^4$ | $b^4$ | $c^2$ | $d^3$ | $e^3$ | $f^1$ |
| E-11 | $a^4$ | $b^4$ | $c^2$ | $d^3$ | $e^4$ | $f^2$ |
| E-12 | $a^4$ | $b^4$ | $c^3$ | $d^3$ | $e^4$ | $f^3$ | each including the tautomers, the stereoisomers, the mixtures, and the salts thereof.

Further, the following Table 2 also shows, exemplarily and in the order of increasing preference from the first line to the last line, such embodiments E-13 to E-24 of the compounds according to the invention that are considered preferred. This means that embodiment E-24, represented by the entries in the last row of Table 2, is the most preferred embodiment.

TABLE 2

Even preferred individual embodiments E-13 to E-24 of the invention

|   | $R^1$ | $R^2$ | $R^3/R^4$ | $R^5$ | $R^6/R^7$ | $R^8$ |
|---|---|---|---|---|---|---|
| E-13 | $a^{1'}$ | $b^{1'}$ | $c^{1'}$ | $d^{1'}$ | $e^{1'}$ | $f^{1'}$ |
| E-14 | $a^{1'}$ | $b^{1'}$ | $c^{1'}$ | $d^{2'}$ | $e^{1'}$ | $f^{1'}$ |
| E-15 | $a^{2'}$ | $b^{1'}$ | $c^{1'}$ | $d^{2'}$ | $e^{1'}$ | $f^{1'}$ |
| E-16 | $a^{2'}$ | $b^{2'}$ | $c^{1'}$ | $d^{2'}$ | $e^{1'}$ | $f^{2'}$ |
| E-17 | $a^{2'}$ | $b^{2'}$ | $c^{1'}$ | $d^{2'}$ | $e^{2'}$ | $f^{1'}$ |
| E-18 | $a^{2'}$ | $b^{3'}$ | $c^{2'}$ | $d^{3'}$ | $e^{2'}$ | $f^{1'}$ |
| E-19 | $a^{3'}$ | $b^{3'}$ | $c^{2'}$ | $d^{3'}$ | $e^{2'}$ | $f^{2'}$ |
| E-20 | $a^{3'}$ | $b^{3'}$ | $c^{2'}$ | $d^{3'}$ | $e^{3'}$ | $f^{2'}$ |
| E-21 | $a^{3'}$ | $b^{4'}$ | $c^{2'}$ | $d^{3'}$ | $e^{3'}$ | $f^{2'}$ |
| E-22 | $a^{4'}$ | $b^{4'}$ | $c^{2'}$ | $d^{3'}$ | $e^{3'}$ | $f^{1'}$ |
| E-23 | $a^{4'}$ | $b^{4'}$ | $c^{2'}$ | $d^{3'}$ | $e^{4'}$ | $f^{2'}$ |
| E-24 | $a^{4'}$ | $b^{4'}$ | $c^{3'}$ | $d^{3'}$ | $e^{4'}$ | $f^{3'}$ | each including the tautomers, the stereoisomers, the mixtures, and the salts thereof.

Another preferred embodiment of the compounds of formula I according to this invention refers to compounds of formula I*

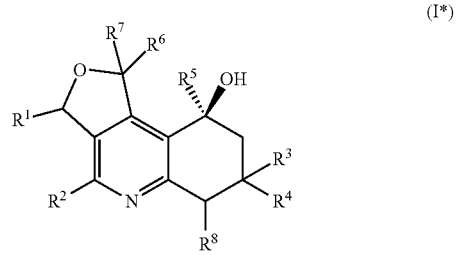

(I*)

wherein the variables $R^1$-$R^8$ are defined as hereinbefore and hereinafter, their tautomers, their stereoisomers, mixtures thereof, and the salts thereof.

This embodiment also includes compounds of formula I*, wherein the variables $R^1$-$R^8$ are selected from above definitions a) ($a^1$) to f) ($f^3$) or a') ($a^{1'}$) to f') ($f^{3'}$), their tautomers, their stereoisomers, mixtures thereof, and the salts thereof.

Particularly, this embodiment refers to compounds of formula I* as defined by the embodiment E-1, E-2, E-3, E-4, E-5, E-6, E-7, E-8, E-9, E-10, E-11 or E-12 in Table 1, and the salts thereof.

Even particularly, this embodiment refers to compounds of formula I* as defined by the embodiment E-13, E-14, E-15, E-16, E-17, E-18, E-19, E-20, E-21, E-22, E-23 or E-24 in Table 2, and the salts thereof.

An embodiment of the compounds of formula I according to this invention refers to compounds of formula I**

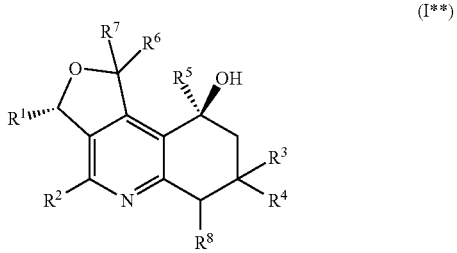

(I**)

wherein the variables $R^1$-$R^8$ are defined as hereinbefore and hereinafter, their tautomers, their stereoisomers, mixtures thereof, and the salts thereof.

This embodiment also includes compounds of formula I**, wherein the variables $R^1$-$R^8$ are selected from above definitions a) ($a^1$) to f) ($f^3$) or a') ($a^{1'}$) to f') ($f^{3'}$), their tautomers, their stereoisomers, mixtures thereof, and the salts thereof.

Particularly, this embodiment refers to compounds of formula I** as defined by the embodiment E-1, E-2, E-3, E-4, E-5, E-6, E-7, E-8, E-9, E-10, E-11 or E-12 in Table 1, and the salts thereof.

Even particularly, this embodiment refers to compounds of formula I** as defined by the embodiment E-13, E-14, E-15, E-16, E-17, E-18, E-19, E-20, E-21, E-22, E-23 or E-24 in Table 2, and the salts thereof.

A preferred embodiment of the compounds of formula I according to this invention refers to compounds of formula I***

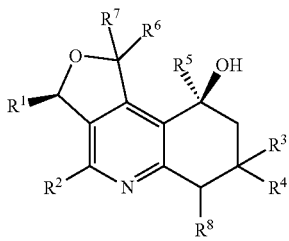

(I***)

wherein the variables $R^1$-$R^8$ are defined as hereinbefore and hereinafter, their tautomers, their stereoisomers, mixtures thereof, and the salts thereof.

This embodiment also includes compounds of formula I***, wherein the variables $R^1$-$R^8$ are selected from above definitions a) ($a^1$) to f) ($f^3$) or a') ($a^{1'}$) to f') ($f^{3'}$), their tautomers, their stereoisomers, mixtures thereof, and the salts thereof.

Particularly, this embodiment refers to compounds of formula I*** as defined by the embodiment E-1, E-2, E-3, E-4, E-5, E-6, E-7, E-8, E-9, E-10, E-11 or E-12 in Table 1, and the salts thereof.

Even particularly, this embodiment refers to compounds of formula I*** as defined by the embodiment E-13, E-14, E-15, E-16, E-17, E-18, E-19, E-20, E-21, E-22, E-23 or E-24 in Table 2, and the salts thereof.

A further embodiment of the compounds of formula I according to this invention refers to compounds of formula I****

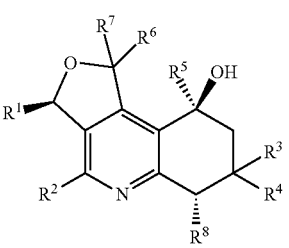

(I****)

wherein the variables $R^1$-$R^8$ are defined as hereinbefore and hereinafter, their tautomers, their stereoisomers, mixtures thereof, and the salts thereof.

This embodiment also includes compounds of formula I****, wherein the variables $R^1$-$R^8$ are selected from above definitions a) ($a^1$) to f) ($f^3$) or a') ($a^{1'}$) to f') ($f^{3'}$), their tautomers, their stereoisomers, mixtures thereof, and the salts thereof.

Particularly, this embodiment refers to compounds of formula I**** as defined by the embodiment E-1, E-2, E-3, E-4, E-5, E-6, E-7, E-8, E-9, E-10, E-11 or E-12 in Table 1, and the salts thereof.

Even particularly, this embodiment refers to compounds of formula I**** as defined by the embodiment E-13, E-14, E-15, E-16, E-17, E-18, E-19, E-20, E-21, E-22, E-23 or E-24 in Table 2, and the salts thereof.

A more preferred embodiment of the compounds of formula I according to this invention refers to compounds of formula I*****

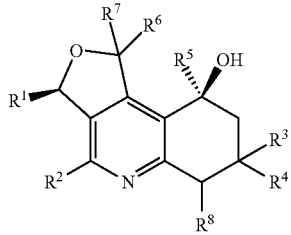

(I*****)

wherein the variables $R^1$-$R^8$ are defined as hereinbefore and hereinafter, their tautomers, their stereoisomers, mixtures thereof, and the salts thereof.

This embodiment also includes compounds of formula I*****, wherein the variables $R^1$-$R^8$ are selected from above definitions a) ($a^1$) to f) ($f^3$) or a') ($a^{1'}$) to f') ($f^{3'}$), their tautomers, their stereoisomers, mixtures thereof, and the salts thereof.

Particularly, this embodiment refers to compounds of formula I***** as defined by the embodiment E-1, E-2, E-3, E-4, E-5, E-6, E-7, E-8, E-9, E-10, E-11 or E-12 in Table 1, and the salts thereof.

Even particularly, this embodiment refers to compounds of formula I***** as defined by the embodiment E-13, E-14, E-15, E-16, E-17, E-18, E-19, E-20, E-21, E-22, E-23 or E-24 in Table 2, and the salts thereof.

The invention further includes all mixtures of the stereoisomers mentioned herein independent of the ratio, including the racemates.

A particularly preferred compound according to the invention is a compound selected from the group consisting of:
(3'R,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

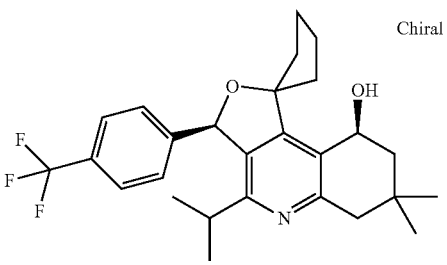 [SMILES: CC(C)c1nc2c(c3c1[C@@H](c1ccc(C(F)(F)F)cc1)OC31CCCC1)[C@@H](O)CC(C)(C)C2]

(3'S,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

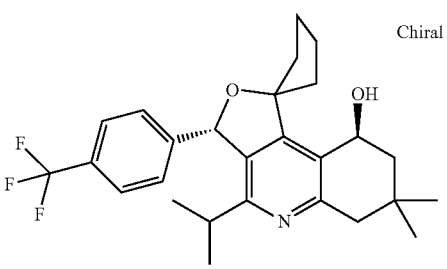 [SMILES: CC(C)c1nc2c(c3c1[C@H](c1ccc(C(F)(F)F)cc1)OC31CCCC1)[C@@H](O)CC(C)(C)C2]

15

(1R,3'S,9'S)-4'-isopropyl-7',7'-dimethyl-3'-(4-(trifluoromethyl)phenyl)-6',7',8',9'-tetrahydro-3'H-spiro[cyclopent[2]ene-1,1'-furo[3,4-c]quinolin]-9'-ol

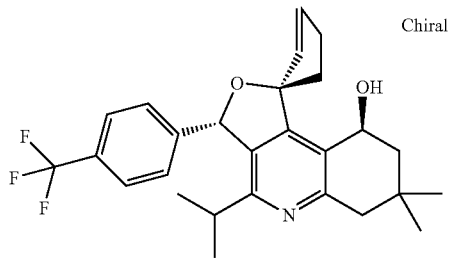

(3R,9S)-4-isopropyl-1,1,7,7-tetramethyl-3-(4-(trifluoromethyl)phenyl)-1,3,6,7,8,9-hexahydrofuro[3,4-c]quinolin-9-ol

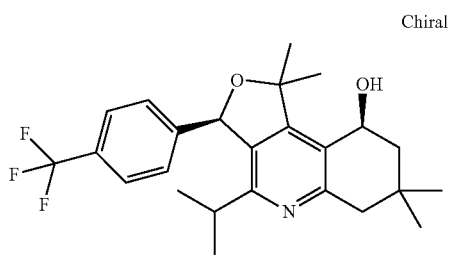 [SMILES: CC(C)c1nc2c(c3c1[C@@H](c1ccc(C(F)(F)F)cc1)OC3(C)C)[C@@H](O)CC(C)(C)C2]

(3'R,9'S)-4'-Isopropyl-7',7'-dimethyl-3'-(4-(trifluoromethyl)phenyl)-6',7',8',9'-tetrahydro-3'H-spiro[cyclohexane-1,1'-furo[3,4-c]quinolin]-9'-ol

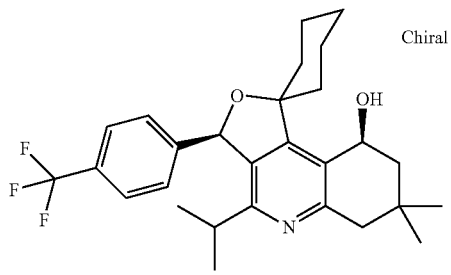 [SMILES: CC(C)c1nc2c(c3c1[C@@H](c1ccc(C(F)(F)F)cc1)OC31CCCCC1)[C@@H](O)CC(C)(C)C2]

(3'R,9'S)-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinolin]-9'-ol

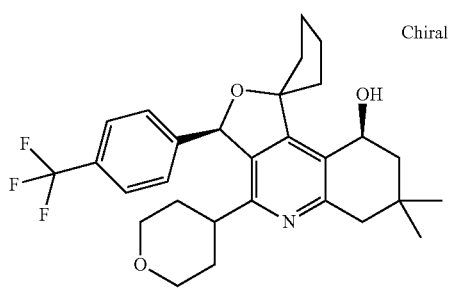 [SMILES: CC1(C)Cc2nc(C3CCOCC3)c3c(c2[C@@H](O)C1)C1(CCCC1)O[C@@H]3c1ccc(C(F)(F)F)cc1]

16

(3'R,9'S)-4'-cyclopentyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

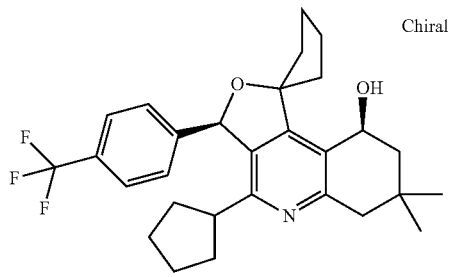 [SMILES: CC1(C)Cc2nc(C3CCCC3)c3c(c2[C@@H](O)C1)C1(CCCC1)O[C@@H]3c1ccc(C(F)(F)F)cc1]

(3'R,9'S)-4'-isopropyl-3'-(4-isopropylphenyl)-7',7'-dimethyl-6',7',8',9'-tetrahydro-3'H-spiro[cyclopentane-1,1'-furo[3,4-c]quinolin]-9'-ol

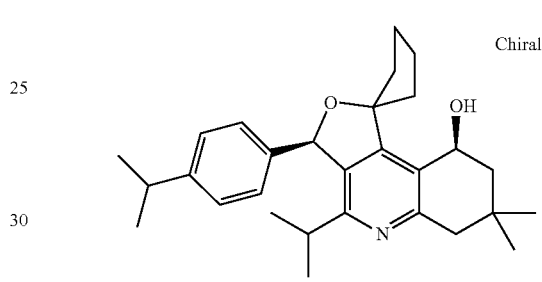

(3'R,9'S)-3'-(4-fluorophenyl)-4'-isopropyl-7',7'-dimethyl-6',7',8',9'-tetrahydro-3'H-spiro[cyclopentane-1,1'-furo[3,4-c]quinolin]-9'-ol

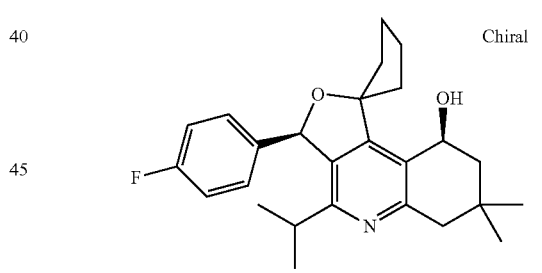

(3'R,9'S)-3'-(4-chlorophenyl)-4'-isopropyl-7',7'-dimethyl-6',7',8',9'-tetrahydro-3'H-spiro[cyclopentane-1,1'-furo[3,4-c]quinolin]-9'-ol

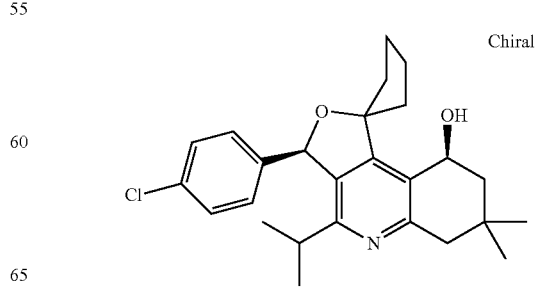

(3'R,9'S)-4'-cyclopentyl-3'-(4-fluorophenyl)-7',7'-dimethyl-6',7',8',9'-tetrahydro-3'H-spiro[cyclopentane-1,1'-furo[3,4-c]quinolin]-9'-ol

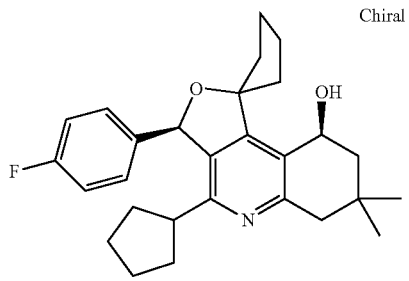 [SMILES: CC1(C)Cc2nc(C3CCCC3)c3c(c2[C@@H](O)C1)C1(CCCC1)O[C@@H]3c1ccc(F)cc1]

(3'R,9'S)-4'-isopropyl-7',7'-dimethyl-3'-p-tolyl-6',7',8',9'-tetrahydro-3'H-spiro[cyclopentane-1,1'-furo[3,4-c]quinolin]-9'-ol

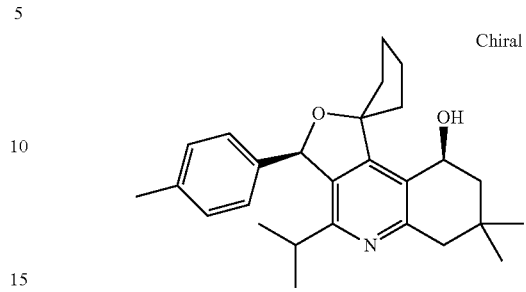

(3'R,9'S)-3'-(4-tert-butylphenyl)-4'-isopropyl-7',7'-dimethyl-6',7',8',9'-tetrahydro-3'H-spiro[cyclopentane-1,1'-furo[3,4-c]quinolin]-9'-ol

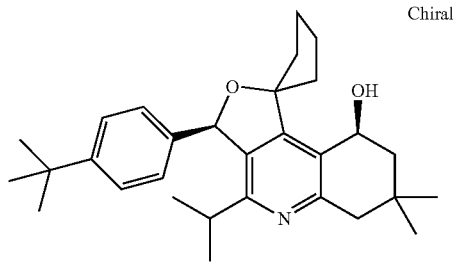 [SMILES: CC(C)c1nc2c(c3c1[C@@H](c1ccc(C(C)(C)C)cc1)OC31CCCC1)[C@@H](O)CC(C)(C)C2]

(3'R,9'S)-4'-isopropyl-7',7'-(propan-1,3-diyl)-3'-(4-(trifluoromethyl)phenyl)-6',7',8',9'-tetrahydro-3'H-spiro[cyclopentane-1,1'-furo[3,4-c]quinolin]-9'-ol

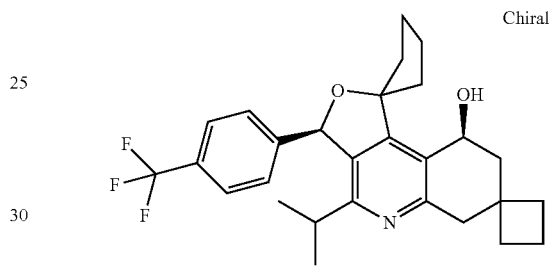

(3'R,9'S)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinolin]-9'-ol

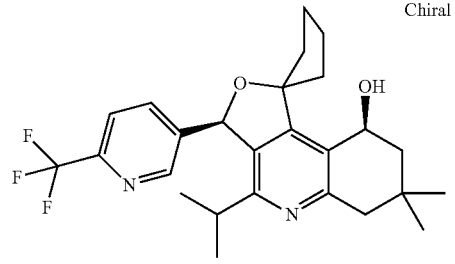 [SMILES: CC(C)c1nc2c(c3c1[C@@H](c1ccc(C(F)(F)F)nc1)OC31CCCC1)[C@@H](O)CC(C)(C)C2]

(3'R,9'S)-3'-(3-fluoro-4-(trifluoromethyl)phenyl)-4'-isopropyl-7',7'-dimethyl-6',7',8',9'-tetrahydro-3'H-spiro[cyclopentane-1,1'-furo[3,4-c]quinolin]-9'-ol

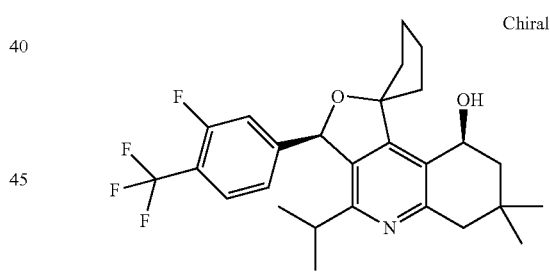

(3'S,9'S)-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinolin]-9'-ol

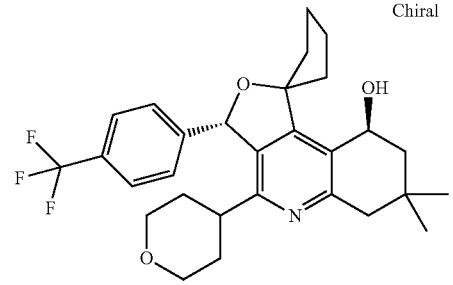 [SMILES: CC1(C)Cc2nc(C3CCOCC3)c3c(c2[C@@H](O)C1)C1(CCCC1)O[C@H]3c1ccc(C(F)(F)F)cc1]

(3'R,9'S)-4'-isopropyl-7',7'-dimethyl-3'-(4-(trifluoromethoxy)phenyl)-6',7',8',9'-tetrahydro-3'H-spiro[cyclopentane-1,1'-furo[3,4-c]quinolin]-9'-ol

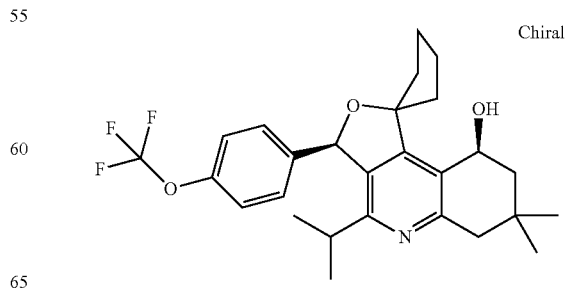

(3R,9S)-3-(4-tert-butylphenyl)-4-isopropyl-1,1,7,7-tetramethyl-1,3,6,7,8,9-hexahydrofuro[3,4-c]quinolin-9-ol

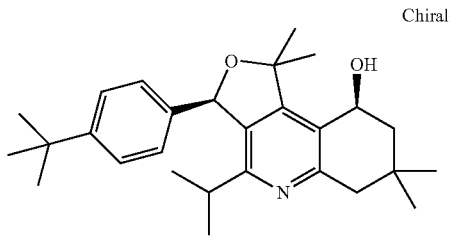 [SMILES: CC(C)c1nc2c(c3c1[C@@H](c1ccc(C(C)(C)C)cc1)OC3(C)C)[C@@H](O)CC(C)(C)C2]

(3R,9S)-3-(4-tert-butylphenyl)-4-cyclopentyl-1,1,7,7-tetramethyl-1,3,6,7,8,9-hexahydrofuro[3,4-c]quinolin-9-ol

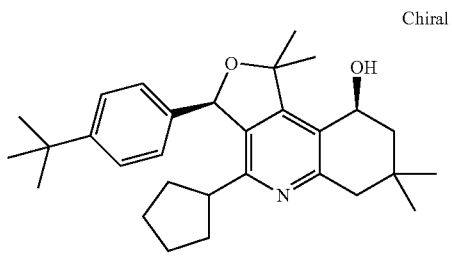 [SMILES: CC1(C)Cc2nc(C3CCCC3)c3c(c2[C@@H](O)C1)C(C)(C)O[C@@H]3c1ccc(C(C)(C)C)cc1]

4-((3'R,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)benzonitrile

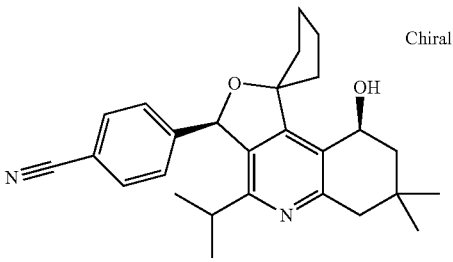 [SMILES: CC(C)c1nc2c(c3c1[C@@H](c1ccc(C#N)cc1)OC31CCCC1)[C@@H](O)CC(C)(C)C2]

(3'S,9'S)-4'-isopropyl-7',7'-dimethyl-3'-(5-(trifluoromethyl)pyridin-2-yl)-6',7',8',9'-tetrahydro-3'H-spiro[cyclopentane-1,1'-furo[3,4-c]quinolin]-9'-ol

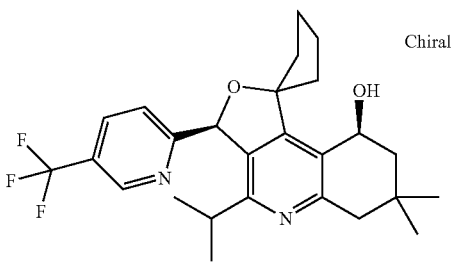 [SMILES: CC(C)c1nc2c(c3c1[C@@H](c1ccc(C(F)(F)F)cn1)OC31CCCC1)[C@@H](O)CC(C)(C)C2]

(3'S,9'R)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

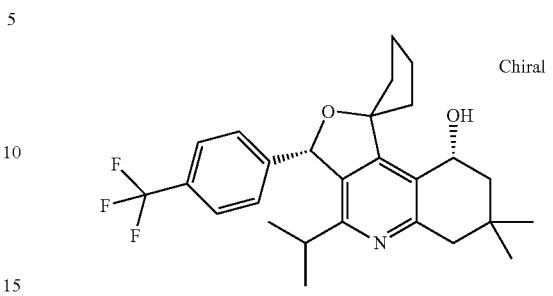

2-(4-((3'R,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile

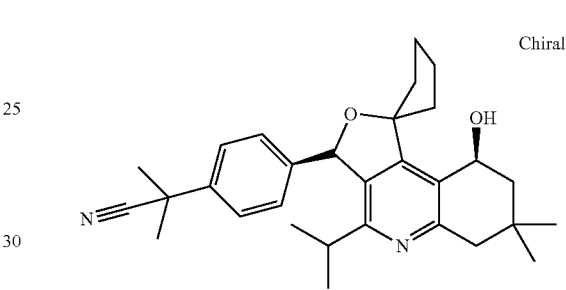

2-(4-((3'S,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile (3'S,9'S)-4'-isopropyl-7',7'-dimethyl-3'-(5-(trifluoromethyl)thiophen-2-yl)-6',7',8',9'-tetrahydro-3'H-spiro[cyclopentane-1,1'-furo[3,4-c]quinolin]-9'-ol

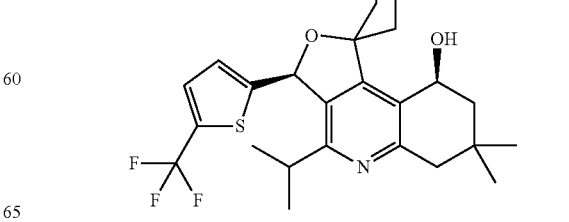

21

(3'R,9'S)-3'-(2-tert-butylpyrimidin-5-yl)-4'-isopropyl-7',7'-dimethyl-6',7',8',9'-tetrahydro-3'H-spiro[cyclopentane-1,1'-furo[3,4-c]quinolin]-9'-ol

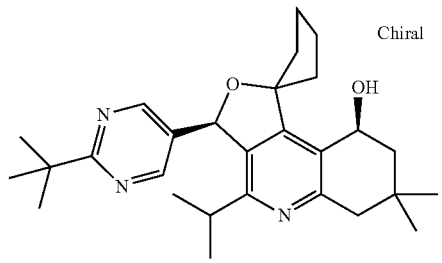 [SMILES: CC(C)c1nc2c(c3c1[C@@H](c1cnc(C(C)(C)C)nc1)OC31CCCC1)[C@@H](O)CC(C)(C)C2]

(3'R,9'S)-3'-(4-(2-hydroxypropan-2-yl)phenyl)-4'-isopropyl-7',7'-dimethyl-6',7',8',9'-tetrahydro-3'H-spiro[cyclopentane-1,1'-furo[3,4-c]quinolin]-9'-ol

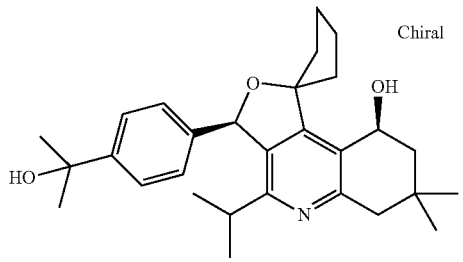 [SMILES: CC(C)c1nc2c(c3c1[C@@H](c1ccc(C(C)(C)O)cc1)OC31CCCC1)[C@@H](O)CC(C)(C)C2]

(3'R,9'S)-3'-(4-isobutylphenyl)-4'-isopropyl-7',7'-dimethyl-6',7',8',9'-tetrahydro-3'H-spiro[cyclopentane-1,1'-furo[3,4-c]quinolin]-9'-ol

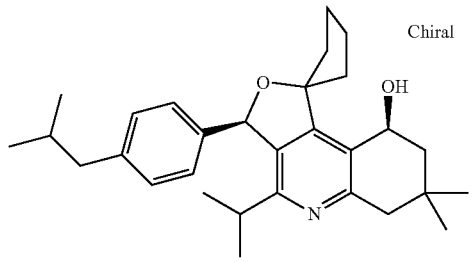 [SMILES: CC(C)Cc1ccc([C@H]2OC3(CCCC3)c3c2c(C(C)C)nc2c3[C@@H](O)CC(C)(C)C2)cc1]

(3'R,9'S)-4'-cyclobutyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

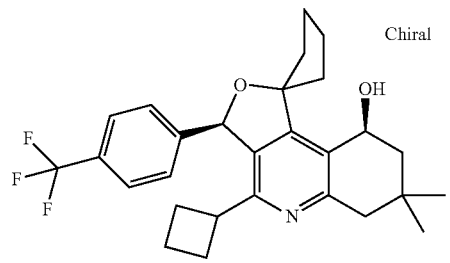 [SMILES: CC1(C)Cc2nc(C3CCC3)c3c(c2[C@@H](O)C1)C1(CCCC1)O[C@@H]3c1ccc(C(F)(F)F)cc1]

22

(3'R,9'S)-4'-cyclopentyl-3'-(4-isopropylphenyl)-7',7'-dimethyl-6',7',8',9'-tetrahydro-3'H-spiro[cyclopentane-1,1'-furo[3,4-c]quinolin]-9'-ol

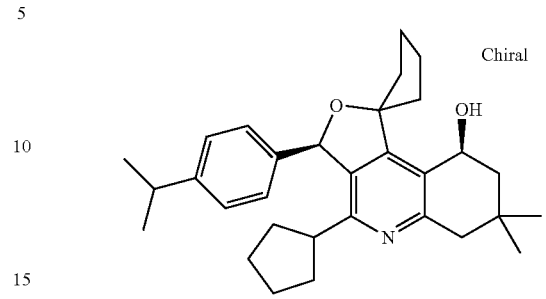

(3R,9S)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-9-ol

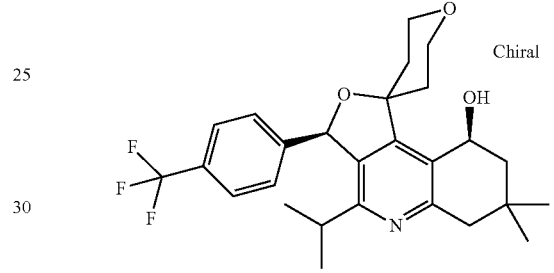

(3'R,9'S)-3'-(3-tert-butylphenyl)-4'-cyclopentyl-7',7'-dimethyl-6',7',8',9'-tetrahydro-3'H-spiro[cyclopentane-1,1'-furo[3,4-c]quinolin]-9'-ol

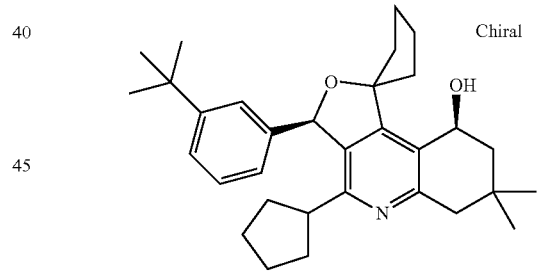

(3'R,9'S)-3'-(4-(1,1-difluoroethyl)phenyl)-4'-isopropyl-7',7'-dimethyl-6',7',8',9'-tetrahydro-3'H-spiro[cyclopentane-1,1'-furo[3,4-c]quinolin]-9'-ol

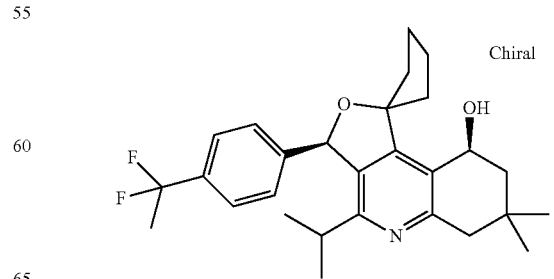

23

(3'R,6'R,9'S)-9'-hydroxy-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate

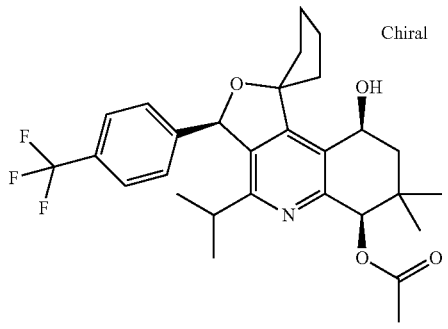 [SMILES: CC(=O)O[C@H]1c2nc(C(C)C)c3c(c2[C@@H](O)CC1(C)C)C1(CCCC1)O[C@@H]3c1ccc(C(F)(F)F)cc1]

(3'R,6'S,9'S)-9'-hydroxy-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate

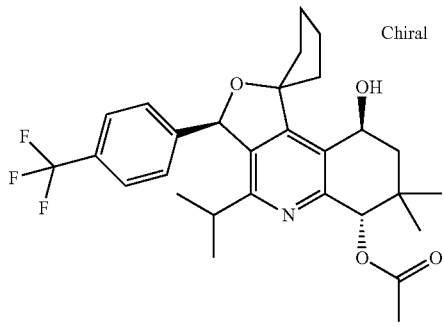 [SMILES: CC(=O)O[C@@H]1c2nc(C(C)C)c3c(c2[C@@H](O)CC1(C)C)C1(CCCC1)O[C@@H]3c1ccc(C(F)(F)F)cc1]

(3'R,6'R,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6',9'-diol

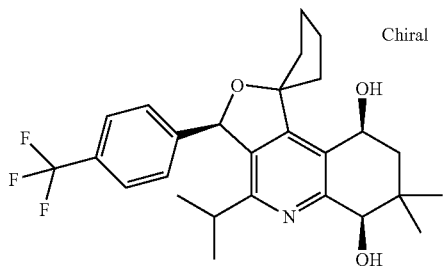 [SMILES: CC(C)c1nc2c(c3c1[C@@H](c1ccc(C(F)(F)F)cc1)OC31CCCC1)[C@@H](O)CC(C)(C)[C@H]2O]

(3'R,6'S,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6',9'-diol

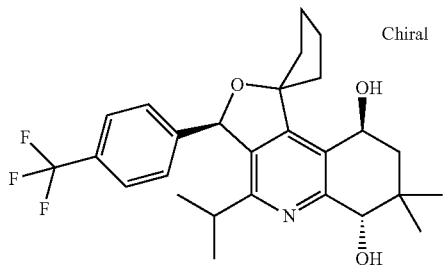 [SMILES: CC(C)c1nc2c(c3c1[C@@H](c1ccc(C(F)(F)F)cc1)OC31CCCC1)[C@@H](O)CC(C)(C)[C@@H]2O]

24

(3'R,9'S)-4'-isopropyl-7',7'-(propan-1,3-diyl)-3'-(4-(isopropyl)phenyl)-6',7',8',9'-tetrahydro-3'H-spiro[cyclopentane-1,1'-furo[3,4-c]quinolin]-9'-ol

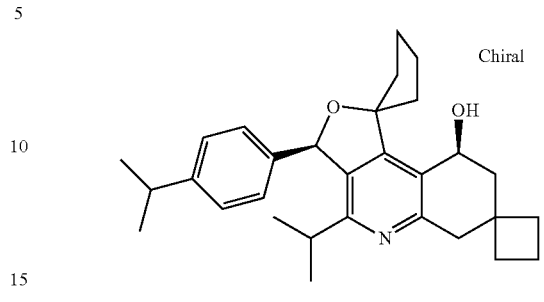

(3'R,9'S)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinolin]-9'-ol

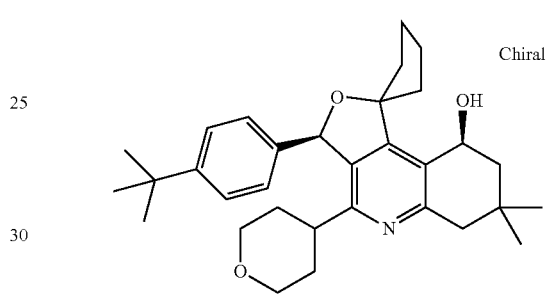

(3'R,9'S)-4'-ethyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

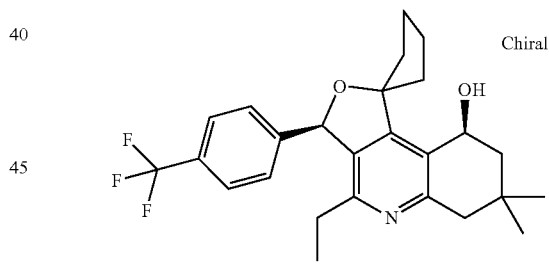

(3'R,6'R,9'S)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline]-6',9'-diol

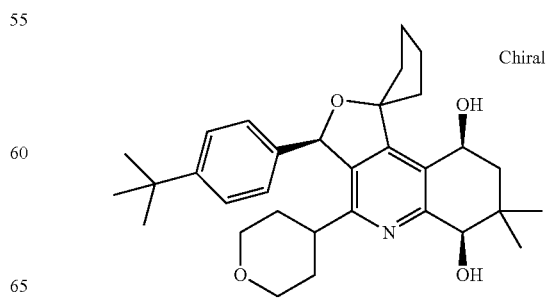

25

(3'R,9'S)-3'-(3,5-difluorophenyl)-4'-isopropyl-7',7'-dimethyl-6',7',8',9'-tetrahydro-3'H-spiro[cyclopentane-1,1'-furo[3,4-c]quinolin]-9'-ol

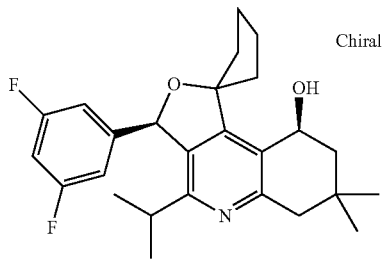 [SMILES: CC(C)c1nc2c(c3c1[C@@H](c1cc(F)cc(F)c1)OC31CCCC1)[C@@H](O)CC(C)(C)C2]

(3R,9S)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-9-ol

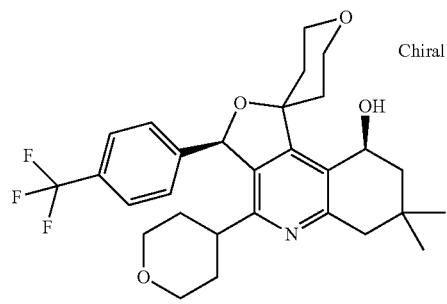 [SMILES: CC1(C)Cc2nc(C3CCOCC3)c3c(c2[C@@H](O)C1)C1(CCOCC1)O[C@@H]3c1ccc(C(F)(F)F)cc1]

(3'R,9'S)-4'-isopropyl-7',7'-dimethyl-3'-(4-(1-methylcyclopropyl)phenyl)-6',7',8',9'-tetrahydro-3'H-spiro[cyclopentane-1,1'-furo[3,4-c]quinolin]-9'-ol

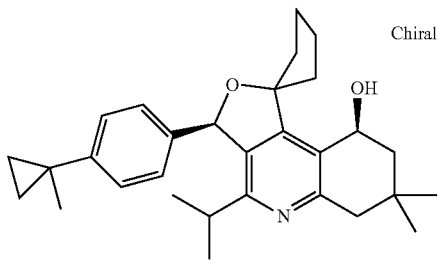 [SMILES: CC(C)c1nc2c(c3c1[C@@H](c1ccc(C4(C)CC4)cc1)OC31CCCC1)[C@@H](O)CC(C)(C)C2]

(3'R,9'S)-4'-isopropyl-7',7'-dimethyl-3'-(3-(trifluoromethyl)phenyl)-6',7',8',9'-tetrahydro-3'H-spiro[cyclopentane-1,1'-furo[3,4-c]quinolin]-9'-ol

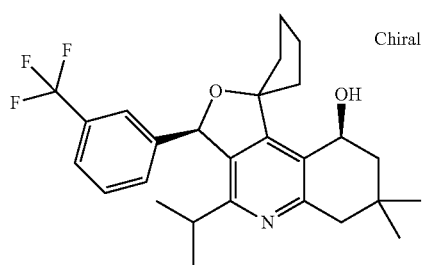 [SMILES: CC(C)c1nc2c(c3c1[C@@H](c1cccc(C(F)(F)F)c1)OC31CCCC1)[C@@H](O)CC(C)(C)C2]

26

(3R,9S)-3-(4-tert-butylphenyl)-4-isopropyl-7,7-dimethyl-2',3',5',6,6',7,8,9-octahydro-3H-spiro[furo[3,4-c]quinoline-1,4'-pyran]-9-ol

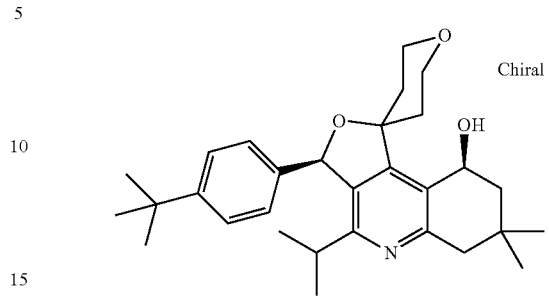

(3'R,9'S)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinolin]-9'-ol

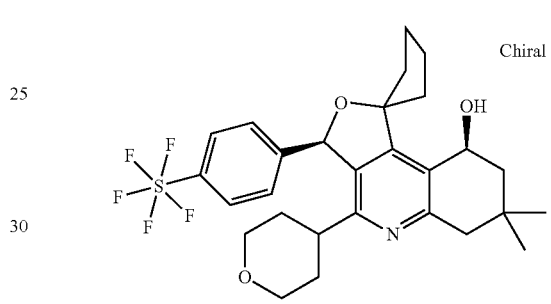

1-(4-((3'R,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)phenyl)cyclopropanecarbonitrile

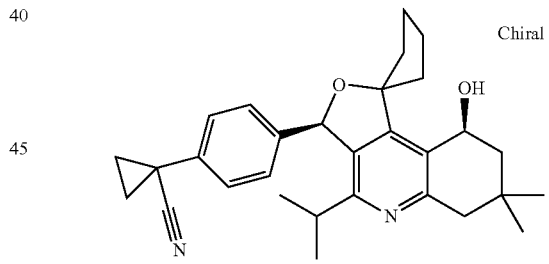

(3'R,9'S)-3'-(4-cyclopropylphenyl)-4'-isopropyl-7',7'-dimethyl-6',7',8',9'-tetrahydro-3'H-spiro[cyclopentane-1,1'-furo[3,4-c]quinolin]-9'-ol

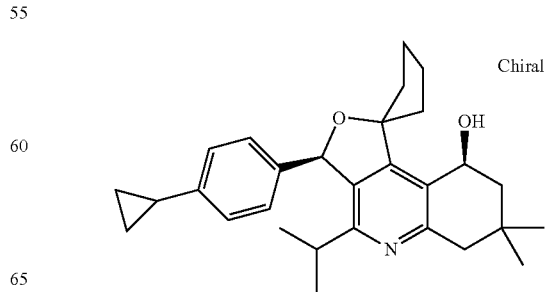

(3'R,6'R,9'S)-9'-hydroxy-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]-6'-yl acetate

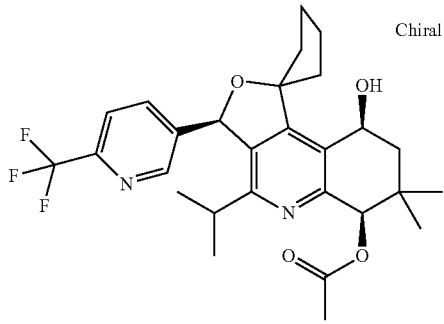 [SMILES: CC(=O)O[C@H]1c2nc(C(C)C)c3c(c2[C@@H](O)CC1(C)C)C1(CCCC1)O[C@@H]3c1ccc(C(F)(F)F)nc1]

(3R,9S)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]-9-ol

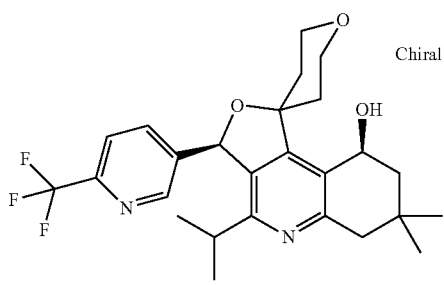 [SMILES: CC(C)c1nc2c(c3c1[C@@H](c1ccc(C(F)(F)F)nc1)OC31CCOCC1)[C@@H](O)CC(C)(C)C2]

(3'R,6'R,9'S)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]-6',9'-diol

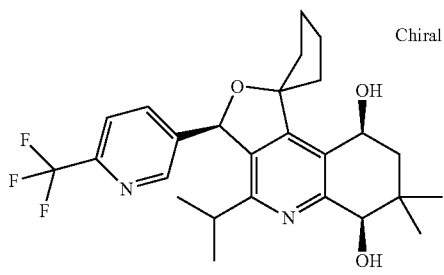 [SMILES: CC(C)c1nc2c(c3c1[C@@H](c1ccc(C(F)(F)F)nc1)OC31CCCC1)[C@@H](O)CC(C)(C)[C@H]2O]

(3R,6R,9S)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-6,9-diol

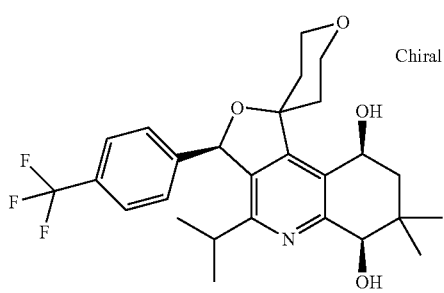 [SMILES: CC(C)c1nc2c(c3c1[C@@H](c1ccc(C(F)(F)F)cc1)OC31CCOCC1)[C@@H](O)CC(C)(C)[C@H]2O]

(3R,6R,9S)-9-hydroxy-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-6-yl acetate

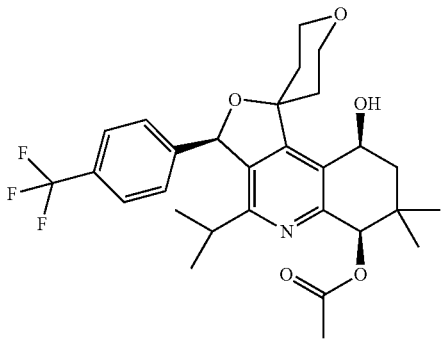

(3'R,6'R,9'S)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6',9'-diol

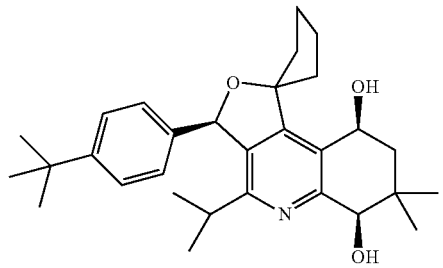

(3'R,6'S,9'S)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6',9'-diol

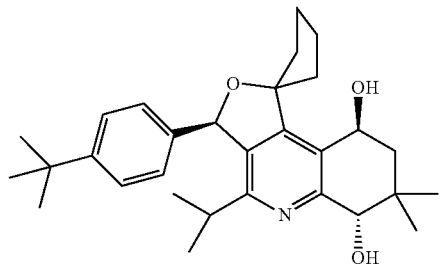

(3S,9S)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]-9-ol

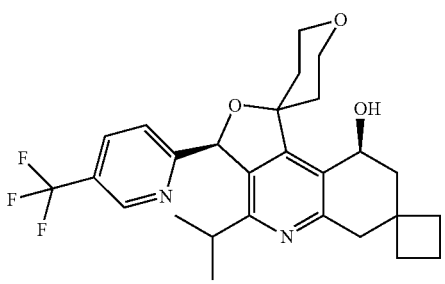

(3R,9S)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-9-ol

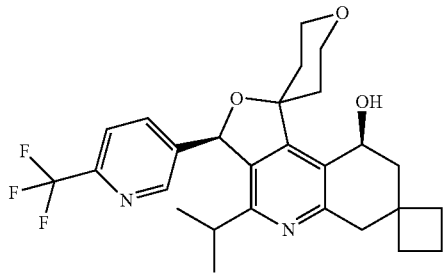

(3R,9S)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]-9-ol

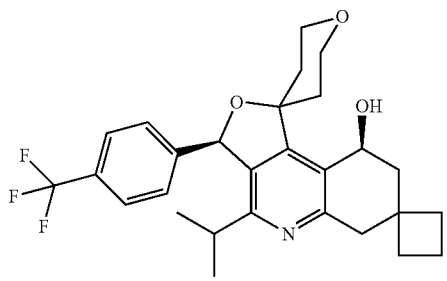

(3R,6R,9S)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]-6,9-diol

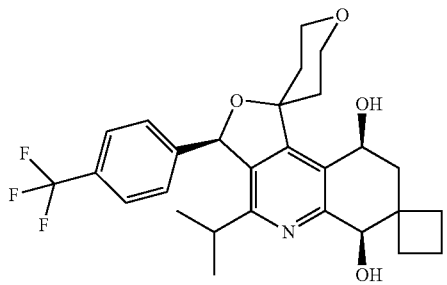

(3S,9S)-3-(2-fluoro-4-(trifluoromethyl)phenyl)-4-isopropyl-7,7-(propan-1,3-diyl)-2',3',5',6,6',7,8,9-octahydro-3H-spiro[furo[3,4-c]quinoline-1,4'-pyran]-9-ol

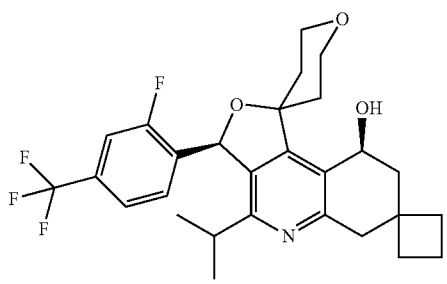

(3R,6R,9S)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-6,9-diol

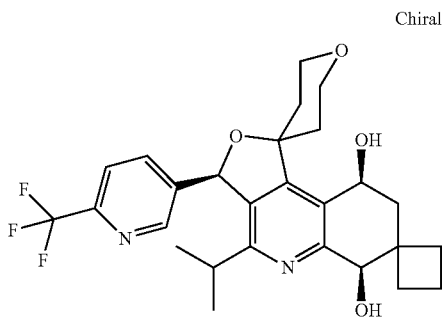 [SMILES: CC(C)c1nc2c(c3c1[C@@H](c1ccc(C(F)(F)F)cc1)OC31CCOCC1)[C@@H](O)CC1(CCC1)[C@H]2O]

(3S,9S)-3-(3-fluoro-5-(trifluoromethyl)pyridin-2-yl)-4-isopropyl-7,7-dimethyl-2',3',5',6,6',7,8,9-octahydro-3H-spiro[furo[3,4-c]quinoline-1,4'-pyran]-9-ol

(3S,6S,9S)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]-6,9-diol

31

(3S,6R,9S)-4-isopropyl-7,7-dimethyl-3-(5-(trifluoromethyl)pyridin-2-yl)-2',3',5',6',7,8,9-octahydro-3H-spiro[furo[3,4-c]quinoline-1,4'-pyran]-6,9-diol

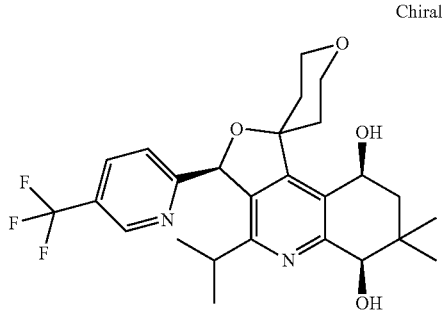

(3R,6S,9S)-4-isopropyl-7,7-dimethyl-3-(6-(trifluoromethyl)pyridin-3-yl)-2',3',5',6',7,8,9-octahydro-3H-spiro[furo[3,4-c]quinoline-1,4'-pyran]-6,9-diol

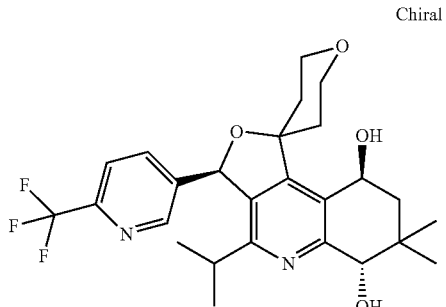 [SMILES: CC(C)c1nc2c(c3c1[C@@H](c1ncc(C(F)(F)F)cc1F)OC31CCOCC1)[C@@H](O)CC(C)(C)C2]

(3R,6R,9S)-4-isopropyl-7,7-dimethyl-3-(6-(trifluoromethyl)pyridin-3-yl)-2',3',5',6',7,8,9-octahydro-3H-spiro[furo[3,4-c]quinoline-1,4'-pyran]-6,9-diol

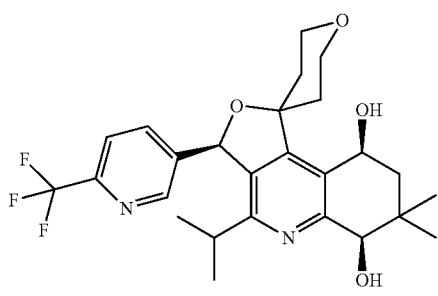

32

(3S,6R,9S)-4-isopropyl-7,7-(propan-1,3-diyl)-3-(5-(trifluoromethyl)pyridin-2-yl)-2',3',5',6',7,8,9-octahydro-3H-spiro[furo[3,4-c]quinoline-1,4'-pyran]-6,9-diol

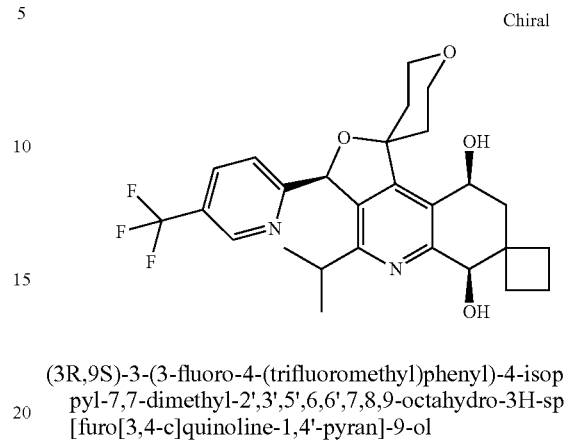

(3R,9S)-3-(3-fluoro-4-(trifluoromethyl)phenyl)-4-isopropyl-7,7-dimethyl-2',3',5',6',7,8,9-octahydro-3H-spiro[furo[3,4-c]quinoline-1,4'-pyran]-9-ol

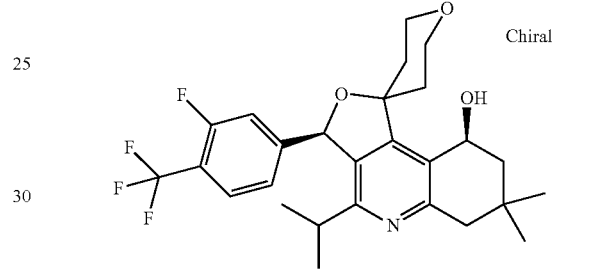

(3S,6R,9S)-3-(2-fluoro-4-(trifluoromethyl)phenyl)-4-isopropyl-7,7-dimethyl-2',3',5',6',7,8,9-octahydro-3H-spiro[furo[3,4-c]quinoline-1,4'-pyran]-6,9-diol

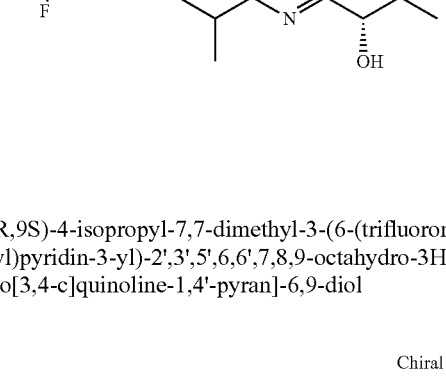

(3S,6S,9S)-3-(2-fluoro-4-(trifluoromethyl)phenyl)-4-isopropyl-7,7-dimethyl-2',3',5',6',7,8,9-octahydro-3H-spiro[furo[3,4-c]quinoline-1,4'-pyran]-6,9-diol

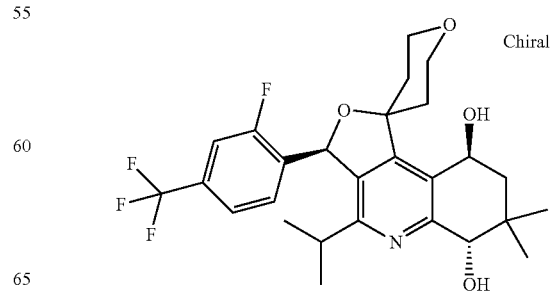

33

(3S,9S)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-9-ol

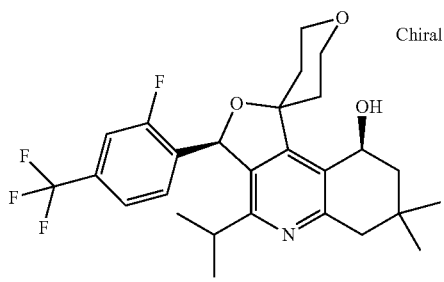 [SMILES: CC(C)c1nc2c(c3c1[C@@H](c1ccc(C(F)(F)F)cc1F)OC31CCOCC1)[C@@H](O)CC(C)(C)C2]

(3S,9S)-3-(5-tert-butyl-4-methylthiazol-2-yl)-4-isopropyl-7,7-dimethyl-2',3',5',6,6',7,8,9-octahydro-3H-spiro[furo[3,4-c]quinoline-1,4'-pyran]-9-ol

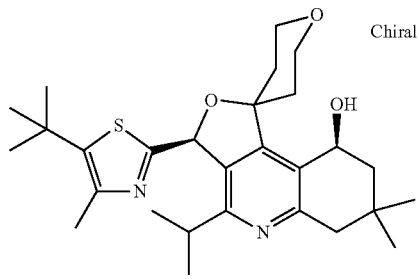 [SMILES: Cc1nc([C@H]2OC3(CCOCC3)c3c2c(C(C)C)nc2c3[C@@H](O)CC(C)(C)C2)sc1C(C)(C)C]

(3S,9S)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-9-ol

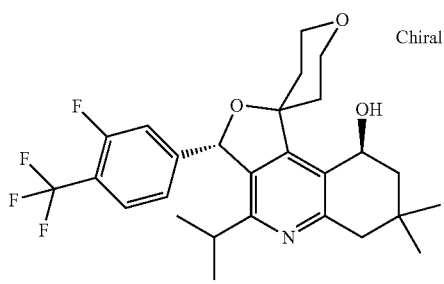 [SMILES: CC(C)c1nc2c(c3c1[C@H](c1ccc(C(F)(F)F)c(F)c1)OC31CCOCC1)[C@@H](O)CC(C)(C)C2]

(3R,6R,9S)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6,9-diol

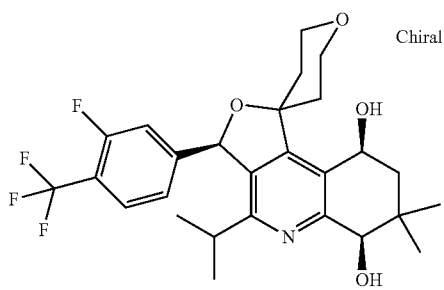 [SMILES: CC(C)c1nc2c(c3c1[C@@H](c1ccc(C(F)(F)F)c(F)c1)OC31CCOCC1)[C@@H](O)CC(C)(C)[C@H]2O]

34

(3R,9S)-4-isopropyl-7,7-(butan-1,4-diyl)-3-(4-(trifluoromethyl)phenyl)-2',3',5',6,6',7,8,9-octahydro-3H-spiro[furo[3,4-c]quinoline-1,4'-pyran]-9-ol

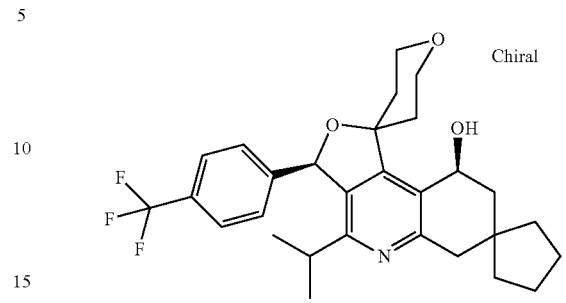

(3R,9S)-3-(4-tert-butoxyphenyl)-4-isopropyl-7,7-dimethyl-2',3',5',6,6',7,8,9-octahydro-3H-spiro[furo[3,4-c]quinoline-1,4'-pyran]-9-ol

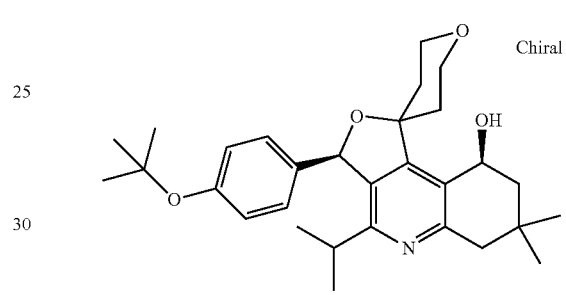

(3R,9S)-3-(4-isopropoxyphenyl)-4-isopropyl-7,7-dimethyl-2',3',5',6,6',7',8',9-octahydro-3H-spiro[furo[3,4-c]quinoline-1,4'-pyran]-9-ol

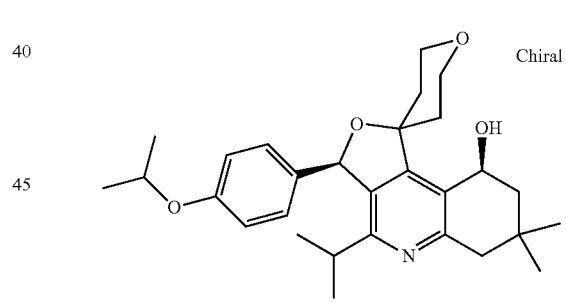

(3'R,9'S)-4'-isopropyl-7',7'-dimethyl-3'-(4-(prop-1-en-2-yl)phenyl)-6',7',8',9'-tetrahydro-3'H-spiro[cyclopentane-1,1'-furo[3,4-c]quinolin]-9'-ol

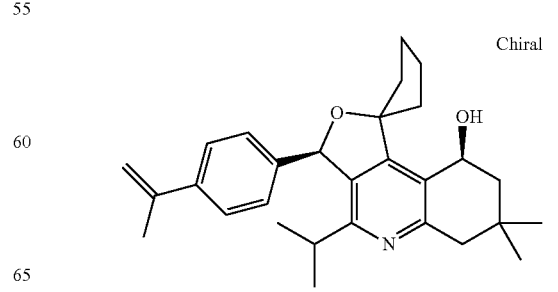

| 35 | 36 |
|---|---|
| (3'R,6'R,9'S)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline]-6',9'-diol | (3R,9S)-3-(4-tert-butylphenyl)-4-isopropyl-7,7-(propan-1,3-diyl)-2',3',5',6,6',7,8,9-octahydro-3H-spiro[furo[3,4-c]quinoline-1,4'-pyran]-9-ol |

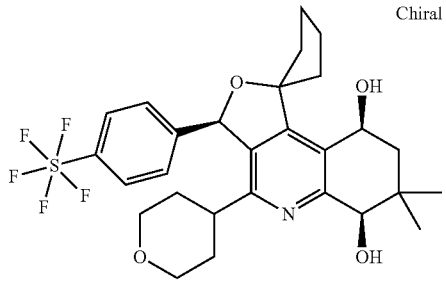 [SMILES: CC1(C)C[C@H](O)c2c(nc(C3CCOCC3)c3c2C2(CCCC2)O[C@@H]3c2ccc(S(F)(F)(F)(F)F)cc2)[C@@H]1O]

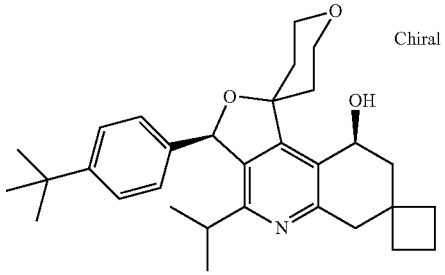

(3R,6R,9S)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]-6,9-diol (3R,9S)-4-isopropyl-7,7-dimethyl-3-(4-(3-methyloxetan-3-yl)phenyl)-2',3',5',6,6',7,8,9-octahydro-3H-spiro[furo[3,4-c]quinoline-1,4'-pyran]-9-ol

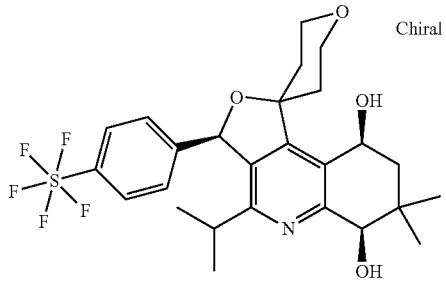 [SMILES: CC(C)c1nc2c(c3c1[C@@H](c1ccc(S(F)(F)(F)(F)F)cc1)OC31CCOCC1)[C@@H](O)CC(C)(C)[C@H]2O]

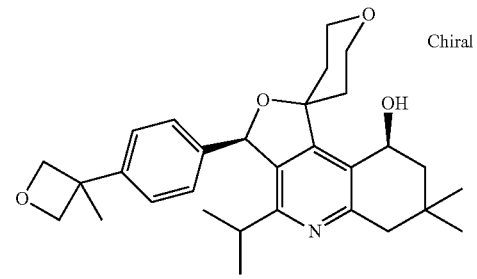

(3R,9S)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran]-9-ol (3'R,9'S)-4'-isopropyl-7',7'-dimethyl-3'-(4-(perfluoroethyl)phenyl)-6',7',8',9'-tetrahydro-3'H-spiro[cyclopentane-1,1'-furo[3,4-c]quinolin]-9'-ol

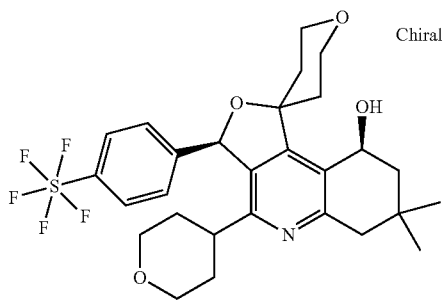 [SMILES: CC1(C)Cc2nc(C3CCOCC3)c3c(c2[C@@H](O)C1)C1(CCOCC1)O[C@@H]3c1ccc(S(F)(F)(F)(F)F)cc1]

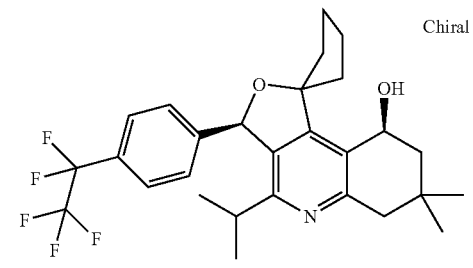

(3'R,9'S)-3'-(4-tert-butylphenyl)-4'-isopropyl-7',7'-(propan-1,3-diyl)-6',7',8',9'-tetrahydro-3'H-spiro[cyclopentane-1,1'-furo[3,4-c]quinolin]-9'-ol 5-((3R,9S)-9-hydroxy-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile

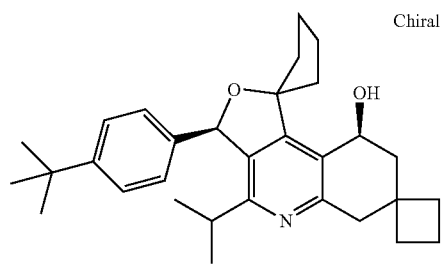 [SMILES: CC(C)c1nc2c(c3c1[C@@H](c1ccc(C(C)(C)C)cc1)OC31CCCC1)[C@@H](O)CC1(CCC1)C2]

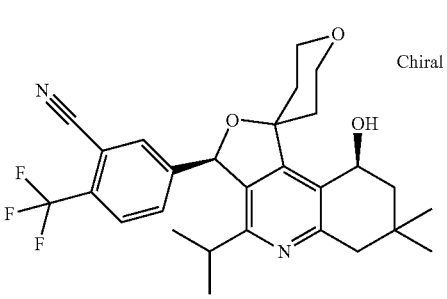 [SMILES: CC(C)c1nc2c(c3c1[C@@H](c1ccc(C(F)(F)F)c(C#N)c1)OC31CCOCC1)[C@@H](O)CC(C)(C)C2]

37

(3S,9S)-4-isopropyl-7,7-dimethyl-3-(5-(trifluoromethyl)py-ridin-2-yl)-2',3',5',6,6',7,8,9-octahydro-3H-spiro[furo[3,4-c]quinoline-1,4'-pyran]-9-ol

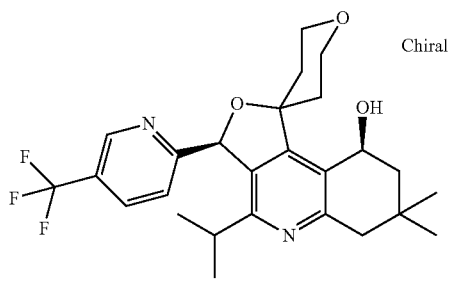 [SMILES: CC(C)c1nc2c(c3c1[C@@H](c1ccc(C(F)(F)F)cn1)OC31CCOCC1)[C@@H](O)CC(C)(C)C2]

(3R,9S)-4-isopropyl-7,7-dimethyl-3-(4-(pentafluorosulfa-nyl)phenyl)-2',3',5',6,6',7,8,9-octahydro-3H-spiro[furo[3,4-c]quinoline-1,4'-pyran]-9-ol

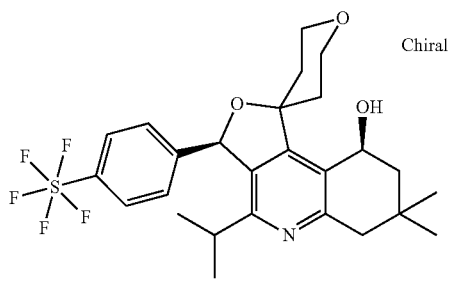 [SMILES: CC(C)c1nc2c(c3c1[C@@H](c1ccc(S(F)(F)(F)(F)F)cc1)OC31CCOCC1)[C@@H](O)CC(C)(C)C2]

(3R,9S)-4-isopropyl-7,7-(propan-1,3-diyl)-3-(4-(pentafluo-rosulfanyl)phenyl)-2',3',5',6,6',7,8,9-octahydro-3H-spiro[furo[3,4-c]quinoline-1,4'-pyran]-9-ol

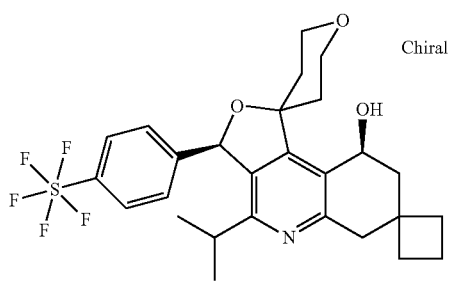 [SMILES: CC(C)c1nc2c(c3c1[C@@H](c1ccc(S(F)(F)(F)(F)F)cc1)OC31CCOCC1)[C@@H](O)CC1(CCC1)C2]

(3R,6R,9S)-4-isopropyl-7,7-(propan-1,3-diyl)-3-(4-(pen-tafluorosulfanyl)phenyl)-2',3',5',6,6',7,8,9-octahydro-3H-spiro[furo[3,4-c]quinoline-1,4'-pyran]-6,9-diol

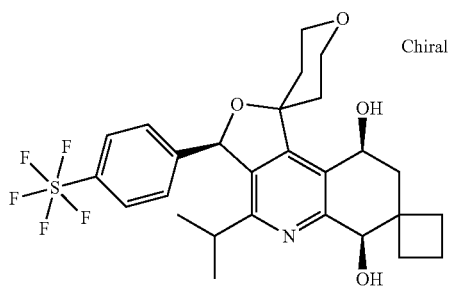 [SMILES: CC(C)c1nc2c(c3c1[C@@H](c1ccc(S(F)(F)(F)(F)F)cc1)OC31CCOCC1)[C@@H](O)CC1(CCC1)[C@H]2O]

38

(3R,9S)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran]-9-ol

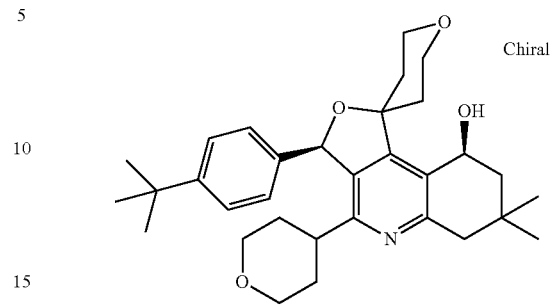

(3'R,9'S)-4'-isopropyl-7',7'-dimethyl-3'-(4-(pentafluorosul-fanyl)phenyl)-6',7',8',9'-tetrahydro-3'H-spiro[cyclopen-tane-1,1'-furo[3,4-c]quinolin]-9'-ol

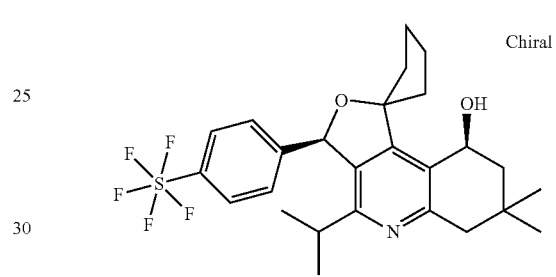

(3R,9S)-4-tert-butyl-7,7-dimethyl-3-(4-(trifluoromethyl)phenyl)-2',3',5',6,6',7,8,9-octahydro-3H-spiro[furo[3,4-c]quinoline-1,4'-pyran]-9-ol

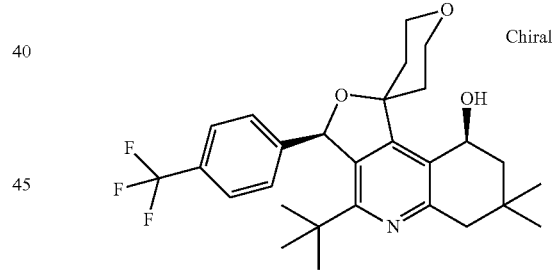

(3R,9S)-4-(1-methoxyethyl)-7,7-dimethyl-3-(4-(trifluorom-ethyl)phenyl)-2',3',5',6,6',7,8,9-octahydro-3H-spiro[furo[3,4-c]quinoline-1,4'-pyran]-9-ol

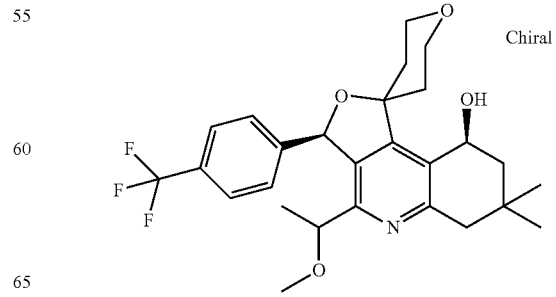

5-((3R,9S)-9-hydroxy-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

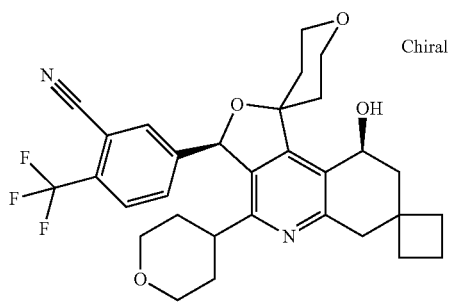 [SMILES: N#Cc1cc([C@H]2OC3(CCOCC3)c3c2c(C2CCOCC2)nc2c3[C@@H](O)CC3(CCC3)C2)ccc1C(F)(F)F]

5-((3R,6R,9S)-6,9-dihydroxy-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

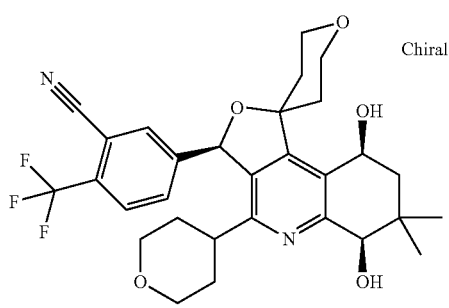 [SMILES: CC1(C)C[C@H](O)c2c(nc(C3CCOCC3)c3c2C2(CCOCC2)O[C@@H]3c2ccc(C(F)(F)F)c(C#N)c2)[C@@H]1O]

(3S,6R,9S)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]-6,9-diol

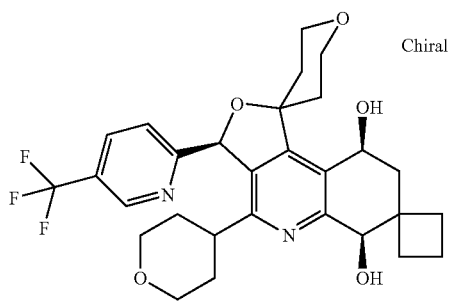 [SMILES: O[C@H]1CC2(CCC2)[C@@H](O)c2nc(C3CCOCC3)c3c(c21)C1(CCOCC1)O[C@@H]3c1ccc(C(F)(F)F)cn1]

(3S,9S)-7,7-dimethyl-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]-9-ol

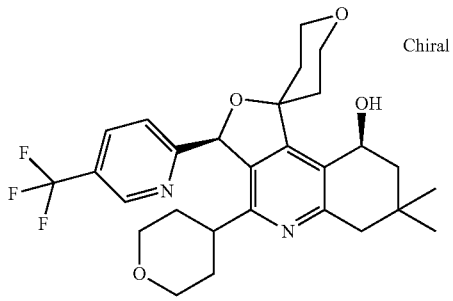 [SMILES: CC1(C)Cc2nc(C3CCOCC3)c3c(c2[C@@H](O)C1)C1(CCOCC1)O[C@@H]3c1ccc(C(F)(F)F)cn1]

5-((3R,9S)-9-hydroxy-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

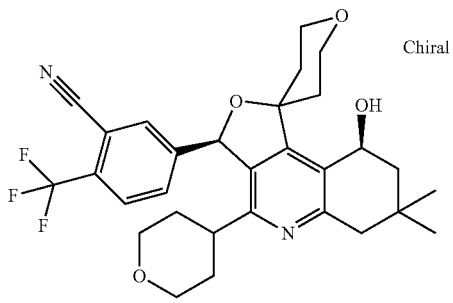 [SMILES: CC1(C)Cc2nc(C3CCOCC3)c3c(c2[C@@H](O)C1)C1(CCOCC1)O[C@@H]3c1ccc(C(F)(F)F)c(C#N)c1]

5-((3R,6R,9S)-6,9-dihydroxy-4-isopropyl-7,7-(propan-1,3-diyl)-2',3',5',6,6',7,8,9-octahydro-3H-spiro[furo[3,4-c]quinoline-1,4'-pyran]-3-yl)-2-(trifluoromethyl)benzonitrile

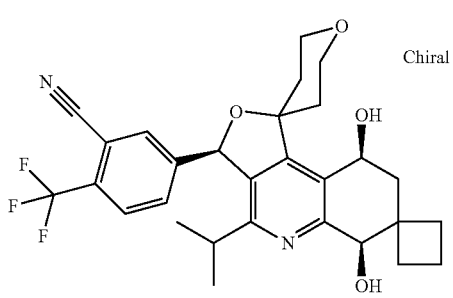 [SMILES: CC(C)c1nc2c(c3c1[C@@H](c1ccc(C(F)(F)F)c(C#N)c1)OC31CCOCC1)[C@@H](O)CC1(CCC1)[C@H]2O]

41

(3R,6R,9S)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-6,9-diol

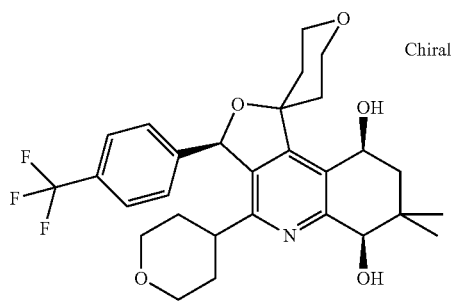 [SMILES: CC1(C)C[C@H](O)c2c(nc(C3CCOCC3)c3c2C2(CCOCC2)O[C@@H]3c2ccc(C(F)(F)F)cc2)[C@@H]1O]

(3R,6R,9S)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran]-6,9-diol

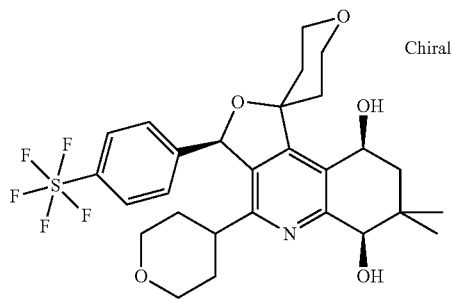 [SMILES: CC1(C)C[C@H](O)c2c(nc(C3CCOCC3)c3c2C2(CCOCC2)O[C@@H]3c2ccc(S(F)(F)(F)(F)F)cc2)[C@@H]1O]

(3R,6R,9S)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]-6,9-diol

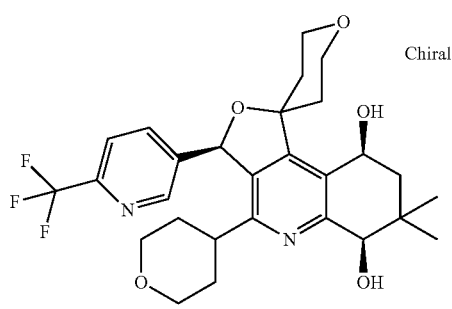 [SMILES: CC1(C)C[C@H](O)c2c(nc(C3CCOCC3)c3c2C2(CCOCC2)O[C@@H]3c2ccc(C(F)(F)F)nc2)[C@@H]1O]

(3R,9S)-4-(methoxymethyl)-7,7-dimethyl-3-(4-(trifluoromethyl)phenyl)-2',3',5',6,6',7,8,9-octahydro-3H-spiro[furo[3,4-c]quinoline-1,4'-pyran]-9-ol

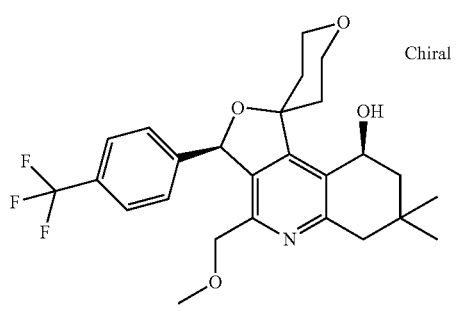 [SMILES: COCc1nc2c(c3c1[C@@H](c1ccc(C(F)(F)F)cc1)OC31CCOCC1)[C@@H](O)CC(C)(C)C2]

42

(3R,6R,9S)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran]-6,9-diol

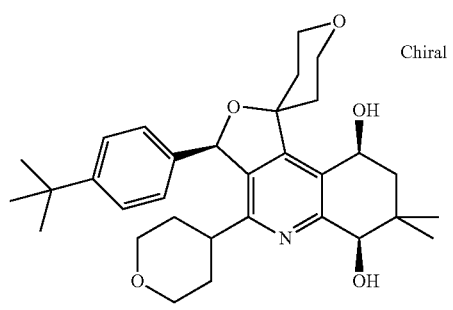 [SMILES: CC(C)(C)c1ccc([C@H]2OC3(CCOCC3)c3c2c(C2CCOCC2)nc2c3[C@@H](O)CC(C)(C)[C@H]2O)cc1]

(3S,9S)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]-9-ol

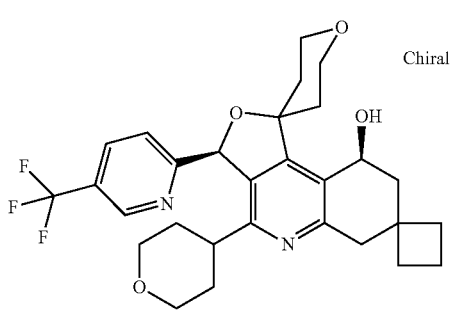 [SMILES: O[C@H]1CC2(CCC2)Cc2nc(C3CCOCC3)c3c(c21)C1(CCOCC1)O[C@@H]3c1ccc(C(F)(F)F)cn1]

(3R,9S)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]-9-ol

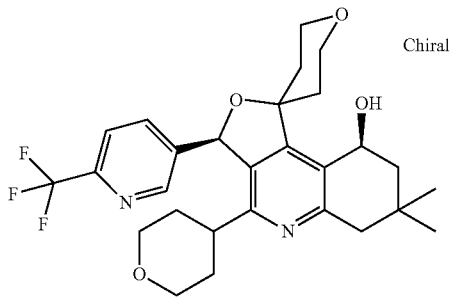 [SMILES: CC1(C)Cc2nc(C3CCOCC3)c3c(c2[C@@H](O)C1)C1(CCOCC1)O[C@@H]3c1ccc(C(F)(F)F)nc1]

(3R,9S)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-9-ol

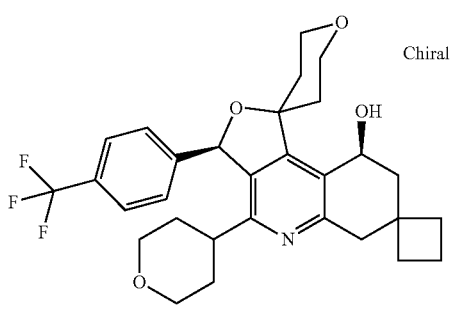 [SMILES: O[C@H]1CC2(CCC2)Cc2nc(C3CCOCC3)c3c(c21)C1(CCOCC1)O[C@@H]3c1ccc(C(F)(F)F)cc1]

(3R,9S)-4-(2-methoxypropan-2-yl)-7,7-dimethyl-3-(4-(trifluoromethyl)phenyl)-2',3',5',6,6',7,8,9-octahydro-3H-spiro[furo[3,4-c]quinoline-1,4'-pyran]-9-ol

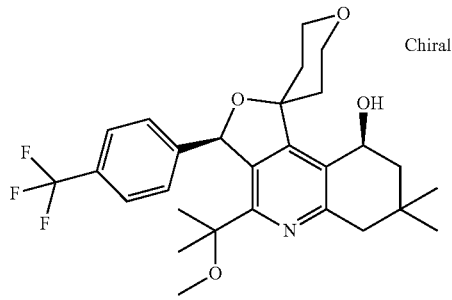 [SMILES: COC(C)(C)c1nc2c(c3c1[C@@H](c1ccc(C(F)(F)F)cc1)OC31CCOCC1)[C@@H](O)CC(C)(C)C2]

(3R,9S)-7,7-(propan-1,3-diyl)-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]-9-ol

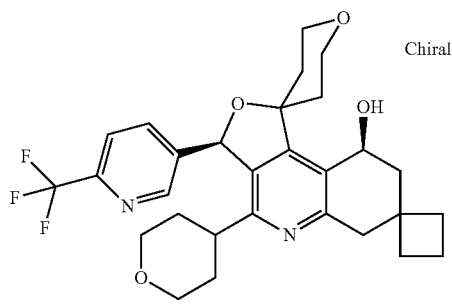 [SMILES: O[C@H]1CC2(CCC2)Cc2nc(C3CCOCC3)c3c(c21)C1(CCOCC1)O[C@@H]3c1ccc(C(F)(F)F)nc1]

5-((3R,9S)-9-hydroxy-4-isopropyl-7,7-(propan-1,3-diyl)-2',3',5',6,6',7,8,9-octahydro-3H-spiro[furo[3,4-c]quinoline-1,4'-pyran]-3-yl)-2-(trifluoromethyl)benzonitrile

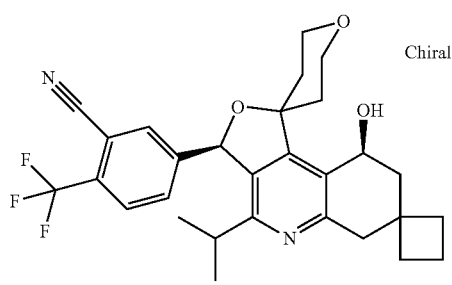 [SMILES: CC(C)c1nc2c(c3c1[C@@H](c1ccc(C(F)(F)F)c(C#N)c1)OC31CCOCC1)[C@@H](O)CC1(CCC1)C2]

5-((3R,6R,9S)-6,9-dihydroxy-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

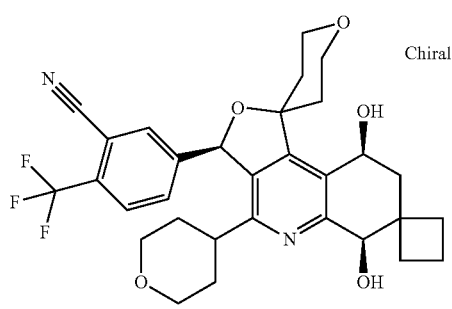 [SMILES: N#Cc1cc([C@H]2OC3(CCOCC3)c3c2c(C2CCOCC2)nc2c3[C@@H](O)CC3(CCC3)[C@H]2O)ccc1C(F)(F)F]

5-((3R,6R,9S)-6,9-dihydroxy-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile

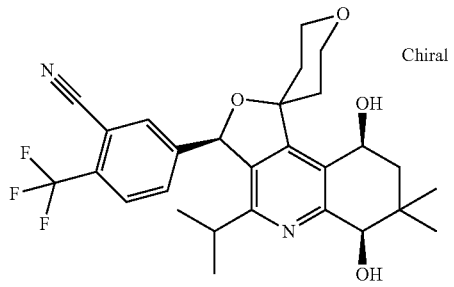 [SMILES: CC(C)c1nc2c(c3c1[C@@H](c1ccc(C(F)(F)F)c(C#N)c1)OC31CCOCC1)[C@@H](O)CC(C)(C)[C@H]2O]

(3R,6R,9S)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-6,9-diol

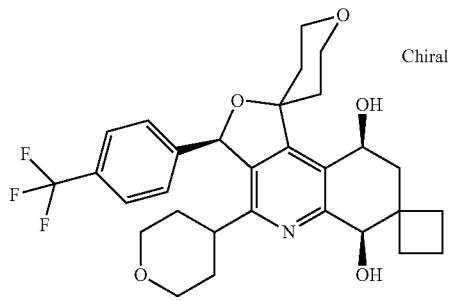 [SMILES: O[C@H]1CC2(CCC2)[C@@H](O)c2nc(C3CCOCC3)c3c(c21)C1(CCOCC1)O[C@@H]3c1ccc(C(F)(F)F)cc1]

(3'S,9'S)-4,4-difluoro-4'-isopropyl-7',7'-dimethyl-3'-(5-(trifluoromethyl)pyridin-2-yl)-6',7',8',9'-tetrahydro-3'H-spiro[cyclohexane-1,1'-furo[3,4-c]quinolin]-9'-ol

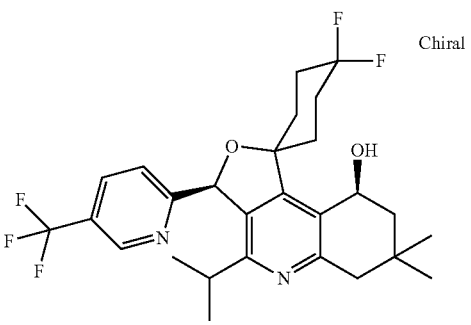 [SMILES: CC(C)c1nc2c(c3c1[C@@H](c1ccc(C(F)(F)F)cn1)OC31CCC(F)(F)CC1)[C@@H](O)CC(C)(C)C2]

and (3'R,9'S)-4,4-difluoro-4'-isopropyl-7',7'-dimethyl-3'-(5-(trifluoromethyl)pyridin-2-yl)-6',7',8',9'-tetrahydro-3'H-spiro[cyclohexane-1,1'-furo[3,4-c]quinolin]-9'-ol

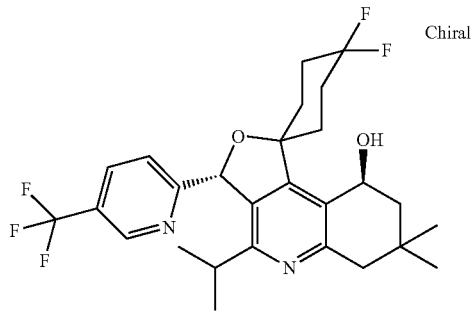 [SMILES: CC(C)c1nc2c(c3c1[C@H](c1ccc(C(F)(F)F)cn1)OC31CCC(F)(F)CC1)[C@@H](O)CC(C)(C)C2]

or a salt thereof.

Some terms used above and below in connection with the compounds according to the invention will now be defined more closely:

The term "substituted" as used herein means that any one or more hydrogens on the designated atom is replaced with a selection from the indicated group, provided that the designated atom's normal valence is not exceeded, and that the substitution results in a stable compound.

The term 1-nC-alkyl, alone or as part of another group, wherein n may have a value of 1 to 6, denotes a saturated, branched or unbranched aliphatic, acyclic hydrocarbon group having 1 to n C atoms. Examples of such groups may include, without being limited to, methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term 2-nC-alkenyl, alone or as part of another group, wherein n may have a value of 2 to 4, denotes an unsaturated, branched or unbranched aliphatic, acyclic hydrocarbon group having 2 to n C atoms and at least one C=C double bond. Examples of such groups may include, without being limited to, ethenyl, prop-1-en-1-yl, prop-1-en-2-yl, but-1-en-1-yl, but-1-en-2-yl, but-2-en-2-yl, etc.

The term halogen within the meaning of the present invention refers to fluorine, chlorine, bromine and iodine, of which fluorine, chlorine and bromine are more worthy to be mentioned.

The term 1-nC-alkoxy, alone or as part of another group, denotes a 1-nC-alkyl-O— group, wherein 1-nC-alkyl is as hereinbefore defined. Examples of such groups may include, without being limited to, methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy, etc.

The term 1-nC-alkoxy-1-nC-alkyl means a 1-nC-alkyl group as defined herein which is substituted by a 1-nC-alkoxy group as defined herein.

The term cyano-1-nC-alkyl means a 1-nC-alkyl group as defined herein which is substituted by a cyano group.

The term hydroxy-1-nC-alkyl means a 1-nC-alkyl group as defined herein which is substituted by a hydroxy group.

A mono- or bicyclic 5- to 10-membered aryl or heteroaryl group, which heteroaryl contains 1 to 4 heteroatoms selected from the group consisting of N, O and S, refers to a mono- or fused bicyclic 5- to 10-membered (fully or partially) aromatic or heteroaromatic ring system optionally comprising 0 to 4 heteroatoms selected from the group consisting of N, O and S.

An aryl group as mentioned herein, alone or as part of another group, refers to a carbocyclic, mono- or fused bicyclic (fully or partially) aromatic ring system having the indicated numbers of ring members. Representative 6- or 10-membered mono- or fused bicyclic aryl groups include, without being limited to, phenyl and naphthyl.

A heteroaryl group as mentioned herein, alone or as part of another group, refers to a heterocyclic, mono- or fused bicyclic (fully or partially) heteroaromatic ring system having the indicated numbers of ring members and containing 1 to 4 heteroatoms selected from nitrogen, oxygen and sulphur.

Representative 5-membered monocyclic heteroaryl groups include, without being limited to, thiophenyl (thienyl), furanyl, pyrrolyl, imidazolyl, pyrazolyl, thiazolyl, isothiazolyl, oxazolyl, isoxazolyl, thiadiazolyl, and oxadiazolyl, Representative 6-membered monocyclic heteroaryl groups include, without being limited to, pyridyl, pyrimidinyl, pyridazinyl, and pyrazinyl.

Representative 9-membered fused bicyclic groups include, without being limited to, indolyl, benzothiophenyl, benzofuranyl, benzimidazolyl, benzopyrazolyl (indazolyl), benzthiazolyl, benzoxazolyl, benzisothiazolyl, and benzisoxazolyl.

Representative 10-membered fused bicyclic heteroaryl groups include, without being limited to, quinolyl, isoquinolyl, and quinazolyl.

Among the 5- to 10-membered aryl or heteroaryl groups mentioned herein, thiophenyl, thiazolyl, phenyl, pyridyl, pyrimidinyl, pyridazinyl, pyrazinyl and naphthyl are more worthy to be mentioned.

The term 3-nC-cycloalkyl, alone or as part of another group, wherein n may have a value of 4 to 7, denotes a saturated, monocyclic, aliphatic hydrocarbon ring group having 3 to n ring C atoms. Examples of such groups may include, without being limited to, cyclopropyl, cyclobutyl, cyclopentyl, cyclohexyl and cycloheptyl, of which cyclopropyl, cyclobutyl, cyclopentyl and cyclohexyl are more worthy to be mentioned.

The term 3-nC-cycloalkane, alone or as part of another group, wherein n may have a value of 4 to 7, denotes a saturated, monocyclic, aliphatic hydrocarbon ring having 3 to n ring C atoms. Examples of such rings may include, without being limited to, a cyclopropane, cyclobutane, cyclopentane, cyclohexane and cycloheptane ring, of which cyclopropane, cyclobutane, cyclopentane and cyclohexane are more worthy to be mentioned.

The term 1-nC-alkyl-3-nC-cycloalkyl means a 3-nC-cycloalkyl group as defined herein which is substituted by a 1-nC-alkyl group as defined herein.

The term cyano-3-nC-cycloalkyl means a 3-nC-cycloalkyl group as defined herein which is substituted by a cyano group.

Completely or partially fluorine-substituted 1-nC-alkyl is, for example difluoromethyl, trifluoromethyl, pentafluoroethyl, 2,2-difluoroethyl, 2,2,2-trifluoroethyl, 1,1-difluoro-1-ethyl or 1,1,1,3,3,3-hexafluoroisopropyl, of which trifluoromethyl is to be emphasized. In an embodiment, partially fluorine-substituted 1-nC-alkyl stands for predominantly fluorine-substituted 1-nC-alkyl. "Predominantly" in this connection means that more than half of the hydrogen atoms of the 1-nC-alkyl groups are replaced by fluorine atoms.

Completely or partially fluorine-substituted 1-nC-alkoxy is, for example difluoromethoxy, trifluoromethoxy, pentafluoroethoxy, 2,2-difluoroethoxy, 2,2,2-trifluoroethoxy or 1,1,1,3,3,3-hexafluorisopropoxy. In an embodiment, partially fluorine-substituted 1-nC-alkoxy stands for predominantly fluorine-substituted 1-nC-alkoxy. "Predominantly" in this connection means that more than half of the hydrogen atoms of the 1-nC-alkoxy groups are replaced by fluorine atoms.

In general, unless otherwise mentioned, heterocyclic groups mentioned herein include all the possible isomeric forms thereof, e.g. tautomers and/or positional isomers thereof. Thus, for example, the term pyridyl includes pyridine-2-yl, pyridine-3-yl and pyridine-4-yl.

Constituents which are substituted as stated herein, may be substituted, unless otherwise noted, at any possible position.

Further, unless otherwise noted, carbocyclic groups which are substituted as mentioned herein may be substituted by their given substituents or parent molecular groups at any possible position.

Further, the heterocyclic groups mentioned herein may be substituted by their given substituents or parent molecular groups, unless otherwise noted, at any possible position, such as e.g. at any substitutable ring carbon or ring nitrogen atom.

Further, unless otherwise noted, rings containing quaternizable amino- or imino-type ring nitrogen atoms (—N═) may be preferably not quaternized on these amino- or imino-type ring nitrogen atoms.

If residues, substituents or groups occur several times in a compound they may have the same or different meanings.

In general, for groups comprising two or more subgroups, the last named subgroup is the radical attachment point, for example, the substituent "1-nC-alkoxy-1-nC-alkyl" means a 1-nC-alkoxy group which is bound to a 1-nC-alkyl group, the latter of which is bound to the core or to the group to which the substituent is attached.

All atoms/elements, including atoms that are part of a group, described herein comprise all stable isotopic forms of the respective element. For instance, whenever hydrogen is mentioned, either explicitly or as part of a group such as methyl, this includes hydrogen and deuterium as stable isotopic forms of the element hydrogen.

Unless otherwise stated, the groups, residues and substituents, particularly $R^1$ to $R^8$, $R^{7'}$, PG, $R^a$, $R^b$, $R^9$ to $R^{11}$ are defined as above and below.

If not otherwise specified, the substituents $R^9$, $R^{10}$ and/or $R^{11}$ can be attached in the ortho, meta or para position with respect to the binding position in which the aryl ring is bonded to the scaffold ring system, whereby emphasis is given to the attachment in the meta or in the para position.

Salts of the compounds of formula I according to the present invention include—depending upon their nature—all acid addition salts and all salts with bases, especially all pharmaceutically acceptable acid addition salts and salts with bases. Particular mention may be made of the physiologically tolerable salts with inorganic or organic acids or bases customarily used in pharmacy. The salts include water-insoluble and, particularly, water-soluble salts.

Inorganic acids suitable for forming pharmaceutically or physiologically acceptable acid addition salts include, by way of example and not limitation, hydrochloric acid, hydrobromic acid, phosphoric acid, sulfuric acid, and the like. Organic acids suitable for forming pharmaceutically or physiologically acceptable acid addition salts include, by way of example and not limitation, citric acid, maleic acid, fumaric acid, succinic acid, lactic acid, tartaric acid, methanesulfonic acid, and the like.

Thus, pharmaceutically or physiologically acceptable acid addition salts with inorganic or organic acids include, by way of example and not limitation, hydrochlorides, hydrobromides, phosphates, sulfates, citrates, maleates, fumarates, succinates, lactates, tartrates, methanesulfonates (mesylates), and the like.

Salts which are unsuitable for pharmaceutical uses but which can be employed, for example, for the isolation or purification of free compounds of formula I or their pharmaceutically acceptable salts, are also included.

Pharmaceutically non-acceptable salts, which can be obtained, for example, as process products during the preparation of the compounds according to this invention e.g. on an industrial scale, are converted into pharmaceutically acceptable salts by processes known to the person skilled in the art.

All isomeric forms (especially all regio- and stereoisomeric forms, e.g. all chiral, enantiomeric, diastereomeric, racemic forms, tautomeric and all geometric isomeric forms) of a compound of formula I are intended within this invention, unless the specific isomer form is specifically indicated. Obviously, the isomer which is pharmacologically most effective and most free from side effects is preferred.

It will be appreciated that the compounds of the present invention contain at least two asymmetrically substituted carbon atoms, and may be isolated as pure diastereomers or diastereomeric mixtures in optically active or racemic forms.

The compounds of formula I are chiral compounds having chiral centers at least in positions 3 and 9, as well as, depending on the meanings of $R^3$ and $R^4$, in position 7, depending on the meanings of $R^8$, in position 6 and, depending on the meanings of $R^6$ and $R^7$, in position 1.

Numbering:

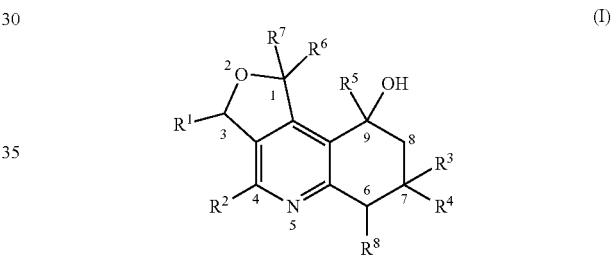

(I)

The invention contemplates all conceivable stereoisomers, particularly the diastereomers and enantiomers mentioned herein, e.g. in substantially pure form, in enriched form (e.g. substantially free of any or all other undesired diastereomers and/or enantiomers) and/or in any mixing ratio, including the racemic forms, as well as the salts thereof.

In general, substantially pure stereoisomers can be obtained according to synthetic principles customary to the skilled person, e.g. by separation of corresponding mixtures, by using stereochemically pure starting materials and/or by stereoselective synthesis.

It is known in the art how to prepare optically active forms, such as by resolution of racemic forms or by synthesis, e.g. from optically active starting materials and/or by using chiral reagents.

Enantiomerically pure compounds of this invention can be prepared via asymmetric synthesis, for example by preparation and separation of appropriate diastereoisomeric compounds/intermediates which can be separated by known methods (e.g. by chromatographic separation or (fractional) crystallization from a suitable solvent), and/or by using chiral reaction components (e.g. chiral reagents, chiral catalysts, chiral ligands, chiral synthons, chiral building blocks, or the like).

Further, it is known to the person skilled in the art how to prepare enantiomerically pure compounds from the corresponding racemic mixtures, such as e.g. by chromatographic separation of the corresponding racemic compounds on chiral separating columns; or by resolution of racemic compounds using an appropriate resolving agent; e.g. by means of diastereomeric salt formation of the racemic compounds with optically active acids or bases, subsequent resolution of the salts and release of the desired compound from the salt; or by derivatization of the corresponding racemic compounds with chiral auxiliary reagents, subsequent diastereomer separation and removal of the chiral auxiliary group; by kinetic resolution of a racemate (e.g. by enzymatic resolution); by enantioselective (preferential) crystallization (or crystallization by entrainment) from a conglomerate of enantiomorphous crystals under suitable conditions; or by (fractional) crystallization from a suitable solvent in the presence of a chiral auxiliary.

Enzymatic Assay

The biological properties of the new compounds may be investigated as follows:

CETP In Vitro Assay

CETP inhibitory activity of compounds of the present invention can be determined in a fluorometric assay purchased from Roar Biomedical, Inc. (New York, N.Y., USA). The compounds of the present invention inhibit CETP-dependent cholesterol ester transfer from HDL to LDL as described here. Recombinant human CETP was partially purified from medium conditioned by CETP expressing CHO cells. In a 384 well format 2.5 μl of compound solution in DMSO was combined with 2 μl of donor solution, 2 μl of acceptor solution and 0.8 μl of recombinant human CETP solution in a total volume of 100 μl with assay buffer and incubated for 3 hours at 37° C. The fluorescence intensity was measured at excitation wavelength of 485 nm and emission wavelength of 535 nm. $IC_{50}$ values are calculated from dose effect curves from compound concentrations between 1 nM and 30 μM.

The compounds of general formula I according to the invention for example have $IC_{50}$ values below 10000 nM, preferably below 2000 nM, more preferably below 400 nM and most preferably below 100 nM. The $IC_{50}$ values of the examples compiled in the experimental part are provided in the following Table 2.

TABLE 2

$IC_{50}$ values for inhibition of CETP by the examples compiled in the experimental part

| Example | $IC_{50}$ [nM] |
|---|---|
| 1 | 54 |
| 1(1) | 1433 |
| 1(2) | 4682 |
| 2 (Diastereomer 1) | 699 |
| 1(3) | 460 |
| 1(4) | 45 |
| 1(5) | 42 |
| 1(6) | 37 |
| 1(7) | 77 |
| 1(8) | 856 |
| 1(9) | 148 |
| 1(10) | 360 |
| 1(11) | 36 |
| 1(12) | 150 |
| 1(13) | 6890 |
| 1(14) | 409 |
| 1(15) | 21 |
| 1(16) | 43 |
| 1(17) | 131 |
| 1(18) | 363 |
| 1(19) | 351 |
| 1(20) | 1077 |
| 1(21) | 124 |

TABLE 2-continued $IC_{50}$ values for inhibition of CETP by the examples compiled in the experimental part

| Example | $IC_{50}$ [nM] |
|---|---|
| 1(22) | 47 |
| 1(23) | 2143 |
| 1(24) | 286 |
| 1(25) | 772 |
| 1(26) | 875 |
| 1(27) | 299 |
| 1(28) | 51 |
| 1(29) | 88 |
| 1(30) | 18 |
| 1(31) | 1073 |
| 1(32) | 62 |
| 1(33) | 229 |
| 1(34) | 137 |
| 3 | 20 |
| 3(1) | 394 |
| 1(35) | 52 |
| 1(36) | 74 |
| 1(37) | 418 |
| 4 | 62 |
| 1(38) | 3315 |
| 1(39) | 56 |
| 1(40) | 37 |
| 1(41) | 524 |
| 1(42) | 25 |
| 1(43) | 22 |
| 1(44) | 69 |
| 1(45) | 122 |
| 1(46) | 1835 |
| 1(47) | 136 |
| 4(1) | 127 |
| 4(2) | 25 |
| 1(48) | 142 |
| 4(3) | 21 |
| 4(4) | 207 |
| 1(49) | 37 |
| 1(52) | 54 |
| 1(50) | 7 |
| 5 | 13 |
| 1(51) | 13 |
| 5(1) | 78 |
| 5(2) | 206 |
| 5(3) | 2695 |
| 5(4) | 183 |
| 5(5) | 418 |
| 1(53) | 23 |
| 4(5) | 15 |
| 6 | 410 |
| 1(55) | 26 |
| 1(56) | 470 |
| 1(54) | 1688 |
| 5(6) | 13 |
| 1(57) | 82 |
| 1(58) | 88 |
| 1(59) | 245 |
| 1(60) | 44 |
| 4(6) | 19 |
| 4(7) | 12 |
| 1(61) | 66 |
| 1(62) | 21 |
| 1(63) | 6 |
| 1(64) | 86 |
| 1(65) | 83 |
| 1(66) | 34 |
| 1(67) | 161 |
| 1(68) | 24 |
| 1(69) | 14 |
| 4(8) | 14 |
| 1(70) | 57 |
| 1(71) | 31 |
| 1(80) | 47 |
| 1(81) | 108 |
| 1(72) | 39 |
| 4(9) | 147 |
| 6(1) | 1216 |
| 1(73) | 1700 |

TABLE 2-continued

IC$_{50}$ values for inhibition of CETP by the
examples compiled in the experimental part

| Example | IC$_{50}$ [nM] |
| --- | --- |
| 1(74) | 100 |
| 4(10) | 15 |
| 4(11) | 255 |
| 4(12) | 70 |
| 6(2) | 1541 |
| 1(82) | 786 |
| 4(13) | 51 |
| 1(75) | 288 |
| 1(76) | 886 |
| 1(77) | 39 |
| 1(83) | 25 |
| 1(78) | 362 |
| 1(79) | 18 |
| 4(14) | 65 |
| 4(15) | 27 |
| 5(7) | 4123 |
| 5(8) | 42 |
| 4(16) | 44 |
| 7 (Diastereomer 1) | 193 |
| 7 (Diastereomer 2) | 1150 |

Indications

The compounds of formula I and their physiologically tolerable salts according to the present invention have valuable pharmacological properties which make them commercially applicable. Thus, for example, these compounds can act as inhibitors of CETP and are expected to be commercially applicable in the therapy of diseases responsive to the inhibition of CETP, such as e.g. any of those diseases mentioned herein.

In view of their ability to inhibit enzyme cholesterol ester transfer protein (CETP), the compounds of general formula I according to the invention and the corresponding pharmaceutically acceptable salts thereof are theoretically suitable for the treatment and/or prevention of all those conditions or diseases which may be affected by the inhibition of the cholesterol ester transfer protein (CETP) activity. Therefore, compounds according to the invention are particularly suitable for the treatment and/or prevention of cardiovascular and/or cardiometabolic and related disorders, in particular atherosclerosis, peripheral vascular disease, dyslipidemia (including e.g. mixed dyslipidemia), hyperbeta-lipoproteinemia, hypoalpha-lipoproteinemia, hypercholesterolemia, hypertriglyceridemia, hyperlipidemia, hypolipoproteinemia, hyperlipoproteinemia, hypo-HDL cholesterolemia, hyper-LDL cholesterolemia, familial hypercholesterolemia, angina, ischemia, cardiac ischemia, stroke, myocardial infarction, reperfusion injury, angioplastic restenosis, hypertension, endothelial dysfunction, vascular complications of diabetes, prevention of diabetes, insulin resistance, obesity, metabolic syndrome, diabetes (especially type 2 diabetes mellitus) or endotoxemia, or arteriosclerosis, coronary heart disease, coronary artery disease, coronary vascular disease or congestive heart failure.

Application Forms and Dosages

The compounds of formula I and their pharmaceutically acceptable salts can be used as medicaments, e.g. in the form of pharmaceutical compositions for enteral, parenteral or topical administration. They may be administered in any of the generally accepted modes of administration available in the art, e.g., perorally, e.g. in the form of tablets, coated tablets, dragees, hard and soft gelatine capsules, solutions, emulsions or suspensions, rectally, e.g. in the form of suppositories, parenterally (including intravenously), e.g. in the form of injection solutions or infusion solutions, or topically, e.g. in the form of ointments, creams or oils. Among the possible modes of administration, oral and intravenous delivery are preferred.

The pharmaceutical compositions according to this invention contain at least one of the compounds of the invention (=active compound), e.g. in a total amount of from 0.1 to 99.9 wt %, 5 to 95 wt %, or 20 to 80 wt %, optionally together with pharmaceutically acceptable excipients.

The person skilled in the art is familiar with pharmaceutically acceptable excipients, such as e.g. diluents, carriers, binders, disintegrants, surfactants, lubricants, vehicles, auxiliaries, adjuvants and/or further additives which are known to be suitable for preparing pharmaceutical compositions, on account of his/her expert knowledge.

As pharmaceutically acceptable excipients, usually any excipients known to be appropriate for pharmaceutical compositions come into consideration. Examples thereof include, but are not limited to, diluents, fillers, binders, disintegrants, lubricants, glidants, solvents, dispersants, emulsifiers, solubilizers, gel formers, ointment bases, antioxidants, preservatives, stabilizers, carriers, thickeners, complexing agents, buffers, pH regulators (e.g. to obtain neutral, alkaline or acidic formulations), permeation promoters, polymers, coating agents, propellants, tonicity adjusting agents, surfactants, colorants, flavorings, sweeteners and dyes.

In general, suitable carrier materials are not only inorganic carrier materials, but also organic carrier materials. Thus, e.g., lactose, starches (e.g. corn starch) or derivatives thereof, talc, silica, polyvinylpyrrolidones, stearic acid or its salts can be used as carrier materials for tablets, coated tablets, dragees and hard gelatine capsules. Suitable carrier materials for soft gelatine capsules are, e.g., vegetable oils, waxes, fats and semi-solid and liquid polyols. Suitable carrier materials for the production of solutions and syrups are, e.g., water, polyols, sucrose, invert sugar and the like. Suitable carrier materials for injection or infusion solutions are, e.g., water, alcohols, polyols, glycerol and vegetable oils. Suitable carrier materials for suppositories are, e.g., natural or hardened oils, waxes, fats and semi-liquid or liquid polyols or polyethylene glycols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

In particular, excipients, carriers and/or diluents of a type appropriate to the desired pharmaceutical composition, formulation or preparation and the desired mode of administration are used.

The pharmaceutical compositions according to this invention can be prepared by processes which are known per se and familiar to the person skilled in the art, e.g. by incorporating the described compounds of formula I or their pharmaceutically acceptable salts (optionally combined with other active substances) optionally together with one or more conventional carriers (e.g. solid or liquid carriers) and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions or suppositories.

The dosage of the compounds of the invention (=active compounds) can vary within wide limits depending on the compound which is to be administered, the nature and gravity of the disease to be treated or prevented, the age and the individual condition of the patient and the mode and frequency of administration, and will, of course, be fitted to the individual requirements in each particular case. Usually, a dosage of the compounds of the invention (=active compounds) in the order of magnitude customary for CETP inhibitors comes into consideration. Expediently, the dosage may be from 0.1 ng/ml to 10 mg/ml, preferably 1 ng/ml to 10 mg/ml, by intravenous route, and 0.1 to 2000 mg, preferably 1 to 100 mg, by oral route, in each case administered 1 to 4 times a day. Depending on the dosage it may be convenient to administer the daily dosage in several dosage units.

Combinations

Besides their use in monotherapy, the compounds according to the invention may also be used in conjunction with other active substances, particularly for the treatment and/or prevention of the diseases, disorders and conditions mentioned above.

Other active substances which are suitable for such a combination include for example those which potentiate the therapeutic effect of a cholesterol ester transfer protein (CETP) inhibitor according to the invention with respect to one of the indications mentioned and/or which allow the dosage of a cholesterol ester transfer protein (CETP) inhibitor according to the invention to be reduced.

Therapeutic agents which are suitable for such a combination include particularly one or more lipid modulating agents. Lipid modulating agents comprise HMG CoA reductase inhibitors (e.g. simvastatin, atorvastatin), fibrates (e.g. bezafibrate, fenofibrate), nicotinic acid and the derivatives thereof, PPAR ($\alpha$, $\gamma$ or $\alpha/\gamma$) agonists or modulators, ACAT inhibitors (e.g. avasimibe), MTP inhibitors, squalene cyclase and squalene synthase inhibitors, LXR agonists or modulators, bile acid-binding substances such (e.g. cholestyramine, colesevelam), cholesterol absorption inhibitors (e.g. ezetimibe), niacin, PCSK9 inhibitors, bile acid reuptake inhibitors and lipase inhibitors.

Other therapeutic agents which are suitable for such a combination include one or more antidiabetic agents as for example metformin, alpha-glucosidase inhibitors (e.g. acarbose, voglibose), PPAR ($\alpha$, $\gamma$ or $\alpha/\gamma$) agonists or modulators, DPP-IV inhibitors (e.g. Sitagliptin, Vildagliptin, Saxagliptin, Alogliptin, Linagliptin), SGLT 2 inhibitors (e.g. dapagliflozin, sergliflozin), GLP-1 or GLP-1 analogues (e.g. exenatide, liraglutide), insulin or insulin analogues, sulphonylureas (e.g. glibenclamide, tolbutamide, glimepiride), thiazolidinediones (e.g. rosiglitazone, pioglitazone), nateglinide, repaglinide, II-$\beta$-HSD inhibitors, glucose-6-phosphatase inhibitors, fructose-1,6-bisphosphatase inhibitors, glycogen phosphorylase inhibitors, glucagon receptor antagonists, inhibitors of phosphoenol pyruvate carboxykinase, glycogen synthase kinase or pyruvate dehydrokinase and glucokinase activators.

Also suitable for such a combination are one or more antiobesity agents including for example sibutramine, tetrahydrolipostatin, leptin, leptin mimetics, antagonists of the cannabinoid) receptor, MCH-1 receptor antagonists, MC4 receptor agonists, NPY5 or NPY2 antagonists or $\beta$3-agonists such as SB-418790 or AD-9677 and agonists of the 5HT2c receptor.

Moreover, combinations with drugs for influencing high blood pressure or chronic heart failure such as e.g. A-II antagonists or ACE inhibitors, ECE inhibitors, diuretics, $\beta$-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable.

Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

The therapeutic agents mentioned herein above as combination partners of the compounds according to this invention are meant to include pharmaceutically acceptable derivatives thereof, such as e.g. their pharmaceutically acceptable salts. The person skilled in the art is aware on the base of his/her expert knowledge of the kind, total daily dosage(s) and administration form(s) of the additional therapeutic agent(s) coadministered. Said total daily dosage(s) can vary within a wide range. Usually, the dosage for the combination partners mentioned above is $\frac{1}{5}$ of the lowest dose normally recommended up to 1/1 of the normally recommended dose.

In practicing the present invention, the compounds according to this invention may be administered in combination therapy separately, sequentially, simultaneously, concurrently or chronologically staggered with one or more further active substances, such as e.g. any of the therapeutic agents mentioned herein above as a combination partner.

In this context, the present invention further relates to a combination comprising a first active ingredient, which is at least one compound according to this invention, and a second active ingredient, which is at least one of the active substances described above as a combination partner, for separate, sequential, simultaneous, concurrent or chronologically staggered use in therapy, particularly for treatment and/or prevention of cardiovascular or related disorders, such as e.g. any of those mentioned herein.

Further, this invention relates to the use of a compound according to this invention combined with at least one of the active substances described above as a combination partner, for preparing a pharmaceutical composition which is suitable for the treatment or prevention of diseases or conditions which may be affected by the inhibition of the cholesterol ester transfer protein (CETP) activity, particularly cardiometabolic and/or cardiovascular disorders, more particularly one of the diseases, disorders or conditions listed above.

Further, this invention relates to a pharmaceutical composition which comprises a compound according to the invention and at least one of the active substances described above as combination partners, optionally together with one or more inert carriers and/or diluents.

The term "combination" according to this invention may be present as a fixed combination, a non-fixed combination, a free combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously, concurrently or chronologically staggered.

The first and second active ingredient of a kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount, particularly for the treatment and/or prevention of the diseases, disorders and conditions mentioned above.

General Synthesis

The compounds according to the invention may be obtained using methods of synthesis known in principle. Preferably the compounds are obtained by the following methods according to the invention which are described in more detail hereinafter.

The synthesis of compounds of formula I, wherein $R^1$-$R^7$ are defined as hereinbefore, wherein $R^1$ may optionally additionally be substituted with alkoxycarbonyl or benzyloxy, $R^8$ denotes hydrogen, can be carried out according to the invention related process a) shown in scheme 1, wherein each $R^a$ denotes independently methyl or ethyl, $R^b$ denotes hydroxyl, chlorine or iodine, Hal denotes bromine or iodine and PG denotes a suitable protecting group or hydrogen, starting from compounds of formula II and III. $R^{7'}$ denotes a progenitor group, which together with the carbon to which it is linked converts into $R^7$ after removal of Hal in compounds of formula XII.

Scheme 1 (Process a)):

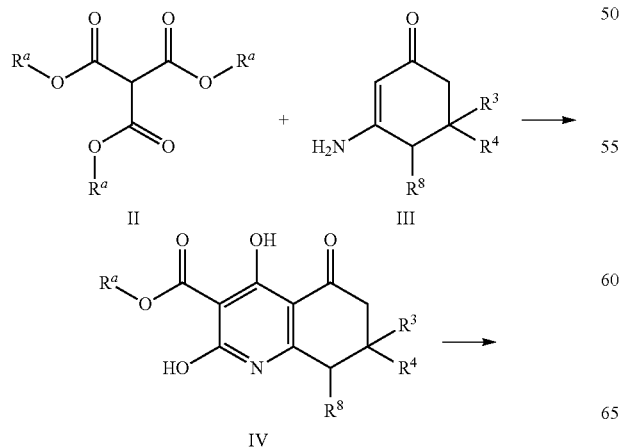

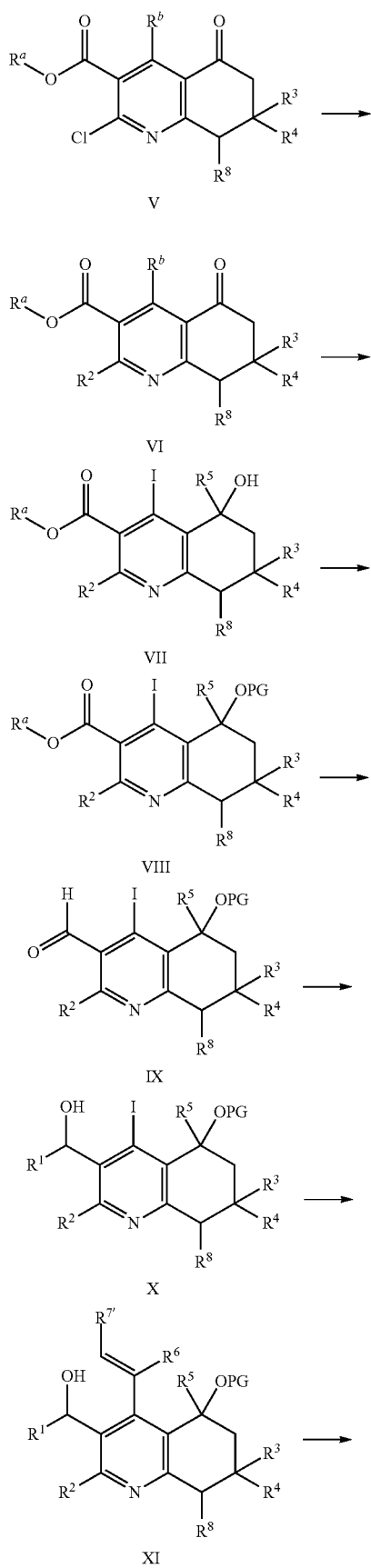

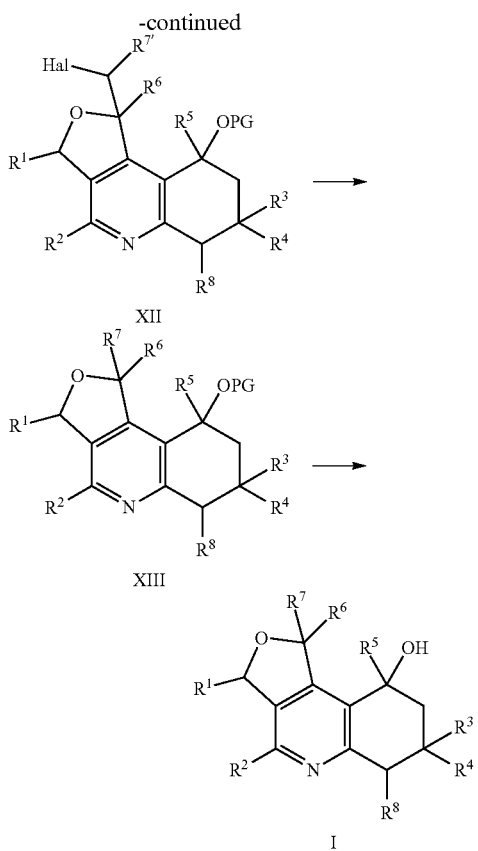

First step is the condensation of triester of formula II, wherein each $R^a$ denotes independently methyl or ethyl (preferably all $R^a$ are identical) with enaminoketones of formula III. This reaction is usually carried out neat at temperatures between 150° C. and 250° C., and yields the bicyclic dihydroxypyridines of formula IV.

Compounds of formula V, wherein $R^b$ is hydroxyl or chlorine, are obtained by chlorination of compounds of formula IV. For example, chlorination of compounds of formula IV with phosphoroxychloride and catalytic amounts of N,N-dimethylformamide at 45° C. gives compounds of formula V, wherein $R^b$ denotes hydroxyl. Analogous chlorination at 80° C. delivers the compounds of formula V, wherein $R^b$ denotes chlorine.

Compounds of formula V can be converted in compounds of formula VI by installing the $R^2$ group via a carbon-carbon-coupling reaction, preferably either by a Negishi reaction or by a Suzuki reaction. In the Negishi reaction compounds of formula V are reacted with suitable (cyclo)alkyl-zinc-halogenide reagents or (cyclo)alkenyl-zinc-halogenide reagents of formula $R^2$—ZnX, wherein X is a halogen (e.g. chlorine) in a suitable solvent such as e.g. toluene, tetrahydrofurane, 1,4-dioxane or diethylether in the presence of a suitable catalyst such as e.g. tetrakis-triphenylphosphine-palladium-(0), bis-tri-tert.-butylphosphine-palladium-(0), 1,1'-bis-(diphenylphosphino)-ferrocene-dichloro-palladium-(II), bis-[1,2-bis-(diphenylphosphino)-ethane]-palladium-(0), or in the presence of a palladium source like e.g. palladium diacetate or tris-(dibenzylideneacetone)-dipalladium-(0) and a suitable ligand like e.g. tri-tert.-butylphosphine, tri-cyclohexylphosphine, di-adamantan-1-yl-butylphosphine, 2-dicyclohexylphosphino-2',6'-diisopropoxy-1,1'biphenyl, 2-dicyclohexylphosphino-2',4',6'-thisopropyl-1,1'-biphenyl or 2-dicyclohexylphosphino-2',6'-dimethoxy-1,1'-biphenyl, at temperatures between 40° C. and 180° C., but preferably between 70° C. and 130° C. The (cyclo)alkyl-zinc-halogenide reagents or (cyclo)alkenyl-zinc-halogenide reagents can optionally be prepared by transmetalation of corresponding (cyclo)alkyl-magnesium-halogenide reagents or (cyclo)alkenyl-magnesium-halogenide reagents, e.g. with zinc chloride in diethylether, tetrahydrofurane or 1,4-dioxane.

The Suzuki reaction is performed by reacting compounds of formula V with a suitable $R^2$-borone reagent, such as e.g. (cyclo)alkyl-boronic acids, (cyclo)alkenyl-boronic acids, (cyclo)alkyl-boronic acid-esters, (cyclo)alkenyl-boronic acid-esters, potassium (cyclo)alkyl-trifluoroborates or potassium (cyclo)alkenyltrifluoroborates. This reaction proceeds in a suitable solvent such as e.g. toluene, N,N-dimethylformamide, acetonitrile, 1,4-dioxane or tetrahydrofurane or mixtures of toluene and tetrahydrofurane in the presence of a suitable base such as e.g. aqueous sodium carbonate, aqueous potassium carbonate, aqueous caesium carbonate, silver carbonate, caesium fluoride, triethylamine or N,N-diisopropyl-N-ethyl-amine and in the presence of a suitable catalyst such as e.g. tetrakis-triphenylphosphine-palladium-(0), bis-tri-tert.-butylphosphine-palladium-(0), 1,1'-bis-(diphenylphosphino)-ferrocene-dichloro-palladium-(II), bis-[1,2-bis-(diphenylphosphino)-ethane]-palladium-(0), or in the presence of a palladium source like e.g. palladium diacetate or tris-(dibenzylideneacetone)-dipalladium-(0) and a suitable ligand like e.g. tri-tert.-butylphosphine, tri-cyclohexylphosphine, di-adamantan-1-yl-butylphosphine, 2-dicyclohexylphosphino-2',6'-diisopropoxy-1,1'biphenyl, 2-dicyclohexylphosphino-2',4',6'-thisopropyl-1,1'-biphenyl or 2-dicyclohexylphosphino-2',6'-dimethoxy-1,1'-biphenyl, at temperatures between 0° C. and 180° C., but preferably between room temperature and 120° C. In the case that (cyclo)alkenylboronic acids, (cyclo)alkenyl-boronic acid-esters, potassium (cyclo)alkenyl-trifluoroborates or (cyclo)alkenyl-zinc-halogenide reagents are employed the reaction is proceeded by a reduction of the double bond. This can be achieved by hydrogenation in the presence of a suitable catalyst such as e.g. palladium on charcoal or palladiumhydroxide on charcoal in a suitable solvent such as e.g. methanol, ethanol, ethylacetate, tetrahydrofurane or 1,4-dioxane but preferably methanol, at temperatures between –20° C. and 100° C. but preferably between 0° C. and 80° C.

Compounds of formula VI, wherein $R^2$ denotes 1-3C-perfluoroalkyl and $R^b$ denotes hydroxyl can be prepared from compounds of formula V, wherein $R^b$ denotes hydroxyl, by the following sequence: Firstly, substitution of chlorine by iodine, for example by a reaction with sodium iodide and acetylchloride in a suitable solvent such as e.g. acetonitrile, N,N-dimethylformamide, 1,4-dioxane or tetrahydrofurane but preferably in acetonitrile, at temperatures between 0° C. and 100° C. but preferably between room temperature and 80° C., delivers the corresponding 2-iodopyridines. These compounds are then reacted with a suitable 1-3C-perfluoroalkyl reagent, such as e.g. 1-3C-perfluoroalkyl-iodide, 1-3C-perfluoroalkyl-trimethylsilane, potassium 1-3C-perfluoroalkyl-carboxylate or methyl 2,2-difluoro-2-(fluorosulfonyl)-acetate, in a suitable solvent such as e.g. N,N-dimethylformamide, N-methylpyrrolidone or dimethylsulfoxide in the presence of a suitable catalyst such as e.g. activated copper, copper-(I)-iodide or mixtures of both and optionally in the presence of potassium fluoride, at temperatures between 50° C. and 200° C., but preferably between 80° C. and 180° C., to obtain the compounds of formula VI, wherein $R^2$ denotes 1-3C-perfluoroalkyl.

Transformation of compounds of formula VI wherein $R^b$ denotes hydroxyl in compounds of formula VI wherein $R^b$ denotes chlorine is done by reacting with phosphoroxychloride and catalytic amounts of N,N-dimethylformamide, at temperatures between 50° C. and 150° C. but preferably between 70° C. and 120° C.

Compounds of formula VI wherein $R^b$ denotes chlorine can be converted in compounds of formula VI wherein $R^b$ denotes iodine. This transformation is done in a suitable solvent such as e.g. acetonitrile, N,N-dimethylformamide, 1,4-dioxane or tetrahydrofurane but preferably in acetonitrile in the presence of sodium iodide and acetylchloride, at temperatures between 0° C. and 100° C. but preferably between room temperature and 80° C.

Reaction of compounds of formula VI wherein $R^b$ denotes iodine with a suitable hydride donating reagent such as e.g. borane-tetrahydrofurane-complex, borane-dimethylsulfide-complex, borane-dimethylaniline-complex, borane-diethylaniline-complex, sodium borohydride, lithium borohydride, lithium aluminium hydride in a suitable solvent such as e.g. diethylether, tetrahydrofurane, 1,4-dioxane or toluene, at temperatures between −78° C. and 100° C., but preferably between −50° C. and 80° C., optionally in the presence of a chiral ligand as for example (1R,2S)-(+)-cis-1-Amino-2-indanol, (1S,2R)-(+)-cis-1-Amino-2-indanol, (R)-1-Methyl-3,3-diphenyl-tetrahydro-pyrrolo[1,2-c][1,3,2]oxazaborole or (S)-1-Methyl-3,3-diphenyl-tetrahydro-pyrrolo[1,2-c][1,3,2]oxazaborole gives the alcohols of formula VII, wherein $R^5$ denotes hydrogen. The reduction in the presence of chiral ligands results in enantiomerically enriched compounds of formula VII. For example the reduction with borane reagents such as e.g. borane-tetrahydrofurane-complex, borane-dimethylsulfide-complex, borane-dimethylaniline-complex or borane-diethylaniline-complex each in the presence of (1R,2S)-(+)-cis-1-Amino-2-indanole gives compounds of formula VII with S-configuration at the newly formed stereocenter as it is known from the literature (see *Tetrahedron: Asymmetry* 1995, 6, 301-306; *Synthesis* 1998, 937-961 or *Angew. Chem.* 1999, 111, 3574-3576).

Likewise, alkylation reaction of compounds of formula VI wherein $R^b$ denotes iodine with a suitable alkyl metal compound, such as e.g. 1-4C-dialkylzinc-, 1-4C-alkylmagnesium halogenide-, or 1-4C-alkyllithium-reagent, particularly 1-2C-dialkylzinc-, 1-2C-alkylmagnesium halogenide-, or 1-2C-alkyllithium-reagent, in a suitable solvent such as e.g. n-hexane, cyclohexane, toluene, diethylether, tetrahydrofurane or 1,4-dioxane, optionally in the presence of a chiral ligand as for example (R)-1-methyl-3,3-diphenyl-tetrahydro-pyrrolo[1,2-c][1,3,2]oxazaborole, (R)-1-methyl-3,3-diphenyl-tetrahydro-pyrrolo[1,2-c][1,3,2]oxazaborole, (−)-3-exo-dimethylamino-isoborneol, (+)-3-exo-dimethylamino-isoborneol or ligands as described in *J. Am. Chem. Soc.* 2002, 124, 10970-10971 or *Tetrahedron* 1998, 54, 5651-5666, at temperatures between −50° C. and 100° C., but preferably between −20° C. and 70° C., gives the corresponding alcohols of formula VII, wherein $R^5$ denotes 1-4C-alkyl, particularly 1-2C-alkyl.

The alcohol group in compounds of formula VII can be temporarily protected with a suitable protecting group, e.g. as a tert.-butyldimethylsilylether by the reaction with tert.-butyldimethylsilylchloride in a suitable solvent such as e.g. N,N-dimethylformamide or acetonitrile in the presence of imidazole, at temperatures between −20° C. and 120° C., but preferably between 0° C. and 80° C., to give the protected derivatives of formula VIII, in which PG stands for this suitable protecting group. This protection can also be carried out by reacting compounds of formula VII with tert.-butyldimethylsilyl-trifluormethansulfonate in the presence of a suitable base such as e.g. pyridine or 2,6-lutidine in a suitable solvent such as e.g. dichloromethane, diethylether, tetrahydrofurane, 1,4-dioxane or toluene, at temperatures between −50° C. and 100° C. but preferably between −30° C. and 50° C. Alternatively any other suitable protecting group as described e.g. in "*Protective Groups in Organic Synthesis*", $2^{nd}$ edition, Greene T. W., Wuts P. G. M.; Wiley-Interscience: New York, 1991 or in "*Protective Groups*", Kocienski P. J.; Thieme: New York, 1994 can be used.

The esters of formula VIII can be converted to the aldehydes of formula IX, e.g. by a two step sequence. First step is the reduction to the alcohol with a suitable reducing agent, such as e.g. diisobutylaluminium hydride or lithiumaluminiumhydride in an aprotic solvent such as e.g. dichloromethane, tetrahydrofurane, 1,4-dioxane or toluene, at temperatures between −78° C. and 100° C., but preferably between −30° C. and 50° C. Second step is the oxidation of the alcohol to the aldehyde, which can be carried out with Dess-Martin-Periodinan (*J. Chem. Soc.* 1983, 48, 4156) or by Swern oxidation (*J. Org. Chem.* 1976, 41, 957). Alternatively this transformation can be performed by reaction with $RuCl_3$ or tetrapropylammonium perrhutenate in the presence of N-methylmorpholin-N-oxide in acetonitrile or dichlormethane, or by an oxidation catalysed by 2,2,6,6-tetramethyl-piperidin-1-oxyl (TEMPO) in the presence of iodine and a base as for example sodium bicarbonate in a solvent such as e.g. dichloromethane, tetrahydrofurane, 1,4-dioxane, benzene or toluene but preferably in toluene optionally as a mixture with water, at temperatures between −30° C. and 80° C. but preferably between 0° C. and 40° C.

Aldehydes of formula IX are transformed to the alcohols of formula X by reaction with a suitable $R^1$-metal reagent, such as e.g. $R^1$-magnesium halogenide- or $R^1$-lithium-reagent, in an aprotic solvent such as e.g. diethylether, tetrahydrofurane, 1,4-dioxane or toluene, at temperatures between −78° C. and 80° C., but preferably between −50° C. and 40° C.

Subsequent reaction of alcohols of formula X with suitable potassium (cyclo)alkenyltrifluoroborates, (cyclo)alkenyl-boronic acids or (cyclo)alkenyl-boronic acid pinacol esters but preferably (cyclo)alkenyl-boronic acid pinacol esters according to a Suzuki reaction, e.g. in a suitable solvent such as e.g. toluene, N,N-dimethylformamide, acetonitrile, 1,4-dioxane or tetrahydrofurane or mixtures of toluene and tetrahydrofurane in the presence of a suitable base such as e.g. aqueous sodium carbonate, aqueous potassium carbonate, aqueous caesium carbonate, silver carbonate, caesium fluoride, triethylamine or N,N-diisopropyl-N-ethyl-amine but preferably caesium fluoride and in the presence of a suitable catalyst such as e.g. tetrakis-triphenylphosphine-palladium-(0), bis-tri-tert.-butylphosphine-palladium-(0), 1,1'-bis-(diphenylphosphino)-ferrocene-dichloro-palladium-(II) or bis-[1,2-bis-(diphenylphosphino)-ethane]-palladium-(0), or in the presence of a suitable palladium source such as e.g. palladium diacetate or tris-(dibenzylideneacetone)-dipalladium-(0) and a suitable ligand such as e.g. tri-tert.-butylphosphine, tricyclohexylphosphine, di-adamantan-1-yl-butylphosphine, 2-dicyclohexylphosphino-2',6'-diisopropoxy-1,1'biphenyl, 2-dicyclohexylphosphino-2',4',6'-thisopropyl-1,1'-biphenyl or 2-dicyclohexylphosphino-2',6'-dimethoxy-1,1'-biphenyl, at temperatures between 0° C. and 180° C., but preferably between room temperature and 120° C., gives compounds of formula XI.

Compounds of formula XI are then reacted with iodine, iodinechloride, N-iodosuccinimide, bromine, bis-(2,4,6-trimethyl-pyridin)-iodonium tetrafluoro borate or N-bromosuccinimide in a suitable solvent such as e.g. dichloromethane, acetonitrile, N,N-dimethylformamide, tetrahydrofurane, 1,4-dioxane or mixtures of acetonitrile and tetrahydrofurane optionally in the presence of a suitable base such as e.g. sodium bicarbonate, sodium carbonate, potassium carbonate, triethylamine or N,N-diisopropyl-N-ethyl-amine and optionally in the presence of silver-(I)-oxide, silver-(I)-nitrate or silver-(I)-trifluoroacetate, at temperatures between −40° C. and 100° C., but preferably between −10° C. and 60° C. to yield the compounds of formula XII, wherein Hal is iodine or bromine.

These compounds of formula XII are reduced to the compounds of formula XIII with a suitable reducing agent, such as e.g. tris-trimethylsilylsilane or tributyltin hydride in the presence of a suitable radical starter such as e.g. azo-bis-isobutyronitrile or dibenzoylperoxide in a suitable solvent such as e.g. carbontetrachloride, benzene or toluene, at temperatures between 80° C. and 150° C. Alternatively compounds of formula XII can be reduced to compounds of formula XIII by hydrogenation in the presence of a suitable catalyst such as e.g. palladium on charcoal or palladiumhydroxide on charcoal in a suitable solvent such as e.g. methanol, ethanol, tetrahydrofurane or 1,4-dioxane but preferably methanol. This reaction may be carried out in the presence of a suitable base such as e.g. triethylamine or N,N-diisopropyl-N-ethyl-amine, at temperatures between −20° C. and 100° C. but preferably between 0° C. and 80° C.

Elimination of hydroiodic acid or hydrobromic acid in compounds of formula XII delivers compounds of formula XIII which contain a double bond. This elimination is performed by reaction with a suitable base such as e.g. triethylamine, N,N-diisopropyl-N-ethyl-amine, sodium methanolate, sodiumethanolate, sodium tert.-butylate, potassium tert.-butylate, lithium diisopropylamide or lithium hexamethyldisilazide, optionally in the presence of a transition metal such as Pd(0), in a suitable solvent such as e.g. methanole, ethanole, tert.-butanole, tetrahydrofurane or 1,4-dioxane, at temperatures between −20° C. and 150° C., preferably between 0° C. and 100° C. The resulting double bond can be reduced or hydrogenated to obtain the corresponding saturated compound of formula XIII using for example a suitable hydrogen source, such as e.g. $Et_3SiH$ in the presence of $F_3CCO_2H$. Deprotection of compounds of formula XIII, wherein PG denotes tert.-butyldimethylsilyl, preferably with a fluoride reagent such as e.g. tetrabutylammonium fluoride or caesium fluoride or with an acid such as e.g. trifluoroacetic acid, hydrochloric acid or sulphuric acid in a suitable solvent such as e.g. dichloromethane, 1,2-dichloroethane, diethylether, tetrahydrofurane, 1,4-dioxane, acetonitrile or toluene, or methanol or water, or mixtures thereof, at temperatures between −50° C. and 120° C., but preferably between −20° C. and 80° C. gives compounds of formula I. Alternatively any other protecting group introduced before can be cleaved by suitable methods as described in the literature e.g. in "Protective Groups in Organic Synthesis", $2^{nd}$ edition, Greene T. W., Wuts P. G. M.; Wiley-Interscience: New York, 1991 or in "Protective Groups", Kocienski P. J.; Thieme: New York, 1994.

The synthesis of compounds of formula I, wherein $R^1$-$R^7$ are defined as hereinbefore, $R^8$ denotes acetoxy, propionyloxy or hydroxy, can be carried out according to the invention related process b) shown in scheme 2, wherein PG denotes a suitable protecting group, starting from compounds of formula XIV, which equal compounds XIII in which $R^8$ denotes hydrogen.

Scheme 2 (Process b)):

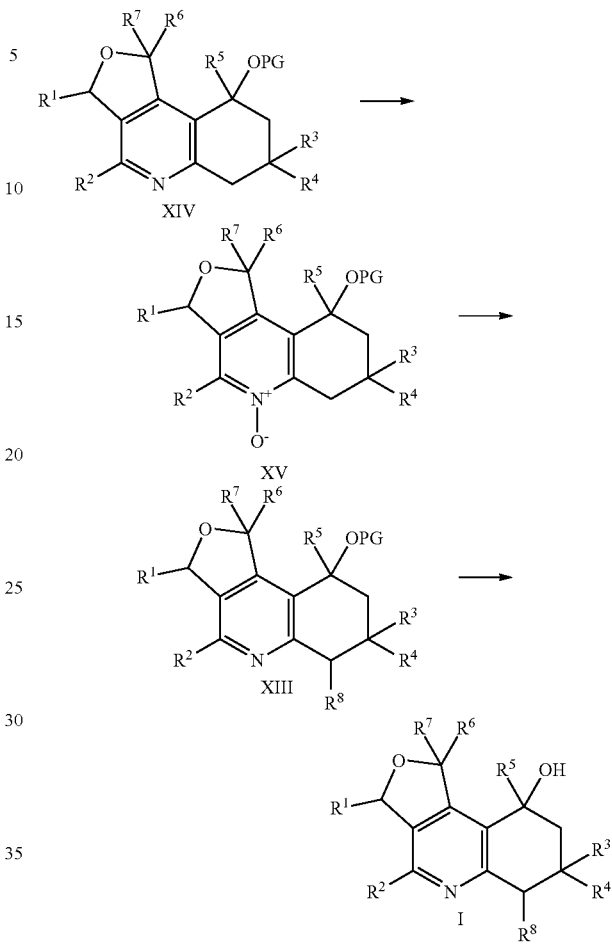

First step is the formation of N-oxides of formula XV. This reaction is performed by treating compounds of formula XIV with a suitable oxidizing reagent, such as e.g. meta-chloroperbenzoic acid (MCPBA), in a suitable solvent such as e.g. dichloromethane, 1,2-dichloroethane, chloroform or tetrachloromethane, at temperatures between −10° C. and 60° C. Compounds of formula XV are then reacted with acetic acid anhydride or propionic acid anhydride at temperatures between 90° C. and 180° C. to deliver compounds of formula XIII, wherein $R^8$ denotes acetoxy or propionyloxy. Deprotection of compounds of formula XIII, wherein PG denotes tert.-butyldimethylsilyl, preferably with a fluoride reagent such as e.g. tetrabutylammonium fluoride or caesium fluoride or with an acid such as e.g. trifluoroacetic acid, hydrochloric acid or sulphuric acid in a suitable solvent such as e.g. dichloromethane, 1,2-dichloroethane, diethylether, tetrahydrofurane, 1,4-dioxane, acetonitrile or toluene, or methanol or water, or mixtures thereof, at temperatures between −50° C. and 120° C., but preferably between −20° C. and 80° C., gives compounds of formula I, wherein $R^8$ denotes acetoxy or propionyloxy. Alternatively any other protecting group introduced before can be cleaved by suitable methods as described in the literature e.g. in "Protective Groups in Organic Synthesis", $2^{nd}$ edition, Greene T. W., Wuts P. G. M.; Wiley-Interscience: New York, 1991 or in "Protective Groups", Kocienski P. J.; Thieme: New York, 1994. Treating compounds of formula I, wherein $R^8$ denotes acetoxy or propionyloxy, with a suitable base such as e.g. sodium carbonate, potassium carbonate, caesium carbonate, lithium hydroxide, sodium hydroxide or potassium hydroxide in a suitable solvent such as e.g. methanol, ethanol, tetrahydrofurane, water or in a mixture of water and methanol or ethanol, at temperatures between 0° C. and 80° C., delivers compounds of formula I, wherein $R^8$ denotes hydroxy. Alternatively these compounds of formula XIII, wherein the —OPG group and the $R^8$ residue are cis configured, can be treated with a suitable base such as e.g. sodium carbonate, potassium carbonate, caesium carbonate, lithium hydroxide, sodium hydroxide or potassium hydroxide in a suitable solvent like methanol, ethanol or water or in a mixture of water and methanol or ethanol, at temperatures between 0° C. and 80° C., to deliver directly compounds of formula I, wherein $R^8$ denotes hydroxy.

In a variant, compounds of formula VIII can be prepared according to the invention related process c) shown in scheme 3, wherein $R^a$, $R^2$, $R^3$, $R^4$ and $R^5$ are defined as described before and $R^8$ denotes hydrogen, starting from compounds of formula V, wherein $R^b$ denotes chlorine.

Scheme 3 (Process c)):

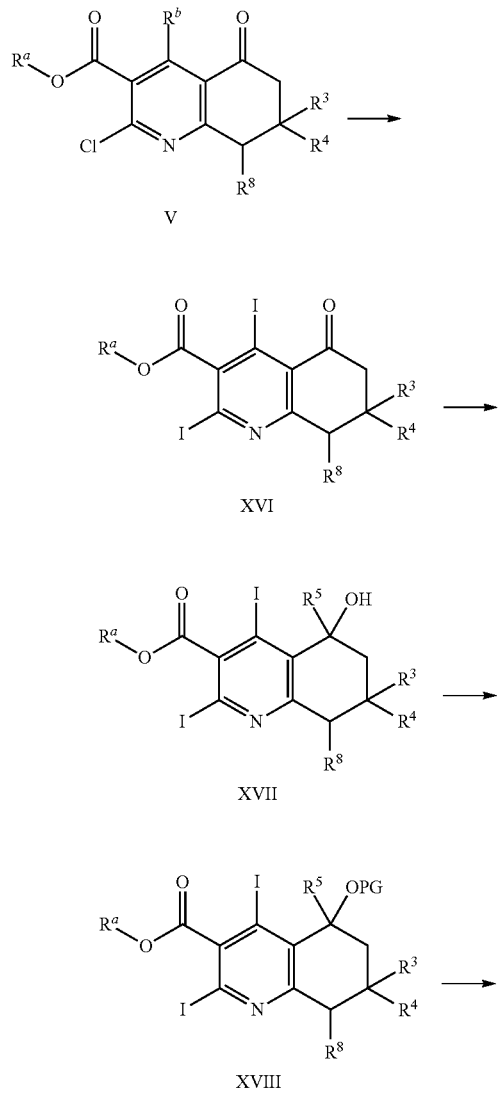

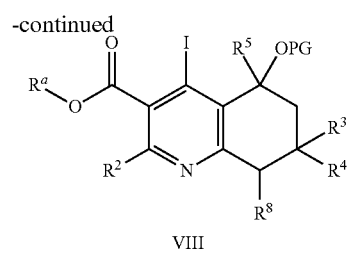

VIII

In this process compounds of formula V, wherein $R^b$ denotes chlorine, are converted into compounds of formula XVI by reacting with a suitable iodination reagent such as e.g. sodium iodide and acetylchloride in a suitable solvent such as e.g. acetonitrile, N,N-dimethylformamide, 1,4-dioxane or tetrahydrofurane but preferably in acetonitrile, at temperatures between 0° C. and 100° C. but preferably between room temperature and 80° C.

Reaction of compounds of formula XVI with a suitable hydride donating reagent such as e.g. borane-tetrahydrofurane-complex, borane-dimethylsulfide-complex, borane-dimethylaniline-complex, borane-diethylaniline-complex, sodium borohydride, lithium borohydride, lithium aluminium hydride in a suitable solvent such as e.g. diethylether, tetrahydrofurane, 1,4-dioxane or toluene, at temperatures between −78° C. and 100° C., but preferably between −50° C. and 80° C., optionally in the presence of a chiral ligand as for example (1R,2S)-(+)-cis-1-Amino-2-indanol, (1S,2R)-(+)-cis-1-Amino-2-indanol, (R)-1-Methyl-3,3-diphenyl-tetrahydro-pyrrolo[1,2-c][1,3,2]oxazaborole or (S)-1-Methyl-3,3-diphenyl-tetrahydro-pyrrolo[1,2-c][1,3,2]oxazaborole gives the alcohols of formula XVII, wherein $R^5$ denotes hydrogen. The reduction in the presence of chiral ligands results in enantiomerically enriched compounds of formula XVII. For example the reduction with borane reagents such as e.g. borane-tetrahydrofurane-complex, borane-dimethylsulfide-complex, borane-dimethylaniline-complex or borane-diethylaniline-complex each in the presence of (1R,2S)-(+)-cis-1-Amino-2-indanole gives compounds of formula XVII with S-configuration at the newly formed stereocenter as it is known from the literature (see *Tetrahedron: Asymmetry* 1995, 6, 301-306; *Synthesis* 1998, 937-961 or *Angew. Chem.* 1999, 111, 3574-3576).

Likewise, alkylation reaction of compounds of formula XVI wherein $R^b$ denotes iodine with a suitable alkyl metal compound, such as e.g. 1-4C-dialkylzinc-, 1-4C-alkylmagnesium halogenide-, or 1-4C-alkyllithium-reagent, particularly 1-2C-dialkylzinc-, 1-2C-alkylmagnesium halogenide-, or 1-2C-alkyllithium-reagent, in a suitable solvent such as e.g. n-hexane, cyclohexane, toluene, diethylether, tetrahydrofurane or 1,4-dioxane, optionally in the presence of a chiral ligand as for example (R)-1-methyl-3,3-diphenyl-tetrahydropyrrolo[1,2-c][1,3,2]oxazaborole, (R)-1-methyl-3,3-diphenyl-tetrahydro-pyrrolo[1,2-c][1,3,2]oxazaborole, (−)-3-exo-dimethylamino-isoborneol, (+)-3-exo-dimethylamino-isoborneol or ligands as described in *J. Am. Chem. Soc.* 2002, 124, 10970-10971 or *Tetrahedron* 1998, 54, 5651-5666, at temperatures between −50° C. and 100° C., but preferably between −20° C. and 70° C., gives the corresponding alcohols of formula XVII, wherein $R^5$ denotes 1-4C-alkyl, particularly 1-2C-alkyl.

The alcohol group in compounds of formula XVII can be temporarily protected with a suitable protecting group, e.g. as a tert.-butyldimethylsilylether by the reaction with tert.-butyldimethylsilylchloride in a suitable solvent such as e.g. N,N-dimethylformamide or acetonitrile in the presence of imidazole, at temperatures between −20° C. and 120° C., but preferably between 0° C. and 80° C., to give the protected derivatives of formula XVIII, in which PG stands for this suitable protecting group. This protection can also be carried out by reacting compounds of formula XVII with tert.-butyldimethylsilyl-trifluormethansulfonate in the presence of a suitable base such as e.g. pyridine or 2,6-lutidine in a suitable solvent such as e.g. dichloromethane, diethylether, tetrahydrofurane, 1,4-dioxane or toluene, at temperatures between −50° C. and 100° C. but preferably between −30° C. and 50° C. Alternatively any other suitable protecting group as described e.g. in "Protective Groups in Organic Synthesis", 2$^{nd}$ edition, Greene T. W., Wuts P. G. M.; Wiley-Interscience: New York, 1991 or in "Protective Groups", Kocienski P. J.; Thieme: New York, 1994 can be used.

Negishi reaction of compounds of formula XVIII with suitable (cyclo)alkyl-zinc-halogenide reagents of formula $R^2$—ZnX, wherein X is a halogen (e.g. chlorine), in a suitable solvent such as e.g. toluene, tetrahydrofurane, 1,4-dioxane or diethylether in the presence of a suitable catalyst such as e.g. tetrakis-triphenylphosphine-palladium-(0), bis-tri-tert.-butylphosphine-palladium-(0), 1,1'-bis-(diphenylphosphino)-ferrocene-dichloro-palladium-(II), bis-[1,2-bis-(diphenylphosphino)-ethane]-palladium-(0), or in the presence of a suitable palladium source such as e.g. palladium diacetate or tris-(dibenzylideneacetone)-dipalladium-(0) and a suitable ligand such as e.g. tri-tert.-butylphosphine, tri-cyclohexylphosphine, di-adamantan-1-yl-butylphosphine, 2-dicyclohexylphosphino-2',6'-diisopropoxy-1,1'biphenyl, 2-dicyclohexylphosphino-2',4',6'-triisopropyl-1,1'-biphenyl or 2-dicyclohexylphosphino-2',6'-dimethoxy-1,1'-biphenyl, at temperatures between 40° C. and 180° C., but preferably between 70° C. and 130° C., delivers compounds of formula VIII. The (cyclo)alkyl-zinc-halogenide reagents may optionally be prepared by transmetalation of corresponding (cyclo)alkyl-magnesium-halogenide reagents, e.g. with zinc chloride in diethylether, tetrahydrofurane or 1,4-dioxane.

Compounds of formula VIII can be transformed into compounds of formula I as shown in invention related process a) in scheme 1, process b) in scheme 2 and as described above.

The synthesis of compounds of formula XI, wherein $R^1$-$R^4$, $R^5$, $R^6$, $R^{7'}$ and PG are defined as described before, $R^8$ denotes hydrogen, can also be carried out according to the invention related process d) shown in scheme 4, starting from compounds of formula VI, wherein $R^b$ denotes chlorine.

Scheme 4 (Process d)):

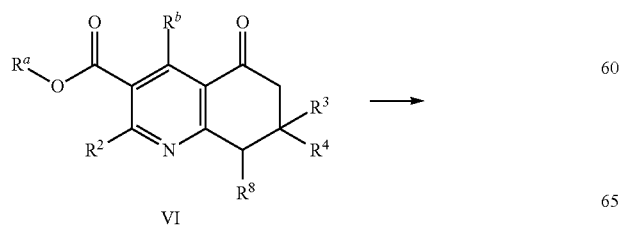

VI

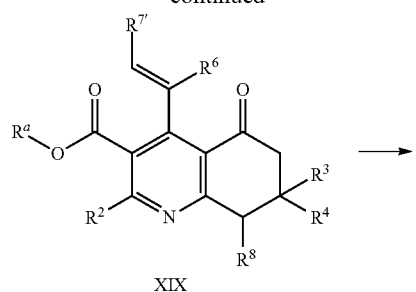

XIX

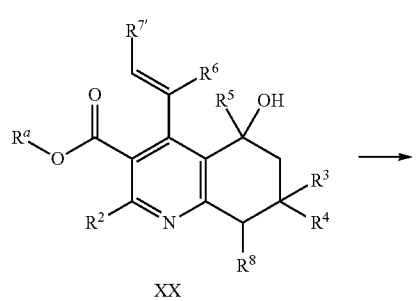

XX

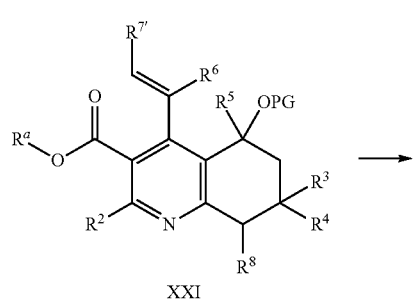

XXI

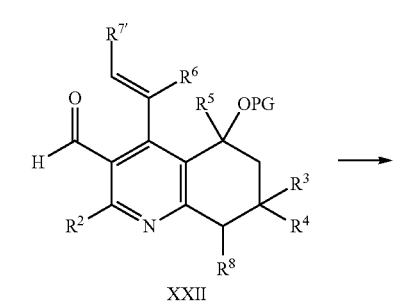

XXII

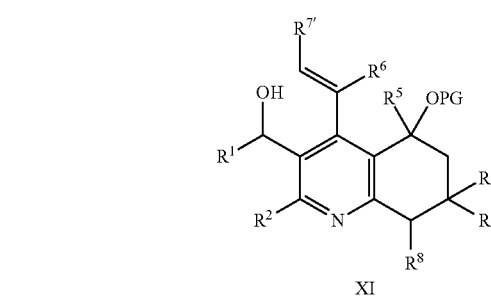

XI

Reaction of ketones of formula VI, wherein $R^b$ denotes chlorine, with suitable potassium (cyclo)alkenyltrifluoroborates, (cyclo)alkenyl-boronic acids or (cyclo)alkenyl-boronic acid pinacol esters but preferably (cyclo)alkenyl-boronic acid pinacol esters according to a Suzuki reaction, e.g. in a suitable solvent such as e.g. toluene, N,N-dimethylformamide, acetonitrile, 1,4-dioxane or tetrahydrofurane or mixtures of toluene and tetrahydrofurane in the presence of a suitable base such as e.g. aqueous sodium carbonate, aqueous potassium carbonate, aqueous caesium carbonate, silver carbonate, caesium fluoride, triethylamine or N,N-diisopropyl-N-ethylamine but preferably caesium fluoride and in the presence of a suitable catalyst such as e.g. tetrakis-triphenylphosphine-palladium-(0), bis-tri-tert.-butylphosphine-palladium-(0), 1,1'-bis-(diphenylphosphino)-ferrocene-dichloro-palladium-(II) or bis-[1,2-bis-(diphenylphosphino)-ethane]-palladium-(0), or in the presence of a suitable palladium source such as e.g. palladium diacetate or tris-(dibenzylideneacetone)-dipalladium-(0) and a suitable ligand such as e.g. tri-tert.-butylphosphine, tri-cyclohexylphosphine, di-adamantan-1-yl-butylphosphine, 2-dicyclohexylphosphino-2',6'-diisopropoxy-1,1'biphenyl, 2-dicyclohexylphosphino-2',4',6'-triisopropyl-1,1'-biphenyl or 2-dicyclohexylphosphino-2',6'-dimethoxy-1,1'-biphenyl, at temperatures between 0° C. and 180° C., but preferably between room temperature and 120° C., gives compounds of formula XIX.

Reaction of compounds of formula XIX with a suitable hydride donating reagent such as e.g. borane-tetrahydrofurane-complex, borane-dimethylsulfide-complex, borane-dimethylaniline-complex, borane-diethylaniline-complex, sodium borohydride, lithium borohydride, lithium aluminium hydride in a suitable solvent such as e.g. diethylether, tetrahydrofurane, 1,4-dioxane or toluene, at temperatures between −78° C. and 100° C., but preferably between −50° C. and 80° C., optionally in the presence of a chiral ligand such as e.g. (1R,2S)-(+)-cis-1-Amino-2-indanol, (1S,2R)-(+)-cis-1-Amino-2-indanol, (R)-1-Methyl-3,3-diphenyl-tetrahydro-pyrrolo[1,2-c][1,3,2]oxazaborole or (S)-1-Methyl-3,3-diphenyl-tetrahydro-pyrrolo[1,2-c][1,3,2]oxazaborole gives the alcohols of formula XX, wherein $R^5$ denotes hydrogen. The reduction in the presence of chiral ligands results in enantiomerically enriched compounds of formula XX. For example the reduction with borane reagents such as e.g. borane-tetrahydrofurane-complex, borane-dimethylsulfide-complex, borane-dimethylaniline-complex or borane-diethylaniline-complex each in the presence of (1R,2S)-(+)-cis-1-Amino-2-indanole gives compounds of formula XX with S-configuration at the newly formed stereocenter as is known from the literature (see *Tetrahedron: Asymmetry* 1995, 6, 301-306; *Synthesis* 1998, 937-961 or *Angew. Chem.* 1999, 111, 3574-3576).

Likewise, alkylation reaction of compounds of formula XIX with a suitable alkyl metal compound, such as e.g. 1-4C-dialkylzinc-, 1-4C-alkylmagnesium halogenide-, or 1-4C-alkyllithium-reagent, particularly 1-2C-dialkylzinc-, 1-2C-alkylmagnesium halogenide-, or 1-2C-alkyllithium-reagent, in a suitable solvent such as e.g. hexane, cyclohexane, toluene, diethylether, tetrahydrofurane or 1,4-dioxane, optionally in the presence of a chiral ligand as for example (R)-1-methyl-3,3-diphenyl-tetrahydro-pyrrolo[1,2-c][1,3,2]oxazaborole, (R)-1-methyl-3,3-diphenyl-tetrahydro-pyrrolo[1,2-c][1,3,2]oxazaborole, (−)-3-exo-dimethylamino-isoborneol, (+)-3-exo-dimethylamino-isoborneol or ligands as described in *J. Am. Chem. Soc.* 2002, 124, 10970-10971 or *Tetrahedron* 1998, 54, 5651-5666, at temperatures between −50° C. and 100° C., but preferably between −20° C. and 70° C., gives the corresponding alcohols of formula XX, wherein $R^5$ denotes 1-4C-alkyl, particularly 1-2C-alkyl.

The alcohol group in compounds of formula XX can be temporarily protected with a suitable protecting group, e.g. as a tert.-butyldimethylsilylether by the reaction with tert.-butyldimethylsilylchloride in a solvent such as e.g. dimethylformamide or acetonitrile in the presence of imidazole, at temperatures between −20° C. and 120° C., but preferably between 0° C. and 80° C., to give the protected derivatives of formula XXI, in which PG stands for this suitable protecting group. This protection can also be carried out by reacting compounds of formula XX with tert.-butyldimethylsilyl-trifluormethansulfonat in the presence of a base such as e.g. pyridine or 2,6-lutidine in a solvent such as e.g. dichloromethane, diethylether, tetrahydrofurane, 1,4-dioxane or toluene, at temperatures between −50° C. and 100° C. but preferably between −30° C. and 50° C. Alternatively any other suitable protecting group as described e.g. in "*Protective Groups in Organic Synthesis*", 2$^{nd}$ edition, Greene T. W., Wuts P. G. M.; Wiley-Interscience: New York, 1991 or in "*Protective Groups*", Kocienski P. J.; Thieme: New York, 1994 can be used.

The esters of formula XXI can be converted to the aldehydes of formula XXII e.g. by a two step sequence. First step is the reduction to the alcohol with a suitable reducing agent, such as e.g. diisobutylamuminium hydride of lithiumaluminiumhydride in an aprotic solvent such as e.g. dichloromethane, tetrahydrofurane, 1,4-dioxane or toluene, at temperatures between −78° C. and 100° C., but preferably between −30° C. and 50° C. Second step is the oxidation of the alcohol to the aldehyde which can be carried out with Dess-Martin-Periodinan (*J. Chem. Soc.* 1983, 48, 4156) or by Swern oxidation (*J. Org. Chem.* 1976, 41, 957). Alternatively this transformation can be performed by reaction with $RuCl_3$ or tetrapropylammonium perrhutenate in the presence of N-methylmorpholin-N-oxide in acetonitrile or dichlormethane, or by an oxidation catalysed by 2,2,6,6-tetramethyl-piperidin-1-oxyl (TEMPO) in the presence of iodine and a base as for example sodium bicarbonate in a solvent like dichloromethane, tetrahydrofurane, 1,4-dioxane, benzene or toluene but preferably in toluene optionally as a mixture with water, at temperatures between −30° C. and 80° C. but preferably between 0° C. and 40° C.

Aldehydes of formula XXII are transformed to the alcohols of formula XI by reaction with a suitable $R^1$-metal reagent, such as e.g. $R^1$-magnesium halogenide- or $R^1$-lithium-reagent, in an aprotic solvent such as e.g. diethylether, tetrahydrofurane, 1,4-dioxane or toluene, at temperatures between −78° C. and 80° C., but preferably between −50° C. and 40° C.

Compounds of formula XI can be transformed into compounds of formula I as shown in invention related process a) in scheme 1, process b) in scheme 2 and described above.

The synthesis of compounds of formula I, wherein $R^1$-$R^7$ are defined as hereinbefore, $R^8$ denotes hydrogen, can also be carried out according to the invention related process e) shown in scheme 5.

Scheme 5 (Process e)):

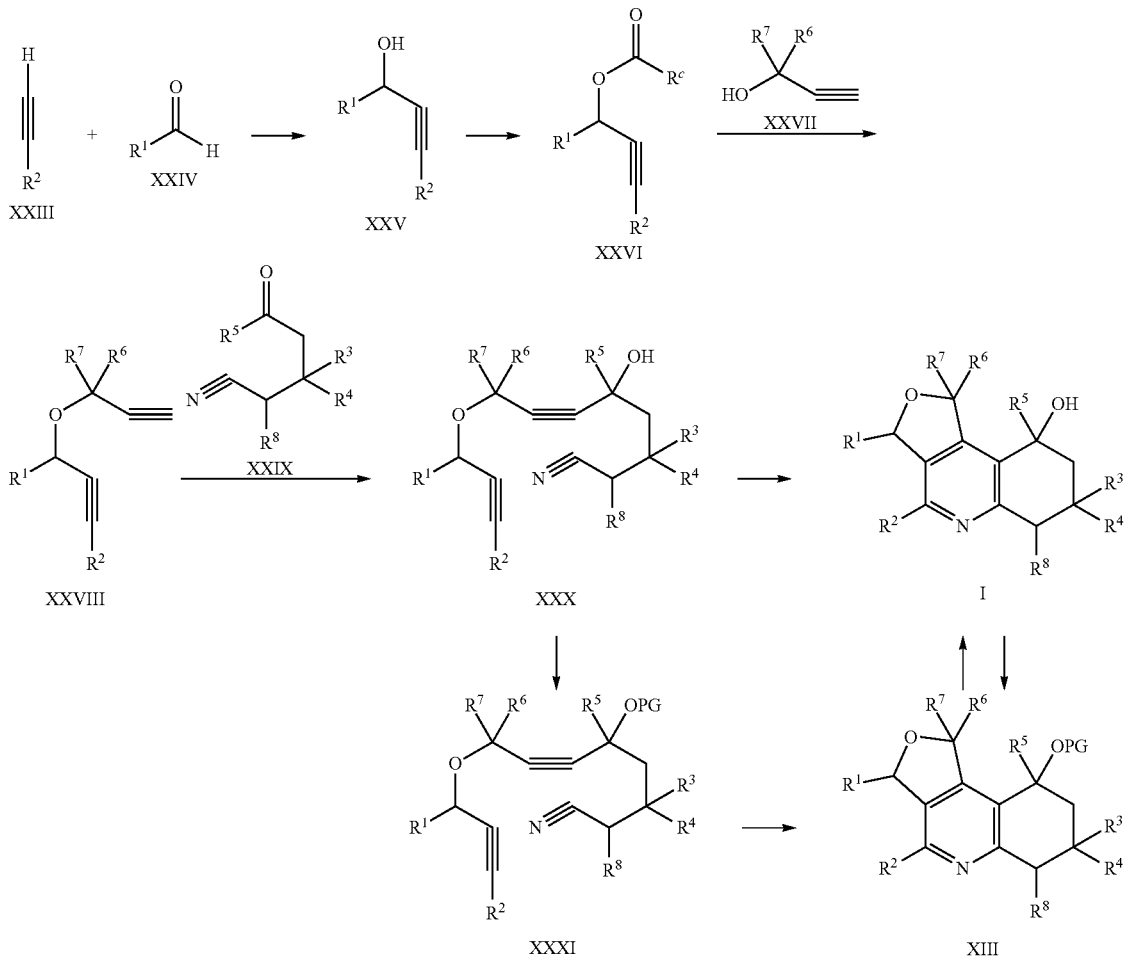

First step is the addition of alkynes of formula XXIII to aldehydes of formula XXIV. For this reaction the alkyne is deprotonated with an organometalspecies such as e.g. n-butyllithium, sec.-butyllithium, tert.-butyllithium, methylmagnesium bromide, ethylmagnesiumbromide or isopropylmagnesium chloride, but preferably n-butyllithium, in a solvent such as e.g. diethylether, tetrahydrofurane or 1,4-dioxane at temperatures between −78° C. and 0° C., but preferably between −78° C. and −20° C. After complete deprotonation the metal-alkyne is reacted with aldehydes of formula XXIV at temperatures between −78° C. and 50° C. The alcohols of formula XXV thus obtained are then acylated to compounds of formula XXVI, wherein Rc is optionally substituted lower alkyl, e.g. by reaction with an acid anhydride such as e.g. acetic anhydride, propionic acid anhydride or trifluoroacetic acid anhydride or by reaction with an acid chloride such as e.g. acetic acid chloride, propionic acid chloride or trifluoroacetic acid chloride in the presence of a base such as e.g. triethylamine, N,N-diisopropyl-N-ethyl-amine, pyridine or 2,6-lutidine, optionally in the presence of an acylation catalyst such as 4-dimethylamino-pyridine (DMAP), in a solvent such as e.g. dichloromethane, 1,2-dichloroethane, diethylether, tetrahydrofurane, 1,4-dioxane, acetonitrile or toluene at temperatures between −78° C. and 40° C. Esters of formula XXVI are then reacted with alcohols of formula XXVII in the presence of an acid such as e.g. methylsulfonic acid or trifluoromethylsulfonic acid or in the presence of a Lewis acid such as e.g. trimethylsilyl-trifluoromethanesulfonate, triethylsilyl-trifluoromethanesulfonate or tert.-butyldimethylsilyl-trifluormethansulfonate, but preferably trimethylsilyl-trifluoromethanesulfonate, in a solvent such as e.g. dichloromethane or 1,2-dichloroethane, at temperatures between −50° C. and room temperature but preferably between −40° C. and 0° C. to give ethers of formula XXVIII. These ethers are then deprotonated with an organometalspecies such as e.g. n-butyllithium, sec.-butyllithium, tert.-butyllithium, methylmagnesium bromide, ethylmagnesiumbromide or isopropylmagnesium chloride, but preferably n-butyllithium, in a solvent such as e.g. diethylether, tetrahydrofurane or 1,4-dioxane at temperatures between −78° C. and 0° C., but preferably between −78° C. and −20° C. After complete deprotonation the metal-alkyne is reacted with carbonyl compounds of formula XXIX at temperatures between −78° C. and 0° C. to give compounds of formula XXX. These are then cyclised, e.g. in the presence of a catalyst such as e.g. cyclopentadienyl-cobalt-dicarbonyl, cyclopentadienyl-cobalt-diethylen-complex, bis-(1,5-cyclooctadien)-rhodium-(I)-tetrafluoroborate or bis-(1,5-cyclooctadien)-rhodium-(I)-trifluoromethanesulfonate, but preferably cyclopentadienyl-cobalt-dicarbonyl, for the rhodium-catalysts additionally in the presence of a ligand such as e.g. 2,2'-bis-(diphenylphosphino)-1,1'-binaphthyl, (S)-(−)-2,2'-bis-(diphenylphosphino)-1,1'-binaphthyl, (R)-(+)-2,2'-bis-(diphenylphosphino)-1,1'-binaphthyl or 2,2'-bis-(diphenylphosphino)-5,5',6,6',7,7',8,8'-octahydro-1,1'-binaphthyl, for the cobalt-catalysts optionally under external irradiation with a tungsten-lamp, in a solvent such as e.g. toluene, xylene, 1,2-dichloroethane or diphenylether, but preferably in toluene, at temperatures between 80° C. and 180° C. to give compounds of formula I. Alternatively this reaction can be performed thermally either neat or in a suitable solvent such as e.g. toluene, xylene or diphenylether at temperatures between 150° C. and 250° C.

The alcohol group in compounds of formula XXX can be temporarily protected with a suitable protecting group, e.g. as a tert.-butyldimethylsilylether by the reaction with tert.-butyldimethylsilylchloride in a suitable solvent such as e.g. N,N-dimethylformamide or acetonitrile in the presence of imidazole, at temperatures between −20° C. and 120° C., but preferably between 0° C. and 80° C., to give the protected derivatives of formula XXXI, in which PG stands for this suitable protecting group. This protection can also be carried out by reacting compounds of formula XXX with tert.-butyldimethylsilyl-trifluormethansulfonate in the presence of a suitable base such as e.g. pyridine or 2,6-lutidine in a suitable solvent such as e.g. dichloromethane, diethylether, tetrahydrofurane, 1,4-dioxane or toluene, at temperatures between −50° C. and 100° C. but preferably between −30° C. and 50° C. Alternatively any other suitable protecting group as described e.g. in "Protective Groups in Organic Synthesis", $2^{nd}$ edition, Greene T. W., Wuts P. G. M.; Wiley-Interscience: New York, 1991 or in "Protective Groups", Kocienski P. J.; Thieme: New York, 1994 can be used. Compounds of formula XXXI can then be cyclised, e.g. in the presence of a catalyst such as e.g. cyclopentadienyl-cobalt-dicarbonyl, cyclopentadienyl-cobalt-diethylen-complex, bis-(1,5-cyclooctadien)-rhodium-(1)-tetrafluoroborate or bis-(1,5-cyclooctadien)-rhodium-(I)-trifluoromethanesulfonate, but preferably cyclopentadienyl-cobalt-dicarbonyl, for the rhodium-catalysts additionally in the presence of a ligand such as e.g. 2,2'-bis-(diphenylphosphino)-1,1'-binaphthyl, (S)-(−)-2,2'-bis-(diphenylphosphino)-1,1'-binaphthyl, (R)-(+)-2,2'-bis-(diphenylphosphino)-1,1'-binaphthyl or 2,2'-bis-(diphenylphosphino)-5,5',6,6',7,7',8,8'-octahydro-1,1'-binaphthyl, for the cobalt-catalysts optionally under external irradiation with a tungsten-lamp, in a solvent such as e.g. toluene, xylene, 1,2-dichloroethane or diphenylether, but preferably in toluene, at temperatures between 80° C. and 180° C. to give compounds of formula XIII. Alternatively this reaction can be performed thermally either neat or in a suitable solvent such as e.g. toluene, xylene or diphenylether at temperatures between 150° C. and 250° C.

Deprotection of compounds of formula XIII, wherein PG denotes tert.-butyldimethylsilyl, preferably with a fluoride reagent such as e.g. tetrabutylammonium fluoride or caesium fluoride or with an acid such as e.g. trifluoroacetic acid, hydrochloric acid or sulphuric acid in a suitable solvent such as e.g. dichloromethane, 1,2-dichloroethane, diethylether, tetrahydrofurane, 1,4-dioxane, acetonitrile or toluene, at temperatures between −50° C. and 120° C., but preferably between −20° C. and 80° C. gives compounds of formula I. Alternatively any other protecting group introduced before can be cleaved by suitable methods as described in the literature e.g. in "Protective Groups in Organic Synthesis", $2^{nd}$ edition, Greene T. W., Wuts P. G. M.; Wiley-Interscience: New York, 1991 or in "Protective Groups", Kocienski P. J.; Thieme: New York, 1994.

Also the alcohol group in compounds of formula I can be protected with a suitable protecting group, e.g. as a tert.-butyldimethylsilylether by the reaction with tert.-butyldimethylsilylchloride in a solvent such as e.g. dimethylformamide or acetonitrile in the presence of imidazole, at temperatures between −20° C. and 120° C., but preferably between 0° C. and 80° C., to give the protected derivatives of formula XIII, in which PG stands for this suitable protecting group. This protection can also be carried out by reacting compounds of formula I with tert.-butyldimethylsilyl-trifluormethansulfonate in the presence of a base such as e.g. pyridine or 2,6-lutidine in a solvent such as e.g. dichloromethane, diethylether, tetrahydrofurane, 1,4-dioxane or toluene, at temperatures between −50° C. and 100° C. but preferably between −30° C. and 50° C. Alternatively any other suitable protecting group as described e.g. in "Protective Groups in Organic Synthesis", $2^{nd}$ edition, Greene T. W., Wuts P. G. M.; Wiley-Interscience: New York, 1991 or in "Protective Groups", Kocienski P. J.; Thieme: New York, 1994 can be used. Compounds of formula XIII can then be transformed into compounds of formula I, wherein $R^8$ denotes acetoxy, propionyloxy or hydroxy, according to invention related process b) shown in scheme 2.

Carbonyl compounds of formula XXIX, wherein $R^3$-$R^5$ are defined as hereinbefore, $R^8$ denotes hydrogen, can be carried out according to the invention related process f) shown in scheme 6.

Scheme 6 (Process f)):

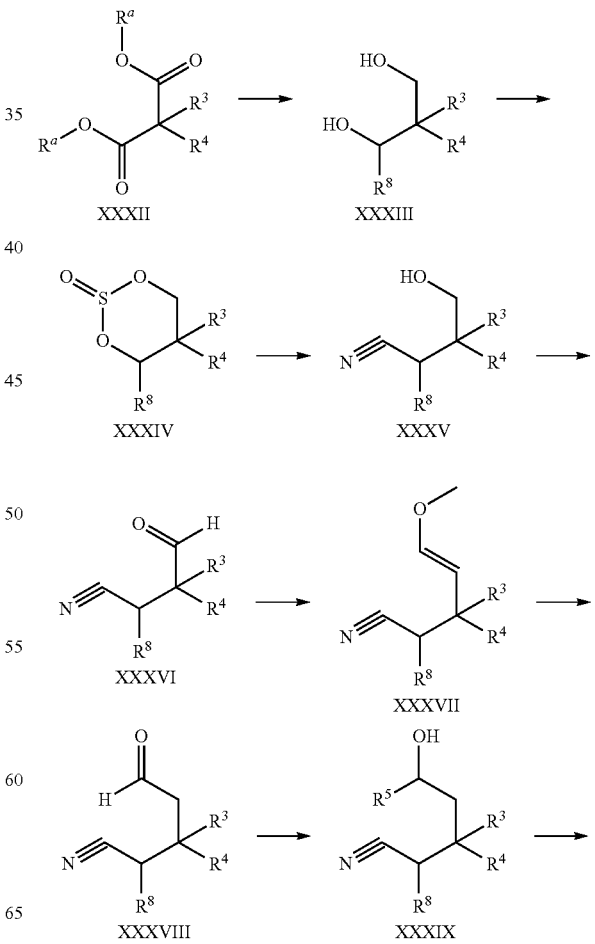

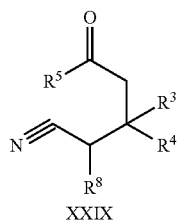

XXIX

First step is the reduction of malonates of formula XXXII, wherein $R^a$ denotes independently methyl or ethyl, to diols of formula XXXIII with a suitable reducing agent, such as e.g. diisobutylamuminium hydride or lithiumaluminiumhydride in an aprotic solvent such as e.g. dichloromethane, tetrahydrofurane, 1,4-dioxane or toluene, at temperatures between −78° C. and 80° C., but preferably between −30° C. and 50° C. Diols of formula XXXIII are then transformed into cyclic sulfites of formula XXXIV by reaction with thionylchloride, optionally in the presence of a base such as e.g. triethylamine, N,N-diisopropyl-N-ethyl-amine or pyridine, in dichloromethane at temperatures between 0° C. and 50° C. Further reaction with sodium cyanide or potassium cyanide e.g. in dimethylsulfoxide or N,N-dimethylformamide at temperatures between 80° C. and 150° C. gives compounds of formula XXXV. The alcohol group in compounds of formula XXXV is then oxidized to the aldehyde group to give compounds of formula XXXVI. This transformation can be carried out with Dess-Martin-Periodinan (*J. Chem. Soc.* 1983, 48, 4156) or by Swern oxidation (*J. Org. Chem.* 1976, 41, 957). Alternatively this transformation can be performed by reaction with $RuCl_3$ or tetrapropylammonium perrhutenate in the presence of N-methylmorpholin-N-oxide in acetonitrile or dichlormethane, or by an oxidation catalysed by 2,2,6,6-tetramethyl-piperidin-1-oxyl (TEMPO) in the presence of iodine and a base such as e.g. sodium bicarbonate in a solvent such as e.g. dichloromethane, tetrahydrofurane, 1,4-dioxane, benzene or toluene but preferably in toluene optionally as a mixture with water, at temperatures between −30° C. and 80° C. but preferably between 0° C. and 40° C. Aldehydes of formula XXXVI are transformed into enolethers of formula XXXVII. For this transformation methoxytriphenylphosphonium chloride is reacted with n-butyllithium or lithiumhexamethyldisilazide in tetrahydrofurane at temperatures between −30° C. and 0° C. The phosphonium-ylide thus formed is reacted with the aldehydes of formula XXXVI at temperatures between −78° C. and room temperature to give compounds of formula XXXVII. Further reaction of enolethers of formula XXXVII with hydrochloric acid in tetrahydrofurane at temperatures between 0° C. and 40° C. gives aldehydes of formula XXXVIII, which equal compounds of formula XXIX for the case that $R^5$ denotes hydrogen. Reaction of these with a suitable alkyl metal compound, such as e.g. 1-4C-alkylmagnesium halogenide- or 1-4C-alkyllithium-reagent, particularly 1-2C-alkylmagnesium halogenide- or 1-2C-alkyllithium-reagent, in a suitable solvent such as e.g. diethylether, tetrahydrofurane or 1,4-dioxane, at temperatures between −78° C. and room temperature gives the alcohols of formula XXXIX, wherein $R^5$ denotes 1-4C-alkyl, particularly 1-2C-alkyl. Oxidation with Dess-Martin-Periodinan (*J. Chem. Soc.* 1983, 48, 4156) or by Swern oxidation (*J. Org. Chem.* 1976, 41, 957) gives compounds of formula XXIX. Alternatively this transformation can be performed by reaction with $RuCl_3$ or tetrapropylammonium perrhutenate in the presence of N-methylmorpholin-N-oxide in acetonitrile or dichlormethane, or by an oxidation catalysed by 2,2,6,6-tetramethyl-piperidin-1-oxyl (TEMPO) in the presence of iodine and a base such as e.g. sodium bicarbonate in a solvent such as e.g. dichloromethane, tetrahydrofurane, 1,4-dioxane, benzene or toluene but preferably in toluene optionally as a mixture with water, at temperatures between −30° C. and 80° C. but preferably between 0° C. and 40°.

The synthesis of compounds of formula I, wherein $R^1$-$R^7$ are defined as hereinbefore, $R^8$ denotes hydrogen, can also be carried out according to the invention related process g) shown in scheme 7.

Scheme 7 (Process g)):

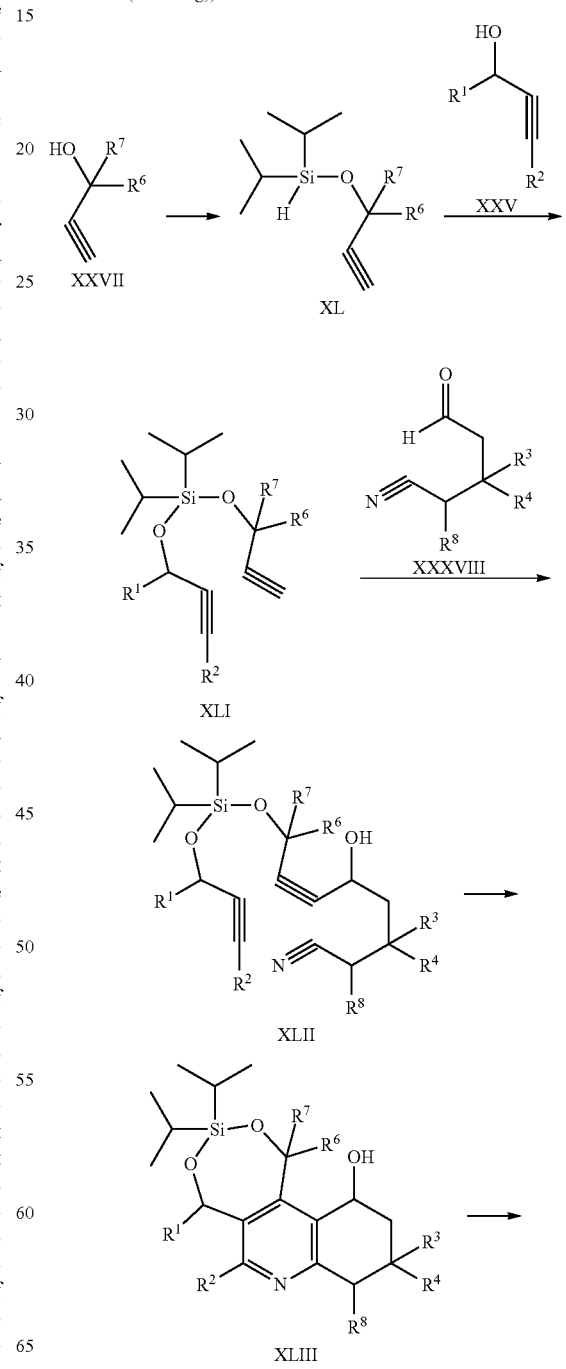

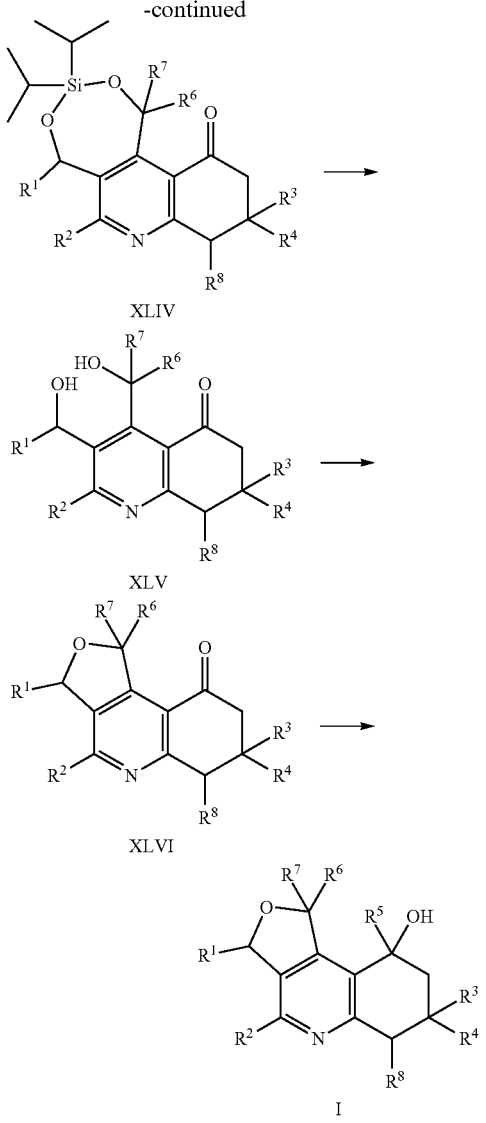

temperature to give compounds of formula XLII. These are then cyclised, e.g. in the presence of a catalyst such as e.g. cyclopentadienyl-cobalt-dicarbonyl, cyclopentadienyl-cobalt-diethylen-complex, bis-(1,5-cyclooctadien)-rhodium-(I)-tetrafluoroborate or bis-(1,5-cyclooctadien)-rhodium-(I)-trifluoromethanesulfonate, but preferably cyclopentadienyl-cobalt-dicarbonyl, for the rhodium-catalysts additionally in the presence of a ligand such as e.g. 2,2'-bis-(diphenylphosphino)-1,1'-binaphthyl, (S)-(−)-2,2'-bis-(diphenylphosphino)-1,1'-binaphthyl, (R)-(+)-2,2'-bis-(diphenylphosphino)-1,1'-binaphthyl or 2,2'-bis-(diphenylphosphino)-5,5', 6,6',7,7',8,8'-octahydro-1,1'-binaphthyl, for the cobalt-catalysts optionally under external irradiation with a tungsten-lamp, in a solvent such as e.g. toluene, xylene, 1,2-dichloroethane or diphenylether, but preferably in toluene, at temperatures between 80° C. and 180° C. to give compounds of formula XLIII. Alternatively this reaction can be performed thermally either neat or in a suitable solvent such as e.g. toluene, xylene or diphenylether at temperatures between 150° C. and 250° C. Oxidation with Dess-Martin-Periodinan (*J. Chem. Soc.* 1983, 48, 4156) or by Swern oxidation (*J. Org. Chem.* 1976, 41, 957) gives ketones of formula XLIV. Alternatively this transformation can be performed by reaction with RuCl$_3$ or tetrapropylammonium perrhutenate in the presence of N-methylmorpholin-N-oxide in acetonitrile or dichlormethane, or by an oxidation catalysed by 2,2,6,6-tetramethyl-piperidin-1-oxyl (TEMPO) in the presence of iodine and a base such as e.g. sodium bicarbonate in a solvent such as e.g. dichloromethane, tetrahydrofurane, 1,4-dioxane, benzene or toluene but preferably in toluene optionally as a mixture with water, at temperatures between −30° C. and 80° C. but preferably between 0° C. and 40°. Cleavage of the silylacetal group in XLIV with tetrabutylammonium fluoride in tetrahydrofurane at temperatures between −10° C. and room temperature gives compounds of formula XLV. Cyclisation to compounds of formula XLVI can then performed by reaction with diethylamino-sulfur-trifluoride (DAST) or bis-(2-methoxyethyl)-amino-sulfur-trifluoride (BAST) in a aprotic solvent such as e.g. dichloromethane or 1,2-dichloroethane at temperatures between −30° C. and 50° C. Reaction of compounds of formula XLVI with a suitable hydride donating reagent such as e.g. borane-tetrahydrofurane-complex, borane-dimethylsulfide-complex, borane-dimethylaniline-complex, borane-diethylaniline-complex, sodium borohydride, lithium borohydride, lithium aluminium hydride in a suitable solvent such as e.g. diethylether, tetrahydrofurane, 1,4-dioxane or toluene, at temperatures between −78° C. and 100° C., but preferably between −50° C. and 80° C., optionally in the presence of a chiral ligand as for example (1R,2S)-(+)-cis-1-Amino-2-indanol, (1S,2R)-(+)-cis-1-Amino-2-indanol, (R)-1-Methyl-3,3-diphenyl-tetrahydro-pyrrolo[1,2-c][1,3,2]oxazaborole or (S)-1-Methyl-3,3-diphenyl-tetrahydro-pyrrolo[1,2-c][1,3,2]oxazaborole gives compounds of formula I, wherein R$^5$ denotes hydrogen. The reduction in the presence of chiral ligands results in enantiomerically enriched compounds of formula I. For example the reduction with borane reagents such as e.g. borane-tetrahydrofurane-complex, borane-dimethylsulfide-complex, borane-dimethylaniline-complex or borane-diethylaniline-complex each in the presence of (1R,2S)-(+)-cis-1-Amino-2-indanole gives compounds of formula I with S-configuration at the newly formed stereocenter as it is known from the literature (see *Tetrahedron: Asymmetry* 1995, 6, 301-306; *Synthesis* 1998, 937-961 or *Angew. Chem.* 1999, 111, 3574-3576). Likewise, alkylation reaction of compounds of formula XLVI with a suitable alkyl metal compound, such as e.g. 1-4C-dialkylzinc-, 1-4C-alkylmagnesium halogenide-, or Compounds of formula XXVII are reacted with chlorodiisopropylsilane in the presence of a base such as e.g. triethylamine or N,N-diisopropyl-N-ethyl-amine in a solvent such as e.g. acetonitrile or N,N-dimethylformamide at temperatures between −10° C. and room temperature. Silylethers XL thus obtained are then reacted N-bromosuccinimide in a solvent such as e.g. dichloromethane or 1,2-dichloroethane at temperatures between −10° C. and room temperature. After complete reaction to this mixture is added a mixture of XXV, a base such as e.g. triethylamine or N,N-diisopropyl-N-ethyl-amine or 4-dimethylaminopyridine (DMAP) in a solvent such as e.g. dichloromethane or 1,2-dichloroethane. The mixture is then heated to temperatures between 50° C. and 100° C. to give compounds of formula XLI. These are then deprotonated with an oganometalspecies such as e.g. e.g. n-butyllithium, sec.-butyllithium, tert.-butyllithium, methylmagnesium bromide, ethylmagnesiumbromide or isopropylmagnesium chloride, but preferably n-butyllithium, in a solvent such as e.g. diethylether, tetrahydrofurane or 1,4-dioxane at temperatures between −78° C. and 0° C., but preferably between −78° C. and −20° C. After complete deprotonation the metal-alkyne is reacted with aldehydes of formula XXXVIII at temperatures between −78° C. and room 1-4C-alkyllithium-reagent, particularly 1-2C-dialkylzinc-, 1-2C-alkylmagnesium halogenide-, or 1-2C-alkyllithium-reagent, in a suitable solvent such as e.g. n-hexane, cyclohexane, toluene, diethylether, tetrahydrofurane or 1,4-dioxane, optionally in the presence of a chiral ligand such as for example (R)-1-methyl-3,3-diphenyl-tetrahydro-pyrrolo[1,2-c][1,3,2]oxazaborole, (R)-1-methyl-3,3-diphenyl-tetrahydro-pyrrolo[1,2-c][1,3,2]oxazaborole, (−)-3-exo-dimethylamino-isoborneol, (+)-3-exo-dimethylamino-isoborneol or ligands as described in *J. Am. Chem. Soc.* 2002, 124, 10970-10971 or *Tetrahedron* 1998, 54, 5651-5666, at temperatures between −50° C. and 100° C., but preferably between −20° C. and 70° C., gives the corresponding compounds of formula I, wherein $R^5$ denotes 1-4C-alkyl, particularly 1-2C-alkyl.

Compounds of formula I can be transformed into compounds of formula XIII according to invention related process e) shown in scheme 5. Compounds of formula XIII can then be transformed into compounds of formula I, wherein $R^8$ denotes acetoxy, propionyloxy or hydroxy, according to invention related process b) shown in scheme 2.

The synthesis of compounds of formula I, wherein $R^1$-$R^7$ are defined as hereinbefore, $R^8$ denotes hydrogen, can be carried out according to the invention related process h) shown in scheme 8.

Scheme 8 (Process h)):

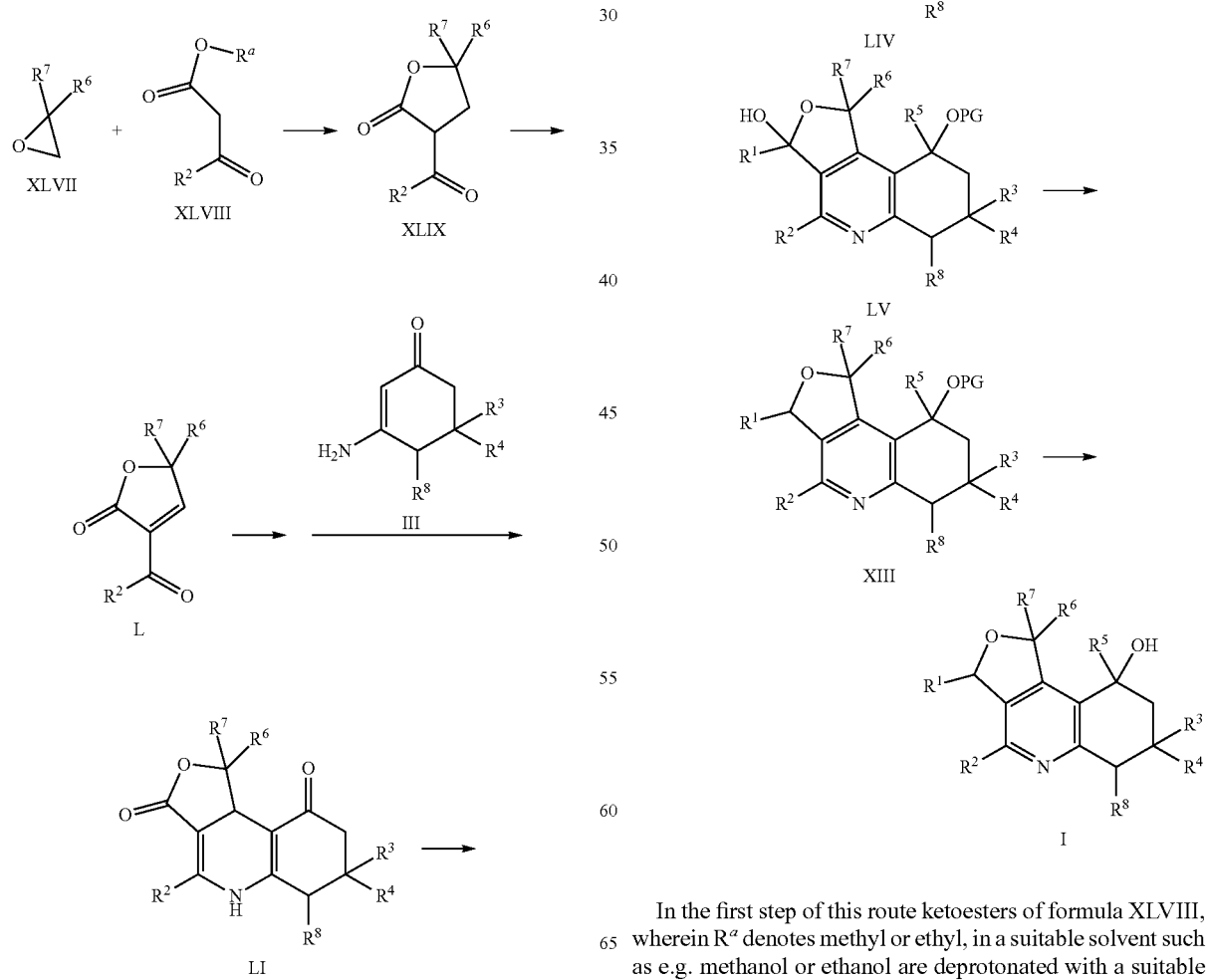

In the first step of this route ketoesters of formula XLVIII, wherein $R^a$ denotes methyl or ethyl, in a suitable solvent such as e.g. methanol or ethanol are deprotonated with a suitable base such as e.g. sodium ethoxide or sodium methoxide and treated with epoxides of formula XLVII at temperatures between −10° C. and 80° C. to give ketolactones XLIX.

Ketolactones XLIX are oxidized to furanones L with a suitable oxidizing reagent such as e.g. 2-iodoxybenzoic acid and 4-methoxypyridine-N-oxide in a suitable solvent such as e.g. dimethylsulfoxide at temperatures between 0° C. and 50° C.

Furanones of formula L are condensed with enaminoketones of formula III, e.g. at temperatures between 150° C. and 250° C. either neat under reduced pressure at or at temperatures between 100° C. and 150° C. in a suitable solvent such as e.g. acetic acid yielding the tricyclic dihydropyridines of formula LI.

Dihydropyridines LI are oxidized to the corresponding tricyclic pyridines of formula LII using a suitable oxidizing reagent such as e.g. 2,3-dichloro-5,6-dicyano-1,4-benzoquinone (DDQ) in a suitable solvent such as e.g. dichloromethane at temperatures between 0° C. and 50° C. Reduction of the ketogroup in tricyclic pyridines of formula LII is carried out with a suitable hydride donating reagent such as e.g. borane-tetrahydrofurane-complex, borane-dimethylsulfide-complex, borane-dimethylaniline-complex, borane-diethylaniline-complex, sodium borohydride, lithium borohydride, lithium aluminium hydride in a suitable solvent such as e.g. diethylether, tetrahydrofurane, 1,4-dioxane or toluene, at temperatures between −78° C. and 100° C., but preferably between −50° C. and 80° C., optionally in the presence of a chiral ligand as for example (1R,2S)-(+)-cis-1-Amino-2-indanol, (1S,2R)-(+)-cis-1-Amino-2-indanol, (R)-1-Methyl-3,3-diphenyl-tetrahydro-pyrrolo[1,2-c][1,3,2]oxazaborole or (S)-1-Methyl-3,3-diphenyl-tetrahydro-pyrrolo[1,2-c][1,3,2]oxazaborole gives the alcohols of formula LIII, wherein $R^5$ denotes hydrogen. The reduction in the presence of chiral ligands results in enantiomerically enriched compounds of formula LIII. For example the reduction with borane reagents such as e.g. borane-tetrahydrofurane-complex, borane-dimethylsulfide-complex, borane-dimethylaniline-complex or borane-diethylaniline-complex each in the presence of (1R,2S)-(+)-cis-1-Amino-2-indanole gives compounds of formula LIII with S-configuration at the newly formed stereocenter as it is known from the literature (see *Tetrahedron: Asymmetry* 1995, 6, 301-306; *Synthesis* 1998, 937-961 or *Angew. Chem.* 1999, 111, 3574-3576).

Likewise, alkylation reaction of compounds of formula LII with a suitable alkyl metal compound, such as e.g. 1-4C-dialkylzinc-, 1-4C-alkylmagnesium halogenide-, or 1-4C-alkyllithium-reagent, particularly 1-2C-dialkylzinc-, 1-2C-alkylmagnesium halogenide-, or 1-2C-alkyllithium-reagent, in a suitable solvent such as e.g. n-hexane, cyclohexane, toluene, diethylether, tetrahydrofurane or 1,4-dioxane, optionally in the presence of a chiral ligand such as for example (R)-1-methyl-3,3-diphenyl-tetrahydro-pyrrolo[1,2-c][1,3,2]oxazaborole, (R)-1-methyl-3,3-diphenyl-tetrahydro-pyrrolo[1,2-c][1,3,2]oxazaborole, (−)-3-exo-dimethylamino-isoborneol, (+)-3-exo-dimethylamino-isoborneol or ligands as described in *J. Am. Chem. Soc.* 2002, 124, 10970-10971 or *Tetrahedron* 1998, 54, 5651-5666, at temperatures between −50° C. and 100° C., but preferably between −20° C. and 70° C., gives the corresponding compounds of formula LIII, wherein $R^5$ denotes 1-4C-alkyl, particularly 1-2C-alkyl.

The alcohol group in compounds of formula LIII can be temporarily protected with a suitable protecting group, e.g. as a tert.-butyldimethylsilylether by the reaction with tert.-butyldimethylsilylchloride in a solvent such as e.g. dimethylformamide or acetonitrile in the presence of imidazole, at temperatures between −20° C. and 120° C., but preferably between 0° C. and 80° C., to give the protected derivatives of formula LIV, in which PG stands for this suitable protecting group. This protection can also be carried out by reacting compounds of formula LIII with tert.-butyldimethylsilyl-trifluormethansulfonat in the presence of a base such as e.g. pyridine or 2,6-lutidine in a solvent such as e.g. dichloromethane, diethylether, tetrahydrofurane, 1,4-dioxane or toluene, at temperatures between −50° C. and 100° C. but preferably between −30° C. and 50° C. Alternatively any other suitable protecting group as described e.g. in "*Protective Groups in Organic Synthesis*", $2^{nd}$ edition, Greene T. W., Wuts P. G. M.; Wiley-Interscience: New York, 1991 or in "*Protective Groups*", Kocienski P. J.; Thieme: New York, 1994 can be used.

Lactones of formula LIV are transformed into lactols of formula LV by reaction with a suitable $R^1$-metal reagent, such as e.g. $R^1$-magnesium halogenide- or $R^1$-lithium-reagent, in an aprotic solvent such as e.g. diethylether, tetrahydrofurane, 1,4-dioxane or toluene, at temperatures between −78° C. and room temperature for lithium reagents or between −50° C. and room temperature for magnesium reagents.

The lactols of formula LV are reduced to the corresponding compounds of formula XIII using a combination of a suitable acid such as e.g. titaniumtetrachloride or borontrifluoride etherate with a suitable hydride donating reagent such as e.g. sodium borohydride, sodium cyanoborohydride or sodium triacetoxyborohydride, but preferably with sodium triacetoxyborohydride, in a suitable solvent such as e.g. diethylether, dichloromethane, toluene or tetrahydrofurane, but preferably tetrahydrofurane, at temperatures between −50° C. and room temperature. The reduction under preferred conditions results in diastereomerically enriched compounds of formula XIII. For example the reduction with borane reagents such as e.g. sodium triacetoxyborohydride in the presence of titaniumtetrachloride gives compounds of formula XIII, in which the newly formed stereocenter has preferably R-configuration as proven by extensive NMR analysis.

Deprotection of compounds of formula XIII, wherein PG denotes tert.-butyldimethylsilyl, preferably with a fluoride reagent such as e.g. tetrabutylammonium fluoride or caesium fluoride or with an acid such as e.g. for example trifluoroacetic acid, hydrochloric acid or sulphuric acid in a suitable solvent such as e.g. dichloromethane, 1,2-dichloroethane, diethylether, tetrahydrofurane, 1,4-dioxane, acetonitrile or toluene, at temperatures between −50° C. and 120° C., but preferably between −20° C. and 80° C. gives compounds of formula I. Alternatively any other protecting group introduced before can be cleaved by suitable methods as described in the literature e.g. in "*Protective Groups in Organic Synthesis*", $2^{nd}$ edition, Greene T. W., Wuts P. G. M.; Wiley-Interscience: New York, 1991 or in "*Protective Groups*", Kocienski P. J.; Thieme: New York, 1994.

Compounds of formula XIII can also be transformed into compounds of formula I, wherein $R^8$ denotes acetoxy, propionyloxy or hydroxy, according to invention related process b) shown in scheme 2.

The synthesis of compounds of formula LXV, wherein $R^1$-$R^7$ are defined as hereinbefore, $R^8$ denotes hydrogen, and $R^b$ is chlorine can be carried out according to the invention related process i) shown in scheme 9.

Scheme 9 (Process i)):

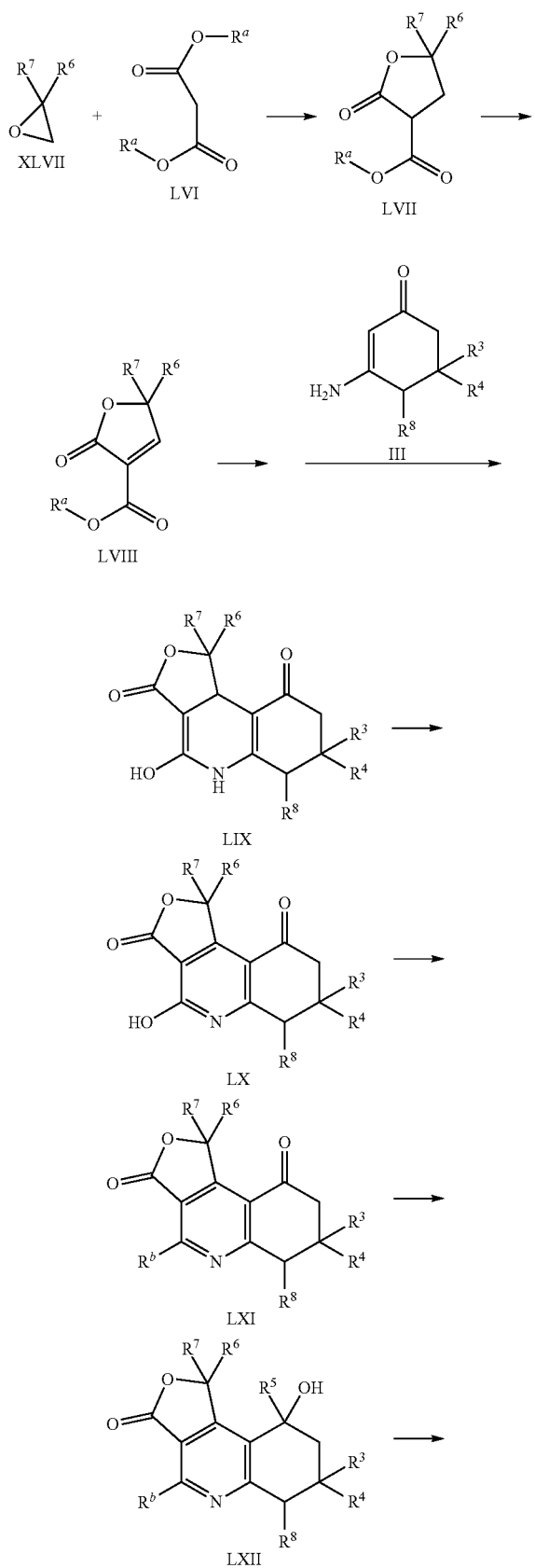

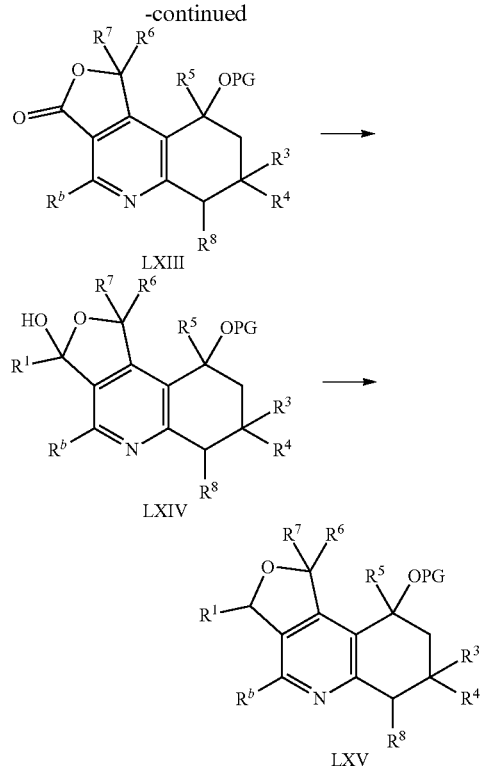

In the first step of this route malonesters of formula LVI, wherein $R^a$ denotes independently methyl or ethyl, in a suitable solvent such as e.g. methanol or ethanol are deprotonated with a suitable base such as e.g. sodium ethoxide or sodium methoxide and treated with epoxides of formula XLVII at temperatures between −10° C. and 80° C. to give lactones LVII.

The lactones LVII are oxidized to furanones LVIII with a suitable oxidizing reagent such as e.g. 2-iodoxybenzoic acid and 4-methoxypyridine-N-oxide in a suitable solvent such as e.g. dimethylsulfoxide at temperatures between 0° C. and 50° C.

Furanones of formula LVIII are condensed with enaminoketones of formula III, e.g. at temperatures between 150° C. and 250° C. either neat under reduced pressure or at temperatures between 100° C. and 150° C. in a suitable solvent such as e.g. acetic acid yielding the tricyclic hydroxo dihydropyridines of formula LIX.

The hydroxo dihydropyridines LIX are oxidized to the corresponding tricyclic hydroxy pyridines of formula LX using a suitable oxidizing reagent such as e.g. 2,3-dichloro-5,6-dicyano-1,4-benzoquinone (DDQ) in a suitable solvent such as e.g. dichloromethane at temperatures between 0° C. and 50° C.

Pyridines of formula LXI, wherein $R^b$ is chlorine, are obtained by chlorination of hydroxy pyridines of formula LX. For example, chlorination of hydroxy pyridines of formula LX with phosphoroxychloride and catalytic amounts of N,N-dimethylformamide at 45° C. gives pyridines of formula LXI, wherein $R^b$ denotes chlorine.

Reduction of the ketogroup in pyridines of formula LXI is carried out with a suitable hydride donating reagent such as e.g. borane-tetrahydrofurane-complex, borane-dimethylsulfide-complex, borane-dimethylaniline-complex, borane-diethylaniline-complex, sodium borohydride, lithium borohydride, lithium aluminium hydride in a suitable solvent such as e.g. diethylether, tetrahydrofurane, 1,4-dioxane or toluene, at temperatures between −78° C. and 100° C., but preferably between −50° C. and 80° C., optionally in the presence of a chiral ligand such as for example (1R,2S)-(+)-cis-1-Amino-2-indanol, (1S,2R)-(+)-cis-1-Amino-2-indanol, (R)-1-Methyl-3,3-diphenyl-tetrahydro-pyrrolo[1,2-c][1,3,2]oxazaborole or (S)-1-Methyl-3,3-diphenyl-tetrahydro-pyrrolo[1,2-c][1,3,2]oxazaborole gives the alcohols of formula LXII, wherein $R^5$ denotes hydrogen. The reduction in the presence of chiral ligands results in enantiomerically enriched compounds of formula LXII. For example the reduction with borane reagents such as e.g. borane-tetrahydrofurane-complex, borane-dimethylsulfide-complex, borane-dimethylaniline-complex or borane-diethylaniline-complex each in the presence of (1R,2S)-(+)-cis-1-Amino-2-indanole gives compounds of formula LXII with S-configuration at the newly formed stereocenter as it is known from the literature (see *Tetrahedron: Asymmetry* 1995, 6, 301-306; *Synthesis* 1998, 937-961 or *Angew. Chem.* 1999, 111, 3574-3576).

Likewise, alkylation reaction of compounds of formula LXI with a suitable alkyl metal compound, such as e.g. 1-4C-dialkylzinc-, 1-4C-alkylmagnesium halogenide-, or 1-4C-alkyllithium-reagent, particularly 1-2C-dialkylzinc-, 1-2C-alkylmagnesium halogenide-, or 1-2C-alkyllithium-reagent, in a suitable solvent such as e.g. n-hexane, cyclohexane, toluene, diethylether, tetrahydrofurane or 1,4-dioxane, optionally in the presence of a chiral ligand as for example (R)-1-methyl-3,3-diphenyl-tetrahydro-pyrrolo[1,2-c][1,3,2]oxazaborole, (R)-1-methyl-3,3-diphenyl-tetrahydro-pyrrolo[1,2-c][1,3,2]oxazaborole, (−)-3-exo-dimethylamino-isoborneol, (+)-3-exo-dimethylamino-isoborneol or ligands as described in *J. Am. Chem. Soc.* 2002, 124, 10970-10971 or *Tetrahedron* 1998, 54, 5651-5666, at temperatures between −50° C. and 100° C., but preferably between −20° C. and 70° C., gives the corresponding compounds of formula LXII, wherein $R^5$ denotes 1-4C-alkyl, particularly 1-2C-alkyl. The alcohol group in compounds of formula LXII can be temporarily protected with a suitable protecting group, e.g. as a tert.-butyldimethylsilylether by the reaction with tert.-butyldimethylsilylchloride in a solvent such as e.g. dimethylformamide or acetonitrile in the presence of imidazole, at temperatures between −20° C. and 120° C., but preferably between 0° C. and 80° C., to give the protected derivatives of formula LXIII, in which PG stands for this suitable protecting group. This protection can also be carried out by reacting compounds of formula LXII with tert.-butyldimethylsilyl-trifluormethansulfonat in the presence of a base such as e.g. pyridine or 2,6-lutidine in a solvent such as e.g. dichloromethane, diethylether, tetrahydrofurane, 1,4-dioxane or toluene, at temperatures between −50° C. and 100° C. but preferably between −30° C. and 50° C. Alternatively any other suitable protecting group as described e.g. in "*Protective Groups in Organic Synthesis*", 2$^{nd}$ edition, Greene T. W., Wuts P. G. M.; Wiley-Interscience: New York, 1991 or in "*Protective Groups*", Kocienski P. J.; Thieme: New York, 1994 can be used.

Lactones of formula LXIII are transformed into lactols of formula LXIV by reaction with a suitable $R^1$-metal reagent, such as e.g. $R^1$-magnesium halogenide- or $R^1$-lithium-reagent, in an aprotic solvent such as e.g. diethylether, tetrahydrofurane, 1,4-dioxane or toluene, at temperatures between −78° C. and room temperature for lithium reagents or between −50° C. and room temperature for magnesium reagents.

The lactols of formula LXIV are reduced to the corresponding compounds of formula LXV using a combination of a suitable acid such as e.g. titaniumtetrachloride or borontrifluoride etherate with a suitable hydride donating reagent such as e.g. sodium borohydride, sodium cyanoborohydride or sodium triacetoxyborohydride, but preferably with sodium triacetoxyborohydride, in a suitable solvent such as e.g. diethylether, dichloromethane, toluene or tetrahydrofurane, but preferably tetrahydrofurane, at temperatures between −50° C. and room temperature. The reduction under preferred conditions results in diastereomerically enriched compounds of formula LXV. For example the reduction with borane reagents such as e.g. sodium triacetoxyborohydride in the presence of titaniumtetrachloride gives compounds of formula LXV, in which the newly formed stereocenter has preferably a R-configuration as proven by extensive NMR analysis.

Compounds of formula LXV can be transformed into compounds of formula I according to the invention related process j) shown in scheme 10, wherein $R^1$, $R^3$-$R^7$ are defined as hereinbefore, $R^8$ denotes hydrogen. $R^{2'}$, $R^{2''}$ and $R^{2'''}$ denote progenitor groups, which together with the carbons to which they are linked convert into $R^2$ in compounds of formula XIII.

Scheme 10 (Process j)):

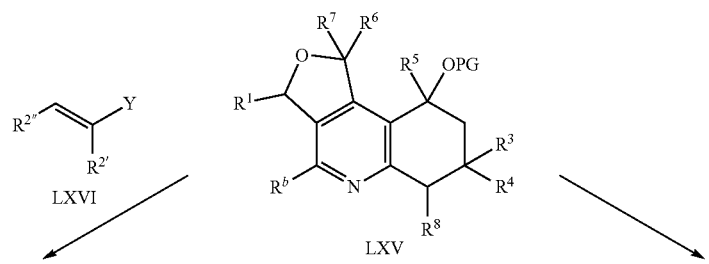

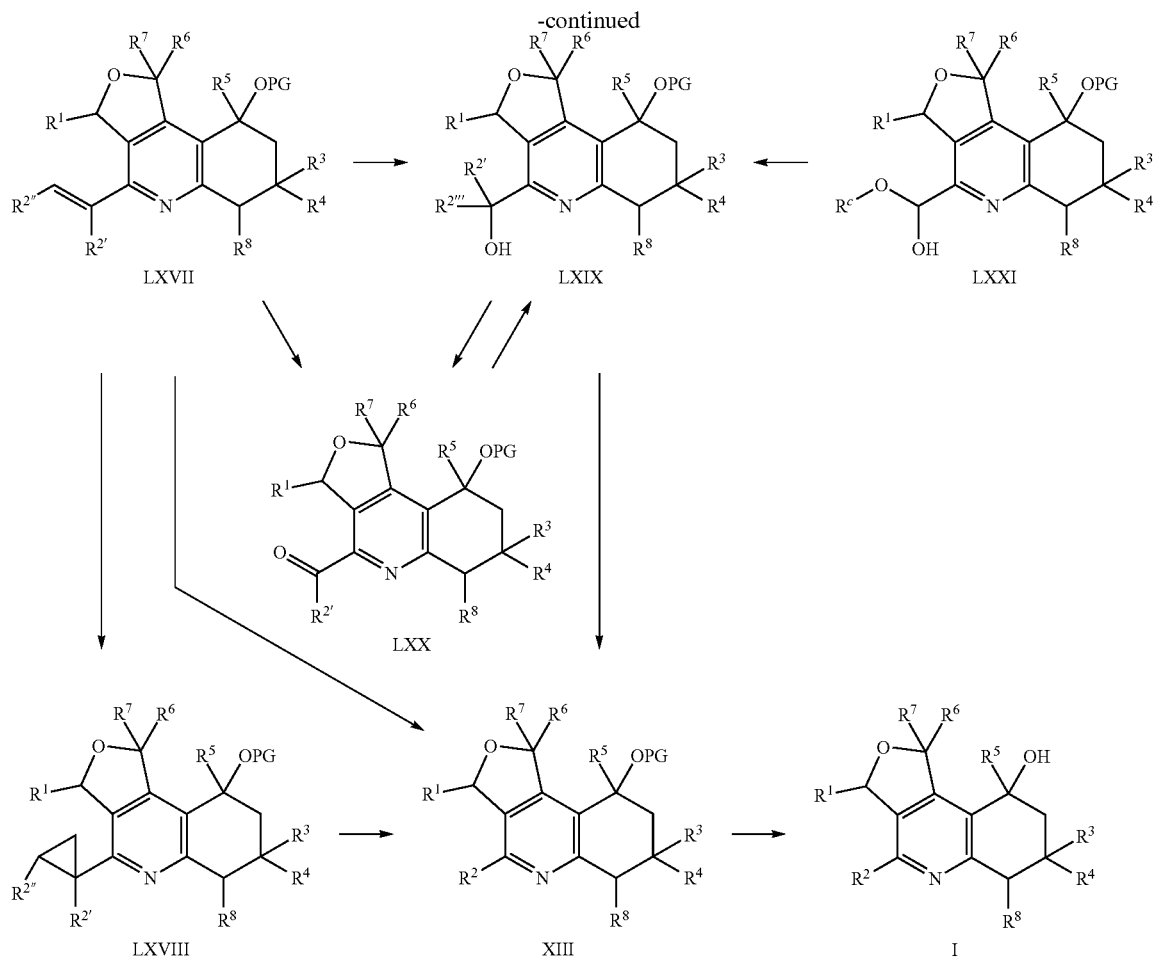

Compounds of formula LXV are converted into compounds of formula LVXII via Negishi coupling with reagents of formula LXVI, wherein Y denotes ZnX, wherein X denotes a halogen (e.g. chlorine). The reaction is performed in a suitable solvent such as e.g. toluene, tetrahydrofurane, 1,4-dioxane or diethylether in the presence of a suitable catalyst such as e.g. tetrakis-triphenylphosphine-palladium-(0), bis-tri-tert.-butylphosphine-palladium-(0), 1,1'-bis-(diphenylphosphino)-ferrocene-dichloro-palladium-(II), bis-[1,2-bis-(diphenylphosphino)-ethane]-palladium-(0), or in the presence of a suitable palladium source such as e.g. palladium diacetate or tris-(dibenzylideneacetone)-dipalladium-(0) and a suitable ligand such as e.g. tri-tert.-butylphosphine, tri-cyclohexylphosphine, di-adamantan-1-yl-butylphosphine, 2-dicyclohexylphosphino-2',6'-diisopropoxy-1,1'biphenyl, 2-dicyclohexylphosphino-2',4',6'-triisopropyl-1,1'-biphenyl or 2-dicyclohexylphosphino-2',6'-dimethoxy-1,1'-biphenyl, at temperatures between 0° C. and 80° C., but preferably at room temperature, delivering compounds of formula LXVII.

Alternatively compounds of formula LXV are converted to compounds of formula LXVII via Suzuki coupling with reagents of formula LXVI, wherein Y denotes a potassium trifluoroborates, boronic acid or boronic acid pinacol ester substituent, in a suitable solvent such as e.g. toluene, N,N-dimethylformamide, acetonitrile, 1,4-dioxane or tetrahydrofurane or mixtures of toluene and tetrahydrofurane in the presence of a suitable base such as e.g. aqueous sodium carbonate, aqueous potassium carbonate, aqueous caesium carbonate, silver carbonate, caesium fluoride, triethylamine or N,N-diisopropyl-N-ethyl-amine but preferably caesium fluoride and in the presence of a suitable catalyst such as e.g. tetrakis-triphenylphosphine-palladium-(0), bis-tri-tert.-butylphosphine-palladium-(0), 1,1'-bis-(diphenylphosphino)-ferrocene-dichloro-palladium-(II) or bis-[1,2-bis-(diphenylphosphino)-ethane]-palladium-(0), or in the presence of a suitable palladium source such as e.g. palladium diacetate or tris-(dibenzylideneacetone)-dipalladium-(0) and a suitable ligand such as e.g. tri-tert.-butylphosphine, tri-cyclohexylphosphine, di-adamantan-1-yl-butylphosphine, 2-dicyclohexylphosphino-2',6'-diisopropoxy-1,1'biphenyl, 2-dicyclohexylphosphino-2',4',6'-triisopropyl-1,1'-biphenyl or 2-dicyclohexylphosphino-2',6'-dimethoxy-1,1'-biphenyl, at temperatures between 0° C. and 180° C., but preferably between room temperature or 120° C. Compounds of formula LXVII can be reduced to compounds of formula XIII by hydrogenation in the presence of a suitable catalyst such as e.g. palladium on charcoal or palladiumhydroxide on charcoal in a suitable solvent such as e.g. methanol, ethanol, tetrahydrofurane or 1,4-dioxane. This reaction may be carried out under hydrogen pressures between 1 bar and 3 bar, optionally in the presence of a suitable base such as e.g. triethylamine or N,N-diisopropyl-N-ethyl-amine, at temperatures between 0° C. and 80° C. but preferably with palladium on charcoal in methanol under 3 bar hydrogen pressure at room temperature. This transformation gives compounds of formula XIII in which the carbon of $R^2$, which is linked to the pyridine, carries two hydrogens for the case that $R^2$ is hydrogen or the carbon of $R^2$, which is linked to the pyridine, carries one hydrogen for the case that $R^2$ is not hydrogen.

Compounds of formula LXVII can be transformed into compounds of formula LXVIII by cyclopropanation in the presence of a suitable reagent such as e.g. diethylzink/diiodomethane, optionally in the presence of trifluoroacetic acid, in a suitable solvent such as e.g. dichloromethane, at temperatures between −20° C. and room temperature.

Compounds of formula LXVIII are reduced to compounds of formula XIII by hydrogenation in the presence of a suitable catalyst such as e.g. palladium on charcoal, palladiumhydroxide on charcoal or platinumdioxide in a suitable solvent such as e.g. acetic acid, methanol, ethanol, tetrahydrofurane or 1,4-dioxane but preferably acetic acid. This reaction may be carried out under hydrogen pressures between 1 bar and 3 bar at temperatures between 0° C. and 100° C. but preferably with platinumdioxide in acetic acid under 3 bar hydrogen pressure at 60° C. This transformation gives compounds of formula XIII in which the carbon of $R^2$, which is linked to the pyridine, carries one hydrogen for the case that $R^2$ is hydrogen or the carbon of $R^2$, which is linked to the pyridine, carries no hydrogen for the case that $R^2$ is not hydrogen.

Alternatively compounds of formula LXVII can be transformed into compounds of formula LXIX, wherein $R^2$ denotes hydrogen by ozonolysis in a suitable solvent such as e.g. dichloromethane at temperatures between −80° C. and −40° C. and subsequent treatment with a suitable reducing agent such as e.g. sodium borohydride in a suitable solvent such as e.g. methanol or ethanol at temperatures between 0° C. and room temperature. For the case that $R^{2'}$ and $R^{2'''}$ denote hydrogen the compounds of formula LXIX can be transformed into compounds of formula LXX by oxidation. This oxidation can be carried out with Dess-Martin-Periodinan (*J. Chem. Soc.* 1983, 48, 4156) or by Swern oxidation (*J. Org. Chem.* 1976, 41, 957). Alternatively this transformation can be performed by reaction with $RuCl_3$ or tetrapropylammonium perrhutenate in the presence of N-methylmorpholin-N-oxide in acetonitrile or dichlormethane, or by an oxidation catalysed by 2,2,6,6-tetramethyl-piperidin-1-oxyl (TEMPO) in the presence of iodine and a base as for example sodium bicarbonate in a solvent such as e.g. dichloromethane, tetrahydrofurane, 1,4-dioxane, benzene or toluene but preferably in toluene optionally as a mixture with water, at temperatures between −30° C. and 80° C. but preferably between 0° C. and 40° C. An alkylation reaction of compounds of formula LXX with a suitable alkyl metal compound, such as e.g. alkylmagnesium halogenide-, or alkyllithium-reagent, in a suitable solvent such as e.g. n-hexane, cyclohexane, toluene, diethylether, tetrahydrofurane or 1,4-dioxane, at temperatures between −80° C. and 60° C., gives the corresponding compounds of formula LXIX, wherein $R^2$ denotes alkyl and $R^2$ denotes hydrogen.

Further oxidation of thus formed compounds of formula LXIX gives ketones of formula LXX wherein $R^{2'}$ denotes alkyl. This oxidation can be carried out with Dess-Martin-Periodinan (*J. Chem. Soc.* 1983, 48, 4156) or by Swern oxidation (*J. Org. Chem.* 1976, 41, 957). Alternatively this transformation can be performed by reaction with $RuCl_3$ or tetrapropylammonium perrhutenate in the presence of N-methylmorpholin-N-oxide in acetonitrile or dichlormethane, or by an oxidation catalysed by 2,2,6,6-tetramethyl-piperidin-1-oxyl (TEMPO) in the presence of iodine and a base as for example sodium bicarbonate in a solvent such as e.g. dichloromethane, tetrahydrofurane, 1,4-dioxane, benzene or toluene but preferably in toluene optionally as a mixture with water, at temperatures between −30° C. and 80° C. but preferably between 0° C. and 40° C. Another alkylation reaction of compounds of formula LXX with a suitable alkyl metal compound, such as e.g. alkylmagnesium halogenide-, or alkyllithium-reagent, in a suitable solvent such as e.g. n-hexane, cyclohexane, toluene, diethylether, tetrahydrofurane or 1,4-dioxane, at temperatures between −80° C. and 60° C., gives the corresponding compounds of formula LXIX, wherein $R^{2'}$ and $R^{2'''}$ denotes alkyl. Deprotonation of the alcohols of formula LXIX with a suitable base such as e.g. sodium hydride, sodium tert.-butoxide or potassium tert.-butoxide in a suitable solvent such as e.g. N,N-dimethylformamide, acetonitrile, dimethylsulfoxide, 1,4-dioxane or tetrahydrofurane and subsequent alkylation with a suitable alkylating reagent such as e.g. an alkyl halogenide, methanesulfonic acid-alkyl-ester, p-toluenesulfonic acid-alkyl-ester or trifluoromethanesulfonic acid-alkyl-ester, but preferably methyl iodide, at temperatures between −10° C. and 60° C. gives compounds of formula XIII, in which the carbon of $R^2$, which is linked to the pyridine, carries an alkoxy group.

Carbonyl compounds of formula LXX can also be formed by reacting compounds of formula LXVII with ozone in a suitable solvent such as e.g. dichloromethane at temperatures between −80° C. and −40° C. and subsequent treatment with a suitable reducing agent such as e.g. triphenylphosphine or dimethylsulfide at temperatures between −80° C. and room temperature. These compounds of formula LXX can then be converted into compounds of formula LXIX as described above.

Alternatively compounds of formula LXV can be converted into compounds of formula LXXI, wherein $R^c$ denotes a methyl- or ethyl-substituent, via carbonylation at a suitable pressure of carbon monoxide such as e.g. 20 bar in a suitable solvent such as e.g. methanol, ethanol or mixtures of methanol or ethanol with N,N-dimethylformamide in the presence of a suitable catalyst such as e.g. bis-tri-tert.-butylphosphine-palladium-(0), 1,1'-bis-(diphenylphosphino)-ferrocene-dichloro-palladium-(II), bis-[1,2-bis-(diphenylphosphino)-ethane]-palladium-(0) at temperatures between room temperature and 120° C., but preferably at 100° C. The ester group in compounds of formula LXXI is then reduced to the hydroxymethyl group in compounds of formula LXIX. This reduction is performed by reaction with a suitable reducing agent, such as e.g. diisobutylamuminium hydride or lithiumaluminiumhydride in an aprotic solvent such as e.g. dichloromethane, tetrahydrofurane, 1,4-dioxane or toluene, at temperatures between −78° C. and 100° C., but preferably between −30° C. and 50° C. The compounds of formula LXIX can then be converted into compounds of formula XIII or LXX as described above.

Starting compounds of formulae II, III, XXIII, XXIV, XXVII, XXXI, XXXII, XLVI and XLVII are known or can be obtained analogously or similarly to known procedures. Compounds of formula III can for example be prepared from their corresponding cyclohexan-1,3-diones analogous as described in *Synthesis* 1983, 902-903. The cyclohexandiones can be prepared analogous to the described procedure in *Angew. Chem.* 1999, 111, 3574-3576.

Besides the strategies presented a host of additional approaches can be envisaged. Therefore, the preceding strategies are in no way meant to restrict the possible synthetic pathways to access the compounds of the invention but are only supposed to show a few routes by way of example.

Besides the hereinbefore described methods for the synthesis of compounds of formula I, additional functional group transformations, which are known to the person skilled in the art, at any stage of the synthesis can be envisaged, if these transformations are compatible to other functional groups and if the so installed functional groups are stable to subsequent transformations in the synthesis.

For example aromatic hydroxy groups can be converted into aromatic sulfonyloxy groups such as methylsulfonyloxy, tosylsulfonyloxy or trifluoromethylsulfonyloxy. This transformation is performed by reacting compounds with aromatic hydroxy group with a sulfonyl anhydride, sulfonylchloride or sulfonylimide in a solvent such as e.g. dichloromethane, 1,2-dichloroethane, diethylether, tetrahydrofurane, 1,4-dioxane, acetonitrile or toluene at temperatures between −78° C. and 40° C., in the presence of a base such as e.g. triethylamine, N,N-diisopropyl-N-ethyl-amine, pyridine or 2,6-lutidine, optionally in the presence of an acylation catalyst as 4-dimethylamino-pyridine (DMAP).

These aromatic sulfonyloxy groups can be further transformed into alkenyl groups or optionally substituted cyclopropyl groups by reacting the compounds with aromatic sulfonyloxy groups with potassium alkenyltrifluoroborates, alkenyl-boronic acids, alkenyl-boronic acid pinacol esters, optionally substituted cyclopropyl-boronic acids or optionally substituted cyclopropyl-boronic acid pinacol esters in toluene, N,N-dimethylformamide, isopropanol, acetonitrile, 1,4-dioxane or tetrahydrofurane or mixtures of toluene and tetrahydrofurane in the presence of a base as such as e.g. aqueous sodium carbonate, aqueous potassium carbonate, aqueous caesium carbonate, silver carbonate, caesium fluoride, triethylamine or N,N-diisopropyl-N-ethyl-amine and in the presence of a catalyst such as e.g. tetrakis-triphenylphosphine-palladium-(0), bis-tri-tert.-butylphosphine-palladium-(0), 1,1'-bis-(diphenylphosphino)-ferrocene-dichloro-palladium-(II) or bis-[1,2-bis-(diphenylphosphino)-ethane]-palladium-(0), or in the presence of a palladium source such as e.g. palladium diacetate or tris-(dibenzylideneacetone)-dipalladium-(0) and a suitable ligand like e.g. tri-tert.-butylphosphine, tri-cyclohexylphosphine, di-adamantan-1-yl-butylphosphine, 2-dicyclohexylphosphino-2',6'-diisopropoxy-1,1'biphenyl, 2-dicyclohexylphosphino-2',4',6'-triisopropyl-1,1'-biphenyl or 2-dicyclohexylphosphino-2',6'-dimethoxy-1,1'-biphenyl at temperatures between 0° C. and 180° C., but preferably between room temperature and 120° C. Alkenyl groups can be transformed into an optionally substituted cyclopropyl group by a Simmons-Smith reaction. This reaction is performed by reacting with bromo-iodomethane or diiodomethane and diethylzinc, optionally in the presence of trifluoroacetic acid, in a solvent such as e.g. dichloromethane, 1,2-dichloroethane, diethylether, tetrahydrofurane, 1,4-dioxane or toluene at temperatures between −50° C. and 80° C., but preferably between −10° C. and room temperature.

Alkoxycarbonyl groups can be transformed into dialkyl-methanol groups. This transformation is performed by reacting with an alkyllithium reagent or with an alkyl-Grignard reagent in a solvent such as e.g. diethylether, tetrahydrofurane, 1,4-dioxane or toluene at temperatures between −50° C. and 80° C., but preferably between −20° C. and room temperature. Alternatively alkoxycarbonyl groups, can be transformed into compounds hydroxymethyl groups. This transformation is performed by reacting with a reducing reagent such as e.g. lithiumaluminium hydride in a solvent like diethylether, tetrahydrofurane, 1,4-dioxane or toluene at temperatures between −50° C. and 80° C., but preferably between −20° C. and 40° C. Hydroxy groups can be further transformed into alkoxy groups by alkylation. This transformation is performed by reacting with an alkylating agent such as e.g. an alkyl halogenide, methanesulfonic acid-alkyl-ester, p-toluenesulfonic acid-alkyl-ester or trifluoromethanesulfonic acid-alkyl-ester in the presence of a base such as e.g. sodium hydride, potassium hydride, sodium hexamethyldisilazide or potassium hexamethyldisilazide in a solvent such as e.g. diethylether, tetrahydrofurane, 1,4-dioxane, N,N-dimethylformamide, acetonitrile or toluene at temperatures between −50° C. and 80° C., but preferably between −20° C. and 50° C.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3rd Ed.) or in "Protecting Groups (Thieme Foundations Organic Chemistry Series N Group" by P. Kocienski (Thieme Medical Publishers, 2000).

In the reactions described hereinbefore, any reactive groups present such as carboxy-, carbonyl-, hydroxy-, amino-, alkylamino- or imino-groups may be protected during the reaction by conventional protecting groups which are cleaved again after the reaction.

For example, a protecting group for a carboxy group may be the methyl-, ethyl-, tert.-butyl- or benzyl-group.

For example, a protecting group for a carbonyl group may be an acetal or ketal like the 1,3-dioxolane- or the 1,3-dioxane-group.

For example, a protecting group for a hydroxy group may be a trimethylsilyl-, tert.-butyldimethylsilyl-, acetyl-, trityl-, benzyl- or tetrahydropyranyl-group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

The cleavage of a carboxymethyl- or a carboxyethyl-group can for example be carried out hydrolytically in an aqueous solvent, e.g. in water, methanol/water, isopropanol/water, acetic acid/water, tetrahydrofuran/water or 1,4-dioxane/water, in the presence of an acid such as trifluoroacetic acid, hydrochloric acid or sulphuric acid or in the presence of an alkali base as for example lithium hydroxide, sodium hydroxide or potassium hydroxide, but preferably sodium hydroxide, or aprotically in the presence of e.g. iodotrimethylsilane, at temperatures between 0 and 120° C., preferably at temperatures between 10 and 100° C.

An acetal or ketal can be cleaved with acetic acid, trifluoroacetic acid, hydrochloric acid, sulphuric acid or pyridiumium-p-toluene sulfonate in mixtures with water or in organic solvents like for example dichloromethane, 1,2-dichloroethane, tetrahydrofurane, 1,4-dioxane, toluene or acetone at temperatures between −20° C. and 150° C., but preferably between 0° C. and 120° C.

A benzyl, methoxybenzyl or benzyloxycarbonyl group is advantageously cleaved hydrogenolytically, e.g. with hydrogen in the presence of a catalyst such as palladium/charcoal in a suitable solvent such as methanol, ethanol, ethyl acetatetetrahydrofurane, 1,4-dioxane or glacial acetic acid, optionally with the addition of an acid such as hydrochloric acid or with the addition of a base such as triethylamine at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as dichloromethane, 1,4-dioxane, methanol or diethylether.

A trimethylsilyl- or tert.-butyldimethylsilyl-group is cleaved with a fluoride reagent like for example tetrabutylammonium fluoride or caesium fluoride or with an acid like for example trifluoroacetic acid, hydrochloric acid or sulphuric acid in a solvent like e.g. dichloromethane, 1,2-dichloroethane, diethylether, tetrahydrofurane, 1,4-dioxane, acetonitrile or toluene at temperatures between −50° C. and 120° C., but preferably between −20° C. and 80° C.

The present invention also relates to intermediates (including their salts, stereoisomers and salts of these stereoisomers), methods and processes which are disclosed herein and which are useful in synthesizing final compounds according to this invention. Thus, the present invention also relates to processes disclosed herein for preparing compounds according to this invention, which processes may be performed as described herein. Said processes may comprise one or more steps of converting and/or reacting the mentioned intermediates with the appropriate reaction partners, suitably under conditions as disclosed herein.

Moreover, the compounds of general formula I or intermediates in the synthesis of compounds of general formula I obtained may be resolved into their enantiomers and/or diastereomers, as mentioned hereinbefore. Thus, for example, cis/trans mixtures may be resolved into their cis and trans isomers, and racemic compounds may be separated into their enantiomers.

Thus, for example, the cis/trans mixtures may be resolved by chromatography into the cis and trans isomers thereof. The compounds of general formula I or intermediates in the synthesis of compounds of general formula I, which occur as racemates may be separated by methods known per se (cf. Allinger N. L. and Eliel E. L. in "Topics in Stereochemistry", Vol. 6, Wiley Interscience, 1971) into their optical antipodes and compounds of general formula I or intermediates in the synthesis of compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoluoyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-methyloxycarbonyl.

Moreover, the compounds of formula I may be converted into the salts thereof, particularly for pharmaceutical use into the pharmaceutically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid. Corresponding processes are known for the skilled person.

When one of the final steps (e.g. removing an acid- or base-labile protecting group from a suitable precursor) or purification is carried out under the presence of an inorganic or organic acid (e.g. hydrochloric, trifluoroacetic, acetic or formic acid or the like) or a base, the compounds of formula I may be obtained—depending on their individual chemical nature and the individual nature of the acid or base used—as free compound or containing said acid or base in an stoechiometric or non-stoechiometric quantity (e.g. as a salt). The acid/base contained can be analyzed according to art-known procedures, e.g. by titration or NMR, and, optionally, removed according to procedures familiar to the skilled person.

Optionally, salts of the compounds of the formula I may be converted into the free compounds. Corresponding processes are known to the skilled person, e.g. via neutralization.

Salts can be obtained by combining or reacting the free compounds with the desired acids or bases, e.g. by dissolving or suspending the free compound in a suitable solvent (e.g. a ketone, such as acetone, methyl ethyl ketone or methyl isobutyl ketone, an ether, such as diethyl ether, diisopropyl ether, tetrahydrofuran or 1,4-dioxane, a chlorinated hydrocarbon, such as methylene chloride or chloroform, a low-molecular-weight aliphatic alcohol, such as methanol, ethanol or isopropanol, or an ester, such as ethyl acetate, or water, or a mixture thereof) which contains the desired acid or base, or to which the desired acid or base is then added. The salts can be obtained by filtering, reprecipitating, precipitating with a nonsolvent for the addition salt or by evaporating the solvent. Salts obtained can be converted to another, e.g. by reaction with an appropriate acid or base or by means of a suitable ion exchanger. Likewise, salts obtained can be converted into the free compounds, which can in turn be converted into salts, by alkalization or by acidification. In this manner, pharmaceutically unacceptable salts can be converted into pharmaceutically acceptable salts.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

The compounds according to the invention are advantageously obtainable using the methods described in the examples that follow, which may also be combined for this purpose with methods known to the skilled person from his/her expert knowledge. Likewise, further compounds according to this invention, whose preparation are not explicitly described in the following examples, can be prepared analogously or similarly to the examples.

Any or all of the compounds according to the present invention which are mentioned as final compounds in the following examples, including the salts, stereoisomers and salts of the stereoisomers thereof, are a particularly interesting subject within the present invention.

Other features and advantages of the present invention will become apparent from the following examples. The following examples serve to illustrate, by way of example, the principles of the invention without restricting it.

EXAMPLES

The following examples serve to further explain the invention without restricting it.

The hereinafter described compounds have been characterized through their characteristic mass after ionisation in a mass-spectrometer, their $R_f$-Value on thin-layer-chromatography plate and/or their retention time on an analytical HPLC.

HPLC Methods:

Method 1: Column: Agilent Zorbax Bonus RP, 50×2.1 mm, 3.5 µm; 1.2 ml/min; UV-Detection: DAD 190-400 nm; Eluent A: Water (0.1% Formic acid), Eluent B: Acetonitrile (0.1% Formic acid)

| Gradient: | |
|---|---|
| Time (min.) | % Eluent B |
| 0.00 | 10 |
| 4.50 | 99 |
| 5.00 | 99 |
| 5.50 | 10 |

Method 2: Column: Agilent Zorbax Bonus RP, 50×2.1 mm, 3.5 µm; 1.2 ml/min; UV-Detection: DAD 190-400 nm; Eluent A: Water (0.1% Formic acid), Eluent B: Acetonitrile (0.1% Formic acid)

| Gradient: | |
|---|---|
| Time (min.) | % Eluent B |
| 0.00 | 10 |
| 1.00 | 75 |
| 1.30 | 75 |
| 2.30 | 99 |
| 4.40 | 99 |
| 5.00 | 10 |

Method 3: Column: Sunfire C18, 30×4.6 mm, 2.5 µm; 3.25 ml/min; UV-Detection: DAD 190-400 nm; Eluent A: Water (0.1% trifluoroacetic acid), Eluent B: Methanol

| Gradient: | |
|---|---|
| Time (min.) | % Eluent B |
| 0.00 | 10 |
| 1.60 | 100 |
| 1.80 | 100 |
| 1.95 | 10 |
| 2.15 | 10 |

Method 4: Column: Merck Chromolith Flash RP18e, 25×4.6 mm, 2 µm, 1.6 ml/min; UV-Detection: 230 nm/254 nm; Eluent A: Water (0.1% Formic acid), Eluent B: Methanol

| Gradient: | |
|---|---|
| Time (min.) | % Eluent B |
| 0.00 | 10 |
| 2.00 | 90 |
| 5.00 | 90 |
| 5.50 | 100 |

Method 5: Column: Merck Chromolith Flash RP18e, 25×4.6 mm, 2 µm, 2.5 ml/min; UV-Detection: 230 nm/254 nm; Eluent A: Water (0.1% Formic acid), Eluent B: Methanol

| Gradient: | |
|---|---|
| Time (min.) | % Eluent B |
| 0.00 | 10 |
| 1.61 | 100 |
| 2.25 | 100 |

Method 6: Column: Merck Chromolith Flash RP18e, 25×4.6 mm, 2 µm, 2.5 ml/min; UV-Detection: 230 nm/254 nm; Eluent A: Water (0.1% Formic acid), Eluent B: Methanol

| Gradient: | |
|---|---|
| Time (min.) | % Eluent B |
| 0.00 | 10 |
| 1.25 | 90 |
| 3.13 | 90 |
| 3.45 | 100 |
| 3.82 | 100 |

Method 7: Column: Agilent Stable Bond SB-C18, 30×4.6 mm, 1.8 µm; 3 ml/min; UV-Detection: DAD 190-400 nm; Eluent A: Water (0.1% Trifluoacetic acid), Eluent B: Methanol

| Gradient: | |
|---|---|
| Time (min.) | % Eluent B |
| 0.00 | 10 |
| 1.80 | 100 |
| 2.00 | 100 |
| 2.15 | 10 |
| 2.35 | 10 |

Method 8: Column: Gemini C18, 50×4.6 mm, 3 µm; 1.3 ml/min; UV-Detection: 254 nm; Eluent A: Water/Acetonitrile 9:1 (0.1% Trifluoacetic acid), Eluent B: Acetonitrile

| Gradient: | |
|---|---|
| Time (min.) | % Eluent B |
| 0.00 | 50 |
| 3.50 | 90 |
| 4.50 | 90 |

Method 9: Column: BEH C18, 50×2.1 mm, 1.7 µm; 0.85 ml/min; UV-Detection: 254 nm; Eluent A: Water/Acetonitrile 9:1 (0.1% Trifluoacetic acid), Eluent B: Acetonitrile

| Gradient: | |
|---|---|
| Time (min.) | % Eluent B |
| 0.00 | 50 |
| 1.20 | 90 |
| 1.66 | 50 |

Method 10: Column: Synergi 4u Hydro-RP, 100×4.6 mm, 4 µm; 1.2 ml/min; UV-Detection: 254 nm; Eluent A: Water/

Acetonitrile 9:1 (10 mM NH$_4$COOH), Eluent B: Water/Acetonitrile 1:9 (10 mM NH$_4$COOH)

Gradient:

| Time (min.) | % Eluent B |
|---|---|
| 0.00 | 0 |
| 1.50 | 0 |
| 11.00 | 100 |
| 28.00 | 100 |

Method 11: Column: Symmetry Shield RP8, 150×4.6 mm, 5 µm; 0.85 ml/min; UV-Detection: 254 nm; Eluent A: Water/Acetonitrile 9:1 (0.1% Formic acid), Eluent B: Water/Acetonitrile 1:9 (0.1% Formic acid)

Gradient:

| Time (min.) | % Eluent B |
|---|---|
| 0.00 | 30 |
| 1.50 | 50 |
| 8.50 | 100 |
| 18.00 | 100 |

Method 12: Column: Symmetry Shield RP8, 150×4.6 mm, 5 µm; 0.85 ml/min; UV-Detection: 254 nm; Eluent A: Water/Acetonitrile 9:1 (0.1% Formic acid), Eluent B: Water/Acetonitrile 1:9 (0.1% Formic acid)

Gradient:

| Time (min.) | % Eluent B |
|---|---|
| 0.00 | 30 |
| 1.50 | 50 |
| 8.50 | 100 |
| 13.50 | 100 |

Method 13: Column: Gemini C18, 50×4.6 mm, 3 µm; 1.3 ml/min; UV-Detection: 254 nm; Eluent A: Water/Acetonitrile 9:1 (0.1% Trifluoacetic acid), Eluent B: Acetonitrile Gradient:

| Time (min.) | % Eluent B |
|---|---|
| 0.00 | 30 |
| 3.50 | 90 |
| 4.50 | 90 |

Method 14: Column: Symmetry Shield RP8, 150×4.6 mm, 5 µm; 1.0 ml/min; UV-Detection: 254 nm; Eluent A: Water/Acetonitrile 9:1 (0.1% Formic acid), Eluent B: Water/Acetonitrile 1:9 (0.1% Formic acid)

Gradient:

| Time (min.) | % Eluent B |
|---|---|
| 0.00 | 5 |
| 1.50 | 5 |
| 11.50 | 95 |
| 13.00 | 95 |

Method 15: Column: Atlantis dC18, 50×4.6 mm, 5 µm; 1.3 ml/min; UV-Detection: 254 nm; Eluent A: Water/Acetonitrile 9:1 (0.1% Trifluoacetic acid), Eluent B: Acetonitrile Gradient:

| Time (min.) | % Eluent B |
|---|---|
| 0.00 | 10 |
| 3.50 | 90 |
| 4.50 | 90 |

Method 16: Column: Synergi Hydro RP80A, 100×4.6 mm, 4 µm; 1.2 ml/min; UV-Detection: 254 nm; Eluent A: Water/Acetonitrile 9:1 (10 mM NH$_4$COOH), Eluent B: Water/Acetonitrile 1:9 (10 mM NH$_4$COOH)

Gradient:

| Time (min.) | % Eluent B |
|---|---|
| 0.00 | 0 |
| 1.50 | 0 |
| 11.50 | 100 |
| 24.50 | 100 |

Method 17: Column: Symmetry Shield RP8, 150×4.6 mm, 5 µm; 0.85 ml/min; UV-Detection: 254 nm; Eluent A: Water/Acetonitrile 9:1 (0.1% Formic acid), Eluent B: Water/Acetonitrile 1:9 (0.1% Formic acid)

Gradient:

| Time (min.) | % Eluent B |
|---|---|
| 0.00 | 30 |
| 1.50 | 50 |
| 8.50 | 100 |
| 18.00 | 100 |

Method 18: Column: Gemini C18, 50×4.6 mm, 3 µm; 1.3 ml/min; UV-Detection: 254 nm; Eluent A: Water/Acetonitrile 9:1 (0.1% Trifluoacetic acid), Eluent B: Acetonitrile Gradient:

| Time (min.) | % Eluent B |
|---|---|
| 0.00 | 70 |
| 3.50 | 90 |
| 4.50 | 90 |

Method 19: Column: Varian Microsorb 100 C18, 30×4.6 mm, UV-Detection: 210-380 nm; Eluent A: Water (0.15% Trifluoacetic acid), Eluent B: Acetonitrile Gradient:

| Time (min.) | % Eluent B | Flow ml/min. |
|---|---|---|
| 0.00 | 5 | 3.5 |
| 0.18 | 5 | 3.5 |
| 2.00 | 98 | 3.5 |
| 2.20 | 98 | 3.5 |
| 2.30 | 5 | 3.5 |
| 2.50 | 5 | 3.5 |
| 2.60 | 5 | 0.5 |

Method 20: Column: Varian Microsorb 100 C18, 30×4.6 mm, UV-Detection: 210-380 nm; Eluent A: Water (0.13% Trifluoacetic acid), Eluent B: Methanol

| Gradient: | | |
| --- | --- | --- |
| Time (min.) | % Eluent B | Flow ml/min. |
| 0.00 | 5 | 2.4 |
| 0.35 | 5 | 2.4 |
| 3.95 | 100 | 2.4 |
| 4.45 | 100 | 2.4 |
| 4.55 | 5 | 2.4 |
| 4.90 | 5 | 2.4 |
| 5.00 | 5 | 0.1 |

Method 21: Column: Varian Microsorb 100 C18, 30×4.6 mm, UV-Detection: 210-380 nm; Eluent A: Water (0.13% Trifluoacetic acid), Eluent B: Acetonitrile

| Gradient: | | |
| --- | --- | --- |
| Time (min.) | % Eluent B | Flow ml/min. |
| 0.00 | 5 | 3.5 |
| 0.18 | 5 | 3.5 |
| 2.00 | 98 | 3.5 |
| 3.00 | 98 | 3.5 |
| 3.10 | 5 | 3.5 |
| 3.30 | 5 | 3.5 |
| 3.50 | 5 | 0.1 |

Method 22: Column: Varian Microsorb 100 C18, 30×4.6 mm, UV-Detection: 210-380 nm; Eluent A: Water (0.13% Trifluoacetic acid), Eluent B: Methanol

| Gradient: | | |
| --- | --- | --- |
| Time (min.) | % Eluent B | Flow ml/min. |
| 0.00 | 5 | 4.8 |
| 0.15 | 5 | 4.8 |
| 2.55 | 100 | 4.8 |
| 2.70 | 100 | 4.8 |
| 2.80 | 5 | 4.8 |
| 2.95 | 5 | 4.8 |
| 3.05 | 5 | 0.1 |

Method 23: Column: Xbridge BEH C18, 30×2.1 mm, UV-Detection: 210-498 nm; Eluent A: Water (0.1% Ammonia), Eluent B: Methanol (0.1% Ammonia)

| Gradient: | | |
| --- | --- | --- |
| Time (min.) | % Eluent B | Flow ml/min. |
| 0.00 | 5 | 0.8 |
| 0.10 | 5 | 0.8 |
| 0.60 | 100 | 1.0 |
| 0.79 | 100 | 1.0 |
| 0.80 | 5 | 0.8 |
| 1.00 | 5 | 0.8 |

Method 24: Column: Waters Xbridge Phenyl, 30×3.0 mm, 2.5 µm; 1.75 ml/min; UV-Detection: 190-400 nm; Temperature: 50° C.; Eluent A: Water (0.1% Trifluoroacetic acid), Eluent B: Methanol

| Gradient: | |
| --- | --- |
| Time (min.) | % Eluent B |
| 0.00 | 10 |
| 1.70 | 100 |
| 1.90 | 100 |
| 2.05 | 10 |
| 2.20 | 10 |

Method 25: Column: Merck Chromolith Speed ROD; RP18e, 50×4.6 mm, 1.5 ml/min; UV-Detection: 190-400 nm; Eluent A: Water (0.1% Formic acid), Eluent B: Acetonitrile (0.1% Formic acid)

| Gradient: | |
| --- | --- |
| Time (min.) | % Eluent B |
| 0.00 | 10 |
| 4.50 | 90 |
| 5.00 | 90 |
| 5.50 | 10 |

Method 26: Column: Waters SunFire C18, 30×4.6 mm, 3.5 µm, 4 ml/min; UV-Detection: 190-400 nm; Eluent A: Water (0.1% Trifluoroacetic acid), Eluent B: Methanol (0.1% Trifluoroacetic acid)

| Gradient: | |
| --- | --- |
| Time (min.) | % Eluent B |
| 0.00 | 5 |
| 0.20 | 5 |
| 1.50 | 100 |
| 1.75 | 100 |
| 1.85 | 5 |

Method 27: Column: Waters XBridge C18, 30×4.6 mm, 3.5 µm, 4 ml/min; UV-Detection: 190-400 nm; Eluent A: Water (0.1% Trifluoroacetic acid), Eluent B: Methanol (0.1% Trifluoroacetic acid)

| Gradient: | |
| --- | --- |
| Time (min.) | % Eluent B |
| 0.00 | 5 |
| 0.20 | 5 |
| 1.50 | 100 |
| 1.90 | 100 |
| 2.00 | 5 |

Method 28: Column: Waters XBridge C18, 30×3.0 mm, 2.5 µm, 2.2 ml/min; UV-Detection: 190-400 nm; Eluent A: Water (0.2% Trifluoroacetic acid), Eluent B: Methanol Gradient:

| Time (min.) | % Eluent B |
|---|---|
| 0.00 | 5 |
| 0.05 | 5 |
| 1.40 | 100 |
| 1.80 | 100 |

Method 29: Column: Waters XBridge C18, 30×3.0 mm, 2.5 µm, 2.2 ml/min; UV-Detection: 190-400 nm; Eluent A: Water (0.2% Ammonia), Eluent B: Methanol Gradient:

| Time (min.) | % Eluent B |
|---|---|
| 0.00 | 5 |
| 0.05 | 5 |
| 1.40 | 100 |
| 1.80 | 100 |

Method 30: Column: HSS C18, 50×2.1 mm, 1.8 µm, 0.7 ml/min; UV-Detection: 254 nm; Eluent A: Water/acetonitrile/trifluoroacetic acid 90:10:0.1, Eluent B: Acetonitrile/water 90:10

Gradient:

| Time (min.) | % Eluent B |
|---|---|
| 0.00 | 0 |
| 0.70 | 100 |
| 2.30 | 100 |
| 2.40 | 0 |
| 2.60 | 0 |

Method 31: Column: HSS C18, 50×2.1 mm, 1.8 µm, 0.7 ml/min; UV-Detection: 254 nm; Eluent A: Water/acetonitrile/trifluoroacetic acid 90:10:0.1, Eluent B: Acetonitrile/water 90:10

Gradient:

| Time (min.) | % Eluent B |
|---|---|
| 0.00 | 0 |
| 1.20 | 100 |
| 1.45 | 100 |
| 1.55 | 0 |
| 1.75 | 0 |

Method 32: Column: Xbridge C8, 30×4.6 mm, 3.5 µm, 4.0 ml/min; UV-Detection: 190-400 nm; Eluent A: Water (0.1% formic acid), Eluent B: Methanol Gradient:

| Time (min.) | % Eluent B |
|---|---|
| 0.00 | 30 |
| 0.05 | 30 |
| 1.50 | 100 |
| 1.55 | 100 |
| 2.40 | 100 |

Method 33: Column: Xbridge C18, 30×4.6 mm, 3.5 µm, 4.0 ml/min; UV-Detection: 190-400 nm; Eluent A: Water (0.1% formic acid), Eluent B: Methanol Gradient:

| Time (min.) | % Eluent B |
|---|---|
| 0.00 | 5 |
| 0.15 | 5 |
| 1.70 | 100 |
| 2.25 | 100 |

Method 34: Column: StableBond C18, 30×3.0 mm, 1.8 µm; UV-Detection: 190-400 nm; Eluent A: Water (0.1% trifluoroacetic acid), Eluent B: Acetonitrile Gradient:

| Time (min.) | % Eluent B | Flow [ml/minute] |
|---|---|---|
| 0.00 | 5 | 1.9 |
| 0.20 | 5 | 1.9 |
| 1.55 | 100 | 1.9 |
| 1.60 | 100 | 2.40 |
| 1.75 | 100 | 2.40 |

Method 35: Column: Xbridge C18, 30×4.6 mm, 3.5 µm, 4.0 ml/min; UV-Detection: 190-400 nm; Eluent A: Water (0.1% trifluoroacetic acid), Eluent B: Methanol (0.1 trifluoroacetic acid)

Gradient:

| Time (min.) | % Eluent B |
|---|---|
| 0.00 | 5 |
| 0.15 | 5 |
| 1.70 | 100 |
| 2.25 | 100 |

Method 36: Column: Merck Chromolith Flash RP18e, 25×4.6 mm, 2 µm, 1.6 ml/min; UV-Detection: 230 nm/254 nm; Eluent A: Water (0.1% Formic acid), Eluent B: Methanol Gradient:

| Time (min.) | % Eluent B |
|---|---|
| 0.00 | 10 |
| 2.50 | 100 |
| 3.50 | 100 |

Thin layer chromatography: Merck; TLC Silica gel 60 $F_{254}$

Preparation of the Starting Compounds

Example I

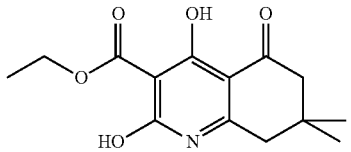 [SMILES: CCOC(=O)c1c(O)nc2c(c1O)C(=O)CC(C)(C)C2]

Ethyl 2,4-dihydroxy-7,7-dimethyl-5-oxo-5,6,7,8-tetrahydroquinoline-3-carboxylate 10 g 3-Amino-5,5-dimethyl-2-cyclohexen-1-one and 25 g 2-Ethoxycarbonyl-malonic acid diethyl ester are combined and heated for 10 minutes at 210° C. (bath temperature). Thereafter the mixture is cooled to room temperature and triturated with diethylether. The crystalline precipitate is collected by filtration and dried in vacuo.

Yield: 9.9 g (49% of theory)
Mass spectrometry (ESI$^+$): m/z=280 [M+H]$^+$
R$_f$-value: 0.45 (silica gel, dichloromethane/methanol 9:1)

Analogously to example I the following compounds are obtained:

(1) Ethyl 2',4'-dihydroxy-5'-oxo-6',8'-dihydro-5'H-spiro[cyclobutane-1,7'-quinoline]-3'-carboxylate

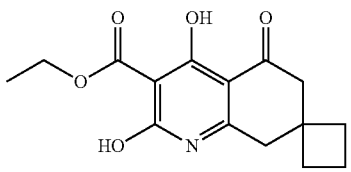 [SMILES: CCOC(=O)c1c(O)nc2c(c1O)C(=O)CC1(CCC1)C2]

Obtained by starting from 8-aminospiro[3.5]non-7-en-6-one.
Mass spectrometry (ESI$^+$): m/z=292 [M+H]$^+$
HPLC (Method 19): Retention time=1.15 min.

(2) Ethyl 2',4'-dihydroxy-5'-oxo-6',8'-dihydro-5'H-spiro[cyclopentane-1,7'-quinoline]-3'-carboxylate

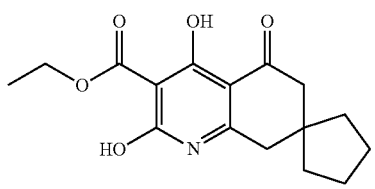

Obtained by starting from 9-aminospiro[4.5]dec-8-en-7-one.
Mass spectrometry (ESI$^+$): m/z=306 [M+H]$^+$
HPLC (Method 36): Retention time=2.30 min.

(3) Ethyl 2',4'-dihydroxy-5'-oxo-6',8'-dihydro-5'H-spiro[cyclobutane-1,7'-quinoline]-3'-carboxylate

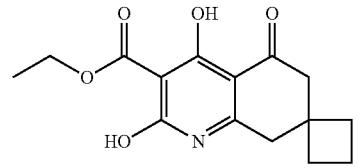

Obtained by starting from 8-aminospiro[3.5]non-7-en-6-one.
Mass spectrometry (ESI$^+$): m/z=292 [M+H]$^+$
HPLC (Method 7): Retention time=1.120 min.

Example II

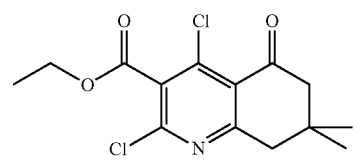 [SMILES: CCOC(=O)c1c(Cl)nc2c(c1O)C(=O)CC(C)(C)C2]

Ethyl 2,4-dichloro-7,7-dimethyl-5-oxo-5,6,7,8-tetrahydroquinoline-3-carboxylate 9.9 g Ethyl 2,4-dihydroxy-7,7-dimethyl-5-oxo-5,6,7,8-tetrahydroquinoline-3-carboxylate are suspended in 50 ml of phosphoroxychloride. After addition of some drops of N,N-dimethylformamide the mixture is heated to 80° C. for 12 hours. Then the phosphoroxychloride is evaporated in vacuo and the residue is dissolved in dichloromethane. After washing with water, saturated aqueous sodium bicarbonate solution and brine the solution is dried with magnesium sulphate. The solvent is evaporated in vacuo and the residue is chromatographed on silica gel cyclohexane/ethylacetate 90:10 to 50:50).

Yield: 6.95 g (62% of theory)
Mass spectrometry (ESI$^+$): m/z=316 [M+H]$^+$
R$_f$-value: 0.44 (silica gel, petrole ether/ethylacetate 4:1)

Example III

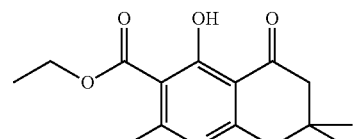

Ethyl 2-chloro-4-hydroxy-7,7-dimethyl-5-oxo-5,6,7,8-tetrahydroquinoline-3-carboxylate 8.35 g ethyl 2,4-dihydroxy-7,7-dimethyl-5-oxo-5,6,7,8-tetrahydroquinoline-3-carboxylate are suspended in 35 ml of phosphoroxychloride. After addition of some drops of N,N-dimethylformamide the mixture is heated to 45° C. for 12 hours. Then the phosphoroxychloride is evaporated in vacuo and the residue is dissolved in dichloromethane. After washing with water, saturated aqueous sodium bicarbonate solution and brine the solution is dried with magnesium sulphate. The solvent is evaporated in vacuo and the residue is chromatographed on silica gel (cyclohexane/ethylacetate 90:10 to 50:50).

Yield: 3.7 g (42% of theory)

Mass spectrometry (ESI$^+$): m/z=298 [M+H]$^+$ $R_f$-value: 0.37 (silica gel, petrole ether/ethylacetate 4:1)

Analogously to example III the following compounds are obtained:

(1) Ethyl 4-chloro-2-isopropyl-7,7-dimethyl-5-oxo-5,6,7,8-tetrahydroquinoline-3-carboxylate

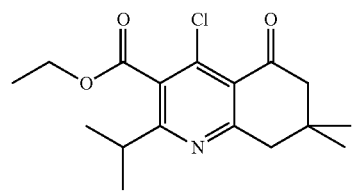 [SMILES: CCOC(=O)c1c(C(C)C)nc2c(c1Cl)C(=O)CC(C)(C)C2]

Obtained by starting from ethyl 4-hydroxy-2-isopropyl-7,7-dimethyl-5-oxo-5,6,7,8-tetrahydroquinoline-3-carboxylate and performing the reaction at 50° C. for 12 hours.

Mass spectrometry (ESI$^+$): m/z=324 [M+H]$^+$ $R_f$-value: 0.46 (silica gel, petrole ether/ethylacetate 4:1)

(2) Ethyl 4-chloro-7,7-dimethyl-5-oxo-2-(tetrahydro-2H-pyran-4-yl)-5,6,7,8-tetrahydroquinoline-3-carboxylate

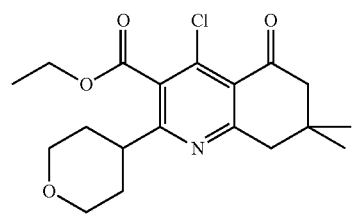 [SMILES: CCOC(=O)c1c(C2CCOCC2)nc2c(c1Cl)C(=O)CC(C)(C)C2]

Obtained by starting from ethyl 4-hydroxy-7,7-dimethyl-5-oxo-2-(tetrahydro-2H-pyran-4-yl)-5,6,7,8-tetrahydroquinoline-3-carboxylate and performing the reaction at 65° C. for 4 hours.

Mass spectrometry (ESI$^+$): m/z=366 [M+H]$^+$

HPLC (Method 1): Retention time=3.236 min.

(3) Ethyl 4-chloro-2-cyclopentyl-7,7-dimethyl-5-oxo-5,6,7,8-tetrahydroquinoline-3-carboxylate

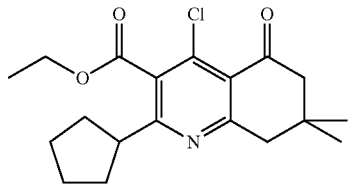 [SMILES: CCOC(=O)c1c(C2CCCC2)nc2c(c1Cl)C(=O)CC(C)(C)C2]

Obtained by starting from ethyl 2-cyclopentyl-4-hydroxy-7,7-dimethyl-5-oxo-5,6,7,8-tetrahydroquinoline-3-carboxylate and performing the reaction at 80° C. for 7 hours.

Mass spectrometry (ESI$^+$): m/z=350 [M+H]$^+$

HPLC (Method 19): Retention time=1.97 min.

(4) Ethyl 4'-chloro-2'-isopropyl-5'-oxo-6',8'-dihydro-5'H-spiro[cyclobutane-1,7'-quinoline]-3'-carboxylate

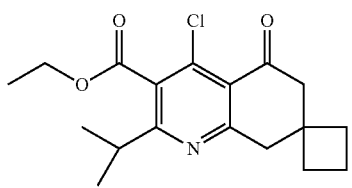 [SMILES: CCOC(=O)c1c(C(C)C)nc2c(c1Cl)C(=O)CC1(CCC1)C2]

Obtained by starting from ethyl 4'-hydroxy-2'-isopropyl-5'-oxo-6',8'-dihydro-5'H-spiro[cyclobutane-1,7'-quinoline]-3'-carboxylate and performing the reaction at 85° C. for 12 hours.

Mass spectrometry (ESI$^+$): m/z=336 [M+H]$^+$

HPLC (Method 20): Retention time=3.62 min.

(5) Ethyl 2'-chloro-4'-hydroxy-5'-oxo-6',8'-dihydro-5'H-spiro[cyclobutane-1,7'-quinoline]-3'-carboxylate

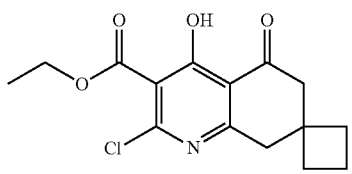 [SMILES: CCOC(=O)c1c(Cl)nc2c(c1O)C(=O)CC1(CCC1)C2]

Obtained by starting from ethyl 2',4'-dihydroxy-5'-oxo-6',8'-dihydro-5'H-spiro[cyclobutane-1,7'-quinoline]-3'-carboxylate and performing the reaction at 80° C. for 2 hours.

Mass spectrometry (ESI$^+$): m/z=310 [M+H]$^+$

HPLC (Method 20): Retention time=3.29 min.

(6) Ethyl 4-chloro-2-cyclobutyl-7,7-dimethyl-5-oxo-5,6,7,8-tetrahydroquinoline-3-carboxylate

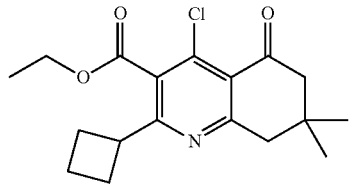 [SMILES: CCOC(=O)c1c(C2CCC2)nc2c(c1Cl)C(=O)CC(C)(C)C2]

Obtained by starting from ethyl 2-cyclobutyl-4-hydroxy-7,7-dimethyl-5-oxo-5,6,7,8-tetrahydroquinoline-3-carboxylate and performing the reaction at 85° C. for 12 hours.

Mass spectrometry (ESI+): m/z=336 [M+H]+

$R_f$-value: 0.52 (silica gel, cyclohexane/ethylacetate 9:1)

(7) Ethyl 4-chloro-2-ethyl-7,7-dimethyl-5-oxo-5,6,7,8-tetrahydroquinoline-3-carboxylate

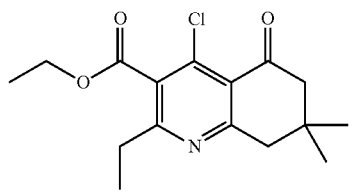

Obtained by starting from ethyl 2-ethyl-4-hydroxy-7,7-dimethyl-5-oxo-5,6,7,8-tetrahydroquinoline-3-carboxylate.

Mass spectrometry (ESI+): m/z=310 [M+H]+

HPLC (Method 20): Retention time=3.14 min.

(8) Ethyl 4'-chloro-2'-isopropyl-5'-oxo-6',8'-dihydro-5'H-spiro[cyclopentane-1,7'-quinoline]-3'-carboxylate

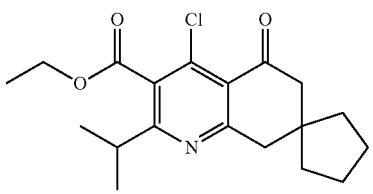 [SMILES: CCOC(=O)c1c(C(C)C)nc2c(c1Cl)C(=O)CC1(CCCC1)C2]

Obtained by starting from ethyl 4'-hydroxy-2'-isopropyl-5'-oxo-6',8'-dihydro-5'H-spiro[cyclopentane-1,7'-quinoline]-3'-carboxylate. The reaction is run at 85° C. for 3 hours Mass spectrometry (ESI+): m/z=350 [M+H]+

HPLC (Method 5): Retention time=1.78 min.

(9) Ethyl 2'-chloro-4'-hydroxy-5'-oxo-6',8'-dihydro-5'H-spiro[cyclopentane-1,7'-quinoline]-3'-carboxylate

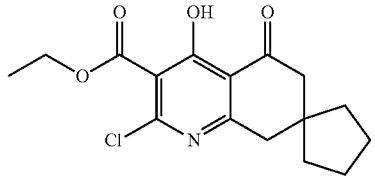 [SMILES: CCOC(=O)c1c(Cl)nc2c(c1O)C(=O)CC1(CCCC1)C2]

Obtained by starting from ethyl 2',4'-dihydroxy-5'-oxo-6',8'-dihydro-5'H-spiro[cyclopentane-1,7'-quinoline]-3'-carboxylate. The reaction is run at 90° C. for 70 minutes.

Mass spectrometry (ESI+): m/z=324 [M+H]+

HPLC (Method 36): Retention time=2.69 min.

(10) Ethyl 4'-chloro-5'-oxo-2'-(tetrahydro-2H-pyran-4-yl)-6',8'-dihydro-5'H-spiro[cyclobutane-1,7'-quinoline]-3'-carboxylate

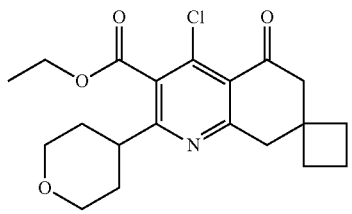 [SMILES: CCOC(=O)c1c(C2CCOCC2)nc2c(c1Cl)C(=O)CC1(CCC1)C2]

Obtained by starting from ethyl 4'-hydroxy-5'-oxo-2'-(tetrahydro-2H-pyran-4-yl)-6',8'-dihydro-5'H-spiro[cyclobutane-1,7'-quinoline]-3'-carboxylate. The reaction is run for 3 hours at 65° C. in acetonitrile as solvent.

Mass spectrometry (ESI+): m/z=378 [M+H]+

HPLC (Method 7): Retention time=1.577 min.

(11) Ethyl 2'-chloro-4'-hydroxy-5'-oxo-6',8'-dihydro-5'H-spiro[cyclobutane-1,7'-quinoline]-3'-carboxylate

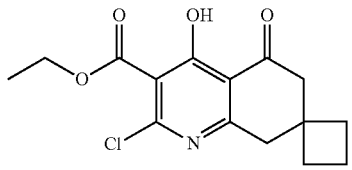 [SMILES: CCOC(=O)c1c(Cl)nc2c(c1O)C(=O)CC1(CCC1)C2]

Obtained by starting from ethyl 2',4'-dihydroxy-5'-oxo-6',8'-dihydro-5'H-spiro[cyclobutane-1,7'-quinoline]-3'-carboxylate. The reaction is run for 12 hours at 75° C. in acetonitrile as solvent.

Mass spectrometry (ESI+): m/z=310 [M+H]+

HPLC (Method 7): Retention time=1.498 min.

Example IV

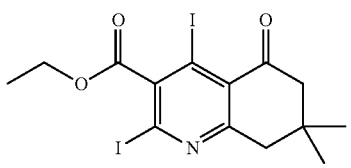 [SMILES: CCOC(=O)c1c(I)nc2c(c1I)C(=O)CC(C)(C)C2]

Ethyl 2,4-diiodo-7,7-dimethyl-5-oxo-5,6,7,8-tetrahydroquinoline-3-carboxylate 6.95 g Ethyl 2,4-dichloro-7,7-dimethyl-5-oxo-5,6,7,8-tetrahydroquinoline-3-carboxylate are dissolved in 100 ml acetonitrile and reacted with 10 g sodium iodide and 1.6 ml acetylchloride for 3 hours at 50° C. The mixture is diluted with diethylether and washed with saturated aqueous sodium bicarbonate solution, saturated aqueous sodium thiosulphate and brine. After drying with magnesium sulphate the solvents are evaporated in vacuo.

Yield: 10.3 g (94% of theory)
Mass spectrometry (ESI$^+$): m/z=500 [M+H]$^+$
HPLC (Method 1): Retention time=3.484 min.

Analogously to example IV the following compounds are obtained:

(1) Ethyl 4-iodo-2-isopropyl-7,7-dimethyl-5-oxo-5,6,7,8-tetrahydroquinoline-3-carboxylate

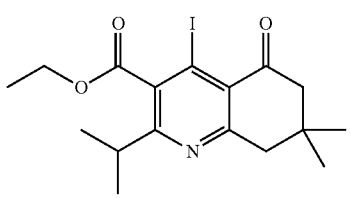 [SMILES: CCOC(=O)c1c(C(C)C)nc2c(c1I)C(=O)CC(C)(C)C2]

Obtained by starting from ethyl 4-chloro-2-isopropyl-7,7-dimethyl-5-oxo-5,6,7,8-tetrahydroquinoline-3-carboxylate.
Mass spectrometry (ESI$^+$): m/z=416 [M+H]$^+$
HPLC (Method 1): Retention time=3.722 min.

(2) Ethyl 4-iodo-7,7-dimethyl-5-oxo-2-(tetrahydro-2H-pyran-4-yl)-5,6,7,8-tetrahydroquinoline-3-carboxylate

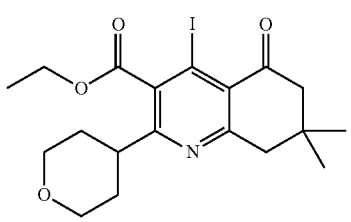 [SMILES: CCOC(=O)c1c(C2CCOCC2)nc2c(c1I)C(=O)CC(C)(C)C2]

Obtained by starting from ethyl 4-chloro-7,7-dimethyl-5-oxo-2-(tetrahydro-2H-pyran-4-yl)-5,6,7,8-tetrahydroquinoline-3-carboxylate.
Mass spectrometry (ESI$^+$): m/z=458 [M+H]$^+$
HPLC (Method 1): Retention time=3.340 min.

(3) Ethyl 2-cyclopentyl-4-iodo-7,7-dimethyl-5-oxo-5,6,7,8-tetrahydroquinoline-3-carboxylate

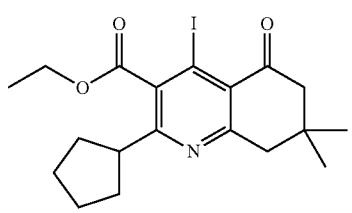

Obtained by starting from ethyl 4-chloro-2-cyclopentyl-7,7-dimethyl-5-oxo-5,6,7,8-tetrahydroquinoline-3-carboxylate.
Mass spectrometry (ESI$^+$): m/z=442 [M+H]$^+$
HPLC (Method 19): Retention time=2.01 min.

(4) Ethyl 4'-iodo-2'-isopropyl-5'-oxo-6',8'-dihydro-5'H-spiro[cyclobutane-1,7'-quinoline]-3'-carboxylate

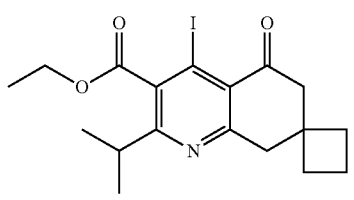 [SMILES: CCOC(=O)c1c(C(C)C)nc2c(c1I)C(=O)CC1(CCC1)C2]

Obtained by starting from ethyl 4'-chloro-2'-isopropyl-5'-oxo-6',8'-dihydro-5'H-spiro[cyclobutane-1,7'-quinoline]-3'-carboxylate.
Mass spectrometry (ESI$^+$): m/z=428 [M+H]$^+$
HPLC (Method 20): Retention time=3.62 min.

(5) Ethyl 2-cyclobutyl-4-iodo-7,7-dimethyl-5-oxo-5,6,7,8-tetrahydroquinoline-3-carboxylate

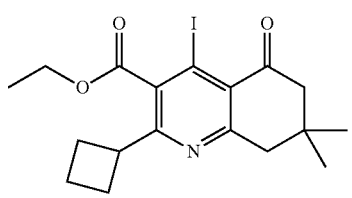 [SMILES: CCOC(=O)c1c(C2CCC2)nc2c(c1I)C(=O)CC(C)(C)C2]

Obtained by starting from ethyl 4-chloro-2-cyclobutyl-7,7-dimethyl-5-oxo-5,6,7,8-tetrahydroquinoline-3-carboxylate.
Mass spectrometry (ESI$^+$): m/z=428 [M+H]$^+$
$R_f$-value: 0.52 (silica gel, cyclohexane/ethylacetate 9:1)

(6) Ethyl 2-ethyl-4-iodo-7,7-dimethyl-5-oxo-5,6,7,8-tetrahydroquinoline-3-carboxylate

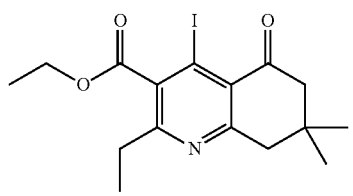 [SMILES: CCOC(=O)c1c(CC)nc2c(c1I)C(=O)CC(C)(C)C2]

Obtained by starting from ethyl 4-chloro-2-ethyl-7,7-dimethyl-5-oxo-5,6,7,8-tetrahydroquinoline-3-carboxylate.

Mass spectrometry (ESI$^+$): m/z=402 [M+H]$^+$

HPLC (Method 20): Retention time=3.18 min.

(7) Ethyl 4'-iodo-2'-isopropyl-5'-oxo-6',8'-dihydro-5'H-spiro[cyclopentane-1,7'-quinoline]-3'-carboxylate

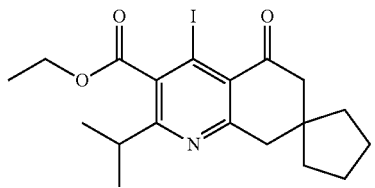 [SMILES: CCOC(=O)c1c(C(C)C)nc2c(c1I)C(=O)CC1(CCCC1)C2]

Obtained by starting from ethyl 4'-chloro-2'-isopropyl-5'-oxo-6',8'-dihydro-5'H-spiro[cyclopentane-1,7'-quinoline]-3'-carboxylate.

Mass spectrometry (ESI$^+$): m/z=442 [M+H]$^+$

HPLC (Method 5): Retention time=1.80 min.

(8) Ethyl 4'-iodo-5'-oxo-2'-(tetrahydro-2H-pyran-4-yl)-6',8'-dihydro-5'H-spiro[cyclobutane-1,7'-quinoline]-3'-carboxylate

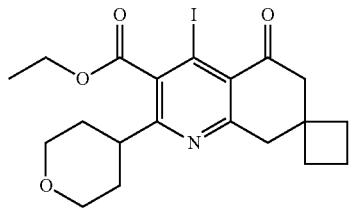 [SMILES: CCOC(=O)c1c(C2CCOCC2)nc2c(c1I)C(=O)CC1(CCC1)C2]

Obtained by starting from ethyl 4'-chloro-5'-oxo-2'-(tetrahydro-2H-pyran-4-yl)-6',8'-dihydro-5'H-spiro[cyclobutane-1,7'-quinoline]-3'-carboxylate.

Mass spectrometry (ESI$^+$): m/z=470 [M+H]$^+$

HPLC (Method 7): Retention time=1.596 min.

Example V

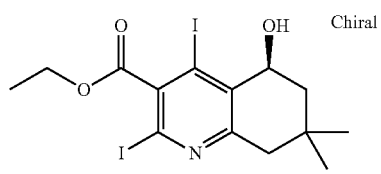 [SMILES: CCOC(=O)c1c(I)nc2c(c1I)[C@@H](O)CC(C)(C)C2]

(S)-Ethyl 5-hydroxy-2,4-diiodo-7,7-dimethyl-5,6,7,8-tetrahydroquinoline-3-carboxylate 500 mg (1R,2S)-(+)-cis-1-Amino-2-indanol are dissolved in 100 ml tetrahydrofurane and to this solution are dropwise added 7.3 ml of a borane-diethylaniline-complex. After completion of gas evolution the solution is cooled to 0° C. and 10.3 g ethyl 2,4-diiodo-7,7-dimethyl-5-oxo-5,6,7,8-tetrahydroquinoline-3-carboxylate in 20 ml tetrahydrofurane are added dropwise. The temperature is raised during 28 hours to room temperature, 20 ml methanol are added dropwise and the mixture is stirred for additional 10 minutes. The solution is diluted with diethylether and washed with 1 N hydrochloric acid, saturated aqueous sodium bicarbonate solution and brine. After drying with magnesium sulphate the solvents are evaporated in vacuo and the residue is chromatographed on silica gel (cyclohexane/ethylacetate 90:10 to 30:70).

Yield: 8.1 g (78% of theory)

Mass spectrometry (ESI$^+$): m/z=502 [M+H]$^+$

HPLC (Method 1): Retention time=3.286 min.

R$_f$-value: 0.21 (silica gel, petrole ether/ethylacetate 4:1)

Analogously to example V the following compounds are obtained:

(1) (S)-Ethyl 5-hydroxy-4-iodo-2-isopropyl-7,7-dimethyl-5,6,7,8-tetrahydroquinoline-3-carboxylate

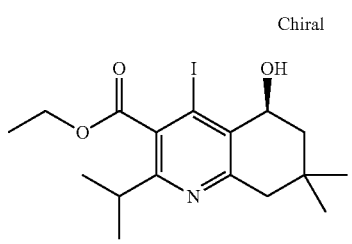 [SMILES: CCOC(=O)c1c(C(C)C)nc2c(c1I)[C@@H](O)CC(C)(C)C2]

Obtained by starting from ethyl 4-iodo-2-isopropyl-7,7-dimethyl-5-oxo-5,6,7,8-tetrahydroquinoline-3-carboxylate.

Mass spectrometry (ESI$^+$): m/z=418 [M+H]$^+$

R$_f$-value: 0.35 (silica gel, petrole ether/ethylacetate 4:1)

(2) (S)-ethyl 5-hydroxy-4-iodo-7,7-dimethyl-2-(tetrahydro-2H-pyran-4-yl)-5,6,7,8-tetrahydroquinoline-3-carboxylate

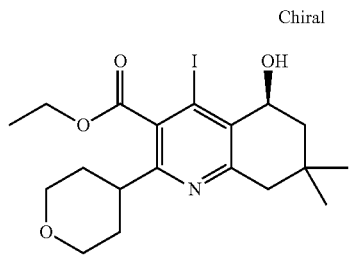 [SMILES: CCOC(=O)c1c(C2CCOCC2)nc2c(c1I)[C@@H](O)CC(C)(C)C2]

Obtained by starting from ethyl 4-iodo-7,7-dimethyl-5-oxo-2-(tetrahydro-2H-pyran-4-yl)-5,6,7,8-tetrahydroquinoline-3-carboxylate.
Mass spectrometry (ESI$^+$): m/z=460 [M+H]$^+$
HPLC (Method 1): Retention time=3.059 min.
$R_f$-value: 0.37 (silica gel, petrole ether/ethylacetate 2:1)

(3) (S)-Ethyl 2-cyclopentyl-5-hydroxy-4-iodo-7,7-dimethyl-5,6,7,8-tetrahydroquinoline-3-carboxylate

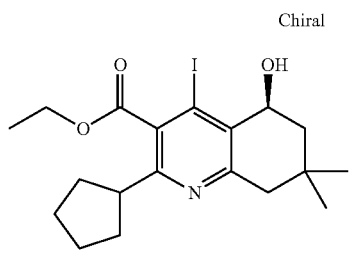 [SMILES: CCOC(=O)c1c(C2CCCC2)nc2c(c1I)[C@@H](O)CC(C)(C)C2]

Obtained by starting from ethyl 2-cyclopentyl-4-iodo-7,7-dimethyl-5-oxo-5,6,7,8-tetrahydroquinoline-3-carboxylate.
Mass spectrometry (ESI$^+$): m/z=444 [M+H]$^+$
HPLC (Method 19): Retention time=1.73 min.

(4) (S)-ethyl 4-cyclopentenyl-5-hydroxy-2-isopropyl-7,7-dimethyl-5,6,7,8-tetrahydroquinoline-3-carboxylate

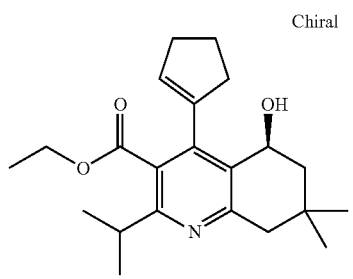 [SMILES: CCOC(=O)c1c(C(C)C)nc2c(c1C1=CCCC1)[C@@H](O)CC(C)(C)C2]

Obtained by starting from ethyl 4-cyclopentenyl-2-isopropyl-7,7-dimethyl-5-oxo-5,6,7,8-tetrahydroquinoline-3-carboxylate.
Mass spectrometry (ESI$^+$): m/z=358 [M+H]$^+$
HPLC (Method 8): Retention time=0.70 min.
$R_f$-value: 0.12 (silica gel, cyclohexane/ethylacetate 9:1)

(5) (S)-ethyl 5'-hydroxy-4'-iodo-2'-isopropyl-6',8'-dihydro-5'H-spiro[cyclobutane-1,7'-quinoline]-3'-carboxylate

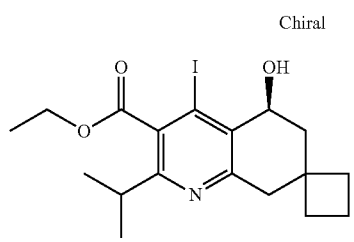 [SMILES: CCOC(=O)c1c(C(C)C)nc2c(c1I)[C@@H](O)CC1(CCC1)C2]

Obtained by starting from ethyl 4'-iodo-2'-isopropyl-5'-oxo-6',8'-dihydro-5'H-spiro[cyclobutane-1,7'-quinoline]-3'-carboxylate.
Mass spectrometry (ESI$^+$): m/z=430 [M+H]$^+$
HPLC (Method 20): Retention time=3.40 min.

(6) (S)-Ethyl 2-cyclobutyl-5-hydroxy-4-iodo-7,7-dimethyl-5,6,7,8-tetrahydroquinoline-3-carboxylate

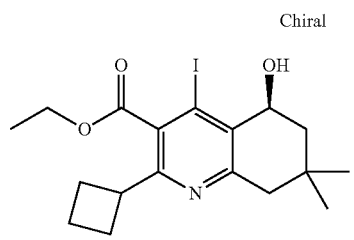 [SMILES: CCOC(=O)c1c(C2CCC2)nc2c(c1I)[C@@H](O)CC(C)(C)C2]

Obtained by starting from ethyl 2-cyclobutyl-4-iodo-7,7-dimethyl-5-oxo-5,6,7,8-tetrahydroquinoline-3-carboxylate.
Mass spectrometry (ESI$^+$): m/z=430 [M+H]$^+$
$R_f$-value: 0.60 (silica gel, cyclohexane/ethylacetate 3:1)

(7) (S)-ethyl 2-ethyl-5-hydroxy-4-iodo-7,7-dimethyl-5,6,7,8-tetrahydroquinoline-3-carboxylate

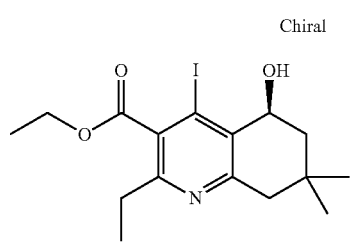 [SMILES: CCOC(=O)c1c(CC)nc2c(c1I)[C@@H](O)CC(C)(C)C2]

Obtained by starting from ethyl 2-ethyl-4-iodo-7,7-dimethyl-5-oxo-5,6,7,8-tetrahydroquinoline-3-carboxylate.
Mass spectrometry (ESI$^+$): m/z=404 [M+H]$^+$
HPLC (Method 20): Retention time=2.64 min.

(8) (S)-Ethyl 5'-hydroxy-4'-iodo-2'-isopropyl-6',8'-dihydro-5'H-spiro[cyclopentane-1,7'-quinoline]-3'-carboxylate

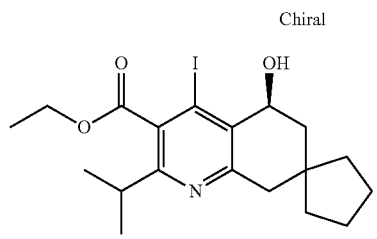 [SMILES: CCOC(=O)c1c(C(C)C)nc2c(c1I)[C@@H](O)CC1(CCCC1)C2]

Obtained by starting from ethyl 4'-iodo-2'-isopropyl-5'-oxo-6',8'-dihydro-5'H-spiro[cyclopentane-1,7'-quinoline]-3'-carboxylate.
Mass spectrometry (ESI$^+$): m/z=444 [M+H]$^+$
HPLC (Method 5): Retention time=1.80 min.

(9) (S)-ethyl 5'-hydroxy-4'-iodo-2'-(tetrahydro-2H-pyran-4-yl)-6',8'-dihydro-5'H-spiro[cyclobutane-1,7'-quinoline]-3'-carboxylate

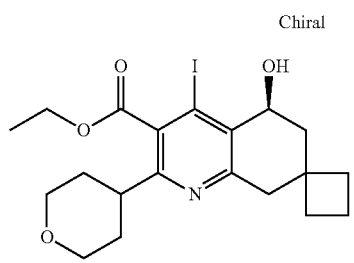 [SMILES: CCOC(=O)c1c(C2CCOCC2)nc2c(c1I)[C@@H](O)CC1(CCC1)C2]

Obtained by starting from ethyl 4'-iodo-5'-oxo-2'-(tetrahydro-2H-pyran-4-yl)-6',8'-dihydro-5'H-spiro[cyclobutane-1,7'-quinoline]-3'-carboxylate.
Mass spectrometry (ESI$^+$): m/z=472 [M+H]$^+$
HPLC (Method 7): Retention time=1.505 min.

Example VI

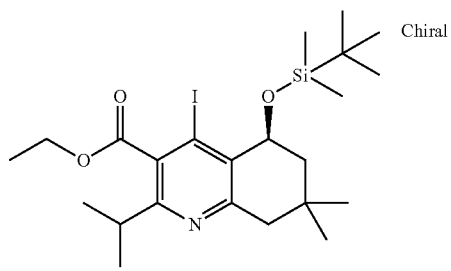 [SMILES: CCOC(=O)c1c(C(C)C)nc2c(c1I)[C@@H](O[Si](C)(C)C(C)(C)C)CC(C)(C)C2]

(S)-Ethyl 5-(tert-butyldimethylsilyloxy)-2,4-diiodo-7,7-dimethyl-5,6,7,8-tetrahydroquinoline-3-carbonylate 8.1 g (S)-Ethyl 5-hydroxy-2,4-diiodo-7,7-dimethyl-5,6,7,8-tetrahydroquinoline-3-carboxylate are dissolved in 70 ml tetrahydrofurane, cooled to 0° C., 3.2 ml 2,6-lutidine and 5 ml trifluoromethanesulfonic acid-tert.-butyldimethylsilylester are added dropwise and the mixture is stirred for further 12 hours while warming to room temperature. The solvents are evaporated in vacuo and the residue is chromatographed on silica gel (cyclohexane/ethylacetate 90:10 to 30:70).

Yield: 9.8 g (99% of theory)
Mass spectrometry (ESI$^+$): m/z=616 [M+H]$^+$
HPLC (Method 1): Retention time=4.916 min.
R$_f$-value: 0.71 (silica gel, petrole ether/ethylacetate 4:1)

Analogously to example VI the following compounds are obtained:

(1) (S)-Ethyl 5-(tert-butyldimethylsilyloxy)-4-iodo-2-isopropyl-7,7-dimethyl-5,6,7,8-tetrahydroquinoline-3-carboxylate

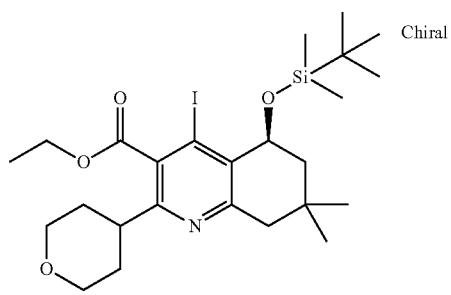 [SMILES: CCOC(=O)c1c(C2CCOCC2)nc2c(c1I)[C@@H](O[Si](C)(C)C(C)(C)C)CC(C)(C)C2]

Obtained by starting from (S)-ethyl 5-hydroxy-4-iodo-2-isopropyl-7,7-dimethyl-5,6,7,8-tetrahydroquinoline-3-carboxylate.
Mass spectrometry (ESI$^+$): m/z=532 [M+H]$^+$
R$_f$-value: 0.45 (silica gel, petrole ether/ethylacetate 16:1)

(2) (S)-ethyl 5-(tert-butyldimethylsilyloxy)-4-iodo-7,7-dimethyl-2-(tetrahydro-2H-pyran-4-yl)-5,6,7,8-tetrahydroquinoline-3-carboxylate Obtained by starting from (S)-ethyl 5-hydroxy-4-iodo-7,7-dimethyl-2-(tetrahydro-2H-pyran-4-yl)-5,6,7,8-tetrahydroquinoline-3-carboxylate.
Mass spectrometry (ESI$^+$): m/z=532 [M+H]$^+$
R$_f$-value: 0.75 (silica gel, petrole ether/ethylacetate 2:1)

(3) (S)-ethyl 5-(tert-butyldimethylsilyloxy)-2-cyclopentyl-4-iodo-7,7-dimethyl-5,6,7,8-tetrahydroquinoline-3-carboxylate

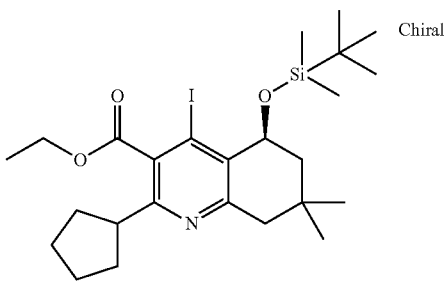 [SMILES: CCOC(=O)c1c(C2CCCC2)nc2c(c1I)[C@@H](O[Si](C)(C)C(C)(C)C)CC(C)(C)C2]

Obtained by starting from (S)-ethyl 2-cyclopentyl-5-hydroxy-4-iodo-7,7-dimethyl-5,6,7,8-tetrahydroquinoline-3-carboxylate.
Mass spectrometry (ESI$^+$): m/z=558 [M+H]$^+$
HPLC (Method 21): Retention time=2.66 min.

(4) (S)-ethyl 5-(tert-butyldimethylsilyloxy)-4-cyclopentenyl-2-isopropyl-7,7-dimethyl-5,6,7,8-tetrahydroquinoline-3-carboxylate

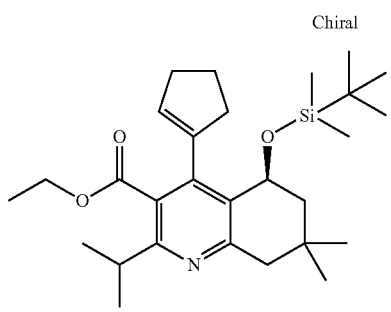 [SMILES: CCOC(=O)c1c(C(C)C)nc2c(c1C1=CCCC1)[C@@H](O[Si](C)(C)C(C)(C)C)CC(C)(C)C2]

Obtained by starting from (S)-ethyl 4-cyclopentenyl-5-hydroxy-2-isopropyl-7,7-dimethyl-5,6,7,8-tetrahydroquinoline-3-carboxylate.
Mass spectrometry (ESI$^+$): m/z=472 [M+H]$^+$
HPLC (Method 8): Retention time=3.38 min.
R$_f$-value: 0.53 (silica gel, cyclohexane/ethylacetate 9:1)

(5) (S)-ethyl 5'-(tert-butyldimethylsilyloxy)-4'-iodo-2'-isopropyl-6',8'-dihydro-5'H-spiro[cyclobutane-1,7'-quinoline]-3'-carboxylate

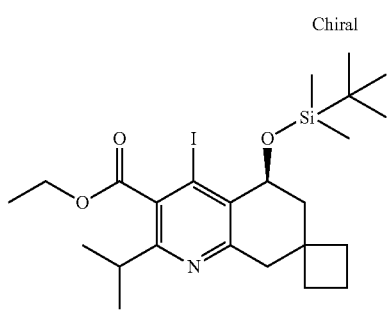 [SMILES: CCOC(=O)c1c(C(C)C)nc2c(c1I)[C@@H](O[Si](C)(C)C(C)(C)C)CC1(CCC1)C2]

Obtained by starting from (S)-ethyl 5'-hydroxy-4'-iodo-2'-isopropyl-6',8'-dihydro-5'H-spiro[cyclobutane-1,7'-quinoline]-3'-carboxylate.
Mass spectrometry (ESI$^+$): m/z=544 [M+H]$^+$
HPLC (Method 20): Retention time=4.31 min.

(6) (S)-Ethyl 5-(tert-butyldimethylsilyloxy)-2-cyclobutyl-4-iodo-7,7-dimethyl-5,6,7,8-tetrahydroquinoline-3-carboxylate

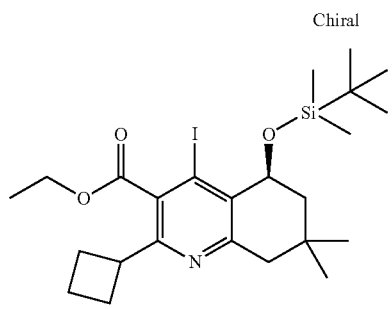 [SMILES: CCOC(=O)c1c(C2CCC2)nc2c(c1I)[C@@H](O[Si](C)(C)C(C)(C)C)CC(C)(C)C2]

Obtained by starting from (S)-ethyl 2-cyclobutyl-5-hydroxy-4-iodo-7,7-dimethyl-5,6,7,8-tetrahydroquinoline-3-carboxylate.
Mass spectrometry (ESI$^+$): m/z=544 [M+H]$^+$
R$_f$-value: 0.75 (silica gel, cyclohexane/ethylacetate 9:1)

(7) (R)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methanol

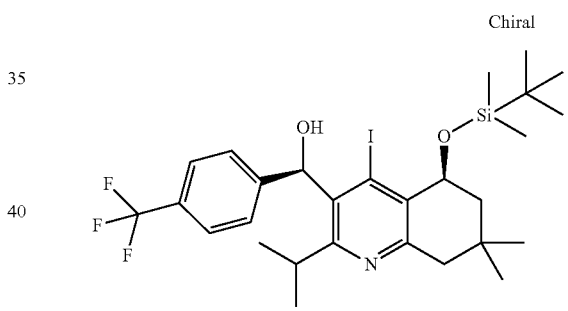

Obtained by starting from (S)-3-((R)-hydroxy(4-(trifluoromethyl)phenyl)methyl)-4-iodo-2-isopropyl-7,7-dimethyl-5,6,7,8-tetrahydroquinolin-5-ol.
Mass spectrometry (ESI$^+$): m/z=634 [M+H]$^+$
HPLC (Method 9): Retention time=2.38 min.

(8) (S)-ethyl 5-(tert-butyldimethylsilyloxy)-2-ethyl-4-iodo-7,7-dimethyl-5,6,7,8-tetrahydroquinoline-3-carboxylate

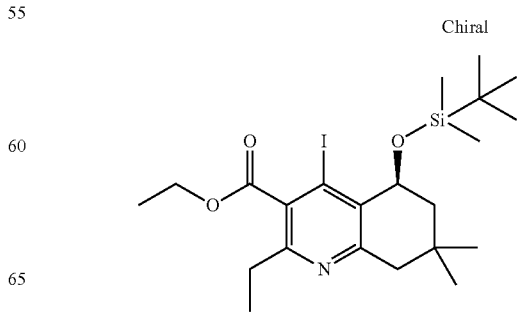

Obtained by starting from (S)-ethyl 2-ethyl-5-hydroxy-4-iodo-7,7-dimethyl-5,6,7,8-tetrahydroquinoline-3-carboxylate.

Mass spectrometry (ESI⁺): m/z=518 [M+H]⁺
HPLC (Method 20): Retention time=4.04 min.

(9) (R)—((S)-5-(tert-butyldimethylsilyloxy)-4-iodo-2-isopropyl-7,7-dimethyl-5,6,7,8-tetrahydroquinolin-3-yl)(4-tert-butylphenyl)methanol

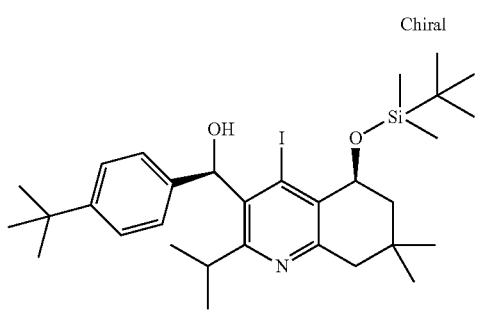 [SMILES: CC(C)c1nc2c(c(I)c1[C@H](O)c1ccc(C(C)(C)C)cc1)[C@@H](O[Si](C)(C)C(C)(C)C)CC(C)(C)C2]

Obtained by starting from (S)-3-((R)-(4-tert-butylphenyl)(hydroxy)methyl)-4-iodo-2-isopropyl-7,7-dimethyl-5,6,7,8-tetrahydroquinolin-5-ol.

Mass spectrometry (ESI⁺): m/z=622 [M+H]⁺
HPLC (Method 13??): Retention time=1.74 min.

(10) (R)—((S)-5'-(tert-butyldimethylsilyloxy)-4'-iodo-2'-isopropyl-6',8'-dihydro-5'H-spiro[cyclobutane-1,7'-quinoline]-3'-yl)(4-(trifluoromethyl)phenyl)methanol

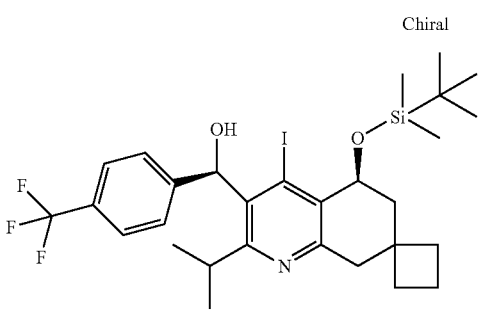 [SMILES: CC(C)c1nc2c(c(I)c1[C@H](O)c1ccc(C(F)(F)F)cc1)[C@@H](O[Si](C)(C)C(C)(C)C)CC1(CCC1)C2]

Obtained by starting from (S)-3'-((R)-hydroxy(4-(trifluoromethyl)phenyl)methyl)-4'-iodo-2'-isopropyl-6',8'-dihydro-5'H-spiro[cyclobutane-1,7'-quinolin]-5'-ol.

Mass spectrometry (ESI⁺): m/z=646 [M+H]⁺
HPLC (Method 13): Retention time=1.63 min.

(11) (S)-Ethyl 5'-(tert-butyldimethylsilyloxy)-4'-iodo-2'-isopropyl-6',8'-dihydro-5'H-spiro[cyclopentane-1,7'-quinoline]-3'-carboxylate

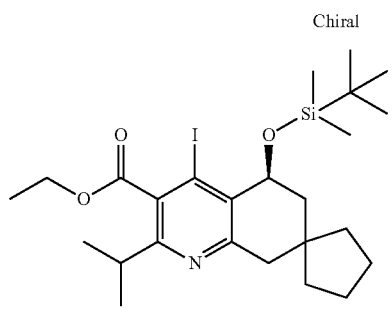 [SMILES: CCOC(=O)c1c(C(C)C)nc2c(c1I)[C@@H](O[Si](C)(C)C(C)(C)C)CC1(CCCC1)C2]

Obtained by starting from ((S)-ethyl 5'-hydroxy-4'-iodo-2'-isopropyl-6',8'-dihydro-5'H-spiro[cyclopentane-1,7'-quinoline]-3'-carboxylate.

Mass spectrometry (ESI⁺): m/z=558 [M+H]⁺
HPLC (Method 5): Retention time=2.08 min.

(12) (R)—((S)-5'-(tert-butyldimethylsilyloxy)-4'-iodo-2'-isopropyl-6',8'-dihydro-5'H-spiro[cyclobutane-1,7'-quinoline]-3'-yl)(4-tert-butylphenyl)methanol

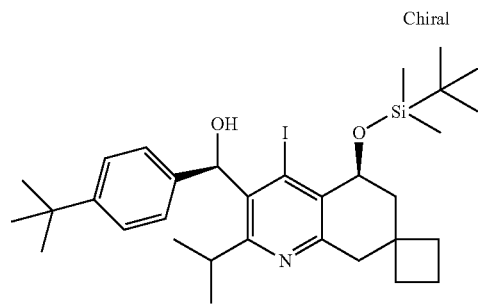 [SMILES: CC(C)c1nc2c(c(I)c1[C@H](O)c1ccc(C(C)(C)C)cc1)[C@@H](O[Si](C)(C)C(C)(C)C)CC1(CCC1)C2]

Obtained by starting from ((S)-3'-((R)-(4-tert-butylphenyl)(hydroxy)methyl)-4'-iodo-2'-isopropyl-6',8'-dihydro-5'H-spiro[cyclobutane-1,7'-quinolin]-5'-ol.

Mass spectrometry (ESI⁺): m/z=634 [M+H]⁺
HPLC (Method 7): Retention time=1.953 min.
$R_f$-value: 0.6 (silica gel, cyclohexane/ethylacetate 9:1)

(13) (S)-ethyl 5'-(tert-butyldimethylsilyloxy)-4'-iodo-2'-(tetrahydro-2H-pyran-4-yl)-6',8'-dihydro-5'H-spiro[cyclobutane-1,7'-quinoline]-3'-carboxylate

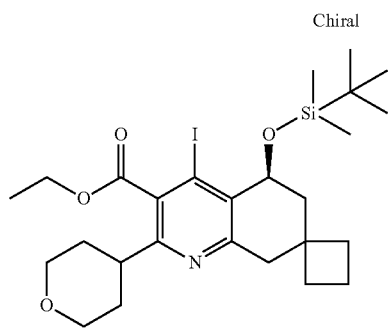 [SMILES: CCOC(=O)c1c(C2CCOCC2)nc2c(c1I)[C@@H](O[Si](C)(C)C(C)(C)C)CC1(CCC1)C2]

Obtained by starting from (S)-ethyl 5'-hydroxy-4'-iodo-2'-(tetrahydro-2H-pyran-4-yl)-6',8'-dihydro-5'H-spiro[cyclobutane-1,7'-quinoline]-3'-carboxylate.
Mass spectrometry (ESI⁺): m/z=586 [M+H]⁺
HPLC (Method 7): Retention time=1.999 min.

(14) (R)—((S)-5'-(tert-butyldimethylsilyloxy)-4'-iodo-2'-(tetrahydro-2H-pyran-4-yl)-6',8'-dihydro-5'H-spiro[cyclobutane-1,7'-quinoline]-3'-yl)(4-(trifluoromethyl)phenyl)methanol

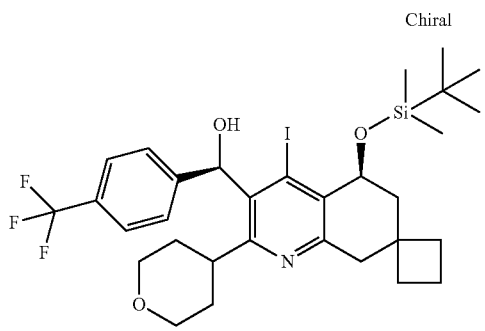 [SMILES: CC(C)(C)[Si](C)(C)O[C@H]1CC2(CCC2)Cc2nc(C3CCOCC3)c([C@H](O)c3ccc(C(F)(F)F)cc3)c(I)c21]

Obtained by starting from (S)-3'-((R)-hydroxy(4-(trifluoromethyl)phenyl)methyl)-4'-iodo-2'-(tetrahydro-2H-pyran-4-yl)-6',8'-dihydro-5'H-spiro[cyclobutane-1,7'-quinolin]-5'-ol
Mass spectrometry (ESI⁺): m/z=688 [M+H]⁺
HPLC (Method 7): Retention time=1.976 min.

Example VII

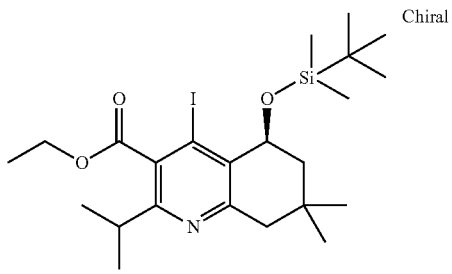 [SMILES: CCOC(=O)c1c(C(C)C)nc2c(c1I)[C@@H](O[Si](C)(C)C(C)(C)C)CC(C)(C)C2]

(S)-Ethyl 5-(tert-butyldimethylsilyloxy)-4-iodo-2-isopropyl-7,7-dimethyl-5,6,7,8-tetrahydroquinoline-3-carboxylate Under argon 9.8 g (S)-ethyl 5-(tert-butyldimethylsilyloxy)-2,4-diiodo-7,7-dimethyl-5,6,7,8-tetrahydroquinoline-3-carboxylate are dissolved in 25 ml toluene and 25 ml tetrahydrofurane. 800 mg 1,1'-bis-(diphenylphosphino)-ferrocene-dichloro-palladium-(II) are added, the mixture is heated to 85° C. and 50 ml of a 0.5 M solution of isopropylzinc-bromide in tetrahydrofurane are added dropwise. After completion of the addition the mixture is heated for 12 hours at reflux. The mixture is cooled to room temperature, diluted with diethylether and washed with saturated ammonium chloride solution and brine. After drying with magnesium sulphate the solvents are evaporated in vacuo and the residue is chromatographed on silica gel (cyclohexane/ethylacetate 90:10 to 60:40).

Yield: 2.63 g (31% of theory)
Mass spectrometry (ESI⁺): m/z=532 [M+H]⁺
$R_f$-value: 0.85 (silica gel, petrole ether/ethylacetate 4:1)
Analogously to example VII the following compounds are obtained:

(1) Ethyl 4-hydroxy-2-isopropyl-7,7-dimethyl-5-oxo-5,6,7,8-tetrahydroquinoline-3-carboxylate

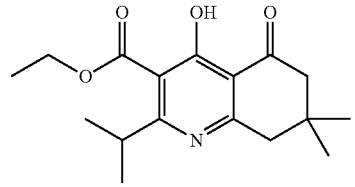 [SMILES: CCOC(=O)c1c(C(C)C)nc2c(c1O)C(=O)CC(C)(C)C2]

Obtained by starting from ethyl 2-chloro-4-hydroxy-7,7-dimethyl-5-oxo-5,6,7,8-tetrahydroquinoline-3-carboxylate
Mass spectrometry (ESI⁺): m/z=306 [M+H]⁺
$R_f$-value: 0.47 (silica gel, petrole ether/ethylacetate 4:1)

(2) Ethyl 2-cyclopentyl-4-hydroxy-7,7-dimethyl-5-oxo-5,6,7,8-tetrahydroquinoline-3-carboxylate

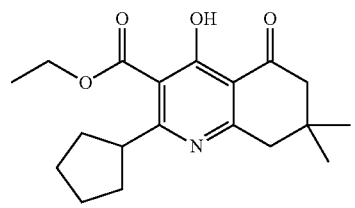 [SMILES: CCOC(=O)c1c(C2CCCC2)nc2c(c1O)C(=O)CC(C)(C)C2]

Obtained by starting from ethyl 2-chloro-4-hydroxy-7,7-dimethyl-5-oxo-5,6,7,8-tetrahydroquinoline-3-carboxylate.
Mass spectrometry (ESI⁺): m/z=332 [M+H]⁺
HPLC (Method 19): Retention time=1.53 min.

(3) Ethyl 4'-hydroxy-2'-isopropyl-5'-oxo-6',8'-dihydro-5'H-spiro[cyclobutane-1,7'-quinoline]-3'-carboxylate

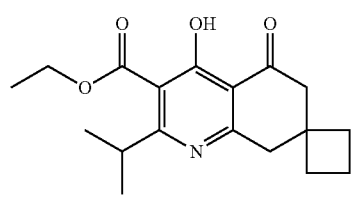

Obtained by starting from ethyl 2'-chloro-4'-hydroxy-5'-oxo-6',8'-dihydro-5'H-spiro[cyclobutane-1,7'-quinoline]-3'-carboxylate.
Mass spectrometry (ESI⁺): m/z=318 [M+H]⁺
HPLC (Method 20): Retention time=2.79 min.

(4) Ethyl 2-cyclobutyl-4-hydroxy-7,7-dimethyl-5-oxo-5,6,7,8-tetrahydroquinoline-3-carboxylate

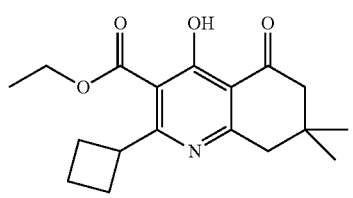 [SMILES: CCOC(=O)c1c(C2CCC2)nc2c(c1O)C(=O)CC(C)(C)C2]

Obtained by starting from ethyl 2-chloro-4-hydroxy-7,7-dimethyl-5-oxo-5,6,7,8-tetrahydroquinoline-3-carboxylate.

Mass spectrometry (ESI⁺): m/z=318 [M+H]⁺

$R_f$-value: 0.60 (silica gel, cyclohexane/ethylacetate 3:1)

(5) Ethyl 2-ethyl-4-hydroxy-7,7-dimethyl-5-oxo-5,6,7,8-tetrahydroquinoline-3-carboxylate

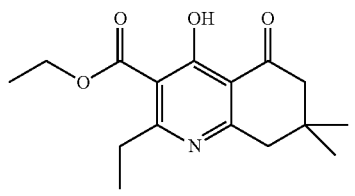 [SMILES: CCOC(=O)c1c(CC)nc2c(c1O)C(=O)CC(C)(C)C2]

Obtained by starting from ethyl 2-chloro-4-hydroxy-7,7-dimethyl-5-oxo-5,6,7,8-tetrahydroquinoline-3-carboxylate. Diethylzinc (1 M in hexane) is used instead of isopropyl-zinc-bromide.

Mass spectrometry (ESI⁺): m/z=292 [M+H]⁺

HPLC (Method 20): Retention time=2.25 min.

(6) Ethyl 4'-hydroxy-2'-isopropyl-5'-oxo-6',8'-dihydro-5'H-spiro[cyclopentane-1,7'-quinoline]-3'-carboxylate

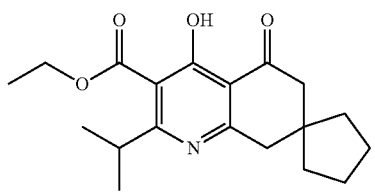

Obtained by starting from ethyl 2'-chloro-4'-hydroxy-5'-oxo-6',8'-dihydro-5'H-spiro[cyclopentane-1,7'-quinoline]-3'-carboxylate.

Mass spectrometry (ESI⁺): m/z=332 [M+H]⁺

HPLC (Method 5): Retention time=1.53 min.

Example VIII

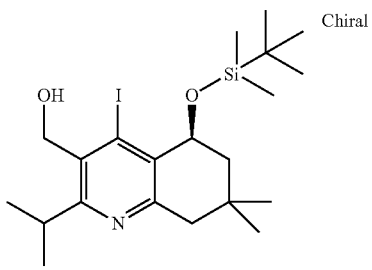 [SMILES: CC(C)c1nc2c(c(I)c1CO)[C@@H](O[Si](C)(C)C(C)(C)C)CC(C)(C)C2]

(S)-(5-(tert-butyldimethylsilyloxy)-4-iodo-2-isopropyl-7,7-dimethyl-5,6,7,8-tetrahydroquinolin-3-yl)methanol 2.63 g (S)-ethyl 5-(tert-butyldimethylsilyloxy)-4-iodo-2-isopropyl-7,7-dimethyl-5,6,7,8-tetrahydroquinoline-3-carboxylate are dissolved in 50 ml dichloromethane and cooled to 0° C. 16.5 ml of a 1 M solution of diisobutylaluminiumhydride in dichloromethane are added dropwise and the solution is stirred for further 2 hours. Then the solution is diluted with dichloromethane and 1 ml of 1 N hydrochloric acid is added dropwise under vigorous stirring. After 5 minutes magnesium sulphate is added and stirring is continued for further 5 minutes. Filtration and evaporation of the solvents in vacuo gives a crude product, which is chromatographed on silica gel (cyclohexane/ethylacetate 90:10 to 60:40).

Yield: 1.96 g (81% of theory)

Mass spectrometry (ESI⁺): m/z=490 [M+H]⁺

HPLC (Method 1): Retention time=4.100 min.

$R_f$-value: 0.55 (silica gel, petrole ether/ethylacetate 4:1)

Analogously to example VIII the following compounds are obtained:

(1) (S)-(5-(tert-butyldimethylsilyloxy)-4-iodo-7,7-dimethyl-2-(tetrahydro-2H-pyran-4-yl)-5,6,7,8-tetrahydroquinolin-3-yl)methanol

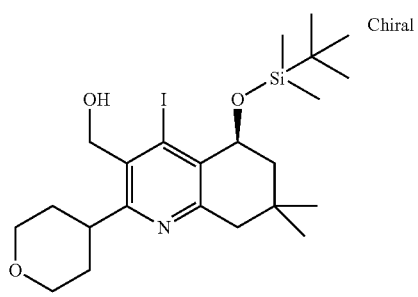 [SMILES: CC1(C)Cc2nc(C3CCOCC3)c(CO)c(I)c2[C@@H](O[Si](C)(C)C(C)(C)C)C1]

Obtained by starting from (S)-ethyl 5-(tert-butyldimethylsilyloxy)-4-iodo-7,7-dimethyl-2-(tetrahydro-2H-pyran-4-yl)-5,6,7,8-tetrahydroquinoline-3-carboxylate.

$R_f$-value: 0.32 (silica gel, petrole ether/ethylacetate 2:1)

(2) (S)-(5-(tert-butyldimethylsilyloxy)-2-cyclopentyl-4-iodo-7,7-dimethyl-5,6,7,8-tetrahydroquinolin-3-yl)methanol

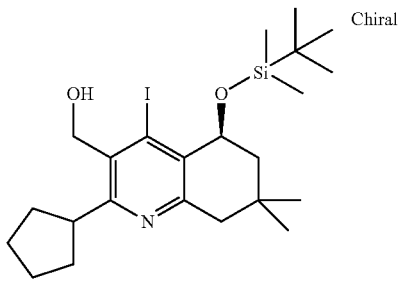 [SMILES: CC1(C)Cc2nc(C3CCCC3)c(CO)c(I)c2[C@@H](O[Si](C)(C)C(C)(C)C)C1]

Obtained by starting from (S)-ethyl 5-(tert-butyldimethylsilyloxy)-2-cyclopentyl-4-iodo-7,7-dimethyl-5,6,7,8-tetrahydroquinoline-3-carboxylate.
Mass spectrometry (ESI⁺): m/z=516 [M+H]⁺
HPLC (Method 21): Retention time=1.84 min.

(3) (S)-(5-(tert-butyldimethylsilyloxy)-4-cyclopentenyl-2-isopropyl-7,7-dimethyl-5,6,7,8-tetrahydroquinolin-3-yl)methanol

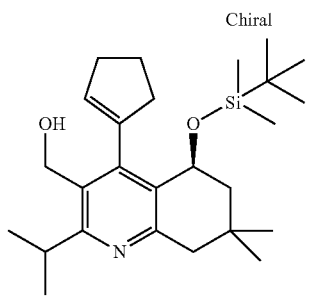 [SMILES: CC(C)c1nc2c(c(C3=CCCC3)c1CO)[C@@H](O[Si](C)(C)C(C)(C)C)CC(C)(C)C2]

Obtained by starting from (S)-ethyl 5-(tert-butyldimethylsilyloxy)-4-cyclopentenyl-2-isopropyl-7,7-dimethyl-5,6,7,8-tetrahydroquinoline-3-carboxylate.
Mass spectrometry (ESI⁺): m/z=430 [M+H]⁺
HPLC (Method 8): Retention time=1.26 min.
R_f-value: 0.17 (silica gel, cyclohexane/ethylacetate 9:1)

(4) (S)-(5'-(tert-butyldimethylsilyloxy)-4'-iodo-2'-isopropyl-6',8'-dihydro-5'H-spiro[cyclobutane-1,7'-quinoline]-3'-yl)methanol

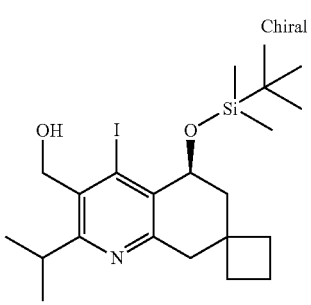 [SMILES: CC(C)c1nc2c(c(I)c1CO)[C@@H](O[Si](C)(C)C(C)(C)C)CC1(CCC1)C2]

Obtained by starting from (S)-ethyl 5'-(tert-butyldimethylsilyloxy)-4'-iodo-2'-isopropyl-6',8'-dihydro-5'H-spiro[cyclobutane-1,7'-quinoline]-3'-carboxylate.
Mass spectrometry (ESI⁺): m/z=502 [M+H]⁺
HPLC (Method 20): Retention time=3.72 min.

(5) (S)-(5-(tert-butyldimethylsilyloxy)-2-cyclobutyl-4-iodo-7,7-dimethyl-5,6,7,8-tetrahydroquinolin-3-yl)methanol

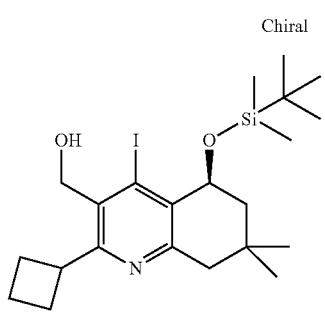 [SMILES: CC1(C)Cc2nc(C3CCC3)c(CO)c(I)c2[C@@H](O[Si](C)(C)C(C)(C)C)C1]

Obtained by starting from (S)-ethyl 5-(tert-butyldimethylsilyloxy)-2-cyclobutyl-4-iodo-7,7-dimethyl-5,6,7,8-tetrahydroquinoline-3-carboxylate.
Mass spectrometry (ESI⁺): m/z=502 [M+H]⁺
R_f-value: 0.20 (silica gel, cyclohexane/ethylacetate 9:1)

(6) (S)-(5-(tert-butyldimethylsilyloxy)-2-ethyl-4-iodo-7,7-dimethyl-5,6,7,8-tetrahydroquinolin-3-yl)methanol

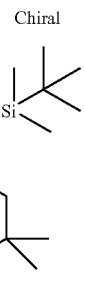

Obtained by starting from (S)-ethyl 5-(tert-butyldimethylsilyloxy)-2-ethyl-4-iodo-7,7-dimethyl-5,6,7,8-tetrahydroquinoline-3-carboxylate.
Mass spectrometry (ESI⁺): m/z=476 [M+H]⁺
HPLC (Method 20): Retention time=3.39 min.

(7) (S)-3'-(hydroxymethyl)-4'-iodo-2'-isopropyl-6',8'-dihydro-5'H-spiro[cyclobutane-1,7'-quinolin]-5'-ol

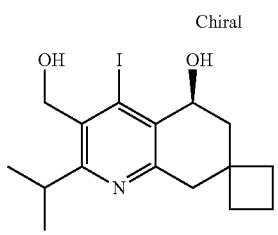 [SMILES: CC(C)c1nc2c(c(I)c1CO)[C@@H](O)CC1(CCC1)C2]

Obtained by starting from (S)-ethyl 5'-hydroxy-4'-iodo-2'-isopropyl-6',8'-dihydro-5'H-spiro[cyclobutane-1,7'-quinoline]-3'-carboxylate.

Mass spectrometry (ESI$^+$): m/z=388 [M+H]$^+$

HPLC (Method 14): Retention time=6.54 min.

(8) (S)-(5-(tert-butyldimethylsilyloxy)-4-(3,6-dihydro-2H-pyran-4-yl)-2-isopropyl-7,7-dimethyl-5,6,7,8-tetrahydroquinolin-3-yl)methanol

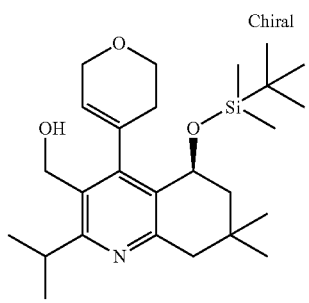 [SMILES: CC(C)c1nc2c(c(C3=CCOCC3)c1CO)[C@@H](O[Si](C)(C)C(C)(C)C)CC(C)(C)C2]

Obtained by starting from (S)-ethyl 5-(tert-butyldimethylsilyloxy)-4-(3,6-dihydro-2H-pyran-4-yl)-2-isopropyl-7,7-dimethyl-5,6,7,8-tetrahydroquinoline-3-carboxylate.

Mass spectrometry (ESI$^+$): m/z=446 [M+H]$^+$

HPLC (Method 24): Retention time=1.457 min.

(9) (S)-(5'-(tert-butyldimethylsilyloxy)-4'-iodo-2'-isopropyl-6',8'-dihydro-5'H-spiro[cyclopentane-1,7'-quinoline]-3-ylmethanol

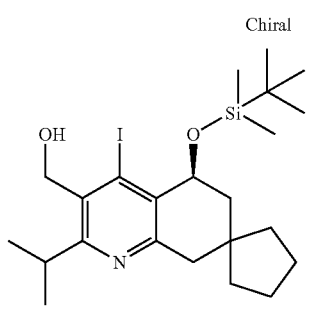 [SMILES: CC(C)c1nc2c(c(I)c1CO)[C@@H](O[Si](C)(C)C(C)(C)C)CC1(CCCC1)C2]

Obtained by starting from (S)-ethyl 5'-(tert-butyldimethylsilyloxy)-4'-iodo-2'-isopropyl-6',8'-dihydro-5'H-spiro[cyclopentane-1,7'-quinoline]-3'-carboxylate.

Mass spectrometry (ESI$^+$): m/z=516 [M+H]$^+$

HPLC (Method 4): Retention time=2.98 min.

(10) (S)-(5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3-ylmethanol

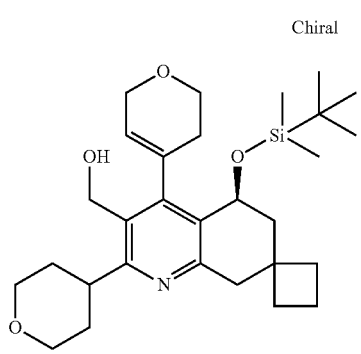 [SMILES: CC(C)(C)[Si](C)(C)O[C@H]1CC2(CCC2)Cc2nc(C3CCOCC3)c(CO)c(C3=CCOCC3)c21]

Obtained by starting from (S)-ethyl 5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-carboxylate.

Mass spectrometry (ESI$^+$): m/z=500 [M+H]$^+$

HPLC (Method 7): Retention time=1.571 min.

(11) (S)-(5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)methanol

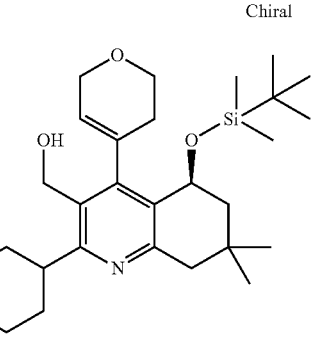

Obtained by starting from (S)-ethyl 5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinoline-3-carboxylate.

Mass spectrometry (ESI$^+$): m/z=488 [M+H]$^+$

HPLC (Method 7): Retention time=1.525 min.

(12) (S)-(5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)methanol

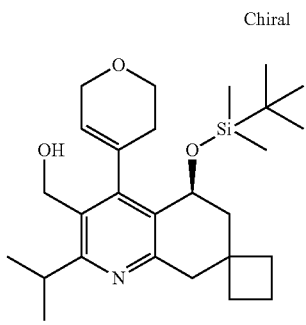 [SMILES: CC(C)c1nc2c(c(C3=CCOCC3)c1CO)[C@@H](O[Si](C)(C)C(C)(C)C)CC1(CCC1)C2]

Obtained by starting from (S)-ethyl 5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-carboxylate.
Mass spectrometry (ESI$^+$): m/z=458 [M+H]$^+$
HPLC (Method 27): Retention time=1.46 min.

(13) (S)-3'-(hydroxymethyl)-4'-iodo-2'-(tetrahydro-2H-pyran-4-yl)-6',8'-dihydro-5'H-spiro[cyclobutane-1,7'-quinolin]-5'-ol

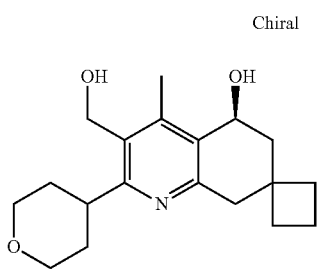 [SMILES: Cc1c(CO)c(C2CCOCC2)nc2c1[C@@H](O)CC1(CCC1)C2]

Obtained by starting from (S)-ethyl 5'-hydroxy-4'-iodo-2'-(tetrahydro-2H-pyran-4-yl)-6',8'-dihydro-5'H-spiro[cyclobutane-1,7'-quinoline]-3'-carboxylate
Mass spectrometry (ESI$^+$): m/z=430 [M+H]$^+$
HPLC (Method 7): Retention time=0.918 min.

Example IX

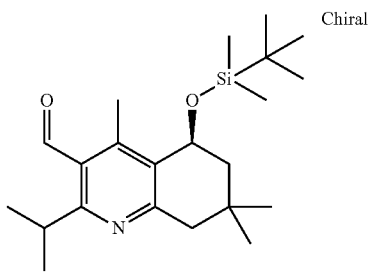 [SMILES: Cc1c(C=O)c(C(C)C)nc2c1[C@@H](O[Si](C)(C)C(C)(C)C)CC(C)(C)C2]

(S)-5-(tert-butyldimethylsilyloxy)-4-iodo-2-isopropyl-7,7-dimethyl-5,6,7,8-tetrahydroquinoline-3-carbaldehyde 1.96 g (S)-(5-(tert-butyldimethylsilyloxy)-4-iodo-2-isopropyl-7,7-dimethyl-5,6,7,8-tetrahydroquinolin-3-yl)methanol are dissolved in 60 ml dichloromethane, cooled to 0° C. and mixed with 15 g 1,1-Dihydro-1,1,1-triacetoxy-1,2-benziodoxol-3(1H)-on (Dess-Martin-Periodinan). The mixture is stirred for 12 hours while warming to room temperature. Then the solvent is evaporated in vacuo and the residue is chromatographed on silica gel (cyclohexane/ethylacetate 95:5 to 80:20).
Yield: 1.17 g (60% of theory)
Mass spectrometry (ESI$^+$): m/z=488 [M+H]$^+$
HPLC (Method 1): Retention time=5.106 min.
R$_f$-value: 0.45 (silica gel, petrole ether/ethylacetate 16:1)
Analogously to example IX the following compounds are obtained:

(1) (S)-5-(tert-butyldimethylsilyloxy)-4-iodo-7,7-dimethyl-2-(tetrahydro-2H-pyran-4-yl)-5,6,7,8-tetrahydroquinoline-3-carbaldehyde

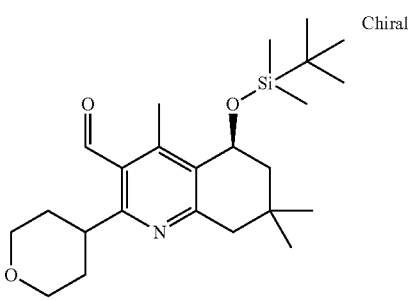 [SMILES: Cc1c(C=O)c(C2CCOCC2)nc2c1[C@@H](O[Si](C)(C)C(C)(C)C)CC(C)(C)C2]

Obtained by starting from (S)-(5-(tert-butyldimethylsilyloxy)-4-iodo-7,7-dimethyl-2-(tetrahydro-2H-pyran-4-yl)-5,6,7,8-tetrahydroquinolin-3-yl)methanol.
Mass spectrometry (ESI$^+$): m/z=530 [M+H]$^+$
R$_f$-value: 0.61 (silica gel, petrole ether/ethylacetate 4:1)

(2) (S)-5-(tert-butyldimethylsilyloxy)-2-cyclopentyl-4-iodo-7,7-dimethyl-5,6,7,8-tetrahydroquinoline-3-carbaldehyde

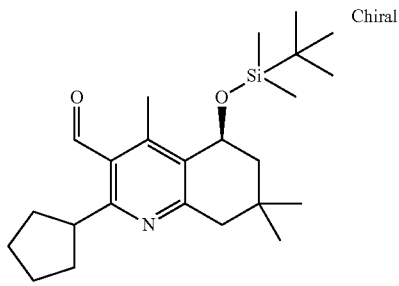 [SMILES: Cc1c(C=O)c(C2CCCC2)nc2c1[C@@H](O[Si](C)(C)C(C)(C)C)CC(C)(C)C2]

Obtained by starting from (S)-(5-(tert-butyldimethylsilyloxy)-2-cyclopentyl-4-iodo-7,7-dimethyl-5,6,7,8-tetrahydroquinolin-3-yl)methanol.
Mass spectrometry (ESI$^+$): m/z=514 [M+H]$^+$
HPLC (Method 21): Retention time=2.67 min.

(3) (S)-5-(tert-butyldimethylsilyloxy)-4-cyclopentenyl-2-isopropyl-7,7-dimethyl-5,6,7,8-tetrahydroquinoline-3-carbaldehyde

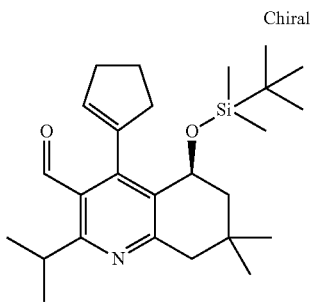 [SMILES: CC(C)c1nc2c(c(C3=CCCC3)c1C=O)[C@@H](O[Si](C)(C)C(C)(C)C)CC(C)(C)C2]

Obtained by starting from (S)-(5-(tert-butyldimethylsilyloxy)-4-cyclopentenyl-2-isopropyl-7,7-dimethyl-5,6,7,8-tetrahydroquinolin-3-yl)methanol.
Mass spectrometry (ESI$^+$): m/z=428 [M+H]$^+$
HPLC (Method 8): Retention time=3.82 min.
R$_f$-value: 0.19 (silica gel, cyclohexane/dichloromethane 6:4)

(4) (S)-5'-(tert-butyldimethylsilyloxy)-4'-iodo-2'-isopropyl-6',8'-dihydro-5'H-spiro[cyclobutane-1,7'-quinoline]-3'-carbaldehyde

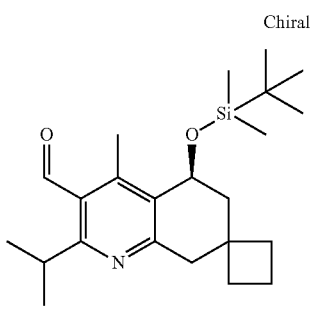 [SMILES: Cc1c(C=O)c(C(C)C)nc2c1[C@@H](O[Si](C)(C)C(C)(C)C)CC1(CCC1)C2]

Obtained by starting from (S)-(5'-(tert-butyldimethylsilyloxy)-4'-iodo-2'-isopropyl-6',8'-dihydro-5'H-spiro[cyclobutane-1,7'-quinoline]-3'-yl)methanol.
Mass spectrometry (ESI$^+$): m/z=500 [M+H]$^+$
HPLC (Method 20): Retention time=4.36 min.

(5) (S)-5-(tert-butyldimethylsilyloxy)-2-cyclobutyl-4-iodo-7,7-dimethyl-5,6,7,8-tetrahydroquinoline-3-carbaldehyde

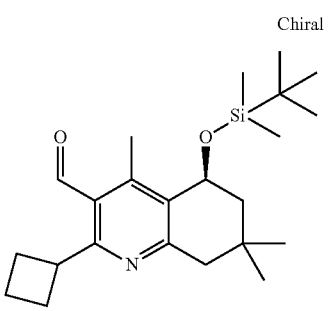 [SMILES: Cc1c(C=O)c(C2CCC2)nc2c1[C@@H](O[Si](C)(C)C(C)(C)C)CC(C)(C)C2]

Obtained by starting from (S)-(5-(tert-butyldimethylsilyloxy)-2-cyclobutyl-4-iodo-7,7-dimethyl-5,6,7,8-tetrahydroquinolin-3-yl)methanol.
Mass spectrometry (ESI$^+$): m/z=500 [M+H]$^+$
R$_f$-value: 0.83 (silica gel, cyclohexane/ethylacetate 9:1)

(6) (S)-5-(tert-butyldimethylsilyloxy)-2-ethyl-4-iodo-7,7-dimethyl-5,6,7,8-tetrahydroquinoline-3-carbaldehyde

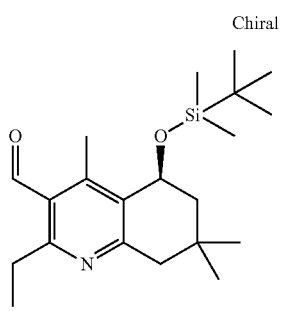 [SMILES: CCc1nc2c(c(C)c1C=O)[C@@H](O[Si](C)(C)C(C)(C)C)CC(C)(C)C2]

Obtained by starting from (S)-(5-(tert-butyldimethylsilyloxy)-2-ethyl-4-iodo-7,7-dimethyl-5,6,7,8-tetrahydroquinolin-3-yl)methanol.
Mass spectrometry (ESI$^+$): m/z=474 [M+H]$^+$
HPLC (Method 20): Retention time=4.04 min.

(7) (S)-ethyl 4-(5-(tert-butyldimethylsilyloxy)-4-cyclopentenyl-2-isopropyl-7,7-dimethyl-5,6,7,8-tetrahydroquinoline-3-carbonyl)benzoate

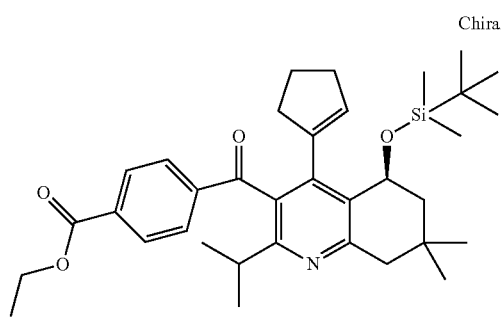

Obtained by starting from ethyl 4-((S)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)benzoate.
Mass spectrometry (ESI$^+$): m/z=576 [M+H]$^+$
R$_f$-value: 0.7 (silica gel, cyclohexane/ethylacetate 9:1)

(8) (S)-5-(tert-butyldimethylsilyloxy)-4-(3,6-dihydro-2H-pyran-4-yl)-2-isopropyl-7,7-dimethyl-5,6,7,8-tetrahydroquinoline-3-carbaldehyde

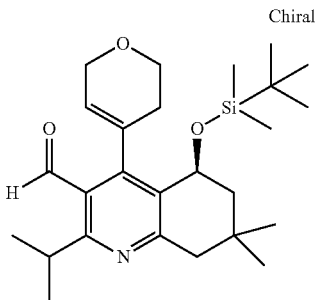 [SMILES: CC(C)c1nc2c(c(C3=CCOCC3)c1C=O)[C@@H](O[Si](C)(C)C(C)(C)C)CC(C)(C)C2]

Obtained by starting from (S)-(5-(tert-butyldimethylsilyloxy)-4-(3,6-dihydro-2H-pyran-4-yl)-2-isopropyl-7,7-dimethyl-5,6,7,8-tetrahydroquinolin-3-yl)methanol.
Mass spectrometry (ESI$^+$): m/z=444 [M+H]$^+$
HPLC (Method 24): Retention time=1.776 min.

(9) ((S)-5'-(tert-butyldimethylsilyloxy)-4'-iodo-2'-isopropyl-6',8'-dihydro-5'H-spiro[cyclopentane-1,7'-quinoline]-3'-carbaldehyde

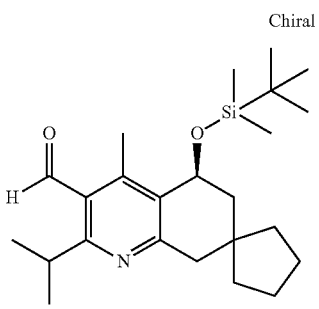

Obtained by starting from (S)-(5'-(tert-butyldimethylsilyloxy)-4'-iodo-2'-isopropyl-6',8'-dihydro-5'H-spiro[cyclopentane-1,7'-quinoline]-3'-ylmethanol.
Mass spectrometry (ESI$^+$): m/z=514 [M+H]$^+$
HPLC (Method 4): Retention time=3.34 min.

(10) (S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-carbaldehyde

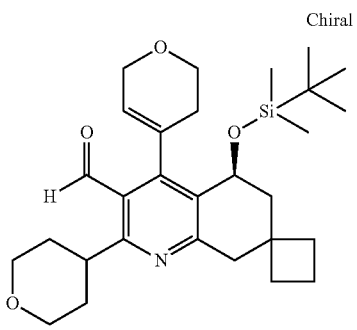 [SMILES: CC(C)(C)[Si](C)(C)O[C@H]1CC2(CCC2)Cc2nc(C3CCOCC3)c(C=O)c(C3=CCOCC3)c21]

Obtained by starting from (S)-(5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3-ylmethanol.
Mass spectrometry (ESI$^+$): m/z=498 [M+H]$^+$
HPLC (Method 7): Retention time=1.931 min.

(11) (S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinoline-3-carbaldehyde

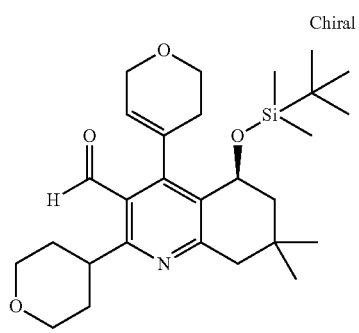 [SMILES: CC1(C)Cc2nc(C3CCOCC3)c(C=O)c(C3=CCOCC3)c2[C@@H](O[Si](C)(C)C(C)(C)C)C1]

Obtained by starting from (S)-(5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)methanol.
Mass spectrometry (ESI$^+$): m/z=486 [M+H]$^+$
HPLC (Method 7): Retention time=1.898 min.

(12) (S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-carbaldehyde

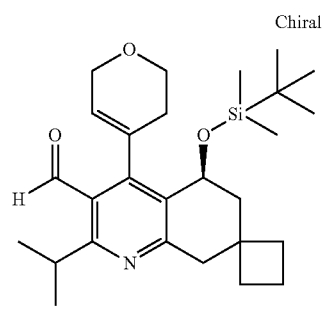

Obtained by starting from (S)-(5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)methanol.
Mass spectrometry (ESI$^+$): m/z=456 [M+H]$^+$
HPLC (Method 2): Retention time=2.771 min.

133

(13) 1-((3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-yl)ethanone

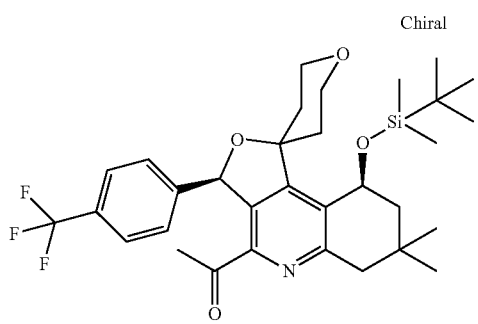 [SMILES: CC(=O)c1nc2c(c3c1[C@@H](c1ccc(C(F)(F)F)cc1)OC31CCOCC1)[C@@H](O[Si](C)(C)C(C)(C)C)CC(C)(C)C2]

Obtained by starting from 1-((3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-ylethanol.

Mass spectrometry (ESI$^+$): m/z=590 [M+H]$^+$

HPLC (Method 29): Retention time=1.618 min.

(14) (3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-carbaldehyde

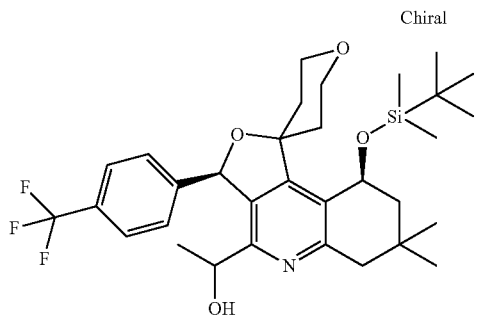 [SMILES: CC(O)c1nc2c(c3c1[C@@H](c1ccc(C(F)(F)F)cc1)OC31CCOCC1)[C@@H](O[Si](C)(C)C(C)(C)C)CC(C)(C)C2]

Obtained by starting from (3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-carbaldehyde. The reaction is run for 1.5 hours at −0° C.

Mass spectrometry (ESI$^+$): m/z=576 [M+H]$^+$

HPLC (Method 29): Retention time=1.582 min.

134

Example X

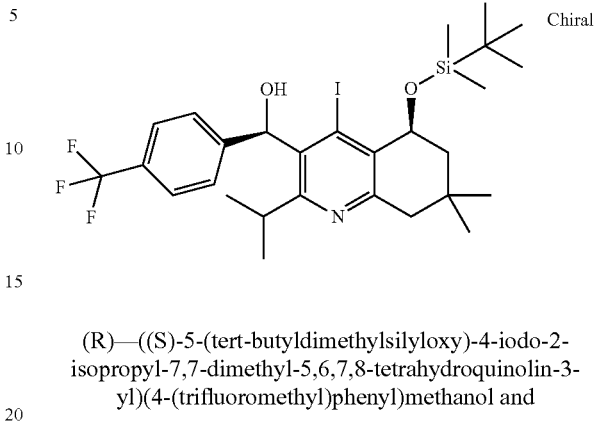

(R)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methanol and

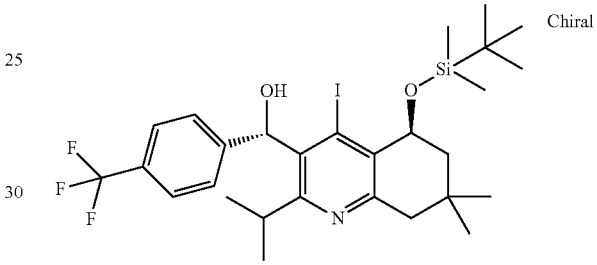

(S)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methanol 1.1 ml 4-iodobenzotrifluoride are dissolved in 60 ml tetrahydrofurane and cooled to −20° C. 3.7 ml of a 2 M solution of isopropylmagnesium chloride in tetrahydrofurane are added dropwise and the solution is stirred for further 5 hours. Then the solution is cooled to −40° C. and 1.17 g (S)-5-(tert-butyldimethylsilyloxy)-4-iodo-2-isopropyl-7,7-dimethyl-5,6,7,8-tetrahydroquinoline-3-carbaldehyde in 5 ml tetrahydrofurane are added dropwise. The mixture is stirred for 12 hours while warming to room temperature. Then it is cooled to 0° C., 10 ml methanol are added and it is stirred for 30 minutes. The solvents are evaporated in vacuo and the residue is chromatographed on silica gel (cyclohexane/ethylacetate 95:5 to 80:20).

(R)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methanol:

Yield: 496 mg (33% of theory)

Mass spectrometry (ESI$^+$): m/z=634 [M+H]$^+$

HPLC (Method 1): Retention time=5.195 min.

R$_f$-value: 0.62 (silica gel, petrole ether/ethylacetate 4:1) and (S)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methan:

782 mg (51% of theory) of

Mass spectrometry (ESI$^+$): m/z=634 [M+H]$^+$

HPLC (Method 1): Retention time=5.256 min.

R$_f$-value: 0.56 (silica gel, petrole ether/ethylacetate 4:1)

Analogously to example X the following compounds are obtained:

(1) (R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol

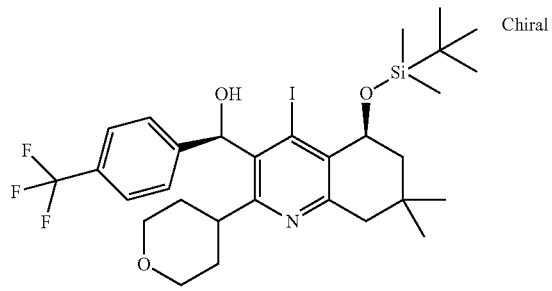 [SMILES: CC1(C)Cc2nc(C3CCOCC3)c([C@H](O)c3ccc(C(F)(F)F)cc3)c(I)c2[C@@H](O[Si](C)(C)C(C)(C)C)C1]

and (S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol

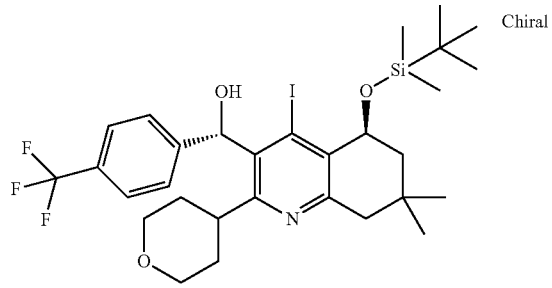 [SMILES: CC1(C)Cc2nc(C3CCOCC3)c([C@@H](O)c3ccc(C(F)(F)F)cc3)c(I)c2[C@@H](O[Si](C)(C)C(C)(C)C)C1]

Obtained by starting from (S)-5-(tert-butyldimethylsilyloxy)-4-iodo-7,7-dimethyl-2-(tetrahydro-2H-pyran-4-yl)-5,6,7,8-tetrahydroquinoline-3-carbaldehyde.

(R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol:

Mass spectrometry (ESI$^+$): m/z=676 [M+H]$^+$

R$_f$-value: 0.49 (silica gel, petrole ether/ethylacetate 4:1)

(S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol:

Mass spectrometry (ESI$^+$): m/z=676 [M+H]$^+$

R$_f$-value: 0.37 (silica gel, petrole ether/ethylacetate 4:1)

(2) (R)—((S)-5'-(tert-butyldimethylsilyloxy)-4'-iodo-2'-isopropyl-6',8'-dihydro-5'H-spiro[cyclobutane-1,7'-quinoline]-3'-yl)(4-(trifluoromethyl)phenyl)methanol

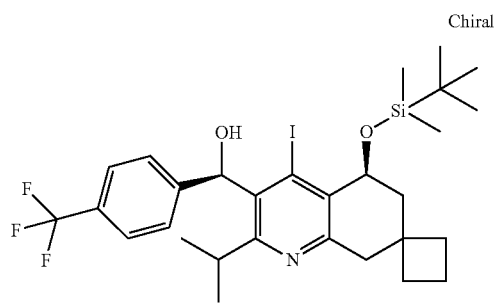 [SMILES: CC(C)c1nc2c(c(I)c1[C@H](O)c1ccc(C(F)(F)F)cc1)[C@@H](O[Si](C)(C)C(C)(C)C)CC1(CCC1)C2]

and (S)—((S)-5'-(tert-butyldimethylsilyloxy)-4'-iodo-2'-isopropyl-6',8'-dihydro-5'H-spiro[cyclobutane-1,7'-quinoline]-3'-yl)(4-(trifluoromethyl)phenyl)methanol

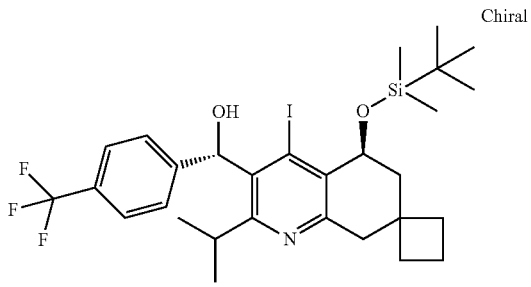 [SMILES: CC(C)c1nc2c(c(I)c1[C@@H](O)c1ccc(C(F)(F)F)cc1)[C@@H](O[Si](C)(C)C(C)(C)C)CC1(CCC1)C2]

Obtained by starting from (S)-5'-(tert-butyldimethylsilyloxy)-4'-iodo-2'-isopropyl-6',8'-dihydro-5'H-spiro[cyclobutane-1,7'-quinoline]-3'-carbaldehyde.

(R)—((S)-5'-(tert-butyldimethylsilyloxy)-4'-iodo-2'-isopropyl-6',8'-dihydro-5'H-spiro[cyclobutane-1,7'-quinoline]-3'-yl)(4-(trifluoromethyl)phenyl)methanol:

Mass spectrometry (ESI$^+$): m/z=646 [M+H]$^+$

HPLC (Method 20): Retention time=4.07 min.

(S)—((S)-5'-(tert-butyldimethylsilyloxy)-4'-iodo-2'-isopropyl-6',8'-dihydro-5'H-spiro[cyclobutane-1,7'-quinoline]-3'-yl)(4-(trifluoromethyl)phenyl)methanol:

Mass spectrometry (ESI$^+$): m/z=646 [M+H]$^+$

HPLC (Method 20): Retention time=4.08 min.

137

(3) (R)—((S)-5-(tert-butyldimethylsilyloxy)-4-iodo-2-isopropyl-7,7-dimethyl-5,6,7,8-tetrahydroquinolin-3-yl)(3-fluoro-4-(trifluoromethyl)phenyl)methanol

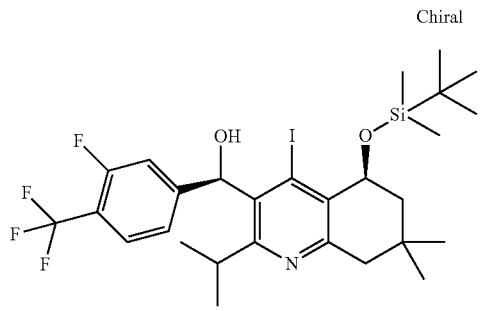 [SMILES: CC(C)c1nc2c(c(I)c1[C@H](O)c1ccc(C(F)(F)F)c(F)c1)[C@@H](O[Si](C)(C)C(C)(C)C)CC(C)(C)C2]

and (S)—((S)-5-(tert-butyldimethylsilyloxy)-4-iodo-2-isopropyl-7,7-dimethyl-5,6,7,8-tetrahydroquinolin-3-yl)(3-fluoro-4-(trifluoromethyl)phenyl)methanol

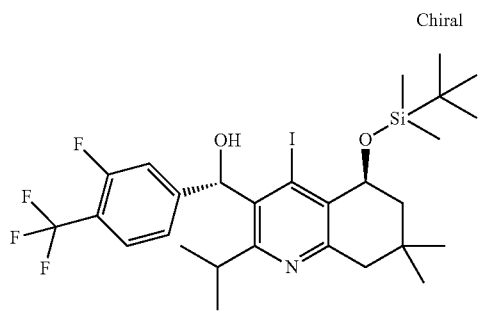 [SMILES: CC(C)c1nc2c(c(I)c1[C@@H](O)c1ccc(C(F)(F)F)c(F)c1)[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 4-bromo-2-fluoro-benzotrifluoride.

(R)—((S)-5-(tert-butyldimethylsilyloxy)-4-iodo-2-isopropyl-7,7-dimethyl-5,6,7,8-tetrahydroquinolin-3-yl)(3-fluoro-4-(trifluoromethyl)phenyl)methanol:

Mass spectrometry (ESI⁺): m/z=652 [M+H]⁺

HPLC (Method 20): Retention time=4.10 min.

(S)—((S)-5-(tert-butyldimethylsilyloxy)-4-iodo-2-isopropyl-7,7-dimethyl-5,6,7,8-tetrahydroquinolin-3-yl)(3-fluoro-4-(trifluoromethyl)phenyl)methanol:

Mass spectrometry (ESI⁺): m/z=652 [M+H]⁺

HPLC (Method 20): Retention time=4.13 min.

138

(4) 4-((R)—((S)-5-(tert-butyldimethylsilyloxy)-4-iodo-2-isopropyl-7,7-dimethyl-5,6,7,8-tetrahydroquinolin-3-yl)(hydroxy)methyl)benzonitrile

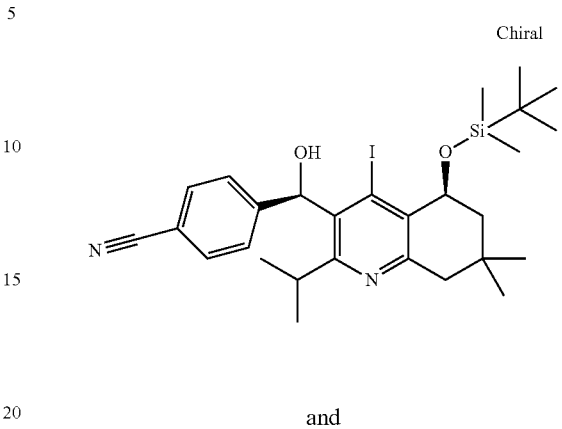

and 4-((S)—((S)-5-(tert-butyldimethylsilyloxy)-4-iodo-2-isopropyl-7,7-dimethyl-5,6,7,8-tetrahydroquinolin-3-yl)(hydroxy)methyl)benzonitrile

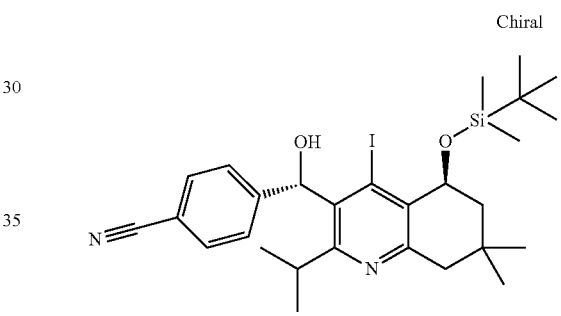

Obtained by starting from (S)-5-(tert-butyldimethylsilyloxy)-4-iodo-2-isopropyl-7,7-dimethyl-5,6,7,8-tetrahydroquinoline-3-carbaldehyde and 4-iodobenzonitrile.

The diastereomers are separated by chromatography on silica gel and are used directly in the next step.

(5) 2-(4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)phenyl)-2-methylpropanenitrile

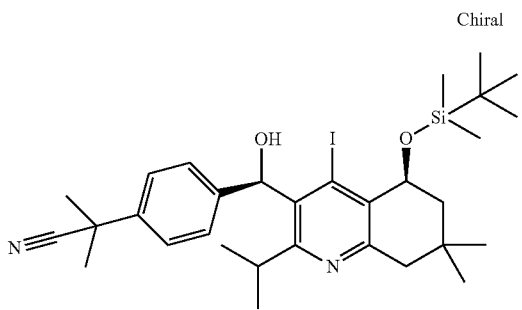 [SMILES: CC(C)c1nc2c(c(I)c1[C@H](O)c1ccc(C(C)(C)C#N)cc1)[C@@H](O[Si](C)(C)C(C)(C)C)CC(C)(C)C2]

2-(4-((S)—((S)-5-(tert-butyldimethylsilyloxy)-4-iodo-2-isopropyl-7,7-dimethyl-5,6,7,8-tetrahydroquinolin-3-yl)(hydroxy)methyl)phenyl)-2-methylpropanenitrile

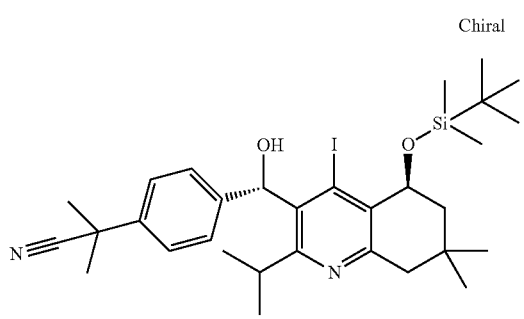 [SMILES: CC(C)c1nc2c(c(I)c1[C@@H](O)c1ccc(C(C)(C)C#N)cc1)[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 2-(4-iodophenyl)-2-methylpropanenitrile. A 1.3 M solution of isopropylmagnesium chloride-lithium chloride complex in tetrahydrofurane is used instead of isopropylmagnesium chloride.

2-(4-((R)—(S)-5-(tert-butyldimethylsilyloxy)-4-cyclopentenyl-2-isopropyl-7,7-dimethyl-5,6,7,8-tetrahydroquinolin-3-yl)(hydroxy)methyl)phenyl)-2-methylpropanenitrile:

Mass spectrometry (ESI+): m/z=633 [M+H]+

$R_f$-value: 0.30 (silica gel, petrole ether/ethylacetate 8:1)

2-(4-((S)—((S)-5-(tert-butyldimethylsilyloxy)-4-iodo-2-isopropyl-7,7-dimethyl-5,6,7,8-tetrahydroquinolin-3-yl)(hydroxy)methyl)phenyl)-2-methylpropanenitrile:

Mass spectrometry (ESI+): m/z=633 [M+H]+

$R_f$-value: 0.24 (silica gel, petrole ether/ethylacetate 8:1)

(6) (R)—((S)-5-(tert-butyldimethylsilyloxy)-4-iodo-2-isopropyl-7,7-dimethyl-5,6,7,8-tetrahydroquinolin-3-yl)(2-tert-butylpyrimidin-5-yl)methanol

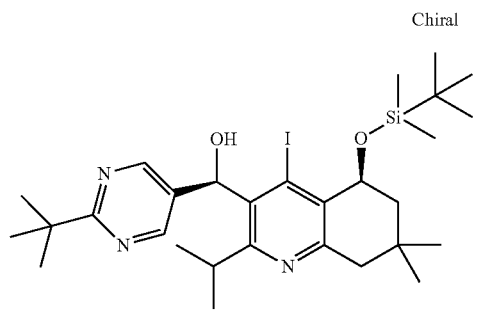 [SMILES: CC(C)c1nc2c(c(I)c1[C@H](O)c1cnc(C(C)(C)C)nc1)[C@@H](O[Si](C)(C)C(C)(C)C)CC(C)(C)C2]

(S)—((S)-5-(tert-butyldimethylsilyloxy)-4-iodo-2-isopropyl-7,7-dimethyl-5,6,7,8-tetrahydroquinolin-3-yl)(2-tert-butylpyrimidin-5-ylmethanol

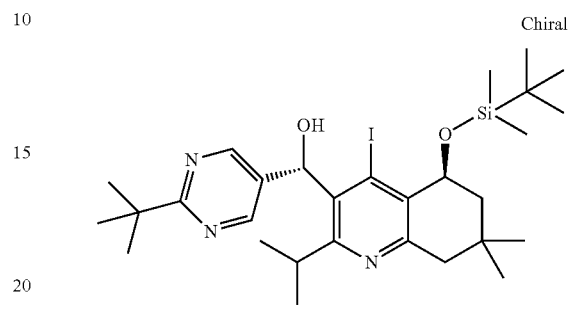

Obtained by starting from 5-bromo-2-tert-butylpyrimidine and (S)-5-(tert-butyldimethylsilyloxy)-4-iodo-2-isopropyl-7,7-dimethyl-5,6,7,8-tetrahydroquinoline-3-carbaldehyde. A 1.3 M solution of isopropylmagnesium chloride-lithium chloride complex in tetrahydrofurane is used instead of isopropylmagnesium chloride.

(R)—((S)-5-(tert-butyldimethylsilyloxy)-4-iodo-2-isopropyl-7,7-dimethyl-5,6,7,8-tetrahydroquinolin-3-yl)(2-tert-butylpyrimidin-5-yl)methanol:

Mass spectrometry (ESI+): m/z=624 [M+H]+

HPLC (Method 10): Retention time=26.06 min.

(S)—((S)-5-(tert-butyldimethylsilyloxy)-4-iodo-2-isopropyl-7,7-dimethyl-5,6,7,8-tetrahydroquinolin-3-yl)(2-tert-butylpyrimidin-5-yl)methanol:

Mass spectrometry (ESI+): m/z=624 [M+H]+

HPLC (Method 10): Retention time=24.93 min.

(7) Ethyl 4-((R)—((S)-5-(tert-butyldimethylsilyloxy)-4-iodo-2-isopropyl-7,7-dimethyl-5,6,7,8-tetrahydroquinolin-3-yl)(hydroxy)methyl)benzoate

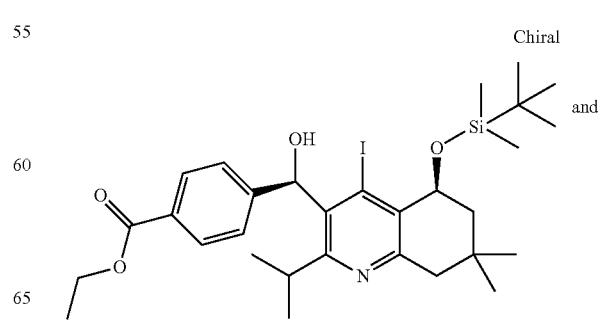

-continued

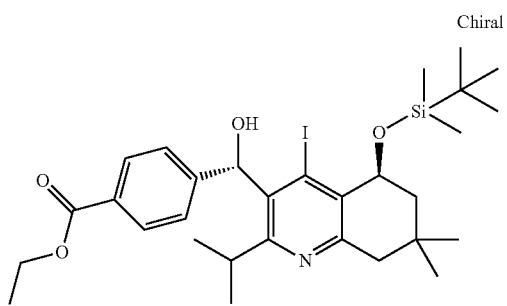

Ethyl 4-((S)—((S)-5-(tert-butyldimethylsilyloxy)-4-iodo-2-isopropyl-7,7-dimethyl-5,6,7,8-tetrahydro-quinolin-3-yl)(hydroxy)methyl)benzoate Obtained by starting from (S)-5-(tert-butyldimethylsilyloxy)-4-iodo-2-isopropyl-7,7-dimethyl-5,6,7,8-tetrahydroquinoline-3-carbaldehyde and ethyl 4-iodobenzoate.

Ethyl 4-((R)—((S)-5-(tert-butyldimethylsilyloxy)-4-iodo-2-isopropyl-7,7-dimethyl-5,6,7,8-tetrahydroquinolin-3-yl)(hydroxy)methyl)benzoate:

Mass spectrometry (ESI$^+$): m/z=638 [M+H]$^+$

R$_f$-value: 0.20 (silica gel, petrole ether/ethylacetate 8:1)

Ethyl 4-((S)—((S)-5-(tert-butyldimethylsilyloxy)-4-iodo-2-isopropyl-7,7-dimethyl-5,6,7,8-tetrahydroquinolin-3-yl)(hydroxy)methyl)benzoate:

Mass spectrometry (ESI$^+$): m/z=638 [M+H]$^+$

R$_f$-value: 0.17 (silica gel, petrole ether/ethylacetate 8:1)

(8) (R)—((S)-5-(tert-butyldimethylsilyloxy)-4-iodo-2-isopropyl-7,7-dimethyl-5,6,7,8-tetrahydroquinolin-3-yl)(4-isobutylphenyl)methanol

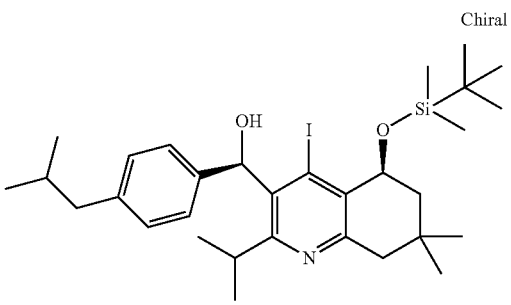 [SMILES: CC(C)Cc1ccc([C@@H](O)c2c(C(C)C)nc3c(c2I)[C@@H](O[Si](C)(C)C(C)(C)C)CC(C)(C)C3)cc1]

and (S)—((S)-5-(tert-butyldimethylsilyloxy)-4-iodo-2-isopropyl-7,7-dimethyl-5,6,7,8-tetrahydroquinolin-3-yl)(4-isobutylphenyl)methanol

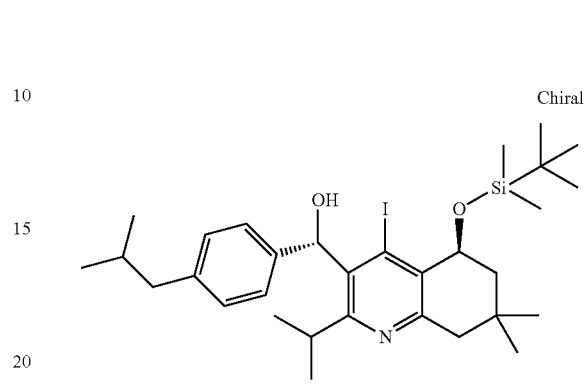

Obtained by starting from (S)-5-(tert-butyldimethylsilyloxy)-4-iodo-2-isopropyl-7,7-dimethyl-5,6,7,8-tetrahydroquinoline-3-carbaldehyde and 1-iodo-4-isobutylbenzene.

(R)—((S)-5-(tert-butyldimethylsilyloxy)-4-iodo-2-isopropyl-7,7-dimethyl-5,6,7,8-tetrahydroquinolin-3-yl)(4-isobutylphenyl)methanol:

Mass spectrometry (ESI$^+$): m/z=622 [M+H]$^+$

R$_f$-value: 0.55 (silica gel, cyclohexane/ethylacetate 9:1)

(S)—((S)-5-(tert-butyldimethylsilyloxy)-4-iodo-2-isopropyl-7,7-dimethyl-5,6,7,8-tetrahydroquinolin-3-yl)(4-isobutylphenyl)methanol:

Mass spectrometry (ESI$^+$): m/z=622 [M+H]$^+$

R$_f$-value: 0.45 (silica gel, cyclohexane/ethylacetate 9:1)

(9) (R)—((S)-5-(tert-butyldimethylsilyloxy)-2-cyclobutyl-4-iodo-7,7-dimethyl-5,6,7,8-tetrahydroquinolin-3-yl)(4-(trifluoromethyl)phenyl)methanol

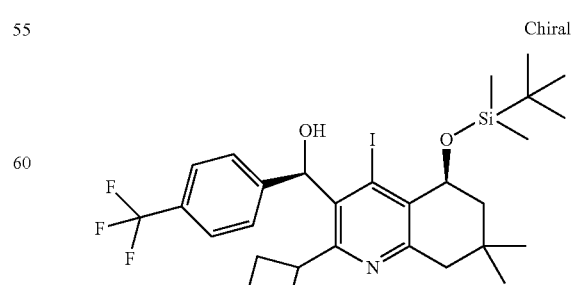

143 and (S)—((S)-5-(tert-butyldimethylsilyloxy)-2-cyclobutyl-4-iodo-7,7-dimethyl-5,6,7,8-tetrahydroquinolin-3-yl)(4-(trifluoromethyl)phenyl)methanol

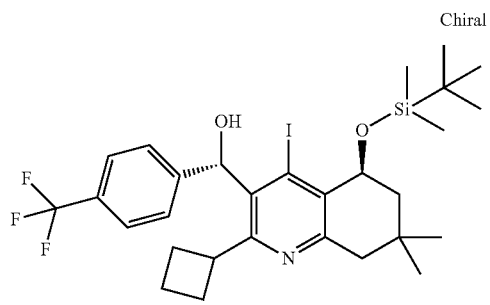 [SMILES: CC1(C)Cc2nc(C3CCC3)c([C@@H](O)c3ccc(C(F)(F)F)cc3)c(I)c2[C@@H](O[Si](C)(C)C(C)(C)C)C1]

Obtained by starting from (S)-5-(tert-butyldimethylsilyloxy)-2-cyclobutyl-4-iodo-7,7-dimethyl-5,6,7,8-tetrahydroquinoline-3-carbaldehyde.

(R)—((S)-5-(tert-butyldimethylsilyloxy)-2-cyclobutyl-4-iodo-7,7-dimethyl-5,6,7,8-tetrahydroquinolin-3-yl)(4-(trifluoromethyl)phenyl)methanol:

Mass spectrometry (ESI$^+$): m/z=646 [M+H]$^+$

R$_f$-value: 0.61 (silica gel, cyclohexane/ethylacetate 9:1)

(S)—((S)-5-(tert-butyldimethylsilyloxy)-2-cyclobutyl-4-iodo-7,7-dimethyl-5,6,7,8-tetrahydroquinolin-3-yl)(4-(trifluoromethyl)phenyl)methanol Mass spectrometry (ESI$^+$): m/z=646 [M+H]$^+$ R$_f$-value: 0.56 (silica gel, cyclohexane/ethylacetate 9:1)

(10) (R)—((S)-5-(tert-butyldimethylsilyloxy)-4-iodo-2-isopropyl-7,7-dimethyl-5,6,7,8-tetrahydroquinolin-3-yl)(4-(1,1-difluoroethyl)phenyl)methanol

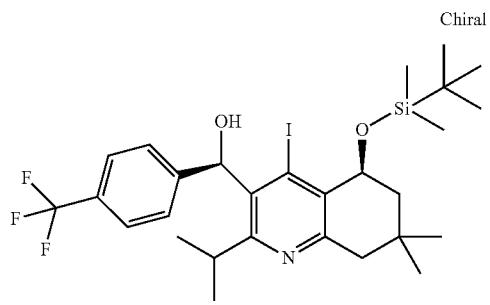 [SMILES: CC(C)c1nc2c(c(I)c1[C@H](O)c1ccc(C(F)(F)F)cc1)[C@@H](O[Si](C)(C)C(C)(C)C)CC(C)(C)C2]

144 and (S)—((S)-5-(tert-butyldimethylsilyloxy)-4-iodo-2-isopropyl-7,7-dimethyl-5,6,7,8-tetrahydroquinolin-3-yl)(4-(1,1-difluoroethyl)phenyl)methanol

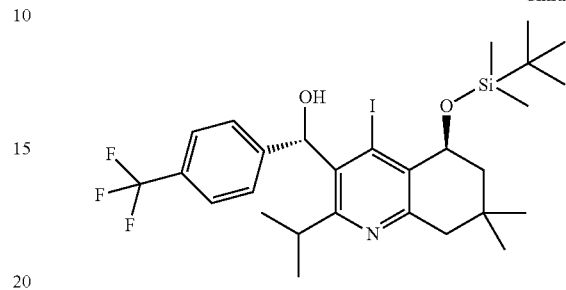

Obtained by starting from (S)-5-(tert-butyldimethylsilyloxy)-4-iodo-2-isopropyl-7,7-dimethyl-5,6,7,8-tetrahydroquinoline-3-carbaldehyde and 1-(1,1-difluoroethyl)-4-iodobenzene.

(R)—((S)-5-(tert-butyldimethylsilyloxy)-4-iodo-2-isopropyl-7,7-dimethyl-5,6,7,8-tetrahydroquinolin-3-yl)(4-(1,1-difluoroethyl)phenyl)methanol:

Mass spectrometry (ESI$^+$): m/z=630 [M+H]$^+$

HPLC (Method 4): Retention time=2.912 min.

(S)—((S)-5-(tert-butyldimethylsilyloxy)-4-iodo-2-isopropyl-7,7-dimethyl-5,6,7,8-tetrahydroquinolin-3-yl)(4-(1,1-difluoroethyl)phenyl)methanol:

Mass spectrometry (ESI$^+$): m/z=630 [M+H]$^+$

HPLC (Method 4): Retention time=2.912 min.

(11) (R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-tert-butylphenyl)methanol

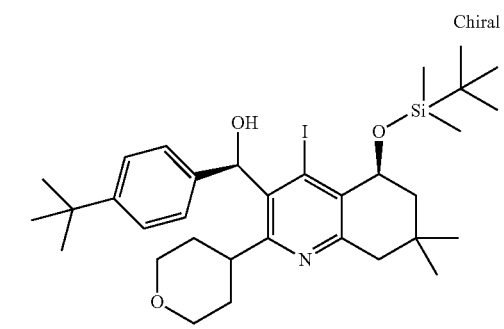 [SMILES: CC1(C)Cc2nc(C3CCOCC3)c([C@H](O)c3ccc(C(C)(C)C)cc3)c(I)c2[C@@H](O[Si](C)(C)C(C)(C)C)C1]

145 and (S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-tert-butylphenyl)methanol

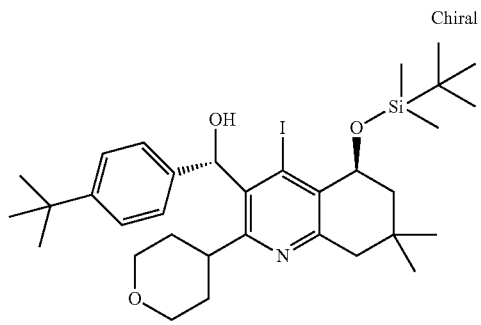 [SMILES: CC1(C)Cc2nc(C3CCOCC3)c([C@@H](O)c3ccc(C(C)(C)C)cc3)c(I)c2[C@@H](O[Si](C)(C)C(C)(C)C)C1]

Obtained by starting from (S)-5-(tert-butyldimethylsilyloxy)-4-iodo-7,7-dimethyl-2-(tetrahydro-2H-pyran-4-yl)-5,6,7,8-tetrahydroquinoline-3-carbaldehyde and 4-tert.-butyl-iodo-benzene.

(R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-tert-butylphenyl)methanol:

Mass spectrometry (ESI$^+$): m/z=664 [M+H]$^+$

R$_f$-value: 0.47 (silica gel, petrole ether/ethylacetate 4:1)

(S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-tert-butylphenyl)methanol:

Mass spectrometry (ESI$^+$): m/z=664 [M+H]$^+$

R$_f$-value: 0.39 (silica gel, petrole ether/ethylacetate 4:1)

(12) (R)—((S)-5-(tert-butyldimethylsilyloxy)-2-ethyl-4-iodo-7,7-dimethyl-5,6,7,8-tetrahydroquinolin-3-yl)(4-(trifluoromethyl)phenyl)methanol

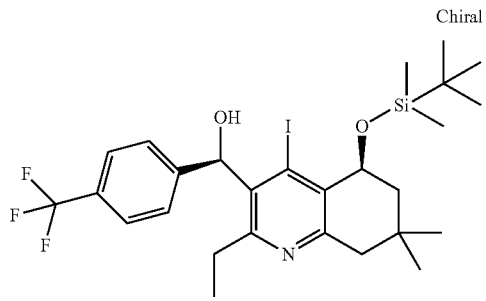 [SMILES: CCc1nc2c(c(I)c1[C@H](O)c1ccc(C(F)(F)F)cc1)[C@@H](O[Si](C)(C)C(C)(C)C)CC(C)(C)C2]

146 and (S)—((S)-5-(tert-butyldimethylsilyloxy)-2-ethyl-4-iodo-7,7-dimethyl-5,6,7,8-tetrahydroquinolin-3-yl)(4-(trifluoromethyl)phenyl)methanol

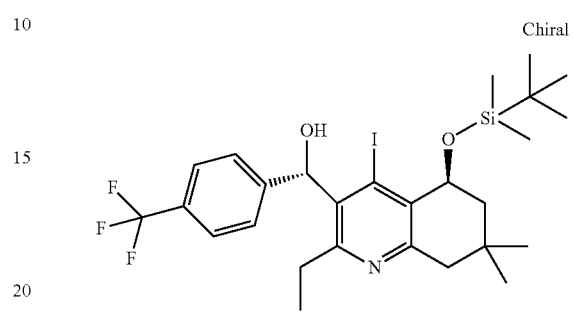

Obtained by starting from (S)-5-(tert-butyldimethylsilyloxy)-2-ethyl-4-iodo-7,7-dimethyl-5,6,7,8-tetrahydroquinoline-3-carbaldehyde.

(R)—((S)-5-(tert-butyldimethylsilyloxy)-2-ethyl-4-iodo-7,7-dimethyl-5,6,7,8-tetrahydroquinolin-3-yl)(4-(trifluoromethyl)phenyl)methanol:

Mass spectrometry (ESI$^+$): m/z=620 [M+H]$^+$

HPLC (Method 20): Retention time=3.75 min.

(S)—((S)-5-(tert-butyldimethylsilyloxy)-2-ethyl-4-iodo-7,7-dimethyl-5,6,7,8-tetrahydroquinolin-3-yl)(4-(trifluoromethyl)phenyl)methanol Mass spectrometry (ESI$^+$): m/z=620 [M+H]$^+$ HPLC (Method 20): Retention time=3.83 min.

(13) (R)—((S)-5-(tert-butyldimethylsilyloxy)-4-iodo-2-isopropyl-7,7-dimethyl-5,6,7,8-tetrahydroquinolin-3-yl)(3,5-difluoro-4-(trimethylsilyl)phenyl)methanol

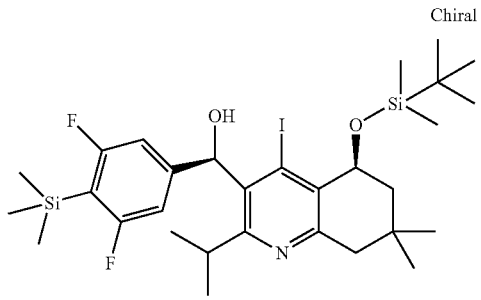 [SMILES: CC(C)c1nc2c(c(I)c1[C@H](O)c1cc(F)c([Si](C)(C)C)c(F)c1)[C@@H](O[Si](C)(C)C(C)(C)C)CC(C)(C)C2]

(S)—((S)-5-(tert-butyldimethylsilyloxy)-4-iodo-2-isopropyl-7,7-dimethyl-5,6,7,8-tetrahydroquinolin-3-yl)(3,5-difluoro-4-(trimethylsilyl)phenyl)methanol (S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol

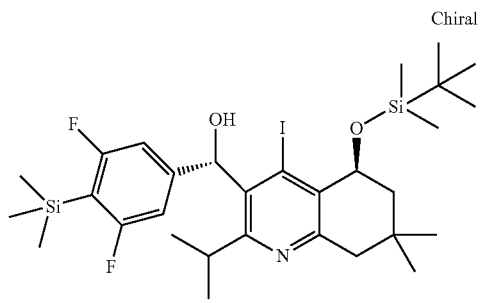 [SMILES: CC(C)c1nc2c(c(I)c1[C@@H](O)c1cc(F)c([Si](C)(C)C)c(F)c1)[C@@H](O[Si](C)(C)C(C)(C)C)CC(C)(C)C2]

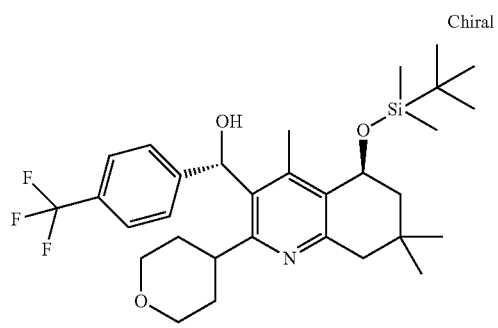

Obtained by starting from (S)-5-(tert-butyldimethylsilyloxy)-4-iodo-2-isopropyl-7,7-dimethyl-5,6,7,8-tetrahydroquinoline-3-carbaldehyde and (4-bromo-2,6-difluorophenyl)trimethylsilane. Isopropylmagnesiumchloride-lithium chloride-complex (1.3 M in tetrahydrofurane) is used instead of isopropylmagnesium chloride. The bromine-magnesium exchange is performed at room temperature for 18 hours and at 40° C. for 4 hours.

(R)—((S)-5-(tert-butyldimethylsilyloxy)-4-iodo-2-isopropyl-7,7-dimethyl-5,6,7,8-tetrahydroquinolin-3-yl)(3,5-difluoro-4-(trimethylsilyl)phenyl)methanol:

Mass spectrometry (ESI$^+$): m/z=674 [M+H]$^+$

HPLC (Method 4): Retention time=3.395 min.

(S)—((S)-5-(tert-butyldimethylsilyloxy)-4-iodo-2-isopropyl-7,7-dimethyl-5,6,7,8-tetrahydroquinolin-3-yl)(3,5-difluoro-4-(trimethylsilyl)phenyl)methanol:

Mass spectrometry (ESI$^+$): m/z=674 [M+H]$^+$

HPLC (Method 4): Retention time=3.307 min.

Obtained by starting from (S)-5-(tert-butyldimethylsilyloxy)-4-iodo-7,7-dimethyl-2-(tetrahydro-2H-pyran-4-yl)-5,6,7,8-tetrahydroquinoline-3-carbaldehyde.

(R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol:

$R_f$-value: 0.45 (silica gel, petrole ether/ethylacetate 4:1)

(S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol:

$R_f$-value: 0.31 (silica gel, petrole ether/ethylacetate 4:1)

(14) (R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol

(15) (R)—((S)-5-(tert-butyldimethylsilyloxy)-4-iodo-2-isopropyl-7,7-dimethyl-5,6,7,8-tetrahydroquinolin-3-yl)(3-(trifluoromethyl)phenyl)methanol

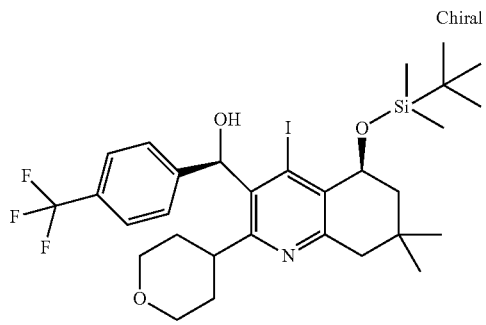 [SMILES: CC1(C)Cc2nc(C3CCOCC3)c([C@H](O)c3ccc(C(F)(F)F)cc3)c(I)c2[C@@H](O[Si](C)(C)C(C)(C)C)C1]

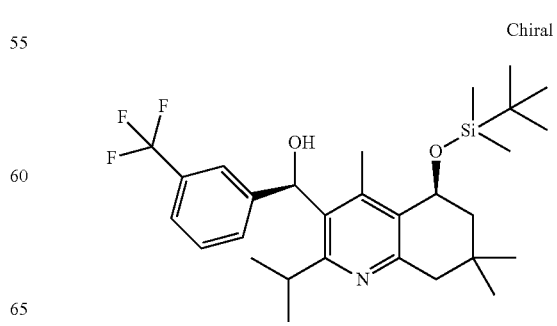

149

(S)—((S)-5-(tert-butyldimethylsilyloxy)-4-iodo-2-isopropyl-7,7-dimethyl-5,6,7,8-tetrahydroquinolin-3-yl)(3-(trifluoromethyl)phenyl)methanol

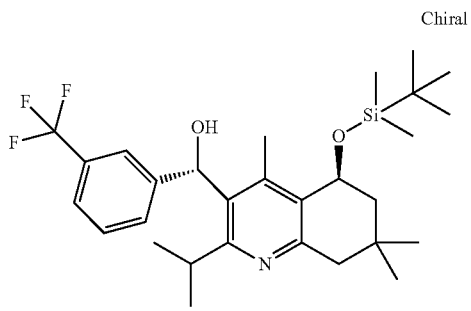 [SMILES: Cc1c([C@@H](O)c2cccc(C(F)(F)F)c2)c(C(C)C)nc2c1[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 1-iodo-3-(trifluoromethyl)benzene.

(R)—((S)-5-(tert-butyldimethylsilyloxy)-4-iodo-2-isopropyl-7,7-dimethyl-5,6,7,8-tetrahydroquinolin-3-yl)(3-(trifluoromethyl)phenyl)methanol:

$R_f$-value: 0.5 (silica gel, petrole ether/ethylacetate 16:1)

(S)—((S)-5-(tert-butyldimethylsilyloxy)-4-iodo-2-isopropyl-7,7-dimethyl-5,6,7,8-tetrahydroquinolin-3-yl)(3-(trifluoromethyl)phenyl)methanol:

$R_f$-value: 0.3 (silica gel, petrole ether/ethylacetate 16:1)

(16) (R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol

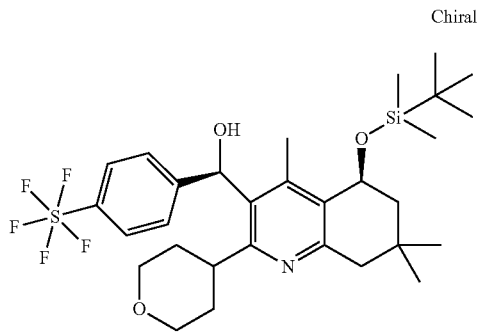 [SMILES: Cc1c([C@H](O)c2ccc(S(F)(F)(F)(F)F)cc2)c(C2CCOCC2)nc2c1[C@@H](O[Si](C)(C)C(C)(C)C)CC(C)(C)C2]

150

(S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol

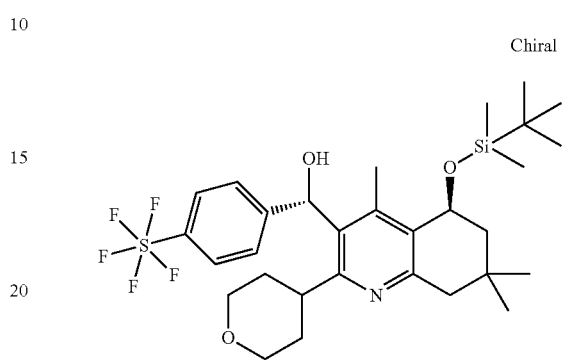

Obtained by starting from (S)-5-(tert-butyldimethylsilyloxy)-4-iodo-7,7-dimethyl-2-(tetrahydro-2H-pyran-4-yl)-5,6,7,8-tetrahydroquinoline-3-carbaldehyde and 1-iodo-4-pentafluorosulfanyl-benzene.

(R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol:

Mass spectrometry (ESI$^+$): m/z=734 [M+H]$^+$ $R_f$-value: 0.25 (silica gel, petrole ether/ethylacetate 4:1)

(S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol:

Mass spectrometry (ESI$^+$): m/z=734 [M+H]$^+$ $R_f$-value: 0.35 (silica gel, petrole ether/ethylacetate 4:1)

(17) (R)—((S)-5'-(tert-butyldimethylsilyloxy)-4'-iodo-2'-isopropyl-6',8'-dihydro-5'H-spiro[cyclopentane-1,7'-quinoline]-3'-yl)(4-(trifluoromethyl)phenyl)methanol

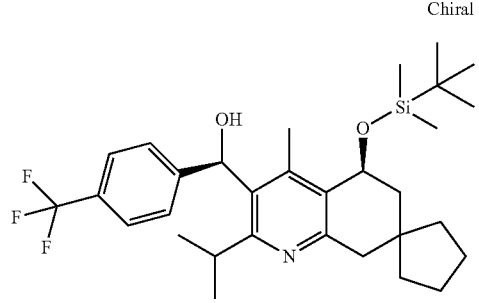 [SMILES: Cc1c([C@H](O)c2ccc(C(F)(F)F)cc2)c(C(C)C)nc2c1[C@@H](O[Si](C)(C)C(C)(C)C)CC1(CCCC1)C2]

151
and (S)—((S)-5'-(tert-butyldimethylsilyloxy)-4'-iodo-2'-isopropyl-6',8'-dihydro-5'H-spiro[cyclopentane-1,7'-quinoline]-3-yl)(4-(trifluoromethyl)phenyl)methanol

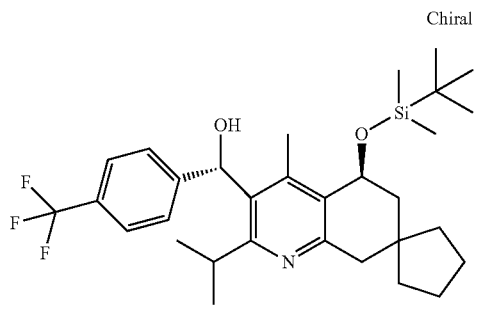 [SMILES: Cc1c([C@@H](O)c2ccc(C(F)(F)F)cc2)c(C(C)C)nc2c1[C@@H](O[Si](C)(C)C(C)(C)C)CC1(CCCC1)C2]

152
and (S)—((S)-5-(tert-butyldimethylsilyloxy)-4-iodo-2-isopropyl-7,7-dimethyl-5,6,7,8-tetrahydroquinolin-3-yl)(4-isopropoxyphenyl)methanol

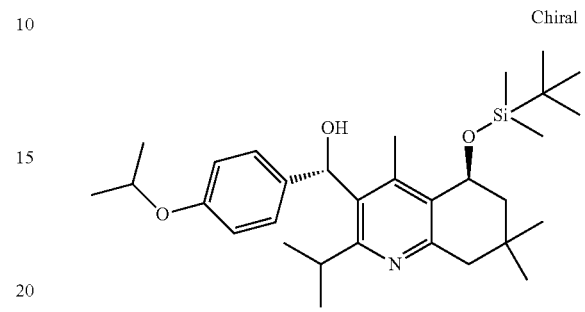

Obtained by starting from (S)-5'-(tert-butyldimethylsilyloxy)-4'-iodo-2'-isopropyl-6',8'-dihydro-5'H-spiro[cyclopentane-1,7'-quinoline]-3'-carbaldehyde. A 1.3 M solution of isopropylmagnesium chloride-lithium chloride-complex in tetrahydrofurane is used instead of a 2 M solution of isopropylmagnesium chloride in tetrahydrofurane.

(R)—((S)-5-(tert-butyldimethylsilyloxy)-4-iodo-2-isopropyl-7,7-(butan-1,4-diyl)-5,6,7,8-tetrahydroquinolin-3-yl)(4-(trifluoromethyl)phenyl)methanol:

Mass spectrometry (ESI$^+$): m/z=660 [M+H]$^+$

HPLC (Method 4): Retention time=3.32 min.

(S)—((S)-5-(tert-butyldimethylsilyloxy)-4-iodo-2-isopropyl-7,7-(butan-1,4-diyl)-5,6,7,8-tetrahydroquinolin-3-yl)(4-(trifluoromethyl)phenyl)methanol:

Mass spectrometry (ESI$^+$): m/z=660 [M+H]$^+$

HPLC (Method 4: Retention time=3.30 min.

(18) (R)—((S)-5-(tert-butyldimethylsilyloxy)-4-iodo-2-isopropyl-7,7-dimethyl-5,6,7,8-tetrahydroquinolin-3-yl)(4-isopropoxyphenyl)methanol Obtained by starting from (S)-5-(tert-butyldimethylsilyloxy)-4-iodo-2-isopropyl-7,7-dimethyl-5,6,7,8-tetrahydroquinoline-3-carbaldehyde and 1-iodo-4-isopropoxybenzene. A 2 M solution of caesium carbonate in water is used instead caesium fluoride. A 1.3 M solution of isopropylmagnesium chloride-lithium chloride-complex in tetrahydrofurane is used instead of a 2 M solution of isopropylmagnesium chloride in tetrahydrofurane.

(R)—((S)-5-(tert-butyldimethylsilyloxy)-4-iodo-2-isopropyl-7,7-dimethyl-5,6,7,8-tetrahydroquinolin-3-yl)(4-isopropoxyphenyl)methanol:

Mass spectrometry (ESI$^+$): m/z=624 [M+H]$^+$ $R_f$-value: 0.5 (silica gel, petrole ether/ethylacetate 9:1)

(S)—((S)-5-(tert-butyldimethylsilyloxy)-4-iodo-2-isopropyl-7,7-dimethyl-5,6,7,8-tetrahydroquinolin-3-yl)(4-isopropoxyphenyl)methanol:

Mass spectrometry (ESI$^+$): m/z=624 [M+H]$^+$ $R_f$-value: 0.4 (silica gel, petrole ether/ethylacetate 9:1)

(19) (R)—((S)-5-(tert-butyldimethylsilyloxy)-4-iodo-2-isopropyl-7,7-dimethyl-5,6,7,8-tetrahydroquinolin-3-yl)(4-(pentafluorosulfanyl)phenyl)methanol

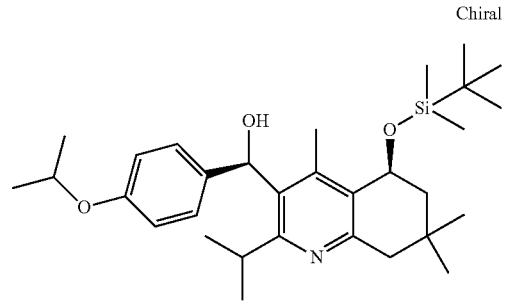 [SMILES: Cc1c([C@H](O)c2ccc(OC(C)C)cc2)c(C(C)C)nc2c1[C@@H](O[Si](C)(C)C(C)(C)C)CC(C)(C)C2]

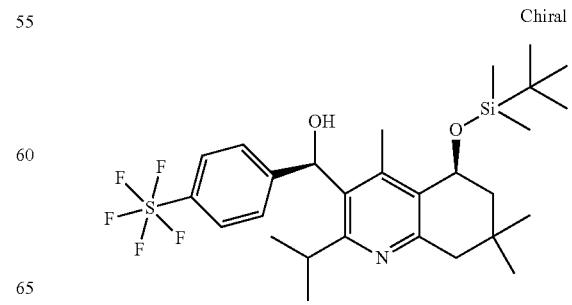

and (S)—((S)-5-(tert-butyldimethylsilyloxy)-4-iodo-2-isopropyl-7,7-dimethyl-5,6,7,8-tetrahydroquinolin-3-yl)(4-(pentafluorosulfanyl)methanol

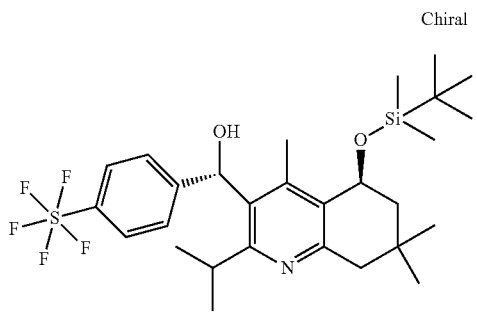 [SMILES: Cc1c([C@@H](O)c2ccc(S(F)(F)(F)(F)F)cc2)c(C(C)C)nc2c1[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 1-iodo-4-pentafluorosulfanylbenzene. A 1.3 M solution of isopropylmagnesium chloride-lithium chloride-complex in tetrahydrofurane is used instead of a 2 M solution of isopropylmagnesium chloride in tetrahydrofurane.

(R)—((S)-5-(tert-butyldimethylsilyloxy)-4-iodo-2-isopropyl-7,7-dimethyl-5,6,7,8-tetrahydroquinolin-3-yl)(4-(pentafluorosulfanyl)phenyl)methanol:

Mass spectrometry (ESI$^+$): m/z=692 [M+H]$^+$

HPLC (Method 7): Retention time=1.951 min.

(S)—((S)-5-(tert-butyldimethylsilyloxy)-4-iodo-2-isopropyl-7,7-dimethyl-5,6,7,8-tetrahydroquinolin-3-yl)(4-(pentafluorosulfanyl)methanol:

Mass spectrometry (ESI$^+$): m/z=692 [M+H]$^+$

HPLC (Method 7): Retention time=1.953 min.

(20) ((S)-5-(tert-butyldimethylsilyloxy)-4-iodo-2-isopropyl-7,7-dimethyl-5,6,7,8-tetrahydroquinolin-3-yl)(4-(3-methyloxetan-3-yl)phenyl)methanol

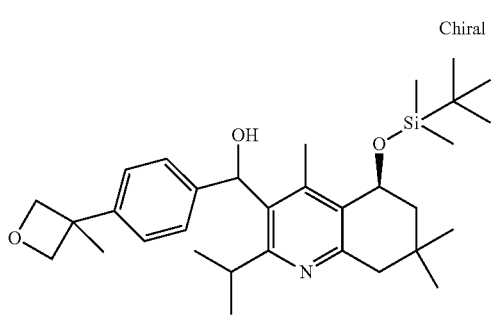 [SMILES: Cc1c(C(O)c2ccc(C3(C)COC3)cc2)c(C(C)C)nc2c1[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 3-(4-iodophenyl)-3-methyloxetane.

Mass spectrometry (ESI$^+$): m/z=636 [M+H]$^+$

HPLC (Method 24): Retention time=1.694 min.

(21) 5-((R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(hydroxy)methyl)-2-(trifluoromethyl)benzonitrile

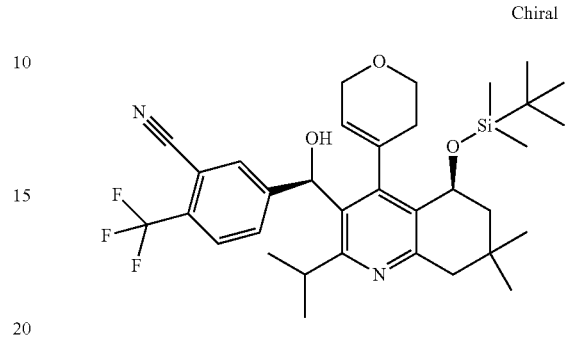

and 5-((S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(hydroxy)methyl)-2-(trifluoromethyl)benzonitrile

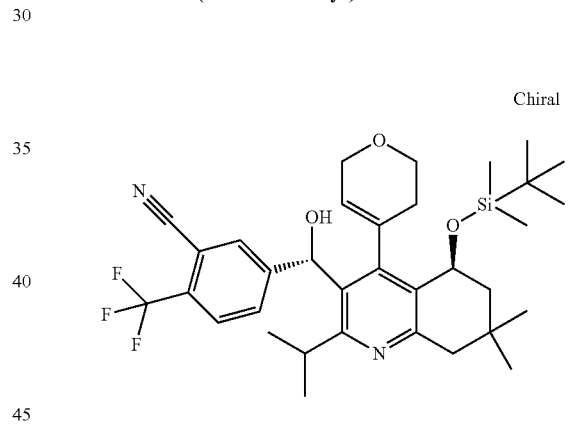

Obtained by starting from (S)-5-(tert-butyldimethylsilyloxy)-4-(3,6-dihydro-2H-pyran-4-yl)-2-isopropyl-7,7-dimethyl-5,6,7,8-tetrahydroquinoline-3-carbaldehyde and 5-iodo-2-(trifluoromethyl)benzonitrile. A 1.3 M solution of isopropylmagnesium chloride-lithium chloride-complex in tetrahydrofurane is used instead of a 2 M solution of isopropylmagnesium chloride in tetrahydrofurane.

5-((R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(hydroxy)methyl)-2-(trifluoromethyl)benzonitrile:

Mass spectrometry (ESI$^+$): m/z=615 [M+H]$^+$

HPLC (Method 7): Retention time=1.612 min.

5-((S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(hydroxy)methyl)-2-(trifluoromethyl)benzonitrile:

Mass spectrometry (ESI$^+$): m/z=615 [M+H]$^+$

HPLC (Method 7): Retention time=1.628 min.

155

(22) (R)—((S)-5-(tert-butyldimethylsilyloxy)-4-iodo-2-isopropyl-7,7-dimethyl-5,6,7,8-tetrahydroquinolin-3-yl)(4-(pentafluorosulfanyl)phenyl)methanol

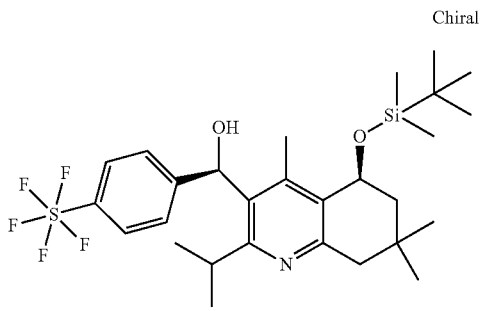 [SMILES: Cc1c([C@H](O)c2ccc(S(F)(F)(F)(F)F)cc2)c(C(C)C)nc2c1[C@@H](O[Si](C)(C)C(C)(C)C)CC(C)(C)C2]

and (S)—((S)-5-(tert-butyldimethylsilyloxy)-4-iodo-2-isopropyl-7,7-dimethyl-5,6,7,8-tetrahydroquinolin-3-yl)(4-(pentafluorosulfanyl)phenyl)methanol

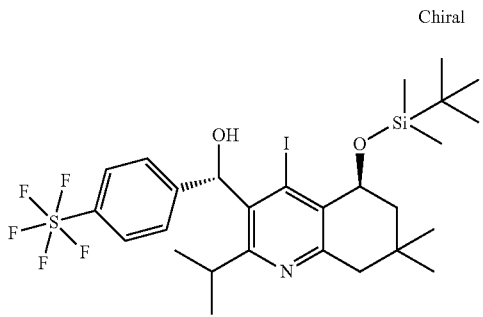 [SMILES: CC(C)c1nc2c(c(I)c1[C@@H](O)c1ccc(S(F)(F)(F)(F)F)cc1)[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 1-iodo-4-pentafluorosulfanyl-benzene. A 1.3 M solution of isopropylmagnesium chloride-lithium chloride-complex in tetrahydrofurane is used instead of a 2 M solution of isopropylmagnesium chloride in tetrahydrofurane.

(R)—((S)-5-(tert-butyldimethylsilyloxy)-4-iodo-2-isopropyl-7,7-dimethyl-5,6,7,8-tetrahydroquinolin-3-yl)(4-(pentafluorosulfanyl)phenyl)methanol:

Mass spectrometry (ESI⁺): m/z=692 [M+H]⁺

HPLC (Method 7): Retention time=1.951 min.

(S)—((S)-5-(tert-butyldimethylsilyloxy)-4-iodo-2-isopropyl-7,7-dimethyl-5,6,7,8-tetrahydroquinolin-3-yl)(4-(pentafluorosulfanyl)phenyl)methanol:

Mass spectrometry (ESI⁺): m/z=692 [M+H]⁺

HPLC (Method 7): Retention time=1.953 min.

156

(23) (R)—((S)-5'-(tert-butyldimethylsilyloxy)-4'-iodo-2'-isopropyl-6',8'-dihydro-5'H-spiro[cyclobutane-1,7'-quinoline]-3'-yl)(4-(pentafluorosulfanyl)phenyl)methanol

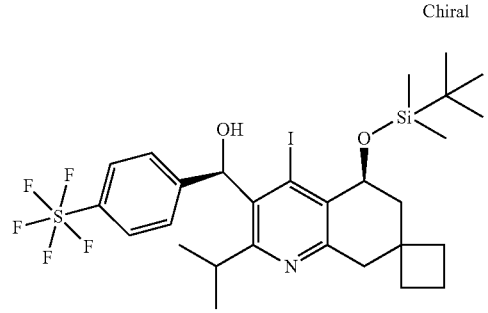 [SMILES: CC(C)c1nc2c(c(I)c1[C@H](O)c1ccc(S(F)(F)(F)(F)F)cc1)[C@@H](O[Si](C)(C)C(C)(C)C)CC1(CCC1)C2]

and (S)—((S)-5'-(tert-butyldimethylsilyloxy)-4'-iodo-2'-isopropyl-6',8'-dihydro-5'H-spiro[cyclobutane-1,7'-quinoline]-3'-yl)(4-(pentafluorosulfanyl)phenyl)methanol

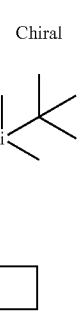

Obtained by starting from (S)-5'-(tert-butyldimethylsilyloxy)-4'-iodo-2'-isopropyl-6',8'-dihydro-5'H-spiro[cyclobutane-1,7'-quinoline]-3'-carbaldehyde and 1-iodo-4-pentafluorosulfanyl-benzene. A 1.3 M solution of isopropylmagnesium chloride-lithium chloride-complex in tetrahydrofurane is used instead of a 2 M solution of isopropylmagnesium chloride in tetrahydrofurane.

(R)—((S)-5'-(tert-butyldimethylsilyloxy)-4'-iodo-2'-isopropyl-6',8'-dihydro-5'H-spiro[cyclobutane-1,7'-quinoline]-3'-yl)(4-(pentafluorosulfanyl)phenyl)methanol:

Mass spectrometry (ESI⁺): m/z=704 [M+H]⁺

HPLC (Method 24): Retention time=1.840 min.

(S)—((S)-5'-(tert-butyldimethylsilyloxy)-4'-iodo-2'-isopropyl-6',8'-dihydro-5'H-spiro[cyclobutane-1,7'-quinoline]-3'-yl)(4-(pentafluorosulfanyl)phenyl)methanol:

Mass spectrometry (ESI⁺): m/z=704 [M+H]⁺

HPLC (Method 24): Retention time=1.838 min.

157

(24) (R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-tert-butylphenyl)methanol

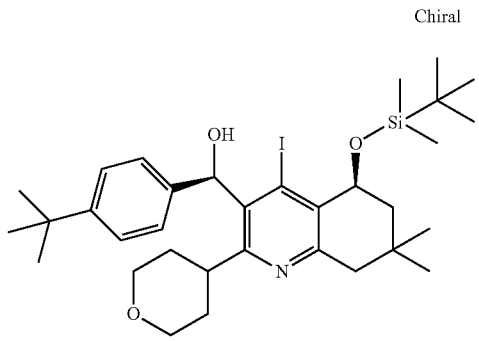 [SMILES: CC1(C)Cc2nc(C3CCOCC3)c([C@H](O)c3ccc(C(C)(C)C)cc3)c(I)c2[C@@H](O[Si](C)(C)C(C)(C)C)C1]

and (S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-tert-butylphenyl)methanol

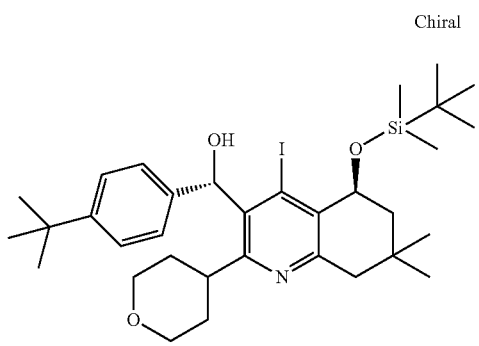 [SMILES: CC1(C)Cc2nc(C3CCOCC3)c([C@@H](O)c3ccc(C(C)(C)C)cc3)c(I)c2[C@@H](O[Si](C)(C)C(C)(C)C)C1]

Obtained by starting from (S)-5-(tert-butyldimethylsilyloxy)-4-iodo-7,7-dimethyl-2-(tetrahydro-2H-pyran-4-yl)-5,6,7,8-tetrahydroquinoline-3-carbaldehyde and 1-tert-butyl-4-iodobenzene.

(R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-tert-butylphenyl)methanol:

Mass spectrometry (ESI⁺): m/z=664 [M+H]⁺

HPLC (Method 24): Retention time=1.864 min.

(S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-tert-butylphenyl)methanol:

Mass spectrometry (ESI⁺): m/z=664 [M+H]⁺

HPLC (Method 24): Retention time=1.846 min.

158

(25) 5-((R)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(hydroxy)methyl)-2-(trifluoromethyl)benzonitrile

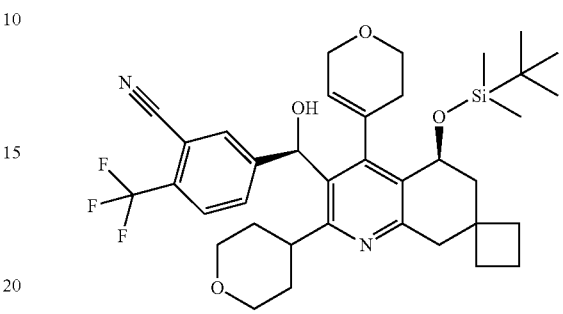

and 5-((S)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(hydroxy)methyl)-2-(trifluoromethyl)benzonitrile Obtained by starting from (S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-carbaldehyde and 5-iodo-2-(trifluoromethyl)benzonitrile. A 1.3 M solution of isopropylmagnesium chloride-lithium chloride-complex in tetrahydrofurane is used instead of a 2 M solution of isopropylmagnesium chloride in tetrahydrofurane.

5-((R)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(hydroxy)methyl)-2-(trifluoromethyl)benzonitrile:

Mass spectrometry (ESI⁺): m/z=669 [M+H]⁺

HPLC (Method 7): Retention time=1.781 min.

5-((S)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(hydroxy)methyl)-2-(trifluoromethyl)benzonitrile:

Mass spectrometry (ESI⁺): m/z=669 [M+H]⁺

HPLC (Method 7): Retention time=1.797 min.

(26) 5-((R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(hydroxy)methyl)-2-(trifluoromethyl)benzonitrile

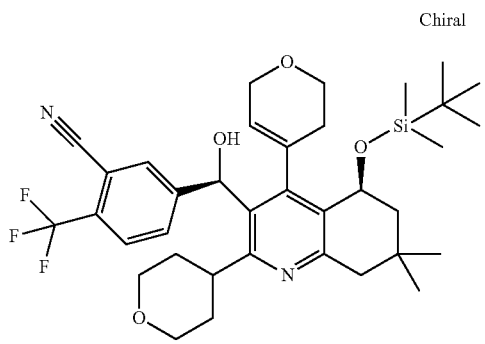 [SMILES: CC1(C)Cc2nc(C3CCOCC3)c([C@H](O)c3ccc(C(F)(F)F)c(C#N)c3)c(C3=CCOCC3)c2[C@@H](O[Si](C)(C)C(C)(C)C)C1]

and 5-((S)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(hydroxy)methyl)-2-(trifluoromethyl)benzonitrile

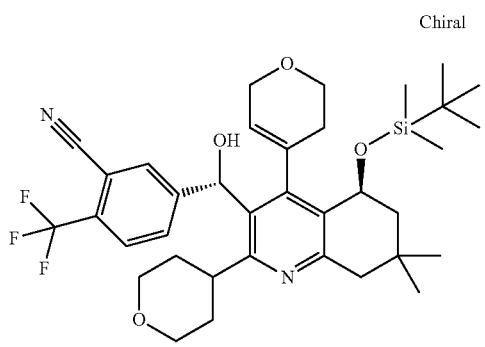 [SMILES: CC1(C)Cc2nc(C3CCOCC3)c([C@@H](O)c3ccc(C(F)(F)F)c(C#N)c3)c(C3=CCOCC3)c2[C@@H](O[Si](C)(C)C(C)(C)C)C1]

Obtained by starting from (S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinoline-3-carbaldehyde and 5-iodo-2-(trifluoromethyl)benzonitrile. A 1.3 M solution of isopropylmagnesium chloride-lithium chloride-complex in tetrahydrofurane is used instead of a 2 M solution of isopropylmagnesium chloride in tetrahydrofurane.

5-((R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(hydroxy)methyl)-2-(trifluoromethyl)benzonitrile:

Mass spectrometry (ESI$^+$): m/z=657 [M+H]$^+$

HPLC (Method 7): Retention time=1.683 min.

5-((S)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(hydroxy)methyl)-2-(trifluoromethyl)benzonitrile:

Mass spectrometry (ESI$^+$): m/z=657 [M+H]$^+$

HPLC (Method 7): Retention time=1.697 min.

(27) 5-((R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(hydroxy)methyl)-2-(trifluoromethyl)benzonitrile

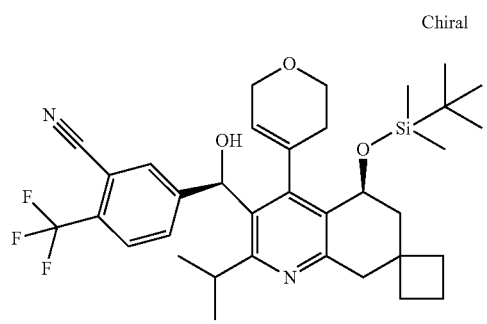 [SMILES: CC(C)c1nc2c(c(C3=CCOCC3)c1[C@H](O)c1ccc(C(F)(F)F)c(C#N)c1)[C@@H](O[Si](C)(C)C(C)(C)C)CC1(CCC1)C2]

and 5-((S)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(hydroxy)methyl)-2-(trifluoromethyl)benzonitrile

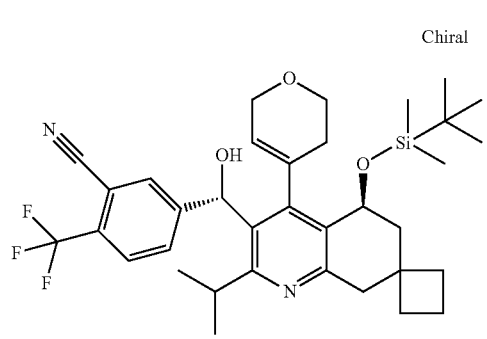 [SMILES: CC(C)c1nc2c(c(C3=CCOCC3)c1[C@@H](O)c1ccc(C(F)(F)F)c(C#N)c1)[C@@H](O[Si](C)(C)C(C)(C)C)CC1(CCC1)C2]

Obtained by starting from (S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-carbaldehyde and 5-iodo-2-(trifluoromethyl)benzonitrile. A 1.3 M solution of isopropylmagnesium chloride-lithium chloride-complex in tetrahydrofurane is used instead of a 2 M solution of isopropylmagnesium chloride in tetrahydrofurane.

5-((R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(hydroxy)methyl)-2-(trifluoromethyl)benzonitrile:

R$_f$-value: 0.23 (silica gel, petrole ether/ethylacetate 4:1)

5-((S)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(hydroxy)methyl)-2-(trifluoromethyl)benzonitrile:

R$_f$-value: 0.18 (silica gel, petrole ether/ethylacetate 4:1)

(28) (S)-3'-((R)-hydroxy(4-(trifluoromethyl)phenyl)methyl)-4'-iodo-2'-(tetrahydro-2H-pyran-4-yl)-6',8'-dihydro-5'H-spiro[cyclobutane-1,7'-quinolin]-5'-ol

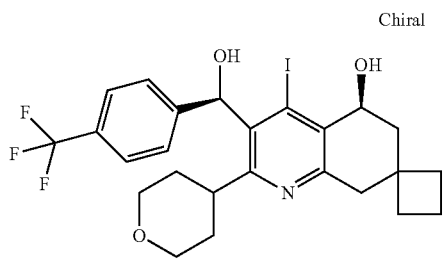 [SMILES: O[C@H](c1ccc(C(F)(F)F)cc1)c1c(C2CCOCC2)nc2c(c1I)[C@@H](O)CC1(CCC1)C2]

and (S)-3'-((S)-hydroxy(4-(trifluoromethyl)phenyl)methyl)-4'-iodo-2'-(tetrahydro-2H-pyran-4-yl)-6',8'-dihydro-5'H-spiro[cyclobutane-1,7'-quinolin]-5'-ol

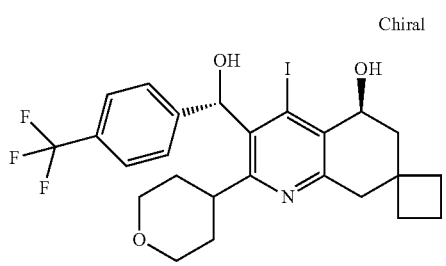 [SMILES: O[C@@H](c1ccc(C(F)(F)F)cc1)c1c(C2CCOCC2)nc2c(c1I)[C@@H](O)CC1(CCC1)C2]

Obtained by starting from (S)-5'-hydroxy-4'-iodo-2'-(tetrahydro-2H-pyran-4-yl)-6',8'-dihydro-5'H-spiro[cyclobutane-1,7'-quinoline]-3'-carbaldehyde (S)-3'-((R)-hydroxy(4-(trifluoromethyl)phenyl)methyl)-4'-iodo-2'-(tetrahydro-2H-pyran-4-yl)-6',8'-dihydro-5'H-spiro[cyclobutane-1,7'-quinolin]-5'-ol:
Mass spectrometry (ESI$^+$): m/z=574 [M+H]$^+$
HPLC (Method 7): Retention time=1.592 min.

(S)-3'-((S)-hydroxy(4-(trifluoromethyl)phenyl)methyl)-4'-iodo-2'-(tetrahydro-2H-pyran-4-yl)-6',8'-dihydro-5'H-spiro[cyclobutane-1,7'-quinolin]-5'-ol:
Mass spectrometry (ESI$^+$): m/z=574 [M+H]$^+$
HPLC (Method 7): Retention time=1.592 min.

Example XI (R)—((S)-5-(tert-butyldimethylsilyloxy)-4-cyclopentenyl-2-isopropyl-7,7-dimethyl-5,6,7,8-tetrahydroquinolin-3-yl)(4-(trifluoromethyl)phenyl)methanol Under argon 490 mg (R)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methanol and 900 mg 2-cyclopent-1-enyl-4,4,5,5-tetramethyl-[1,3,2]dioxaborolane are dissolved in 20 ml tetrahydrofurane. 900 mg caesium fluoride are added and the mixture is purged for 5 minutes with argon. After the addition of 50 mg of 1,1'-bis-(diphenylphosphino)-ferrocene-dichloro-palladium-(II) the mixture is heated to 50° C. for 36 hours. Then the mixture is diluted with diethylether, washed with saturated aqueous ammonium chloride and brine and dried with magnesium sulphate. The solvents are evaporated in vacuo and the residue is chromatographed on silica gel (cyclohexane/ethylacetate 95:5 to 60:40).
Yield: 330 mg (74% of theory)
Mass spectrometry (ESI$^+$): m/z=574 [M+H]$^+$
R$_f$-value: 0.37 (silica gel, petrole ether/ethylacetate 8:1)
Analogously to example XI the following compounds are obtained:

(1) (S)—((S)-5-(tert-butyldimethylsilyloxy)-4-cyclopentenyl-2-isopropyl-7,7-dimethyl-5,6,7,8-tetrahydroquinolin-3-yl)(4-(trifluoromethyl)phenyl)methanol

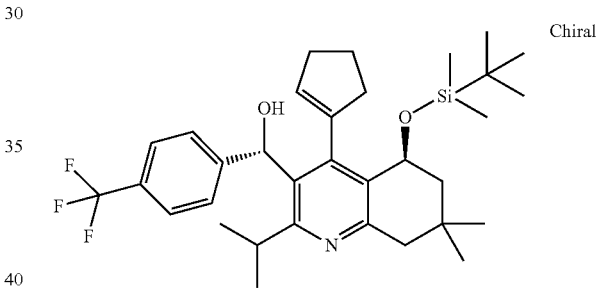

Obtained by starting from (S)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methanol.
Mass spectrometry (ESI$^+$): m/z=574 [M+H]$^+$
R$_f$-value: 0.28 (silica gel, petrole ether/ethylacetate 8:1)

(2) (R)—((S)-5-(tert-butyldimethylsilyloxy)-4-cyclopentenyl-7,7-dimethyl-2-(tetrahydro-2H-pyran-4-yl)-5,6,7,8-tetrahydroquinolin-3-yl)(4-(trifluoromethyl)phenyl)methanol

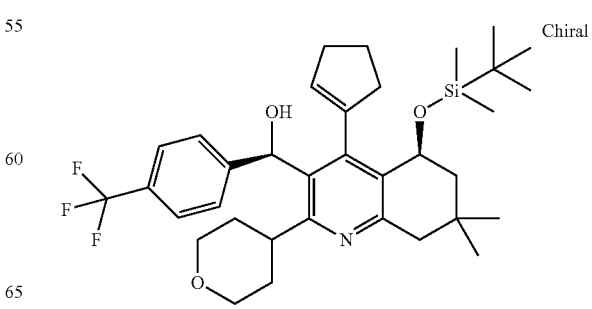

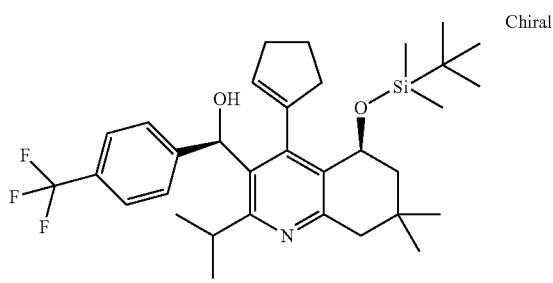 [SMILES: CC(C)c1nc2c(c(C3=CCCC3)c1[C@H](O)c1ccc(C(F)(F)F)cc1)[C@@H](O[Si](C)(C)C(C)(C)C)CC(C)(C)C2]

Obtained by starting from (R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol.

Mass spectrometry (ESI$^+$): m/z=616 [M+H]$^+$
R$_f$-value: 0.37 (silica gel, petrole ether/ethylacetate 4:1)

(3) (R)—((S)-5-(tert-butyldimethylsilyloxy)-4-cyclopentenyl-2-cyclopentyl-7,7-dimethyl-5,6,7,8-tetrahydroquinolin-3-yl)(4-(trifluoromethyl)phenyl)methanol

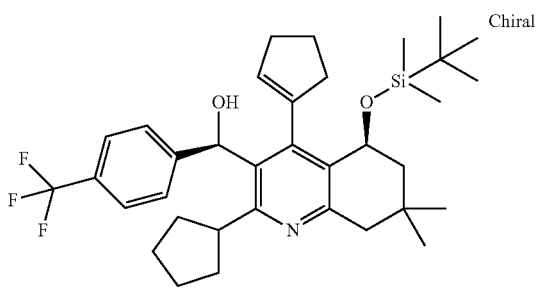 [SMILES: CC1(C)Cc2nc(C3CCCC3)c([C@H](O)c3ccc(C(F)(F)F)cc3)c(C3=CCCC3)c2[C@@H](O[Si](C)(C)C(C)(C)C)C1]

Obtained by starting from (R)—((S)-5-(tert-butyldimethylsilyloxy)-2-cyclopentyl-4-iodo-7,7-dimethyl-5,6,7,8-tetrahydroquinolin-3-yl)(4-(trifluoromethyl)phenyl)methanol.

Mass spectrometry (ESI$^+$): m/z=600 [M+H]$^+$
HPLC (Method 8): Retention time=2.20 min.

(4) (R)—((S)-5-(tert-butyldimethylsilyloxy)-4-cyclopentenyl-2-isopropyl-7,7-dimethyl-5,6,7,8-tetrahydroquinolin-3-yl)(4-fluorophenyl)methanol

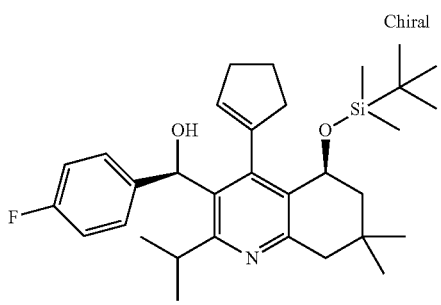 [SMILES: CC(C)c1nc2c(c(C3=CCCC3)c1[C@H](O)c1ccc(F)cc1)[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(4-fluorophenyl)methanol.

Mass spectrometry (ESI$^+$): m/z=524 [M+H]$^+$
HPLC (Method 19): Retention time=2.01 min.

(5) (R)—((S)-5-(tert-butyldimethylsilyloxy)-4-cyclopentenyl-2-isopropyl-7,7-dimethyl-5,6,7,8-tetrahydroquinolin-3-yl)(4-chlorophenyl)methanol

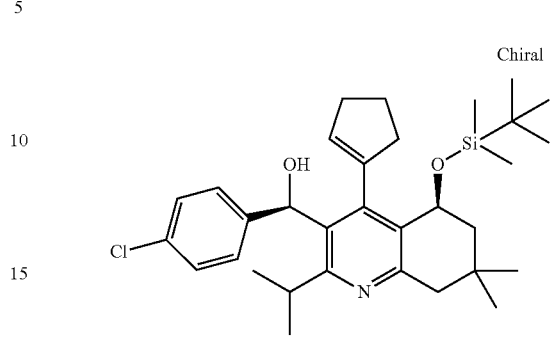

Obtained by starting from (R)—((S)-5-(tert-butyldimethylsilyloxy)-4-iodo-2-isopropyl-7,7-dimethyl-5,6,7,8-tetrahydroquinolin-3-yl)(4-chlorophenyl)methanol.

Mass spectrometry (ESI$^+$): m/z=540 [M+H]$^+$
HPLC (Method 21): Retention time=2.06 min.

(6) (R)—((S)-5-(tert-butyldimethylsilyloxy)-4-cyclopentenyl-2-cyclopentyl-7,7-dimethyl-5,6,7,8-tetrahydroquinolin-3-yl)(4-fluorophenyl)methanol

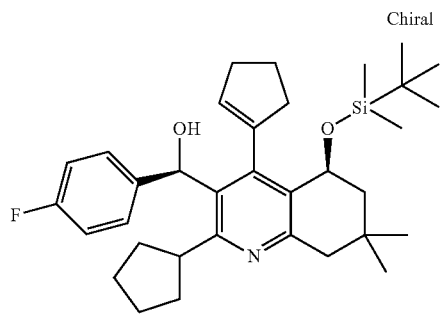 [SMILES: CC1(C)Cc2nc(C3CCCC3)c([C@H](O)c3ccc(F)cc3)c(C3=CCCC3)c2[C@@H](O[Si](C)(C)C(C)(C)C)C1]

Obtained by starting from (R)—((S)-5-(tert-butyldimethylsilyloxy)-2-cyclopentyl-4-iodo-7,7-dimethyl-5,6,7,8-tetrahydroquinolin-3-yl)(4-fluorophenyl)methanol.

Mass spectrometry (ESI$^+$): m/z=550 [M+H]$^+$
HPLC (Method 20): Retention time=3.81 min.

(7) (R)—((S)-5-(tert-butyldimethylsilyloxy)-4-cyclopentenyl-2-isopropyl-7,7-dimethyl-5,6,7,8-tetrahydroquinolin-3-yl)(4-tert-butylphenyl)methanol

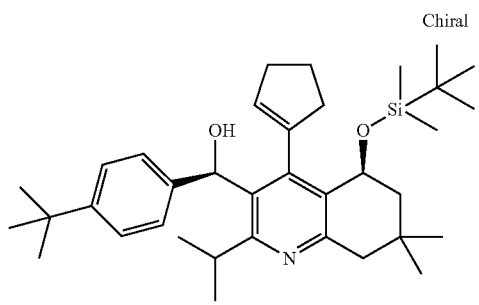 [SMILES: CC(C)c1nc2c(c(C3=CCCC3)c1[C@H](O)c1ccc(C(C)(C)C)cc1)[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(4-tert-butylphenyl)methanol.

Mass spectrometry (ESI⁺): m/z=562 [M+H]⁺

HPLC (Method 21): Retention time=2.20 min.

(8) (S)—((S)-5-(tert-butyldimethylsilyloxy)-4-cyclopentenyl-7,7-dimethyl-2-(tetrahydro-2H-pyran-4-yl)-5,6,7,8-tetrahydroquinolin-3-yl)(4-(trifluoromethyl)phenyl)methanol

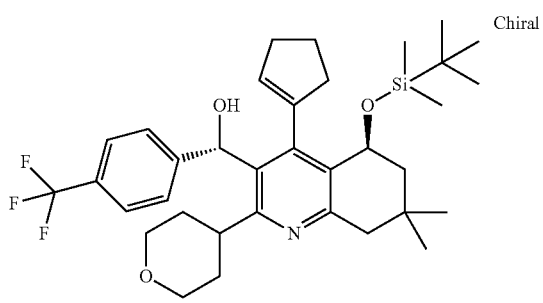 [SMILES: CC1(C)Cc2nc(C3CCOCC3)c([C@@H](O)c3ccc(C(F)(F)F)cc3)c(C3=CCCC3)c2[C@@H](O[Si](C)(C)C(C)(C)C)C1]

Obtained by starting from (S)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol.

Mass spectrometry (ESI⁺): m/z=616 [M+H]⁺

HPLC (Method 1): Retention time=4.180 min.

$R_f$-value: 0.23 (silica gel, petrole ether/ethylacetate 4:1)

(9) (R)—((S)-5-(tert-butyldimethylsilyloxy)-4-cyclopentenyl-2-isopropyl-7,7-dimethyl-5,6,7,8-tetrahydroquinolin-3-yl)(p-tolyl)methanol

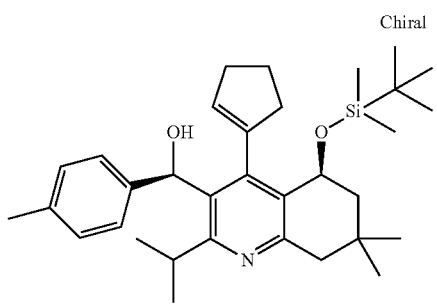 [SMILES: Cc1ccc([C@@H](O)c2c(C(C)C)nc3c(c2C2=CCCC2)[C@@H](O[Si](C)(C)C(C)(C)C)CC(C)(C)C3)cc1]

Obtained by starting from (R)—((S)-5-(tert-butyldimethylsilyloxy)-4-iodo-2-isopropyl-7,7-dimethyl-5,6,7,8-tetrahydroquinolin-3-yl)(p-tolyl)methanol.

Mass spectrometry (ESI⁺): m/z=520 [M+H]⁺

HPLC (Method 20): Retention time=3.79 min.

(10) (R)—((S)-5'-(tert-butyldimethylsilyloxy)-4'-cyclopentenyl-2'-isopropyl-6',8'-dihydro-5'H-spiro[cyclobutane-1,7'-quinoline]-3-yl)(4-(trifluoromethyl)phenyl)methanol

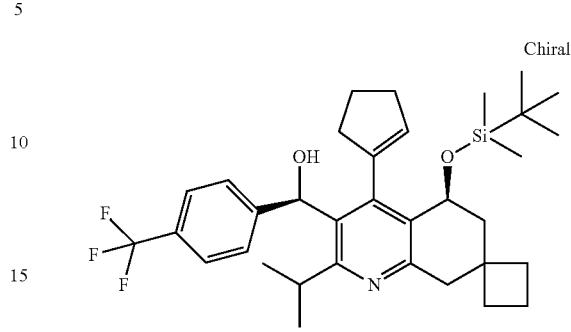

Obtained by starting from (R)—((S)-5'-(tert-butyldimethylsilyloxy)-4'-iodo-2'-isopropyl-6',8'-dihydro-5'H-spiro[cyclobutane-1,7'-quinoline]-3-yl)(4-(trifluoromethyl)phenyl)methanol.

Mass spectrometry (ESI⁺): m/z=586 [M+H]⁺

HPLC (Method 20): Retention time=3.82 min.

(11) (R)—((S)-5-(tert-butyldimethylsilyloxy)-4-cyclopentenyl-2-isopropyl-7,7-dimethyl-5,6,7,8-tetrahydroquinolin-3-yl)(3-fluoro-4-(trifluoromethyl)phenyl)methanol

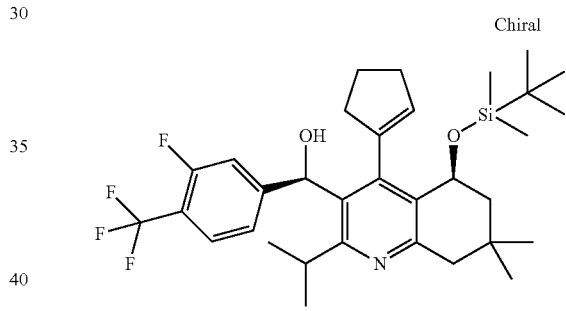

Obtained by starting from (R)—((S)-5-(tert-butyldimethylsilyloxy)-4-iodo-2-isopropyl-7,7-dimethyl-5,6,7,8-tetrahydroquinolin-3-yl)(3-fluoro-4-(trifluoromethyl)phenyl)methanol.

Mass spectrometry (ESI⁺): m/z=592 [M+H]⁺

HPLC (Method 20): Retention time=3.80 min.

(12) (R)—((S)-5-(tert-butyldimethylsilyloxy)-4-cyclopentenyl-2-isopropyl-7,7-dimethyl-5,6,7,8-tetrahydroquinolin-3-yl)(4-(trifluoromethoxy)phenyl)methanol

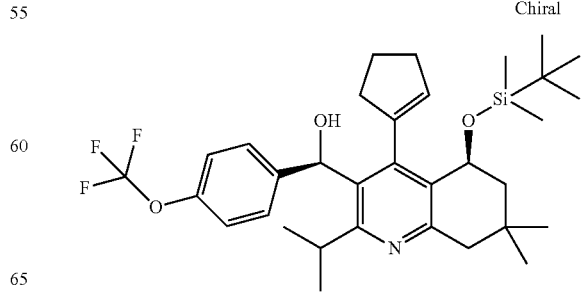

Obtained by starting from (R)—((S)-5-(tert-butyldimethylsilyloxy)-4-iodo-2-isopropyl-7,7-dimethyl-5,6,7,8-tetrahydroquinolin-3-yl)(4-(trifluoromethoxy)phenyl)methanol.

Mass spectrometry (ESI⁺): m/z=590 [M+H]⁺

HPLC (Method 20): Retention time=3.80 min.

(13) 4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)benzonitrile

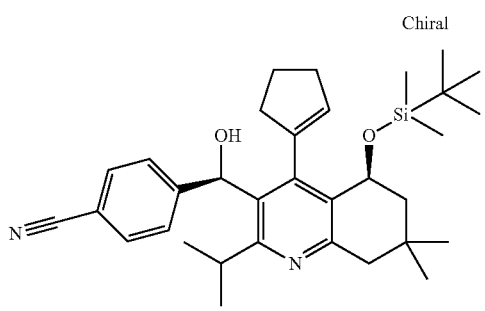 [SMILES: CC(C)c1nc2c(c(C3=CCCC3)c1[C@H](O)c1ccc(C#N)cc1)[C@@H](O[Si](C)(C)C(C)(C)C)CC(C)(C)C2]

Obtained by starting from 4-((R)—((S)-5-(tert-butyldimethylsilyloxy)-4-iodo-2-isopropyl-7,7-dimethyl-5,6,7,8-tetrahydroquinolin-3-yl)(hydroxy)methyl)benzonitrile.

Mass spectrometry (ESI⁺): m/z=531 [M+H]⁺

HPLC (Method 11): Retention time=7.51 min.

(14) 2-(4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)phenyl)-2-methylpropanenitrile

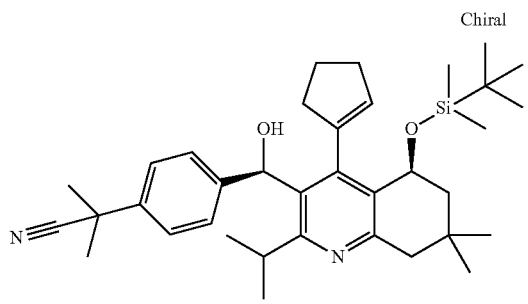 [SMILES: CC(C)c1nc2c(c(C3=CCCC3)c1[C@H](O)c1ccc(C(C)(C)C#N)cc1)[C@@H](O[Si](C)(C)C(C)(C)C)CC(C)(C)C2]

Obtained by starting from 2-(4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)phenyl)-2-methylpropanenitrile.

Mass spectrometry (ESI⁺): m/z=573 [M+H]⁺

HPLC (Method 1): Retention time=3.506 min.

R$_f$-value: 0.42 (silica gel, petrole ether/ethylacetate 4:1)

(15) 2-(4-((S)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)phenyl)-2-methylpropanenitrile

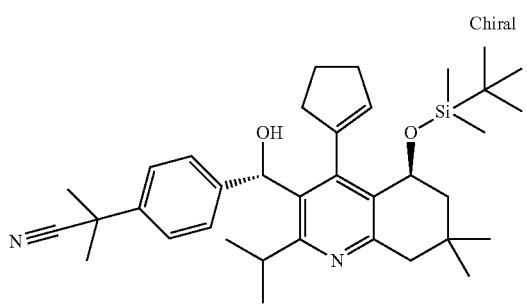 [SMILES: CC(C)c1nc2c(c(C3=CCCC3)c1[C@@H](O)c1ccc(C(C)(C)C#N)cc1)[C@@H](O[Si](C)(C)C(C)(C)C)CC(C)(C)C2]

Obtained by starting from 2-(4-((S)—((S)-5-(tert-butyldimethylsilyloxy)-4-iodo-2-isopropyl-7,7-dimethyl-5,6,7,8-tetrahydroquinolin-3-yl)(hydroxy)methyl)phenyl)-2-methylpropanenitrile.

Mass spectrometry (ESI⁺): m/z=573 [M+H]⁺

HPLC (Method 1): Retention time=3.440 min.

R$_f$-value: 0.38 (silica gel, petrole ether/ethylacetate 4:1)

(16) (S)—((S)-5-(tert-butyldimethylsilyloxy)-4-cyclopentenyl-2-isopropyl-7,7-dimethyl-5,6,7,8-tetrahydroquinolin-3-yl)(5-(trifluoromethyl)thiophen-2-yl)methanol

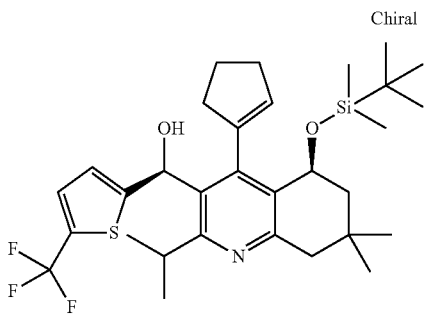 [SMILES: CC(C)c1nc2c(c(C3=CCCC3)c1[C@H](O)c1ccc(C(F)(F)F)s1)[C@@H](O[Si](C)(C)C(C)(C)C)CC(C)(C)C2]

Obtained by starting from (S)—((S)-5-(tert-butyldimethylsilyloxy)-4-iodo-2-isopropyl-7,7-dimethyl-5,6,7,8-tetrahydroquinolin-3-yl)(5-(trifluoromethyl)thiophen-2-yl)methanol.

Mass spectrometry (ESI⁺): m/z=580 [M+H]⁺

HPLC (Method 11): Retention time=10.04 min.

R$_f$-value: 0.38 (silica gel, petrole ether/ethylacetate 4:1)

(17) Ethyl 4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)benzoate

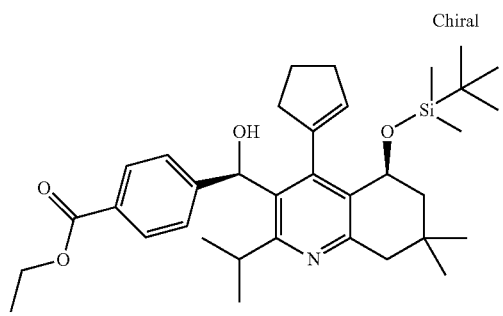 [SMILES: CCOC(=O)c1ccc([C@@H](O)c2c(C(C)C)nc3c(c2C2=CCCC2)[C@@H](O[Si](C)(C)C(C)(C)C)CC(C)(C)C3)cc1]

Obtained by starting from ethyl 4-((R)—((S)-5-(tert-butyldimethylsilyloxy)-4-iodo-2-isopropyl-7,7-dimethyl-5,6,7,8-tetrahydroquinolin-3-yl)(hydroxy)methyl)benzoate.

Mass spectrometry (ESI$^+$): m/z=578 [M+H]$^+$

HPLC (Method 1): Retention time=3.637 min.

R$_f$-value: 0.45 (silica gel, petrole ether/ethylacetate 4:1)

(18) (R)—((S)-5-(tert-butyldimethylsilyloxy)-4-cyclopentenyl-2-isopropyl-7,7-dimethyl-5,6,7,8-tetrahydroquinolin-3-yl)(4-isobutylphenyl)methanol

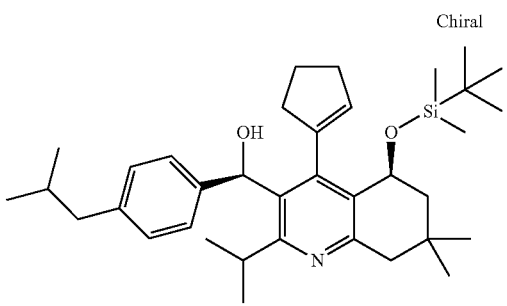 [SMILES: CC(C)Cc1ccc([C@@H](O)c2c(C(C)C)nc3c(c2C2=CCCC2)[C@@H](O[Si](C)(C)C(C)(C)C)CC(C)(C)C3)cc1]

Obtained by starting from (R)—((S)-5-(tert-butyldimethylsilyloxy)-4-iodo-2-isopropyl-7,7-dimethyl-5,6,7,8-tetrahydroquinolin-3-yl)(4-isobutylphenyl)methanol.

Mass spectrometry (ESI$^+$): m/z=562 [M+H]$^+$

R$_f$-value: 0.65 (silica gel, cyclohexane/ethylacetate 9:1)

(19) (R)—((S)-5-(tert-butyldimethylsilyloxy)-2-cyclobutyl-4-cyclopentenyl-7,7-dimethyl-5,6,7,8-tetrahydroquinolin-3-yl)(4-(trifluoromethyl)phenyl)methanol

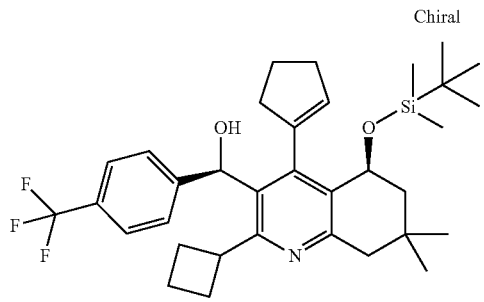 [SMILES: CC1(C)Cc2nc(C3CCC3)c([C@H](O)c3ccc(C(F)(F)F)cc3)c(C3=CCCC3)c2[C@@H](O[Si](C)(C)C(C)(C)C)C1]

Obtained by starting from (R)—((S)-5-(tert-butyldimethylsilyloxy)-2-cyclobutyl-4-iodo-7,7-dimethyl-5,6,7,8-tetrahydroquinolin-3-yl)(4-(trifluoromethyl)phenyl)methanol.

Mass spectrometry (ESI$^+$): m/z=586 [M+H]$^+$

R$_f$-value: 0.50 (silica gel, cyclohexane/ethylacetate 9:1)

(20) (R)—((S)-5-(tert-butyldimethylsilyloxy)-4-cyclopentenyl-2-cyclopentyl-7,7-dimethyl-5,6,7,8-tetrahydroquinolin-3-yl)(4-isopropylphenyl)methanol

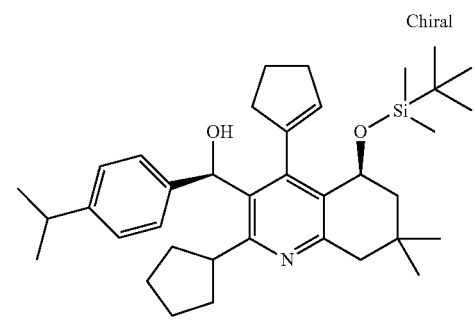 [SMILES: CC(C)c1ccc([C@@H](O)c2c(C3CCCC3)nc3c(c2C2=CCCC2)[C@@H](O[Si](C)(C)C(C)(C)C)CC(C)(C)C3)cc1]

and (S)—((S)-5-(tert-butyldimethylsilyloxy)-4-cyclopentenyl-2-cyclopentyl-7,7-dimethyl-5,6,7,8-tetrahydroquinolin-3-yl)(4-isopropylphenyl)methanol

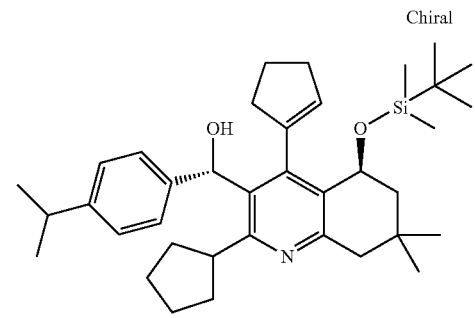 [SMILES: CC(C)c1ccc([C@H](O)c2c(C3CCCC3)nc3c(c2C2=CCCC2)[C@@H](O[Si](C)(C)C(C)(C)C)CC(C)(C)C3)cc1]

Obtained by starting from ((S)-5-(tert-butyldimethylsilyloxy)-2-cyclopentyl-4-iodo-7,7-dimethyl-5,6,7,8-tetrahydroquinolin-3-yl)(4-isopropylphenyl)methanol.

(R)—((S)-5-(tert-butyldimethylsilyloxy)-4-cyclopentenyl-2-cyclopentyl-7,7-dimethyl-5,6,7,8-tetrahydroquinolin-3-yl)(4-isopropylphenyl)methanol:

R$_f$-value: 0.11 (silica gel, petrole ether/ethylacetate 95:5)

(S)—((S)-5-(tert-butyldimethylsilyloxy)-4-cyclopentenyl-2-cyclopentyl-7,7-dimethyl-5,6,7,8-tetrahydroquinolin-3-yl)(4-isopropylphenyl)methanol R$_f$-value: 0.08 (silica gel, petrole ether/ethylacetate 95:5)

(21) (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(trifluoromethyl)phenyl)methanol

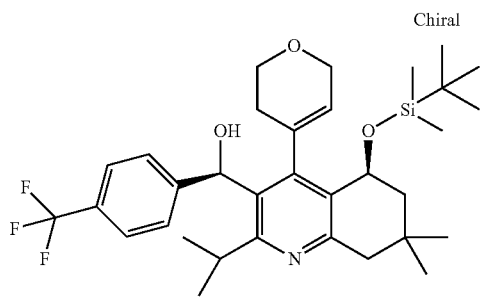 [SMILES: CC(C)c1nc2c(c(C3=CCOCC3)c1[C@H](O)c1ccc(C(F)(F)F)cc1)[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methanol and 2-(3,6-dihydro-2H-pyran-4-yl)-4,4,5,5-tetramethyl-1,3,2-dioxaborolane.

Mass spectrometry (ESI$^+$): m/z=590 [M+H]$^+$

HPLC (Method 12): Retention time=7.86 min.

(22) (R)—((S)-5-(tert-butyldimethylsilyloxy)-4-cyclopentenyl-2-cyclopentyl-7,7-dimethyl-5,6,7,8-tetrahydroquinolin-3-yl)(3-tert-butylphenyl)methanol

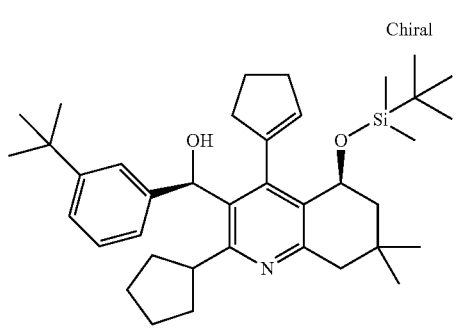 [SMILES: CC1(C)Cc2nc(C3CCCC3)c([C@H](O)c3cccc(C(C)(C)C)c3)c(C3=CCCC3)c2[C@@H](O[Si](C)(C)C(C)(C)C)C1]

and (S)—((S)-5-(tert-butyldimethylsilyloxy)-4-cyclopentenyl-2-cyclopentyl-7,7-dimethyl-5,6,7,8-tetrahydroquinolin-3-yl)(3-tert-butylphenyl)methanol

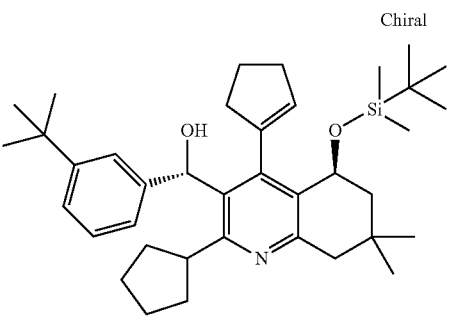 [SMILES: CC1(C)Cc2nc(C3CCCC3)c([C@@H](O)c3cccc(C(C)(C)C)c3)c(C3=CCCC3)c2[C@@H](O[Si](C)(C)C(C)(C)C)C1]

Obtained by starting from ((S)-5-(tert-butyldimethylsilyloxy)-2-cyclopentyl-4-iodo-7,7-dimethyl-5,6,7,8-tetrahydroquinolin-3-yl)(3-tert-butylphenyl)methanol.

(R)—((S)-5-(tert-butyldimethylsilyloxy)-4-cyclopentenyl-2-cyclopentyl-7,7-dimethyl-5,6,7,8-tetrahydroquinolin-3-yl)(3-tert-butylphenyl)methanol:

R$_f$-value: 0.4 (silica gel, petrole ether/ethylacetate 9:1)

(S)—((S)-5-(tert-butyldimethylsilyloxy)-4-cyclopentenyl-2-cyclopentyl-7,7-dimethyl-5,6,7,8-tetrahydroquinolin-3-yl)(3-tert-butylphenyl)methanol R$_f$-value: 0.3 (silica gel, petrole ether/ethylacetate 9:1)

(23) (R)—((S)-5-(tert-butyldimethylsilyloxy)-4-cyclopentenyl-2-isopropyl-7,7-dimethyl-5,6,7,8-tetrahydroquinolin-3-yl)(4-(1,1-difluoroethyl)phenyl)methanol

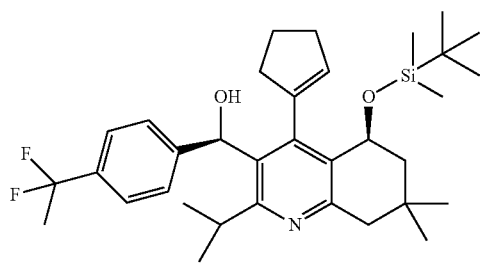

Obtained by starting from (R)—((S)-5-(tert-butyldimethylsilyloxy)-4-iodo-2-isopropyl-7,7-dimethyl-5,6,7,8-tetrahydroquinolin-3-yl)(4-(1,1-difluoroethyl)phenyl)methanol.

Mass spectrometry (ESI$^+$): m/z=570 [M+H]$^+$

HPLC (Method 4): Retention time=2.687 min.

173

(24) (R)—((S)-5'-(tert-butyldimethylsilyloxy)-4'-cyclopentenyl-2'-isopropyl-6',8'-dihydro-5'H-spiro[cyclobutane-1,7'-quinoline]-3'-yl)(4-isopropylphenyl)methanol

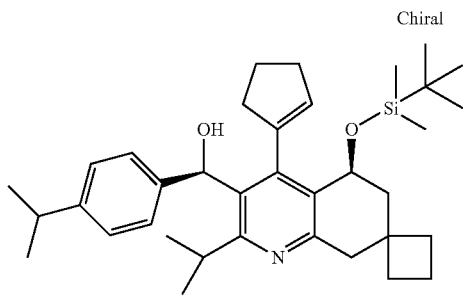 [SMILES: CC(C)c1ccc([C@@H](O)c2c(C(C)C)nc3c(c2C2=CCCC2)[C@@H](O[Si](C)(C)C(C)(C)C)CC2(CCC2)C3)cc1]

Obtained by starting from (R)—((S)-5'-(tert-butyldimethylsilyloxy)-4'-iodo-2'-isopropyl-6',8'-dihydro-5'H-spiro[cyclobutane-1,7'-quinoline]-3'-yl)(4-isopropylphenyl)methanol.

Mass spectrometry (ESI$^+$): m/z=560 [M+H]$^+$

HPLC (Method 20): Retention time=3.91 min.

(25) (R)—((S)-5-(tert-butyldimethylsilyloxy)-4-cyclopentenyl-7,7-dimethyl-2-(tetrahydro-2H-pyran-4-yl)-5,6,7,8-tetrahydroquinolin-3-yl)(4-tert-butylphenyl)methanol

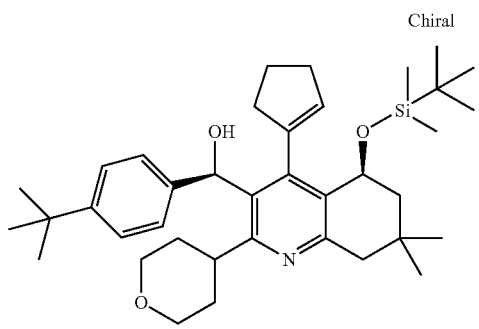 [SMILES: CC1(C)Cc2nc(C3CCOCC3)c([C@H](O)c3ccc(C(C)(C)C)cc3)c(C3=CCCC3)c2[C@@H](O[Si](C)(C)C(C)(C)C)C1]

Obtained by starting from (R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-tert-butylphenyl)methanol.

Mass spectrometry (ESI$^+$): m/z=604 [M+H]$^+$

HPLC (Method 2): Retention time=2.321 min.

R$_f$-value: 0.45 (silica gel, petrole ether/ethylacetate 4:1)

174

(26) (R)—((S)-5-(tert-butyldimethylsilyloxy)-4-cyclopentenyl-2-ethyl-7,7-dimethyl-5,6,7,8-tetrahydroquinolin-3-yl)(4-(trifluoromethyl)phenyl)methanol

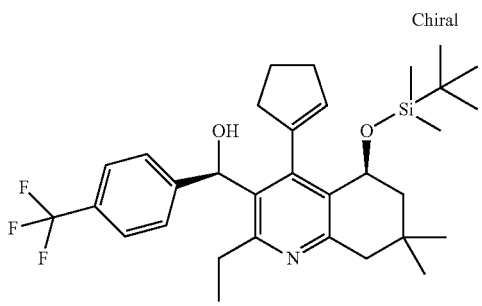 [SMILES: CCc1nc2c(c(C3=CCCC3)c1[C@H](O)c1ccc(C(F)(F)F)cc1)[C@@H](O[Si](C)(C)C(C)(C)C)CC(C)(C)C2]

Obtained by starting from (R)—((S)-5-(tert-butyldimethylsilyloxy)-2-ethyl-4-iodo-7,7-dimethyl-5,6,7,8-tetrahydroquinolin-3-yl)(4-(trifluoromethyl)phenyl)methanol.

Mass spectrometry (ESI$^+$): m/z=560 [M+H]$^+$

HPLC (Method 20): Retention time=3.94 min.

(27) (R)—((S)-5-(tert-butyldimethylsilyloxy)-4-cyclopentenyl-2-isopropyl-7,7-dimethyl-5,6,7,8-tetrahydroquinolin-3-yl)(3,5-difluoro-4-(trimethylsilyl)phenyl)methanol

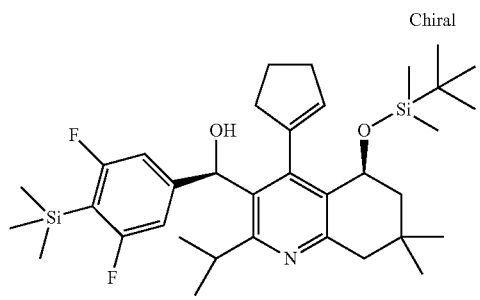 [SMILES: CC(C)c1nc2c(c(C3=CCCC3)c1[C@H](O)c1cc(F)c([Si](C)(C)C)c(F)c1)[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(3,5-difluoro-4-(trimethylsilyl)phenyl)methanol.

Mass spectrometry (ESI$^+$): m/z=614 [M+H]$^+$

HPLC (Method 4): Retention time=3.081 min.

(28) (R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(4-(trifluoromethyl)phenyl)methanol

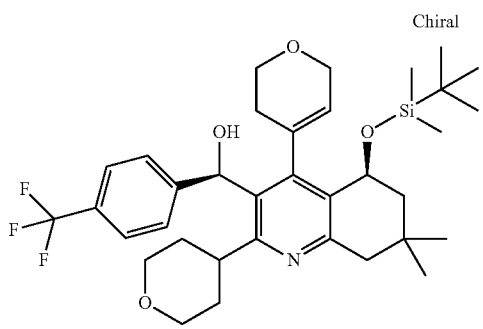 [SMILES: CC1(C)Cc2nc(C3CCOCC3)c([C@H](O)c3ccc(C(F)(F)F)cc3)c(C3=CCOCC3)c2[C@@H](O[Si](C)(C)C(C)(C)C)C1]

Obtained by starting from (R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol and 2-(3,6-dihydro-2H-pyran-4-yl)-4,4,5,5-tetramethyl-1,3,2-dioxaborolane.

Mass spectrometry (ESI$^+$): m/z=632 [M+H]$^+$

HPLC (Method 1): Retention time=3.340 min.

R$_f$-value: 0.25 (silica gel, petrole ether/ethylacetate 4:1)

(29) (R)-(4-(benzyloxy)phenyl)((S)-5-(tert-butyldimethylsilyloxy)-4-cyclopentenyl-2-isopropyl-7,7-dimethyl-5,6,7,8-tetrahydroquinolin-3-yl)methanol

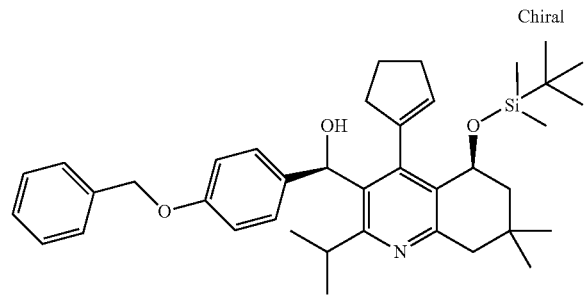 [SMILES: CC(C)c1nc2c(c(C3=CCCC3)c1[C@H](O)c1ccc(OCc3ccccc3)cc1)[C@@H](O[Si](C)(C)C(C)(C)C)CC(C)(C)C2]

Obtained by starting from (R)-(4-(benzyloxy)phenyl)((S)-5-(tert-butyldimethylsilyloxy)-4-iodo-2-isopropyl-7,7-dimethyl-5,6,7,8-tetrahydroquinolin-3-ylmethanol.

Mass spectrometry (ESI$^+$): m/z=612 [M+H]$^+$

R$_f$-value: 0.4 (silica gel, cyclohexane/ethylacetate 9:1)

(30) (R)—((S)-5-(tert-butyldimethylsilyloxy)-4-cyclopentenyl-2-isopropyl-7,7-dimethyl-5,6,7,8-tetrahydroquinolin-3-yl)(3-(trifluoromethyl)phenyl)methanol

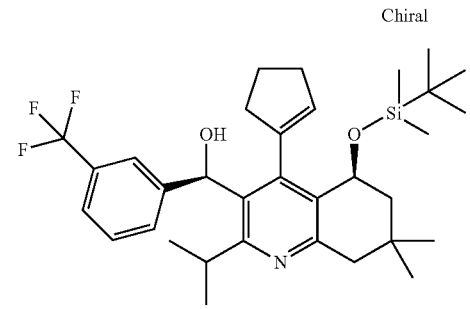 [SMILES: CC(C)c1nc2c(c(C3=CCCC3)c1[C@H](O)c1cccc(C(F)(F)F)c1)[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(3-(trifluoromethyl)phenyl)methanol.

HPLC (Method 4): Retention time=2.77 min.

(31) (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-tert-butylphenyl)methanol

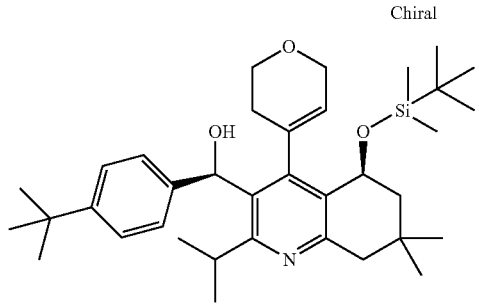 [SMILES: CC(C)c1nc2c(c(C3=CCOCC3)c1[C@H](O)c1ccc(C(C)(C)C)cc1)[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(4-tert-butylphenyl)methanol and 2-(3,6-dihydro-2H-pyran-4-yl)-4,4,5,5-tetramethyl-1,3,2-dioxaborolane.

Mass spectrometry (ESI$^+$): m/z=578 [M+H]$^+$

HPLC (Method 12): Retention time=8.08 min.

(32) (R)—((S)-5-(tert-butyldimethylsilyloxy)-4-cyclopentenyl-7,7-dimethyl-2-(tetrahydro-2H-pyran-4-yl)-5,6,7,8-tetrahydroquinolin-3-yl)(4-(pentafluorosulfanyl)phenyl)methanol

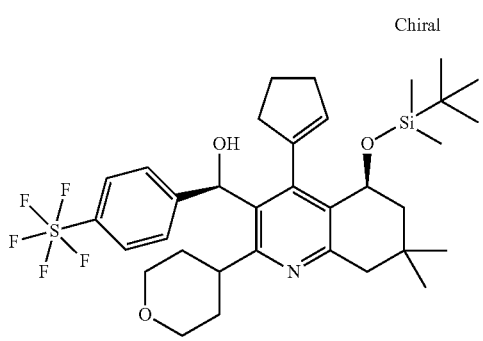 [SMILES: CC1(C)Cc2nc(C3CCOCC3)c([C@H](O)c3ccc(S(F)(F)(F)(F)F)cc3)c(C3=CCCC3)c2[C@@H](O[Si](C)(C)C(C)(C)C)C1]

Obtained by starting from (R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-(trifluoromethyl)phenyl)methanol.

Mass spectrometry (ESI+): m/z=674 [M+H]+

HPLC (Method 7): Retention time=1.840 min.

(33) ethyl 4-((S)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)benzoate

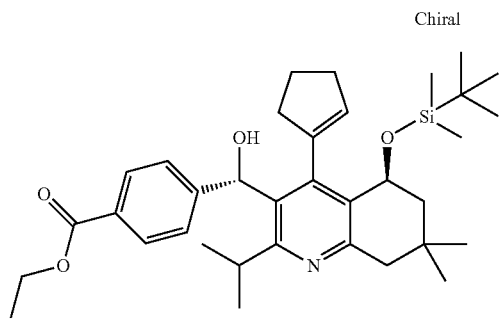 [SMILES: CCOC(=O)c1ccc([C@H](O)c2c(C(C)C)nc3c(c2C2=CCCC2)[C@@H](O[Si](C)(C)C(C)(C)C)CC(C)(C)C3)cc1]

Obtained by starting from ethyl 4-((S)—((S)-5-(tert-butyldimethylsilyloxy)-4-iodo-2-isopropyl-7,7-dimethyl-5,6,7,8-tetrahydroquinolin-3-yl)(hydroxy)methyl)benzoate.

Mass spectrometry (ESI+): m/z=578 [M+H]+

$R_f$-value: 0.35 (silica gel, cyclohexane/ethylacetate 9:1)

(34) (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(6-(trifluoromethyl)pyridin-3-yl)methanol

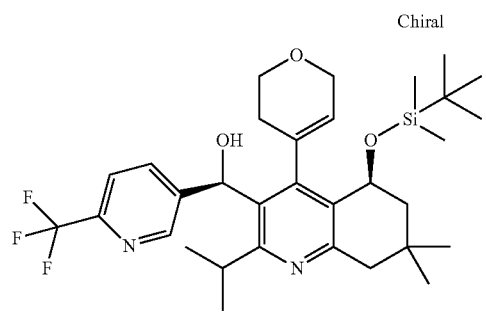 [SMILES: CC(C)c1nc2c(c(C3=CCOCC3)c1[C@H](O)c1ccc(C(F)(F)F)nc1)[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(6-(trifluoromethyl)pyridin-3-yl)methanol and 2-(3,6-dihydro-2H-pyran-4-yl)-4,4,5,5-tetramethyl-1,3,2-dioxaborolane.

Mass spectrometry (ESI+): m/z=591 [M+H]+

HPLC (Method 12): Retention time=8.74 min.

(35) (S)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(5-(trifluoromethyl)pyridin-2-yl)methanol

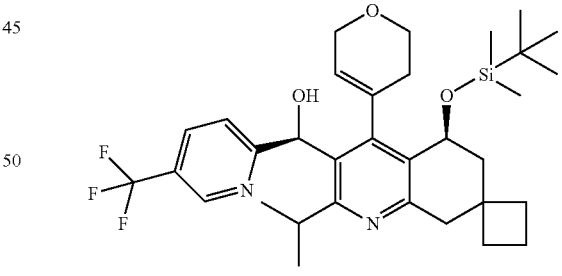

Obtained by starting from (S)—((S)-5'-(tert-butyldimethylsilyloxy)-4'-iodo-2'-isopropyl-6',8'-dihydro-5'H-spiro[cyclobutane-1,7'-quinoline]-3'-yl)(5-(trifluoromethyl)pyridin-2-yl)methanol and 2-(3,6-dihydro-2H-pyran-4-yl)-4,4,5,5-tetramethyl-1,3,2-dioxaborolane.

Mass spectrometry (ESI+): m/z=603 [M+H]+

HPLC (Method 9): Retention time=1.62 min.

(36) ((R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(4-(trifluoromethyl)phenyl)methanol

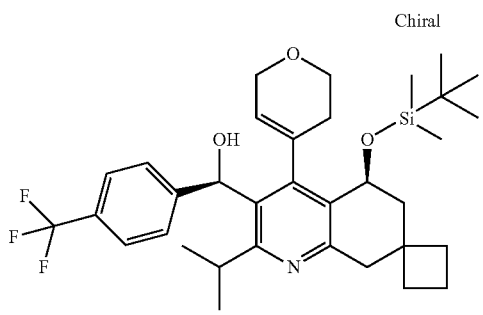 [SMILES: CC(C)c1nc2c(c(C3=CCOCC3)c1[C@H](O)c1ccc(C(F)(F)F)cc1)[C@@H](O[Si](C)(C)C(C)(C)C)CC1(CCC1)C2]

Obtained by starting from (R)—((S)-5'-(tert-butyldimethylsilyloxy)-4'-iodo-2'-isopropyl-6',8'-dihydro-5'H-spiro[cyclobutane-1,7'-quinoline]-3'-yl)(4-(trifluoromethyl)phenyl)methanol and 2-(3,6-dihydro-2H-pyran-4-yl)-4,4,5,5-tetramethyl-1,3,2-dioxaborolane.

Mass spectrometry (ESI+): m/z=602 [M+H]+

HPLC (Method 9): Retention time=1.78 min.

(37) (S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-carbaldehyde

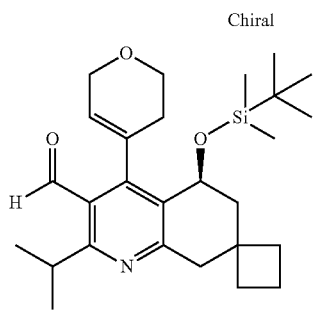 [SMILES: CC(C)c1nc2c(c(C3=CCOCC3)c1C=O)[C@@H](O[Si](C)(C)C(C)(C)C)CC1(CCC1)C2]

Obtained by starting from (S)-5'-(tert-butyldimethylsilyloxy)-4'-iodo-2'-isopropyl-6',8'-dihydro-5'H-spiro[cyclobutane-1,7'-quinoline]-3'-carbaldehyde and 2-(3,6-dihydro-2H-pyran-4-yl)-4,4,5,5-tetramethyl-1,3,2-dioxaborolane.

Mass spectrometry (ESI+): m/z=456 [M+H]+

HPLC (Method 13): Retention time=1.84 min.

(38) (S)-ethyl 5-(tert-butyldimethylsilyloxy)-4-(3,6-dihydro-2H-pyran-4-yl)-2-isopropyl-7,7-dimethyl-5,6,7,8-tetrahydroquinoline-3-carboxylate

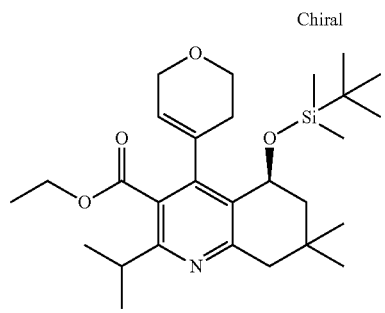 [SMILES: CCOC(=O)c1c(C(C)C)nc2c(c1C1=CCOCC1)[C@@H](O[Si](C)(C)C(C)(C)C)CC(C)(C)C2]

Obtained by starting from (S)-ethyl 5-(tert-butyldimethylsilyloxy)-4-iodo-2-isopropyl-7,7-dimethyl-5,6,7,8-tetrahydroquinoline-3-carboxylate and 2-(3,6-dihydro-2H-pyran-4-yl)-4,4,5,5-tetramethyl-1,3,2-dioxaborolane.

Mass spectrometry (ESI+): m/z=488 [M+H]+

HPLC (Method 24): Retention time=1.755 min.

(39) (R)—((S)-5'-(tert-butyldimethylsilyloxy)-4'-(3,6-dihydro-2H-pyran-4-yl)-2'-isopropyl-6',8'-dihydro-5'H-spiro[cyclopentane-1,7'-quinoline]-3-yl)(4-(trifluoromethyl)phenyl)methanol

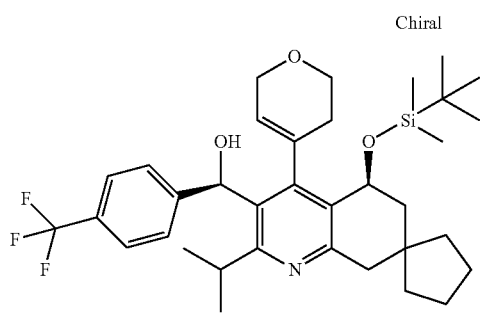 [SMILES: CC(C)c1nc2c(c(C3=CCOCC3)c1[C@H](O)c1ccc(C(F)(F)F)cc1)[C@@H](O[Si](C)(C)C(C)(C)C)CC1(CCCC1)C2]

Obtained by starting from (R)—((S)-5'-(tert-butyldimethylsilyloxy)-4'-iodo-2'-isopropyl-6',8'-dihydro-5'H-spiro[cyclopentane-1,7'-quinoline]-3'-yl)(4-(trifluoromethyl)phenyl)methanol and 2-(3,6-dihydro-2H-pyran-4-yl)-4,4,5,5-tetramethyl-1,3,2-dioxaborolane. The crude product is used directly in the next step.

Mass spectrometry (ESI+): m/z=616 [M+H]+

HPLC (Method 4): Retention time=1.98 min.

(40) (R)-(4-tert-butoxyphenyl)((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)methanol

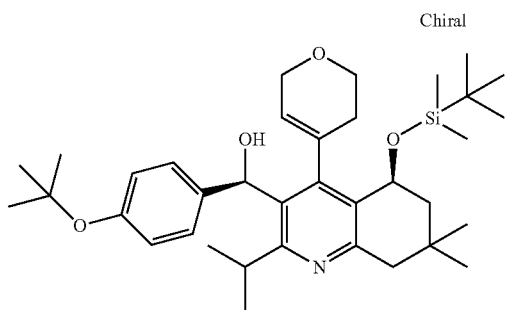 [SMILES: CC(C)c1nc2c(c(C3=CCOCC3)c1[C@H](O)c1ccc(OC(C)(C)C)cc1)[C@@H](O[Si](C)(C)C(C)(C)C)CC(C)(C)C2]

Obtained by starting from (R)-(4-tert-butoxyphenyl)((S)-5-(tert-butyldimethylsilyloxy)-4-iodo-2-isopropyl-7,7-dimethyl-5,6,7,8-tetrahydroquinolin-3-yl)methanol and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 5:1.

Mass spectrometry (ESI$^+$): m/z=594 [M+H]$^+$
HPLC (Method 4): Retention time=2.69 min.

(41) (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-isopropoxyphenyl)methanol

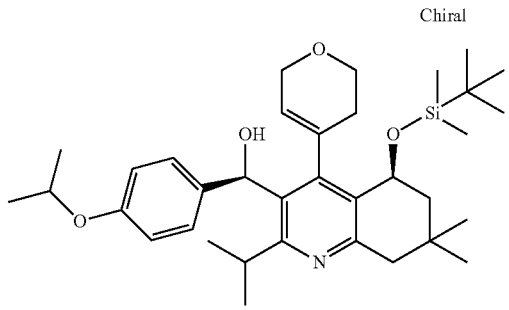 [SMILES: CC(C)Oc1ccc([C@@H](O)c2c(C(C)C)nc3c(c2C2=CCOCC2)[C@@H](O[Si](C)(C)C(C)(C)C)CC(C)(C)C3)cc1]

Obtained by starting from (R)—((S)-5-(tert-butyldimethylsilyloxy)-4-iodo-2-isopropyl-7,7-dimethyl-5,6,7,8-tetrahydroquinolin-3-yl)(4-isopropoxyphenyl)methanol and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 5:1.

Mass spectrometry (ESI$^+$): m/z=580 [M+H]$^+$
HPLC (Method 4): Retention time=2.555 min.

(42) (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(pentafluorosulfanyl)phenyl)methanol

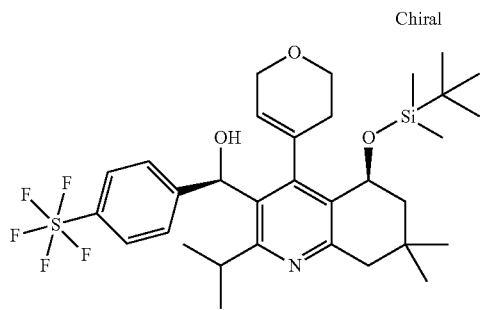 [SMILES: CC(C)c1nc2c(c(C3=CCOCC3)c1[C@H](O)c1ccc(S(F)(F)(F)(F)F)cc1)[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(4-(pentafluorosulfanyl)phenyl)methanol and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 4:1.

Mass spectrometry (ESI$^+$): m/z=648 [M+H]$^+$
HPLC (Method 24): Retention time=1.636 min.
R$_f$-value: 0.46 (silica gel, petrole ether/ethylacetate 4:1)

(43) (R)—((S)-5'-(tert-butyldimethylsilyloxy)-4'-cyclopentenyl-2'-isopropyl-6',8'-dihydro-5'H-spiro[cyclobutane-1,7'-quinoline]-3'-yl)(4-tert-butylphenyl)methanol

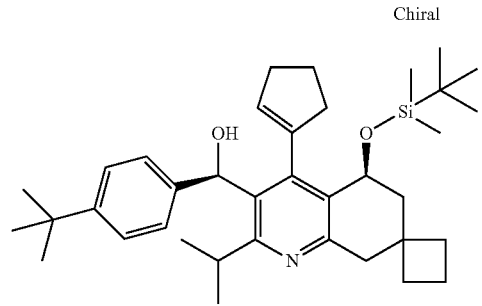 [SMILES: CC(C)c1nc2c(c(C3=CCCC3)c1[C@H](O)c1ccc(C(C)(C)C)cc1)[C@@H](O[Si](C)(C)C(C)(C)C)CC1(CCC1)C2]

Obtained by starting from (R)—((S)-5'-(tert-butyldimethylsilyloxy)-4'-iodo-2'-isopropyl-6',8'-dihydro-5'H-spiro[cyclobutane-1,7'-quinoline]-3'-yl)(4-tert-butylphenyl)methanol.

Mass spectrometry (ESI$^+$): m/z=574 [M+H]$^+$
HPLC (Method 7): Retention time=1.832 min.
R$_f$-value: 0.5 (silica gel, cyclohexane/ethylacetate 9:1)

(44) (R)—((S)-5'-(tert-butyldimethylsilyloxy)-4'-(3, 6-dihydro-2H-pyran-4-yl)-2'-isopropyl-6',8'-dihydro-5'H-spiro[cyclobutane-1,7'-quinoline]-3'-yl)(4-tert-butylphenyl)methanol

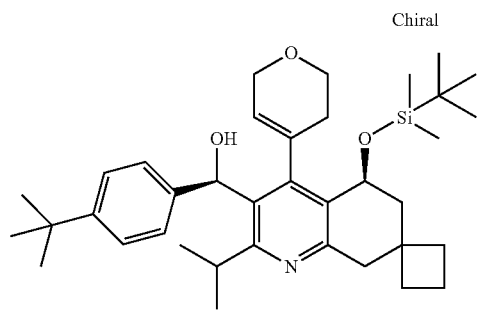 [SMILES: CC(C)c1nc2c(c(C3=CCOCC3)c1[C@H](O)c1ccc(C(C)(C)C)cc1)[C@@H](O[Si](C)(C)C(C)(C)C)CC1(CCC1)C2]

Obtained by starting from (R)—((S)-5'-(tert-butyldimethylsilyloxy)-4'-iodo-2'-isopropyl-6',8'-dihydro-5'H-spiro[cyclobutane-1,7'-quinoline]-3'-yl)(4-tert-butylphenyl)methanol and 2-(3,6-dihydro-2H-pyran-4-yl)-4,4,5,5-tetramethyl-1,3,2-dioxaborolane.
Mass spectrometry (ESI+): m/z=590 [M+H]+
HPLC (Method 7): Retention time=1.758 min.

(45) (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(3-methyloxetan-3-yl)phenyl)methanol

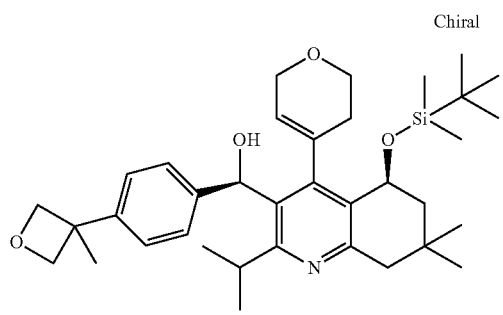 [SMILES: CC(C)c1nc2c(c(C3=CCOCC3)c1[C@H](O)c1ccc(C3(C)COC3)cc1)[C@@H](O[Si](C)(C)C(C)(C)C)CC(C)(C)C2]

and (S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(3-methyloxetan-3-yl)phenyl)methanol

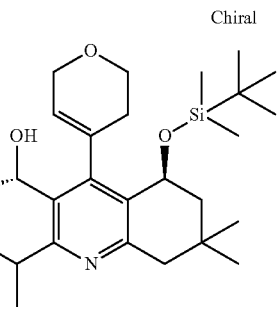

Obtained by starting from ((S)-5-(tert-butyldimethylsilyloxy)-4-iodo-2-isopropyl-7,7-dimethyl-5,6,7,8-tetrahydroquinolin-3-yl)(4-(3-methyloxetan-3-yl)phenyl)methanol and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 4:1.

(R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(3-methyloxetan-3-yl)phenyl)methanol:
Mass spectrometry (ESI+): m/z=592 [M+H]+
HPLC (Method 24): Retention time=1.527 min.
$R_f$-value: 0.48 (silica gel, petrole ether/ethylacetate 2:1)

(S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(3-methyloxetan-3-yl)phenyl)methanol:
Mass spectrometry (ESI+): m/z=592 [M+H]+
HPLC (Method 24): Retention time=1.567 min.
$R_f$-value: 0.40 (silica gel, petrole ether/ethylacetate 2:1)

(46) (R)—((S)-5-(tert-butyldimethylsilyloxy)-4-cyclopentenyl-2-isopropyl-7,7-dimethyl-5,6,7,8-tetrahydroquinolin-3-yl)(4-(perfluoroethyl)phenyl)methanol

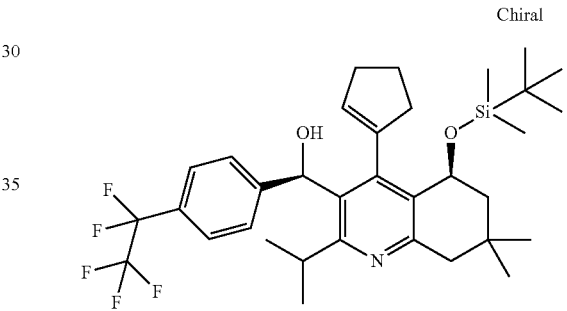

Obtained by starting from (R)—((S)-5-(tert-butyldimethylsilyloxy)-4-iodo-2-isopropyl-7,7-dimethyl-5,6,7,8-tetrahydroquinolin-3-yl)(4-(perfluoroethyl)phenyl)methanol.
Mass spectrometry (ESI+): m/z=624 [M+H]+
HPLC (Method 7): Retention time=1.790 min.

(47) (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(pentafluorosulfanyl)phenyl)methanol

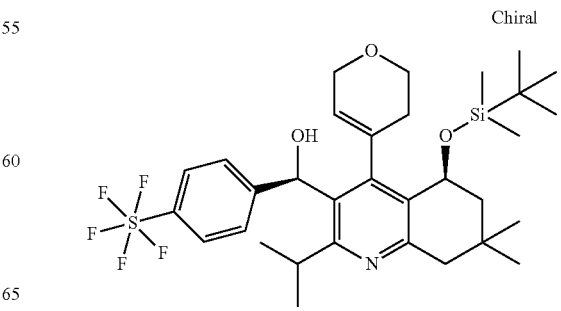

Obtained by starting from (R)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methanol and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 4:1.

Mass spectrometry (ESI$^+$): m/z=648 [M+H]$^+$
HPLC (Method 24): Retention time=1.636 min.
R$_f$-value: 0.43 (silica gel, petrole ether/ethylacetate 4:1)

(48) (R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(4-(pentafluorosulfanyl)phenyl)methanol

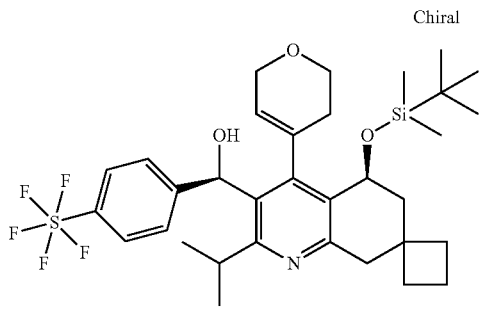 [SMILES: CC(C)c1nc2c(c(C3=CCOCC3)c1[C@H](O)c1ccc(S(F)(F)(F)(F)F)cc1)[C@@H](O[Si](C)(C)C(C)(C)C)CC1(CCC1)C2]

Obtained by starting from (R)—((S)-5'-(tert-butyldimethylsilyloxy)-4'-iodo-2'-isopropyl-6',8'-dihydro-5'H-spiro[cyclobutane-1,7'-quinoline]-3'-yl)(4-(pentafluorosulfanyl)phenyl)methanol and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 4:1.

Mass spectrometry (ESI$^+$): m/z=660 [M+H]$^+$
HPLC (Method 24): Retention time=1.642 min.

(49) (R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(4-tert-butylphenyl)methanol

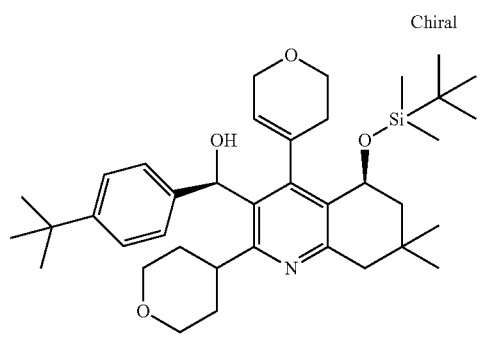 [SMILES: CC1(C)Cc2nc(C3CCOCC3)c([C@H](O)c3ccc(C(C)(C)C)cc3)c(C3=CCOCC3)c2[C@@H](O[Si](C)(C)C(C)(C)C)C1]

Obtained by starting from (R)—((S)-5-(tert-butyldimethylsilyloxy)-4-iodo-7,7-dimethyl-2-(tetrahydro-2H-pyran-4-yl)-5,6,7,8-tetrahydroquinolin-3-yl)(4-tert-butylphenyl)methanol and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 4:1.

Mass spectrometry (ESI$^+$): m/z=620 [M+H]$^+$
HPLC (Method 24): Retention time=1.653 min.

(50) (R)—((S)-4-cyclopentenyl-2-isopropyl-7,7-dimethyl-5-(2,3,3-trimethylbutan-2-yloxy)-5,6,7,8-tetrahydroquinolin-3-yl)(4-(pentafluorosulfanyl)phenyl)methanol

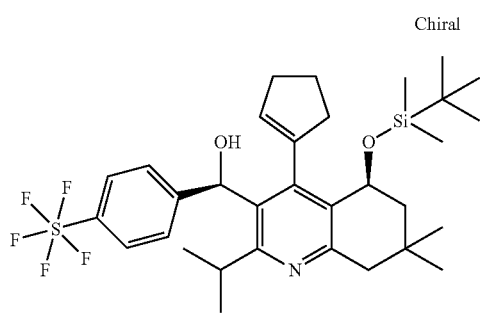 [SMILES: CC(C)c1nc2c(c(C3=CCCC3)c1[C@H](O)c1ccc(S(F)(F)(F)(F)F)cc1)[C@@H](O[Si](C)(C)C(C)(C)C)CC(C)(C)C2]

Obtained by starting from (R)—((S)-4-iodo-2-isopropyl-7,7-dimethyl-5-(2,3,3-trimethylbutan-2-yloxy)-5,6,7,8-tetrahydroquinolin-3-yl)(4-(pentafluorosulfanyl)phenyl)methanol.

Mass spectrometry (ESI$^+$): m/z=632 [M+H]$^+$
HPLC (Method 4): Retention time=2.840 min.

(51) (S)-ethyl 5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-carboxylate

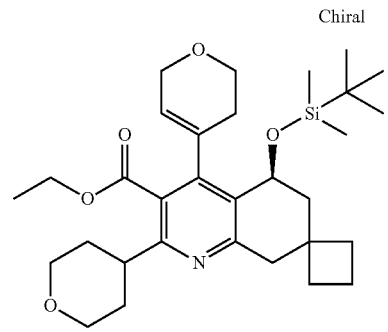 [SMILES: CCOC(=O)c1c(C2CCOCC2)nc2c(c1C1=CCOCC1)[C@@H](O[Si](C)(C)C(C)(C)C)CC1(CCC1)C2]

Obtained by starting from (S)-ethyl 5'-(tert-butyldimethylsilyloxy)-4'-iodo-2'-(tetrahydro-2H-pyran-4-yl)-6',8'-dihydro-5'H-spiro[cyclobutane-1,7'-quinoline]-3'-carboxylate and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 4:1.

Mass spectrometry (ESI$^+$): m/z=542 [M+H]$^+$
HPLC (Method 7): Retention time=1.943 min.

(52) (S)-ethyl 5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinoline-3-carboxylate

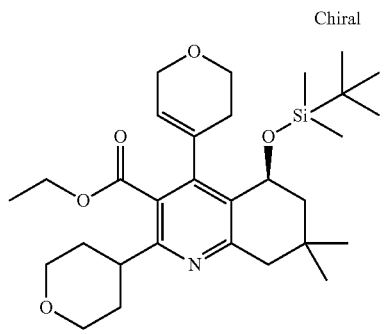 [SMILES: CCOC(=O)c1c(C2CCOCC2)nc2c(c1C1=CCOCC1)[C@@H](O[Si](C)(C)C(C)(C)C)CC(C)(C)C2]

Obtained by starting from (S)-ethyl 5-(tert-butyldimethylsilyloxy)-4-iodo-7,7-dimethyl-2-(tetrahydro-2H-pyran-4-yl)-5,6,7,8-tetrahydroquinoline-3-carboxylate and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 4:1.

Mass spectrometry (ESI$^+$): m/z=530 [M+H]$^+$

HPLC (Method 7): Retention time=1.918 min.

(53) S)-ethyl 5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-carboxylate

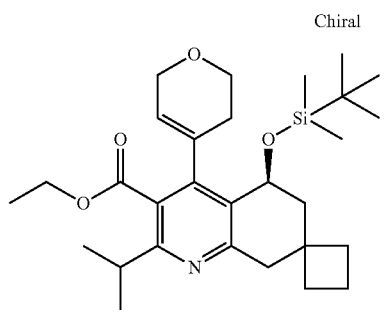 [SMILES: CCOC(=O)c1c(C(C)C)nc2c(c1C1=CCOCC1)[C@@H](O[Si](C)(C)C(C)(C)C)CC1(CCC1)C2]

Obtained by starting from (S)-ethyl 5'-(tert-butyldimethylsilyloxy)-4'-iodo-2'-isopropyl-6',8'-dihydro-5'H-spiro[cyclobutane-1,7'-quinoline]-3'-carboxylate and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 4:1.

Mass spectrometry (ESI$^+$): m/z=500 [M+H]$^+$

HPLC (Method 27): Retention time=1.74 min.

(54) (R)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(4-(trifluoromethyl)phenyl)methanol

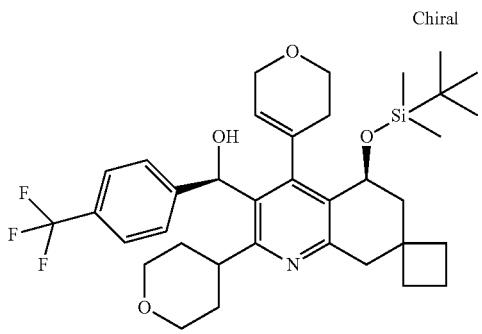 [SMILES: CC(C)(C)[Si](C)(C)O[C@H]1CC2(CCC2)Cc2nc(C3CCOCC3)c([C@H](O)c3ccc(C(F)(F)F)cc3)c(C3=CCOCC3)c21]

Obtained by starting from (R)—((S)-5'-(tert-butyldimethylsilyloxy)-4'-iodo-2'-(tetrahydro-2H-pyran-4-yl)-6',8'-dihydro-5'H-spiro[cyclobutane-1,7'-quinoline]-3'-yl)(4-(trifluoromethyl)phenyl)methanol and 2-(3,6-dihydro-2H-pyran-4-yl)-4,4,5,5-tetramethyl-1,3,2-dioxaborolane. A 2 M solution of caesium carbonate in water is used instead caesium fluoride. The reaction is run in tetrahydrofurane/toluene 4:1.

Mass spectrometry (ESI$^+$): m/z=644 [M+H]$^+$

HPLC (Method 7): Retention time=1.762 min.

(55) (3R,9S)-9-(tert-butyldimethylsilyloxy)-4-(3,6-dihydro-2H-pyran-4-yl)-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]

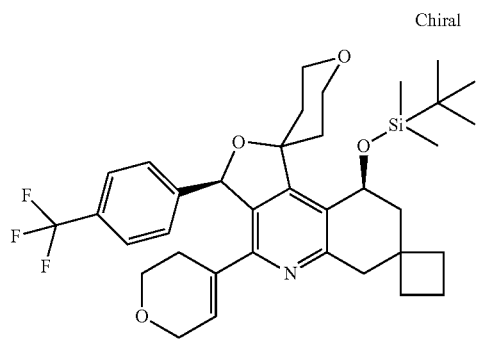 [SMILES: CC(C)(C)[Si](C)(C)O[C@H]1CC2(CCC2)Cc2nc(C3=CCOCC3)c3c(c21)C1(CCOCC1)O[C@@H]3c1ccc(C(F)(F)F)cc1]

Obtained by starting from (3R,9S)-9-(tert-butyldimethylsilyloxy)-4-chloro-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]. A 2 M solution of caesium carbonate in water is used instead caesium fluoride. The reaction is run in tetrahydrofurane/toluene 2:1.

Mass spectrometry (ESI$^+$): m/z=642 [M+H]$^+$

HPLC (Method 34): Retention time=1.432 min.

(56) (S)-5-(tert-butyldimethylsilyloxy)-4-(4,4-difluorocyclohex-1-enyl)-2-isopropyl-7,7-dimethyl-5,6,7,8-tetrahydroquinoline-3-carbaldehyde

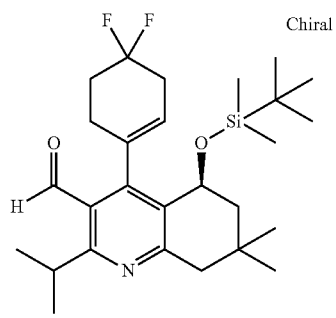 [SMILES: CC(C)c1nc2c(c(C3=CCC(F)(F)CC3)c1C=O)[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 2-(4,4-difluorocyclohex-1-enyl)-4,4,5,5-tetramethyl-1,3,2-dioxaborolane (WO2010/057121).

Mass spectrometry (ESI⁺): m/z=478 [M+H]⁺

HPLC (Method 30): Retention time=2.23 min.

Example XII

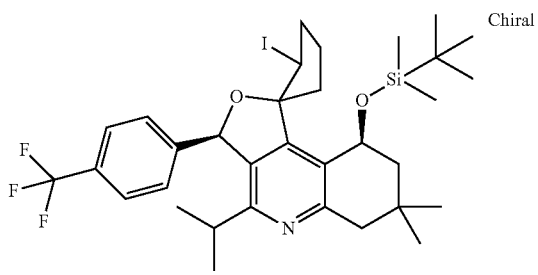 [SMILES: CC(C)c1nc2c(c3c1[C@@H](c1ccc(C(F)(F)F)cc1)OC31CCCC1I)[C@@H](O[Si](C)(C)C(C)(C)C)CC(C)(C)C2]

(3'R,9'S)-9'-(tert-butyldimethylsilyloxy)-2-iodo-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]

105 mg (R)—((S)-5-(tert-butyldimethylsilyloxy)-4-cyclopentenyl-2-isopropyl-7,7-dimethyl-5,6,7,8-tetrahydroquinolin-3-yl)(4-(trifluoromethyl)phenyl)methanol are dissolved in 4 ml dichloromethane, mixed with 500 µl of a 1 M solution of iodinechloride in dichloromethane and stirred for 24 hours. Then the solution is diluted with diethylether and washed with saturated aqueous sodium bicarbonate solution, saturated aqueous sodium thiosulphate solution and brine. After drying with magnesium sulphate the solvents are evaporated in vacuo and the residue is chromatographed on silica gel (cyclohexane/ethylacetate 98:2 to 80:20).

Yield: 64 mg (50% of theory)

Mass spectrometry (ESI⁺): m/z=700 [M+H]⁺

$R_f$-value: 0.57 (silica gel, petrole ether/ethylacetate 8:1)

Analogously to example XII the following compounds are obtained:

(1) (3'S,9'S)-9'-(tert-butyldimethylsilyloxy)-2-iodo-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]

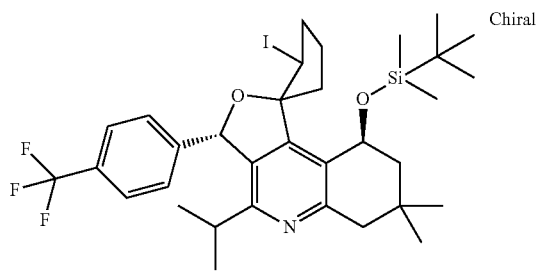 [SMILES: CC(C)c1nc2c(c3c1[C@H](c1ccc(C(F)(F)F)cc1)OC31CCCC1I)[C@@H](O[Si](C)(C)C(C)(C)C)CC(C)(C)C2]

Obtained by starting from (S)—((S)-5-(tert-butyldimethylsilyloxy)-4-cyclopentenyl-2-isopropyl-7,7-dimethyl-5,6,7,8-tetrahydroquinolin-3-yl)(4-(trifluoromethyl)phenyl)methanol.

Mass spectrometry (ESI⁺): m/z=700 [M+H]⁺

$R_f$-value: 0.63 (silica gel, petrole ether/ethylacetate 8:1)

(2) (3R,9S)-9-(tert-butyldimethylsilyloxy)-1-(iodomethyl)-4-isopropyl-1,7,7-trimethyl-3-(4-(trifluoromethyl)phenyl)-1,3,6,7,8,9-hexahydrofuro[3,4-c]quinoline

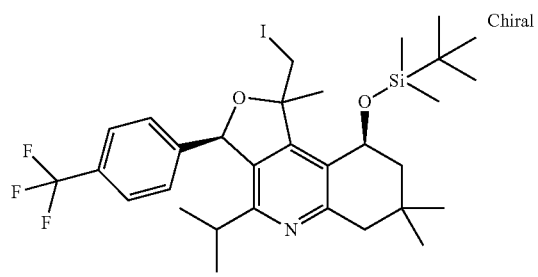 [SMILES: CC(C)c1nc2c(c3c1[C@@H](c1ccc(C(F)(F)F)cc1)OC3(C)CI)[C@@H](O[Si](C)(C)C(C)(C)C)CC(C)(C)C2]

Obtained by starting from (R)—((S)-5-(tert-butyldimethylsilyloxy)-2-isopropyl-7,7-dimethyl-4-(prop-1-en-2-yl)-5,6,7,8-tetrahydroquinolin-3-yl)(4-(trifluoromethyl)phenyl)methanol.

Mass spectrometry (ESI⁺): m/z=674 [M+H]⁺

HPLC (Method 1): Retention time=5.069 min.

$R_f$-value: 0.65 (silica gel, petrole ether/ethylacetate 8:1)

(3) (3'R,9'S)-9'-(tert-butyldimethylsilyloxy)-2-iodo-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinoline]

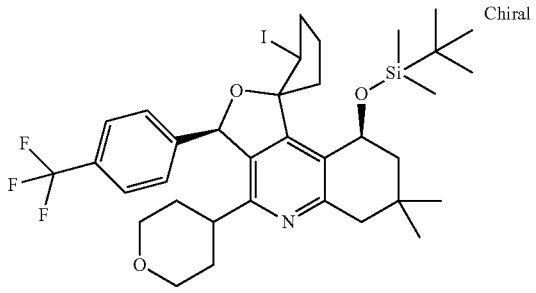 [SMILES: CC1(C)Cc2nc(C3CCOCC3)c3c(c2[C@@H](O[Si](C)(C)C(C)(C)C)C1)C1(CCCC1I)O[C@@H]3c1ccc(C(F)(F)F)cc1]

Obtained by starting from (R)—((S)-5-(tert-butyldimethylsilyloxy)-4-cyclopentenyl-7,7-dimethyl-2-(tetrahydro-2H-pyran-4-yl)-5,6,7,8-tetrahydroquinolin-3-yl)(4-(trifluoromethyl)phenyl)methanol.
Mass spectrometry (ESI⁺): m/z=742 [M+H]⁺
HPLC (Method 1): Retention time=5.170 min.
$R_f$-value: 0.62 (silica gel, petrole ether/ethylacetate 4:1)

(4) (3'R,9'S)-9'-(tert-butyldimethylsilyloxy)-4'-cyclopentyl-2-iodo-7',7'-dimethyl-3'-(4-(trifluoromethyl)phenyl)-6',7',8',9'-tetrahydro-3'H-spiro[cyclopentane-1,1'-furo[3,4-c]quinoline]

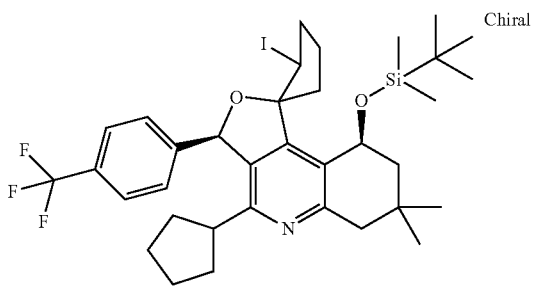 [SMILES: CC1(C)Cc2nc(C3CCCC3)c3c(c2[C@@H](O[Si](C)(C)C(C)(C)C)C1)C1(CCCC1I)O[C@@H]3c1ccc(C(F)(F)F)cc1]

Obtained by starting from (R)—((S)-5-(tert-butyldimethylsilyloxy)-4-cyclopentenyl-2-cyclopentyl-7,7-dimethyl-5,6,7,8-tetrahydroquinolin-3-yl)(4-(trifluoromethyl)phenyl)methanol.
Mass spectrometry (ESI⁺): m/z=726 [M+H]⁺
HPLC (Method 9): Retention time=2.73 min.

(5) (3'R,9'S)-9'-(tert-butyldimethylsilyloxy)-2-iodo-4'-isopropyl-3'-(4-isopropylphenyl)-7',7'-dimethyl-6',7',8',9'-tetrahydro-3'H-spiro[cyclopentane-1,1'-furo[3,4-c]quinoline]

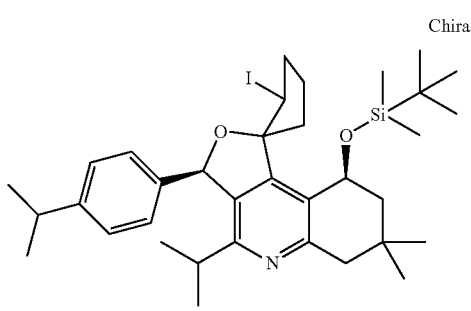

Obtained by starting from (3'R,9'S)-9'-(tert-butyldimethylsilyloxy)-2-iodo-4'-isopropyl-3'-(4-isopropylphenyl)-7',7'-dimethyl-6',7',8',9'-tetrahydro-3'H-spiro[cyclopentane-1,1'-furo[3,4-c]quinoline].
Mass spectrometry (ESI⁺): m/z=674 [M+H]⁺
HPLC (Method 8): Retention time=3.51 min.

(6) (3'R,9'S)-9'-(tert-butyldimethylsilyloxy)-3'-(4-fluorophenyl)-2-iodo-4'-isopropyl-7',7'-dimethyl-6',7',8',9'-tetrahydro-3'H-spiro[cyclopentane-1,1'-furo[3,4-c]quinoline]

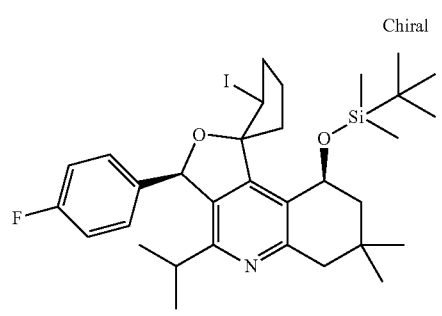 [SMILES: CC(C)c1nc2c(c3c1[C@@H](c1ccc(F)cc1)OC31CCCC1I)[C@@H](O[Si](C)(C)C(C)(C)C)CC(C)(C)C2]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(4-fluorophenyl)methanol.
Mass spectrometry (ESI⁺): m/z=650 [M+H]⁺
HPLC (Method 21): Retention time=2.17 min.

(7) (3'R,9'S)-9'-(tert-butyldimethylsilyloxy)-3'-(4-chlorophenyl)-2-iodo-4'-isopropyl-7',7'-dimethyl-6',7',8',9'-tetrahydro-3'H-spiro[cyclopentane-1,1'-furo[3,4-c]quinoline]

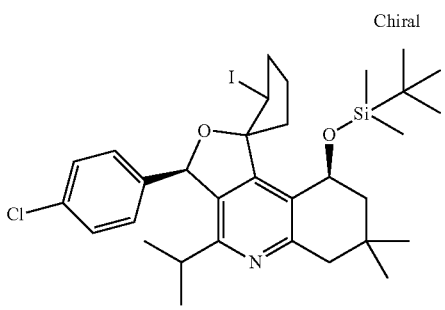 [SMILES: CC(C)c1nc2c(c3c1[C@@H](c1ccc(Cl)cc1)OC31CCCC1I)[C@@H](O[Si](C)(C)C(C)(C)C)CC(C)(C)C2]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(4-chlorophenyl)methanol.
Mass spectrometry (ESI⁺): m/z=666 [M+H]⁺
HPLC (Method 21): Retention time=2.15 min.

(8) (3'R,9'S)-9'-(tert-butyldimethylsilyloxy)-4'-cyclopentyl-3'-(4-fluorophenyl)-2-iodo-7',7'-dimethyl-6',7',8',9'-tetrahydro-3'H-spiro[cyclopentane-1,1'-furo[3,4-c]quinoline]

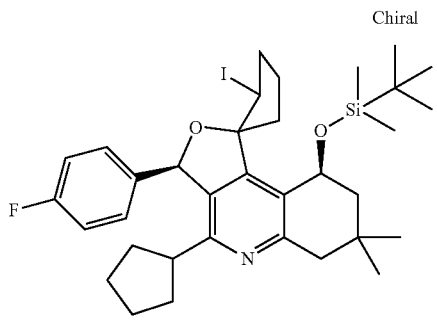

Obtained by starting from (R)—((S)-5-(tert-butyldimethylsilyloxy)-4-cyclopentenyl-2-cyclopentyl-7,7-dimethyl-5,6,7,8-tetrahydroquinolin-3-yl)(4-fluorophenyl)methanol.
Mass spectrometry (ESI$^+$): m/z=676 [M+H]$^+$
HPLC (Method 20): Retention time=4.18 min.

(9) (3'R,9'S)-9'-(tert-butyldimethylsilyloxy)-3'-(4-tert-butylphenyl)-2-iodo-4'-isopropyl-7',7'-dimethyl-6',7',8',9'-tetrahydro-3'H-spiro[cyclopentane-1,1'-furo[3,4-c]quinoline]

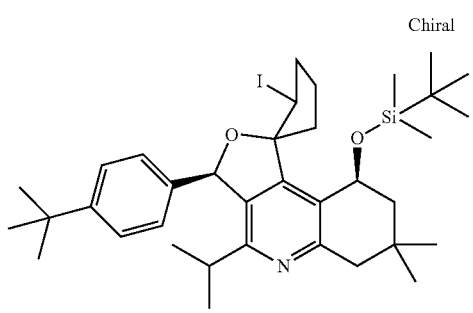 [SMILES: CC(C)c1nc2c(c3c1[C@@H](c1ccc(C(C)(C)C)cc1)OC31CCCC1I)[C@@H](O[Si](C)(C)C(C)(C)C)CC(C)(C)C2]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(4-tert-butylphenyl)methanol.
Mass spectrometry (ESI$^+$): m/z=688 [M+H]$^+$

(10) (3'R,9'S)-9'-(tert-butyldimethylsilyloxy)-2-iodo-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]

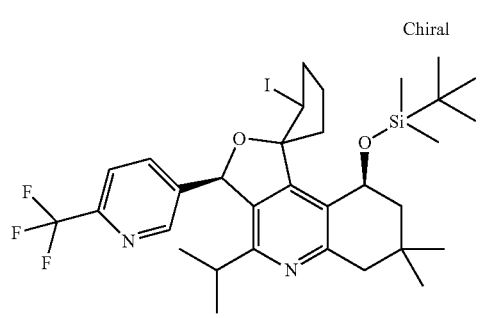 [SMILES: CC(C)c1nc2c(c3c1[C@@H](c1ccc(C(F)(F)F)nc1)OC31CCCC1I)[C@@H](O[Si](C)(C)C(C)(C)C)CC(C)(C)C2]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(6-(trifluoromethyl)pyridin-3-yl)methanol.
Mass spectrometry (ESI$^+$): m/z=701 [M+H]$^+$
HPLC (Method 8): Retention time=3.17 min.

(11) (3'S,9'S)-9'-(tert-butyldimethylsilyloxy)-2-iodo-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinoline]

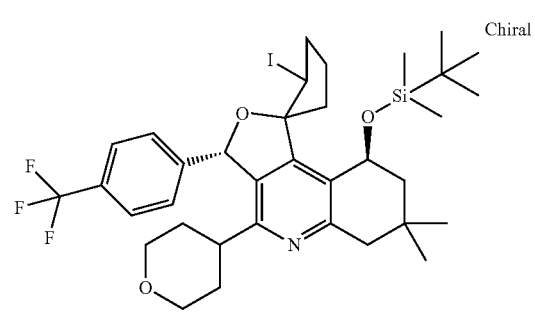 [SMILES: CC1(C)Cc2nc(C3CCOCC3)c3c(c2[C@@H](O[Si](C)(C)C(C)(C)C)C1)C1(CCCC1I)O[C@H]3c1ccc(C(F)(F)F)cc1]

Obtained by starting from (S)—((S)-5-(tert-butyldimethylsilyloxy)-4-cyclopentenyl-7,7-dimethyl-2-(tetrahydro-2H-pyran-4-yl)-5,6,7,8-tetrahydroquinolin-3-yl)(4-(trifluoromethyl)phenyl)methanol.
Mass spectrometry (ESI$^+$): m/z=742 [M+H]$^+$
HPLC (Method 1): Retention time=5.196 min.
$R_f$-value: 0.28 (silica gel, petrole ether/ethylacetate 8:1)

(12) (3'R,9'S)-9'-(tert-butyldimethylsilyloxy)-2-iodo-4'-isopropyl-7',7'-dimethyl-3'-p-tolyl-6',7',8',9'-tetrahydro-3'H-spiro[cyclopentane-1,1'-furo[3,4-c]quinoline]

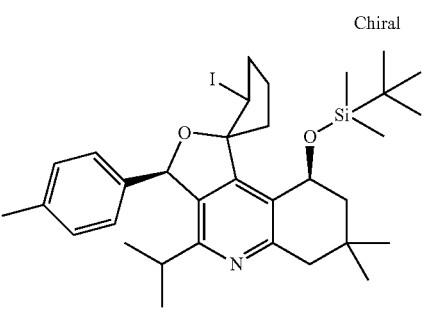 [SMILES: Cc1ccc([C@H]2OC3(CCCC3I)c3c2c(C(C)C)nc2c3[C@@H](O[Si](C)(C)C(C)(C)C)CC(C)(C)C2)cc1]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(p-tolyl)methanol.
Mass spectrometry (ESI$^+$): m/z=646 [M+H]$^+$
HPLC (Method 20): Retention time=4.05 min.

(13) (3'R,9'S)-9'-(tert-butyldimethylsilyloxy)-2-iodo-4'-isopropyl-7',7'-(propan-1,3-diyl)-3'-(4-(trifluoromethyl)phenyl)-6',7',8',9'-tetrahydro-3'H-spiro[cyclopentane-1,1'-furo[3,4-c]quinoline]

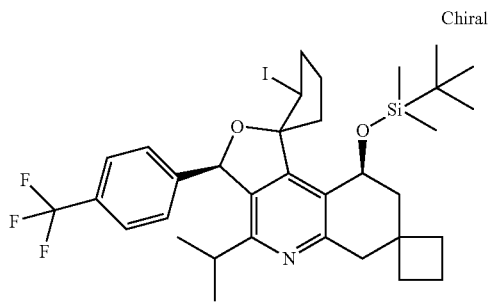 [SMILES: CC(C)c1nc2c(c3c1[C@@H](c1ccc(C(F)(F)F)cc1)OC31CCCC1I)[C@@H](O[Si](C)(C)C(C)(C)C)CC1(CCC1)C2]

Obtained by starting from (R)—((S)-5'-(tert-butyldimethylsilyloxy)-4'-cyclopentenyl-2'-isopropyl-6',8'-dihydro-5'H-spiro[cyclobutane-1,7'-quinoline]-3'-yl)(4-(trifluoromethyl)phenyl)methanol.

Mass spectrometry (ESI⁺): m/z=712 [M+H]⁺

HPLC (Method 20): Retention time=4.22 min.

(14) (3'R,9'S)-9'-(tert-butyldimethylsilyloxy)-3'-(3-fluoro-4-(trifluoromethyl)phenyl)-2-iodo-4'-isopropyl-7',7'-dimethyl-6',7',8',9'-tetrahydro-3'H-spiro[cyclopentane-1,1'-furo[3,4-c]quinoline]

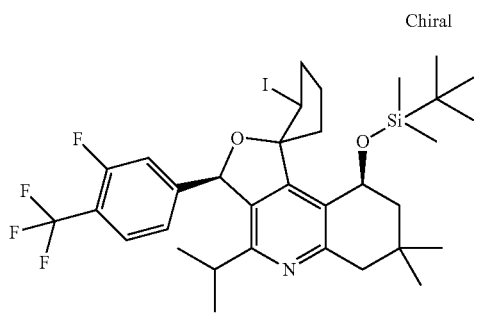 [SMILES: CC(C)c1nc2c(c3c1[C@@H](c1ccc(C(F)(F)F)c(F)c1)OC31CCCC1I)[C@@H](O[Si](C)(C)C(C)(C)C)CC(C)(C)C2]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(3-fluoro-4-(trifluoromethyl)phenyl)methanol.

Mass spectrometry (ESI⁺): m/z=718 [M+H]⁺

HPLC (Method 20): Retention time=4.23 min.

(15) (3'R,9'S)-9'-(tert-butyldimethylsilyloxy)-2-iodo-4'-isopropyl-7',7'-dimethyl-3'-(4-(trifluoromethoxy)phenyl)-6',7',8',9'-tetrahydro-3'H-spiro[cyclopentane-1,1'-furo[3,4-c]quinoline]

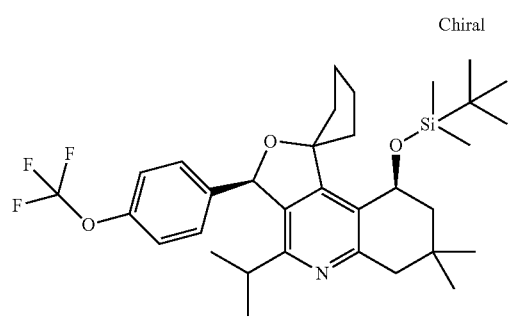 [SMILES: CC(C)c1nc2c(c3c1[C@@H](c1ccc(OC(F)(F)F)cc1)OC31CCCC1)[C@@H](O[Si](C)(C)C(C)(C)C)CC(C)(C)C2]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(4-(trifluoromethoxy)phenyl)methanol.

Mass spectrometry (ESI⁺): m/z=716 [M+H]⁺

HPLC (Method 20): Retention time=4.17 min.

(16) (3R,9S)-9-(tert-butyldimethylsilyloxy)-3-(4-tert-butylphenyl)-1-(iodomethyl)-4-isopropyl-1,7,7-trimethyl-1,3,6,7,8,9-hexahydrofuro[3,4-c]quinoline

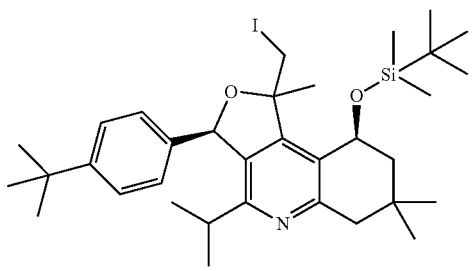

Obtained by starting from (R)—((S)-5-(tert-butyldimethylsilyloxy)-2-isopropyl-7,7-dimethyl-4-(prop-1-en-2-yl)-5,6,7,8-tetrahydroquinolin-3-yl)(4-tert-butylphenyl)methanol.

Mass spectrometry (ESI⁺): m/z=662 [M+H]⁺

HPLC (Method 19): Retention time=2.09 min.

197

(17) (3R,9S)-9-(tert-butyldimethylsilyloxy)-3-(4-tert-butylphenyl)-4-cyclopentyl-1-(iodomethyl)-1,7,7-trimethyl-1,3,6,7,8,9-hexahydrofuro[3,4-c]quinoline

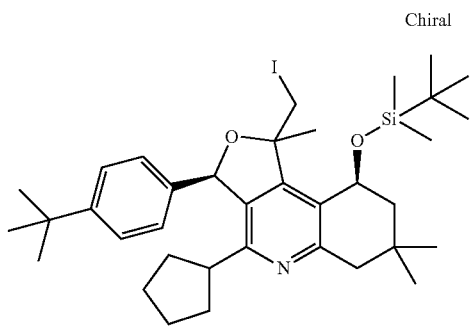 [SMILES: CC1(C)Cc2nc(C3CCCC3)c3c(c2[C@@H](O[Si](C)(C)C(C)(C)C)C1)C(C)(CI)O[C@@H]3c1ccc(C(C)(C)C)cc1]

Obtained by starting from (R)—((S)-5-(tert-butyldimethylsilyloxy)-2-cyclopentyl-7,7-dimethyl-4-(prop-1-en-2-yl)-5,6,7,8-tetrahydroquinolin-3-yl)(4-tert-butylphenyl)methanol.

Mass spectrometry (ESI$^+$): m/z=688 [M+H]$^+$

HPLC (Method 19): Retention time=2.17 min.

(18) 4-((3'R,9'S)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]-3'-yl)benzonitrile

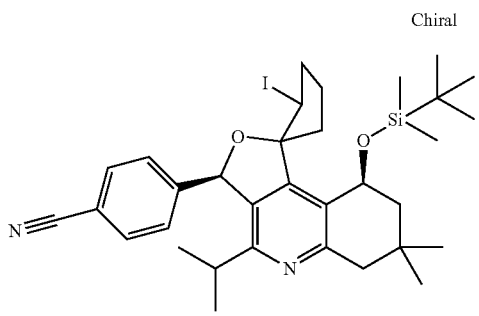 [SMILES: CC(C)c1nc2c(c3c1[C@@H](c1ccc(C#N)cc1)OC31CCCC1I)[C@@H](O[Si](C)(C)C(C)(C)C)CC(C)(C)C2]

Obtained by starting from 4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)benzonitrile. The crude product is used directly in the next step.

HPLC (Method 9): Retention time=2.39 min.

198

(19) (3'S,9'S)-9'-(tert-butyldimethylsilyloxy)-2-iodo-4'-isopropyl-7',7'-dimethyl-3'-(5-(trifluoromethyl)pyridin-2-yl)-6',7',8',9'-tetrahydro-3'H-spiro[cyclopentane-1,1'-furo[3,4-c]quinoline]

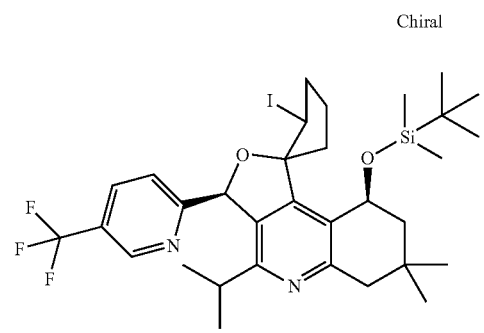 [SMILES: CC(C)c1nc2c(c3c1[C@@H](c1ccc(C(F)(F)F)cn1)OC31CCCC1I)[C@@H](O[Si](C)(C)C(C)(C)C)CC(C)(C)C2]

Obtained by starting from (S)—((S)-5-(tert-butyldimethylsilyloxy)-4-cyclopentenyl-2-isopropyl-7,7-dimethyl-5,6,7,8-tetrahydroquinolin-3-yl)(5-(trifluoromethyl)pyridin-2-yl)methanol.

Mass spectrometry (ESI$^+$): m/z=701 [M+H]$^+$

HPLC (Method 8): Retention time=3.47 min.

(20) 2-(4-((3'R,9'S)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile

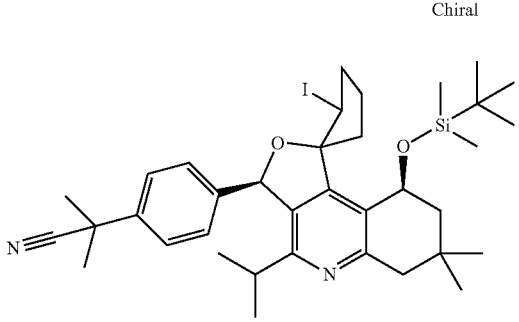 [SMILES: CC(C)c1nc2c(c3c1[C@@H](c1ccc(C(C)(C)C#N)cc1)OC31CCCC1I)[C@@H](O[Si](C)(C)C(C)(C)C)CC(C)(C)C2]

Obtained by starting from 2-(4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)phenyl)-2-methylpropanenitrile.

Mass spectrometry (ESI$^+$): m/z=699 [M+H]$^+$

HPLC (Method 1): Retention time=4.856 min.

R$_f$-value: 0.30 (silica gel, petrole ether/ethylacetate 8:1)

(21) 2-(4-((3'S,9'S)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile

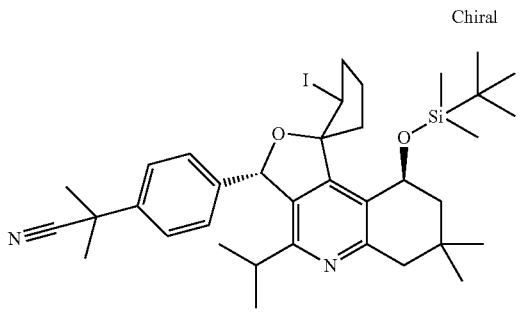 [SMILES: CC(C)c1nc2c(c3c1[C@H](c1ccc(C(C)(C)C#N)cc1)OC31CCCC1I)[C@@H](O[Si](C)(C)C(C)(C)C)CC(C)(C)C2]

Obtained by starting from 2-(4-((S)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)phenyl)-2-methylpropanenitrile.

Mass spectrometry (ESI+): m/z=699 [M+H]+

HPLC (Method 1): Retention time=4.917 min.

$R_f$-value: 0.28 (silica gel, petrole ether/ethylacetate 8:1)

(22) Ethyl 4-((3'R,9'S)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]-3'-yl)benzoate

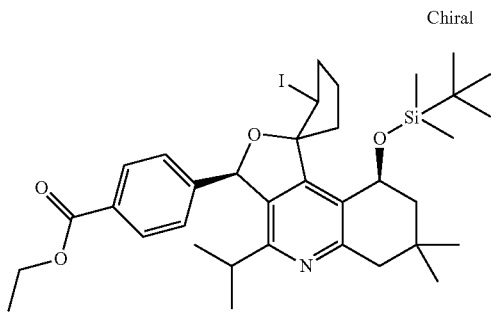 [SMILES: CCOC(=O)c1ccc([C@H]2OC3(CCCC3I)c3c2c(C(C)C)nc2c3[C@@H](O[Si](C)(C)C(C)(C)C)CC(C)(C)C2)cc1]

Obtained by starting from ethyl 4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)benzoate.

Mass spectrometry (ESI+): m/z=704 [M+H]+

HPLC (Method 1): Retention time=5.120 min.

$R_f$-value: 0.62 (silica gel, petrole ether/ethylacetate 4:1)

(23) (3'R,9'S)-9'-(tert-butyldimethylsilyloxy)-2-iodo-3'-(4-isobutylphenyl)-4'-isopropyl-7',7'-dimethyl-6',7',8',9'-tetrahydro-3'H-spiro[cyclopentane-1,1'-furo[3,4-c]quinoline]

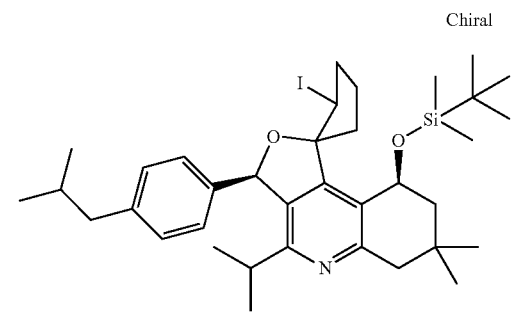 [SMILES: CC(C)Cc1ccc([C@H]2OC3(CCCC3I)c3c2c(C(C)C)nc2c3[C@@H](O[Si](C)(C)C(C)(C)C)CC(C)(C)C2)cc1]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(4-isobutylphenyl)methanol.

Mass spectrometry (ESI+): m/z=688 [M+H]+

$R_f$-value: 0.90 (silica gel, cyclohexane/ethylacetate 9:1)

(24) (3'R,9'S)-9'-(tert-butyldimethylsilyloxy)-4'-cyclobutyl-2-iodo-7',7'-dimethyl-3'-(4-(trifluoromethyl)phenyl)-6',7',8',9'-tetrahydro-3'H-spiro[cyclopentane-1,1'-furo[3,4-c]quinoline]

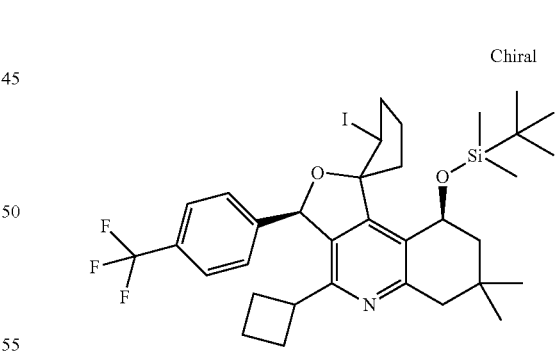

Obtained by starting from (R)—((S)-5-(tert-butyldimethylsilyloxy)-2-cyclobutyl-4-cyclopentenyl-7,7-dimethyl-5,6,7,8-tetrahydroquinolin-3-yl)(4-(trifluoromethyl)phenyl)methanol.

Mass spectrometry (ESI+): m/z=712 [M+H]+

$R_f$-value: 0.80 (silica gel, cyclohexane/ethylacetate 9:1)

(25) (3'R,9'S)-9'-(tert-butyldimethylsilyloxy)-4'-cyclopentyl-2-iodo-3'-(4-isopropylphenyl)-7',7'-dimethyl-6',7',8',9'-tetrahydro-3'H-spiro[cyclopentane-1,1'-furo[3,4-c]quinoline]

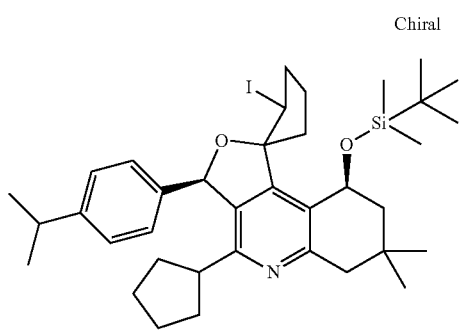 [SMILES: CC(C)c1ccc([C@H]2OC3(CCCC3I)c3c2c(C2CCCC2)nc2c3[C@@H](O[Si](C)(C)C(C)(C)C)CC(C)(C)C2)cc1]

Obtained by starting from (R)—((S)-5-(tert-butyldimethylsilyloxy)-4-cyclopentenyl-2-cyclopentyl-7,7-dimethyl-5,6,7,8-tetrahydroquinolin-3-yl)(4-isopropylphenyl)methanol.

Mass spectrometry (ESI$^+$): m/z=700 [M+H]$^+$

HPLC (Method 4): Retention time=3.904 min.

(26) (3'R,9'S)-9'-(tert-butyldimethylsilyloxy)-3'-(3-tert-butylphenyl)-4'-cyclopentyl-2-iodo-7',7'-dimethyl-6',7',8',9'-tetrahydro-3'H-spiro[cyclopentane-1,1'-furo[3,4-c]quinoline]

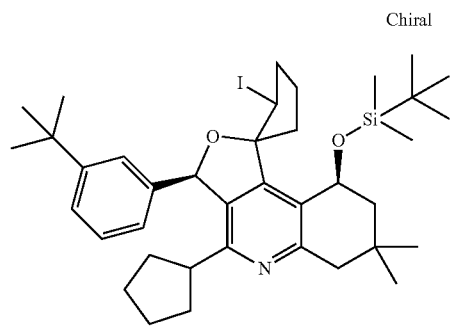 [SMILES: CC1(C)Cc2nc(C3CCCC3)c3c(c2[C@@H](O[Si](C)(C)C(C)(C)C)C1)C1(CCCC1I)O[C@@H]3c1cccc(C(C)(C)C)c1]

Obtained by starting from (R)—((S)-5-(tert-butyldimethylsilyloxy)-4-cyclopentenyl-2-cyclopentyl-7,7-dimethyl-5,6,7,8-tetrahydroquinolin-3-yl)(3-tert-butylphenyl)methanol.

HPLC (Method 4): Retention time=4.107 min.

(27) (3'R,9'S)-9'-(tert-butyldimethylsilyloxy)-3'-(4-(1,1-difluoroethyl)phenyl)-2-iodo-4'-isopropyl-7',7'-dimethyl-6',7',8',9'-tetrahydro-3'H-spiro[cyclopentane-1,1'-furo[3,4-c]quinoline]

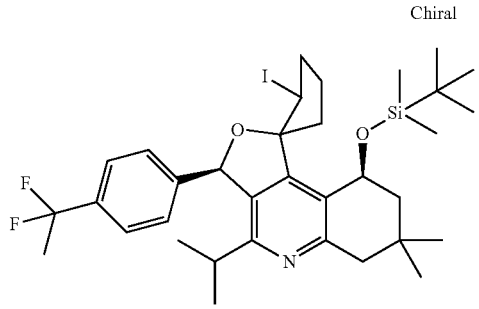 [SMILES: CC(C)c1nc2c(c3c1[C@@H](c1ccc(C(C)(F)F)cc1)OC31CCCC1I)[C@@H](O[Si](C)(C)C(C)(C)C)CC(C)(C)C2]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(4-(1,1-difluoroethyl)phenyl)methanol.

Mass spectrometry (ESI$^+$): m/z=696 [M+H]$^+$

HPLC (Method 4): Retention time=3.240 min.

(28) (3'R,9'S)-9'-(tert-butyldimethylsilyloxy)-2-iodo-4'-isopropyl-7',7'-(propan-1,3-diyl)-3'-(4-(isopropyl)phenyl)-6',7',8',9'-tetrahydro-3'H-spiro[cyclopentane-1,1'-furo[3,4-c]quinoline]

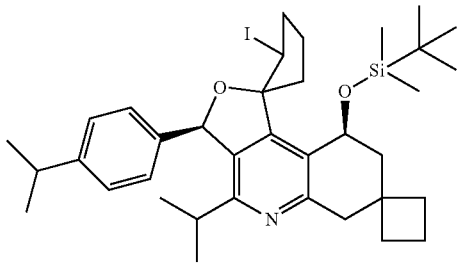

Obtained by starting from (S)-4'-cyclopentenyl-3'-((R)-hydroxy(4-isopropylphenyl)methyl)-2'-isopropyl-6',8'-dihydro-5'H-spiro[cyclobutane-1,7'-quinolin]-5'-ol.

Mass spectrometry (ESI$^+$): m/z=686 [M+H]$^+$

HPLC (Method 20): Retention time=4.19 min.

(29) (3'R,9'S)-9'-(tert-butyldimethylsilyloxy)-4'-ethyl-2-iodo-7',7'-dimethyl-3'-(4-(trifluoromethyl)phenyl)-6',7',8',9'-tetrahydro-3'H-spiro[cyclopentane-1,1'-furo[3,4-c]quinoline]

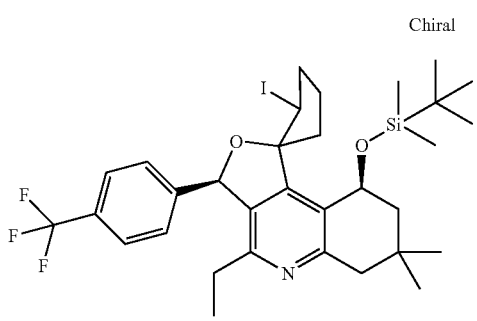 [SMILES: CCc1nc2c(c3c1[C@@H](c1ccc(C(F)(F)F)cc1)OC31CCCC1I)[C@@H](O[Si](C)(C)C(C)(C)C)CC(C)(C)C2]

Obtained by starting from (R)—((S)-5-(tert-butyldimethylsilyloxy)-4-cyclopentenyl-2-ethyl-7,7-dimethyl-5,6,7,8-tetrahydroquinolin-3-yl)(4-(trifluoromethyl)phenyl)methanol.

Mass spectrometry (ESI+): m/z=686 [M+H]+

HPLC (Method 20): Retention time=4.18 min.

(30) (3'R,9'S)-9'-(tert-butyldimethylsilyloxy)-3'-(3,5-difluoro-4-(trimethylsilyl)phenyl)-2-iodo-4'-isopropyl-7',7'-dimethyl-6',7',8',9'-tetrahydro-3'H-spiro[cyclopentane-1,1'-furo[3,4-c]quinoline]

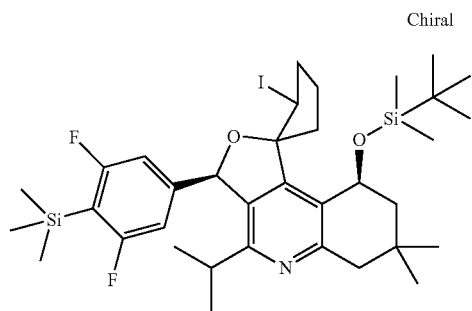 [SMILES: CC(C)c1nc2c(c3c1[C@@H](c1cc(F)c([Si](C)(C)C)c(F)c1)OC31CCCC1I)[C@@H](O[Si](C)(C)C(C)(C)C)CC(C)(C)C2]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(3,5-difluoro-4-(trimethylsilyl)phenyl)methanol.

Mass spectrometry (ESI+): m/z=740 [M+H]+

HPLC (Method 6): Retention time=4.125 min.

(31) (3'R,9'S)-9'-(tert-butyldimethylsilyloxy)-2-iodo-4'-isopropyl-7',7'-dimethyl-3'-(3-(trifluoromethyl)phenyl)-6',7',8',9'-tetrahydro-3'H-spiro[cyclopentane-1,1'-furo[3,4-c]quinoline]

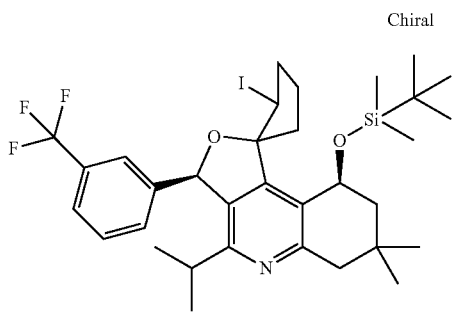 [SMILES: CC(C)c1nc2c(c3c1[C@@H](c1cccc(C(F)(F)F)c1)OC31CCCC1I)[C@@H](O[Si](C)(C)C(C)(C)C)CC(C)(C)C2]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(3-(trifluoromethyl)phenyl)methanol.

HPLC (Method 4): Retention time=3.26 min.

(32) 2-(4-((3'R,9'S)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]-3'-yl)phenyl)acetonitrile

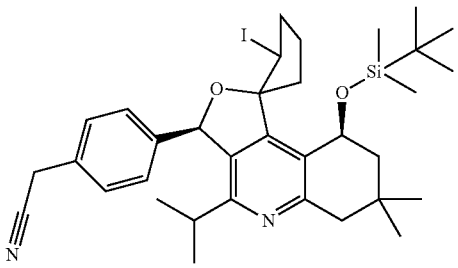

Obtained by starting from 2-(4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)phenyl)acetonitrile.

Mass spectrometry (ESI+): m/z=671 [M+H]+

(33) (3'R,9'S)-2-iodo-4'-isopropyl-7',7'-dimethyl-3'-(4-(pentafluorosulfanyl)phenyl)-9'-(2,3,3-trimethylbutan-2-yloxy)-6',7',8',9'-tetrahydro-3'H-spiro[cyclopentane-1,1'-furo[3,4-c]quinoline]

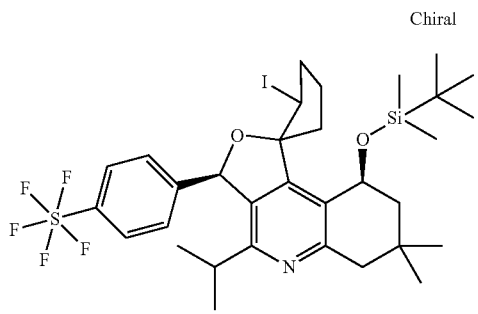 [SMILES: CC(C)c1nc2c(c3c1[C@@H](c1ccc(S(F)(F)(F)(F)F)cc1)OC31CCCC1I)[C@@H](O[Si](C)(C)C(C)(C)C)CC(C)(C)C2]

Obtained by starting from (R)—((S)-4-cyclopentenyl-2-isopropyl-7,7-dimethyl-5-(2,3,3-trimethylbutan-2-yloxy)-5,6,7,8-tetrahydroquinolin-3-yl)(4-(pentafluorosulfanyl)phenyl)methanol.

Mass spectrometry (ESI$^+$): m/z=758 [M+H]$^+$

HPLC (Method 4): Retention time=3.345 min.

Example XIII

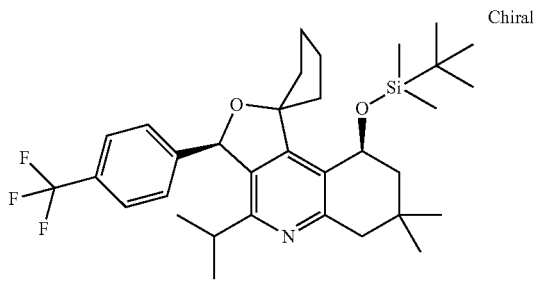 [SMILES: CC(C)c1nc2c(c3c1[C@@H](c1ccc(C(F)(F)F)cc1)OC31CCCC1)[C@@H](O[Si](C)(C)C(C)(C)C)CC(C)(C)C2]

(3'R,9'S)-9'-(tert-butyldimethylsilyloxy)-4'-isopropyl-,7',7'-dimethyl-3'-(4-(trifluoromethyl)phenyl)-6',7',8',9'-tetrahydro-3'H-spiro[cyclopentane-1,1'-furo[3,4-c]quinoline]

To a solution of 60 mg (3'R,9'S)-9'-(tert-butyldimethylsilyloxy)-2-iodo-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline] in 5 ml methanol are added 25 µl triethylamine and 90 mg of 10% palladium on charcoal. The mixture is hydrogenated at 10 bar for 12 hours. After filtration the solvent is evaporated in vacuo and the residue is chromatographed on silica gel (cyclohexane/ethylacetate 98:5 to 80:20).

Yield: 32 mg (65% of theory)

Mass spectrometry (ESI$^+$): m/z=574 [M+H]$^+$

HPLC (Method 2): Retention time=2.797 min.

R$_f$-value: 0.52 (silica gel, petrole ether/ethylacetate 8:1)

Analogously to example XIII the following compounds are obtained:

(1) a) (3'S,9'S)-9'-(tert-butyldimethylsilyloxy)-4'-isopropyl-,7',7'-dimethyl-3'-(4-(trifluoromethyl)phenyl)-6',7',8',9'-tetrahydro-3'H-spiro[cyclopentane-1,1'-furo[3,4-c]quinoline]

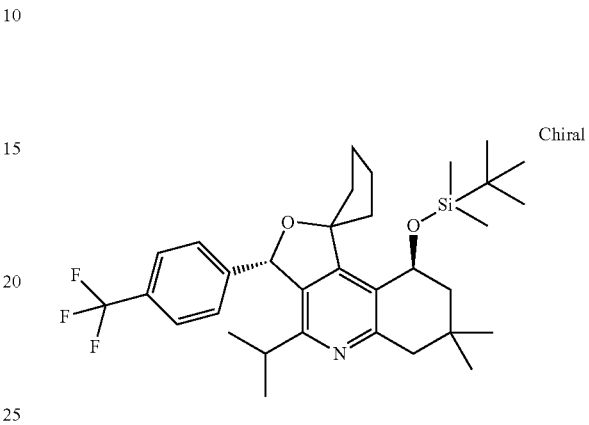

Obtained by starting from (3'S,9'S)-9'-(tert-butyldimethylsilyloxy)-2-iodo-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline].

Mass spectrometry (ESI$^+$): m/z=574 [M+H]$^+$

HPLC (Method 2): Retention time=2.814 min.

R$_f$-value: 0.50 (silica gel, petrole ether/ethylacetate 8:1)

As a side product in this reaction is obtained:

b) (1R,3'S,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopent[2]ene-1,1'-furo[3,4-c]quinoline]

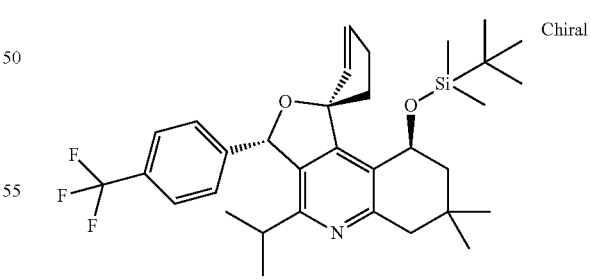

Mass spectrometry (ESI$^+$): m/z=572 [M+H]$^+$

HPLC (Method 2): Retention time=2.707 min.

R$_f$-value: 0.42 (silica gel, petrole ether/ethylacetate 8:1)

(2) (3R,9S)-9-(tert-butyldimethylsilyloxy)-4-isopropyl-1,1,7,7-tetramethyl-3-(4-(trifluoromethyl)phenyl)-1,3,6,7,8,9-hexahydrofuro[3,4-c]quinoline

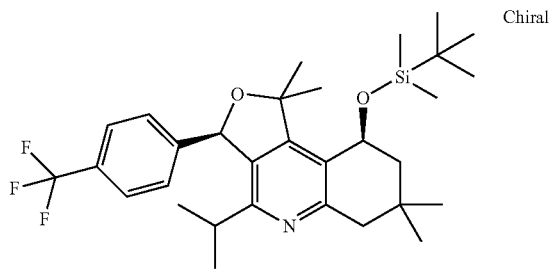 [SMILES: CC(C)c1nc2c(c3c1[C@@H](c1ccc(C(F)(F)F)cc1)OC3(C)C)[C@@H](O[Si](C)(C)C(C)(C)C)CC(C)(C)C2]

Obtained by starting from (3R,9S)-9-(tert-butyldimethylsilyloxy)-1-(iodomethyl)-4-isopropyl-1,7,7-trimethyl-3-(4-(trifluoromethyl)phenyl)-1,3,6,7,8,9-hexahydrofuro[3,4-c]quinoline.
Mass spectrometry (ESI⁺): m/z=548 [M+H]⁺
HPLC (Method 1): Retention time=4.440 min.
$R_f$-value: 0.54 (silica gel, petrole ether/ethylacetate 8:1)

(3) (3'R,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclohexane-1,1'-furo[3,4-c]quinoline]

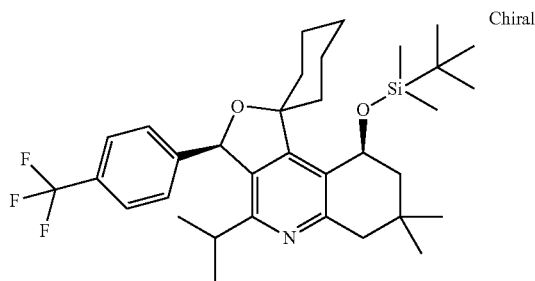 [SMILES: CC(C)c1nc2c(c3c1[C@@H](c1ccc(C(F)(F)F)cc1)OC31CCCCC1)[C@@H](O[Si](C)(C)C(C)(C)C)CC(C)(C)C2]

Obtained by starting from (3'R,9'S)-2-bromo-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclohexane-1,1'-furo[3,4-c]quinoline].
Mass spectrometry (ESI⁺): m/z=588 [M+H]⁺
HPLC (Method 1): Retention time=4.780 min.

(4) (3'R,9'S)-9'-(tert-butyldimethylsilyloxy)-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinoline]

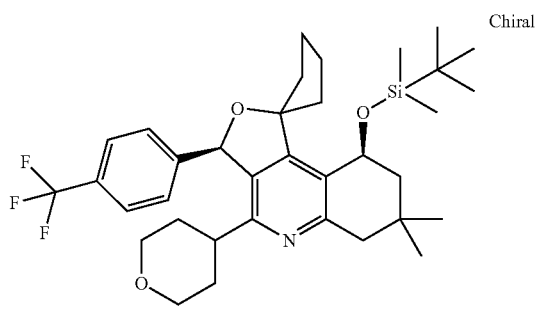 [SMILES: CC1(C)Cc2nc(C3CCOCC3)c3c(c2[C@@H](O[Si](C)(C)C(C)(C)C)C1)C1(CCCC1)O[C@@H]3c1ccc(C(F)(F)F)cc1]

Obtained by starting from (3'R,9'S)-9'-(tert-butyldimethylsilyloxy)-2-iodo-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinoline].
Mass spectrometry (ESI⁺): m/z=616 [M+H]⁺
HPLC (Method 1): Retention time=4.744 min.
$R_f$-value: 0.62 (silica gel, petrole ether/ethylacetate 4:1)

(5) (3'R,9'S)-9'-(tert-butyldimethylsilyloxy)-4'-cyclopentyl-7',7'-dimethyl-3'-(4-(trifluoromethyl)phenyl)-6',7',8',9'-tetrahydro-3'H-spiro[cyclopentane-1,1'-furo[3,4-c]quinoline]

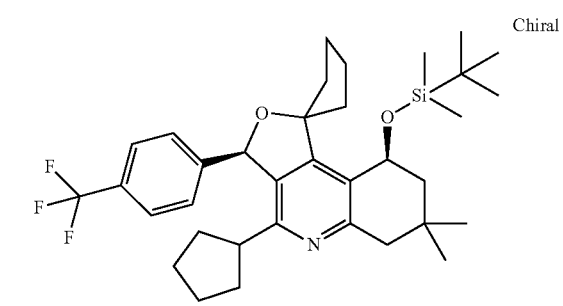 [SMILES: CC1(C)Cc2nc(C3CCCC3)c3c(c2[C@@H](O[Si](C)(C)C(C)(C)C)C1)C1(CCCC1)O[C@@H]3c1ccc(C(F)(F)F)cc1]

Obtained by starting from (3'R,9'S)-9'-(tert-butyldimethylsilyloxy)-4'-cyclopentyl-2-iodo-7',7'-dimethyl-3'-(4-(trifluoromethyl)phenyl)-6',7',8',9'-tetrahydro-3'H-spiro[cyclopentane-1,1'-furo[3,4-c]quinoline].
Mass spectrometry (ESI⁺): m/z=600 [M+H]⁺
HPLC (Method 9): Retention time=2.35 min.

(6) (3'R,9'S)-9'-(tert-butyldimethylsilyloxy)-4'-isopropyl-3'-(4-isopropylphenyl)-7',7'-dimethyl-6',7',8',9'-tetrahydro-3'H-spiro[cyclopentane-1,1'-furo[3,4-c]quinoline]

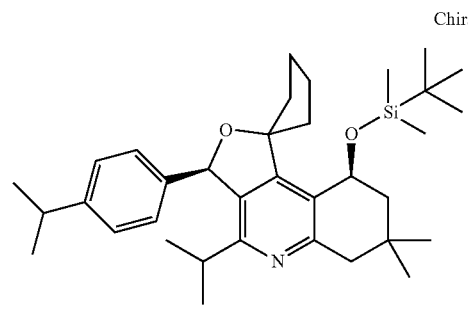

Obtained by starting from (3'R,9'S)-9'-(tert-butyldimethylsilyloxy)-2-iodo-4'-isopropyl-3'-(4-isopropylphenyl)-7',7'-dimethyl-6',7',8',9'-tetrahydro-3'H-spiro[cyclopentane-1,1'-furo[3,4-c]quinoline].
Mass spectrometry (ESI⁺): m/z=548 [M+H]⁺
HPLC (Method 8): Retention time=2.71 min.

(7) (3'R,9'S)-9'-(tert-butyldimethylsilyloxy)-3'-(4-fluorophenyl)-4'-isopropyl-7',7'-dimethyl-6',7',8',9'-tetrahydro-3'H-spiro[cyclopentane-1,1'-furo[3,4-c]quinoline]

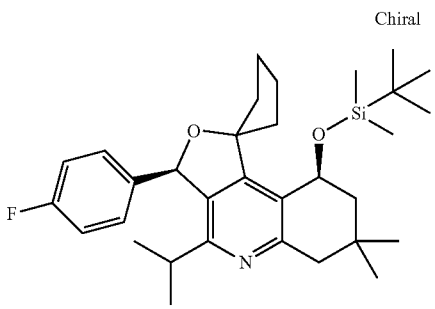 [SMILES: CC(C)c1nc2c(c3c1[C@@H](c1ccc(F)cc1)OC31CCCC1)[C@@H](O[Si](C)(C)C(C)(C)C)CC(C)(C)C2]

Obtained by starting from (3'R,9'S)-9'-(tert-butyldimethylsilyloxy)-3'-(4-fluorophenyl)-2-iodo-4'-isopropyl-7',7'-dimethyl-6',7',8',9'-tetrahydro-3'H-spiro[cyclopentane-1,1'-furo[3,4-c]quinoline].

Mass spectrometry (ESI$^+$): m/z=524 [M+H]$^+$

HPLC (Method 21): Retention time=2.07 min.

(8) (3'R,9'S)-9'-(tert-butyldimethylsilyloxy)-3'-(4-chlorophenyl)-4'-isopropyl-7',7'-dimethyl-6',7',8',9'-tetrahydro-3'H-spiro[cyclopentane-1,1'-furo[3,4-c]quinoline]

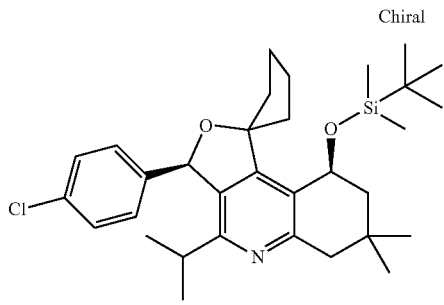 [SMILES: CC(C)c1nc2c(c3c1[C@@H](c1ccc(Cl)cc1)OC31CCCC1)[C@@H](O[Si](C)(C)C(C)(C)C)CC(C)(C)C2]

Obtained by starting from (3'R,9'S)-9'-(tert-butyldimethylsilyloxy)-3'-(4-chlorophenyl)-2-iodo-4'-isopropyl-7',7'-dimethyl-6',7',8',9'-tetrahydro-3'H-spiro[cyclopentane-1,1'-furo[3,4-c]quinoline].

Mass spectrometry (ESI$^+$): m/z=540 [M+H]$^+$

HPLC (Method 20): Retention time=4.05 min.

(9) (3'R,9'S)-9'-(tert-butyldimethylsilyloxy)-4'-cyclopentyl-3'-(4-fluorophenyl)-7',7'-dimethyl-6',7',8',9'-tetrahydro-3'H-spiro[cyclopentane-1,1'-furo[3,4-c]quinoline]

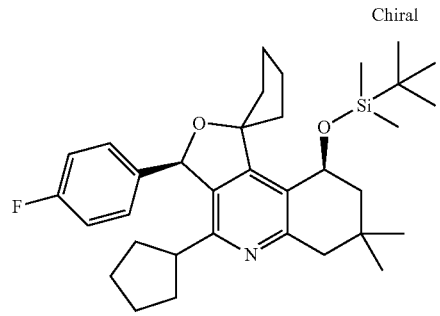 [SMILES: CC1(C)Cc2nc(C3CCCC3)c3c(c2[C@@H](O[Si](C)(C)C(C)(C)C)C1)C1(CCCC1)O[C@@H]3c1ccc(F)cc1]

Obtained by starting from (3'R,9'S)-9'-(tert-butyldimethylsilyloxy)-4'-cyclopentyl-3'-(4-fluorophenyl)-2-iodo-7',7'-dimethyl-6',7',8',9'-tetrahydro-3'H-spiro[cyclopentane-1,1'-furo[3,4-c]quinoline].

Mass spectrometry (ESI$^+$): m/z=550 [M+H]$^+$

HPLC (Method 20): Retention time=4.00 min.

(10) (3'R,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline]

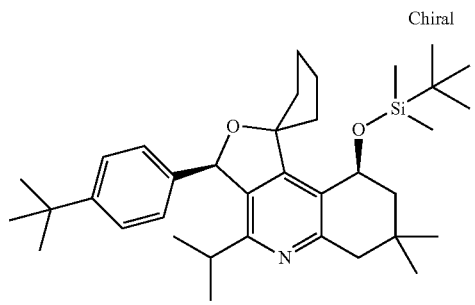 [SMILES: CC(C)c1nc2c(c3c1[C@@H](c1ccc(C(C)(C)C)cc1)OC31CCCC1)[C@@H](O[Si](C)(C)C(C)(C)C)CC(C)(C)C2]

Obtained by starting from (3'R,9'S)-9'-(tert-butyldimethylsilyloxy)-3'-(4-tert-butylphenyl)-2-iodo-4'-isopropyl-7',7'-dimethyl-6',7',8',9'-tetrahydro-3'H-spiro[cyclopentane-1,1'-furo[3,4-c]quinoline].

Mass spectrometry (ESI$^+$): m/z=562 [M+H]$^+$

(11) (3'R,9'S)-9'-(tert-butyldimethylsilyloxy)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]

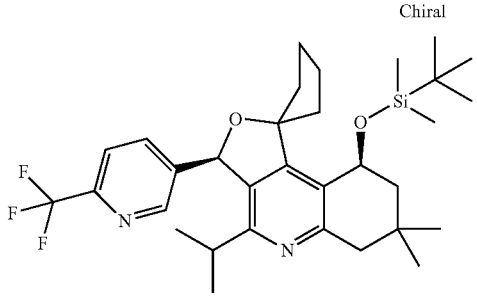 [SMILES: CC(C)c1nc2c(c3c1[C@@H](c1ccc(C(F)(F)F)nc1)OC31CCCC1)[C@@H](O[Si](C)(C)C(C)(C)C)CC(C)(C)C2]

Obtained by starting from (3'R,9'S)-9'-(tert-butyldimethyl-silyloxy)-2-iodo-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline].

Mass spectrometry (ESI⁺): m/z=575 [M+H]⁺

HPLC (Method 8): Retention time=2.69 min.

(12) (3'S,9'S)-9'-(tert-butyldimethylsilyloxy)-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinoline]

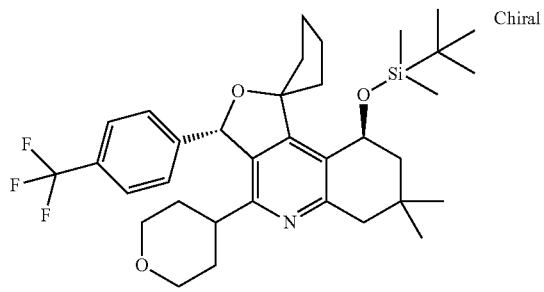 [SMILES: CC1(C)Cc2nc(C3CCOCC3)c3c(c2[C@@H](O[Si](C)(C)C(C)(C)C)C1)C1(CCCC1)O[C@H]3c1ccc(C(F)(F)F)cc1]

Obtained by starting from (3'S,9'S)-9'-(tert-butyldimethyl-silyloxy)-2-iodo-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinoline].

Mass spectrometry (ESI⁺): m/z=616 [M+H]⁺

HPLC (Method 1): Retention time=4.696 min.

R$_f$-value: 0.50 (silica gel, petrole ether/ethylacetate 4:1)

(13) (3'R,9'S)-9'-(tert-butyldimethylsilyloxy)-4'-isopropyl-7',7'-dimethyl-3'-p-tolyl-6',7',8',9'-tetrahydro-3'H-spiro[cyclopentane-1,1'-furo[3,4-c]quinoline]

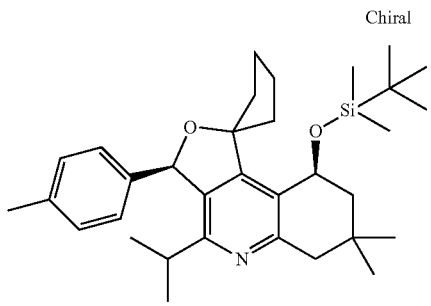 [SMILES: Cc1ccc([C@H]2OC3(CCCC3)c3c2c(C(C)C)nc2c3[C@@H](O[Si](C)(C)C(C)(C)C)CC(C)(C)C2)cc1]

Obtained by starting from (3'R,9'S)-9'-(tert-butyldimethyl-silyloxy)-2-iodo-4'-isopropyl-7',7'-dimethyl-3'-p-tolyl-6',7',8',9'-tetrahydro-3'H-spiro[cyclopentane-1,1'-furo[3,4-c]quinoline].

Mass spectrometry (ESI⁺): m/z=520 [M+H]⁺

HPLC (Method 20): Retention time=3.89 min.

(14) (3'R,9'S)-9'-(tert-butyldimethylsilyloxy)-4'-isopropyl-,7',7'-(propan-1,3-diyl)-3'-(4-(trifluoromethyl)phenyl)-6',7',8',9'-tetrahydro-3'H-spiro[cyclopentane-1,1'-furo[3,4-c]quinoline]

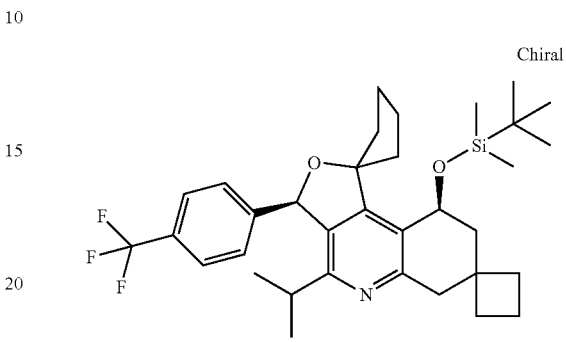

Obtained by starting from (3'R,9'S)-9'-(tert-butyldimethyl-silyloxy)-2-iodo-4'-isopropyl-7',7'-(propan-1,3-diyl)-3'-(4-(trifluoromethyl)phenyl)-6',7',8',9'-tetrahydro-3'H-spiro[cyclopentane-1,1'-furo[3,4-c]quinoline].

Mass spectrometry (ESI⁺): m/z=586 [M+H]⁺

HPLC (Method 20): Retention time=4.03 min.

(15) (3'R,9'S)-9'-(tert-butyldimethylsilyloxy)-3'-(3-fluoro-4-(trifluoromethyl)phenyl)-4'-isopropyl-7',7'-dimethyl-6',7',8',9'-tetrahydro-3'H-spiro[cyclopentane-1,1'-furo[3,4-c]quinoline]

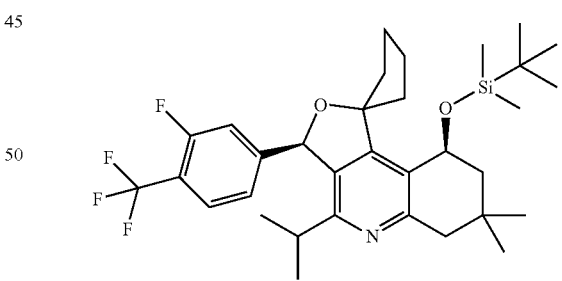

Obtained by starting from (3'R,9'S)-9'-(tert-butyldimethyl-silyloxy)-3'-(3-fluoro-4-(trifluoromethyl)phenyl)-2-iodo-4'-isopropyl-7',7'-dimethyl-6',7',8',9'-tetrahydro-3'H-spiro[cyclopentane-1,1'-furo[3,4-c]quinoline].

Mass spectrometry (ESI⁺): m/z=592 [M+H]⁺

HPLC (Method 20): Retention time=4.06 min.

(16) (3'R,9'S)-9'-(tert-butyldimethylsilyloxy)-4'-isopropyl-7',7'-dimethyl-3'-(4-(trifluoromethoxy)phenyl)-6',7',8',9'-tetrahydro-3'H-spiro[cyclopentane-1,1'-furo[3,4-c]quinoline]

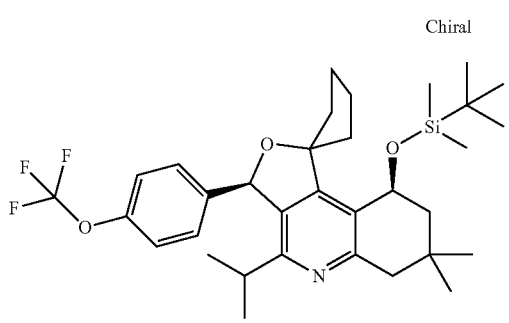 [SMILES: CC(C)c1nc2c(c3c1[C@@H](c1ccc(OC(F)(F)F)cc1)OC31CCCC1)[C@@H](O[Si](C)(C)C(C)(C)C)CC(C)(C)C2]

Obtained by starting from (3'R,9'S)-9'-(tert-butyldimethylsilyloxy)-2-iodo-4'-isopropyl-7',7'-dimethyl-3'-(4-(trifluoromethoxy)phenyl)-6',7',8',9'-tetrahydro-3'H-spiro[cyclopentane-1,1'-furo[3,4-c]quinoline].

Mass spectrometry (ESI$^+$): m/z=590 [M+H]$^+$

HPLC (Method 20): Retention time=4.01 min.

(17) (3R,9S)-9-(tert-butyldimethylsilyloxy)-3-(4-tert-butylphenyl)-4-isopropyl-1,1,7,7-tetramethyl-1,3,6,7,8,9-hexahydrofuro[3,4-c]quinoline

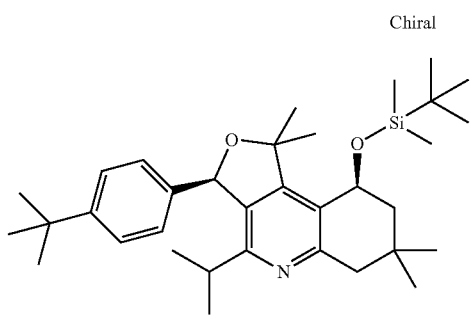 [SMILES: CC(C)c1nc2c(c3c1[C@@H](c1ccc(C(C)(C)C)cc1)OC3(C)C)[C@@H](O[Si](C)(C)C(C)(C)C)CC(C)(C)C2]

Obtained by starting from (3R,9S)-9-(tert-butyldimethylsilyloxy)-3-(4-tert-butylphenyl)-1-(iodomethyl)-4-isopropyl-1,7,7-trimethyl-1,3,6,7,8,9-hexahydrofuro[3,4-c]quinoline.

Mass spectrometry (ESI$^+$): m/z=536 [M+H]$^+$

HPLC (Method 19): Retention time=2.05 min.

(18) (3R,9S)-9-(tert-butyldimethylsilyloxy)-3-(4-tert-butylphenyl)-4-cyclopentyl-1,1,7,7-tetramethyl-1,3,6,7,8,9-hexahydrofuro[3,4-c]quinoline

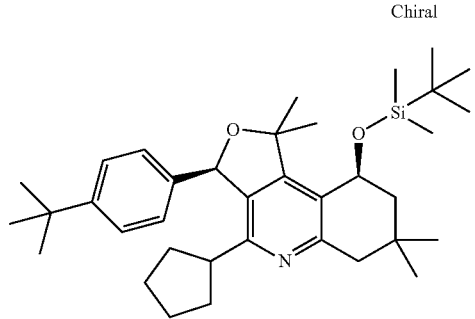 [SMILES: CC1(C)Cc2nc(C3CCCC3)c3c(c2[C@@H](O[Si](C)(C)C(C)(C)C)C1)C(C)(C)O[C@@H]3c1ccc(C(C)(C)C)cc1]

Obtained by starting from (3R,9S)-9-(tert-butyldimethylsilyloxy)-3-(4-tert-butylphenyl)-4-cyclopentyl-1-(iodomethyl)-1,7,7-trimethyl-1,3,6,7,8,9-hexahydrofuro[3,4-c]quinoline.

Mass spectrometry (ESI$^+$): m/z=562 [M+H]$^+$

HPLC (Method 22): Retention time=2.48 min.

(19) 4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)benzonitrile

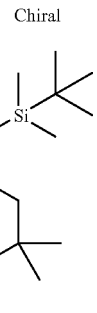

Obtained by starting from 4-((3'R,9'S)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]-3'-yl)benzonitrile.

Mass spectrometry (ESI$^+$): m/z=531 [M+H]$^+$

HPLC (Method 9): Retention time=1.86 min.

(20) (3'S,9'S)-9'-(tert-butyldimethylsilyloxy)-4'-isopropyl-7',7'-dimethyl-3'-(5-(trifluoromethyl)pyridin-2-yl)-6',7',8',9'-tetrahydro-3'H-spiro[cyclopentane-1,1'-furo[3,4-c]quinoline]

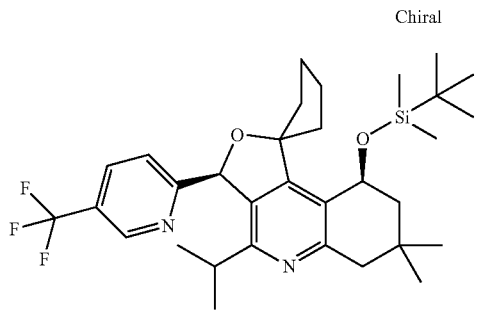 [SMILES: CC(C)c1nc2c(c3c1[C@@H](c1ccc(C(F)(F)F)cn1)OC31CCCC1)[C@@H](O[Si](C)(C)C(C)(C)C)CC(C)(C)C2]

Obtained by starting from (3'S,9'S)-9'-(tert-butyldimethylsilyloxy)-2-iodo-4'-isopropyl-7',7'-dimethyl-3'-(5-(trifluoromethyl)pyridin-2-yl)-6',7',8',9'-tetrahydro-3'H-spiro[cyclopentane-1,1'-furo[3,4-c]quinoline].

Mass spectrometry (ESI$^+$): m/z=575 [M+H]$^+$

HPLC (Method 8): Retention time=2.53 min.

$R_f$-value: 0.43 (silica gel, cyclohexane/ethylacetate 9:1)

(21) 2-(4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile

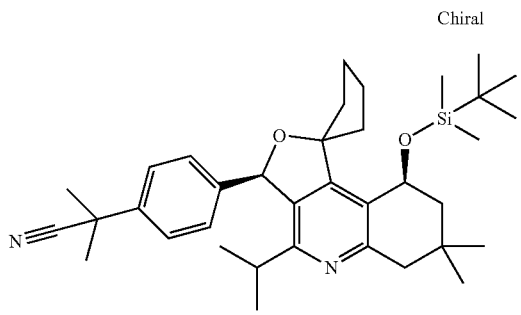 [SMILES: CC(C)c1nc2c(c3c1[C@@H](c1ccc(C(C)(C)C#N)cc1)OC31CCCC1)[C@@H](O[Si](C)(C)C(C)(C)C)CC(C)(C)C2]

Obtained by starting from 2-(4-((3'R,9'S)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile.

Mass spectrometry (ESI$^+$): m/z=573 [M+H]$^+$

HPLC (Method 1): Retention time=4.119 min.

$R_f$-value: 0.44 (silica gel, petrole ether/ethylacetate 4:1)

(22) 2-(4-((3'S,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile

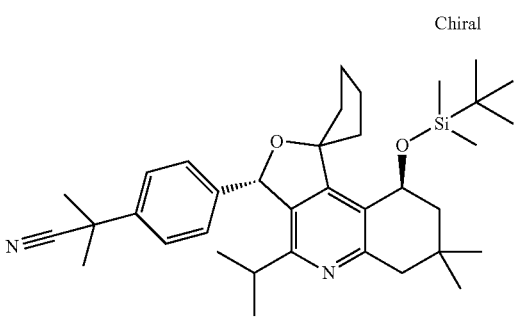 [SMILES: CC(C)c1nc2c(c3c1[C@H](c1ccc(C(C)(C)C#N)cc1)OC31CCCC1)[C@@H](O[Si](C)(C)C(C)(C)C)CC(C)(C)C2]

Obtained by starting from 2-(4-((3'S,9'S)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile.

Mass spectrometry (ESI$^+$): m/z=573 [M+H]$^+$

HPLC (Method 1): Retention time=4.117 min.

$R_f$-value: 0.45 (silica gel, petrole ether/ethylacetate 4:1)

(23) (3'S,9'S)-9'-(tert-butyldimethylsilyloxy)-4'-isopropyl-7',7'-dimethyl-3'-(5-(trifluoromethyl)thiophen-2-yl)-6',7',8',9'-tetrahydro-3'H-spiro[cyclopentane-1,1'-furo[3,4-c]quinoline]

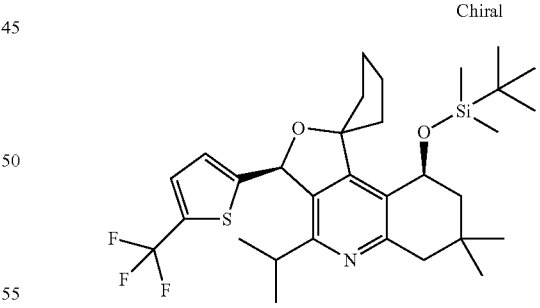

Obtained by starting from (3'S,9'S)-9'-(tert-butyldimethylsilyloxy)-2-iodo-4'-isopropyl-7',7'-dimethyl-3'-(5-(trifluoromethyl)thiophen-2-yl)-6',7',8',9'-tetrahydro-3'H-spiro[cyclopentane-1,1'-furo[3,4-c]quinoline].

Mass spectrometry (ESI$^+$): m/z=580 [M+H]$^+$

HPLC (Method 11): Retention time=14.89 min.

(24) (3'R,9'S)-9'-(tert-butyldimethylsilyloxy)-3'-(2-tert-butylpyrimidin-5-yl)-4'-isopropyl-7',7'-dimethyl-6',7',8',9'-tetrahydro-3'H-spiro[cyclopentane-1,1'-furo[3,4-c]quinoline]

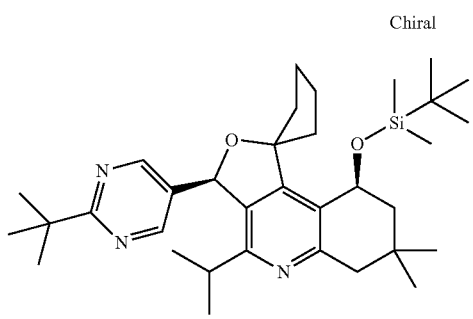 [SMILES: CC(C)c1nc2c(c3c1[C@@H](c1cnc(C(C)(C)C)nc1)OC31CCCC1)[C@@H](O[Si](C)(C)C(C)(C)C)CC(C)(C)C2]

Obtained by starting from (3'R,9'S)-9'-(tert-butyldimethylsilyloxy)-3'-(2-tert-butylpyrimidin-5-yl)-2-iodo-4'-isopropyl-7',7'-dimethyl-6',7',8',9'-tetrahydro-3'H-spiro[cyclopentane-1,1'-furo[3,4-c]quinoline].

Mass spectrometry (ESI⁺): m/z=564 [M+H]⁺

(25) Ethyl 4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)benzoate

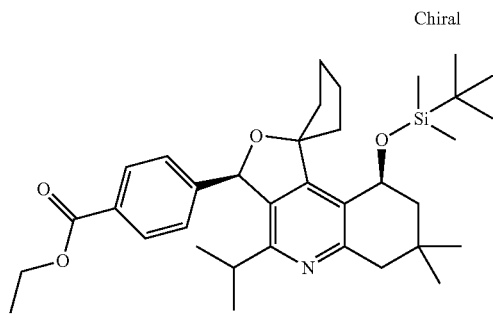 [SMILES: CCOC(=O)c1ccc([C@H]2OC3(CCCC3)c3c2c(C(C)C)nc2c3[C@@H](O[Si](C)(C)C(C)(C)C)CC(C)(C)C2)cc1]

Obtained by starting from ethyl 4-((3'R,9'S)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]-3'-yl)benzoate.

Mass spectrometry (ESI⁺): m/z=578 [M+H]⁺

HPLC (Method 1): Retention time=4.512 min.

R$_f$-value: 0.63 (silica gel, petrole ether/ethylacetate 4:1)

(26) (3'R,9'S)-9'-(tert-butyldimethylsilyloxy)-3'-(4-isobutylphenyl)-4'-isopropyl-7',7'-dimethyl-6',7',8',9'-tetrahydro-3'H-spiro[cyclopentane-1,1'-furo[3,4-c]quinoline]

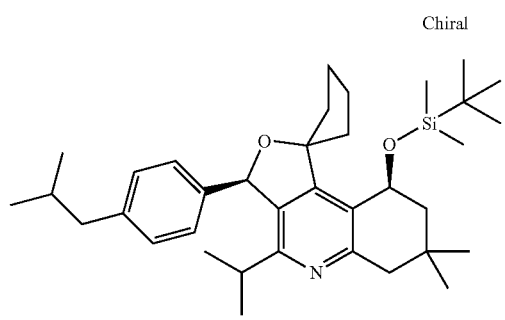 [SMILES: CC(C)Cc1ccc([C@H]2OC3(CCCC3)c3c2c(C(C)C)nc2c3[C@@H](O[Si](C)(C)C(C)(C)C)CC(C)(C)C2)cc1]

Obtained by starting from (3'R,9'S)-9'-(tert-butyldimethylsilyloxy)-2-iodo-3'-(4-isobutylphenyl)-4'-isopropyl-7',7'-dimethyl-6',7',8',9'-tetrahydro-3'H-spiro[cyclopentane-1,1'-furo[3,4-c]quinoline].

Mass spectrometry (ESI⁺): m/z=562 [M+H]⁺

R$_f$-value: 0.80 (silica gel, cyclohexane/ethylacetate 9:1)

(27) (3'R,9'S)-9'-(tert-butyldimethylsilyloxy)-4'-cyclobutyl-7',7'-dimethyl-3'-(4-(trifluoromethyl)phenyl)-6',7',8',9'-tetrahydro-3'H-spiro[cyclopentane-1,1'-furo[3,4-c]quinoline]

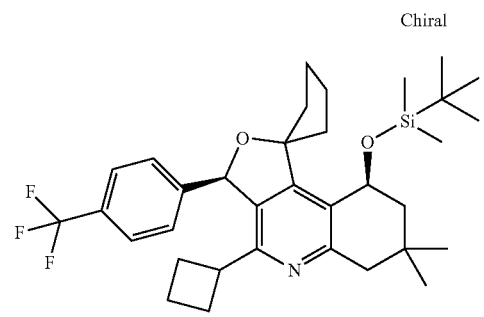 [SMILES: CC1(C)Cc2nc(C3CCC3)c3c(c2[C@@H](O[Si](C)(C)C(C)(C)C)C1)C1(CCCC1)O[C@@H]3c1ccc(C(F)(F)F)cc1]

Obtained by starting from (3'R,9'S)-9'-(tert-butyldimethylsilyloxy)-4'-cyclobutyl-2-iodo-7',7'-dimethyl-3'-(4-(trifluoromethyl)phenyl)-6',7',8',9'-tetrahydro-3'H-spiro[cyclopentane-1,1'-furo[3,4-c]quinoline].

Mass spectrometry (ESI⁺): m/z=586 [M+H]⁺

R$_f$-value: 0.70 (silica gel, cyclohexane/ethylacetate 9:1)

(28) (3'R,9'S)-9'-(tert-butyldimethylsilyloxy)-4'-cyclopentyl-3'-(4-isopropylphenyl)-7',7'-dimethyl-6',7',8',9'-tetrahydro-3'H-spiro[cyclopentane-1,1'-furo[3,4-c]quinoline]

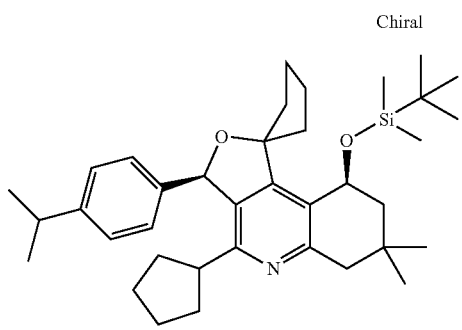 [SMILES: CC(C)c1ccc([C@H]2OC3(CCCC3)c3c2c(C2CCCC2)nc2c3[C@@H](O[Si](C)(C)C(C)(C)C)CC(C)(C)C2)cc1]

Obtained by starting from (3'R,9'S)-9'-(tert-butyldimethylsilyloxy)-4'-cyclopentyl-2-iodo-3'-(4-isopropylphenyl)-7',7'-dimethyl-6',7',8',9'-tetrahydro-3'H-spiro[cyclopentane-1,1'-furo[3,4-c]quinoline].

Mass spectrometry (ESI$^+$): m/z=574 [M+H]$^+$

HPLC (Method 5): Retention time=2.083 min.

(29) (3R,9S)-9-(tert-butyldimethylsilyloxy)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]

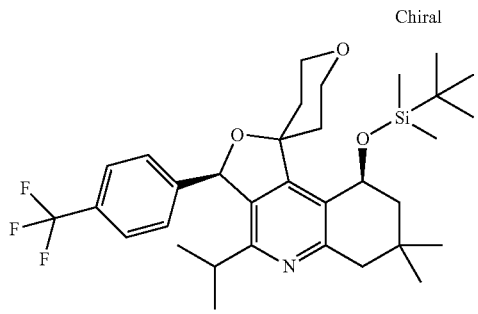 [SMILES: CC(C)c1nc2c(c3c1[C@@H](c1ccc(C(F)(F)F)cc1)OC31CCOCC1)[C@@H](O[Si](C)(C)C(C)(C)C)CC(C)(C)C2]

Obtained by starting from (3R,9S)-9-(tert-butyldimethylsilyloxy)-3'-iodo-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran].

Mass spectrometry (ESI$^+$): m/z=590 [M+H]$^+$

HPLC (Method 9): Retention time=1.99 min.

(30) (3'R,9'S)-9'-(tert-butyldimethylsilyloxy)-3'-(3-tert-butylphenyl)-4'-cyclopentyl-7',7'-dimethyl-6',7',8',9'-tetrahydro-3'H-spiro[cyclopentane-1,1'-furo[3,4-c]quinoline]

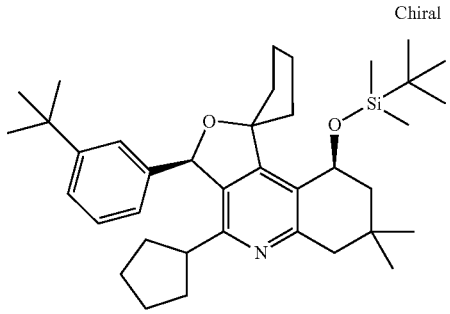 [SMILES: CC1(C)Cc2nc(C3CCCC3)c3c(c2[C@@H](O[Si](C)(C)C(C)(C)C)C1)C1(CCCC1)O[C@@H]3c1cccc(C(C)(C)C)c1]

Obtained by starting from (3'R,9'S)-9'-(tert-butyldimethylsilyloxy)-3'-(3-tert-butylphenyl)-4'-cyclopentyl-2-iodo-7',7'-dimethyl-6',7',8',9'-tetrahydro-3'H-spiro[cyclopentane-1,1'-furo[3,4-c]quinoline].

HPLC (Method 4): Retention time=3.539 min.

(31) (3'R,9'S)-9'-(tert-butyldimethylsilyloxy)-3'-(4-(1,1-difluoroethyl)phenyl)-4'-isopropyl-7',7'-dimethyl-6',7',8',9'-tetrahydro-3'H-spiro[cyclopentane-1,1'-furo[3,4-c]quinoline]

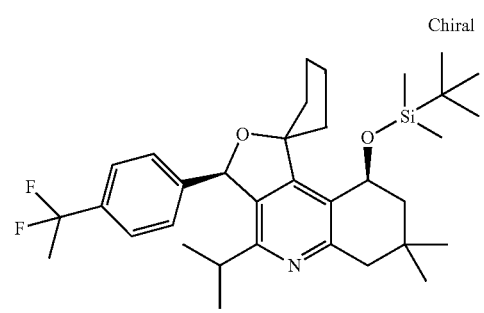 [SMILES: CC(C)c1nc2c(c3c1[C@@H](c1ccc(C(C)(F)F)cc1)OC31CCCC1)[C@@H](O[Si](C)(C)C(C)(C)C)CC(C)(C)C2]

Obtained by starting from (3'R,9'S)-9'-(tert-butyldimethylsilyloxy)-3'-(4-(1,1-difluoroethyl)phenyl)-2-iodo-4'-isopropyl-7',7'-dimethyl-6',7',8',9'-tetrahydro-3'H-spiro[cyclopentane-1,1'-furo[3,4-c]quinoline].

Mass spectrometry (ESI$^+$): m/z=570 [M+H]$^+$

HPLC (Method 4): Retention time=2.942 min.

(32) (3'R,9'S)-9'-(tert-butyldimethylsilyloxy)-4'-isopropyl-,7',7'-(propan-1,3-diyl)-3'-(4-(isopropyl)phenyl)-6',7',8',9'-tetrahydro-3'H-spiro[cyclopentane-1,1'-furo[3,4-c]quinoline]

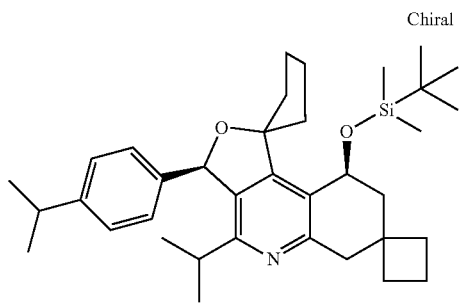 [SMILES: CC(C)c1ccc([C@H]2OC3(CCCC3)c3c2c(C(C)C)nc2c3[C@@H](O[Si](C)(C)C(C)(C)C)CC3(CCC3)C2)cc1]

Obtained by starting from (3'R,9'S)-9'-(tert-butyldimethylsilyloxy)-2-iodo-4'-isopropyl-7',7'-(propan-1,3-diyl)-3'-(4-(isopropyl)phenyl)-6',7',8',9'-tetrahydro-3'H-spiro[cyclopentane-1,1'-furo[3,4-c]quinoline].

Mass spectrometry (ESI$^+$): m/z=560 [M+H]$^+$

HPLC (Method 22): Retention time=2.51 min.

(33) (3'R,9'S)-9'-(tert-butyldimethylsilyloxy)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline]

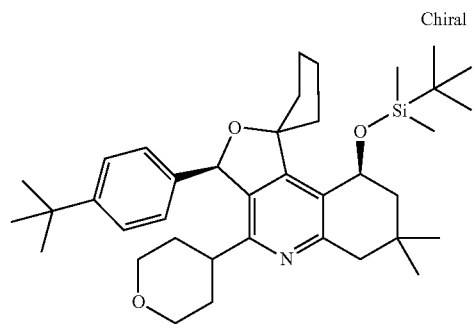 [SMILES: CC1(C)Cc2nc(C3CCOCC3)c3c(c2[C@@H](O[Si](C)(C)C(C)(C)C)C1)C1(CCCC1)O[C@@H]3c1ccc(C(C)(C)C)cc1]

Obtained by starting from (3'R,9'S)-9'-(tert-butyldimethylsilyloxy)-3'-(4-tert-butylphenyl)-2-iodo-7',7'-dimethyl-4'-(tetrahydro-2H-pyran-4-yl)-6',7',8',9'-tetrahydro-3'H-spiro[cyclopentane-1,1'-furo[3,4-c]quinoline].

Mass spectrometry (ESI$^+$): m/z=604 [M+H]$^+$

HPLC (Method 2): Retention time=2.876 min.

R$_f$-value: 0.63 (silica gel, petrole ether/ethylacetate 4:1)

(34) (3'R,9'S)-9'-(tert-butyldimethylsilyloxy)-4'-ethyl-7',7'-dimethyl-3'-(4-(trifluoromethyl)phenyl)-6',7',8',9'-tetrahydro-3'H-spiro[cyclopentane-1,1'-furo[3,4-c]quinoline]

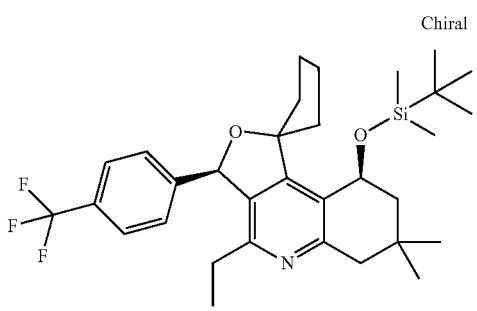 [SMILES: CCc1nc2c(c3c1[C@@H](c1ccc(C(F)(F)F)cc1)OC31CCCC1)[C@@H](O[Si](C)(C)C(C)(C)C)CC(C)(C)C2]

Obtained by starting from (3'R,9'S)-9'-(tert-butyldimethylsilyloxy)-4'-ethyl-2-iodo-7',7'-dimethyl-3'-(4-(trifluoromethyl)phenyl)-6',7',8',9'-tetrahydro-3'H-spiro[cyclopentane-1,1'-furo[3,4-c]quinoline].

Mass spectrometry (ESI$^+$): m/z=560 [M+H]$^+$

HPLC (Method 19): Retention time=2.00 min.

(35) (3'R,9'S)-9'-(tert-butyldimethylsilyloxy)-3'-(3,5-difluoro-4-(trimethylsilyl)phenyl)-4'-isopropyl-7',7'-dimethyl-6',7',8',9'-tetrahydro-3'H-spiro[cyclopentane-1,1'-furo[3,4-c]quinoline]

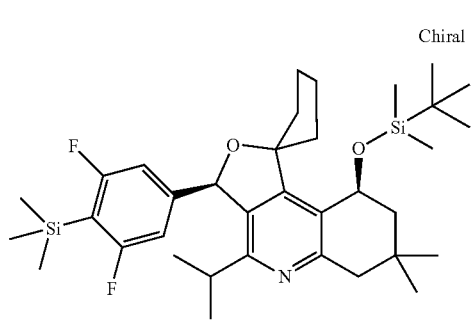 [SMILES: CC(C)c1nc2c(c3c1[C@@H](c1cc(F)c([Si](C)(C)C)c(F)c1)OC31CCCC1)[C@@H](O[Si](C)(C)C(C)(C)C)CC(C)(C)C2]

Obtained by starting from (3'R,9'S)-9'-(tert-butyldimethylsilyloxy)-3'-(3,5-difluoro-4-(trimethylsilyl)phenyl)-2-iodo-4'-isopropyl-7',7'-dimethyl-6',7',8',9'-tetrahydro-3'H-spiro[cyclopentane-1,1'-furo[3,4-c]quinoline].

Mass spectrometry (ESI$^+$): m/z=614 [M+H]$^+$

HPLC (Method 7): Retention time=2.017 min.

223

(36) (3R,9S)-9-(tert-butyldimethylsilyloxy)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]

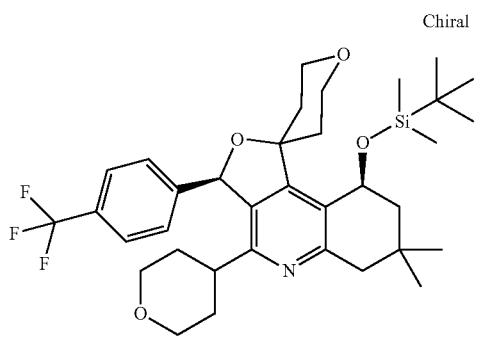 [SMILES: CC1(C)Cc2nc(C3CCOCC3)c3c(c2[C@@H](O[Si](C)(C)C(C)(C)C)C1)C1(CCOCC1)O[C@@H]3c1ccc(C(F)(F)F)cc1]

Obtained by starting from (3R,9S)-9-(tert-butyldimethylsilyloxy)-3'-iodo-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran].

Mass spectrometry (ESI$^+$): m/z=632 [M+H]$^+$

(37) 4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenol

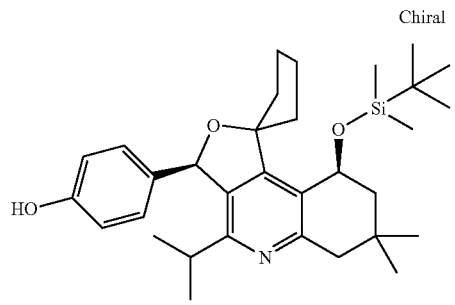 [SMILES: CC(C)c1nc2c(c3c1[C@@H](c1ccc(O)cc1)OC31CCCC1)[C@@H](O[Si](C)(C)C(C)(C)C)CC(C)(C)C2]

Obtained by starting from (3'R,9'S)-3'-(4-(benzyloxy)phenyl)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline].

Mass spectrometry (ESI$^+$): m/z=522 [M+H]$^+$

R$_f$-value: 0.29 (silica gel, cyclohexane/ethylacetate 9:1)

224

(38) (3'R,9'S)-9'-(tert-butyldimethylsilyloxy)-4'-isopropyl-7',7'-dimethyl-3'-(3-(trifluoromethyl)phenyl)-6',7',8',9'-tetrahydro-3'H-spiro[cyclopentane-1,1'-furo[3,4-c]quinoline]

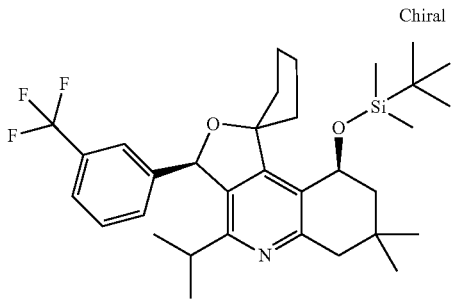 [SMILES: CC(C)c1nc2c(c3c1[C@@H](c1cccc(C(F)(F)F)c1)OC31CCCC1)[C@@H](O[Si](C)(C)C(C)(C)C)CC(C)(C)C2]

Obtained by starting from (3'R,9'S)-9'-(tert-butyldimethylsilyloxy)-2-iodo-4'-isopropyl-7',7'-dimethyl-3'-(3-(trifluoromethyl)phenyl)-6',7',8',9'-tetrahydro-3'H-spiro[cyclopentane-1,1'-furo[3,4-c]quinoline].

HPLC (Method 4): Retention time=3.08 min.

(39) (3R,9S)-9-(tert-butyldimethylsilyloxy)-3-(4-tert-butylphenyl)-4-isopropyl-7,7-dimethyl-2',3',5',6,6',7,8,9-octahydro-3H-spiro[furo[3,4-c]quinoline-1,4'-pyran]

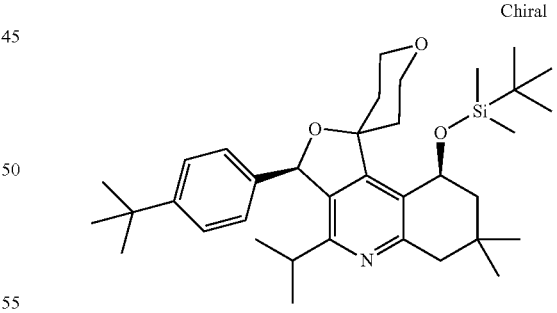

Obtained by starting from (3R,9S)-9-(tert-butyldimethylsilyloxy)-3-(4-tert-butylphenyl)-3'-iodo-4-isopropyl-7,7-dimethyl-2',3',5',6,6',7,8,9-octahydro-3H-spiro[furo[3,4-c]quinoline-1,4'-pyran].

Mass spectrometry (ESI$^+$): m/z=578 [M+H]$^+$

HPLC (Method 12): Retention time=12.18 min.

(40) (3'R,9'S)-9'-(tert-butyldimethylsilyloxy)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline]

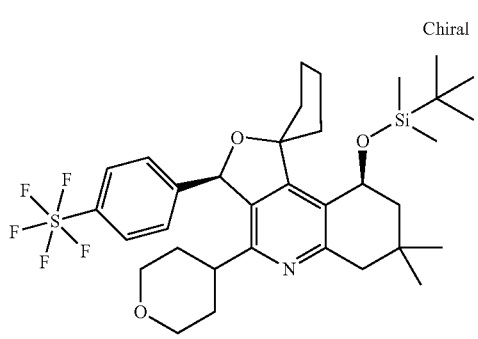 [SMILES: CC1(C)Cc2nc(C3CCOCC3)c3c(c2[C@@H](O[Si](C)(C)C(C)(C)C)C1)C1(CCCC1)O[C@@H]3c1ccc(S(F)(F)(F)(F)F)cc1]

Obtained by starting from (3'R,9'S)-9'-(tert-butyldimethylsilyloxy)-2-iodo-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline].

Mass spectrometry (ESI$^+$): m/z=674 [M+H]$^+$

HPLC (Method 1): Retention time=4.766 min.

(41) 2-(4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)acetonitrile

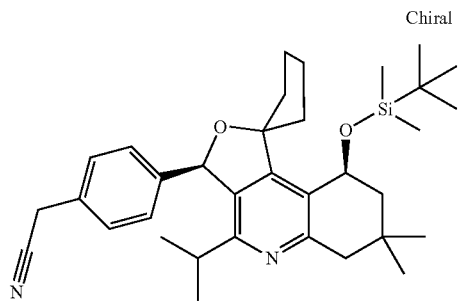 [SMILES: CC(C)c1nc2c(c3c1[C@@H](c1ccc(CC#N)cc1)OC31CCCC1)[C@@H](O[Si](C)(C)C(C)(C)C)CC(C)(C)C2]

Obtained by starting from 2-(4-((3'R,9'S)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]-3'-yl)phenyl)acetonitrile.

Mass spectrometry (ESI$^+$): m/z=545 [M+H]$^+$

R$_f$-value: 0.2 (silica gel, cyclohexane/ethylacetate 9:1)

(42) (3R,9S)-9-(tert-butyldimethylsilyloxy)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]

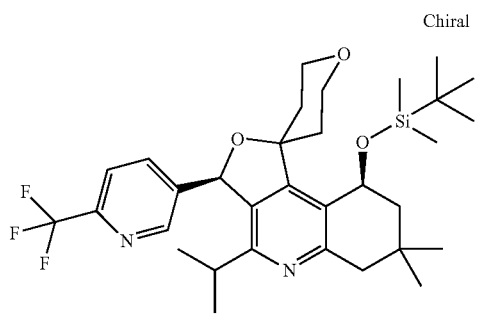 [SMILES: CC(C)c1nc2c(c3c1[C@@H](c1ccc(C(F)(F)F)nc1)OC31CCOCC1)[C@@H](O[Si](C)(C)C(C)(C)C)CC(C)(C)C2]

Obtained by starting from (3R,9S)-9-(tert-butyldimethylsilyloxy)-3'-iodo-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]. 10% palladiumhydroxide on charcoal is used instead of 10% palladium on charcoal.

Mass spectrometry (ESI$^+$): m/z=591 [M+H]$^+$

HPLC (Method 12): Retention time=12.42 min.

(43) (3S,9S)-9-(tert-butyldimethylsilyloxy)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]

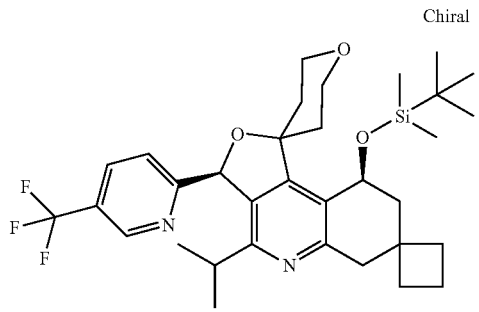 [SMILES: CC(C)c1nc2c(c3c1[C@@H](c1ccc(C(F)(F)F)cn1)OC31CCOCC1)[C@@H](O[Si](C)(C)C(C)(C)C)CC1(CCC1)C2]

Obtained by starting from (3S,9S)-9-(tert-butyldimethylsilyloxy)-3'-iodo-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]. 10% palladiumhydroxide on charcoal is used instead of 10% palladium on charcoal.

Mass spectrometry (ESI$^+$): m/z=603 [M+H]$^+$

HPLC (Method 12): Retention time=11.80 min.

227

(44) (3R,9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]

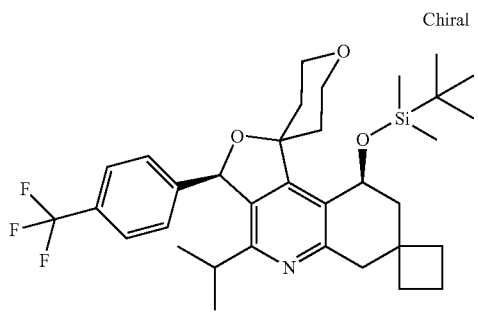 [SMILES: CC(C)c1nc2c(c3c1[C@@H](c1ccc(C(F)(F)F)cc1)OC31CCOCC1)[C@@H](O[Si](C)(C)C(C)(C)C)CC1(CCC1)C2]

Obtained by starting from (3R,9S)-9-(tert-butyldimethylsilyloxy)-3'-iodo-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran].

Mass spectrometry (ESI$^+$): m/z=602 [M+H]$^+$

HPLC (Method 9): Retention time=2.61 min.

(45) (3S,9S)-9-(tert-butyldimethylsilyloxy)-3-(3-fluoro-5-(trifluoromethyl)pyridin-2-yl)-4-isopropyl-7,7-dimethyl-2',3',5',6,6',7,8,9-octahydro-3H-spiro[furo[3,4-c]quinoline-1,4'-pyran]

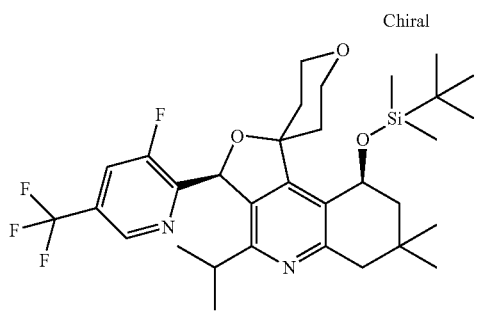 [SMILES: CC(C)c1nc2c(c3c1[C@@H](c1ncc(C(F)(F)F)cc1F)OC31CCOCC1)[C@@H](O[Si](C)(C)C(C)(C)C)CC(C)(C)C2]

Obtained by starting from (3S,9S)-9-(tert-butyldimethylsilyloxy)-3-(3-fluoro-5-(trifluoromethyl)pyridin-2-yl)-3'-iodo-4-isopropyl-7,7-dimethyl-2',3',5',6,6',7,8,9-octahydro-3H-spiro[furo[3,4-c]quinoline-1,4'-pyran]. 10% palladiumhydroxide on charcoal is used instead of 10% palladium on charcoal.

Mass spectrometry (ESI$^+$): m/z=609 [M+H]$^+$

HPLC (Method 9): Retention time=2.35 min.

228

(46) (3S,9S)-9-(tert-butyldimethylsilyloxy)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]

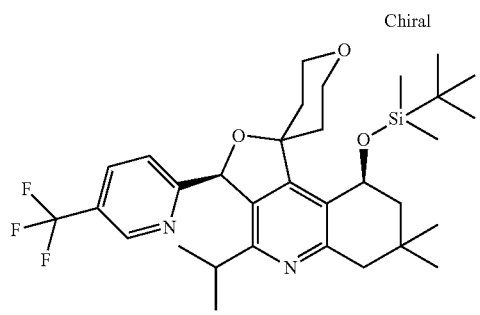 [SMILES: CC(C)c1nc2c(c3c1[C@@H](c1ccc(C(F)(F)F)cn1)OC31CCOCC1)[C@@H](O[Si](C)(C)C(C)(C)C)CC(C)(C)C2]

Obtained by starting from (3S,9S)-9-(tert-butyldimethylsilyloxy)-3'-iodo-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran].

Mass spectrometry (ESI$^+$): m/z=591 [M+H]$^+$

HPLC (Method 24): Retention time=1.684 min.

(47) (3R,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]

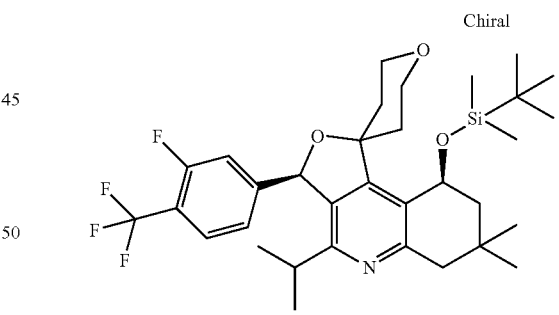

Obtained by starting from (3R,9S)-9-(tert-butyldimethylsilyloxy)-3-(3-fluoro-4-(trifluoromethyl)phenyl)-3'-iodo-4-isopropyl-7,7-dimethyl-2',3',5',6,6',7,8,9-octahydro-3H-spiro[furo[3,4-c]quinoline-1,4'-pyran]. 10% palladiumhydroxide on charcoal is used instead of 10% palladium on charcoal.

Mass spectrometry (ESI$^+$): m/z=608 [M+H]$^+$

HPLC (Method 12): Retention time=14.10 min.

(48) ((3S,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]

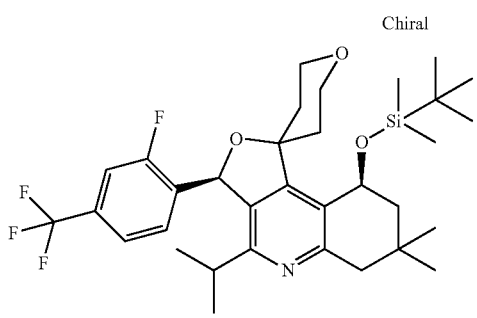 [SMILES: CC(C)c1nc2c(c3c1[C@@H](c1ccc(C(F)(F)F)cc1F)OC31CCOCC1)[C@@H](O[Si](C)(C)C(C)(C)C)CC(C)(C)C2]

Obtained by starting from (3S,9S)-9-(tert-butyldimethylsilyloxy)-3-(2-fluoro-4-(trifluoromethyl)phenyl)-3'-iodo-4-isopropyl-7,7-dimethyl-2',3',5',6,6',7,8,9-octahydro-3H-spiro[furo[3,4-c]quinoline-1,4'-pyran].

Mass spectrometry (ESI⁺): m/z=608 [M+H]⁺

HPLC (Method 9): Retention time=2.71 min.

(49) (3S,9S)-3-(5-tert-butyl-4-methylthiazol-2-yl)-9-(tert-butyldimethylsilyloxy)-4-isopropyl-7,7-dimethyl-2',3',5',6,6',7,8,9-octahydro-3H-spiro[furo[3,4-c]quinoline-1,4'-pyran]

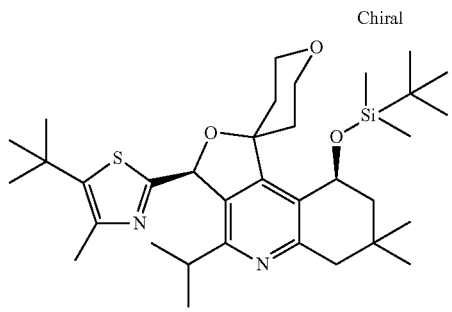 [SMILES: Cc1nc([C@H]2OC3(CCOCC3)c3c2c(C(C)C)nc2c3[C@@H](O[Si](C)(C)C(C)(C)C)CC(C)(C)C2)sc1C(C)(C)C]

Obtained by starting from (3S,9S)-3-(5-tert-butyl-4-methylthiazol-2-yl)-9-(tert-butyldimethylsilyloxy)-3'-iodo-4-isopropyl-7,7-dimethyl-2',3',5',6,6',7,8,9-octahydro-3H-spiro[furo[3,4-c]quinoline-1,4'-pyran].

Mass spectrometry (ESI⁺): m/z=599 [M+H]⁺

HPLC (Method 9): Retention time=2.79 min.

(50) (3R,9S)-9-(tert-butyldimethylsilyloxy)-4-isopropyl-7,7-(butan-1,4-diyl)-3-(4-(trifluoromethyl)phenyl)-2',3',5',6,6',7,8,9-octahydro-3H-spiro[furo[3,4-c]quinoline-1,4'-pyran]

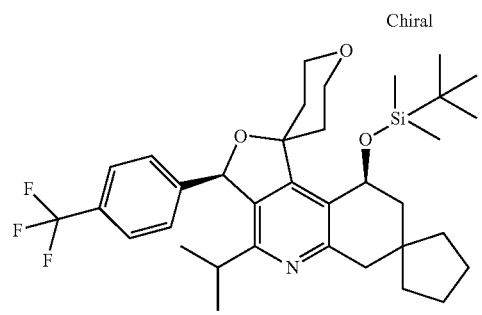 [SMILES: CC(C)c1nc2c(c3c1[C@@H](c1ccc(C(F)(F)F)cc1)OC31CCOCC1)[C@@H](O[Si](C)(C)C(C)(C)C)CC1(CCCC1)C2]

Obtained by starting from (3R,9S)-9-(tert-butyldimethylsilyloxy)-3'-iodo-4-isopropyl-7,7-(butan-1,4-diyl)-3-(4-(trifluoromethyl)phenyl)-2',3',5',6,6',7,8,9-octahydro-3H-spiro[furo[3,4-c]quinoline-1,4'-pyran]. The crude product is used directly in the next step.

Mass spectrometry (ESI⁺): m/z=616 [M+H]⁺

HPLC (Method 4): Retention time=3.30 min.

(51) (3R,9S)-3-(4-tert-butoxyphenyl)-9-(tert-butyldimethylsilyloxy)-4-isopropyl-7,7-dimethyl-2',3',5',6,6',7,8,9-octahydro-3H-spiro[furo[3,4-c]quinoline-1,4'-pyran]

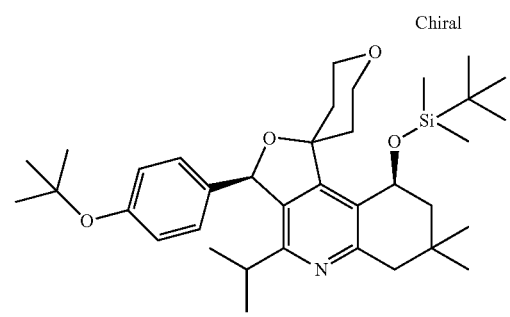 [SMILES: CC(C)c1nc2c(c3c1[C@@H](c1ccc(OC(C)(C)C)cc1)OC31CCOCC1)[C@@H](O[Si](C)(C)C(C)(C)C)CC(C)(C)C2]

Obtained by starting from (3R,9S)-3-(4-tert-butoxyphenyl)-9-(tert-butyldimethylsilyloxy)-3'-iodo-4-isopropyl-7,7-dimethyl-2',3',5',6,6',7,8,9-octahydro-3H-spiro[furo[3,4-c]quinoline-1,4'-pyran]. The crude product is used directly in the next step.

Mass spectrometry (ESI⁺): m/z=NACHTRAGEN [M+H]⁺

HPLC (Method NACHTRAGEN): Retention time=NACHTRAGEN min.

(52) (3R,9S)-9-(tert-butyldimethylsilyloxy)-3-(4-isopropoxyphenyl)-4-isopropyl-7,7-dimethyl-2',3',5',6,6',7,8,9-octahydro-3H-spiro[furo[3,4-c]quinoline-1,4'-pyran]

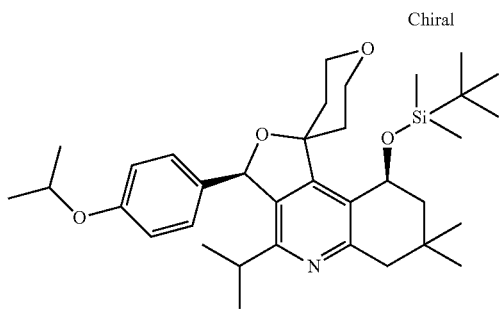 [SMILES: CC(C)Oc1ccc([C@H]2OC3(CCOCC3)c3c2c(C(C)C)nc2c3[C@@H](O[Si](C)(C)C(C)(C)C)CC(C)(C)C2)cc1]

Obtained by starting from (3R,9S)-9-(tert-butyldimethylsilyloxy)-3'-iodo-3-(4-isopropoxyphenyl)-4-isopropyl-7,7-dimethyl-2',3',5',6,6',7,8,9-octahydro-3H-spiro[furo[3,4-c]quinoline-1,4'-pyran].

Mass spectrometry (ESI$^+$): m/z=580 [M+H]$^+$

HPLC (Method 4): Retention time=2.93 min.

(53) (3R,9S)-9-(tert-butyldimethylsilyloxy)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran]

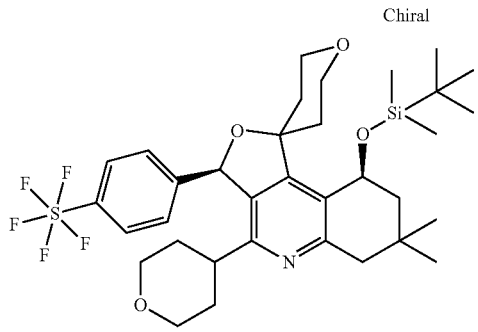 [SMILES: CC1(C)Cc2nc(C3CCOCC3)c3c(c2[C@@H](O[Si](C)(C)C(C)(C)C)C1)C1(CCOCC1)O[C@@H]3c1ccc(S(F)(F)(F)(F)F)cc1]

Obtained by starting from (3R,9S)-9-(tert-butyldimethylsilyloxy)-3'-iodo-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran].

Mass spectrometry (ESI$^+$): m/z=690 [M+H]$^+$

HPLC (Method 24): Retention time=1.831 min.

(54) (3R,9S)-9-(tert-butyldimethylsilyloxy)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]

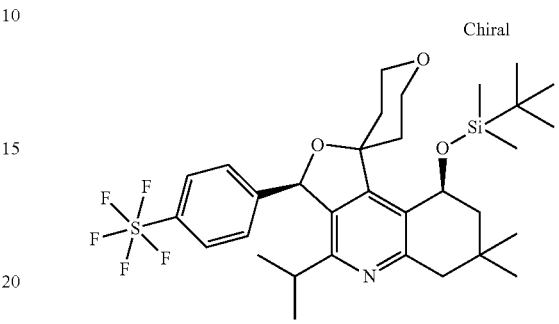

Obtained by starting from (3R,9S)-9-(tert-butyldimethylsilyloxy)-3'-iodo-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran].

Mass spectrometry (ESI$^+$): m/z=648 [M+H]$^+$

HPLC (Method 24): Retention time=1.777 min.

(55) (3'R,9'S)-9'-(tert-butyldimethylsilyloxy)-3'-(4-tert-butylphenyl)-4'-isopropyl-7',7'-(propan-1,3-diyl)-6',7',8',9'-tetrahydro-3'H-spiro[cyclopentane-1,1'-furo[3,4-c]quinoline]

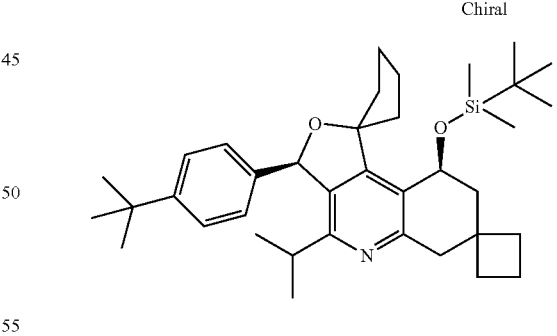

Obtained by starting from (3'R,9'S)-9'-(tert-butyldimethylsilyloxy)-3'-(4-tert-butylphenyl)-2-iodo-4'-isopropyl-7',7'-(propan-1,3-diyl)-6',7',8',9'-tetrahydro-3'H-spiro[cyclopentane-1,1'-furo[3,4-c]quinoline].

Mass spectrometry (ESI$^+$): m/z=574 [M+H]$^+$

HPLC (Method 7): Retention time=1.940 min.

R$_f$-value: 0.7 (silica gel, cyclohexane/ethylacetate 9:1)

233

(56) (3R,9S)-9-(tert-butyldimethylsilyloxy)-3-(4-tert-butylphenyl)-4-isopropyl-7,7-(propan-1,3-diyl)-2',3',5',6,6',7,8,9-octahydro-3H-spiro[furo[3,4-c]quinoline-1,4'-pyran]

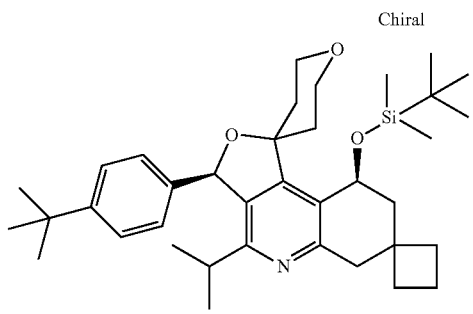 [SMILES: CC(C)c1nc2c(c3c1[C@@H](c1ccc(C(C)(C)C)cc1)OC31CCOCC1)[C@@H](O[Si](C)(C)C(C)(C)C)CC1(CCC1)C2]

Obtained by starting from (3R,9S)-9-(tert-butyldimethylsilyloxy)-3-(4-tert-butylphenyl)-3'-iodo-4-isopropyl-7,7-(propan-1,3-diyl)-2',3',5',6,6',7,8,9-octahydro-3H-spiro[furo[3,4-c]quinoline-1,4'-pyran].

Mass spectrometry (ESI$^+$): m/z=590 [M+H]$^+$

HPLC (Method 7): Retention time=1.936 min.

R$_f$-value: 0.55 (silica gel, cyclohexane/ethylacetate 9:1)

(57) (3R,9S)-9-(tert-butyldimethylsilyloxy)-4-isopropyl-7,7-dimethyl-3-(4-(3-methyloxetan-3-yl)phenyl)-2',3',5',6,6',7,8,9-octahydro-3H-spiro[furo[3,4-c]quinoline-1,4'-pyran]

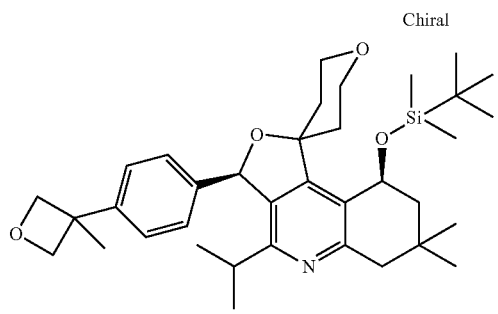 [SMILES: CC(C)c1nc2c(c3c1[C@@H](c1ccc(C4(C)COC4)cc1)OC31CCOCC1)[C@@H](O[Si](C)(C)C(C)(C)C)CC(C)(C)C2]

Obtained by starting from (3R,9S)-9-(tert-butyldimethylsilyloxy)-3'-iodo-4-isopropyl-7,7-dimethyl-3-(4-(3-methyloxetan-3-yl)phenyl)-2',3',5',6,6',7,8,9-octahydro-3H-spiro[furo[3,4-c]quinoline-1,4'-pyran].

Mass spectrometry (ESI$^+$): m/z=592 [M+H]$^+$

HPLC (Method 24): Retention time=1.648 min.

234

(58) (3'R,9'S)-9'-(tert-butyldimethylsilyloxy)-4'-isopropyl-7',7'-dimethyl-3'-(4-(perfluoroethyl)phenyl)-6',7',8',9'-tetrahydro-3'H-spiro[cyclopentane-1,1'-furo[3,4-c]quinoline]

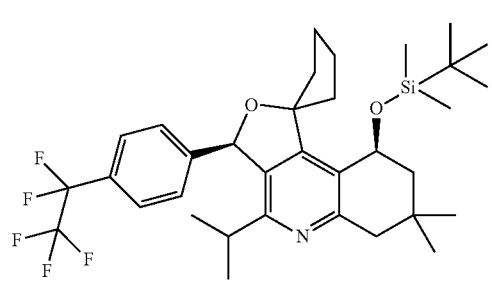

Obtained by starting from (3'R,9'S)-9'-(tert-butyldimethylsilyloxy)-2-iodo-4'-isopropyl-7',7'-dimethyl-3'-(4-(perfluoroethyl)phenyl)-6',7',8',9'-tetrahydro-3'H-spiro[cyclopentane-1,1'-furo[3,4-c]quinoline].

Mass spectrometry (ESI$^+$): m/z=624 [M+H]$^+$

HPLC (Method 7): Retention time=1.949 min.

(59) 5-((3R,9S)-9-(tert-butyldimethylsilyloxy)-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile

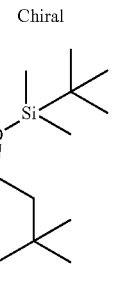

Obtained by starting from 5-((3R,9S)-9-(tert-butyldimethylsilyloxy)-3'-iodo-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=615 [M+H]$^+$

HPLC (Method 7): Retention time=1.798 min.

(60) (3S,9S)-9-(tert-butyldimethylsilyloxy)-4-isopropyl-7,7-dimethyl-3-(5-(trifluoromethyl)pyridin-2-yl)-2',3',5',6',7,8,9-octahydro-3H-spiro[furo[3,4-c]quinoline-1,4'-pyran]

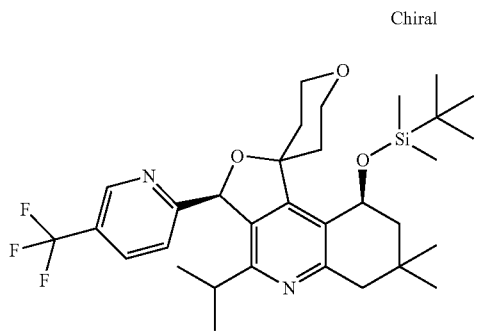 [SMILES: CC(C)c1nc2c(c3c1[C@@H](c1ccc(C(F)(F)F)cn1)OC31CCOCC1)[C@@H](O[Si](C)(C)C(C)(C)C)CC(C)(C)C2]

Obtained by starting from (3S,9S)-9-(tert-butyldimethylsilyloxy)-3'-iodo-4-isopropyl-7,7-dimethyl-3-(5-(trifluoromethyl)pyridin-2-yl)-2',3',5',6',7,8,9-octahydro-3H-spiro[furo[3,4-c]quinoline-1,4'-pyran].

Mass spectrometry (ESI$^+$): m/z=591 [M+H]$^+$

R$_f$-value: 0.4 (silica gel, cyclohexane/ethylacetate 9:1)

(61) (3R,9S)-9-(tert-butyldimethylsilyloxy)-4-isopropyl-7,7-dimethyl-3-(4-(pentafluorosulfanyl)phenyl)-2',3',5',6',7,8,9-octahydro-3H-spiro[furo[3,4-c]quinoline-1,4'-pyran]

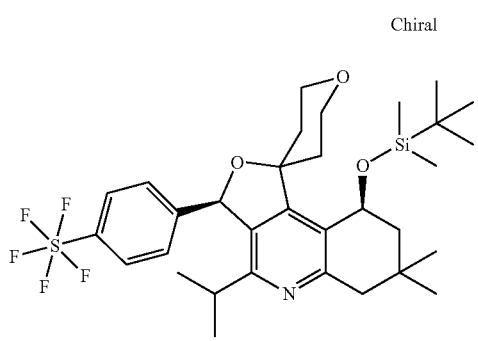 [SMILES: CC(C)c1nc2c(c3c1[C@@H](c1ccc(S(F)(F)(F)(F)F)cc1)OC31CCOCC1)[C@@H](O[Si](C)(C)C(C)(C)C)CC(C)(C)C2]

Obtained by starting from (3R,9S)-9-(tert-butyldimethylsilyloxy)-3'-iodo-4-isopropyl-7,7-dimethyl-3-(4-(pentafluorosulfanyl)phenyl)-2',3',5',6',7,8,9-octahydro-3H-spiro[furo[3,4-c]quinoline-1,4'-pyran].

Mass spectrometry (ESI$^+$): m/z=648 [M+H]$^+$

HPLC (Method 24): Retention time=1.777 min.

R$_f$-value: 0.58 (silica gel, petrole ether/ethylacetate 4:1)

(62) (3R,9S)-9-(tert-butyldimethylsilyloxy)-4-isopropyl-7,7-(propan-1,3-diyl)-3-(4-(pentafluorosulfanyl)phenyl)-2',3',5',6',7,8,9-octahydro-3H-spiro[furo[3,4-c]quinoline-1,4'-pyran]

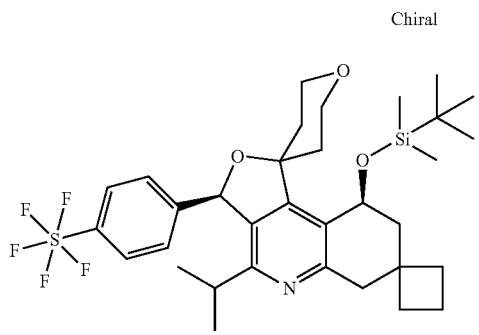 [SMILES: CC(C)c1nc2c(c3c1[C@@H](c1ccc(S(F)(F)(F)(F)F)cc1)OC31CCOCC1)[C@@H](O[Si](C)(C)C(C)(C)C)CC1(CCC1)C2]

Obtained by starting from (3R,9S)-9-(tert-butyldimethylsilyloxy)-3'-iodo-4-isopropyl-7,7-(propan-1,3-diyl)-3-(4-(pentafluorosulfanyl)phenyl)-2',3',5',6',7,8,9-octahydro-3H-spiro[furo[3,4-c]quinoline-1,4'-pyran].

Mass spectrometry (ESI$^+$): m/z=660 [M+H]$^+$

HPLC (Method 24): Retention time=1.809 min.

(63) (3R,9S)-9-(tert-butyldimethylsilyloxy)-3-(4-tert-butylphenyl)-7,7-dimethyl-4-(tetrahydro-2H-pyran-4-yl)-2',3',5',6',7,8,9-octahydro-3H-spiro[furo[3,4-c]quinoline-1,4'-pyran]

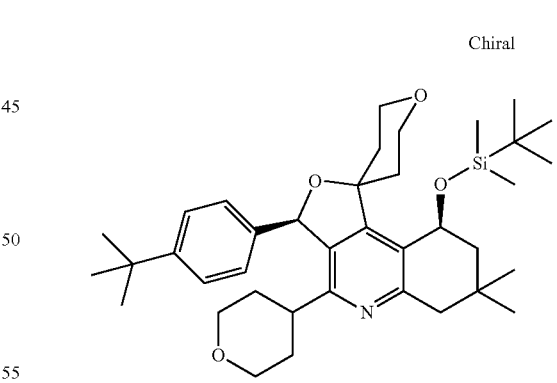

Obtained by starting from (3R,9S)-9-(tert-butyldimethylsilyloxy)-3-(4-tert-butylphenyl)-3'-iodo-7,7-dimethyl-4-(tetrahydro-2H-pyran-4-yl)-2',3',5',6',7,8,9-octahydro-3H-spiro[furo[3,4-c]quinoline-1,4'-pyran].

Mass spectrometry (ESI$^+$): m/z=620 [M+H]$^+$

HPLC (Method 24): Retention time=1.806 min.

237

(64) (3'R,9'S)-4'-isopropyl-7',7'-dimethyl-3'-(4-(pentafluorosulfanyl)phenyl)-9'-(2,3,3-trimethylbutan-2-yloxy)-6',7',8',9'-tetrahydro-3'H-spiro[cyclopentane-1,1'-furo[3,4-c]quinoline]

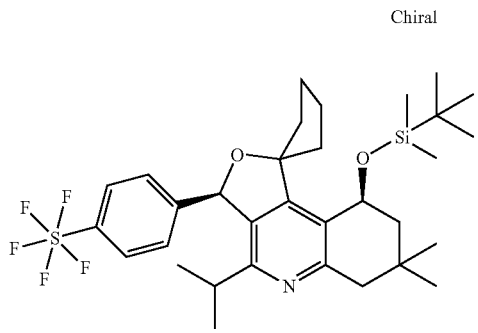 [SMILES: CC(C)c1nc2c(c3c1[C@@H](c1ccc(S(F)(F)(F)(F)F)cc1)OC31CCCC1)[C@@H](O[Si](C)(C)C(C)(C)C)CC(C)(C)C2]

Obtained by starting from (3'R,9'S)-2-iodo-4'-isopropyl-7',7'-dimethyl-3'-(4-(pentafluorosulfanyl)phenyl)-9'-(2,3,3-trimethylbutan-2-yloxy)-6',7',8',9'-tetrahydro-3'H-spiro[cyclopentane-1,1'-furo[3,4-c]quinoline].

Mass spectrometry (ESI$^+$): m/z=632 [M+H]$^+$

HPLC (Method 4): Retention time=3.295 min.

(65) 5-((3R,9S)-9-(tert-butyldimethylsilyloxy)-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-O-2-(trifluoromethyl)benzonitrile

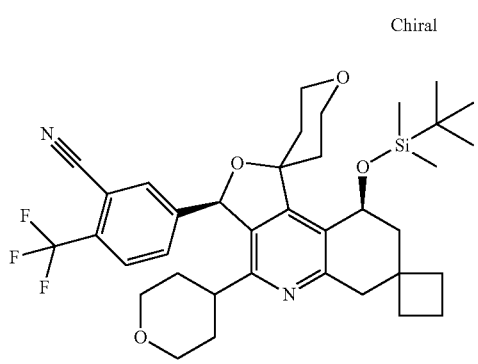 [SMILES: CC(C)(C)[Si](C)(C)O[C@H]1CC2(CCC2)Cc2nc(C3CCOCC3)c3c(c21)C1(CCOCC1)O[C@@H]3c1ccc(C(F)(F)F)c(C#N)c1]

Obtained by starting from 5-((3R,9S)-9-(tert-butyldimethylsilyloxy)-3'-iodo-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=669 [M+H]$^+$

HPLC (Method 7): Retention time=1.902 min.

238

(66) 5-((3R,9S)-9-(tert-butyldimethylsilyloxy)-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

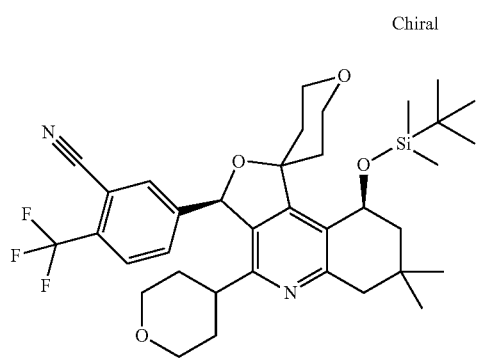 [SMILES: CC1(C)Cc2nc(C3CCOCC3)c3c(c2[C@@H](O[Si](C)(C)C(C)(C)C)C1)C1(CCOCC1)O[C@@H]3c1ccc(C(F)(F)F)c(C#N)c1]

Obtained by starting from 5-((3R,9S)-9-(tert-butyldimethylsilyloxy)-3'-iodo-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=657 [M+H]$^+$

HPLC (Method 26): Retention time=1.75 min.

(67) (3S,9S)-9-(tert-butyldimethylsilyloxy)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]

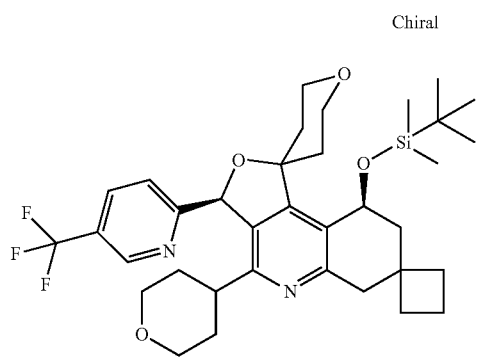 [SMILES: CC(C)(C)[Si](C)(C)O[C@H]1CC2(CCC2)Cc2nc(C3CCOCC3)c3c(c21)C1(CCOCC1)O[C@@H]3c1ccc(C(F)(F)F)cn1]

Obtained by starting from (3S,9S)-9-(tert-butyldimethylsilyloxy)-3'-iodo-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran].

Mass spectrometry (ESI$^+$): m/z=645 [M+H]$^+$

HPLC (Method 7): Retention time=1.814 min.

239

(68) (3S,9S)-9-(tert-butyldimethylsilyloxy)-7,7-dimethyl-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]

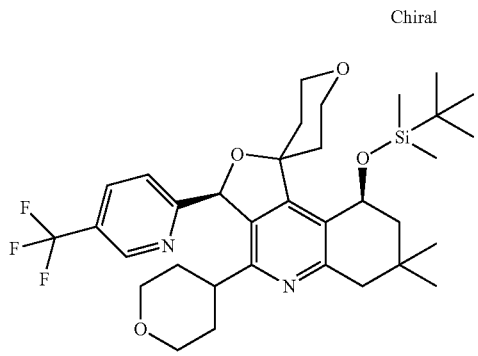 [SMILES: CC1(C)Cc2nc(C3CCOCC3)c3c(c2[C@@H](O[Si](C)(C)C(C)(C)C)C1)C1(CCOCC1)O[C@@H]3c1ccc(C(F)(F)F)cn1]

Obtained by starting from (3S,9S)-9-(tert-butyldimethylsilyloxy)-3'-iodo-7,7-dimethyl-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran].

Mass spectrometry (ESI$^+$): m/z=633 [M+H]$^+$

HPLC (Method 7): Retention time=1.873 min.

(69) 5-((3R,9S)-9-(tert-butyldimethylsilyloxy)-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

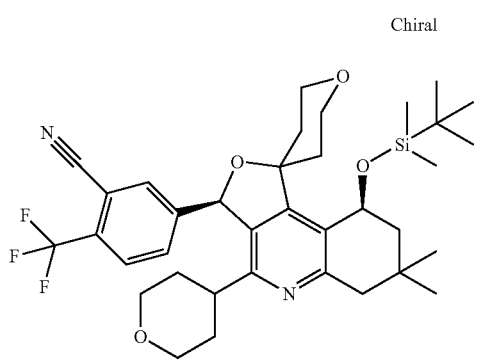 [SMILES: CC1(C)Cc2nc(C3CCOCC3)c3c(c2[C@@H](O[Si](C)(C)C(C)(C)C)C1)C1(CCOCC1)O[C@@H]3c1ccc(C(F)(F)F)c(C#N)c1]

Obtained by starting from 5-((3R,9S)-9-(tert-butyldimethylsilyloxy)-3'-iodo-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=657 [M+H]$^+$

HPLC (Method V002_001 A12_Sf_S_M): Retention time=1.75 min.

240

(70) 5-((3R,9S)-9-(tert-butyldimethylsilyloxy)-4-isopropyl-7,7-(propan-1,3-diyl)-2',3',5',6,6',7,8,9-octahydro-3H-spiro[furo[3,4-c]quinoline-1,4'-pyran]-3-yl)-2-(trifluoromethyl)benzonitrile

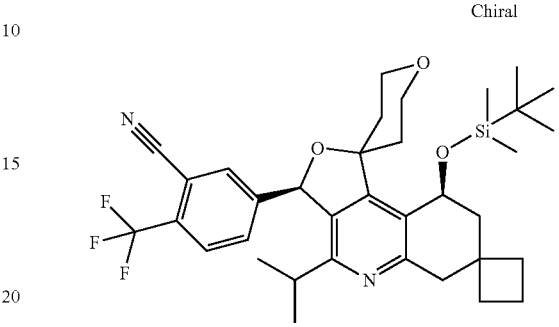

Obtained by starting from 5-((3R,9S)-9-(tert-butyldimethylsilyloxy)-3'-iodo-4-isopropyl-7,7-(propan-1,3-diyl)-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=627 [M+H]$^+$

HPLC (Method 27): Retention time=1.67 min.

(71) (3R,9S)-9-(tert-butyldimethylsilyloxy)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]

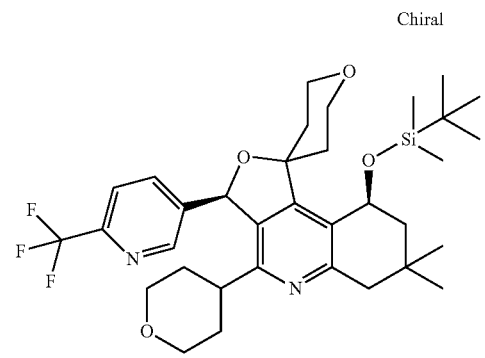 [SMILES: CC1(C)Cc2nc(C3CCOCC3)c3c(c2[C@@H](O[Si](C)(C)C(C)(C)C)C1)C1(CCOCC1)O[C@@H]3c1ccc(C(F)(F)F)nc1]

Obtained by starting from (3R,9S)-9-(tert-butyldimethylsilyloxy)-3'-iodo-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran].

Mass spectrometry (ESI$^+$): m/z=633 [M+H]$^+$

HPLC (Method 7): Retention time=1.797 min.

(72) (3R,9S)-9-(tert-butyldimethylsilyloxy)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]

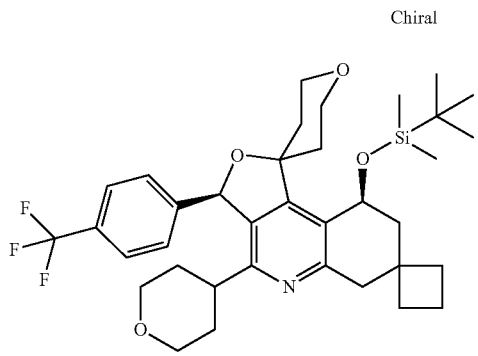 [SMILES: CC(C)(C)[Si](C)(C)O[C@H]1CC2(CCC2)Cc2nc(C3CCOCC3)c3c(c21)C1(CCOCC1)O[C@@H]3c1ccc(C(F)(F)F)cc1]

Obtained by starting from (3R,9S)-9-(tert-butyldimethylsilyloxy)-3'-iodo-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran].

Mass spectrometry (ESI+): m/z=644 [M+H]+

HPLC (Method 7): Retention time=1.939 min.

(73) (3R,9S)-9-(tert-butyldimethylsilyloxy)-7,7-(propan-1,3-diyl)-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]

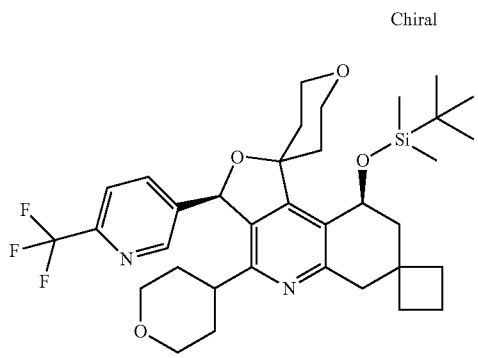 [SMILES: CC(C)(C)[Si](C)(C)O[C@H]1CC2(CCC2)Cc2nc(C3CCOCC3)c3c(c21)C1(CCOCC1)O[C@@H]3c1ccc(C(F)(F)F)nc1]

Obtained by starting from (3R,9S)-9-(tert-butyldimethylsilyloxy)-3'-iodo-7,7-(propan-1,3-diyl)-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran].

Mass spectrometry (ESI+): m/z=645 [M+H]+

HPLC (Method 7): Retention time=1.898 min.

(74) (3'R,9'S)-9'-(tert-butyldimethylsilyloxy)-4,4-difluoro-4'-isopropyl-7',7'-dimethyl-3-(5-(trifluoromethyl)pyridin-2-yl)-6',7',8',9'-tetrahydro-3'H-spiro[cyclohexane-1,1'-furo[3,4-c]quinoline]

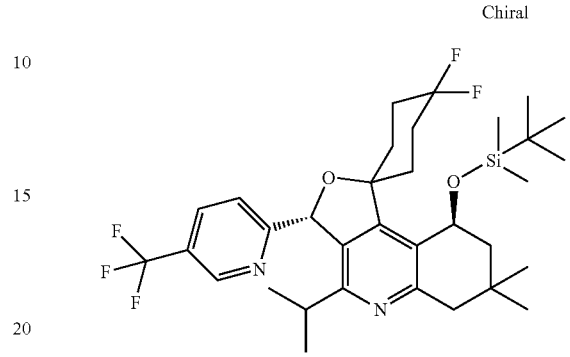

Obtained by starting from (3'R,9'S)-9'-(tert-butyldimethylsilyloxy)-4,4-difluoro-2-iodo-4'-isopropyl-7',7'-dimethyl-3'-(5-(trifluoromethyl)pyridin-2-yl)-6',7',8',9'-tetrahydro-3'H-spiro[cyclohexane-1,1'-furo[3,4-c]quinoline]. 10% palladiumhydroxide on charcoal is used instead of 10% palladium on charcoal.

Mass spectrometry (ESI+): m/z=625 [M+H]+

HPLC (Method 13): Retention time=1.23 min.

R$_f$-value: 0.30 (silica gel, n-hexane/diethylether 95:5)

Example XIV

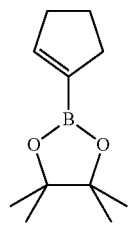

2-Cyclopent-1-enyl-4,4,5,5-tetramethyl-[1,3,2]dioxaborolane

Under argon 4.31 g 1-chlor-1-cyclopenten and 12.5 g bis-(pinacolato)-diboron are dissolved 160 ml 1,4-dioxane, mixed with 8 g potassium acetate and purged for 5 minutes with argon. 370 mg Tris-(dibenzylidenaceton)-dipalladium-(0) ([Pd$_2$ dba$_3$]) and 780 mg 2-cyclohexylphosphino-2',4',6'-triisopropyl-1,1'-biphenyl are added and the mixture is heated for 3 hours to 110° C. After cooling to room temperature it is diluted with diethylether and washed with water and brine. The organic phase is dried with magnesium sulphate and the solvents are evaporated in vacuo. The residue is triturated with petrole ether. After removing the precipitate by filtration the solvent of the mother liquor is evaporated in vacuo.

Yield: 13.1 g (99% of theory)

Mass spectrometry (EI): m/z=194 [M]+

Example XV

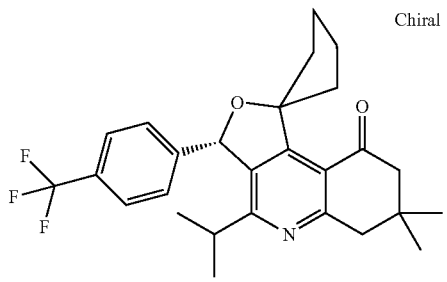 [SMILES: CC(C)c1nc2c(c3c1[C@H](c1ccc(C(F)(F)F)cc1)OC31CCCC1)C(=O)CC(C)(C)C2]

(S)-4'-isopropyl-7',7'-dimethyl-3'-(4-(trifluoromethyl)phenyl)-7',8'-dihydro-3'H-spiro[cyclopentane-1,1'-furo[3,4-c]quinolin]-9'(6'H)-one 72 mg (3'S,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol are dissolved in 3 ml dichloromethane and mixed with 650 µl of a 15% solution of 1,1-dihydro-1,1,1-triacetoxy-1,2-benziodoxol-3(1H)-on (Dess-Martin-Periodinan) in dichloromethane. The mixture is stirred for 4 hours. Then the solvent is evaporated in vacuo and the residue is chromatographed on silica gel (cyclohexane/ethylacetate 95:5 to 80:20).

Yield: 57 mg (80% of theory)
Mass spectrometry (ESI$^+$): m/z=458 [M+H]$^+$
R$_f$-value: 0.43 (silica gel, petrole ether/ethylacetate 8:1)

Example XVI

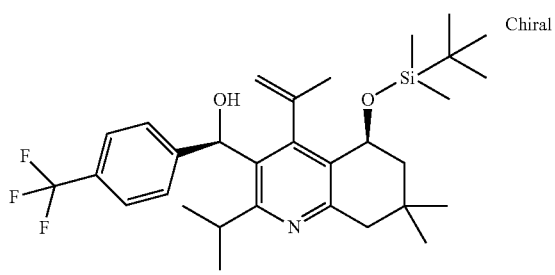 [SMILES: C=C(C)c1c([C@H](O)c2ccc(C(F)(F)F)cc2)c(C(C)C)nc2c1[C@@H](O[Si](C)(C)C(C)(C)C)CC(C)(C)C2]

(R)—((S)-5-(tert-butyldimethylsilyloxy)-2-isopropyl-7,7-dimethyl-4-(prop-1-en-2-yl)-5,6,7,8-tetrahydroquinolin-3-yl)(4-(trifluoromethyl)phenyl)methanol Under argon 450 mg (R)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methanol and 250 mg potassium isopropenyltrifluoroborate are dissolved in 5 ml tetrahydrofurane and 1 ml toluene. 1.5 ml of a 2 M solution of sodium carbonate are added and the mixture is purged for 5 minutes with argon. After the addition of 50 mg of 1,1'-bis-(diphenylphosphino)-ferrocene-dichloro-palladium-(II) the mixture is heated to 100° C. for 12 hours. Then the mixture is diluted with diethylether, washed with saturated aqueous ammonium chloride and brine and dried with magnesium sulphate. The solvents are evaporated in vacuo and the residue is chromatographed on silica gel (cyclohexane/ethylacetate 95:5 to 70:30).

Yield: 285 mg (73% of theory)
Mass spectrometry (ESI$^+$): m/z=548 [M+H]$^+$
R$_f$-value: 0.44 (silica gel, petrole ether/ethylacetate 8:1)

Analogously to example XVI the following compounds are obtained:

(1) (R)—((S)-5-(tert-butyldimethylsilyloxy)-4-cyclohexenyl-2-isopropyl-7,7-dimethyl-5,6,7,8-tetrahydroquinolin-3-yl)(4-(trifluoromethyl)phenyl)methanol

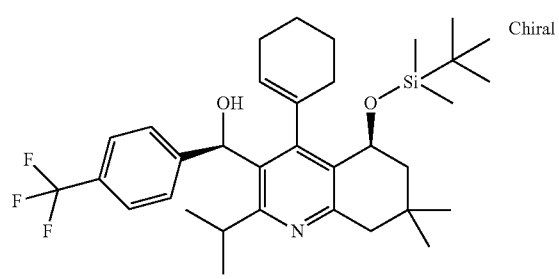 [SMILES: CC(C)c1nc2c(c(C3=CCCCC3)c1[C@H](O)c1ccc(C(F)(F)F)cc1)[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(4-(trifluoromethyl)phenyl)methanol and potassium cyclohex-1-ene-1-yl-trifluoroborane.

Mass spectrometry (ESI$^+$): m/z=588 [M+H]$^+$
R$_f$-value: 0.42 (silica gel, petrole ether/ethylacetate 8:1)

(2) (R)—((S)-5-(tert-butyldimethylsilyloxy)-2-isopropyl-7,7-dimethyl-4-(prop-1-en-2-yl)-5,6,7,8-tetrahydroquinolin-3-yl)(4-tert-butylphenyl)methanol

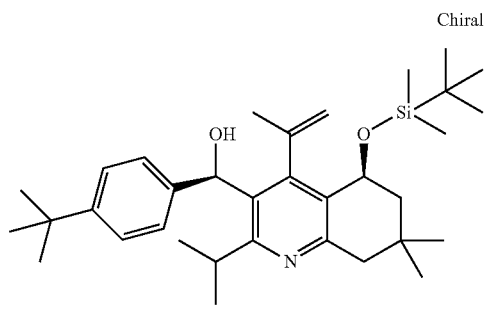 [SMILES: C=C(C)c1c([C@H](O)c2ccc(C(C)(C)C)cc2)c(C(C)C)nc2c1[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(4-tert-butylphenyl)methanol.

Mass spectrometry (ESI$^+$): m/z=536 [M+H]$^+$
HPLC (Method 20): Retention time=3.81 min.

(3) (R)—((S)-5-(tert-butyldimethylsilyloxy)-2-cyclopentyl-7,7-dimethyl-4-(prop-1-en-2-yl)-5,6,7,8-tetrahydroquinolin-3-yl)(4-tert-butylphenyl)methanol

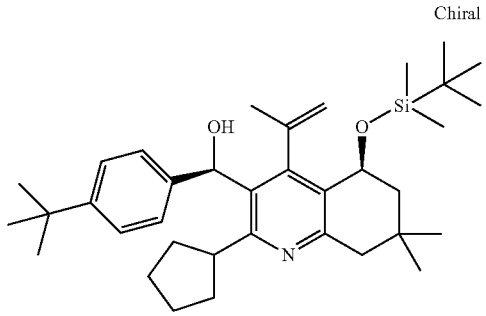 [SMILES: C=C(C)c1c([C@H](O)c2ccc(C(C)(C)C)cc2)c(C2CCCC2)nc2c1[C@@H](O[Si](C)(C)C(C)(C)C)CC(C)(C)C2]

and (S)—((S)-5-(tert-butyldimethylsilyloxy)-2-cyclopentyl-7,7-dimethyl-4-(prop-1-en-2-yl)-5,6,7,8-tetrahydroquinolin-3-yl)(4-tert-butylphenyl)methanol

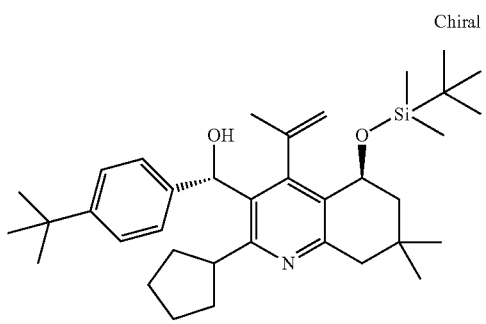 [SMILES: C=C(C)c1c([C@@H](O)c2ccc(C(C)(C)C)cc2)c(C2CCCC2)nc2c1[C@@H](O[Si](C)(C)C(C)(C)C)CC(C)(C)C2]

Obtained by starting from a diastereomic mixture of ((5S)-5-(tert-butyldimethylsilyloxy)-2-cyclopentyl-4-iodo-7,7-dimethyl-5,6,7,8-tetrahydroquinolin-3-yl)(4-tert-butylphenyl)methanol.

(R)—((S)-5-(tert-butyldimethylsilyloxy)-2-cyclopentyl-7,7-dimethyl-4-(prop-1-en-2-yl)-5,6,7,8-tetrahydroquinolin-3-yl)(4-tert-butylphenyl)methanol:

Mass spectrometry (ESI$^+$): m/z=562 [M+H]$^+$

HPLC (Method 22): Retention time=2.37 min.

(S)—((S)-5-(tert-butyldimethylsilyloxy)-2-cyclopentyl-7,7-dimethyl-4-(prop-1-en-2-yl)-5,6,7,8-tetrahydroquinolin-3-yl)(4-tert-butylphenyl)methanol:

Mass spectrometry (ESI$^+$): m/z=562 [M+H]$^+$

HPLC (Method 22): Retention time=2.46 min.

Example XVII

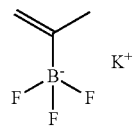

Potassium Isopropenyltrifluoroborate 8.59 g Isopropenylboronic acid are dissolved in 160 ml diethylether and under intensive stirring 27.4 g potassium hydrogenfluoride are added. Afterwards 12.6 ml water are added dropwise and the mixture is stirred for 12 hours at room temperature. The mixture is diluted with acetone and filtered through a plug of celite. The mother liquor is evaporated in vacuo. The residue is dissolved in a small amount of warm acetone. Then diethylether is added to start crystallisation. The crystals are collected by filtration and dried in vacuo. This material is directly used in the next steps.

Yield: 7.45 g (50% of theory)

Analogously to example XVII the following compounds are obtained:

(1) Potassium cyclohex-1-ene-1-yl-trifluoroborate

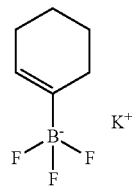

Obtained by starting from cyclohex-1-ene-1-boronic acid. The obtained crystals are directly used in the next steps.

Example XVIII

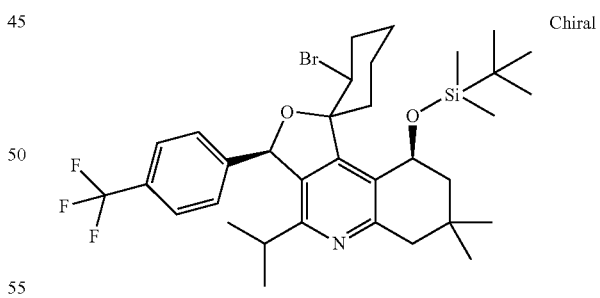

(3'R,9'S)-2-bromo-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclohexane-1,1'-furo[3,4-c]quinoline]

60 mg (R)—((S)-5-(tert-butyldimethylsilyloxy)-4-cyclohexenyl-2-isopropyl-7,7-dimethyl-5,6,7,8-tetrahydroquinolin-3-yl)(4-(trifluoromethyl)phenyl)methanol are dissolved in 2 ml dichloromethane, cooled to 0° C., treated dropwise with 25 µl of bromine and stirred for 1.5 hours at room temperature. Then the solution is diluted with diethylether and washed with saturated aqueous sodium thiosulphate solution and brine. After drying with magnesium sulphate the solvents are evaporated in vacuo and the residue is chromatographed on silica gel (cyclohexane/ethylacetate 98:2 to 80:20).

Yield: 25 mg (37% of theory)

Mass spectrometry (ESI⁺): m/z=666 [M+H]⁺

HPLC (Method 1): Retention time=5.305 min.

$R_f$-value: 0.68 (silica gel, petrole ether/ethylacetate 8:1)

Example XIX

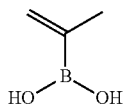

Isopropenylboronic Acid 17 ml Trimethylborate are dissolved in 60 ml tetrahydrofurane, cooled to 0° C. and treated dropwise with 100 ml of a 0.5 M solution of isopropenylmagnesium bromide in tetrahydrofurane. After stirring for 2 hours at room temperature the mixture is cooled to 0° C. and treated dropwise with 250 ml 1 M hydrochloric acid. The aqueous phase is extracted twice with diethylether, the combined organic phases are dried with magnesium sulphate and the solvents are evaporated in vacuo. The crude product is used directly in the next steps.

Example XX

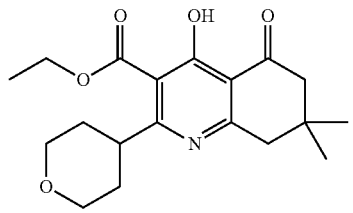 [SMILES: CCOC(=O)c1c(C2CCOCC2)nc2c(c1O)C(=O)CC(C)(C)C2]

Ethyl 4-hydroxy-7,7-dimethyl-5-oxo-2-(tetrahydro-2H-pyran-4-yl)-5,6,7,8-tetrahydroquinoline-3-carboxylate 880 mg Ethyl 2-(3,6-dihydro-2H-pyran-4-yl)-4-hydroxy-7,7-dimethyl-5-oxo-5,6,7,8-tetrahydroquinoline-3-carboxylate are dissolved in 20 ml ethylacetate, mixed with 120 mg palladium on charcoal (10%) and hydrogenated at 3 bar for 5 hours at room temperature. Then the catalyst is removed by filtration, the solvents are removed in vacuo and the residue thus obtained is directly used in the next steps.

Yield: 885 mg (100% of theory)

Mass spectrometry (ESI⁺): m/z=348 [M+H]⁺

HPLC (Method 1): Retention time=2.130 min.

Analogously to example XX the following compounds are obtained:

(1) Ethyl 4'-hydroxy-5'-oxo-2'-(tetrahydro-2H-pyran-4-yl)-6',8'-dihydro-5'H-spiro[cyclobutane-1,7'-quinoline]-3'-carboxylate

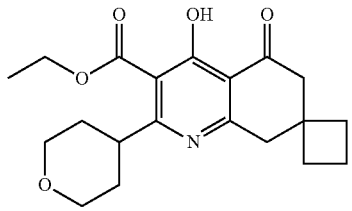 [SMILES: CCOC(=O)c1c(C2CCOCC2)nc2c(c1O)C(=O)CC1(CCC1)C2]

Obtained by starting from ethyl 2'-(3,6-dihydro-2H-pyran-4-yl)-4'-hydroxy-5'-oxo-6',8'-dihydro-5'H-spiro[cyclobutane-1,7'-quinoline]-3'-carboxylate.

Mass spectrometry (ESI⁺): m/z=360 [M+H]⁺

HPLC (Method 7): Retention time=1.346 min.

(2) (3R,9S)-9-(tert-butyldimethylsilyloxy)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]

Chiral

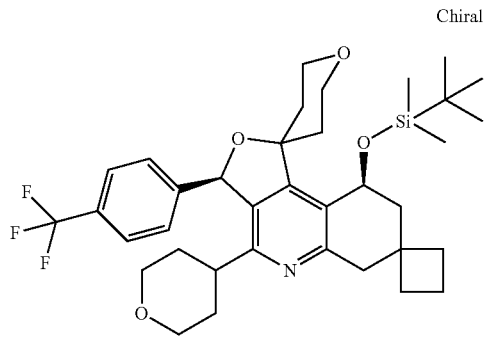 [SMILES: CC(C)(C)[Si](C)(C)O[C@H]1CC2(CCC2)Cc2nc(C3CCOCC3)c3c(c21)C1(CCOCC1)O[C@@H]3c1ccc(C(F)(F)F)cc1]

Obtained by starting from (3R,9S)-9-(tert-butyldimethylsilyloxy)-4-(3,6-dihydro-2H-pyran-4-yl)-7,7-(propan-1,3-diyl)-3-(4-(trifluoromethyl)phenyl)-2',3',5',6,6',7,8,9-octahydro-3H-spiro[furo[3,4-c]quinoline-1,4'-pyran].

Mass spectrometry (ESI⁺): m/z=644 [M+H]⁺

HPLC (Method 33): Retention time=2.061 min.

Example XXI

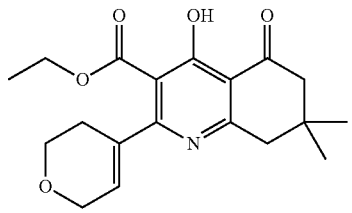 [SMILES: CCOC(=O)c1c(C2=CCOCC2)nc2c(c1O)C(=O)CC(C)(C)C2]

Ethyl 2-(3,6-dihydro-2H-pyran-4-yl)-4-hydroxy-7,7-dimethyl-5-oxo-5,6,7,8-tetrahydroquinoline-3-carboxylate 1 g Ethyl 2-chloro-4-hydroxy-7,7-dimethyl-5-oxo-5,6,7,8-tetrahydroquinoline-3-carboxylate and 800 mg 2-(3,6-dihydro-2H-pyran-4-yl)-4,4,5,5-tetramethyl-1,3,2-dioxaborolane are dissolved in 10 ml tetrahydrofuran and 2 ml toluene. 3.5 ml of a 2 M solution of sodium carbonate in water are added and the mixture is purged for 15 minutes with argon. Afterwards 100 mg 1,1'-bis-(diphenylphosphino)-ferrocene-dichloro-palladium-(II) are added and the mixture is stirred for 1.5 hours at 100° C. The mixture is diluted with diethylether, and the organic phase is washed with half saturated solution of ethylenediaminetetraacetic acid in a 1 M solution of sodium hydroxide in water, saturated ammonium chloride and brine. After drying with magnesium sulphate the solvents are evaporated in vacuo and the residue is chromatographed on silica gel (cyclohexane/ethylacetate 70:30 to 10:90).

Yield: 890 mg (77% of theory)

Mass spectrometry (ESI$^+$): m/z=346 [M+H]$^+$

HPLC (Method 1): Retention time=1.952 min.

Analogously to example XXI the following compounds are obtained:

(1) Ethyl 2'-(3,6-dihydro-2H-pyran-4-yl)-4'-hydroxy-5'-oxo-6',8'-dihydro-5'H-spiro[cyclobutane-1,7'-quinoline]-3'-carboxylate

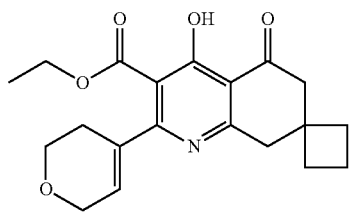 [SMILES: CCOC(=O)c1c(C2=CCOCC2)nc2c(c1O)C(=O)CC1(CCC1)C2]

Obtained by starting from ethyl 2'-chloro-4'-hydroxy-5'-oxo-6',8'-dihydro-5'H-spiro[cyclobutane-1,7'-quinoline]-3'-carboxylate. 1,4-Dioxane is used instead of tetrahydrofurane and caesium carbonate instead of sodium carbonate.

Mass spectrometry (ESI$^+$): m/z=358 [M+H]$^+$

HPLC (Method 7): Retention time=1.226 min.

Example XXII

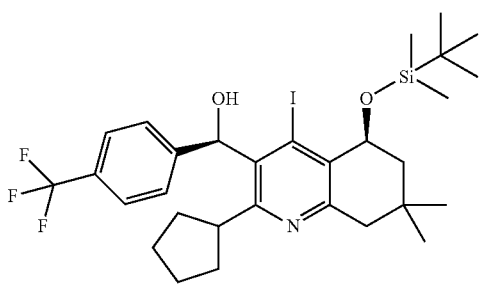

(R)—((S)-5-(tert-butyldimethylsilyloxy)-2-cyclopentyl-4-iodo-7,7-dimethyl-5,6,7,8-tetrahydroquinolin-3-yl)(4-(trifluoromethyl)phenyl)methanol and

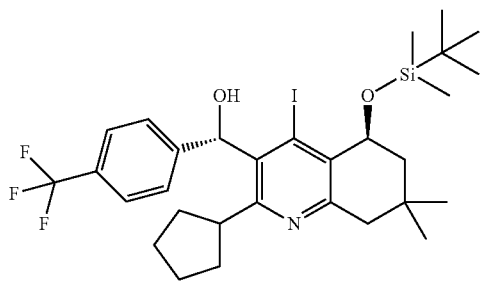

(S)—((S)-5-(tert-butyldimethylsilyloxy)-2-cyclopentyl-4-iodo-7,7-dimethyl-5,6,7,8-tetrahydroquinolin-3-yl)(4-(trifluoromethyl)phenyl)methanol To 300 mg magnesium turnings and 2 crystals of iodine were added 1 ml tetrahydrofurane. Afterwards a few drops of a solution of 2 ml 4-bromobenzotrifluoride in 15 ml tetrahydrofurane were added and the mixture was gently heated to start the reaction. Then the rest of the 4-bromobenzotrifluoride solution is added dropwise. After complete formation the Grignard reagent is added dropwise via syringe to a solution of 880 mg (S)-5-(tert-butyldimethylsilyloxy)-2-cyclopentyl-4-iodo-7,7-dimethyl-5,6,7,8-tetrahydroquinoline-3-carbaldehyde in 10 ml tetrahydrofurane at −50° C. The reaction is stirred for 1 hour at −50° C. and then quenched by dropwise addition of 10 ml methanol. The mixture is partitioned between dichloromethane and saturated ammonium chloride. The organic phase is washed with brine and dried with sodium sulphate. The solvents are evaporated in vacuo and the residue is chromatographed on silica gel (cyclohexane/ethylacetate 100:0 to 95:5).

Yield: 190 mg (17% of theory) (R)—((S)-5-(tert-butyldimethylsilyloxy)-2-cyclopentyl-4-iodo-7,7-dimethyl-5,6,7,8-tetrahydroquinolin-3-yl)(4-(trifluoromethyl)phenyl)methanol Mass spectrometry (ESI$^+$): m/z=660 [M+H]$^+$ HPLC (Method 17): Retention time=13.60 min.

and

Yield: 430 mg (38% of theory) (S)—((S)-5-(tert-butyldimethylsilyloxy)-2-cyclopentyl-4-iodo-7,7-dimethyl-5,6,7,8-tetrahydroquinolin-3-yl)(4-(trifluoromethyl)phenyl)methanol Mass spectrometry (ESI$^+$): m/z=660 [M+H]$^+$ HPLC (Method 17): Retention time=14.23 min.

Analogously to example XXII the following compounds are obtained:

(1) (R)—((S)-5-(tert-butyldimethylsilyloxy)-4-iodo-2-isopropyl-7,7-dimethyl-5,6,7,8-tetrahydroquinolin-3-yl)(4-isopropylphenyl)methanol

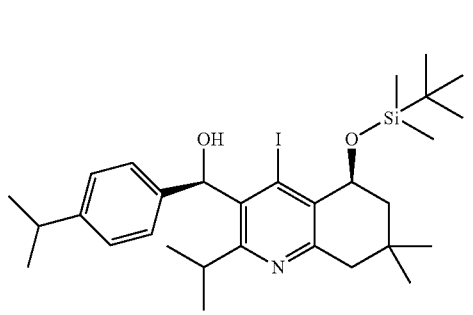

and (S)—((S)-5-(tert-butyldimethylsilyloxy)-4-iodo-2-isopropyl-7,7-dimethyl-5,6,7,8-tetrahydroquinolin-3-yl)(4-isopropylphenyl)methanol

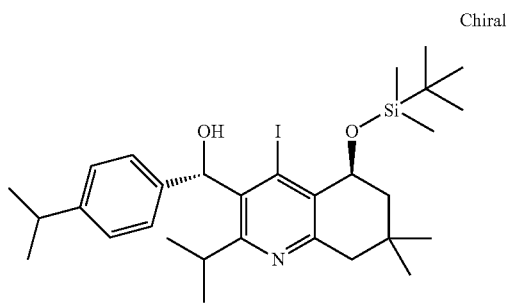 [SMILES: CC(C)c1ccc([C@H](O)c2c(C(C)C)nc3c(c2I)[C@@H](O[Si](C)(C)C(C)(C)C)CC(C)(C)C3)cc1]

Obtained by starting from (S)-5-(tert-butyldimethylsilyloxy)-4-iodo-2-isopropyl-7,7-dimethyl-5,6,7,8-tetrahydroquinoline-3-carbaldehyde and 1-bromo-4-isopropylbenzene.

$R_f$-value: 0.18 (silica gel, cyclohexane/ethylacetate 95:5)
(R)—((S)-5-(tert-butyldimethylsilyloxy)-4-iodo-2-isopropyl-7,7-dimethyl-5,6,7,8-tetrahydroquinolin-3-yl)(4-isopropylphenyl)methanol $R_f$-value: 0.15 (silica gel, cyclohexane/ethylacetate 95:5)
(S)—((S)-5-(tert-butyldimethylsilyloxy)-4-iodo-2-isopropyl-7,7-dimethyl-5,6,7,8-tetrahydroquinolin-3-yl)(4-isopropylphenyl)methanol (2) (S)-3-((R)-hydroxy(4-(trifluoromethyl)phenyl)methyl)-4-iodo-2-isopropyl-7,7-dimethyl-5,6,7,8-tetrahydroquinolin-5-ol

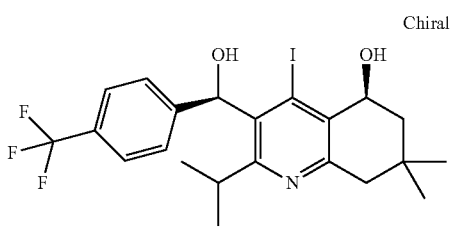 [SMILES: CC(C)c1nc2c(c(I)c1[C@H](O)c1ccc(C(F)(F)F)cc1)[C@@H](O)CC(C)(C)C2]

and (S)-3-((S)-hydroxy(4-(trifluoromethyl)phenyl)methyl)-4-iodo-2-isopropyl-7,7-dimethyl-5,6,7,8-tetrahydroquinolin-5-ol

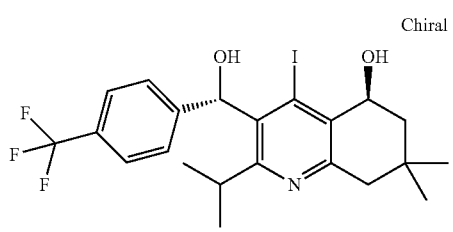 [SMILES: CC(C)c1nc2c(c(I)c1[C@@H](O)c1ccc(C(F)(F)F)cc1)[C@@H](O)CC(C)(C)C2]

Obtained by starting from (S)-5-hydroxy-4-iodo-2-isopropyl-7,7-dimethyl-5,6,7,8-tetrahydroquinoline-3-carbaldehyde.

(S)-3-((R)-hydroxy(4-(trifluoromethyl)phenyl)methyl)-4-iodo-2-isopropyl-7,7-dimethyl-5,6,7,8-tetrahydroquinolin-5-ol:

HPLC (Method 18): Retention time=1.78 min.

(S)-3-((S)-hydroxy(4-(trifluoromethyl)phenyl)methyl)-4-iodo-2-isopropyl-7,7-dimethyl-5,6,7,8-tetrahydroquinolin-5-ol:

HPLC (Method 18): Retention time=1.96 min.

253

(3) (S)-3'-((R)-hydroxy(4-(trifluoromethyl)phenyl)methyl)-4'-iodo-2'-isopropyl-6',8'-dihydro-5'H-spiro[cyclobutane-1,7'-quinolin]-5'-ol

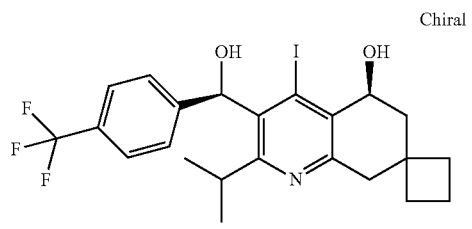 [SMILES: CC(C)c1nc2c(c(I)c1[C@H](O)c1ccc(C(F)(F)F)cc1)[C@@H](O)CC1(CCC1)C2]

and (S)-3'-((S)-hydroxy(4-(trifluoromethyl)phenyl)methyl)-4'-iodo-2'-isopropyl-6',8'-dihydro-5'H-spiro[cyclobutane-1,7'-quinolin]-5'-ol

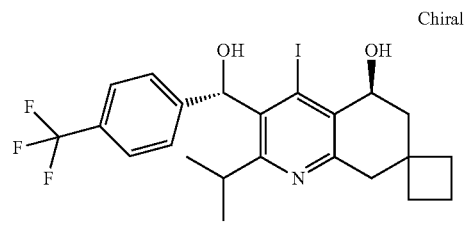 [SMILES: CC(C)c1nc2c(c(I)c1[C@@H](O)c1ccc(C(F)(F)F)cc1)[C@@H](O)CC1(CCC1)C2]

Obtained by starting from (S)-5'-hydroxy-4'-iodo-2'-isopropyl-6',8'-dihydro-5'H-spiro[cyclobutane-1,7'-quinoline]-3'-carbaldehyde.

(S)-3'-((R)-hydroxy(4-(trifluoromethyl)phenyl)methyl)-4'-iodo-2'-isopropyl-6',8'-dihydro-5'H-spiro[cyclobutane-1,7'-quinolin]-5'-ol:
Mass spectrometry (ESI+): m/z=532 [M+H]+
HPLC (Method 18): Retention time=1.90 min.
(S)-3'-((S)-hydroxy(4-(trifluoromethyl)phenyl)methyl)-4'-iodo-2'-isopropyl-6',8'-dihydro-5'H-spiro[cyclobutane-1,7'-quinolin]-5'-ol:
Mass spectrometry (ESI+): m/z=532 [M+H]+
HPLC (Method 18): Retention time=2.04 min.

(4) (R)—((S)-5-(tert-butyldimethylsilyloxy)-4-iodo-2-isopropyl-7,7-dimethyl-5,6,7,8-tetrahydroquinolin-3-yl)(4-(perfluoroethyl)phenyl)methanol

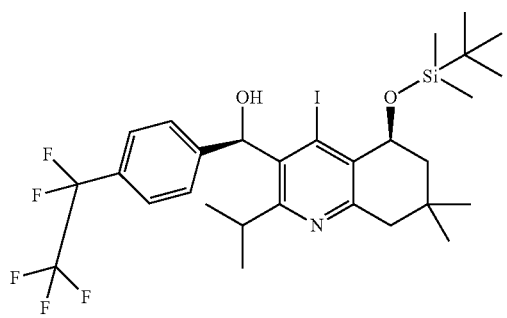

254 and (S)—((S)-5-(tert-butyldimethylsilyloxy)-4-iodo-2-isopropyl-7,7-dimethyl-5,6,7,8-tetrahydroquinolin-3-yl)(4-(perfluoroethyl)phenyl)methanol

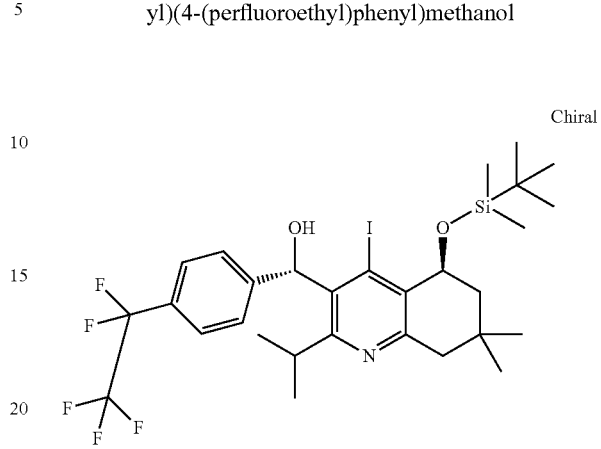

Obtained by starting from (S)-5-(tert-butyldimethylsilyloxy)-4-iodo-2-isopropyl-7,7-dimethyl-5,6,7,8-tetrahydroquinoline-3-carbaldehyde and 1-bromo-4-(perfluoroethyl)benzene.

(R)—((S)-5-(tert-butyldimethylsilyloxy)-4-iodo-2-isopropyl-7,7-dimethyl-5,6,7,8-tetrahydroquinolin-3-yl)(4-(perfluoroethyl)phenyl)methanol:
Mass spectrometry (ESI+): m/z=684 [M+H]+
HPLC (Method 2): Retention time=3.133 min.
(S)—((S)-5-(tert-butyldimethylsilyloxy)-4-iodo-2-isopropyl-7,7-dimethyl-5,6,7,8-tetrahydroquinolin-3-yl)(4-(perfluoroethyl)phenyl)methanol:
Mass spectrometry (ESI+): m/z=684 [M+H]+
HPLC (Method 2): Retention time=3.258 min.

Example XXIII

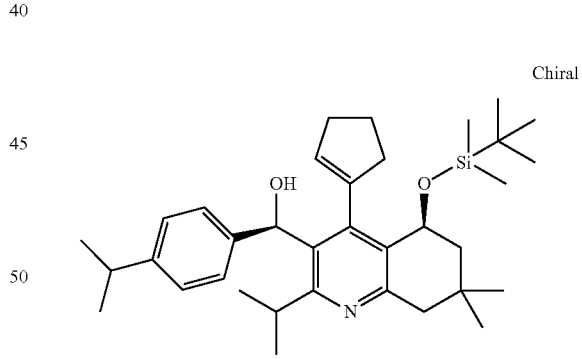

(R)—((S)-5-(tert-butyldimethylsilyloxy)-4-cyclopentenyl-2-isopropyl-7,7-dimethyl-5,6,7,8-tetrahydroquinolin-3-yl)(4-isopropylphenyl)methanol Under argon in a microwave vial 60 mg (R)—((S)-5-(tert-butyldimethylsilyloxy)-4-iodo-2-isopropyl-7,7-dimethyl-5,6,7,8-tetrahydroquinolin-3-yl)(4-isopropylphenyl)methanol and 57 mg 2-cyclopent-1-enyl-4,4,5,5-tetramethyl-[1,3,2]dioxaborolane are dissolved in 2 ml 1,2-dimethoxyethane and 197 μl of a 2 M solution of sodium carbonate in water. 11 mg Tetrakis-triphenylpalladium-(0) are added, the vial is closed and the mixture is heated for 30 minutes at 110° C. Then the mixture is diluted with ethylacetate and washed with water and brine. After drying with sodium sulphate the solvents are evaporated in vacuo and the residue is chromatographed on silica gel (cyclohexane/ethylacetate 100:0 to 95:5).

Yield: 30 mg (55% of theory)

Mass spectrometry (ESI⁺): m/z=548 [M+H]⁺

HPLC (Method 8): Retention time=2.14 min.

$R_f$-value: 0.4 (silica gel, cyclohexane/ethylacetate 95:5)

Analogously to example XXIII the following compounds are obtained:

(1) Ethyl 4-cyclopentenyl-2-isopropyl-7,7-dimethyl-5-oxo-5,6,7,8-tetrahydroquinoline-3-carboxylate

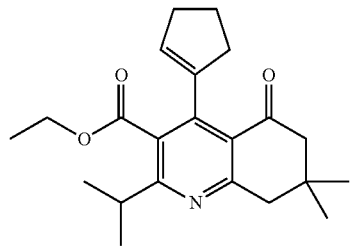 [SMILES: CCOC(=O)c1c(C(C)C)nc2c(c1C1=CCCC1)C(=O)CC(C)(C)C2]

Obtained by starting from ethyl 4-chloro-2-isopropyl-7,7-dimethyl-5-oxo-5,6,7,8-tetrahydroquinoline-3-carboxylate.

Mass spectrometry (ESI⁺): m/z=356 [M+H]⁺

HPLC (Method 8): Retention time=3.16 min.

(2) (S)—((S)-5-(tert-butyldimethylsilyloxy)-4-cyclopentenyl-2-isopropyl-7,7-dimethyl-5,6,7,8-tetrahydroquinolin-3-yl)(5-(trifluoromethyl)pyridin-2-yl)methanol

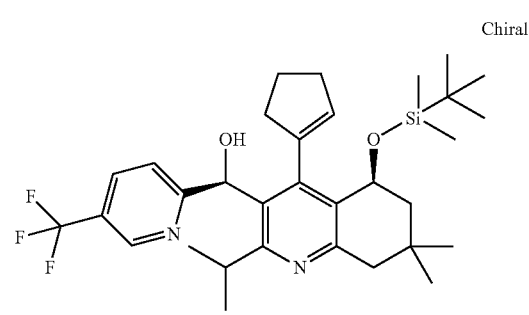 [SMILES: CC(C)c1nc2c(c(C3=CCCC3)c1[C@H](O)c1ccc(C(F)(F)F)cn1)[C@@H](O[Si](C)(C)C(C)(C)C)CC(C)(C)C2]

Obtained by starting from (S)—((S)-5-(tert-butyldimethylsilyloxy)-4-iodo-2-isopropyl-7,7-dimethyl-5,6,7,8-tetrahydroquinolin-3-yl)(5-(trifluoromethyl)pyridin-2-yl)methanol.

Mass spectrometry (ESI⁺): m/z=575 [M+H]⁺

HPLC (Method 8): Retention time=2.13 min.

$R_f$-value: 0.2 (silica gel, cyclohexane/ethylacetate 95:5)

(3) (R)—((S)-5-(tert-butyldimethylsilyloxy)-4-cyclopentenyl-2-isopropyl-7,7-dimethyl-5,6,7,8-tetrahydroquinolin-3-yl)(2-tert-butylpyrimidin-5-yl)methanol

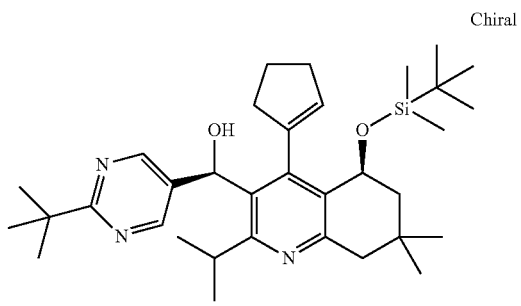 [SMILES: CC(C)c1nc2c(c(C3=CCCC3)c1[C@H](O)c1cnc(C(C)(C)C)nc1)[C@@H](O[Si](C)(C)C(C)(C)C)CC(C)(C)C2]

Obtained by starting from (R)—((S)-5-(tert-butyldimethylsilyloxy)-4-iodo-2-isopropyl-7,7-dimethyl-5,6,7,8-tetrahydroquinolin-3-yl)(2-tert-butylpyrimidin-5-yl)methanol. Potassium carbonate is used instead of sodium carbonate.

HPLC (Method 8): Retention time=2.14 min.

Example XXIV

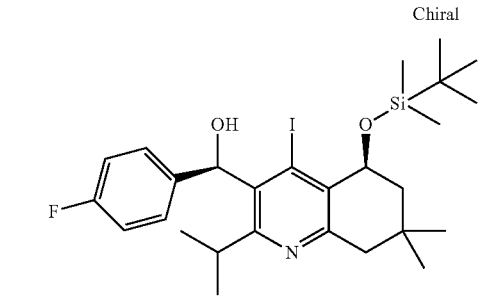

(R)—((S)-5-(tert-butyldimethylsilyloxy)-4-iodo-2-isopropyl-7,7-dimethyl-5,6,7,8-tetrahydroquinolin-3-yl)(4-fluorophenyl)methanol and

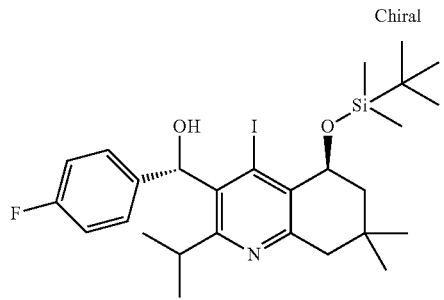 [SMILES: CC(C)c1nc2c(c(I)c1[C@@H](O)c1ccc(F)cc1)[C@@H](O[Si](C)(C)C(C)(C)C)CC(C)(C)C2]

(S)—((S)-5-(tert-butyldimethylsilyloxy)-4-iodo-2-isopropyl-7,7-dimethyl-5,6,7,8-tetrahydroquinolin-3-yl)(4-fluorophenyl)methanol Under argon 1.6 g (S)-5-(tert-butyldimethylsilyloxy)-4-iodo-2-isopropyl-7,7-dimethyl-5,6,7,8-tetrahydroquinoline-3-carbaldehyde are dissolved in 20 ml tetrahydrofurane, cooled to −50° C. and treated dropwise with 6.5 ml of a 1 M solution of 4-fluorophenyl-magnesium bromide in tetrahydrofurane. After stirring for 1 hour the reaction is quenched by addition of 5 ml methanol. The mixture is stirred for 12 hours while warming to room temperature. The solvents are evaporated in vacuo and the residue is chromatographed on silica gel (cyclohexane/ethylacetate 100:0 to 95:5).

(R)—((S)-5-(tert-butyldimethylsilyloxy)-4-iodo-2-isopropyl-7,7-dimethyl-5,6,7,8-tetrahydroquinolin-3-yl)(4-fluorophenyl)methanol:
  Yield: 682 mg (36% of theory)
  Mass spectrometry (ESI$^+$): m/z=584 [M+H]$^+$
  HPLC (Method 19): Retention time=1.96 min.
and
(S)—((S)-5-(tert-butyldimethylsilyloxy)-4-iodo-2-isopropyl-7,7-dimethyl-5,6,7,8-tetrahydroquinolin-3-yl)(4-fluorophenyl)methanol:
  Yield: 1.13 g (59% of theory)
  Mass spectrometry (ESI$^+$): m/z=584 [M+H]$^+$
  HPLC (Method 19): Retention time=1.98 min.

Analogously to example XXIV the following compounds are obtained:

(1) (R)—((S)-5-(tert-butyldimethylsilyloxy)-4-iodo-2-isopropyl-7,7-dimethyl-5,6,7,8-tetrahydroquinolin-3-yl)(4-chlorophenyl)methanol

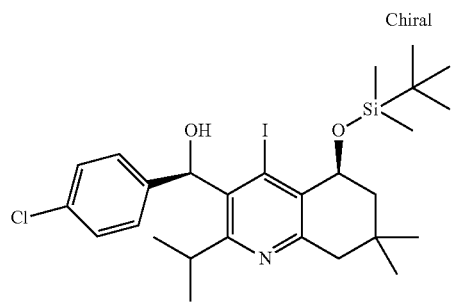 [SMILES: CC(C)c1nc2c(c(I)c1[C@H](O)c1ccc(Cl)cc1)[C@@H](O[Si](C)(C)C(C)(C)C)CC(C)(C)C2]

and (S)—((S)-5-(tert-butyldimethylsilyloxy)-4-iodo-2-isopropyl-7,7-dimethyl-5,6,7,8-tetrahydroquinolin-3-yl)(4-chlorophenyl)methanol

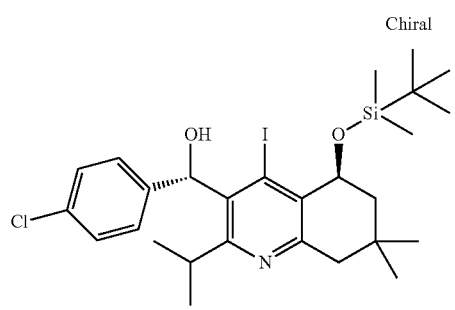 [SMILES: CC(C)c1nc2c(c(I)c1[C@@H](O)c1ccc(Cl)cc1)[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 4-chlorophenylmagnesium bromide.

(R)—((S)-5-(tert-butyldimethylsilyloxy)-4-iodo-2-isopropyl-7,7-dimethyl-5,6,7,8-tetrahydroquinolin-3-yl)(4-chlorophenyl)methanol:
  Mass spectrometry (ESI$^+$): m/z=600 [M+H]$^+$
  HPLC (Method 19): Retention time=2.05 min.
(S)—((S)-5-(tert-butyldimethylsilyloxy)-4-iodo-2-isopropyl-7,7-dimethyl-5,6,7,8-tetrahydroquinolin-3-yl)(4-chlorophenyl)methanol:
  Mass spectrometry (ESI$^+$): m/z=600 [M+H]$^+$
  HPLC (Method 19): Retention time=2.07 min.

(2) (R)—((S)-5-(tert-butyldimethylsilyloxy)-2-cyclopentyl-4-iodo-7,7-dimethyl-5,6,7,8-tetrahydroquinolin-3-yl)(4-fluorophenyl)methanol

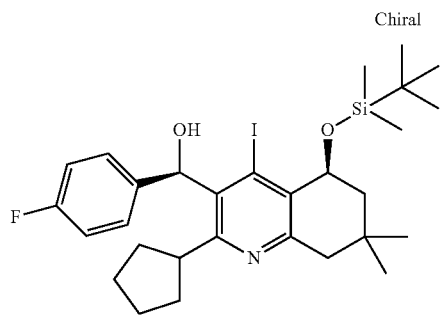 [SMILES: CC1(C)Cc2nc(C3CCCC3)c([C@H](O)c3ccc(F)cc3)c(I)c2[C@@H](O[Si](C)(C)C(C)(C)C)C1]

and (S)—((S)-5-(tert-butyldimethylsilyloxy)-2-cyclopentyl-4-iodo-7,7-dimethyl-5,6,7,8-tetrahydroquinolin-3-yl)(4-fluorophenyl)methanol

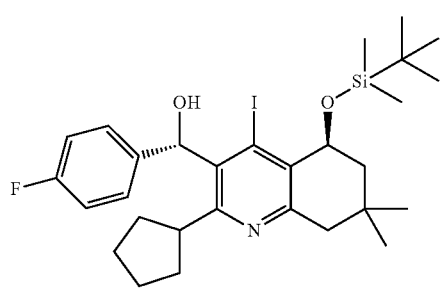

Obtained by starting from (S)-5-(tert-butyldimethylsilyloxy)-2-cyclopentyl-4-iodo-7,7-dimethyl-5,6,7,8-tetrahydroquinoline-3-carbaldehyde and 4-fluorophenylmagnesium bromide.

(R)—((S)-5-(tert-butyldimethylsilyloxy)-2-cyclopentyl-4-iodo-7,7-dimethyl-5,6,7,8-tetrahydroquinolin-3-yl)(4-fluorophenyl)methanol:
  Mass spectrometry (ESI$^+$): m/z=600 [M+H]$^+$
  HPLC (Method 19): Retention time=2.03 min.

(S)—((S)-5-(tert-butyldimethylsilyloxy)-2-cyclopentyl-4-iodo-7,7-dimethyl-5,6,7,8-tetrahydroquinolin-3-yl)(4-fluorophenyl)methanol:

Mass spectrometry (ESI$^+$): m/z=600 [M+H]$^+$

HPLC (Method 19): Retention time=2.05 min.

(3) (R)—((S)-5-(tert-butyldimethylsilyloxy)-4-iodo-2-isopropyl-7,7-dimethyl-5,6,7,8-tetrahydroquinolin-3-yl)(4-tert-butylphenyl)methanol

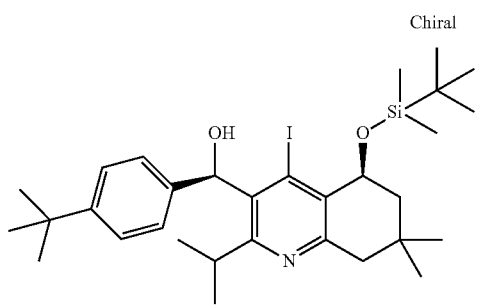 [SMILES: CC(C)c1nc2c(c(I)c1[C@H](O)c1ccc(C(C)(C)C)cc1)[C@@H](O[Si](C)(C)C(C)(C)C)CC(C)(C)C2]

and (S)—((S)-5-(tert-butyldimethylsilyloxy)-4-iodo-2-isopropyl-7,7-dimethyl-5,6,7,8-tetrahydroquinolin-3-yl)(4-tert-butylphenyl)methanol

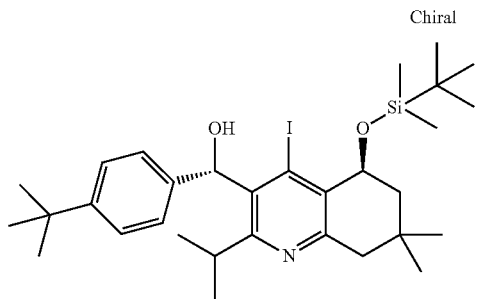 [SMILES: CC(C)c1nc2c(c(I)c1[C@@H](O)c1ccc(C(C)(C)C)cc1)[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 4-tert.-butylphenylmagnesium bromide. (R)—((S)-5-(tert-butyldimethylsilyloxy)-4-iodo-2-isopropyl-7,7-dimethyl-5,6,7,8-tetrahydroquinolin-3-yl)(4-tert-butylphenyl)methanol:

Mass spectrometry (ESI$^+$): m/z=622 [M+H]$^+$

HPLC (Method 19): Retention time=2.17 min.

(S)—((S)-5-(tert-butyldimethylsilyloxy)-4-iodo-2-isopropyl-7,7-dimethyl-5,6,7,8-tetrahydroquinolin-3-yl)(4-tert-butylphenyl)methanol:

Mass spectrometry (ESI$^+$): m/z=622 [M+H]$^+$

HPLC (Method 21): Retention time=2.23 min.

(4) (R)—((S)-5-(tert-butyldimethylsilyloxy)-4-iodo-2-isopropyl-7,7-dimethyl-5,6,7,8-tetrahydroquinolin-3-yl)(p-tolylmethanol

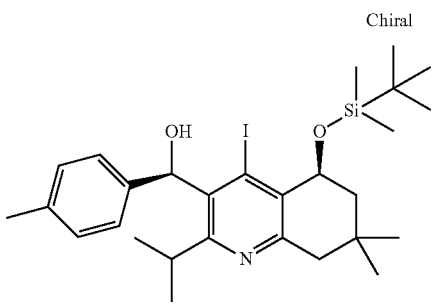 [SMILES: Cc1ccc([C@@H](O)c2c(C(C)C)nc3c(c2I)[C@@H](O[Si](C)(C)C(C)(C)C)CC(C)(C)C3)cc1]

and (S)—((S)-5-(tert-butyldimethylsilyloxy)-4-iodo-2-isopropyl-7,7-dimethyl-5,6,7,8-tetrahydroquinolin-3-yl)(p-tolylmethanol

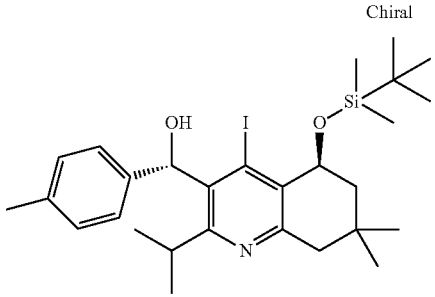 [SMILES: Cc1ccc([C@H](O)c2c(C(C)C)nc3c(c2I)[C@@H](O[Si](C)(C)C(C)(C)C)CC(C)(C)C3)cc1]

Obtained by starting from (S)-5-(tert-butyldimethylsilyloxy)-4-iodo-2-isopropyl-7,7-dimethyl-5,6,7,8-tetrahydroquinoline-3-carbaldehyde and p-tolylmagnesium bromide.

(R)—((S)-5-(tert-butyldimethylsilyloxy)-4-iodo-2-isopropyl-7,7-dimethyl-5,6,7,8-tetrahydroquinolin-3-yl)(4-tert-butylphenyl)methanol:

Mass spectrometry (ESI$^+$): m/z=580 [M+H]$^+$

HPLC (Method 20): Retention time=3.90 min.

(S)—((S)-5-(tert-butyldimethylsilyloxy)-4-iodo-2-isopropyl-7,7-dimethyl-5,6,7,8-tetrahydroquinolin-3-yl)(4-tert-butylphenyl)methanol:

Mass spectrometry (ESI$^+$): m/z=580 [M+H]$^+$

HPLC (Method 20): Retention time=3.90 min.

(5) (R)—((S)-5-(tert-butyldimethylsilyloxy)-4-iodo-2-isopropyl-7,7-dimethyl-5,6,7,8-tetrahydroquinolin-3-yl)(4-(trifluoromethoxy)phenyl)methanol

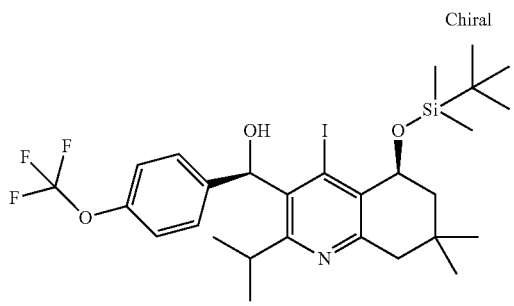 [SMILES: CC(C)c1nc2c(c(I)c1[C@H](O)c1ccc(OC(F)(F)F)cc1)[C@@H](O[Si](C)(C)C(C)(C)C)CC(C)(C)C2]

and (S)—((S)-5-(tert-butyldimethylsilyloxy)-4-iodo-2-isopropyl-7,7-dimethyl-5,6,7,8-tetrahydroquinolin-3-yl)(4-(trifluoromethoxy)phenyl)methanol

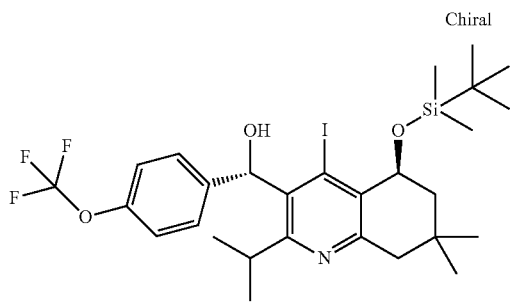 [SMILES: CC(C)c1nc2c(c(I)c1[C@@H](O)c1ccc(OC(F)(F)F)cc1)[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 4-trifluormethoxyphenylmagnesium bromide.

(R)—((S)-5-(tert-butyldimethylsilyloxy)-4-iodo-2-isopropyl-7,7-dimethyl-5,6,7,8-tetrahydroquinolin-3-yl)(4-(trifluoromethoxy)phenyl)methanol:

Mass spectrometry (ESI⁺): m/z=650 [M+H]⁺

HPLC (Method 20): Retention time=4.03 min.

(S)—((S)-5-(tert-butyldimethylsilyloxy)-4-iodo-2-isopropyl-7,7-dimethyl-5,6,7,8-tetrahydroquinolin-3-yl)(4-(trifluoromethoxy)phenyl)methanol:

Mass spectrometry (ESI⁺): m/z=650 [M+H]⁺

HPLC (Method 20): Retention time=4.06 min.

(6) ((5S)-5-(tert-butyldimethylsilyloxy)-2-cyclopentyl-4-iodo-7,7-dimethyl-5,6,7,8-tetrahydroquinolin-3-yl)(4-tert-butylphenyl)methanol

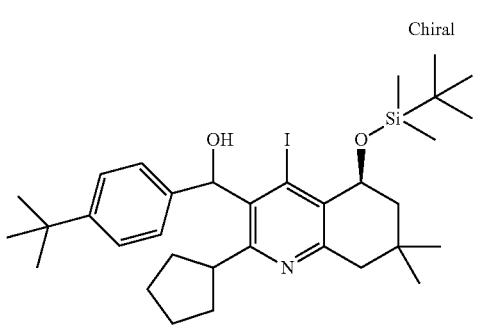 [SMILES: CC1(C)Cc2nc(C3CCCC3)c(C(O)c3ccc(C(C)(C)C)cc3)c(I)c2[C@@H](O[Si](C)(C)C(C)(C)C)C1]

Obtained by starting from (S)-5-(tert-butyldimethylsilyloxy)-2-cyclopentyl-4-iodo-7,7-dimethyl-5,6,7,8-tetrahydroquinoline-3-carbaldehyde and 4-tert.-butylphenylmagnesium bromide. The product is obtained as a diastereomic mixture, which is used directly in the next step.

Mass spectrometry (ESI⁺): m/z=648 [M+H]⁺

HPLC (Method 20): Retention time=4.10 min.

(7) ((S)-5-(tert-butyldimethylsilyloxy)-2-cyclopentyl-4-iodo-7,7-dimethyl-5,6,7,8-tetrahydroquinolin-3-yl)(4-isopropylphenyl)methanol

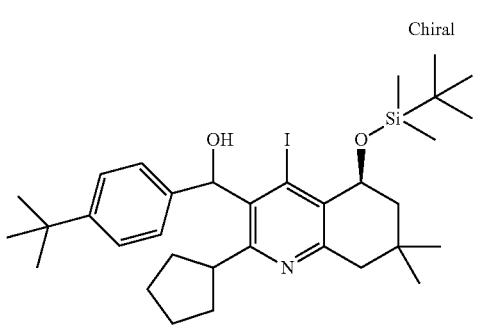 [SMILES: CC1(C)Cc2nc(C3CCCC3)c(C(O)c3ccc(C(C)(C)C)cc3)c(I)c2[C@@H](O[Si](C)(C)C(C)(C)C)C1]

Obtained by starting from (S)-5-(tert-butyldimethylsilyloxy)-2-cyclopentyl-4-iodo-7,7-dimethyl-5,6,7,8-tetrahydroquinoline-3-carbaldehyde and 4-iso-propylphenylmagnesium bromide. The product is obtained as a diastereomic mixture, which is used directly in the next step.

Mass spectrometry (ESI⁺): m/z=634 [M+H]⁺

HPLC (Method 6): Retention time=3.891 min. (Isomer-1)

HPLC (Method 6): Retention time=4.067 min. (Isomer-2)

(8) ((S)-5-(tert-butyldimethylsilyloxy)-2-cyclopentyl-4-iodo-7,7-dimethyl-5,6,7,8-tetrahydroquinolin-3-yl)(3-tert-butylphenyl)methanol

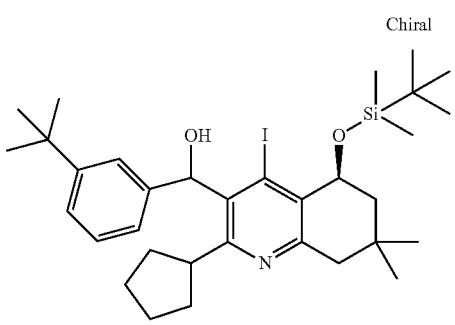 [SMILES: CC1(C)Cc2nc(C3CCCC3)c(C(O)c3cccc(C(C)(C)C)c3)c(I)c2[C@@H](O[Si](C)(C)C(C)(C)C)C1]

Obtained by starting from (S)-5-(tert-butyldimethylsilyloxy)-2-cyclopentyl-4-iodo-7,7-dimethyl-5,6,7,8-tetrahydroquinoline-3-carbaldehyde and 3-tert.-butylphenylmagnesium bromide. The product is obtained as a diastereomic mixture, which is used directly in the next step.

HPLC (Method 4): Retention time=3.294 min. (Isomer-1)
HPLC (Method 4): Retention time=3.335 min. (Isomer-2)

(9) (R)—((S)-5'-(tert-butyldimethylsilyloxy)-4'-iodo-2'-isopropyl-6',8'-dihydro-5'H-spiro[cyclobutane-1,7'-quinoline]-3'-yl)(4-isopropylphenyl)methanol

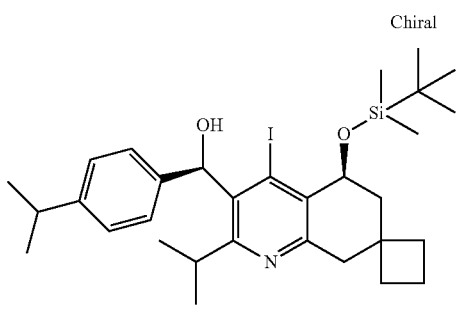 [SMILES: CC(C)c1ccc([C@@H](O)c2c(C(C)C)nc3c(c2I)[C@@H](O[Si](C)(C)C(C)(C)C)CC2(CCC2)C3)cc1]

and (S)—((S)-5'-(tert-butyldimethylsilyloxy)-4'-iodo-2'-isopropyl-6',8'-dihydro-5'H-spiro[cyclobutane-1,7'-quinoline]-3'-yl)(4-isopropylphenyl)methanol

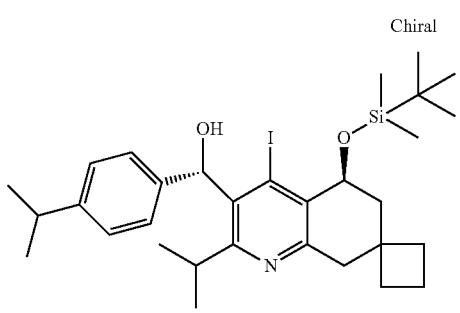 [SMILES: CC(C)c1ccc([C@H](O)c2c(C(C)C)nc3c(c2I)[C@@H](O[Si](C)(C)C(C)(C)C)CC2(CCC2)C3)cc1]

Obtained by starting from (S)-5'-(tert-butyldimethylsilyloxy)-4'-iodo-2'-isopropyl-6',8'-dihydro-5'H-spiro[cyclobutane-1,7'-quinoline]-3'-carbaldehyde and 4-isopropylphenylmagnesiumbromide.

(R)—((S)-5'-(tert-butyldimethylsilyloxy)-4'-iodo-2'-isopropyl-6',8'-dihydro-5'H-spiro[cyclobutane-1,7'-quinoline]-3-yl)(4-isopropylphenyl)methanol:
Mass spectrometry (ESI⁺): m/z=620 [M+H]⁺
HPLC (Method 20): Retention time=4.04 min.

(S)—((S)-5'-(tert-butyldimethylsilyloxy)-4'-iodo-2'-isopropyl-6',8'-dihydro-5'H-spiro[cyclobutane-1,7'-quinoline]-3-yl)(4-isopropylphenyl)methanol:
Mass spectrometry (ESI⁺): m/z=620 [M+H]⁺
HPLC (Method 20): Retention time=4.05 min.

(10) (R)-(4-(benzyloxy)phenyl)((S)-5-(tert-butyldimethylsilyloxy)-4-iodo-2-isopropyl-7,7-dimethyl-5,6,7,8-tetrahydroquinolin-3-yl)methanol

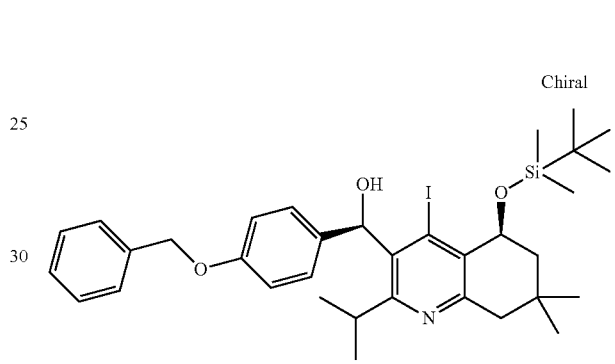

and (S)-(4-(benzyloxy)phenyl)((S)-5-(tert-butyldimethylsilyloxy)-4-iodo-2-isopropyl-7,7-dimethyl-5,6,7,8-tetrahydroquinolin-3-ylmethanol

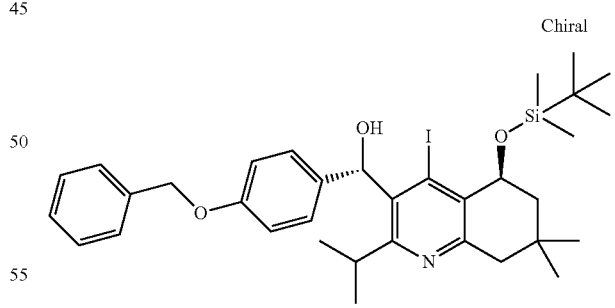

Obtained by starting from (S)-5-(tert-butyldimethylsilyloxy)-4-iodo-2-isopropyl-7,7-dimethyl-5,6,7,8-tetrahydroquinoline-3-carbaldehyde and 4-benzyloxyphenylmagnesium bromide.

(R)-(4-(benzyloxy)phenyl)((S)-5-(tert-butyldimethylsilyloxy)-4-iodo-2-isopropyl-7,7-dimethyl-5,6,7,8-tetrahydroquinolin-3-yl)methanol:
Mass spectrometry (ESI⁺): m/z=672 [M+H]⁺
$R_f$-value: 0.60 (silica gel, cyclohexane/ethylacetate 9:1)

(S)-(4-(benzyloxy)phenyl)((S)-5-(tert-butyldimethylsilyloxy)-4-iodo-2-isopropyl-7,7-dimethyl-5,6,7,8-tetrahydroquinolin-3-yl)methanol:

Mass spectrometry (ESI+): m/z=672 [M+H]+

$R_f$-value: 0.55 (silica gel, cyclohexane/ethylacetate 9:1)

(11) (R)-(4-tert-butoxyphenyl)((S)-5-(tert-butyldimethylsilyloxy)-4-iodo-2-isopropyl-7,7-dimethyl-5,6,7,8-tetrahydroquinolin-3-yl)methanol

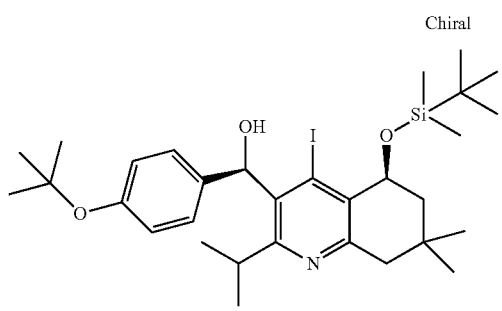 [SMILES: CC(C)c1nc2c(c(I)c1[C@H](O)c1ccc(OC(C)(C)C)cc1)[C@@H](O[Si](C)(C)C(C)(C)C)CC(C)(C)C2]

and (S)-(4-tert-butoxyphenyl)((S)-5-(tert-butyldimethylsilyloxy)-4-iodo-2-isopropyl-7,7-dimethyl-5,6,7,8-tetrahydroquinolin-3-yl)methanol

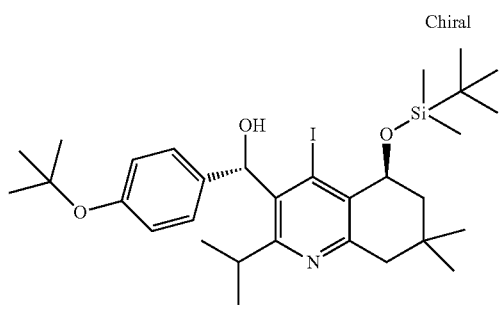 [SMILES: CC(C)c1nc2c(c(I)c1[C@@H](O)c1ccc(OC(C)(C)C)cc1)[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde. A 0.5 M solution of (4-tert-butoxyphenyl)magnesium bromide in tetrahydrofurane is used instead of 1 M solution of 4-fluorophenyl-magnesium bromide in tetrahydrofurane.

(R)-(4-tert-butoxyphenyl)((S)-5-(tert-butyldimethylsilyloxy)-4-iodo-2-isopropyl-7,7-dimethyl-5,6,7,8-tetrahydroquinolin-3-yl)methanol:

Mass spectrometry (ESI+): m/z=638 [M+H]+

$R_f$-value: 0.5 (silica gel, petrole ether/ethylacetate 9:1)

(S)-(4-tert-butoxyphenyl)((S)-5-(tert-butyldimethylsilyloxy)-4-iodo-2-isopropyl-7,7-dimethyl-5,6,7,8-tetrahydroquinolin-3-yl)methanol:

Mass spectrometry (ESI+): m/z=638 [M+H]+

$R_f$-value: 0.4 (silica gel, petrole ether/ethylacetate 9:1)

(12) (S)-3'-((R)-(4-tert-butylphenyl)(hydroxy)methyl)-4'-iodo-2'-isopropyl-6',8'-dihydro-5'H-spiro[cyclobutane-1,7'-quinolin]-5'-ol

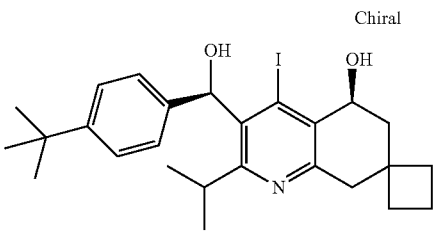 [SMILES: CC(C)c1nc2c(c(I)c1[C@H](O)c1ccc(C(C)(C)C)cc1)[C@@H](O)CC1(CCC1)C2]

Obtained by starting from (S)-5'-hydroxy-4'-iodo-2'-isopropyl-6',8'-dihydro-5'H-spiro[cyclobutane-1,7'-quinoline]-3'-carbaldehyde and 4-tert.-butylphenylmagnesium bromide.

Mass spectrometry (ESI+): m/z=520 [M+H]+

HPLC (Method 7): Retention time=1.590 min.

Example XXV

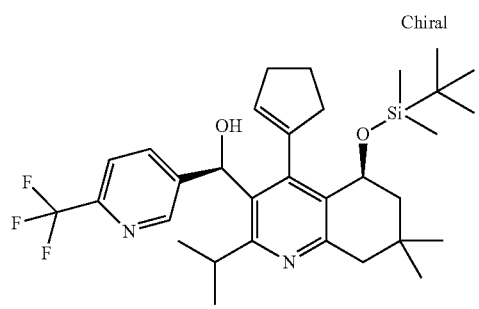 [SMILES: CC(C)c1nc2c(c(C3=CCCC3)c1[C@H](O)c1ccc(C(F)(F)F)nc1)[C@@H](O[Si](C)(C)C(C)(C)C)CC(C)(C)C2]

(R)—((S)-5-(tert-butyldimethylsilyloxy)-4-cyclopentenyl-2-isopropyl-7,7-dimethyl-5,6,7,8-tetrahydroquinolin-3-yl)(6-(trifluoromethyl)pyridin-3-yl)methanol and

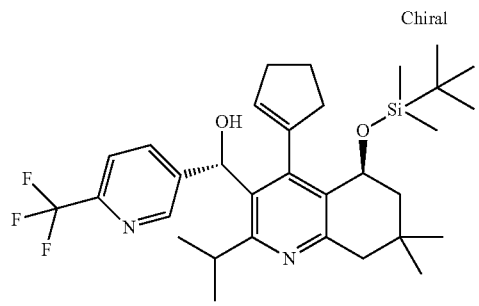 [SMILES: CC(C)c1nc2c(c(C3=CCCC3)c1[C@@H](O)c1ccc(C(F)(F)F)nc1)[C@@H](O[Si](C)(C)C(C)(C)C)CC(C)(C)C2]

(S)—((S)-5-(tert-butyldimethylsilyloxy)-4-cyclopentenyl-2-isopropyl-7,7-dimethyl-5,6,7,8-tetrahydrquinolin-3-yl)(6-(trifluoromethyl)pyridin-3-yl)methanol 91 mg Magnesium turnings and 79 mg lithium chloride are placed in a flask and dried in vacuo with a heat gun. After cooling back to room temperature the flask is refilled with argon.

Thereafter 5 ml tetrahydrofurane and 9 µl of a 1 M solution of diisobutylaluminiumhydride in hexane are added successively. The mixture is stirred 5 minutes, then treated with 436 mg of 5-bromo-2-trifluoromethylpyridine in 5 ml tetrahydrofurane and stirred for 30 minutes. This mixture is added dropwise at 0° C. to a solution of 200 mg (S)-5-(tert-butyldimethylsilyloxy)-4-cyclopentenyl-2-isopropyl-7,7-dimethyl-5,6,7,8-tetrahydroquinoline-3-carbaldehyde in 1 ml tetrahydrofurane. The reaction is stirred for 1 hour and then quenched by addition of saturated ammonium chloride. The mixture is extracted 3 times with ethylacetate and the combined organic phases are dried with sodium sulphate. After evaporation of the solvents in vacuo the residue is chromatographed on silica gel (pentane/diethylether 98:2 to 70:30).

Yield: 65 mg (24% of theory) (R)—((S)-5-(tert-butyldimethylsilyloxy)-4-cyclopentenyl-2-isopropyl-7,7-dimethyl-5,6,7,8-tetrahydroquinolin-3-yl)(6-(trifluoromethyl)pyridin-3-yl)methanol Mass spectrometry (ESI$^+$): m/z=575 [M+H]$^+$ R$_f$-value: 0.18 (silica gel, pentane/diethylether 8:2)
and Yield: 117 mg (44% of theory) (S)—((S)-5-(tert-butyldimethylsilyloxy)-4-cyclopentenyl-2-isopropyl-7,7-dimethyl-5,6,7,8-tetrahydroquinolin-3-yl)(6-(trifluoromethyl)pyridin-3-yl)methanol R$_f$-value: 0.26 (silica gel, pentane/diethylether 8:2)

Analogously to example XXV the following compounds are obtained:

(1) (R)—((S)-5-(tert-butyldimethylsilyloxy)-4-iodo-2-isopropyl-7,7-dimethyl-5,6,7,8-tetrahydroquinolin-3-yl)(6-(trifluoromethyl)pyridin-3-yl)methanol

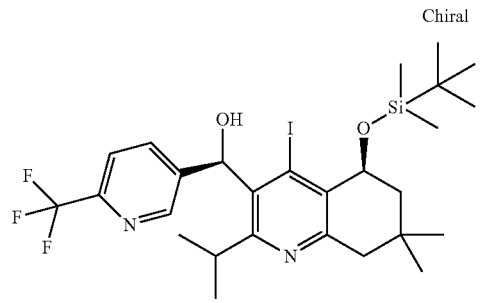 [SMILES: CC(C)c1nc2c(c(I)c1[C@H](O)c1ccc(C(F)(F)F)nc1)[C@@H](O[Si](C)(C)C(C)(C)C)CC(C)(C)C2]

and (S)—((S)-5-(tert-butyldimethylsilyloxy)-4-iodo-2-isopropyl-7,7-dimethyl-5,6,7,8-tetrahydroquinolin-3-yl)(6-(trifluoromethyl)pyridin-3-yl)methanol

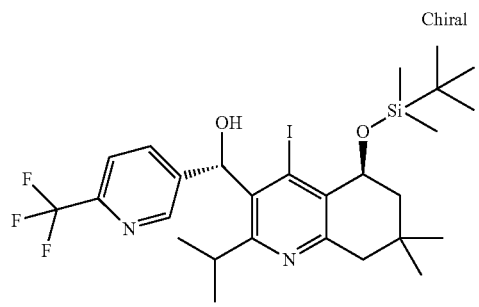 [SMILES: CC(C)c1nc2c(c(I)c1[C@@H](O)c1ccc(C(F)(F)F)nc1)[C@@H](O[Si](C)(C)C(C)(C)C)CC(C)(C)C2]

Obtained by starting from (S)-5-(tert-butyldimethylsilyloxy)-4-iodo-2-isopropyl-7,7-dimethyl-5,6,7,8-tetrahydroquinoline-3-carbaldehyde and 5-bromo-2-(trifluoromethyl)pyridine.

(R)—((S)-5-(tert-butyldimethylsilyloxy)-4-iodo-2-isopropyl-7,7-dimethyl-5,6,7,8-tetrahydroquinolin-3-yl)(6-(trifluoromethyl)pyridin-3-yl)methanol:

Mass spectrometry (ESI$^+$): m/z=635 [M+H]$^+$

HPLC (Method 9): Retention time=3.33 min.

(S)—((S)-5-(tert-butyldimethylsilyloxy)-4-iodo-2-isopropyl-7,7-dimethyl-5,6,7,8-tetrahydroquinolin-3-yl)(6-(trifluoromethyl)pyridin-3-yl)methanol:

Mass spectrometry (ESI$^+$): m/z=635 [M+H]$^+$

HPLC (Method 9): Retention time=3.36 min.

Example XXVI

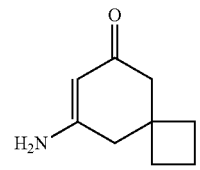

8-Aminospiro[3.5]non-7-en-6-one 10 g 8-hydroxyspiro[3.5]non-7-en-6-one and 10.1 g ammonium acetate are dissolved in 100 ml toluene and 3.2 ml acetic acid. The mixture is refluxed for 2 hours using a Dean-Stark trap. After cooling to room temperature the mixture is cautiously added to 200 ml of a saturated solution of sodium bicarbonate and 100 g ice. Then the mixture is stirred for 15 minutes, the solid product is collected by filtration and dried at 50° C. in vacuo.

Yield: 8.5 g (86% of theory)

Mass spectrometry (ESI$^+$): m/z=152 [M+H]$^+$

HPLC (Method 19): Retention time=0.81 min.

Analogously to example XXVI the following compounds are obtained:

(1) 9-Aminospiro[4.5]dec-8-en-7-one

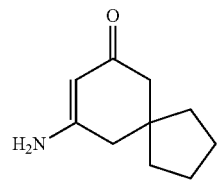

Obtained by starting from spiro[4.5]decane-7,9-dione.
Mass spectrometry (ESI⁺): m/z=166 [M+H]⁺
HPLC (Method 36): Retention time=1.54 min.

Example XXVII

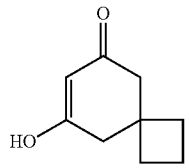

8-hydroxyspiro[3.5]non-7-en-6-one 2.6 g Sodium are added in portions to 50 ml methanol. After complete dissolution the solution is heated to 60° C. 12.7 ml Dimethylmalonate are added and the mixture is refluxed for 10 minutes. Then 12.3 g 1-cyclobutylidenepropan-2-one are added and the mixture is refluxed for 4 hours. After recooling to room temperature a solution of 14 g potassium hydroxide in 65 ml water is added and the mixture is refluxed for 1 hour. The mixture is cooled to room temperature and the pH is adjusted to 2 by careful addition of half saturated hydrochloric acid. Then it is stirred for 1 hour at room temperature, 3 hours at 60° C. and 12 hours at room temperature. The precipitate is collected by filtration and washed with water and diisopropylether and dried in vacuo to give 10.6 g product. The methanol of the mother liquor is evaporated in vacuo, 50 ml 1,4-dioxane are added and the mixture is refluxed for 1 hour. The 1,4-dioxane is evaporated in vacuo and the precipitate is collected by filtration, washed with water and diisopropylether and dried in vacuo to give 3.2 g product.
Yield: 13.8 g (82% of theory)
Mass spectrometry (ESI⁺): m/z=153 [M+H]⁺
R$_f$-value: 0.37 (silica gel, dichloromethane/methanol 9:1)

Example XXVIII

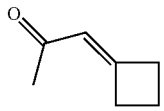

1-Cyclobutylidenepropan-2-one

A mixture of 55 g 1-(triphenylphosphoraniliden)-2-propanone in 85 ml silicone oil is heated to 100° C. 2 g benzoic acid and 11.4 g cyclobutanone are added and the mixture is stirred for 12 hours at 110° C. From this mixture the product is obtained by distillation (boiling point 70-74° C. at 30 mbar).
Yield: 12.3 g (68% of theory)
Mass spectrometry (ESI⁺): m/z=111 [M+H]⁺
R$_f$-value: 0.34 (silica gel, cyclohexane/ethylacetate 9:1)

Example XXIX

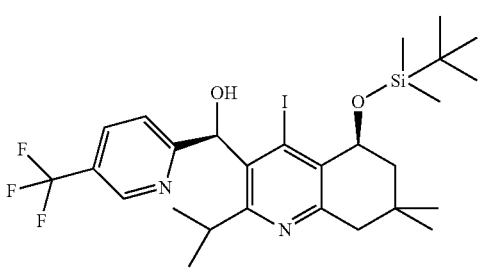

(S)—((S)-5-(tert-butyldimethylsilyloxy)-4-iodo-2-isopropyl-7,7-dimethyl-5,6,7,8-tetrahydroquinolin-3-yl)(5-(trifluoromethyl)pyridin-2-yl)methanol and

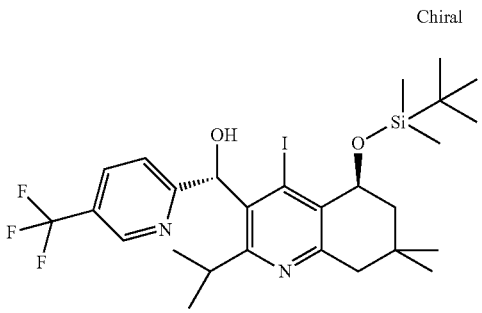 [SMILES: CC(C)c1nc2c(c(I)c1[C@@H](O)c1ccc(C(F)(F)F)cn1)[C@@H](O[Si](C)(C)C(C)(C)C)CC(C)(C)C2]

(R)—((S)-5-(tert-butyldimethylsilyloxy)-4-iodo-2-isopropyl-7,7-dimethyl-5,6,7,8-tetrahydroquinolin-3-yl)(5-(trifluoromethyl)pyridin-2-yl)methanol 1.23 ml of a 2.5 M solution of n-butyllithium in toluene are added dropwise to a solution of 695 mg 2-bromo-5-trifluoromethylpyridine in 10 ml toluene at −80° C. The mixture is stirred for 1 hour and then a solution of 600 mg (S)-5-(tert-butyldimethylsilyloxy)-4-iodo-2-isopropyl-7,7-dimethyl-5,6,7,8-tetrahydroquinoline-3-carbaldehyde in 1 ml toluene is added dropwise. After stirring the mixture for 1 hour at −80° C. the reaction is quenched by addition of a saturated aqueous ammonium chloride solution. The phases are separated and the aqueous phase is extracted for three times with ethylacetate. The combined organic phases are dried with magnesium sulphate and the solvents are evaporated in vacuo. The residue is chromatographed on silica gel (pentane/diethylether 100:0 to 70:30).

(S)—((S)-5-(tert-butyldimethylsilyloxy)-4-iodo-2-isopropyl-7,7-dimethyl-5,6,7,8-tetrahydroquinolin-3-yl)(5-(trifluoromethyl)pyridin-2-yl)methanol:
Yield: 186 mg (24% of theory)
Mass spectrometry (ESI$^+$): m/z=635 [M+H]$^+$
HPLC (Method 11): Retention time=12.61 min.
$R_f$-value: 0.53 (silica gel, pentane/diethylether 4:1)

(R)—((S)-5-(tert-butyldimethylsilyloxy)-4-iodo-2-isopropyl-7,7-dimethyl-5,6,7,8-tetrahydroquinolin-3-yl)(5-(trifluoromethyl)pyridin-2-yl)methanol:
Yield: 350 mg (45% of theory)
Mass spectrometry (ESI$^+$): m/z=635 [M+H]$^+$
HPLC (Method 11): Retention time=12.92 min.
$R_f$-value: 0.35 (silica gel, pentane/diethylether 4:1)

Analogously to example XXIX the following compounds are obtained:

(1) (S)—((S)-5-(tert-butyldimethylsilyloxy)-4-iodo-2-isopropyl-7,7-dimethyl-5,6,7,8-tetrahydroquinolin-3-yl)(5-(trifluoromethyl)thiophen-2-yl)methanol

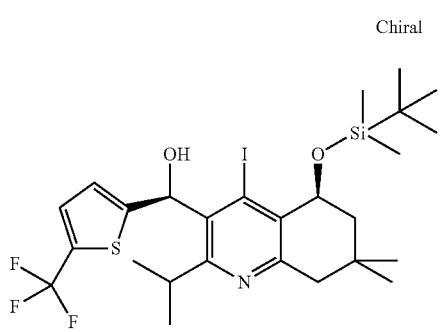 [SMILES: CC(C)c1nc2c(c(I)c1[C@H](O)c1ccc(C(F)(F)F)s1)[C@@H](O[Si](C)(C)C(C)(C)C)CC(C)(C)C2]

Chiral and (R)—((S)-5-(tert-butyldimethylsilyloxy)-4-iodo-2-isopropyl-7,7-dimethyl-5,6,7,8-tetrahydroquinolin-3-yl)(5-(trifluoromethyl)thiophen-2-yl)methanol

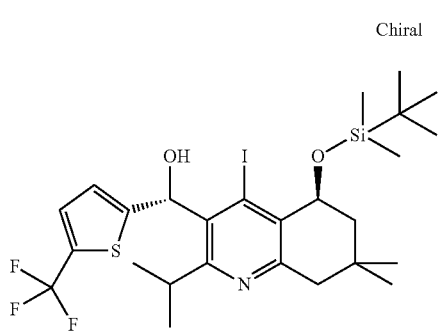 [SMILES: CC(C)c1nc2c(c(I)c1[C@@H](O)c1ccc(C(F)(F)F)s1)[C@@H](O[Si](C)(C)C(C)(C)C)CC(C)(C)C2]

Chiral

Obtained by starting from (S)-5-(tert-butyldimethylsilyloxy)-4-iodo-2-isopropyl-7,7-dimethyl-5,6,7,8-tetrahydroquinoline-3-carbaldehyde and 2-bromo-5-(trifluoromethyl)thiophene.

(S)—((S)-5-(tert-butyldimethylsilyloxy)-4-iodo-2-isopropyl-7,7-dimethyl-5,6,7,8-tetrahydroquinolin-3-yl)(5-(trifluoromethyl)thiophen-2-yl)methanol:
Mass spectrometry (ESI$^+$): m/z=640 [M+H]$^+$
HPLC (Method 11): Retention time=14.89 min.

(R)—((S)-5-(tert-butyldimethylsilyloxy)-4-iodo-2-isopropyl-7,7-dimethyl-5,6,7,8-tetrahydroquinolin-3-yl)(5-(trifluoromethyl)thiophen-2-yl)methanol:
Mass spectrometry (ESI$^+$): m/z=640 [M+H]$^+$
HPLC (Method 11): Retention time=15.09 min.

(2) (S)—((S)-5'-(tert-butyldimethylsilyloxy)-4'-iodo-2'-isopropyl-6',8'-dihydro-5'H-spiro[cyclobutane-1,7'-quinoline]-3'-yl)(5-(trifluoromethyl)pyridin-2-yl)methanol

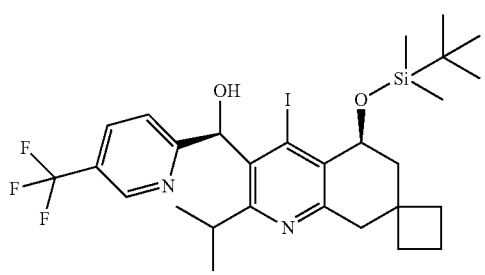

Chiral and (R)—((S)-5'-(tert-butyldimethylsilyloxy)-4'-iodo-2'-isopropyl-6',8'-dihydro-5'H-spiro[cyclobutane-1,7'-quinoline]-3'-yl)(5-(trifluoromethyl)pyridin-2-yl)methanol

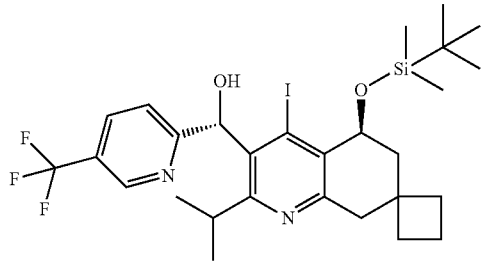

Chiral

Obtained by starting from (S)-5'-(tert-butyldimethylsilyloxy)-4'-iodo-2'-isopropyl-6',8'-dihydro-5'H-spiro[cyclobutane-1,7'-quinoline]-3'-carbaldehyde and 2-bromo-5-(trifluoromethyl)pyridine.

(S)—((S)-5'-(tert-butyldimethylsilyloxy)-4'-iodo-2'-isopropyl-6',8'-dihydro-5'H-spiro[cyclobutane-1,7'-quinoline]-3'-yl)(5-(trifluoromethyl)pyridin-2-yl)methanol:
Mass spectrometry (ESI$^+$): m/z=647 [M+H]$^+$
$R_f$-value: 0.17 (silica gel, n-hexane/diethylether 9:1)

(R)—((S)-5'-(tert-butyldimethylsilyloxy)-4'-iodo-2'-isopropyl-6',8'-dihydro-5'H-spiro[cyclobutane-1,7'-quinoline]-3'-yl)(5-(trifluoromethyl)pyridin-2-yl)methanol:
Mass spectrometry (ESI⁺): m/z=647 [M+H]⁺
$R_f$-value: 0.11 (silica gel, n-hexane/diethylether 9:1)

(3) (S)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(2-fluoro-4-(trifluoromethyl)phenyl)methanol

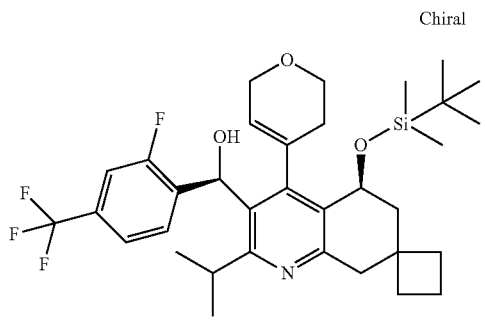 [SMILES: CC(C)c1nc2c(c(C3=CCOCC3)c1[C@H](O)c1ccc(C(F)(F)F)cc1F)[C@@H](O[Si](C)(C)C(C)(C)C)CC1(CCC1)C2]

and (R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(2-fluoro-4-(trifluoromethyl)phenyl)methanol

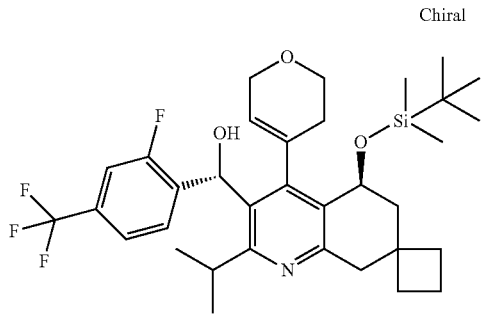 [SMILES: CC(C)c1nc2c(c(C3=CCOCC3)c1[C@@H](O)c1ccc(C(F)(F)F)cc1F)[C@@H](O[Si](C)(C)C(C)(C)C)CC1(CCC1)C2]

Obtained by starting from (S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-carbaldehyde and 1-bromo-2-fluoro-4-(trifluoromethyl)benzene. Tetrahydrofurane is used instead of toluene.
(S)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(2-fluoro-4-(trifluoromethyl)phenyl)methanol:
Mass spectrometry (ESI⁺): m/z=620 [M+H]⁺
HPLC (Method 9): Retention time=1.78 min.
(R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(2-fluoro-4-(trifluoromethyl)phenyl)methanol:
Mass spectrometry (ESI⁺): m/z=620 [M+H]⁺
HPLC (Method 9): Retention time=1.87 min.

(4) (R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(6-(trifluoromethyl)pyridin-3-yl)methanol

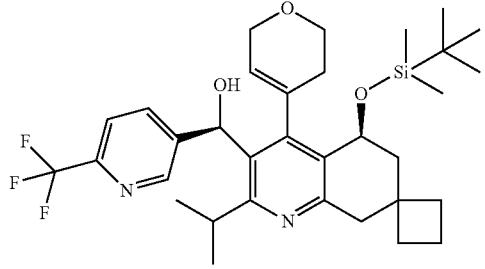

and (S)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(6-(trifluoromethyl)pyridin-3-yl)methanol

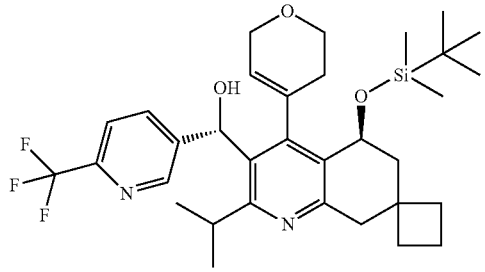

Obtained by starting from (S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-carbaldehyde and 5-bromo-2-(trifluoromethyl)pyridine.
(R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(6-(trifluoromethyl)pyridin-3-yl)methanol:
Mass spectrometry (ESI⁺): m/z=603 [M+H]⁺
HPLC (Method 30): Retention time=1.38 min.
(S)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(6-(trifluoromethyl)pyridin-3-yl)methanol:
Mass spectrometry (ESI⁺): m/z=603 [M+H]⁺
HPLC (Method 30): Retention time=1.40 min.

(5) (S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(3-fluoro-5-(trifluoromethyl)pyridin-2-yl)methanol

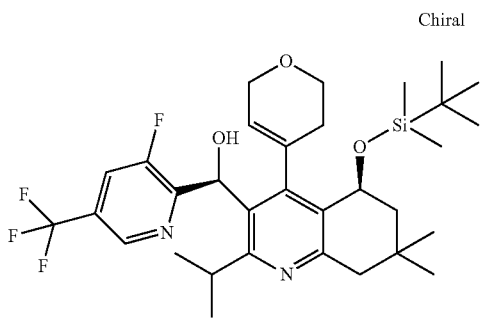 [SMILES: CC(C)c1nc2c(c(C3=CCOCC3)c1[C@H](O)c1ncc(C(F)(F)F)cc1F)[C@@H](O[Si](C)(C)C(C)(C)C)CC(C)(C)C2]

Obtained by starting from (S)-5-(tert-butyldimethylsilyloxy)-4-(3,6-dihydro-2H-pyran-4-yl)-2-isopropyl-7,7-dimethyl-5,6,7,8-tetrahydroquinoline-3-carbaldehyde and 2-bromo-3-fluoro-5-(trifluoromethyl)pyridine.
Mass spectrometry (ESI⁺): m/z=609 [M+H]⁺
HPLC (Method 12): Retention time=8.83 min.

(6) (S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(5-(trifluoromethyl)pyridin-2-yl)methanol

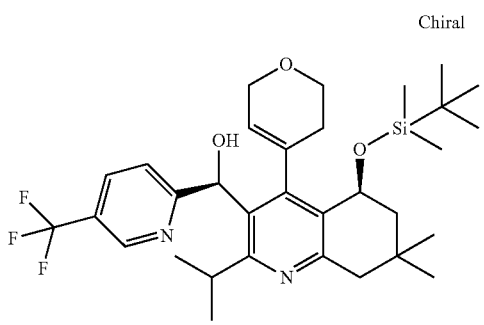 [SMILES: CC(C)c1nc2c(c(C3=CCOCC3)c1[C@H](O)c1ccc(C(F)(F)F)cn1)[C@@H](O[Si](C)(C)C(C)(C)C)CC(C)(C)C2]

and (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(5-(trifluoromethyl)pyridin-2-yl)methanol

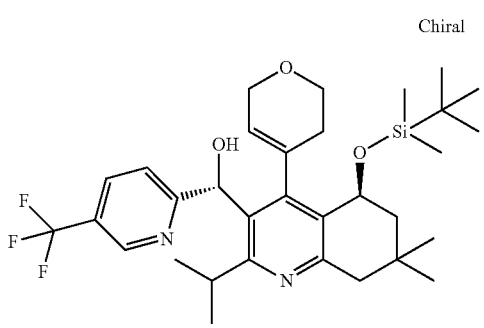 [SMILES: CC(C)c1nc2c(c(C3=CCOCC3)c1[C@@H](O)c1ccc(C(F)(F)F)cn1)[C@@H](O[Si](C)(C)C(C)(C)C)CC(C)(C)C2]

Obtained by starting from (S)-5-(tert-butyldimethylsilyloxy)-4-(3,6-dihydro-2H-pyran-4-yl)-2-isopropyl-7,7-dimethyl-5,6,7,8-tetrahydroquinoline-3-carbaldehyde and 2-bromo-5-(trifluoromethyl)pyridine.

(S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(5-(trifluoromethyl)pyridin-2-yl)methanol:
Mass spectrometry (ESI⁺): m/z=591 [M+H]⁺
HPLC (Method 9): Retention time=1.49 min.

(R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(5-(trifluoromethyl)pyridin-2-yl)methanol:
Mass spectrometry (ESI⁺): m/z=591 [M+H]⁺
HPLC (Method 9): Retention time=1.64 min.

(7) (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(3-fluoro-4-(trifluoromethyl)phenyl)methanol

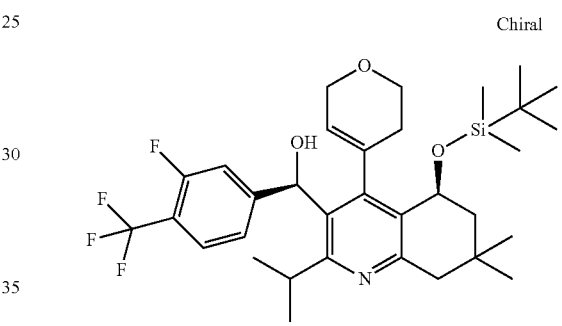

and (S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(3-fluoro-4-(trifluoromethyl)phenyl)methanol

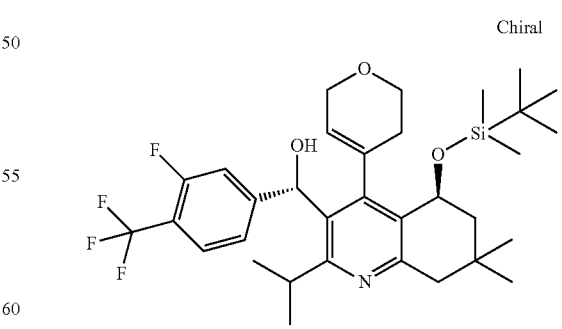

Obtained by starting from (S)-5-(tert-butyldimethylsilyloxy)-4-(3,6-dihydro-2H-pyran-4-yl)-2-isopropyl-7,7-dimethyl-5,6,7,8-tetrahydroquinoline-3-carbaldehyde and 4-bromo-2-fluoro-1-(trifluoromethyl)benzene. Diethylether is used instead of toluene.

(R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(3-fluoro-4-(trifluoromethyl)phenyl)methanol:

Mass spectrometry (ESI⁺): m/z=608 [M+H]⁺
HPLC (Method 12): Retention time=9.94 min.

(S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(3-fluoro-4-(trifluoromethyl)phenyl)methanol:

Mass spectrometry (ESI⁺): m/z=608 [M+H]⁺
HPLC (Method 12): Retention time=10.23 min.

(8) (S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(2-fluoro-4-(trifluoromethyl)phenyl)methanol

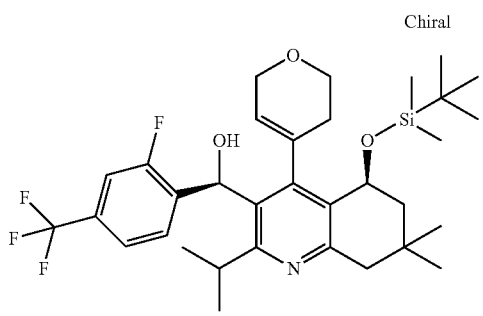 [SMILES: CC(C)c1nc2c(c(C3=CCOCC3)c1[C@H](O)c1ccc(C(F)(F)F)cc1F)[C@@H](O[Si](C)(C)C(C)(C)C)CC(C)(C)C2]

and (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(2-fluoro-4-(trifluoromethyl)phenyl)methanol

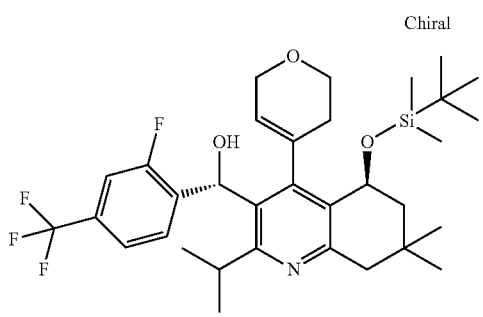 [SMILES: CC(C)c1nc2c(c(C3=CCOCC3)c1[C@@H](O)c1ccc(C(F)(F)F)cc1F)[C@@H](O[Si](C)(C)C(C)(C)C)CC(C)(C)C2]

Obtained by starting from (S)-5-(tert-butyldimethylsilyloxy)-4-(3,6-dihydro-2H-pyran-4-yl)-2-isopropyl-7,7-dimethyl-5,6,7,8-tetrahydroquinoline-3-carbaldehyde and 1-bromo-2-fluoro-4-(trifluoromethyl)benzene.

(S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(2-fluoro-4-(trifluoromethyl)phenyl)methanol:

Mass spectrometry (ESI⁺): m/z=608 [M+H]⁺
HPLC (Method 9): Retention time=1.70 min.

(R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(2-fluoro-4-(trifluoromethyl)phenyl)methanol Mass spectrometry (ESI⁺): m/z=608 [M+H]⁺
HPLC (Method 9): Retention time=1.81 min.

(9) (S)-(5-tert-butyl-4-methylthiazol-2-yl)((S)-5-(tert-butyldimethylsilyloxy)-4-(3,6-dihydro-2H-pyran-4-yl)-2-isopropyl-7,7-dimethyl-5,6,7,8-tetrahydroquinolin-3-ylmethanol

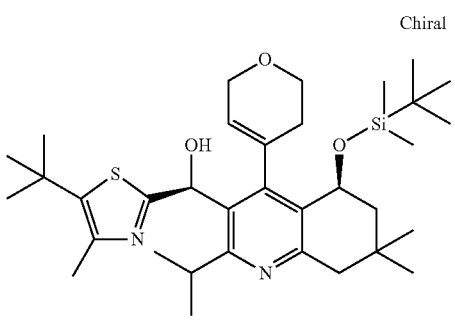 [SMILES: Cc1nc([C@@H](O)c2c(C(C)C)nc3c(c2C2=CCOCC2)[C@@H](O[Si](C)(C)C(C)(C)C)CC(C)(C)C3)sc1C(C)(C)C]

and (R)-(5-tert-butyl-4-methylthiazol-2-yl)((S)-5-(tert-butyldimethylsilyloxy)-4-(3,6-dihydro-2H-pyran-4-yl)-2-isopropyl-7,7-dimethyl-5,6,7,8-tetrahydroquinolin-3-ylmethanol

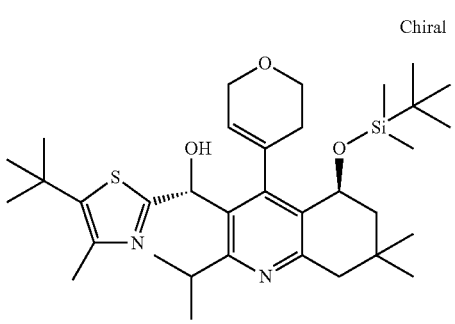 [SMILES: Cc1nc([C@H](O)c2c(C(C)C)nc3c(c2C2=CCOCC2)[C@@H](O[Si](C)(C)C(C)(C)C)CC(C)(C)C3)sc1C(C)(C)C]

Obtained by starting from (S)-5-(tert-butyldimethylsilyloxy)-4-(3,6-dihydro-2H-pyran-4-yl)-2-isopropyl-7,7-dimethyl-5,6,7,8-tetrahydroquinoline-3-carbaldehyde and 2-bromo-5-tert-butyl-4-methylthiazole.

(S)-(5-tert-butyl-4-methylthiazol-2-yl)((S)-5-(tert-butyldimethylsilyloxy)-4-(3,6-dihydro-2H-pyran-4-yl)-2-isopropyl-7,7-dimethyl-5,6,7,8-tetrahydroquinolin-3-ylmethanol:

Mass spectrometry (ESI⁺): m/z=599 [M+H]⁺
HPLC (Method 9): Retention time=1.67 min.

(R)-(5-tert-butyl-4-methylthiazol-2-yl)((S)-5-(tert-butyldimethylsilyloxy)-4-(3,6-dihydro-2H-pyran-4-yl)-2-isopropyl-7,7-dimethyl-5,6,7,8-tetrahydroquinolin-3-ylmethanol:

Mass spectrometry (ESI⁺): m/z=599 [M+H]⁺
HPLC (Method 9): Retention time=1.97 min.

(10) (S)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(5-(trifluoromethyl)pyridin-2-yl)methanol

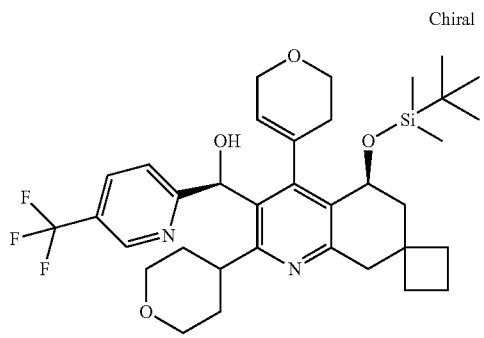 [SMILES: CC(C)(C)[Si](C)(C)O[C@H]1CC2(CCC2)Cc2nc(C3CCOCC3)c([C@H](O)c3ccc(C(F)(F)F)cn3)c(C3=CCOCC3)c21]

and (R)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(5-(trifluoromethyl)pyridin-2-yl)methanol

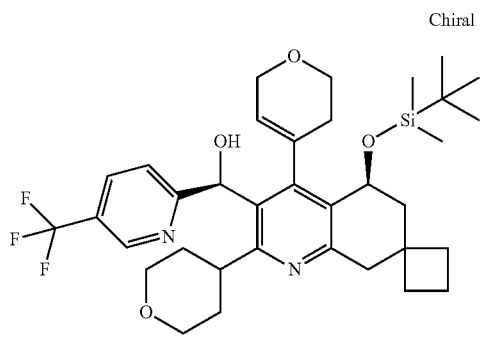 [SMILES: CC(C)(C)[Si](C)(C)O[C@H]1CC2(CCC2)Cc2nc(C3CCOCC3)c([C@H](O)c3ccc(C(F)(F)F)cn3)c(C3=CCOCC3)c21]

Obtained by starting from (S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-carbaldehyde and 2-bromo-5-(trifluoromethyl)pyridine.

(S)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(5-(trifluoromethyl)pyridin-2-yl)methanol:

Mass spectrometry (ESI$^+$): m/z=645 [M+H]$^+$

HPLC (Method 7): Retention time=1.714 min.

(R)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(5-(trifluoromethyl)pyridin-2-yl)methanol:

Mass spectrometry (ESI$^+$): m/z=645 [M+H]$^+$

HPLC (Method 7): Retention time=1.732 min.

(11) (S)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(5-(trifluoromethyl)pyridin-2-ylmethanol

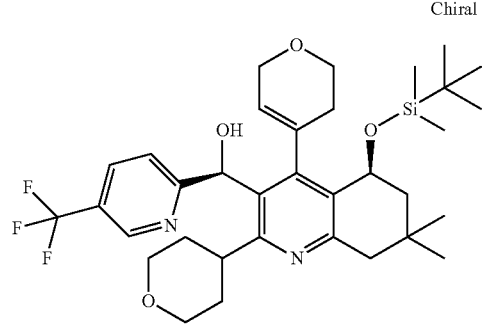 [SMILES: CC1(C)Cc2nc(C3CCOCC3)c([C@H](O)c3ccc(C(F)(F)F)cn3)c(C3=CCOCC3)c2[C@@H](O[Si](C)(C)C(C)(C)C)C1]

and (R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(5-(trifluoromethyl)pyridin-2-ylmethanol

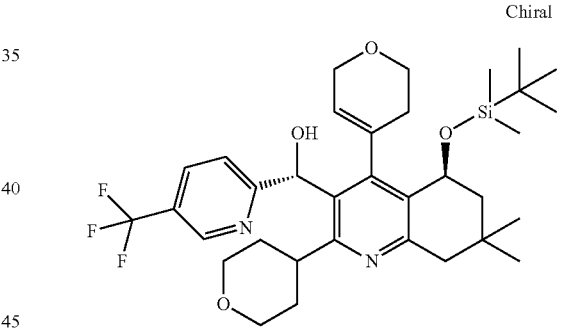

Obtained by starting from (S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinoline-3-carbaldehyde and 2-bromo-5-(trifluoromethyl)pyridine.

(S)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(5-(trifluoromethyl)pyridin-2-ylmethanol:

Mass spectrometry (ESI$^+$): m/z=633 [M+H]$^+$

HPLC (Method 7): Retention time=1.692 min.

(R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(5-(trifluoromethyl)pyridin-2-yl)methanol:

Mass spectrometry (ESI$^+$): m/z=633 [M+H]$^+$

HPLC (Method 7): Retention time=1.719 min.

281

(12) (R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(6-(trifluoromethyl)pyridin-3-yl)methanol

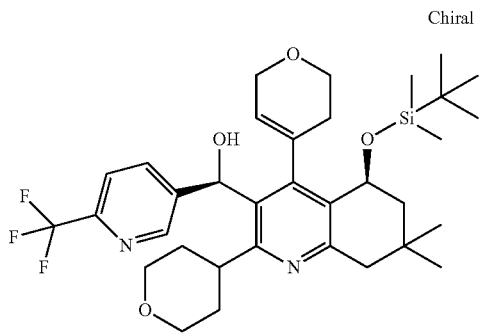 [SMILES: CC1(C)Cc2nc(C3CCOCC3)c([C@H](O)c3ccc(C(F)(F)F)nc3)c(C3=CCOCC3)c2[C@@H](O[Si](C)(C)C(C)(C)C)C1]

and (S)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(6-(trifluoromethyl)pyridin-3-yl)methanol

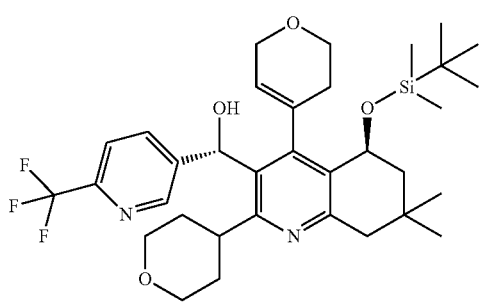

Obtained by starting from (S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinoline-3-carbaldehyde and 5-bromo-2-(trifluoromethyl)pyridine.

(R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(6-(trifluoromethyl)pyridin-3-yl)methanol:

Mass spectrometry (ESI$^+$): m/z=633 [M+H]$^+$

HPLC (Method 7): Retention time=1.728 min.

(S)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(6-(trifluoromethyl)pyridin-3-yl)methanol:

Mass spectrometry (ESI$^+$): m/z=633 [M+H]$^+$

HPLC (Method 7): Retention time=1.741 min.

282

(13) (R)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(6-(trifluoromethyl)pyridin-3-yl)methanol

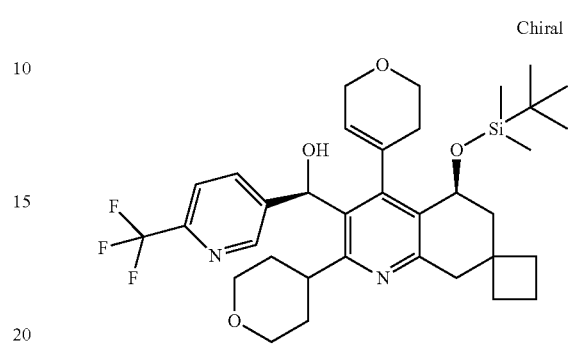

and (S)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(6-(trifluoromethyl)pyridin-3-ylmethanol

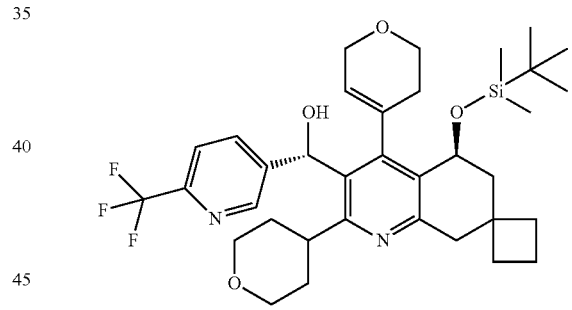

Obtained by starting from (S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-carbaldehyde and 5-bromo-2-(trifluoromethyl)pyridine.

(R)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(6-(trifluoromethyl)pyridin-3-ylmethanol:

Mass spectrometry (ESI$^+$): m/z=645 [M+H]$^+$

HPLC (Method 7): Retention time=1.755 min.

(S)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(6-(trifluoromethyl)pyridin-3-yl)methanol:

Mass spectrometry (ESI$^+$): m/z=645 [M+H]$^+$

HPLC (Method 7): Retention time=1.770 min.

(14) (R)—((S)-5-(tert-butyldimethylsilyloxy)-4-(4,4-difluorocyclohex-1-enyl)-2-isopropyl-7,7-dimethyl-5,6,7,8-tetrahydroquinolin-3-yl)(5-(trifluoromethyl)pyridin-2-yl)methanol

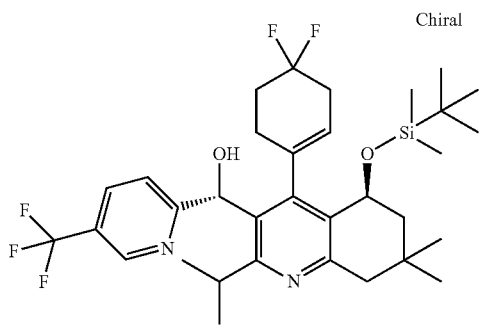 [SMILES: CC(C)c1nc2c(c(C3=CCC(F)(F)CC3)c1[C@@H](O)c1ccc(C(F)(F)F)cn1)[C@@H](O[Si](C)(C)C(C)(C)C)CC(C)(C)C2]

and (S)—((S)-5-(tert-butyldimethylsilyloxy)-4-(4,4-difluorocyclohex-1-enyl)-2-isopropyl-7,7-dimethyl-5,6,7,8-tetrahydroquinolin-3-yl)(5-(trifluoromethyl)pyridin-2-yl)methanol

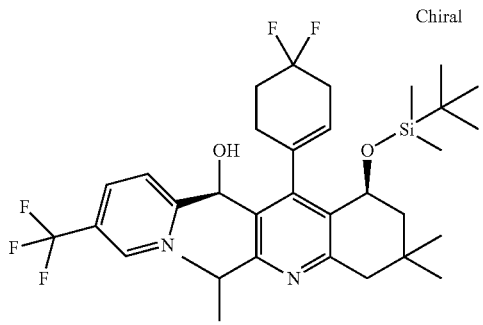 [SMILES: CC(C)c1nc2c(c(C3=CCC(F)(F)CC3)c1[C@H](O)c1ccc(C(F)(F)F)cn1)[C@@H](O[Si](C)(C)C(C)(C)C)CC(C)(C)C2]

Obtained by starting from (S)-5-(tert-butyldimethylsilyloxy)-4-(4,4-difluorocyclohex-1-enyl)-2-isopropyl-7,7-dimethyl-5,6,7,8-tetrahydroquinoline-3-carbaldehyde and 2-bromo-5-(trifluoromethyl)pyridine.

(R)—((S)-5-(tert-butyldimethylsilyloxy)-4-(4,4-difluorocyclohex-1-enyl)-2-isopropyl-7,7-dimethyl-5,6,7,8-tetrahydroquinolin-3-yl)(5-(trifluoromethyl)pyridin-2-yl)methanol:

Mass spectrometry (ESI$^+$): m/z=625 [M+H]$^+$

HPLC (Method 13): Retention time=0.69 min.

(S)—((S)-5-(tert-butyldimethylsilyloxy)-4-(4,4-difluorocyclohex-1-enyl)-2-isopropyl-7,7-dimethyl-5,6,7,8-tetrahydroquinolin-3-yl)(5-(trifluoromethyl)pyridin-2-yl)methanol:

Mass spectrometry (ESI$^+$): m/z=625 [M+H]$^+$

HPLC (Method 30): Retention time=1.92 min.

Example XXX

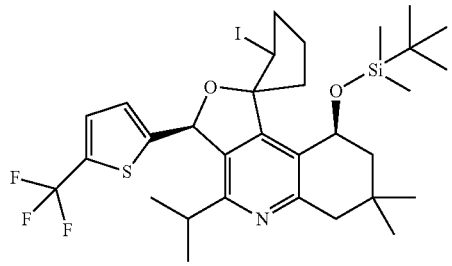

(3'S,9'S)-9'-(tert-butyldimethylsilyloxy)-2-iodo-4'-isopropyl-7',7'-dimethyl-3'-(5-(trifluoromethyl)thiophen-2-yl)-6',7',8',9'-tetrahydro-3'H-spiro[cyclopentane-1,1'-furo[3,4-c]quinoline]

To a solution of 67 mg (S)—((S)-5-(tert-butyldimethylsilyloxy)-4-cyclopentenyl-2-isopropyl-7,7-dimethyl-5,6,7,8-tetrahydroquinolin-3-yl)(5-(trifluoromethyl)thiophen-2-yl)methanol in 1 ml tetrahydrofurane and 1 ml acetonitrile are added under nitrogen 29 mg sodium bicarbonate and a solution of 88 mg of iodine in 200 µl tetrahydrofurane and the reaction is monitored by thin layer chromatography. In the case of low conversion the same amounts of sodium bicarbonate and iodine solution are added up to two times. The mixture is then diluted with diethylether and washed with saturated aqueous sodium sulfite solution and brine. After drying with sodium sulphate the solvents are evaporated in vacuo and the residue is chromatographed on silica gel (cyclohexane/ethylacetate 98:2 to 80:20).

Yield: 50 mg (61% of theory)

Mass spectrometry (ESI$^+$): m/z=706 [M+H]$^+$

Analogously to example XXX the following compounds are obtained:

(1) (3'R,9'S)-9'-(tert-butyldimethylsilyloxy)-3'-(2-tert-butylpyrimidin-5-yl)-2-iodo-4'-isopropyl-7',7'-dimethyl-6',7',8',9'-tetrahydro-3'H-spiro[cyclopentane-1,1'-furo[3,4-c]quinoline]

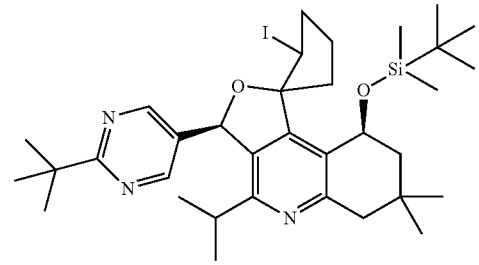

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(2-tert-butylpyrimidin-5-yl)methanol.

Mass spectrometry (ESI$^+$): m/z=690 [M+H]$^+$

(2) (3R,9S)-9-(tert-butyldimethylsilyloxy)-3'-iodo-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]

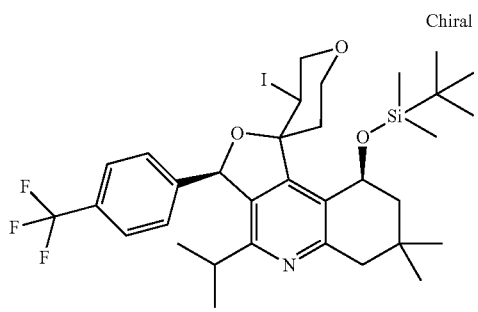 [SMILES: CC(C)c1nc2c(c3c1[C@@H](c1ccc(C(F)(F)F)cc1)OC31CCOCC1I)[C@@H](O[Si](C)(C)C(C)(C)C)CC(C)(C)C2]

Obtained by starting from (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(trifluoromethyl)phenyl)methanol.

Mass spectrometry (ESI$^+$): m/z=716 [M+H]$^+$

HPLC (Method 9): Retention time=2.40 min.

(3) (3'R,9'S)-9'-(tert-butyldimethylsilyloxy)-3'-(4-tert-butylphenyl)-2-iodo-7',7'-dimethyl-4'-(tetrahydro-2H-pyran-4-yl)-6',7',8',9'-tetrahydro-3'H-spiro[cyclopentane-1,1'-furo[3,4-c]quinoline]

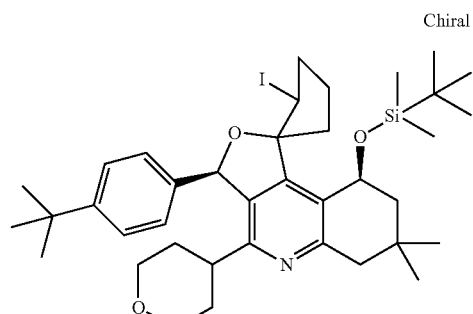

Obtained by starting from (R)—((S)-5-(tert-butyldimethylsilyloxy)-4-cyclopentenyl-7,7-dimethyl-2-(tetrahydro-2H-pyran-4-yl)-5,6,7,8-tetrahydroquinolin-3-yl)(4-tert-butylphenyl)methanol. The reaction is conducted in tetrahydrofurane.

Mass spectrometry (ESI$^+$): m/z=730 [M+H]$^+$

HPLC (Method 2): Retention time=3.340 min.

R$_f$-value: 0.76 (silica gel, petrole ether/ethylacetate 4:1)

(4) (3R,9S)-9-(tert-butyldimethylsilyloxy)-3'-iodo-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]

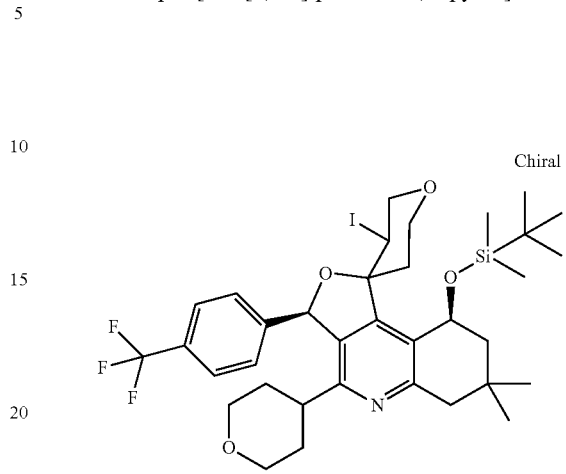

Obtained by starting from (R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(4-(trifluoromethyl)phenyl)methanol.

Mass spectrometry (ESI$^+$): m/z=758 [M+H]$^+$

HPLC (Method 7): Retention time=1.998 min.

(5) (3'R,9'S)-3'-(4-(benzyloxy)phenyl)-9'-(tert-butyldimethylsilyloxy)-2-iodo-4'-isopropyl-7',7'-dimethyl-6',7',8',9'-tetrahydro-3'H-spiro[cyclopentane-1,1'-furo[3,4-c]quinoline]

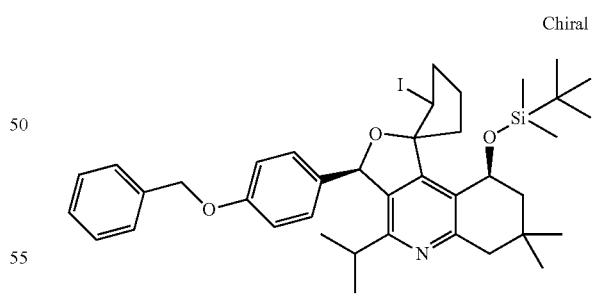

Obtained by starting from (R)-(4-(benzyloxy)phenyl)((S)-5-(tert-butyldimethylsilyloxy)-4-cyclopentenyl-2-isopropyl-7,7-dimethyl-5,6,7,8-tetrahydroquinolin-3-yl)methanol.

Mass spectrometry (ESI$^+$): m/z=738 [M+H]$^+$

R$_f$-value: 0.7 (silica gel, cyclohexane/ethylacetate 9:1)

(6) (3R,9S)-9-(tert-butyldimethylsilyloxy)-3-(4-tert-butylphenyl)-3'-iodo-4-isopropyl-7,7-dimethyl-2',3',5',6,6',7,8,9-octahydro-3H-spiro[furo[3,4-c]quinoline-1,4'-pyran]

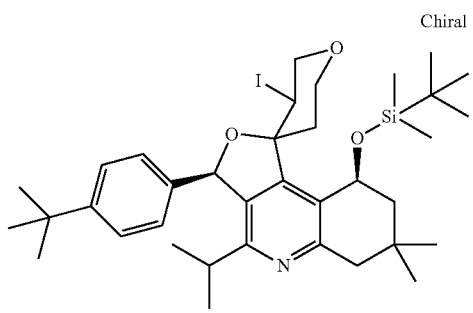 [SMILES: CC(C)c1nc2c(c3c1[C@@H](c1ccc(C(C)(C)C)cc1)OC31CCOCC1I)[C@@H](O[Si](C)(C)C(C)(C)C)CC(C)(C)C2]

Obtained by starting from (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-tert-butylphenyl)methanol.

Mass spectrometry (ESI$^+$): m/z=704 [M+H]$^+$

HPLC (Method 12): Retention time=15.12 min.

(7) (3'R,9'S)-9'-(tert-butyldimethylsilyloxy)-2-iodo-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline]

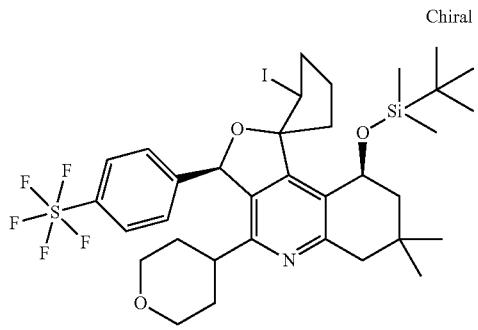 [SMILES: CC1(C)Cc2nc(C3CCOCC3)c3c(c2[C@@H](O[Si](C)(C)C(C)(C)C)C1)C1(CCCC1I)O[C@@H]3c1ccc(S(F)(F)(F)(F)F)cc1]

Obtained by starting from (R)—((S)-5-(tert-butyldimethylsilyloxy)-4-cyclopentenyl-7,7-dimethyl-2-(tetrahydro-2H-pyran-4-yl)-5,6,7,8-tetrahydroquinolin-3-yl)(4-(pentafluorosulfanyl)phenyl)methanol.

Mass spectrometry (ESI$^+$): m/z=800 [M+H]$^+$

HPLC (Method 7): Retention time=2.060 min.

(8) (3R,9S)-9-(tert-butyldimethylsilyloxy)-3'-iodo-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]

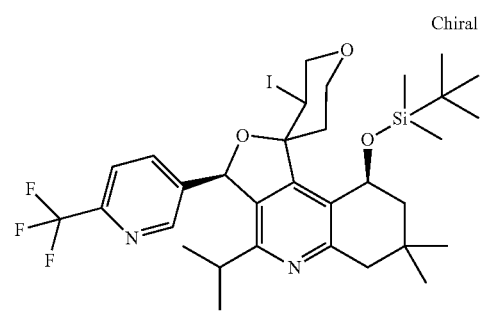 [SMILES: CC(C)c1nc2c(c3c1[C@@H](c1ccc(C(F)(F)F)nc1)OC31CCOCC1I)[C@@H](O[Si](C)(C)C(C)(C)C)CC(C)(C)C2]

Obtained by starting from (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(6-(trifluoromethyl)pyridin-3-yl)methanol.

Mass spectrometry (ESI$^+$): m/z=717 [M+H]$^+$

HPLC (Method 12): Retention time=14.57 min.

(9) (3S,9S)-9-(tert-butyldimethylsilyloxy)-3'-iodo-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]

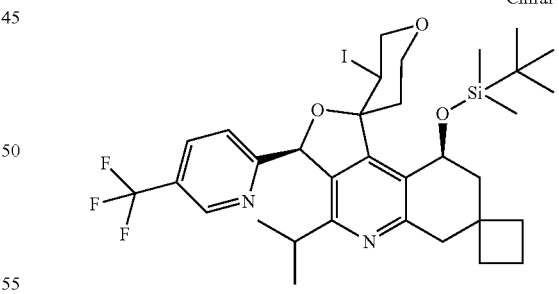

Obtained by starting from (S)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(5-(trifluoromethyl)pyridin-2-yl)methanol.

Mass spectrometry (ESI$^+$): m/z=729 [M+H]$^+$

HPLC (Method 12): Retention time=14.18 min.

(10) (3R,9S)-9-(tert-butyldimethylsilyloxy)-3'-iodo-4-isopropyl-7,7-(propan-1,3-diyl)-3-(4-(trifluoromethyl)phenyl)-2',3',5',6',7,8,9-octahydro-3H-spiro[furo[3,4-c]quinoline-1,4'-pyran]

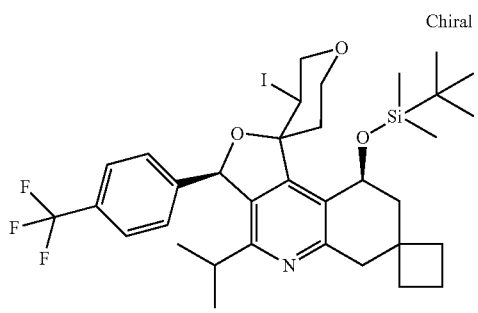 [SMILES: CC(C)c1nc2c(c3c1[C@@H](c1ccc(C(F)(F)F)cc1)OC31CCOCC1I)[C@@H](O[Si](C)(C)C(C)(C)C)CC1(CCC1)C2]

Obtained by starting from (R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(4-(trifluoromethyl)phenyl)methanol.

Mass spectrometry (ESI$^+$): m/z=728 [M+H]$^+$

HPLC (Method 13): Retention time=1.76 min.

(11) (3S,9S)-9-(tert-butyldimethylsilyloxy)-3-(2-fluoro-4-(trifluoromethyl)phenyl)-3'-iodo-4-isopropyl-7,7-(propan-1,3-diyl)-2',3',5',6',7,8,9-octahydro-3H-spiro[furo[3,4-c]quinoline-1,4'-pyran]

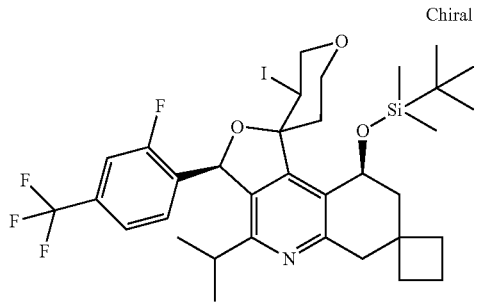 [SMILES: CC(C)c1nc2c(c3c1[C@@H](c1ccc(C(F)(F)F)cc1F)OC31CCOCC1I)[C@@H](O[Si](C)(C)C(C)(C)C)CC1(CCC1)C2]

Obtained by starting from (S)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(2-fluoro-4-(trifluoromethyl)phenyl)methanol.

Mass spectrometry (ESI$^+$): m/z=746 [M+H]$^+$

HPLC (Method 9): Retention time=3.83 min.

(12) (3R,9S)-9-(tert-butyldimethylsilyloxy)-3'-iodo-4-isopropyl-7,7-(propan-1,3-diyl)-3-(6-(trifluoromethyl)pyridin-3-yl)-2',3',5',6',7,8,9-octahydro-3H-spiro[furo[3,4-c]quinoline-1,4'-pyran]

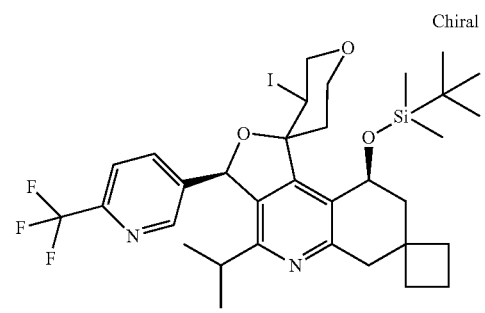 [SMILES: CC(C)c1nc2c(c3c1[C@@H](c1ccc(C(F)(F)F)nc1)OC31CCOCC1I)[C@@H](O[Si](C)(C)C(C)(C)C)CC1(CCC1)C2]

Obtained by starting from (R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(6-(trifluoromethyl)pyridin-3-yl)methanol.

Mass spectrometry (ESI$^+$): m/z=729 [M+H]$^+$

HPLC (Method 12): Retention time=15.88 min.

(13) (3S,9S)-9-(tert-butyldimethylsilyloxy)-3-(3-fluoro-5-(trifluoromethyl)pyridin-2-yl)-3'-iodo-4-isopropyl-7,7-dimethyl-2',3',5',6',7,8,9-octahydro-3H-spiro[furo[3,4-c]quinoline-1,4'-pyran]

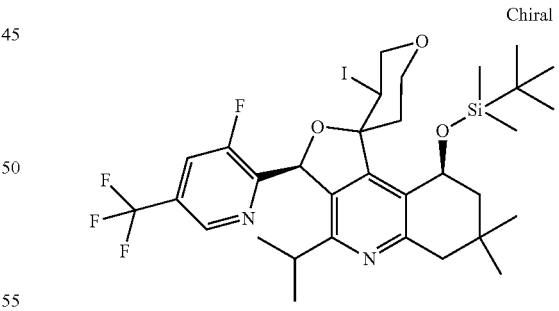

Obtained by starting from (S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(3-fluoro-5-(trifluoromethyl)pyridin-2-yl)methanol.

Mass spectrometry (ESI$^+$): m/z=735 [M+H]$^+$

HPLC (Method 9): Retention time=3.37 min.

(14) (3S,9S)-9-(tert-butyldimethylsilyloxy)-3'-iodo-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]

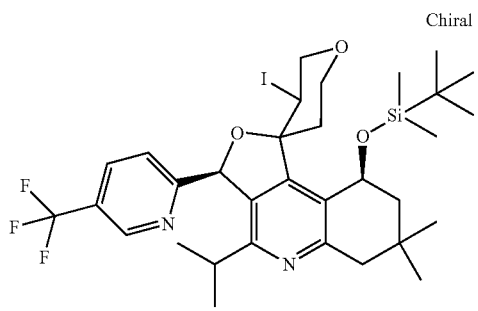 [SMILES: CC(C)c1nc2c(c3c1[C@@H](c1ccc(C(F)(F)F)cn1)OC31CCOCC1I)[C@@H](O[Si](C)(C)C(C)(C)C)CC(C)(C)C2]

Obtained by starting from (S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(5-(trifluoromethyl)pyridin-2-yl)methanol. Lithium carbonate is used instead of sodium bicarbonate.

Mass spectrometry (ESI$^+$): m/z=717 [M+H]$^+$

HPLC (Method 24): Retention time=1.802 min.

(15) (3R,9S)-9-(tert-butyldimethylsilyloxy)-3-(3-fluoro-4-(trifluoromethyl)phenyl)-3'-iodo-4-isopropyl-7,7-dimethyl-2',3',5',6,6',7,8,9-octahydro-3H-spiro[furo[3,4-c]quinoline-1,4'-pyran]

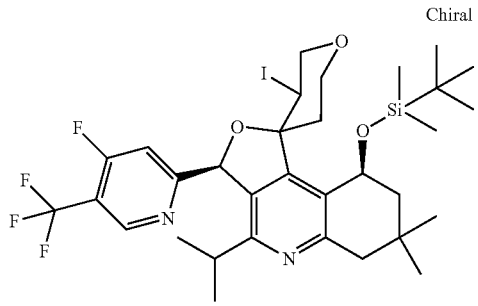 [SMILES: CC(C)c1nc2c(c3c1[C@@H](c1cc(F)c(C(F)(F)F)cn1)OC31CCOCC1I)[C@@H](O[Si](C)(C)C(C)(C)C)CC(C)(C)C2]

Obtained by starting from (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(3-fluoro-4-(trifluoromethyl)phenyl)methanol.

Mass spectrometry (ESI$^+$): m/z=734 [M+H]$^+$

HPLC (Method 12): Retention time=17.47 min.

(16) (3S,9S)-9-(tert-butyldimethylsilyloxy)-3-(3-fluoro-4-(trifluoromethyl)phenyl)-3'-iodo-4-isopropyl-7,7-dimethyl-2',3',5',6,6',7,8,9-octahydro-3H-spiro[furo[3,4-c]quinoline-1,4'-pyran]

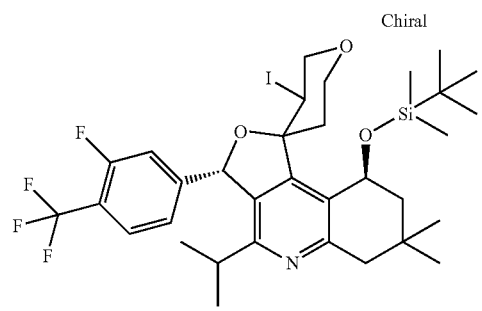 [SMILES: CC(C)c1nc2c(c3c1[C@H](c1ccc(C(F)(F)F)c(F)c1)OC31CCOCC1I)[C@@H](O[Si](C)(C)C(C)(C)C)CC(C)(C)C2]

Obtained by starting from (S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(3-fluoro-4-(trifluoromethyl)phenyl)methanol.

Mass spectrometry (ESI$^+$): m/z=734 [M+H]$^+$

HPLC (Method 12): Retention time=18.45 min.

(17) (3S,9S)-9-(tert-butyldimethylsilyloxy)-3-(2-fluoro-4-(trifluoromethyl)phenyl)-3'-iodo-4-isopropyl-7,7-dimethyl-2',3',5',6,6',7,8,9-octahydro-3H-spiro[furo[3,4-c]quinoline-1,4'-pyran]

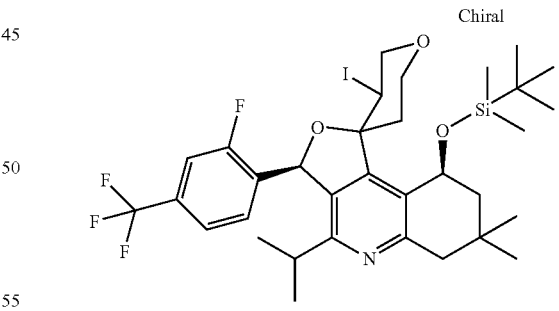

Obtained by starting from (S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(2-fluoro-4-(trifluoromethyl)phenyl)methanol.

Mass spectrometry (ESI$^+$): m/z=734 [M+H]$^+$

HPLC (Method 13): Retention time=1.76 min.

(18) (3S,9S)-3-(5-tert-butyl-4-methylthiazol-2-yl)-9-(tert-butyldimethylsilyloxy)-3'-iodo-4-isopropyl-7,7-dimethyl-2',3',5',6',7,8,9-octahydro-3H-spiro[furo[3,4-c]quinoline-1,4'-pyran]

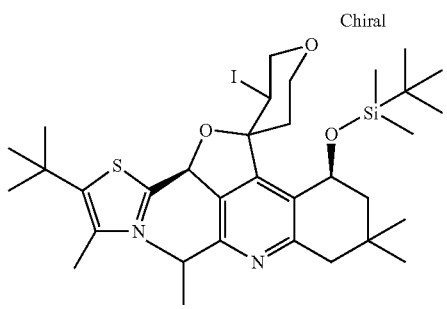 [SMILES: Cc1nc([C@H]2OC3(CCOCC3I)c3c2c(C(C)C)nc2c3[C@@H](O[Si](C)(C)C(C)(C)C)CC(C)(C)C2)sc1C(C)(C)C]

Obtained by starting from (S)-(5-tert-butyl-4-methylthiazol-2-yl)((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)methanol.

Mass spectrometry (ESI⁺): m/z=725 [M+H]⁺

HPLC (Method 9): Retention time=3.77 min.

(19) (3R,9S)-9-(tert-butyldimethylsilyloxy)-3'-iodo-4-isopropyl-7,7-(butan-1,4-diyl)-3-(4-(trifluoromethyl)phenyl)-2',3',5',6',7,8,9-octahydro-3H-spiro[furo[3,4-c]quinoline-1,4'-pyran]

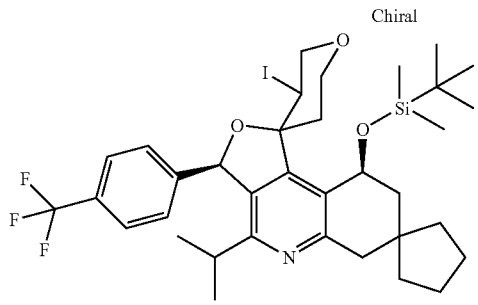 [SMILES: CC(C)c1nc2c(c3c1[C@@H](c1ccc(C(F)(F)F)cc1)OC31CCOCC1I)[C@@H](O[Si](C)(C)C(C)(C)C)CC1(CCCC1)C2]

Obtained by starting from (R)—((S)-5'-(tert-butyldimethylsilyloxy)-4'-(3,6-dihydro-2H-pyran-4-yl)-2'-isopropyl-6',8'-dihydro-5'H-spiro[cyclopentane-1,7'-quinoline]-3'-yl)(4-(trifluoromethyl)phenyl)methanol. The crude product is used directly in the next step.

Mass spectrometry (ESI⁺): m/z=742 [M+H]⁺

HPLC (Method 4): Retention time=2.04 min.

(20) (3R,9S)-3-(4-tert-butoxyphenyl)-9-(tert-butyldimethylsilyloxy)-3-iodo-4-isopropyl-7,7-dimethyl-2',3',5',6',7,8,9-octahydro-3H-spiro[furo[3,4-c]quinoline-1,4'-pyran]

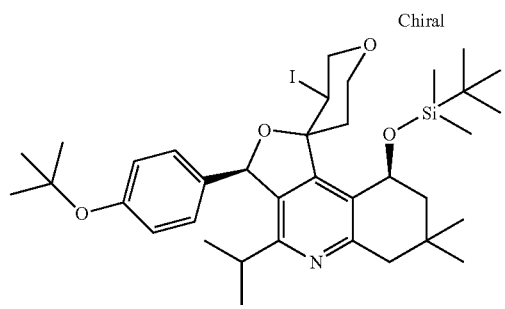 [SMILES: CC(C)c1nc2c(c3c1[C@@H](c1ccc(OC(C)(C)C)cc1)OC31CCOCC1I)[C@@H](O[Si](C)(C)C(C)(C)C)CC(C)(C)C2]

Obtained by starting from (R)-(4-tert-butoxyphenyl)((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)methanol.

Mass spectrometry (ESI⁺): m/z=720 [M+H]⁺

$R_f$-value: 0.37 (silica gel, petrole ether/ethylacetate 4:1)

(21) (3R,9S)-9-(tert-butyldimethylsilyloxy)-3-iodo-3-(4-isopropoxyphenyl)-4-isopropyl-7,7-dimethyl-2',3',5',6',7,8,9-octahydro-3H-spiro[furo[3,4-c]quinoline-1,4'-pyran]

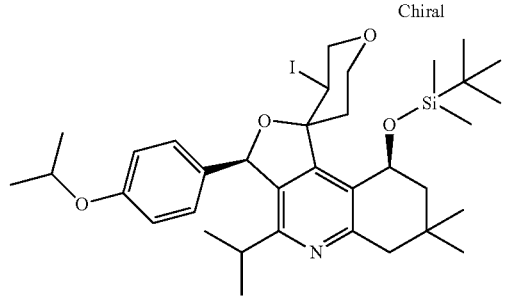 [SMILES: CC(C)Oc1ccc([C@H]2OC3(CCOCC3I)c3c2c(C(C)C)nc2c3[C@@H](O[Si](C)(C)C(C)(C)C)CC(C)(C)C2)cc1]

Obtained by starting from (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-isopropoxyphenyl)methanol.

Mass spectrometry (ESI⁺): m/z=706 [M+H]⁺

HPLC (Method 4): Retention time=3.042 min.

(22) (3R,9S)-9-(tert-butyldimethylsilyloxy)-3-iodo-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]

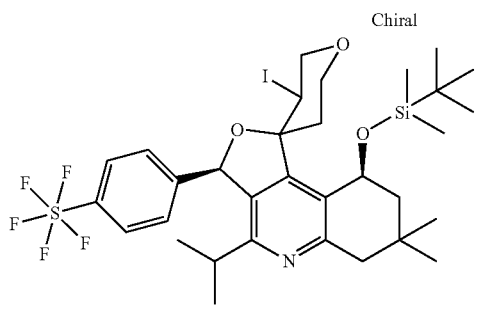 [SMILES: CC(C)c1nc2c(c3c1[C@@H](c1ccc(S(F)(F)(F)(F)F)cc1)OC31CCOCC1I)[C@@H](O[Si](C)(C)C(C)(C)C)CC(C)(C)C2]

Obtained by starting from (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(pentafluorosulfanyl)phenyl)methanol.

Mass spectrometry (ESI+): m/z=774 [M+H]+

HPLC (Method 24): Retention time=1.855 min.

(23) (3'R,9'S)-9'-(tert-butyldimethylsilyloxy)-3'-(4-tert-butylphenyl)-2-iodo-4'-isopropyl-7',7'-(propan-1,3-diyl)-6',7',8',9'-tetrahydro-3'H-spiro[cyclopentane-1,1'-furo[3,4-c]quinoline]

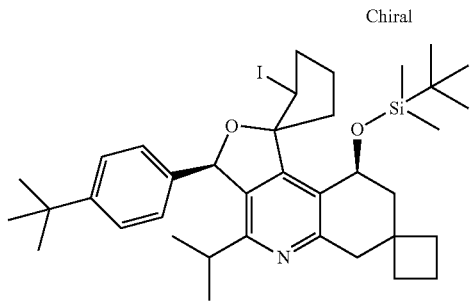 [SMILES: CC(C)c1nc2c(c3c1[C@@H](c1ccc(C(C)(C)C)cc1)OC31CCCC1I)[C@@H](O[Si](C)(C)C(C)(C)C)CC1(CCC1)C2]

Obtained by starting from (R)—((S)-5'-(tert-butyldimethylsilyloxy)-4'-cyclopentenyl-2'-isopropyl-6',8'-dihydro-5'H-spiro[cyclobutane-1,7'-quinoline]-3'-yl)(4-tert-butylphenyl)methanol.

Mass spectrometry (ESI+): m/z=700 [M+H]+

HPLC (Method 7): Retention time=2.031 min.

R$_f$-value: 0.85 (silica gel, cyclohexane/ethylacetate 9:1)

(24) (3R,9S)-9-(tert-butyldimethylsilyloxy)-3-(4-tert-butylphenyl)-3'-iodo-4-isopropyl-7,7-(propan-1,3-diyl)-2',3',5',6,6',7,8,9-octahydro-3H-spiro[furo[3,4-c]quinoline-1,4'-pyran]

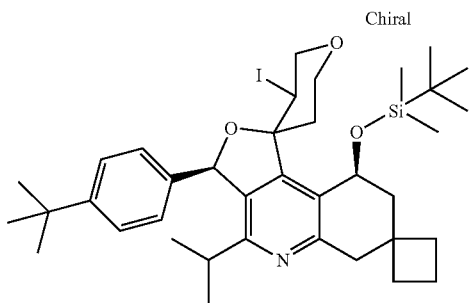 [SMILES: CC(C)c1nc2c(c3c1[C@@H](c1ccc(C(C)(C)C)cc1)OC31CCOCC1I)[C@@H](O[Si](C)(C)C(C)(C)C)CC1(CCC1)C2]

Obtained by starting from (R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(4-tert-butylphenyl)methanol.

Mass spectrometry (ESI+): m/z=716 [M+H]+

HPLC (Method 7): Retention time=2.007 min.

R$_f$-value: 0.9 (silica gel, cyclohexane/ethylacetate 3:1)

(25) (3R,9S)-9-(tert-butyldimethylsilyloxy)-3'-iodo-4-isopropyl-7,7-dimethyl-3-(4-(3-methyloxetan-3-yl)phenyl)-2',3',5',6,6',7,8,9-octahydro-3H-spiro[furo[3,4-c]quinoline-1,4'-pyran]

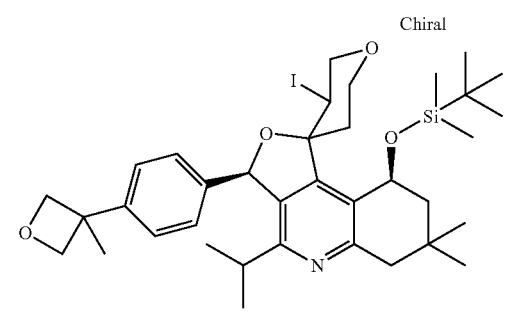 [SMILES: CC(C)c1nc2c(c3c1[C@@H](c1ccc(C4(C)COC4)cc1)OC31CCOCC1I)[C@@H](O[Si](C)(C)C(C)(C)C)CC(C)(C)C2]

Obtained by starting from (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(3-methyloxetan-3-yl)phenyl)methanol. Lithium carbonate is used instead of sodium bicarbonate.

Mass spectrometry (ESI+): m/z=718 [M+H]+

HPLC (Method 24): Retention time=1.746 min.

(26) (3'R,9'S)-9'-(tert-butyldimethylsilyloxy)-2-iodo-4'-isopropyl-7',7'-dimethyl-3'-(4-(perfluoroethyl)phenyl)-6',7',8',9'-tetrahydro-3'H-spiro[cyclopentane-1,1'-furo[3,4-c]quinoline]

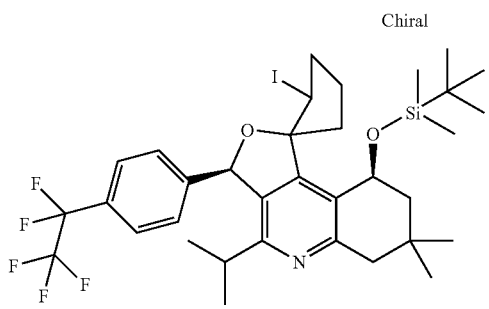 [SMILES: CC(C)c1nc2c(c3c1[C@@H](c1ccc(C(F)(F)C(F)(F)F)cc1)OC31CCCC1I)[C@@H](O[Si](C)(C)C(C)(C)C)CC(C)(C)C2]

Obtained by starting from (R)—((S)-5-(tert-butyldimethylsilyloxy)-4-cyclopentenyl-2-isopropyl-7,7-dimethyl-5,6,7,8-tetrahydroquinolin-3-yl)(4-(perfluoroethyl)phenyl)methanol.

Mass spectrometry (ESI$^+$): m/z=750 [M+H]$^+$

HPLC (Method 7): Retention time=2.034 min.

(27) 5-((3R,9S)-9-(tert-butyldimethylsilyloxy)-3'-iodo-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile

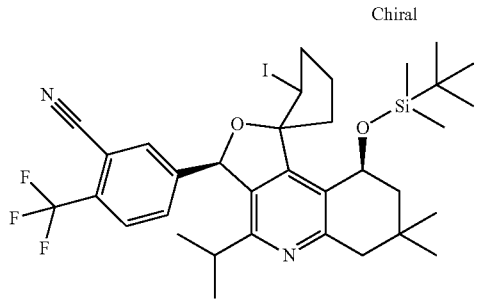 [SMILES: CC(C)c1nc2c(c3c1[C@@H](c1ccc(C(F)(F)F)c(C#N)c1)OC31CCCC1I)[C@@H](O[Si](C)(C)C(C)(C)C)CC(C)(C)C2]

Obtained by starting from 5-((R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(hydroxy)methyl)-2-(trifluoromethyl)benzonitrile.

Mass spectrometry (ESI$^+$): m/z=741 [M+H]$^+$

HPLC (Method 7): Retention time=1.856 min.

(28) (3S,9S)-9-(tert-butyldimethylsilyloxy)-3'-iodo-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]

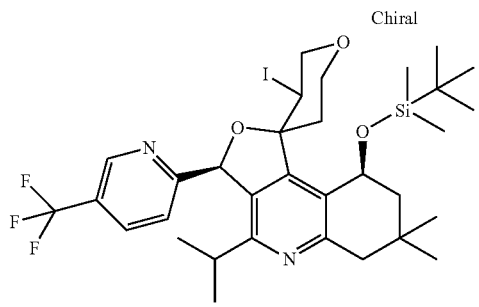 [SMILES: CC(C)c1nc2c(c3c1[C@@H](c1ccc(C(F)(F)F)cn1)OC31CCOCC1I)[C@@H](O[Si](C)(C)C(C)(C)C)CC(C)(C)C2]

Obtained by starting from (S)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(5-(trifluoromethyl)pyridin-2-yl)methanol.

Mass spectrometry (ESI$^+$): m/z=717 [M+H]$^+$

HPLC (Method 7): Retention time=1.943 min.

R$_f$-value: 0.52 (silica gel, cyclohexane/ethylacetate 9:1)

(29) (3R,9S)-9-(tert-butyldimethylsilyloxy)-3'-iodo-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]

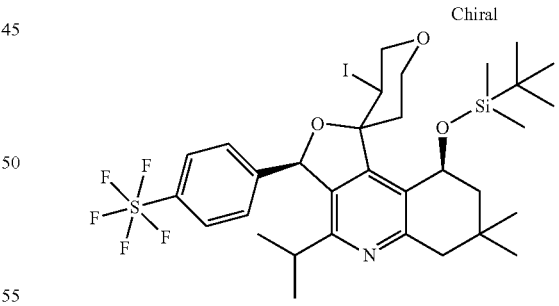

Obtained by starting from (R)—((S)-5-(tert-butyldimethylsilyloxy)-4-(3,6-dihydro-2H-pyran-4-yl)-2-isopropyl-7,7-dimethyl-5,6,7,8-tetrahydroquinolin-3-yl)(4-(pentafluorosulfanyl)phenyl)methanol.

Mass spectrometry (ESI$^+$): m/z=774 [M+H]$^+$

HPLC (Method 24): Retention time=1.855 min.

(30) (3R,9S)-9-(tert-butyldimethylsilyloxy)-3'-iodo-4-isopropyl-7,7-(propan-1,3-diyl)-3-(4-(pentafluorosulfanyl)phenyl)-2',3',5',6,6',7,8,9-octahydro-3H-spiro[furo[3,4-c]quinoline-1,4'-pyran]

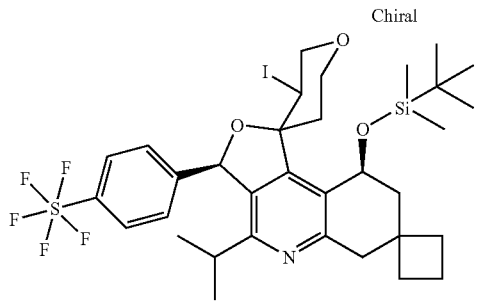 [SMILES: CC(C)c1nc2c(c3c1[C@@H](c1ccc(S(F)(F)(F)(F)F)cc1)OC31CCOCC1I)[C@@H](O[Si](C)(C)C(C)(C)C)CC1(CCC1)C2]

Obtained by starting from (R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3'-yl)(4-(pentafluorosulfanyl)phenyl)methanol. Lithium carbonate is used instead of sodium bicarbonate.

Mass spectrometry (ESI$^+$): m/z=786 [M+H]$^+$

HPLC (Method 24): Retention time=1.879 min.

(31) (3R,9S)-9-(tert-butyldimethylsilyloxy)-3-(4-tert-butylphenyl)-3'-iodo-7,7-dimethyl-4-(tetrahydro-2H-pyran-4-yl)-2',3',5',6,6',7,8,9-octahydro-3H-spiro[furo[3,4-c]quinoline-1,4'-pyran]

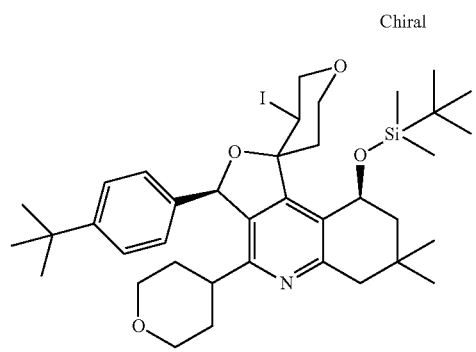 [SMILES: CC1(C)Cc2nc(C3CCOCC3)c3c(c2[C@@H](O[Si](C)(C)C(C)(C)C)C1)C1(CCOCC1I)O[C@@H]3c1ccc(C(C)(C)C)cc1]

Obtained by starting from (R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(4-tert-butylphenyl)methanol. Lithium carbonate is used instead of sodium bicarbonate.

Mass spectrometry (ESI$^+$): m/z=746 [M+H]$^+$

HPLC (Method 24): Retention time=1.879 min.

(32) 5-((3R,9S)-9-(tert-butyldimethylsilyloxy)-3'-iodo-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

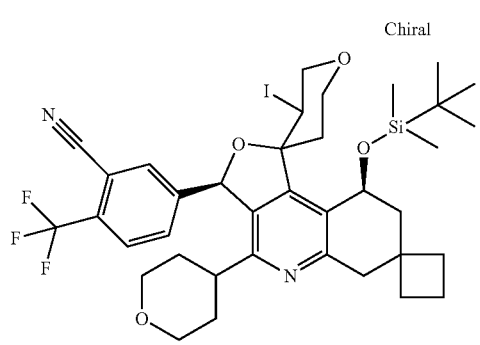 [SMILES: CC(C)(C)[Si](C)(C)O[C@H]1CC2(CCC2)Cc2nc(C3CCOCC3)c3c(c21)C1(CCOCC1I)O[C@@H]3c1ccc(C(F)(F)F)c(C#N)c1]

Obtained by starting from 5-((R)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(hydroxy)methyl)-2-(trifluoromethyl)benzonitrile. Lithium carbonate is used instead of sodium bicarbonate.

Mass spectrometry (ESI$^+$): m/z=795 [M+H]$^+$

HPLC (Method 7): Retention time=1.952 min.

(33) 5-((3R,9S)-9-(tert-butyldimethylsilyloxy)-3'-iodo-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

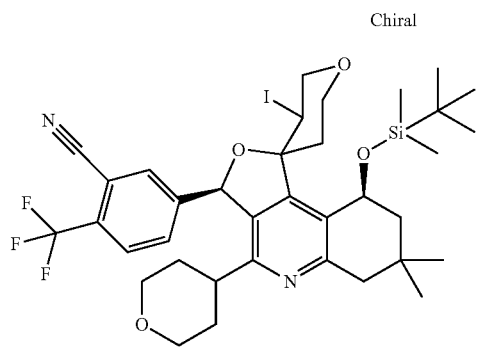 [SMILES: CC1(C)Cc2nc(C3CCOCC3)c3c(c2[C@@H](O[Si](C)(C)C(C)(C)C)C1)C1(CCOCC1I)O[C@@H]3c1ccc(C(F)(F)F)c(C#N)c1]

Obtained by starting from 5-((R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(hydroxy)methyl)-2-(trifluoromethyl)benzonitrile.

Mass spectrometry (ESI$^+$): m/z=783 [M+H]$^+$

HPLC (Method 7): Retention time=1.853 min.

(34) (3S,9S)-9-(tert-butyldimethylsilyloxy)-3'-iodo-7,7-(propan-1,3-diyl)-4-(tetrahydro-2H-pyran-4-yl)-3-(5-(trifluoromethyl)pyridin-2-yl)-2',3',5',6',7,8,9-octahydro-3H-spiro[furo[3,4-c]quinoline-1,4'-pyran]

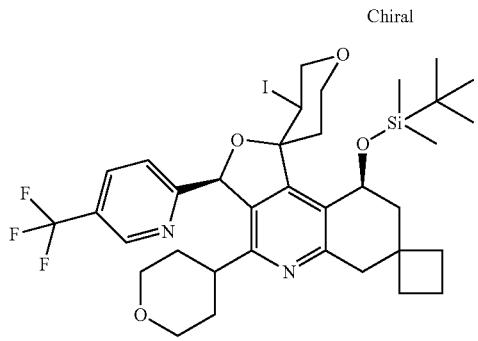 [SMILES: CC(C)(C)[Si](C)(C)O[C@H]1CC2(CCC2)Cc2nc(C3CCOCC3)c3c(c21)C1(CCOCC1I)O[C@@H]3c1ccc(C(F)(F)F)cn1]

Obtained by starting from (S)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3-yl)(5-(trifluoromethyl)pyridin-2-yl)methanol. Lithium carbonate is used instead of sodium bicarbonate.

Mass spectrometry (ESI⁺): m/z=771 [M+H]⁺

HPLC (Method 7): Retention time=1.891 min.

(35) (3S,9S)-9-(tert-butyldimethylsilyloxy)-3'-iodo-7,7-dimethyl-4-(tetrahydro-2H-pyran-4-yl)-3-(5-(trifluoromethyl)pyridin-2-yl)-2',3',5',6',7,8,9-octahydro-3H-spiro[furo[3,4-c]quinoline-1,4'-pyran]

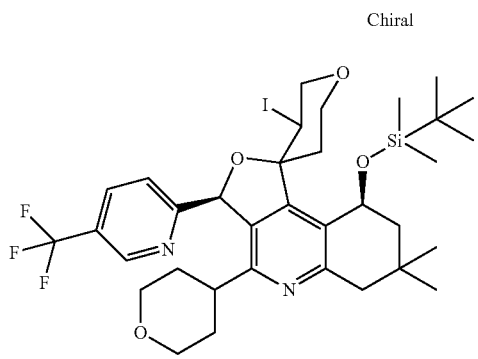 [SMILES: CC1(C)Cc2nc(C3CCOCC3)c3c(c2[C@@H](O[Si](C)(C)C(C)(C)C)C1)C1(CCOCC1I)O[C@@H]3c1ccc(C(F)(F)F)cn1]

Obtained by starting from (S)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(5-(trifluoromethyl)pyridin-2-yl)methanol. Lithium carbonate is used instead of sodium bicarbonate.

Mass spectrometry (ESI⁺): m/z=759 [M+H]⁺

HPLC (Method 7): Retention time=1.958 min.

(36) 5-((3R,9S)-9-(tert-butyldimethylsilyloxy)-3'-iodo-7,7-dimethyl-4-(tetrahydro-2H-pyran-4-yl)-2',3',5',6',7,8,9-octahydro-3H-spiro[furo[3,4-c]quinoline-1,4'-pyran]-3-yl)-2-(trifluoromethyl)benzonitrile

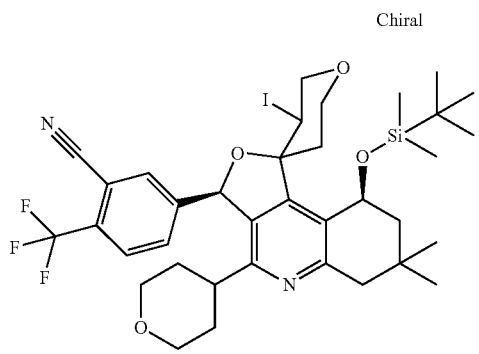 [SMILES: CC1(C)Cc2nc(C3CCOCC3)c3c(c2[C@@H](O[Si](C)(C)C(C)(C)C)C1)C1(CCOCC1I)O[C@@H]3c1ccc(C(F)(F)F)c(C#N)c1]

Obtained by starting from 5-((R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(hydroxy)methyl)-2-(trifluoromethyl)benzonitrile. Lithium carbonate is used instead of sodium bicarbonate.

Mass spectrometry (ESI⁺): m/z=783 [M+H]⁺

HPLC (Method 7): Retention time=1.853 min.

(37) 5-((3R,9S)-9-(tert-butyldimethylsilyloxy)-3'-iodo-4-isopropyl-7,7-(propan-1,3-diyl)-2',3',5',6',7,8,9-octahydro-3H-spiro[furo[3,4-c]quinoline-1,4'-pyran]-3-yl)-2-(trifluoromethyl)benzonitrile

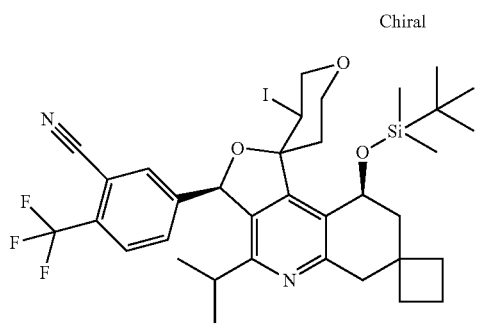 [SMILES: CC(C)c1nc2c(c3c1[C@@H](c1ccc(C(F)(F)F)c(C#N)c1)OC31CCOCC1I)[C@@H](O[Si](C)(C)C(C)(C)C)CC1(CCC1)C2]

Obtained by starting from 5-((R)—((S)-5'-(tert-butyldimethylsilyloxy)-4'-(3,6-dihydro-2H-pyran-4-yl)-2'-isopropyl-6',8'-dihydro-5'H-spiro[cyclobutane-1,7'-quinoline]-3-yl)(hydroxy)methyl)-2-(trifluoromethyl)benzonitrile. Lithium carbonate is used instead of sodium bicarbonate.

Mass spectrometry (ESI⁺): m/z=753 [M+H]⁺

HPLC (Method 27): Retention time=1.73 min.

303

(38) (3R,9S)-9-(tert-butyldimethylsilyloxy)-3'-iodo-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]

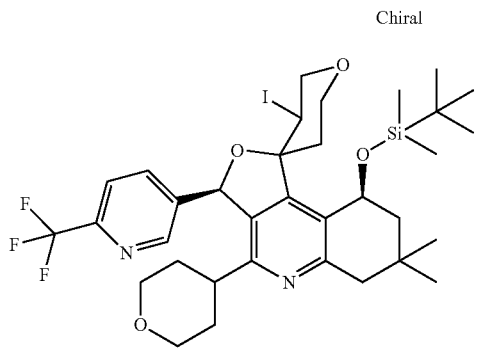 [SMILES: CC1(C)Cc2nc(C3CCOCC3)c3c(c2[C@@H](O[Si](C)(C)C(C)(C)C)C1)C1(CCOCC1I)O[C@@H]3c1ccc(C(F)(F)F)nc1]

Obtained by starting from (R)—((S)-5-(tert-butyldimethylsilyloxy)-4-(3,6-dihydro-2H-pyran-4-yl)-7,7-dimethyl-2-(tetrahydro-2H-pyran-4-yl)-5,6,7,8-tetrahydroquinolin-3-yl)(6-(trifluoromethyl)pyridin-3-yl)methanol. Lithium carbonate is used instead of sodium bicarbonate.

Mass spectrometry (ESI$^+$): m/z=759 [M+H]$^+$

HPLC (Method 7): Retention time=1.853 min.

(39) (3R,9S)-9-(tert-butyldimethylsilyloxy)-3'-iodo-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]

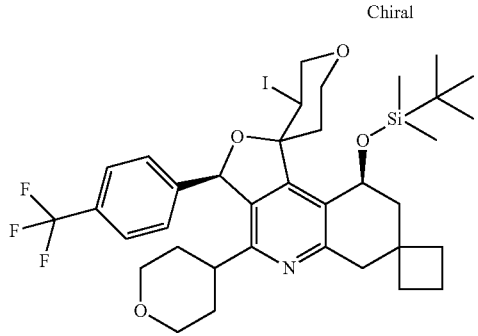 [SMILES: CC(C)(C)[Si](C)(C)O[C@H]1CC2(CCC2)Cc2nc(C3CCOCC3)c3c(c21)C1(CCOCC1I)O[C@@H]3c1ccc(C(F)(F)F)cc1]

Obtained by starting from (R)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(4-(trifluoromethyl)phenyl)methanol. Lithium carbonate is used instead of sodium bicarbonate.

Mass spectrometry (ESI$^+$): m/z=770 [M+H]$^+$

HPLC (Method 7): Retention time=1.991 min.

304

(40) (3R,9S)-9-(tert-butyldimethylsilyloxy)-3'-iodo-7,7-(propan-1,3-diyl)-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]

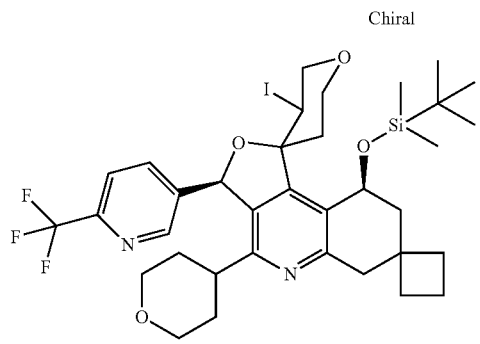 [SMILES: CC(C)(C)[Si](C)(C)O[C@H]1CC2(CCC2)Cc2nc(C3CCOCC3)c3c(c21)C1(CCOCC1I)O[C@@H]3c1ccc(C(F)(F)F)nc1]

Obtained by starting from (R)—((S)-5'-(tert-butyldimethylsilyloxy)-4'-(3,6-dihydro-2H-pyran-4-yl)-2'-(tetrahydro-2H-pyran-4-yl)-6',8'-dihydro-5'H-spiro[cyclobutane-1,7'-quinoline]-3'-yl)(6-(trifluoromethyl)pyridin-3-yl)methanol. Lithium carbonate is used instead of sodium bicarbonate.

Mass spectrometry (ESI$^+$): m/z=771 [M+H]$^+$

HPLC (Method 7): Retention time=1.955 min.

(41) (3'R,9'S)-9'-(tert-butyldimethylsilyloxy)-4,4-difluoro-2-iodo-4'-isopropyl-7',7'-dimethyl-3'-(5-(trifluoromethyl)pyridin-2-yl)-6',7',8',9'-tetrahydro-3'H-spiro[cyclohexane-1,1'-furo[3,4-c]quinoline]

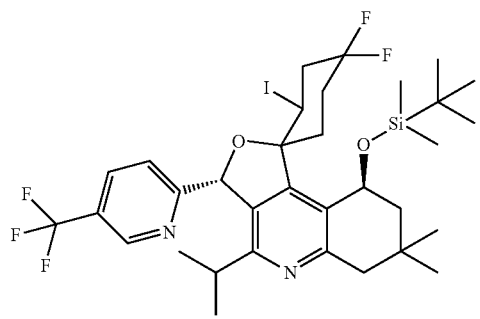

Obtained by starting from (R)—((S)-5-(tert-butyldimethylsilyloxy)-4-(4,4-difluorocyclohex-1-enyl)-2-isopropyl-7,7-dimethyl-5,6,7,8-tetrahydroquinolin-3-yl)(5-(trifluoromethyl)pyridin-2-yl)methanol.

Mass spectrometry (ESI$^+$): m/z=751 [M+H]$^+$

HPLC (Method 13): Retention time=1.80 min.

R$_f$-value: 0.52 (silica gel, n-hexane/diethylether 95:5)

Example XXXI

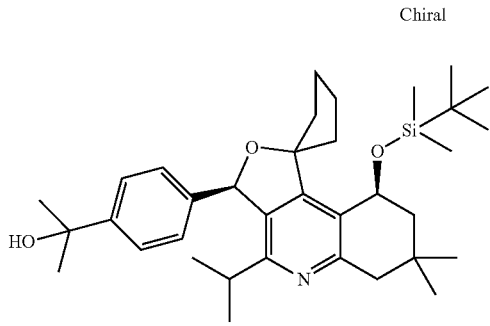 [SMILES: CC(C)c1nc2c(c3c1[C@@H](c1ccc(C(C)(C)O)cc1)OC31CCCC1)[C@@H](O[Si](C)(C)C(C)(C)C)CC(C)(C)C2]

2-(4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)propan-2-ol 110 mg Ethyl 4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)benzoate are dissolved in 3 ml tetrahydrofurane, cooled to −5° C. and treated dropwise with 820 µl of a 1.4 M solution of methylmagnesium bromide in toluene/tetrahydrofurane (72:25). The mixture is warmed to room temperature during 1 hour, then recooled to 0° C. and the reaction is quenched by addition 1 ml methanol. The solvents are evaporated in vacuo and the residue is chromatographed on silica gel (petrole ether/ethylacetate 90:10 to 50:50).

Yield: 72 mg (67% of theory)

Mass spectrometry (ESI$^+$): m/z=564 [M+H]$^+$

HPLC (Method 1): Retention time=3.646 min.

Example XXXII

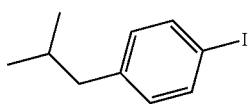

1-Iodo-4-isobutylbenzene 1.67 g 1-(4-Iodophenyl)-2-methylpropan-1-ol are dissolved in 5 ml trifluoroacetic acid and 5 ml triethylsilane. The mixture is stirred for 12 hours at 50° C., the solvents are evaporated in vacuo and the residue is chromatographed on silica gel (cyclohexane/ethylacetate 100:0 to 66:34).

Yield: 1.30 g (83% of theory)

Mass spectrometry (EI$^+$): m/z=260 [M]$^+$

R$_f$-value: 0.90 (silica gel, cyclohexane/ethylacetate 9:1)

Example XXXIII

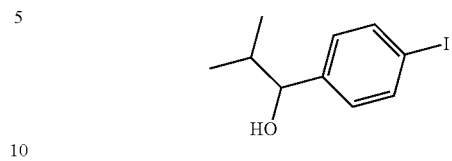

1-(4-Iodophenyl)-2-methylpropan-1-ol 2.5 g 4-Iodobenzaldehyde are dissolved in 25 ml diethylether, cooled to 0° C. and treated dropwise with 6.0 ml of a 2 M solution of isopropylmagnesium chloride in tetrahydrofurane. The temperature is slowly raised to room temperature and the mixture is stirred for further 12 hours. Then the reaction is quenched by addition of half saturated aqueous ammonium chloride. The aqueous phase is twice extracted with ethylacetate and the combined organic phases are washed twice with saturated aqueous ammonium chloride and brine. After drying with magnesium sulphate the solvents are evaporated in vacuo and the residue is chromatographed on silica gel (cyclohexane/ethylacetate 100:0 to 40:60).

Yield: 703 mg (24% of theory)

Mass spectrometry (ESI$^+$): m/z=259 [M+H−H$_2$O]$^+$

Example XXXIV

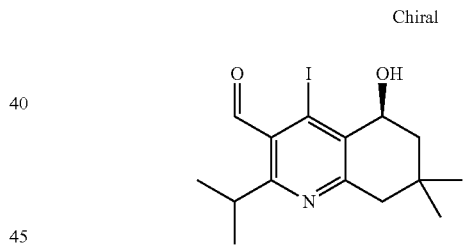

(S)-5-hydroxy-4-iodo-2-isopropyl-7,7-dimethyl-5,6,7,8-tetrahydroquinoline-3-carbaldehyde Under nitrogen 1.4 g (S)-3-(hydroxymethyl)-4-iodo-2-isopropyl-7,7-dimethyl-5,6,7,8-tetrahydroquinolin-5-ol are dissolved in 25 ml toluene and treated successively with a solution of 940 mg sodium bicarbonate in 25 ml of water, 1.9 g iodine and 60 mg 2,2,6,6-tetramethyl-piperidin-1-oxyl (TEMPO). The mixture is stirred for 20 hours at room temperature, diluted with diethylether and washed with a 10% aqueous solution of sodium sulfite and a 5% aqueous solution of sodium bicarbonate. After drying with sodium sulphate the solvents are evaporated in vacuo and the residue is chromatographed on silica gel (hexane/ethylacetate 8:2).

Yield: 1.2 g (86% of theory)

Mass spectrometry (ESI$^+$): m/z=374 [M+H]$^+$

HPLC (Method 8): Retention time=1.61 min.

Analogously to example XXXIV the following compounds are obtained:

(1) (S)-5'-hydroxy-4'-iodo-2'-isopropyl-6',8'-dihydro-5'H-spiro[cyclobutane-1,7'-quinoline]-3'-carbaldehyde

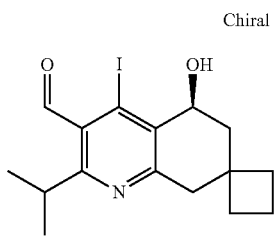 [SMILES: CC(C)c1nc2c(c(I)c1C=O)[C@@H](O)CC1(CCC1)C2]

Obtained by starting from (S)-3'-(hydroxymethyl)-4'-iodo-2'-isopropyl-6',8'-dihydro-5'H-spiro[cyclobutane-1,7'-quinolin]-5'-ol.
Mass spectrometry (ESI$^+$): m/z=386 [M+H]$^+$
HPLC (Method 9): Retention time=1.71 min.

(2) (S)-5'-hydroxy-4'-iodo-2'-(tetrahydro-2H-pyran-4-yl)-6',8'-dihydro-5'H-spiro[cyclobutane-1,7'-quinoline]-3'-carbaldehyde

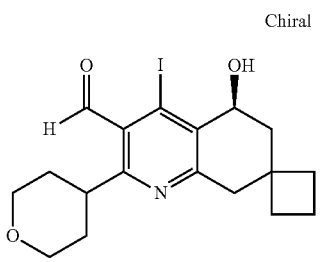 [SMILES: O=Cc1c(C2CCOCC2)nc2c(c1I)[C@@H](O)CC1(CCC1)C2]

Obtained by starting from (S)-3'-(hydroxymethyl)-4'-iodo-2'-(tetrahydro-2H-pyran-4-yl)-6',8'-dihydro-5'H-spiro[cyclobutane-1,7'-quinolin]-5'-ol
Mass spectrometry (ESI$^+$): m/z=428 [M+H]$^+$
HPLC (Method 7): Retention time=1.454 min.

Example XXXV

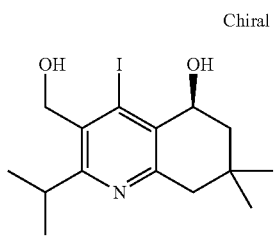 [SMILES: CC(C)c1nc2c(c(I)c1CO)[C@@H](O)CC(C)(C)C2]

(1) (S)-3-(hydroxymethyl)-4-iodo-2-isopropyl-7,7-dimethyl-5,6,7,8-tetrahydroquinolin-5-ol To a solution of 1.67 g (S)-(5-(tert-butyldimethylsilyloxy)-4-iodo-2-isopropyl-7,7-dimethyl-5,6,7,8-tetrahydroquinolin-3-ylmethanol in 50 ml tetrahydrofurane are added 6.8 ml of a 1 M solution of tetrabutylammonium fluoride in tetrahydrofurane. The solution is stirred for 2 hours at room temperature, then the solvent is evaporated in vacuo and the residue is redissolved in dichloromethane. After washing successively with water, saturated aqueous sodium bicarbonate and brine the organic phase is dried with sodium sulphate. The solvents are evaporated in vacuo and the residue is chromatographed on silica gel (cyclohexane/ethylacetate 3:1).
Yield: 980 mg (77% of theory)
Mass spectrometry (ESI$^+$): m/z=376 [M+H]$^+$
HPLC (Method 18): Retention time=0.46 min.

Analogously to example XXXV the following compounds are obtained:

(1) (3'R,6'R,9'S)-3'-(4-tert-butylphenyl)-9'-hydroxy-4'-isopropyl-7',7'-dimethyl-6',7',8',9'-tetrahydro-3'H-spiro[cyclopentane-1,1'-furo[3,4-c]quinoline]-6'-yl acetate

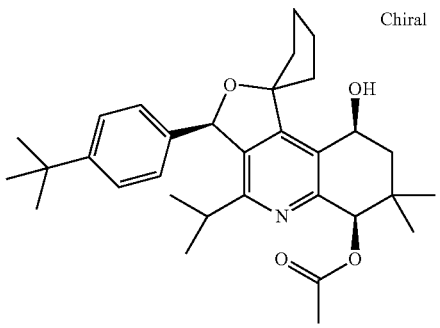 [SMILES: CC(=O)O[C@H]1c2nc(C(C)C)c3c(c2[C@@H](O)CC1(C)C)C1(CCCC1)O[C@@H]3c1ccc(C(C)(C)C)cc1]

Obtained by starting from (3'R,6'R,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6'-yl acetate.
Mass spectrometry (ESI$^+$): m/z=506 [M+H]$^+$
HPLC (Method 9): Retention time=3.05 min.

(2) (3'R,6'S,9'S)-3'-(4-tert-butylphenyl)-9'-hydroxy-4'-isopropyl-7',7'-dimethyl-6',7',8',9'-tetrahydro-3'H-spiro[cyclopentane-1,1'-furo[3,4-c]quinoline]-6'-yl acetate

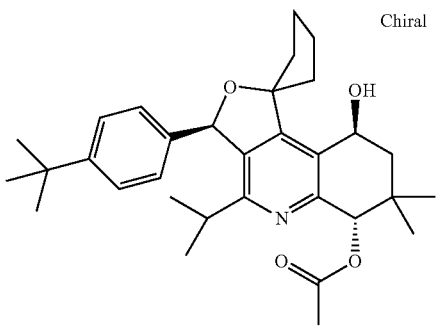 [SMILES: CC(=O)O[C@@H]1c2nc(C(C)C)c3c(c2[C@@H](O)CC1(C)C)C1(CCCC1)O[C@@H]3c1ccc(C(C)(C)C)cc1]

Obtained by starting from (3'R,6'S,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6'-yl acetate.
Mass spectrometry (ESI$^+$): m/z=506 [M+H]$^+$
HPLC (Method 9): Retention time=3.53 min.

Example XXXVI

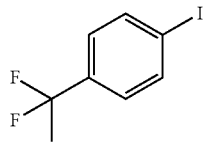

1-(1,1-Difluoroethyl)-4-iodobenzene 2.2 g 4-Iodoacetophenone are dissolved in 4.5 ml tetrahydrodurane and 20 ml methanol, treated with 3.0 g [bis(2-methoxyethyl)amino]sulfur-trifluoride (BAST) dissolved in 3 ml tetrahydrofurane and stirred for 4 days at 50° C. The mixture is then partitioned between dichloromethane and saturated aqueous sodium bicarbonate. The aqueous phase is extracted three times with dichloromethane and the combined organic phases are dried with sodium sulphate. The solvents are evaporated in vacuo and the residue is chromatographed on silica gel (petrole ether/ethylacetate 100:0 to 98:2).

Yield: 1 g (42% of theory)
HPLC (Method 5): Retention time=1.573 min.

Example XXXVII

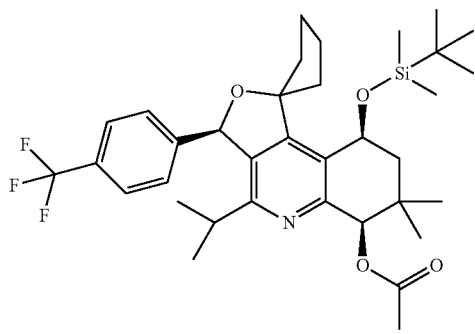

(3'R,6'R,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate and

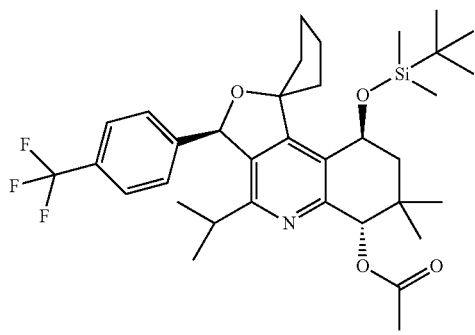

(3'R,6'S,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate 250 mg (3'R,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]5'-oxide and 3 ml acetic acid anhydride are mixed and heated for 2 hours at 130° C. Excess acetic acid anhydride is removed in vacuo and the residue is diluted with diethylether. After washing with saturated aqueous sodium bicarbonate the organic phase is dried with sodium sulphate. The solvent is evaporated in vacuo and the residue is chromatographed on silica gel (hexane/ethylacetate 95:5).

(3'R,6'R,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate:

Yield: 140 mg (52% of theory)
Mass spectrometry (ESI$^+$): m/z=632 [M+H]$^+$
HPLC (Method 13): Retention time=2.95 min.

(3'R,6'S,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate:

Yield: 50 mg (19% of theory)
Mass spectrometry (ESI$^+$): m/z=632 [M+H]$^+$
HPLC (Method 13): Retention time=3.08 min.

Analogously to example XXXVII the following compounds are obtained:

(1) (3'R,6'R,9'S)-9'-(tert-butyldimethylsilyloxy)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline]-6'-yl acetate

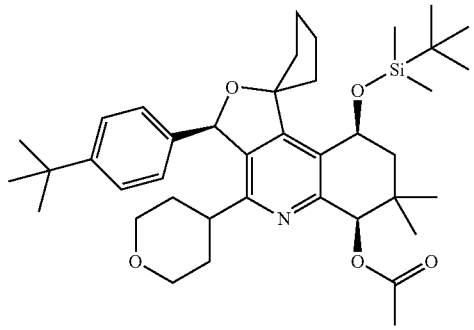

Obtained starting from (3'R,9'S)-9'-(tert-butyldimethylsilyloxy)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline]5'-oxide. Additionally (3'R,6'S,9'S)-9'-(tert-butyldimethylsilyloxy)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline]-6'-yl acetate as a mixture with meta-chlorobenzoic acid is obtained.

Mass spectrometry (ESI$^+$): m/z=662 [M+H]$^+$
R$_f$-value: 0.69 (silica gel, petrole ether/ethylacetate 2:1)

(2) (3'R,6'R,9'S)-9'-(tert-butyldimethylsilyloxy)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]-6'-yl acetate

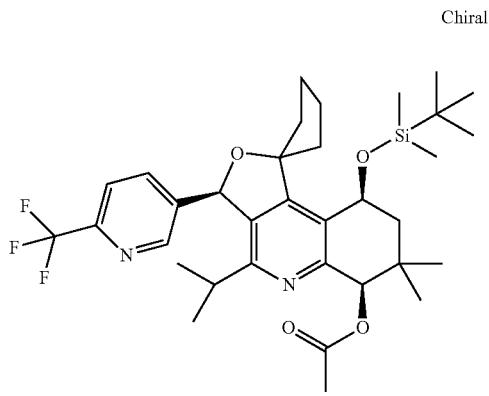 [SMILES: CC(=O)O[C@H]1c2nc(C(C)C)c3c(c2[C@@H](O[Si](C)(C)C(C)(C)C)CC1(C)C)C1(CCCC1)O[C@@H]3c1ccc(C(F)(F)F)nc1]

Obtained by starting from (3'R,9'S)-9'-(tert-butyldimethylsilyloxy)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]5'-oxide.

Mass spectrometry (ESI+): m/z=633 [M+H]+
HPLC (Method 13): Retention time=2.70 min.

(3) (3R,6R,9S)-9-(tert-butyldimethylsilyloxy)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-6-yl acetate

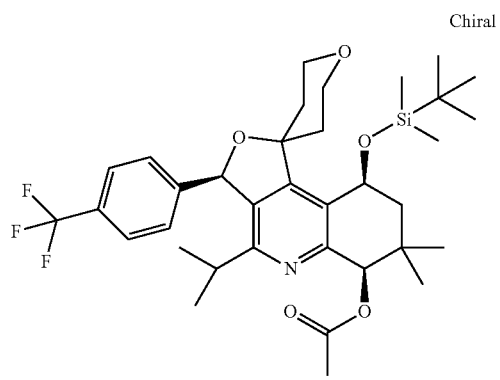 [SMILES: CC(=O)O[C@H]1c2nc(C(C)C)c3c(c2[C@@H](O[Si](C)(C)C(C)(C)C)CC1(C)C)C1(CCOCC1)O[C@@H]3c1ccc(C(F)(F)F)cc1]

Obtained by starting from (3R,9S)-9-(tert-butyldimethylsilyloxy)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]5-oxide.

Mass spectrometry (ESI+): m/z=648 [M+H]+
HPLC (Method 13): Retention time=2.67 min.

(4) (3'R,6'R,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6'-yl acetate

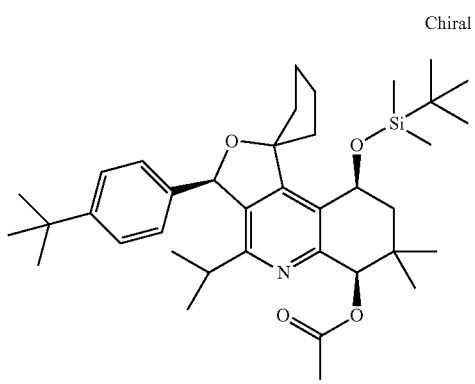 [SMILES: CC(=O)O[C@H]1c2nc(C(C)C)c3c(c2[C@@H](O[Si](C)(C)C(C)(C)C)CC1(C)C)C1(CCCC1)O[C@@H]3c1ccc(C(C)(C)C)cc1]

and (3'R,6'S,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6'-yl acetate

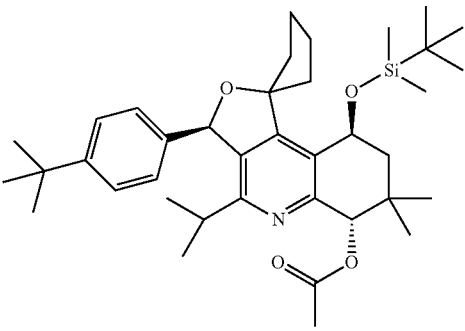

Obtained by starting from (3'R,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline]5'-oxide.

(3'R,6'R,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6'-yl acetate:

Mass spectrometry (ESI+): m/z=620 [M+H]+
HPLC (Method 13): Retention time=3.16 min.

(3'R,6'S,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6'-yl acetate:

Mass spectrometry (ESI+): m/z=620 [M+H]+
HPLC (Method 13): Retention time=3.52 min.

313

(5) (3R,6R,9S)-9-(tert-butyldimethylsilyloxy)-4-isopropyl-7,7-(propan-1,3-diyl)-3-(4-(trifluoromethyl)phenyl)-2',3',5',6',7,8,9-octahydro-3H-spiro[furo[3,4-c]quinoline-1,4'-pyran]-6-yl acetate

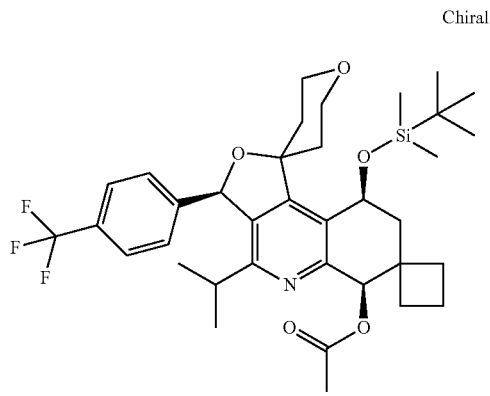 [SMILES: CC(=O)O[C@H]1c2nc(C(C)C)c3c(c2[C@@H](O[Si](C)(C)C(C)(C)C)CC12CCC2)C1(CCOCC1)O[C@@H]3c1ccc(C(F)(F)F)cc1]

and (3R,6S,9S)-9-(tert-butyldimethylsilyloxy)-4-isopropyl-7,7-(propan-1,3-diyl)-3-(4-(trifluoromethyl)phenyl)-2',3',5',6',7,8,9-octahydro-3H-spiro[furo[3,4-c]quinoline-1,4'-pyran]-6-yl acetate

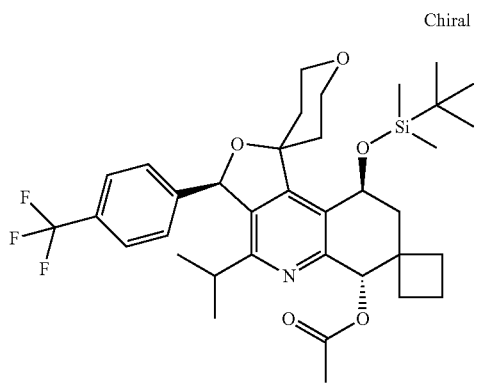 [SMILES: CC(=O)O[C@@H]1c2nc(C(C)C)c3c(c2[C@@H](O[Si](C)(C)C(C)(C)C)CC12CCC2)C1(CCOCC1)O[C@@H]3c1ccc(C(F)(F)F)cc1]

Obtained by starting from (3R,9S)-9-(tert-butyldimethylsilyloxy)-4-isopropyl-7,7-(propan-1,3-diyl)-3-(4-(trifluoromethyl)phenyl)-2',3',5',6',7,8,9-octahydro-3H-spiro[furo[3,4-c]quinoline-1,4'-pyran]5-oxide.

(3R,6R,9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]-6-yl acetate:

Mass spectrometry (ESI$^+$): m/z=660 [M+H]$^+$

HPLC (Method 30): Retention time=1.66 min.

(3R,6S,9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]-6-yl acetate:

Mass spectrometry (ESI$^+$): m/z=660 [M+H]$^+$

HPLC (Method 30): Retention time=1.66 min.

314

(6) (3R,6R,9S)-9-(tert-butyldimethylsilyloxy)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-6-yl acetate

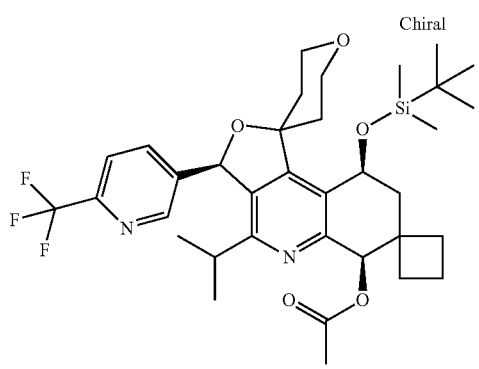 [SMILES: CC(=O)O[C@H]1c2nc(C(C)C)c3c(c2[C@@H](O[Si](C)(C)C(C)(C)C)CC12CCC2)C1(CCOCC1)O[C@@H]3c1ccc(C(F)(F)F)nc1]

and (3R,6S,9S)-9-(tert-butyldimethylsilyloxy)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-6-yl acetate

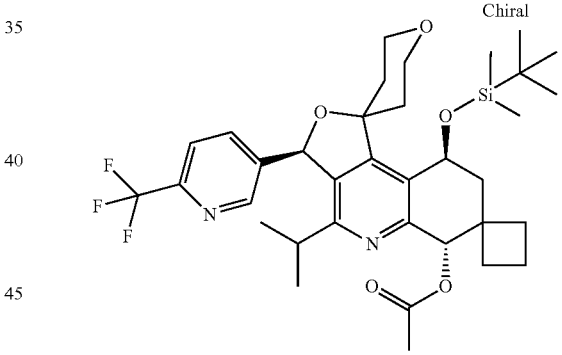

Obtained by starting from (3R,9S)-9-(tert-butyldimethylsilyloxy)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]5-oxide.

(3R,6R,9S)-9-(tert-butyldimethylsilyloxy)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-6-yl acetate:

Mass spectrometry (ESI$^+$): m/z=661 [M+H]$^+$

HPLC (Method 30): Retention time=1.32 min.

(3R,6S,9S)-9-(tert-butyldimethylsilyloxy)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-6-yl acetate:

Mass spectrometry (ESI$^+$): m/z=661 [M+H]$^+$

HPLC (Method 30): Retention time=1.33 min.

315

(7) (3S,6R,9S)-9-(tert-butyldimethylsilyloxy)-4-isopropyl-7,7-dimethyl-3-(5-(trifluoromethyl)pyridin-2-yl)-2',3',5',6',7,8,9-octahydro-3H-spiro[furo[3,4-c]quinoline-1,4'-pyran]-6-yl acetate

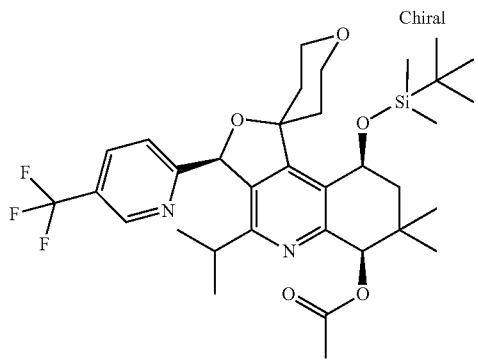 [SMILES: CC(=O)O[C@H]1c2nc(C(C)C)c3c(c2[C@@H](O[Si](C)(C)C(C)(C)C)CC1(C)C)C1(CCOCC1)O[C@@H]3c1ccc(C(F)(F)F)cn1]

and (3S,6S,9S)-9-(tert-butyldimethylsilyloxy)-4-isopropyl-7,7-dimethyl-3-(5-(trifluoromethyl)pyridin-2-yl)-2',3',5',6',7,8,9-octahydro-3H-spiro[furo[3,4-c]quinoline-1,4'-pyran]-6-yl acetate

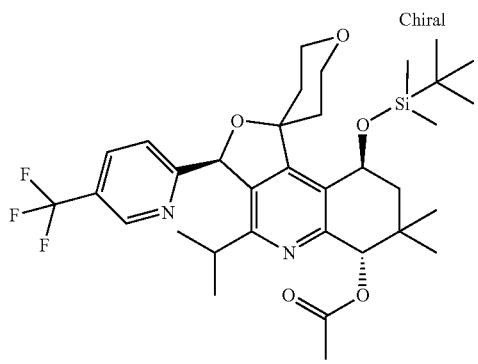 [SMILES: CC(=O)O[C@@H]1c2nc(C(C)C)c3c(c2[C@@H](O[Si](C)(C)C(C)(C)C)CC1(C)C)C1(CCOCC1)O[C@@H]3c1ccc(C(F)(F)F)cn1]

Obtained by starting from (3S,9S)-9-(tert-butyldimethylsilyloxy)-4-isopropyl-7,7-dimethyl-3-(5-(trifluoromethyl)pyridin-2-yl)-2',3',5',6',7,8,9-octahydro-3H-spiro[furo[3,4-c]quinoline-1,4'-pyran]5-oxide.

(3S,6R,9S)-9-(tert-butyldimethylsilyloxy)-4-isopropyl-7,7-dimethyl-3-(5-(trifluoromethyl)pyridin-2-yl)-2',3',5',6',7,8,9-octahydro-3H-spiro[furo[3,4-c]quinoline-1,4'-pyran]-6-yl acetate:

Mass spectrometry (ESI⁺): m/z=649 [M+H]⁺

HPLC (Method 13): Retention time=2.44 min.

(3S,6S,9S)-9-(tert-butyldimethylsilyloxy)-4-isopropyl-7,7-dimethyl-3-(5-(trifluoromethyl)pyridin-2-yl)-2',3',5',6',7,8,9-octahydro-3H-spiro[furo[3,4-c]quinoline-1,4'-pyran]-6-yl acetate:

Mass spectrometry (ESI⁺): m/z=649 [M+H]⁺

HPLC (Method 13): Retention time=2.60 min.

316

(8) (3R,6R,9S)-9-(tert-butyldimethylsilyloxy)-4-isopropyl-7,7-dimethyl-3-(6-(trifluoromethyl)pyridin-3-yl)-2',3',5',6',7,8,9-octahydro-3H-spiro[furo[3,4-c]quinoline-1,4'-pyran]-6-yl acetate

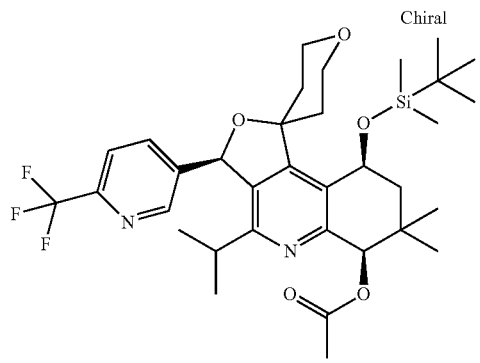 [SMILES: CC(=O)O[C@H]1c2nc(C(C)C)c3c(c2[C@@H](O[Si](C)(C)C(C)(C)C)CC1(C)C)C1(CCOCC1)O[C@@H]3c1ccc(C(F)(F)F)nc1]

and (3R,6S,9S)-9-(tert-butyldimethylsilyloxy)-4-isopropyl-7,7-dimethyl-3-(6-(trifluoromethyl)pyridin-3-yl)-2',3',5',6',7,8,9-octahydro-3H-spiro[furo[3,4-c]quinoline-1,4'-pyran]-6-yl acetate

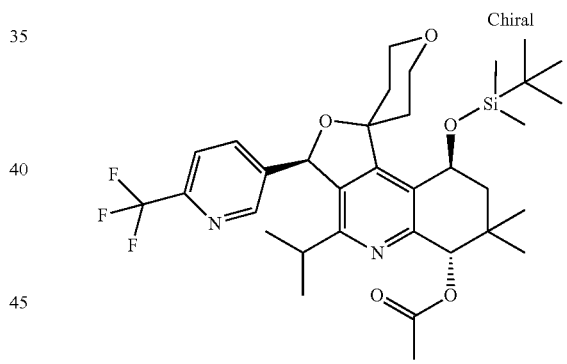

Obtained by starting from (3R,9S)-9-(tert-butyldimethylsilyloxy)-4-isopropyl-7,7-dimethyl-3-(6-(trifluoromethyl)pyridin-3-yl)-2',3',5',6',7,8,9-octahydro-3H-spiro[furo[3,4-c]quinoline-1,4'-pyran]5-oxide.

(3R,6R,9S)-9-(tert-butyldimethylsilyloxy)-4-isopropyl-7,7-dimethyl-3-(6-(trifluoromethyl)pyridin-3-yl)-2',3',5',6',7,8,9-octahydro-3H-spiro[furo[3,4-c]quinoline-1,4'-pyran]-6-yl acetate:

Mass spectrometry (ESI⁺): m/z=649 [M+H]⁺

HPLC (Method 12): Retention time=13.09 min.

(3R,6S,9S)-9-(tert-butyldimethylsilyloxy)-4-isopropyl-7,7-dimethyl-3-(6-(trifluoromethyl)pyridin-3-yl)-2',3',5',6',7,8,9-octahydro-3H-spiro[furo[3,4-c]quinoline-1,4'-pyran]-6-yl acetate:

Mass spectrometry (ESI⁺): m/z=649 [M+H]⁺

HPLC (Method 13): Retention time=2.48 min.

317

(9) (3S,6R,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate

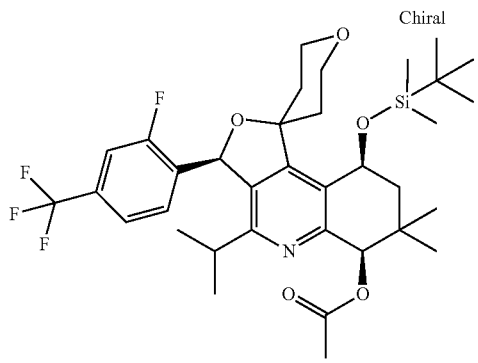 [SMILES: CC(=O)O[C@H]1c2nc(C(C)C)c3c(c2[C@@H](O[Si](C)(C)C(C)(C)C)CC1(C)C)C1(CCOCC1)O[C@@H]3c1ccc(C(F)(F)F)cc1F]

and (3S,6S,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate

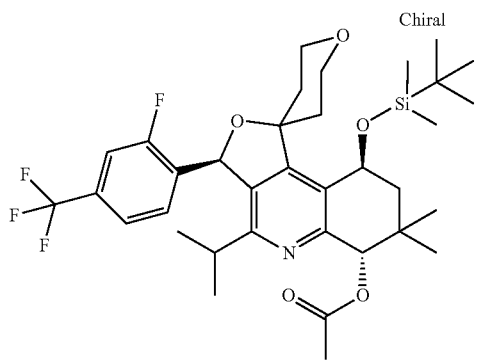 [SMILES: CC(=O)O[C@@H]1c2nc(C(C)C)c3c(c2[C@@H](O[Si](C)(C)C(C)(C)C)CC1(C)C)C1(CCOCC1)O[C@@H]3c1ccc(C(F)(F)F)cc1F]

Obtained by starting from (3S,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]5-oxide.

(3S,6R,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate:

Mass spectrometry (ESI$^+$): m/z=666 [M+H]$^+$

HPLC (Method 30): Retention time=1.76 min.

(3S,6S,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate:

Mass spectrometry (ESI$^+$): m/z=666 [M+H]$^+$

HPLC (Method 30): Retention time=1.76 min.

318

(10) (3R,6R,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate

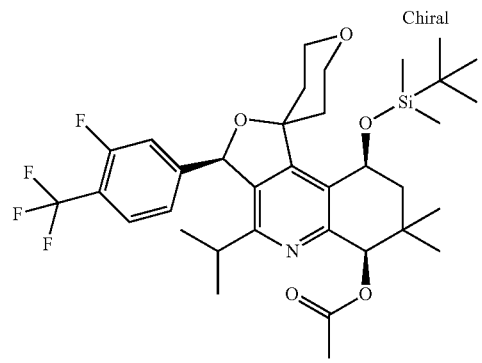 [SMILES: CC(=O)O[C@H]1c2nc(C(C)C)c3c(c2[C@@H](O[Si](C)(C)C(C)(C)C)CC1(C)C)C1(CCOCC1)O[C@@H]3c1ccc(C(F)(F)F)c(F)c1]

and (3R,6S,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate

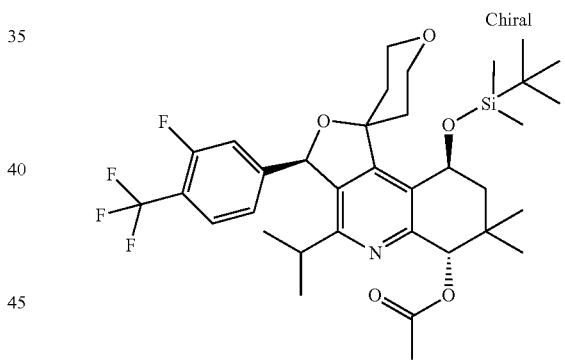

Obtained by starting from (3R,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]5-oxide.

(3R,6R,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate:

Mass spectrometry (ESI$^+$): m/z=666 [M+H]$^+$

HPLC (Method 13): Retention time=2.68 min.

(3R,6S,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate:

Mass spectrometry (ESI$^+$): m/z=666 [M+H]$^+$

HPLC (Method 13): Retention time=2.69 min.

(11) (3'R,6'R,9'S)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline]-6',9'-diol

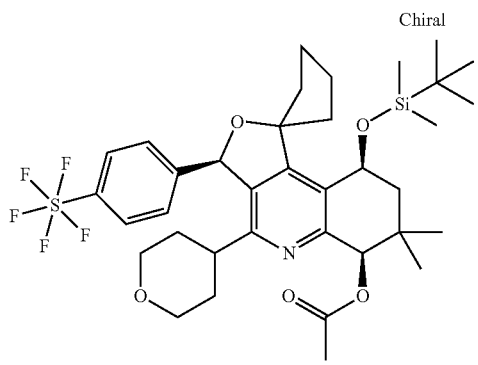 [SMILES: CC(=O)O[C@H]1c2nc(C3CCOCC3)c3c(c2[C@@H](O[Si](C)(C)C(C)(C)C)CC1(C)C)C1(CCCC1)O[C@@H]3c1ccc(S(F)(F)(F)(F)F)cc1]

Obtained by starting from (3'R,9'S)-9'-(tert-butyldimethylsilyloxy)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline]5'-oxide.

Mass spectrometry (ESI$^+$): m/z=732 [M+H]$^+$

HPLC (Method 7): Retention time=2.015 min.

(12) (3R,6R,9S)-9-(tert-butyldimethylsilyloxy)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]-6-yl acetate

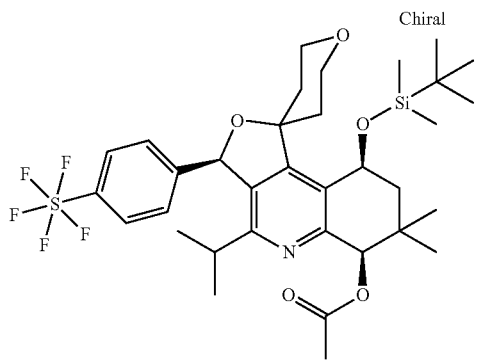 [SMILES: CC(=O)O[C@H]1c2nc(C(C)C)c3c(c2[C@@H](O[Si](C)(C)C(C)(C)C)CC1(C)C)C1(CCOCC1)O[C@@H]3c1ccc(S(F)(F)(F)(F)F)cc1]

Obtained by starting from (3R,9S)-9-(tert-butyldimethylsilyloxy)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]5-oxide.

Mass spectrometry (ESI$^+$): m/z=706 [M+H]$^+$

HPLC (Method 24): Retention time=1.924 min.

(13) (3R,6R,9S)-4-isopropyl-7,7-(propan-1,3-diyl)-3-(4-(pentafluorosulfanyl)phenyl)-9-(2,3,3-trimethylbutan-2-yloxy)-2',3',5',6,6',7,8,9-octahydro-3H-spiro[furo[3,4-c]quinoline-1,4'-pyran]-6-yl acetate

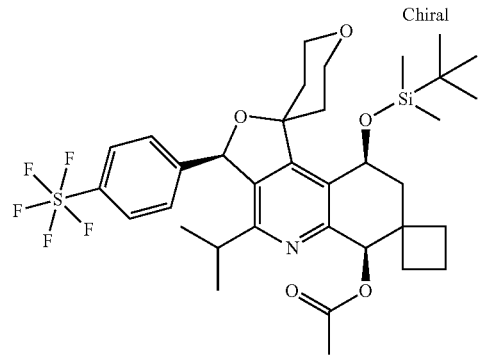 [SMILES: CC(=O)O[C@H]1c2nc(C(C)C)c3c(c2[C@@H](O[Si](C)(C)C(C)(C)C)CC12CCC2)C1(CCOCC1)O[C@@H]3c1ccc(S(F)(F)(F)(F)F)cc1]

Obtained by starting from (3R,9S)-9-(tert-butyldimethylsilyloxy)-4-isopropyl-7,7-(propan-1,3-diyl)-3-(4-(pentafluorosulfanyl)phenyl)-2',3',5',6,6',7,8,9-octahydro-3H-spiro[furo[3,4-c]quinoline-1,4'-pyran]5-oxide.

Mass spectrometry (ESI$^+$): m/z=718 [M+H]$^+$

HPLC (Method 24): Retention time=1.933 min.

(14) (3R,6R,9S)-9-(tert-butyldimethylsilyloxy)-3-(3-cyano-4-(trifluoromethyl)phenyl)-7,7-dimethyl-4-(tetrahydro-2H-pyran-4-yl)-2',3',5',6,6',7,8,9-octahydro-3H-spiro[furo[3,4-c]quinoline-1,4'-pyran]-6-yl acetate

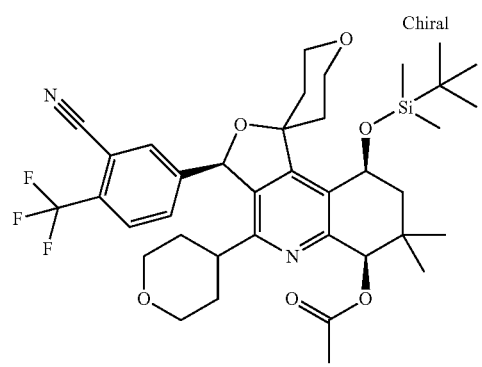 [SMILES: CC(=O)O[C@H]1c2nc(C3CCOCC3)c3c(c2[C@@H](O[Si](C)(C)C(C)(C)C)CC1(C)C)C1(CCOCC1)O[C@@H]3c1ccc(C(F)(F)F)c(C#N)c1]

Obtained by starting from (3R,9S)-9-(tert-butyldimethylsilyloxy)-3-(3-cyano-4-(trifluoromethyl)phenyl)-7,7-dimethyl-4-(tetrahydro-2H-pyran-4-yl)-2',3',5',6,6',7,8,9-octahydro-3H-spiro[furo[3,4-c]quinoline-1,4'-pyran]5-oxide.

Mass spectrometry (ESI$^+$): m/z=715 [M+H]$^+$

HPLC (Method 2): Retention time=2.583 min.

321

(15) (3S,6R,9S)-9-(tert-butyldimethylsilyloxy)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]-6-yl acetate

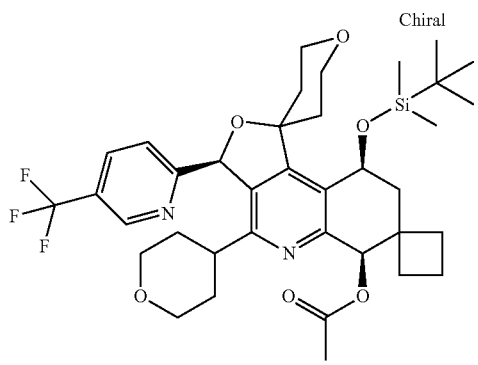 [SMILES: CC(=O)O[C@H]1c2nc(C3CCOCC3)c3c(c2[C@@H](O[Si](C)(C)C(C)(C)C)CC12CCC2)C1(CCOCC1)O[C@@H]3c1ccc(C(F)(F)F)cn1]

Obtained by starting from (3S,9S)-9-(tert-butyldimethylsilyloxy)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]5-oxide.

Mass spectrometry (ESI⁺): m/z=703 [M+H]⁺

HPLC (Method 7): Retention time=1.828 min.

(16) (3R,6R,9S)-9-(tert-butyldimethylsilyloxy)-3-(3-cyano-4-(trifluoromethyl)phenyl)-4-isopropyl-7,7-(propan-1,3-diyl)-2',3',5',6,6',7,8,9-octahydro-3H-spiro[furo[3,4-c]quinoline-1,4'-pyran]-6-yl acetate

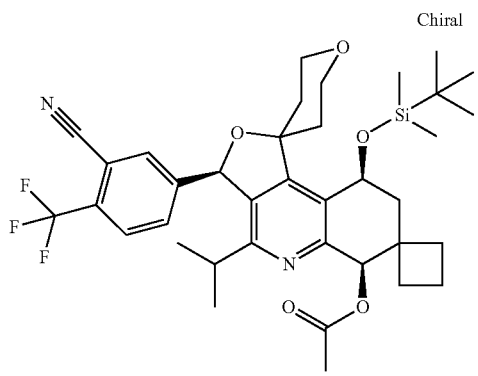 [SMILES: CC(=O)O[C@H]1c2nc(C(C)C)c3c(c2[C@@H](O[Si](C)(C)C(C)(C)C)CC12CCC2)C1(CCOCC1)O[C@@H]3c1ccc(C(F)(F)F)c(C#N)c1]

Obtained by starting from (3R,9S)-9-(tert-butyldimethylsilyloxy)-3-(3-cyano-4-(trifluoromethyl)phenyl)-4-isopropyl-7,7-(propan-1,3-diyl)-2',3',5',6,6',7,8,9-octahydro-3H-spiro[furo[3,4-c]quinoline-1,4'-pyran]5-oxide.

Mass spectrometry (ESI⁺): m/z=685 [M+H]⁺

HPLC (Method 27): Retention time=1.73 min.

322

(17) (3R,6R,9S)-9-(tert-butyldimethylsilyloxy)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-6-yl acetate

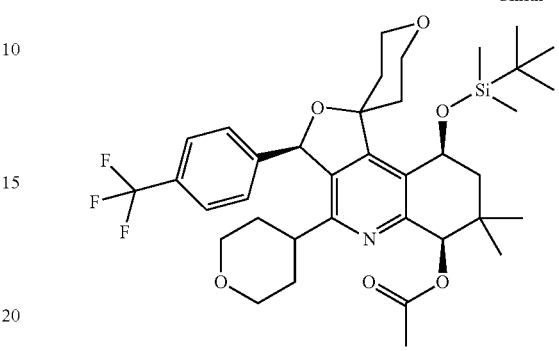

Obtained by starting from (3R,9S)-9-(tert-butyldimethylsilyloxy)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]5-oxide.

Mass spectrometry (ESI⁺): m/z=690 [M+H]⁺

HPLC (Method 28): Retention time=1.57 min.

(18) (3R,6R,9S)-9-(tert-butyldimethylsilyloxy)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran]-6-yl acetate Obtained by starting from (3R,9S)-9-(tert-butyldimethylsilyloxy)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran]5-oxide.

Mass spectrometry (ESI⁺): m/z=748 [M+H]⁺

HPLC (Method 24): Retention time=1.911 min.

323

(19) (3R,6R,9S)-9-(tert-butyldimethylsilyloxy)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]-6-yl acetate

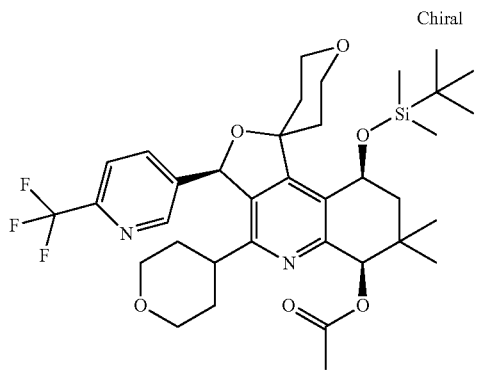 [SMILES: CC(=O)O[C@H]1c2nc(C3CCOCC3)c3c(c2[C@@H](O[Si](C)(C)C(C)(C)C)CC1(C)C)C1(CCOCC1)O[C@@H]3c1ccc(C(F)(F)F)nc1]

Obtained by starting from (3R,9S)-9-(tert-butyldimethylsilyloxy)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]5-oxide.

Mass spectrometry (ESI$^+$): m/z=691 [M+H]$^+$

HPLC (Method 7): Retention time=1.786 min.

(20) (3R,6R,9S)-9-(tert-butyldimethylsilyloxy)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran]-6-yl acetate

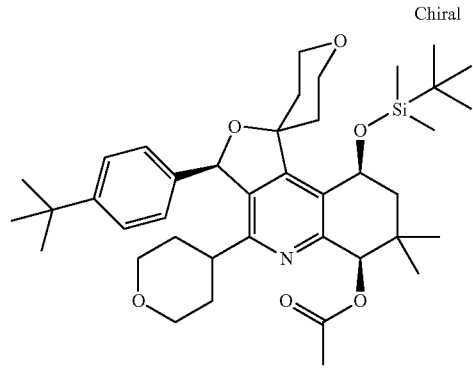 [SMILES: CC(=O)O[C@H]1c2nc(C3CCOCC3)c3c(c2[C@@H](O[Si](C)(C)C(C)(C)C)CC1(C)C)C1(CCOCC1)O[C@@H]3c1ccc(C(C)(C)C)cc1]

Obtained by starting from (3R,9S)-9-(tert-butyldimethylsilyloxy)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran]5-oxide.

Mass spectrometry (ESI$^+$): m/z=678 [M+H]$^+$

HPLC (Method 24): Retention time=1.941 min.

324

(21) (3R,6R,9S)-9-(tert-butyldimethylsilyloxy)-3-(3-cyano-4-(trifluoromethyl)phenyl)-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-6-yl acetate

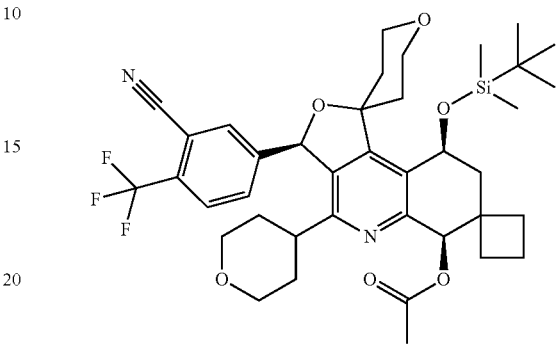

Obtained by starting from (3R,9S)-9-(tert-butyldimethylsilyloxy)-3-(3-cyano-4-(trifluoromethyl)phenyl)-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]5-oxide.

Mass spectrometry (ESI$^+$): m/z=727 [M+H]$^+$

HPLC (Method 28): Retention time=1.54 min.

(22) (3R,6R,9S)-9-(tert-butyldimethylsilyloxy)-3-(3-cyano-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate

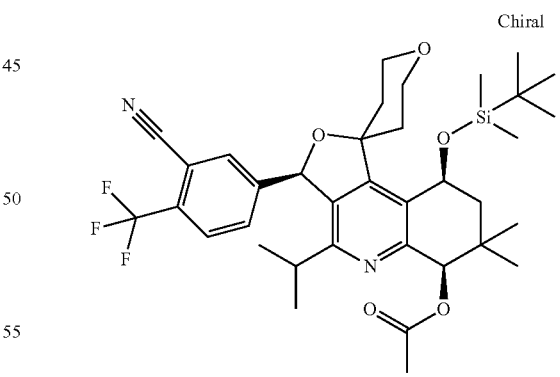

Obtained by starting from (3R,9S)-9-(tert-butyldimethylsilyloxy)-3-(3-cyano-4-(trifluoromethyl)phenyl)-4-isopropyl-7,7-dimethyl-2',3',5',6,6',7,8,9-octahydro-3H-spiro[furo[3,4-c]quinoline-1,4'-pyran]5-oxide.

Mass spectrometry (ESI$^+$): m/z=673 [M+H]$^+$

HPLC (Method 27): Retention time=1.73 min.

325

(23) (3S,6R,9S)-9-(tert-butyldimethylsilyloxy)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]-6-yl acetate

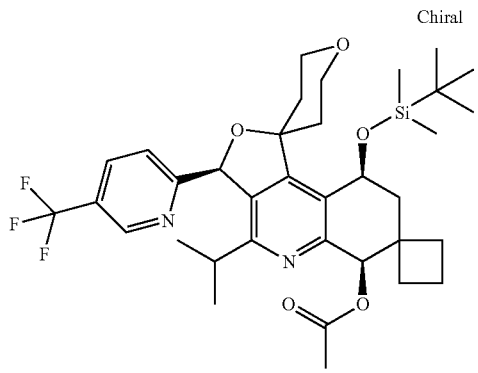 [SMILES: CC(=O)O[C@H]1c2nc(C(C)C)c3c(c2[C@@H](O[Si](C)(C)C(C)(C)C)CC12CCC2)C1(CCOCC1)O[C@@H]3c1ccc(C(F)(F)F)cn1]

and (3S,6S,9S)-9-(tert-butyldimethylsilyloxy)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]-6-yl acetate

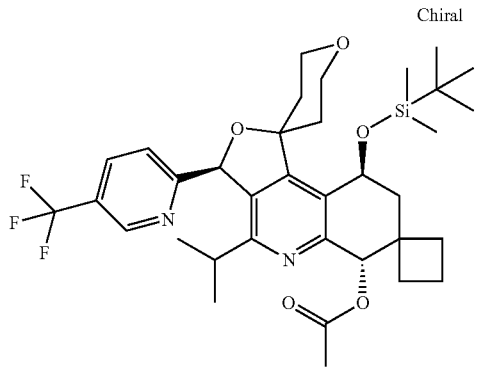 [SMILES: CC(=O)O[C@@H]1c2nc(C(C)C)c3c(c2[C@@H](O[Si](C)(C)C(C)(C)C)CC12CCC2)C1(CCOCC1)O[C@@H]3c1ccc(C(F)(F)F)cn1]

Obtained by starting from (3S,9S)-9-(tert-butyldimethylsilyloxy)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]5-oxide.

(3S,6R,9S)-9-(tert-butyldimethylsilyloxy)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]-6-yl acetate:

Mass spectrometry (ESI$^+$): m/z=661 [M+H]$^+$
HPLC (Method 13): Retention time=2.48 min.

(3S,6S,9S)-9-(tert-butyldimethylsilyloxy)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]-6-yl acetate:

Mass spectrometry (ESI$^+$): m/z=661 [M+H]$^+$
HPLC (Method 13): Retention time=2.63 min.

326

(24) (3R,6R,9S)-9-(tert-butyldimethylsilyloxy)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-6-yl acetate

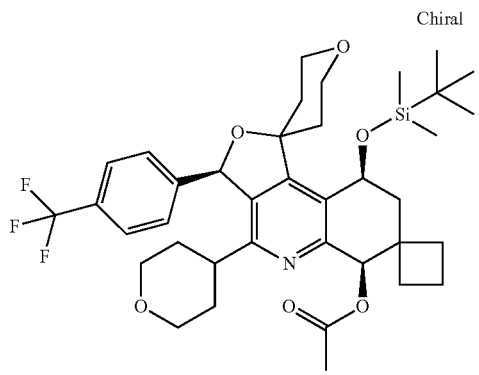 [SMILES: CC(=O)O[C@H]1c2nc(C3CCOCC3)c3c(c2[C@@H](O[Si](C)(C)C(C)(C)C)CC12CCC2)C1(CCOCC1)O[C@@H]3c1ccc(C(F)(F)F)cc1]

Obtained by starting from (3R,9S)-9-(tert-butyldimethylsilyloxy)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]5-oxide.

Mass spectrometry (ESI$^+$): m/z=702 [M+H]$^+$
HPLC (Method 33): Retention time=2.030 min.

Example XXXVIII

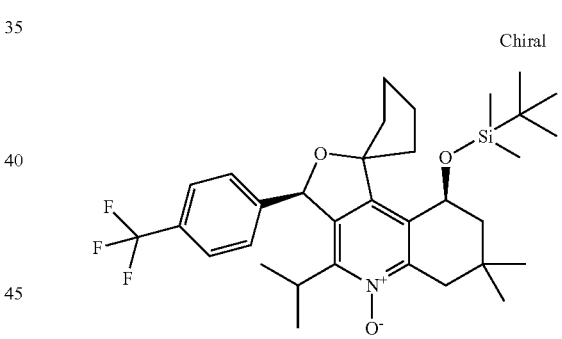

(3'R,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]5'-oxide 280 mg (3'R,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline] are dissolved in 5 ml chloroform and treated with 80 mg of meta-chloroperbenzoic acid (MCPBA) (<77%). The mixture is stirred for 18 hours and then partitioned between dichloromethane and a solution of sodium sulfite in water (5%). The organic phase is washed with saturated aqueous sodium bicarbonate and dried with sodium sulphate. After evaporation of the solvents the residue is chromatographed on silica gel (hexane/ethylacetate 4:1).

Yield: 280 mg (97% of theory)
Mass spectrometry (ESI$^+$): m/z=590 [M+H]$^+$
HPLC (Method 13): Retention time=2.71 min.

Analogously to example XXXVIII the following compounds are obtained:

(1) (3'R,9'S)-9'-(tert-butyldimethylsilyloxy)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline]5'-oxide

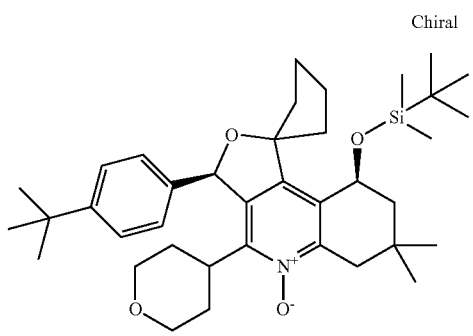 [SMILES: CC1(C)Cc2c(c3c(c(C4CCOCC4)[n+]2[O-])[C@@H](c2ccc(C(C)(C)C)cc2)OC32CCCC2)[C@@H](O[Si](C)(C)C(C)(C)C)C1]

Obtained starting from (3'R,9'S)-9'-(tert-butyldimethylsilyloxy)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline]. Dichloromethane is used as solvent.

Mass spectrometry (ESI⁺): m/z=620 [M+H]⁺

HPLC (Method 1): Retention time=4.909 min.

$R_f$-value: 0.62 (silica gel, petrole ether/ethylacetate 1:2)

(2) (3'R,9'S)-9'-(tert-butyldimethylsilyloxy)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]5'-oxide

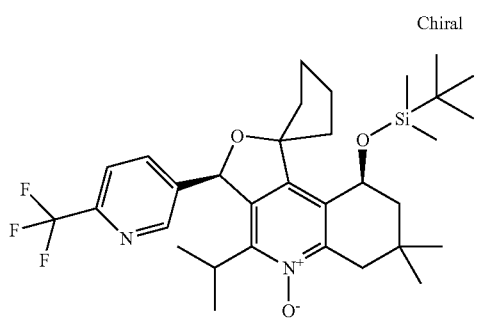 [SMILES: CC(C)c1c2c(c3c([n+]1[O-])CC(C)(C)C[C@@H]3O[Si](C)(C)C(C)(C)C)C1(CCCC1)O[C@@H]2c1ccc(C(F)(F)F)nc1]

Obtained by starting from (3'R,9'S)-9'-(tert-butyldimethylsilyloxy)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline].

Mass spectrometry (ESI⁺): m/z=591 [M+H]⁺

HPLC (Method 12): Retention time=12.25 min.

(3) (3R,9S)-9-(tert-butyldimethylsilyloxy)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]5-oxide

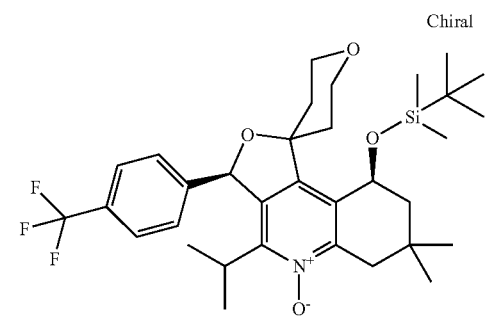 [SMILES: CC(C)c1c2c(c3c([n+]1[O-])CC(C)(C)C[C@@H]3O[Si](C)(C)C(C)(C)C)C1(CCOCC1)O[C@@H]2c1ccc(C(F)(F)F)cc1]

Obtained by starting from (3R,9S)-9-(tert-butyldimethylsilyloxy)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran].

Mass spectrometry (ESI⁺): m/z=606 [M+H]⁺

HPLC (Method 13): Retention time=2.35 min.

(4) (3'R,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline]5'-oxide

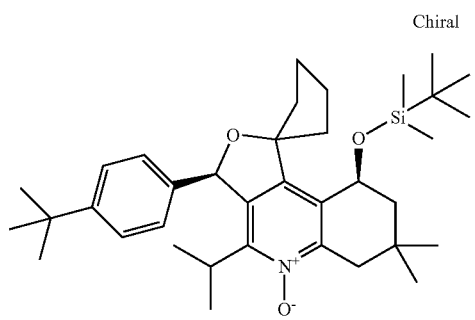 [SMILES: CC(C)c1c2c(c3c([n+]1[O-])CC(C)(C)C[C@@H]3O[Si](C)(C)C(C)(C)C)C1(CCCC1)O[C@@H]2c1ccc(C(C)(C)C)cc1]

Obtained by starting from (3'R,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline].

Mass spectrometry (ESI⁺): m/z=578 [M+H]⁺

HPLC (Method 13): Retention time=3.18 min.

329

(5) (3R,9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]5-oxide

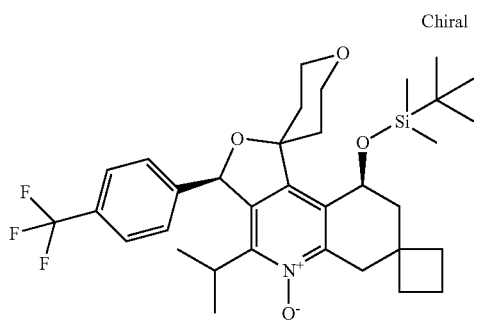

Obtained by starting from (3R,9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran].

Mass spectrometry (ESI$^+$): m/z=618 [M+H]$^+$

HPLC (Method 30): Retention time=1.24 min.

(6) (3R,9S)-9-(tert-butyldimethylsilyloxy)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]5-oxide

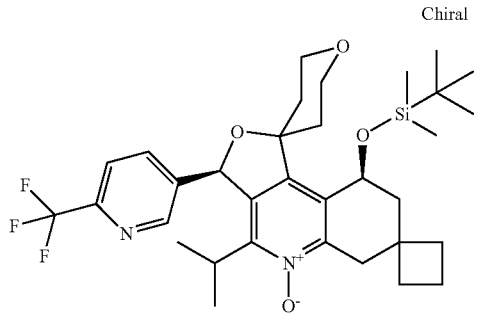 [SMILES: CC(C)c1c2c(c3c([n+]1[O-])CC1(CCC1)C[C@@H]3O[Si](C)(C)C(C)(C)C)C1(CCOCC1)O[C@@H]2c1ccc(C(F)(F)F)nc1]

Obtained by starting from (3R,9S)-9-(tert-butyldimethylsilyloxy)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran].

Mass spectrometry (ESI$^+$): m/z=619 [M+H]$^+$

HPLC (Method 12): Retention time=12.25 min.

330

(7) (3S,9S)-9-(tert-butyldimethylsilyloxy)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]5-oxide

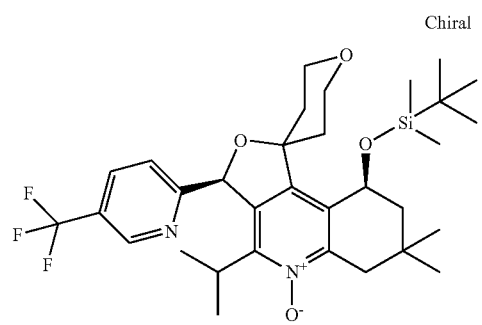

Obtained by starting from (3S,9S)-9-(tert-butyldimethylsilyloxy)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran].

Mass spectrometry (ESI$^+$): m/z=607 [M+H]$^+$

HPLC (Method 13): Retention time=2.06 min.

(8) (3R,9S)-9-(tert-butyldimethylsilyloxy)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]5-oxide

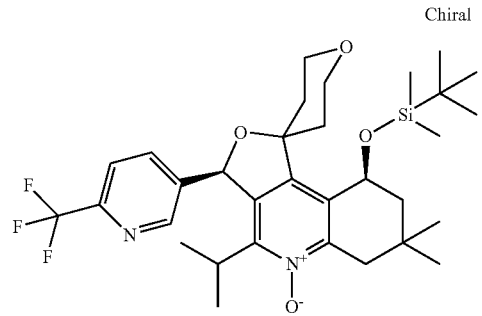 [SMILES: CC(C)c1c2c(c3c([n+]1[O-])CC(C)(C)C[C@@H]3O[Si](C)(C)C(C)(C)C)C1(CCOCC1)O[C@@H]2c1ccc(C(F)(F)F)nc1]

Obtained by starting from (3R,9S)-9-(tert-butyldimethylsilyloxy)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran].

Mass spectrometry (ESI$^+$): m/z=607 [M+H]$^+$

HPLC (Method 13): Retention time=2.04 min.

331

(9) (3S,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]5-oxide

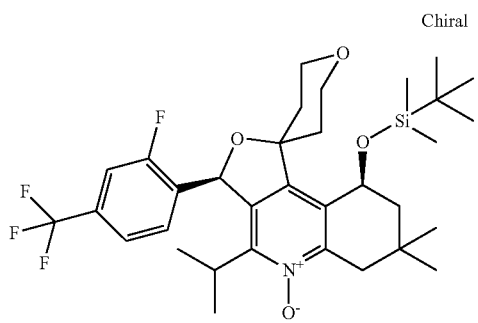 [SMILES: CC(C)c1c2c(c3c([n+]1[O-])CC(C)(C)C[C@@H]3O[Si](C)(C)C(C)(C)C)C1(CCOCC1)O[C@@H]2c1ccc(C(F)(F)F)cc1F]

Obtained by starting from (3S,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran].

Mass spectrometry (ESI⁺): m/z=624 [M+H]⁺

HPLC (Method 30): Retention time=2.06 min.

(10) (3R,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]5-oxide

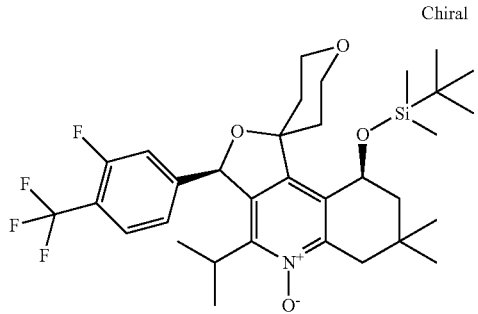 [SMILES: CC(C)c1c2c(c3c([n+]1[O-])CC(C)(C)C[C@@H]3O[Si](C)(C)C(C)(C)C)C1(CCOCC1)O[C@@H]2c1ccc(C(F)(F)F)c(F)c1]

Obtained by starting from (3R,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran].

Mass spectrometry (ESI⁺): m/z=624 [M+H]⁺

HPLC (Method 13): Retention time=2.38 min.

332

(11) (3'R,9'S)-9'-(tert-butyldimethylsilyloxy)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline]5'-oxide

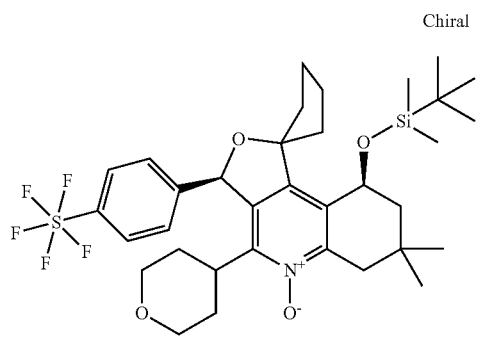 [SMILES: CC1(C)Cc2c(c3c(c(C4CCOCC4)[n+]2[O-])[C@@H](c2ccc(S(F)(F)(F)(F)F)cc2)OC32CCCC2)[C@@H](O[Si](C)(C)C(C)(C)C)C1]

Obtained by starting from (3'R,9'S)-9'-(tert-butyldimethylsilyloxy)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline].

Mass spectrometry (ESI⁺): m/z=690 [M+H]⁺

HPLC (Method 7): Retention time=1.971 min.

$R_f$-value: 0.57 (silica gel, petrole ether/ethylacetate 1:2)

(12) (3R,9S)-9-(tert-butyldimethylsilyloxy)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]5-oxide

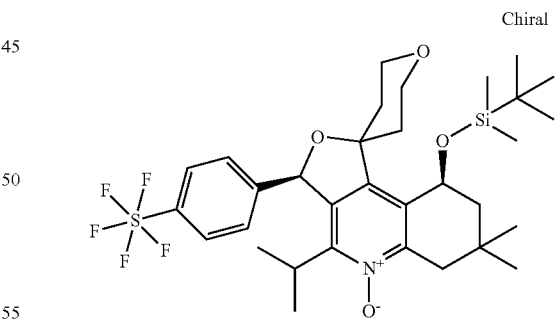

Obtained by starting from (3R,9S)-9-(tert-butyldimethylsilyloxy)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran].

Mass spectrometry (ESI⁺): m/z=664 [M+H]⁺

HPLC (Method 24): Retention time=1.840 min.

333

(13) (3R,9S)-9-(tert-butyldimethylsilyloxy)-4-isopropyl-7,7-(propan-1,3-diyl)-3-(4-(pentafluorosulfanyl)phenyl)-2',3',5',6,6',7,8,9-octahydro-3H-spiro[furo[3,4-c]quinoline-1,4'-pyran]5-oxide

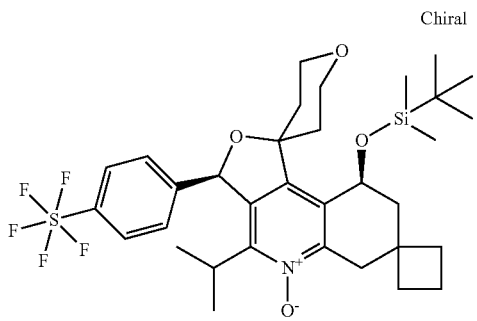 [SMILES: CC(C)c1c2c(c3c([n+]1[O-])CC1(CCC1)C[C@@H]3O[Si](C)(C)C(C)(C)C)C1(CCOCC1)O[C@@H]2c1ccc(S(F)(F)(F)(F)F)cc1]

Obtained by starting from (3R,9S)-4-isopropyl-7,7-(propan-1,3-diyl)-3-(4-(pentafluorosulfanyl)phenyl)-9-(2,3,3-trimethylbutan-2-yloxy)-2',3',5',6,6',7,8,9-octahydro-3H-spiro[furo[3,4-c]quinoline-1,4'-pyran].

Mass spectrometry (ESI$^+$): m/z=676 [M+H]$^+$

HPLC (Method 24): Retention time=1.869 min.

(14) (3R,9S)-9-(tert-butyldimethylsilyloxy)-3-(3-cyano-4-(trifluoromethyl)phenyl)-7,7-dimethyl-4-(tetrahydro-2H-pyran-4-yl)-2',3',5',6,6',7,8,9-octahydro-3H-spiro[furo[3,4-c]quinoline-1,4'-pyran]5-oxide

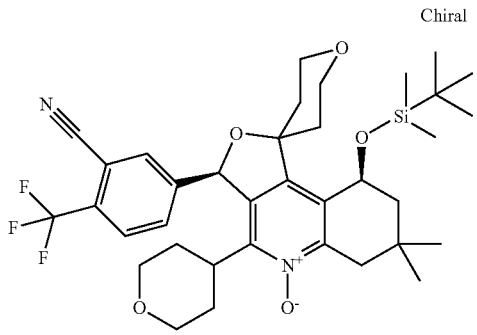 [SMILES: CC1(C)Cc2c(c3c(c(C4CCOCC4)[n+]2[O-])[C@@H](c2ccc(C(F)(F)F)c(C#N)c2)OC32CCOCC2)[C@@H](O[Si](C)(C)C(C)(C)C)C1]

Obtained by starting from 5-((3R,9S)-9-(tert-butyldimethylsilyloxy)-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=673 [M+H]$^+$

HPLC (Method 27): Retention time=1.65 min.

334

(15) (3S,9S)-9-(tert-butyldimethylsilyloxy)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]5-oxide

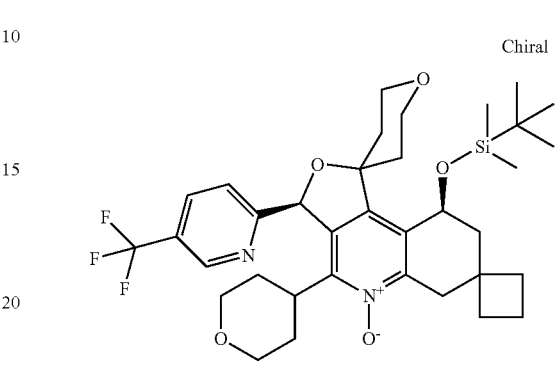

Obtained by starting from (3S,9S)-9-(tert-butyldimethylsilyloxy)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran].

Mass spectrometry (ESI$^+$): m/z=661 [M+H]$^+$

HPLC (Method 7): Retention time=1.784 min.

(16) 3R,9S)-9-(tert-butyldimethylsilyloxy)-3-(3-cyano-4-(trifluoromethyl)phenyl)-4-isopropyl-7,7-(propan-1,3-diyl)-2',3',5',6,6',7,8,9-octahydro-3H-spiro[furo[3,4-c]quinoline-1,4'-pyran]5-oxide

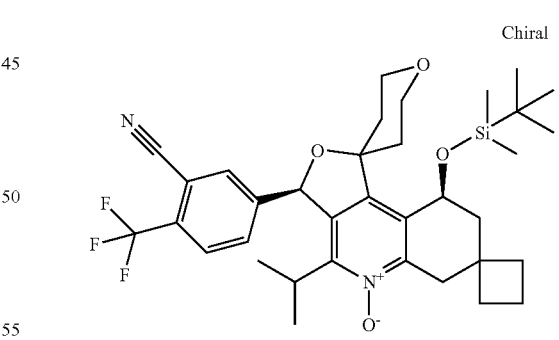

Obtained by starting from 5-((3R,9S)-9-(tert-butyldimethylsilyloxy)-4-isopropyl-7,7-(propan-1,3-diyl)-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=643 [M+H]$^+$

HPLC (Method 27): Retention time=1.70 min.

(17) (3R,9S)-9-(tert-butyldimethylsilyloxy)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]5-oxide

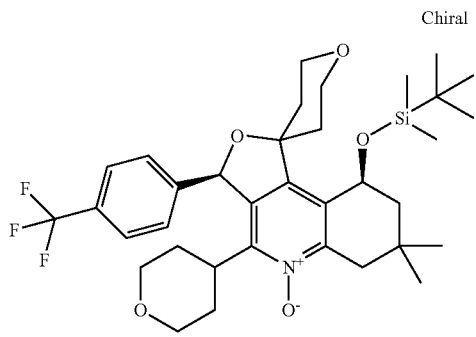 [SMILES: CC1(C)Cc2c(c3c(c(C4CCOCC4)[n+]2[O-])[C@@H](c2ccc(C(F)(F)F)cc2)OC32CCOCC2)[C@@H](O[Si](C)(C)C(C)(C)C)C1]

Obtained by starting from (3R,9S)-9-(tert-butyldimethylsilyloxy)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran].

Mass spectrometry (ESI$^+$): m/z=648 [M+H]$^+$

HPLC (Method 28): Retention time=1.52 min.

(18) (3R,9S)-9-(tert-butyldimethylsilyloxy)-7,7-dimethyl-4-(tetrahydro-2H-pyran-4-yl)-3-(4-(pentafluorosulfanyl)-2',3',5',6,6',7,8,9-octahydro-3H-spiro[furo[3,4-c]quinoline-1,4'-pyran]5-oxide

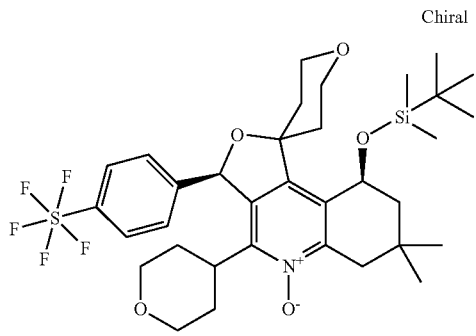 [SMILES: CC1(C)Cc2c(c3c(c(C4CCOCC4)[n+]2[O-])[C@@H](c2ccc(S(F)(F)(F)(F)F)cc2)OC32CCOCC2)[C@@H](O[Si](C)(C)C(C)(C)C)C1]

Obtained by starting from (3R,9S)-9-(tert-butyldimethylsilyloxy)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran].

Mass spectrometry (ESI$^+$): m/z=706 [M+H]$^+$

HPLC (Method 24): Retention time=1.830 min.

(19) (3R,9S)-9-(tert-butyldimethylsilyloxy)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]5-oxide

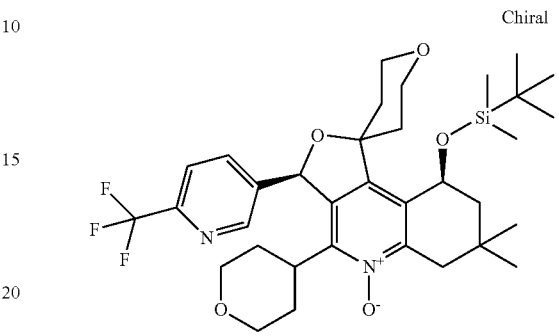

Obtained by starting from (3R,9S)-9-(tert-butyldimethylsilyloxy)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran].

Mass spectrometry (ESI$^+$): m/z=649 [M+H]$^+$

HPLC (Method 7): Retention time=1.727 min.

(20) (3R,9S)-9-(tert-butyldimethylsilyloxy)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran]5-oxide

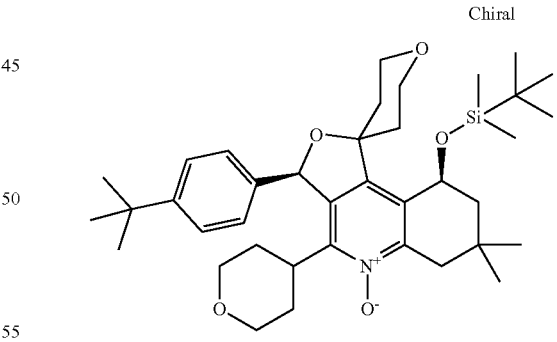

Obtained by starting from (3R,9S)-9-(tert-butyldimethylsilyloxy)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran].

Mass spectrometry (ESI$^+$): m/z=636 [M+H]$^+$

HPLC (Method 24): Retention time=1.861 min.

(21) (3R,9S)-9-(tert-butyldimethylsilyloxy)-3-(3-cyano-4-(trifluoromethyl)phenyl)-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]5-oxide

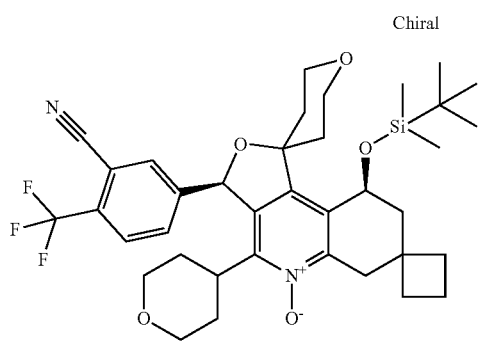 [SMILES: CC(C)(C)[Si](C)(C)O[C@H]1CC2(CCC2)Cc2c1c1c(c(C3CCOCC3)[n+]2[O-])[C@@H](c2ccc(C(F)(F)F)c(C#N)c2)OC12CCOCC2]

Obtained by starting from 5-((3R,9S)-9-(tert-butyldimethylsilyloxy)-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=685 [M+H]$^+$

HPLC (Method 28): Retention time=1.50 min.

(22) (3R,9S)-9-(tert-butyldimethylsilyloxy)-3-(3-cyano-4-(trifluoromethyl)phenyl)-4-isopropyl-7,7-dimethyl-2',3',5',6,6',7,8,9-octahydro-3H-spiro[furo[3,4-c]quinoline-1,4'-pyran]5-oxide

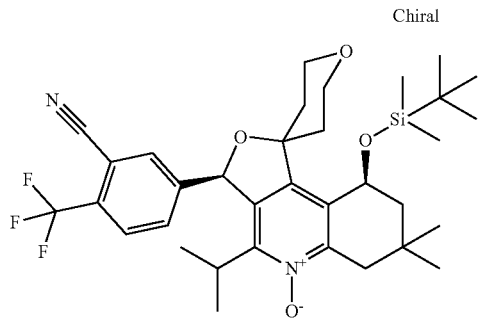 [SMILES: CC(C)c1c2c(c3c([n+]1[O-])CC(C)(C)C[C@@H]3O[Si](C)(C)C(C)(C)C)C1(CCOCC1)O[C@@H]2c1ccc(C(F)(F)F)c(C#N)c1]

Obtained by starting from 5-((3R,9S)-9-(tert-butyldimethylsilyloxy)-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=631 [M+H]$^+$

HPLC (Method 28): Retention time=1.50 min.

(23) (3S,9S)-9-(tert-butyldimethylsilyloxy)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]5-oxide

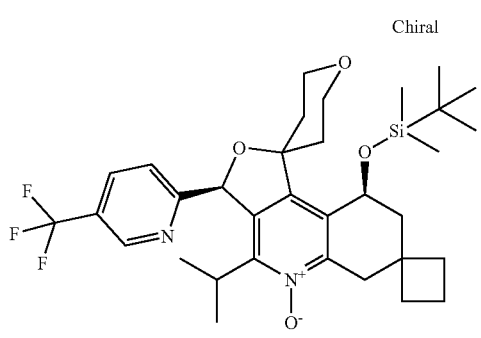 [SMILES: CC(C)c1c2c(c3c([n+]1[O-])CC1(CCC1)C[C@@H]3O[Si](C)(C)C(C)(C)C)C1(CCOCC1)O[C@@H]2c1ccc(C(F)(F)F)cn1]

Obtained by starting from (3S,9S)-9-(tert-butyldimethylsilyloxy)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran].

Mass spectrometry (ESI$^+$): m/z=619 [M+H]$^+$

HPLC (Method 13): Retention time=2.24 min.

(24) (3R,9S)-9-(tert-butyldimethylsilyloxy)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]5-oxide

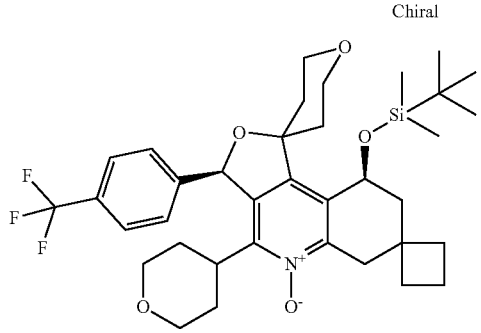 [SMILES: CC(C)(C)[Si](C)(C)O[C@H]1CC2(CCC2)Cc2c1c1c(c(C3CCOCC3)[n+]2[O-])[C@@H](c2ccc(C(F)(F)F)cc2)OC12CCOCC2]

Obtained by starting from (3R,9S)-9-(tert-butyldimethylsilyloxy)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran].

Mass spectrometry (ESI$^+$): m/z=660 [M+H]$^+$

HPLC (Method 33): Retention time=1.992 min.

Example XXXIX

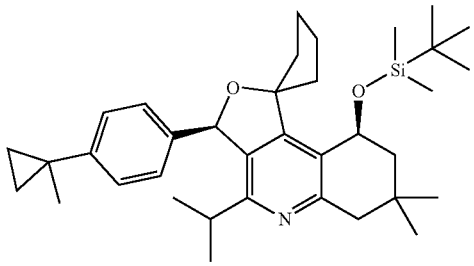

(3'R,9'S)-9'-(tert-butyldimethylsilyloxy)-4'-isopropyl-7',7'-dimethyl-3'-(4-(1-methylcyclopropyl)phenyl)-6',7',8',9'-tetrahydro-3'H-spiro[cyclopentane-1,1'-furo[3,4-c]quinoline]

43 μl of 1 M solution of diethylzinc in hexane are dissolved in 330 μl dichloromethane cooled to 0° C. and treated with a solution of 3.3 μl trifluoroacetic acid in 330 μl dichloromethane. The mixture is stirred for 20 minutes and is then treated with a solution of 3.3 μl diiodomethane in 170 μl dichloromethane. After stirring for 20 minutes a solution of 11 mg (3'R,9'S)-9'-(tert-butyldimethylsilyloxy)-4'-isopropyl-7',7'-dimethyl-3'-(4-(prop-1-en-2-yl)phenyl)-6',7',8',9'-tetrahydro-3'H-spiro[cyclopentane-1,1'-furo[3,4-c]quinoline] in 170 μl dichloromethane is added. Then the mixture is stirred for 12 hours while warming to room temperature. After cooling to 0° C. the reaction is quenched with saturated aqueous sodium bicarbonate. The aqueous phase is extracted three times with dichloromethane. The combined organic phases are washed with brine and are dried with magnesium sulphate. The solvents are evaporated in vacuo and the residue is chromatographed on silica gel (cyclohexane/ethylacetate 100:0 to 95:5).

Yield: 6 mg (53% of theory)
$R_f$-value: 0.7 (silica gel, cyclohexane/ethylacetate 9:1)

Analogously to example XXXIX the following compounds are obtained:

(1) (3'R,9'S)-9'-(tert-butyldimethylsilyloxy)-3'-(4-cyclopropylphenyl)-4'-isopropyl-7',7'-dimethyl-6',7',8',9'-tetrahydro-3'H-spiro[cyclopentane-1,1'-furo[3,4-c]quinoline]

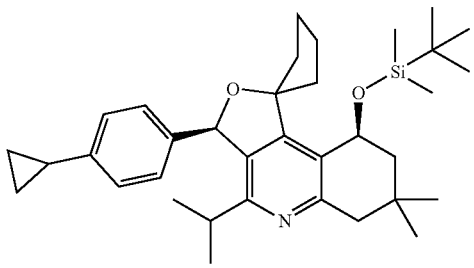

Obtained by starting from (3'R,9'S)-9'-(tert-butyldimethylsilyloxy)-4'-isopropyl-7',7'-dimethyl-3'-(4-vinylphenyl)-6',7',8',9'-tetrahydro-3'H-spiro[cyclopentane-1,1'-furo[3,4-c]quinoline].

Mass spectrometry (ESI⁺): m/z=546 [M+H]⁺
$R_f$-value: 0.71 (silica gel, cyclohexane/ethylacetate 9:1)

Example XL

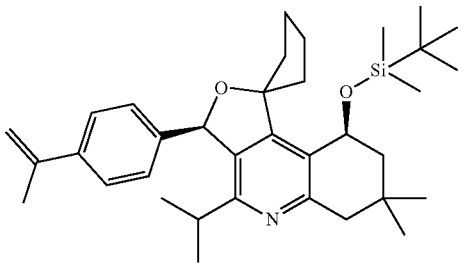

(3'R,9'S)-9'-(tert-butyldimethylsilyloxy)-4'-isopropyl-7',7'-dimethyl-3'-(4-(prop-1-en-2-yl)phenyl)-6',7',8',9'-tetrahydro-3'H-spiro[cyclopentane-1,1'-furo[3,4-c]quinoline]

25 mg 4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl trifluoromethanesulfonate are dissolved in 1 ml tetrahydrofurane. 7 mg potassium isopropenyltrifluoroborate, and 6 μl triethylamine are added. The mixture is purged for 5 minutes with argon. The 2 mg 1,1'-bis-(diphenylphosphino)-ferrocene-dichloro-palladium-(II) are added and the mixture is stirred for 6 hours at 80° C. After cooling to room temperature further 7 mg potassium isopropenyltrifluoroborate, and 6 μl triethylamine are added. The mixture is again purged for 5 minutes with argon and then stirred for 12 hours at 80° C. Then the mixture is diluted with ethylacetate and washed with water and brine. After drying with magnesium sulphate the solvents are evaporated in vacuo and the residue is chromatographed on silica gel (cyclohexane/ethylacetate 100:0 to 95:5).

Yield: 11 mg (53% of theory)
Mass spectrometry (ESI⁺): m/z=546 [M+H]⁺
$R_f$-value: 0.69 (silica gel, cyclohexane/ethylacetate 9:1)

Analogously to example XL the following compounds are obtained:

(1) (3'R,9'S)-9'-(tert-butyldimethylsilyloxy)-4'-isopropyl-7',7'-dimethyl-3'-(4-vinylphenyl)-6',7',8',9'-tetrahydro-3'H-spiro[cyclopentane-1,1'-furo[3,4-c]quinoline]

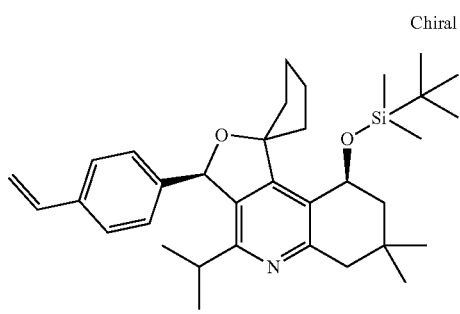 [SMILES: C=Cc1ccc([C@H]2OC3(CCCC3)c3c2c(C(C)C)nc2c3[C@@H](O[Si](C)(C)C(C)(C)C)CC(C)(C)C2)cc1]

Obtained by starting from 4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl trifluoromethanesulfonate.

Mass spectrometry (ESI⁺): m/z=532 [M+H]⁺
$R_f$-value: 0.7 (silica gel, cyclohexane/ethylacetate 9:1)

Example XLI

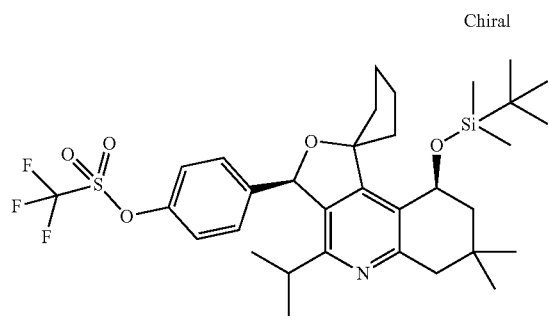 [SMILES: CC(C)c1nc2c(c3c1[C@@H](c1ccc(OS(=O)(=O)C(F)(F)F)cc1)OC31CCCC1)[C@@H](O[Si](C)(C)C(C)(C)C)CC(C)(C)C2]

4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl trifluoromethanesulfonate 56 mg 4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenol are dissolved in 3 ml dichloromethane, treated with 24 μl triethylamine, 45 mg 1,1,1-trifluoro-N-phenyl-N-(trifluoromethylsulfonyl)methanesulfonamide and 1 mg 4-dimethylamino-pyridine (DMAP) and stirred at 40° C. for 4 hours. Then the mixture is diluted with dichloromethane, washed with saturated aqueous sodium bicarbonate and dried with magnesium sulphate. After evaporation of the solvents in vacuo the residue is chromatographed on silica gel (cyclohexane/ethylacetate 100:0 to 90:10).

Yield: 25 mg (36% of theory)
Mass spectrometry (ESI⁺): m/z=654 [M+H]⁺
$R_f$-value: 0.64 (silica gel, cyclohexane/ethylacetate 9:1)

Example XLII

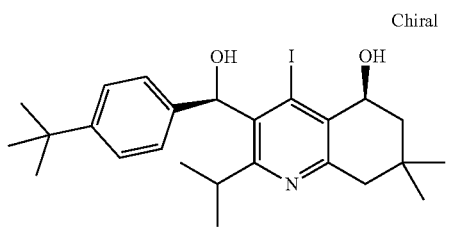 [SMILES: CC(C)c1nc2c(c(I)c1[C@H](O)c1ccc(C(C)(C)C)cc1)[C@@H](O)CC(C)(C)C2]

(S)-3-((R)-(4-tert-butylphenyl)(hydroxy)methyl)-4-iodo-2-isopropyl-7,7-dimethyl-5,6,7,8-tetrahydroquinolin-5-ol and

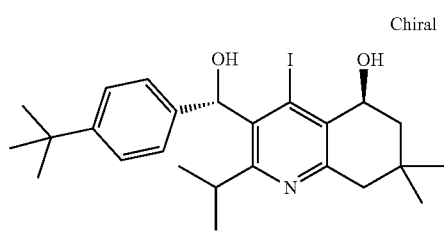 [SMILES: CC(C)c1nc2c(c(I)c1[C@@H](O)c1ccc(C(C)(C)C)cc1)[C@@H](O)CC(C)(C)C2]

(S)-3-((S)-(4-tert-butylphenyl)(hydroxy)methyl)-4-iodo-2-isopropyl-7,7-dimethyl-5,6,7,8-tetrahydroquinolin-5-ol Under nitrogen 400 mg (S)-5-hydroxy-4-iodo-2-isopropyl-7,7-dimethyl-5,6,7,8-tetrahydroquinoline-3-carbaldehyde are dissolved in 5 ml tetrahydrofurane, cooled to −50° C. and treated dropwise with 2.15 ml of a 2 M solution of 4-tert.-butylphenyl-magnesium bromide in tetrahydrofurane. After stirring for 1 hour and warming to −20° C. the reaction is recooled to −50° C. and then quenched by addition of 5 ml methanol. After raising the temperature to −10° C. saturated aqueous ammonium chloride is added. The mixture is twice extracted with ethylacetate. The combined organic phases are washed with water and dried with sodium sulphate. The solvents are evaporated in vacuo and the residue is chromatographed on silica gel (hexane/ethylacetate 4:1).

(S)-3-((R)-(4-tert-butylphenyl)(hydroxy)methyl)-4-iodo-2-isopropyl-7,7-dimethyl-5,6,7,8-tetrahydroquinolin-5-ol:
Yield: 360 mg (66% of theory)
Mass spectrometry (ESI⁺): m/z=508 [M+H]⁺
HPLC (Method 8): Retention time=0.83 min.
and
(S)-3-((S)-(4-tert-butylphenyl)(hydroxy)methyl)-4-iodo-2-isopropyl-7,7-dimethyl-5,6,7,8-tetrahydroquinolin-5-ol:
Yield: 80 mg (15% of theory)
Mass spectrometry (ESI⁺): m/z=508 [M+H]⁺
HPLC (Method 8): Retention time=0.75 min.

Example XLIII

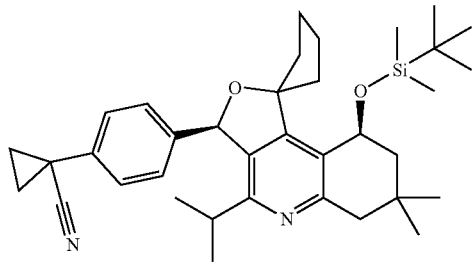

1-(4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)cyclopropanecarbonitrile 15 mg 2-(4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)acetonitrile, 0.4 mg triethylbenzylammonium chloride and 7.2 μl dibromoethane are dissolved in 20 μl dichloromethane and 20 μl of a 50% aqueous sodium hydroxide solution. The mixture is stirred for 12 hours at room temperature. Then 1 mg triethylbenzylammonium chloride, 50 μl dichloromethane and 14 μl dibromoethane are added and stirring is continued for 5 hours. Again 14 μl dibromoethane are added and the mixture is stirred for 48 hours. Afterwards the mixture is diluted with ethylacetate and washed three times with water and with brine. After drying with magnesium sulphate the solvents are evaporated in vacuo. The crude product (10 mg) is directly used in the next step.

$R_f$-value: 0.45 (silica gel, cyclohexane/ethylacetate 4:1)

Example XLIV

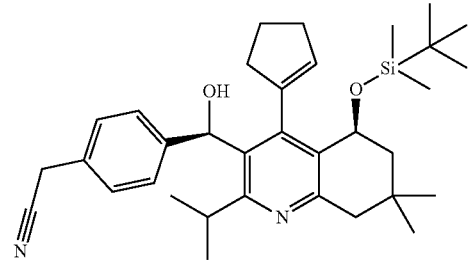

2-(4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)phenyl)acetonitrile 130 mg 4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)benzyl methanesulfonate are dissolved in 3 ml N,N-dimethylformamide. 25 mg sodium cyanide are added and the mixture is stirred for 48 hours at room temperature. Further 13 mg sodium cyanide are added and the mixture is stirred for 3 hours at 80° C. The solvent is evaporated in vacuo and the residue is diluted with ethylacetate. After washing twice with water and with brine the organic phase is dried with magnesium sulphate. The solvents are evaporated in vacuo and the residue is chromatographed on silica gel (cyclohexane/ethylacetate 100:0 to 60:40).

Yield: 57 mg (49% of theory)

Mass spectrometry (ESI+): m/z=545 [M+H]+

$R_f$-value: 0.7 (silica gel, cyclohexane/ethylacetate 2:1)

Example XLV

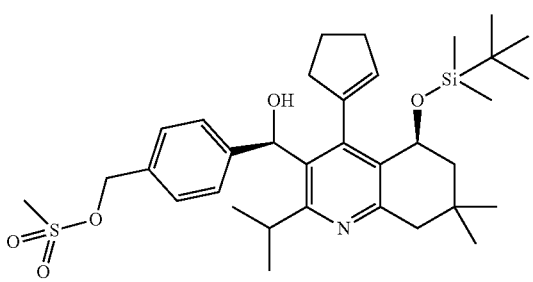

4-((R)—((S)-5-(tert-butyldimethylsilyloxy)-4-cyclopentenyl-2-isopropyl-7,7-dimethyl-5,6,7,8-tetrahydroquinolin-3-yl)(hydroxy)methyl)benzyl methanesulfonate 113 mg (R)—((S)-5-(tert-butyldimethylsilyloxy)-4-cyclopentenyl-2-isopropyl-7,7-dimethyl-5,6,7,8-tetrahydroquinolin-3-yl)(4-(hydroxymethyl)phenyl)methanol are dissolved in 2 ml dichloromethane and cooled to 0° C. Successively 17 μl methanesulfonyl chloride and a solution of 38 μl N,N-diisopropyl-N-ethyl-amine in 1 ml dichloromethane are added dropwise. The mixture is stirred for 2 hours and further 17 μl methanesulfonyl chloride and a solution of 38 μl N,N-diisopropyl-N-ethyl-amine in 1 ml dichloromethane are added successively. The mixture is stirred for 1 hour and then the solvent is evaporated in vacuo. The crude product (130 mg) is directly used in the next step.

$R_f$-value: 0.8 (silica gel, cyclohexane/ethylacetate 1:1)

Example XLVI

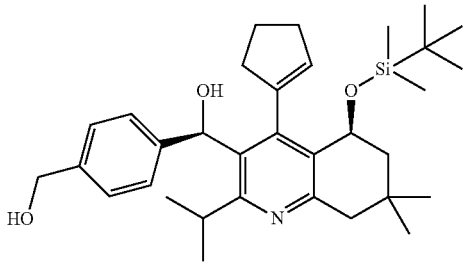

(R)—((S)-5-(tert-butyldimethylsilyloxy)-4-cyclopen-
tenyl-2-isopropyl-7,7-dimethyl-5,6,7,8-tetrahydro-
quinolin-3-yl)(4-(hydroxymethyl)phenyl)methanol and

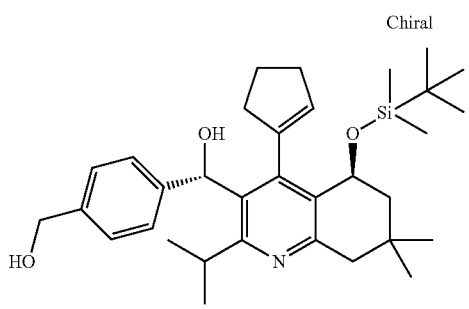 [SMILES: CC(C)c1nc2c(c(C3=CCCC3)c1[C@@H](O)c1ccc(CO)cc1)[C@@H](O[Si](C)(C)C(C)(C)C)CC(C)(C)C2]

(S)—((S)-5-(tert-butyldimethylsilyloxy)-4-cyclopen-
tenyl-2-isopropyl-7,7-dimethyl-5,6,7,8-tetrahydro-
quinolin-3-yl)(4-(hydroxymethyl)phenyl)methanol 410 mg (S)-ethyl 4-(5-(tert-butyldimethylsilyloxy)-4-cy-clopentenyl-2-isopropyl-7,7-dimethyl-5,6,7,8-tetrahydro-quinoline-3-carbonyl)benzoate are dissolved in 5 ml tetrahydrofurane and treated dropwise with 1.5 ml of a 1 M solution of lithiumaluminium hydride in tetrahydrofurane. The mixture is stirred for 8 hours at room temperature, cooled to 0° C. and the reaction is quenched by careful addition of 130 μl water and 130 μl of 4 M aqueous sodium hydroxide. After diluting with ethylacetate the mixture is dried with magnesium sulphate and filtered. The solvents are evaporated in vacuo and the residue is chromatographed on silica gel (cyclohexane/ethylacetate 100:0 to 60:40).

(R)—((S)-5-(tert-butyldimethylsilyloxy)-4-cyclopente-nyl-2-isopropyl-7,7-dimethyl-5,6,7,8-tetrahydroquinolin-3-yl)(4-(hydroxymethyl)phenyl)methanol:

Yield: 113 mg (30% of theory)
Mass spectrometry (ESI$^+$): m/z=536 [M+H]$^+$
HPLC (Method 2): Retention time=1.716 min.
R$_f$-value: 0.41 (silica gel, cyclohexane/ethylacetate 2:1)

(S)—((S)-5-(tert-butyldimethylsilyloxy)-4-cyclopente-nyl-2-isopropyl-7,7-dimethyl-5,6,7,8-tetrahydroquinolin-3-yl)(4-(hydroxymethyl)phenyl)methanol:

Yield: 147 mg (39% of theory)
Mass spectrometry (ESI$^+$): m/z=536 [M+H]$^+$
HPLC (Method 2): Retention time=1.705 min.
R$_f$-value: 0.036 (silica gel, cyclohexane/ethylacetate 2:1)

Analogously to example XLVI the following compounds are obtained:

(1) (R)—((S)-5-(tert-butyldimethylsilyloxy)-4-iodo-
2-isopropyl-7,7-dimethyl-5,6,7,8-tetrahydroquinolin-
3-yl)(6-(trifluoromethyl)pyridin-3-yl)methanol

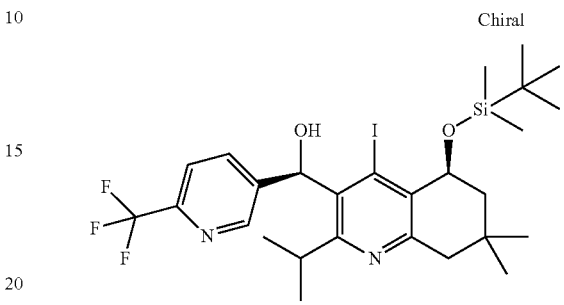

Obtained by starting from (S)-(5-(tert-butyldimethylsily-loxy)-4-iodo-2-isopropyl-7,7-dimethyl-5,6,7,8-tetrahydro-quinolin-3-yl)(6-(trifluoromethyl)pyridin-3-yl)methanone. Lithiumaluminium hydride is added at −10° C. The reaction is run for 1.5 hours at 0° C. The product is used directly in the next step.

Example XLVII

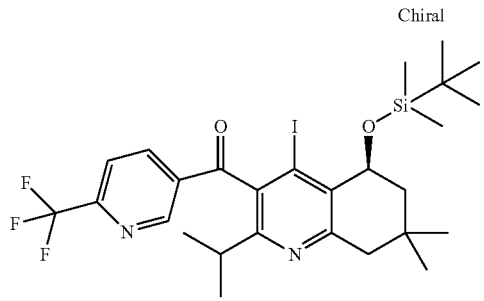 [SMILES: CC(C)c1nc2c(c(I)c1C(=O)c1ccc(C(F)(F)F)nc1)[C@@H](O[Si](C)(C)C(C)(C)C)CC(C)(C)C2]

(S)-(5-(tert-butyldimethylsilyloxy)-4-iodo-2-isopro-
pyl-7,7-dimethyl-5,6,7,8-tetrahydroquinolin-3-yl)(6-
(trifluoromethyl)pyridin-3-yl)methanone 1.3 g (S)—((S)-5-(tert-butyldimethylsilyloxy)-4-iodo-2-isopropyl-7,7-dimethyl-5,6,7,8-tetrahydroquinolin-3-yl)(6-(trifluoromethyl)pyridin-3-yl)methanol are dissolved in 20 ml dichloromethane, cooled to 0° C. and mixed with 1.13 g 1,1-dihydro-1,1,1-triacetoxy-1,2-benziodoxol-3(1H)-on (Dess-Martin-Periodinan). The mixture is stirred for 12 hours while warming to room temperature. 10 ml of a solution of sodium hydrogensulfite (10%) and 10 ml of a saturated solution of sodium hydrogencarbonate are added. The mixture is stirred vigorously for 15 minutes. The organic phase is separated and dried with sodium sulphate. The solvent is evaporated in vacuo and the crude product is used directly in the next step.

Yield: 1.24 g (96% of theory)
Mass spectrometry (ESI$^+$): m/z=633 [M+H]$^+$
HPLC (Method 13): Retention time=2.96 min.

Example XLVIII

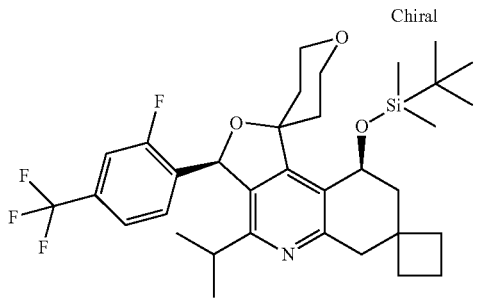 [SMILES: CC(C)c1nc2c(c3c1[C@@H](c1ccc(C(F)(F)F)cc1F)OC31CCOCC1)[C@@H](O[Si](C)(C)C(C)(C)C)CC1(CCC1)C2]

(3S,9S)-9-(tert-butyldimethylsilyloxy)-3-(2-fluoro-4-(trifluoromethyl)phenyl)-4-isopropyl-7,7-(propan-1,3-diyl)-2',3',5',6,6',7,8,9-octahydro-3H-spiro[furo[3,4-c]quinoline-1,4'-pyran]

92 mg (3S,9S)-9-(tert-butyldimethylsilyloxy)-3-(2-fluoro-4-(trifluoromethyl)phenyl)-3'-iodo-4-isopropyl-7,7-(propan-1,3-diyl)-2',3',5',6,6',7,8,9-octahydro-3H-spiro[furo[3,4-c]quinoline-1,4'-pyran] are dissolved in 5 ml methanol. 36 µl triethylamine and 13 mg 10% palladium on charcoal are added and the mixture is hydrogenated at 3 bar for 3 hours. The catalyst is then removed by filtration and the solvents are evaporated in vacuo. The residue is taken up in 50 ml dichloromethane and cooled to 0° C. 165 µl Trifluoroacetic acid and 35 µl triethylsilane are added. Then the temperature is raised to room temperature and the mixture is stirred for 6 hours. The solvents are evaporated in vacuo and the residue is partitioned between dichloromethane and saturated aqueous sodium bicarbonate solution. After drying the organic phase with magnesium sulphate the solvents are evaporated in vacuo to obtain the product, Yield: 60 mg (79% of theory)
Mass spectrometry (ESI⁺): m/z=620 [M+H]⁺
HPLC (Method 9): Retention time=2.86 min.

Analogously to example XLVIII the following compounds are obtained:

(1) (3R,9S)-9-(tert-butyldimethylsilyloxy)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]

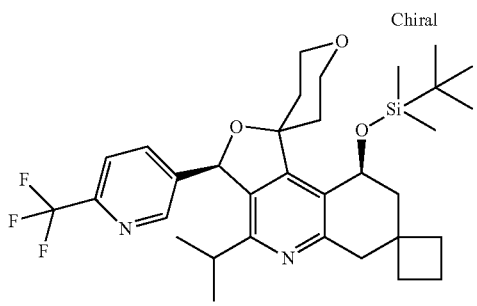 [SMILES: CC(C)c1nc2c(c3c1[C@@H](c1ccc(C(F)(F)F)nc1)OC31CCOCC1)[C@@H](O[Si](C)(C)C(C)(C)C)CC1(CCC1)C2]

Obtained by starting from (3R,9S)-9-(tert-butyldimethylsilyloxy)-3'-iodo-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]. 10% palladium hydroxide on charcoal is used instead of 10% palladium on charcoal.

Mass spectrometry (ESI⁺): m/z=603 [M+H]⁺
HPLC (Method 30): Retention time=1.45 min.

(2) (3S,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]

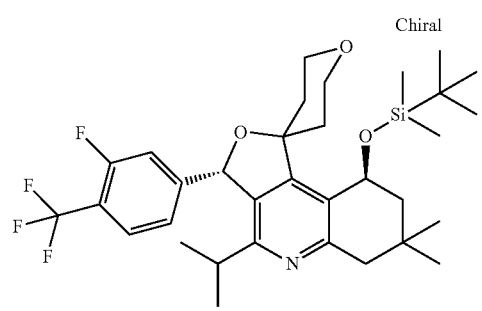 [SMILES: CC(C)c1nc2c(c3c1[C@H](c1ccc(C(F)(F)F)c(F)c1)OC31CCOCC1)[C@@H](O[Si](C)(C)C(C)(C)C)CC(C)(C)C2]

Obtained by starting from (3S,9S)-9-(tert-butyldimethylsilyloxy)-3-(3-fluoro-4-(trifluoromethyl)phenyl)-3'-iodo-4-isopropyl-7,7-dimethyl-2',3',5',6,6',7,8,9-octahydro-3H-spiro[furo[3,4-c]quinoline-1,4'-pyran]. 10% palladiumhydroxide on charcoal is used instead of 10% palladium on charcoal.

Mass spectrometry (ESI⁺): m/z=608 [M+H]⁺
HPLC (Method 30): Retention time=2.06 min.

Example XLIX

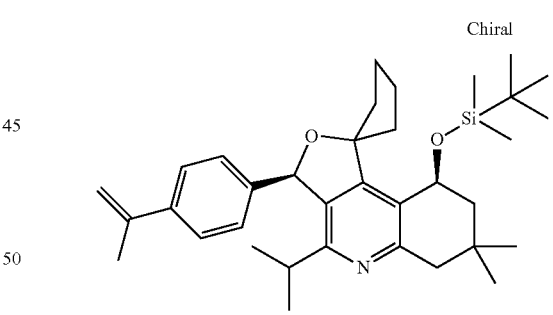

(3'R,9'S)-9'-(tert-butyldimethylsilyloxy)-3'-(4-(2-fluoropropan-2-yl)phenyl)-4'-isopropyl-7',7'-dimethyl-6',7',8',9'-tetrahydro-3'H-spiro[cyclopentane-1,1'-furo[3,4-c]quinoline]

22 mg 2-(4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)propan-2-ol are dissolved in 1 ml dichloromethane and cooled to 0° C. Then 50 mg bis(2-methoxyethyl)amino]sulfur-trifluoride (BAST) are added and the mixture is stirred for 2 hours at room temperature. After cooling to −40° C. methanol (1 ml) is added. The mixture is stirred for 5 minutes and then the solvent is evaporated in vacuo. The residue is chromatographed on silica gel (petrole ether/ethylacetate 95:5 to 50:50).

Yield: 11 mg (50% of theory)
Mass spectrometry (ESI$^+$): m/z=566 [M+H]$^+$
HPLC (Method 1): Retention time=4.418 min.
R$_f$-value: 0.72 (silica gel, petrole ether/ethylacetate 8:1)

Example L

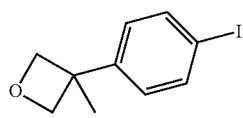

3-(4-iodophenyl)-3-methyloxetane

In a microwave vial 1.21 g 2-(4-iodophenyl)-2-methylpropane-1,3-diol are dissolved in 8 ml tetrahydrofurane and treated with 1.6 g triphenylphosphine and 1.1 g 1,1'-(azodicarbonyl)dipiperidine. The mixture is heated to 120° C. for 24 hours. Then the solvent is evaporated in vacuo and the residue is chromatographed on silica gel (petrole ether/ethylacetate 95:5 to 40:60).

Yield: 180 mg (16% of theory)
HPLC (Method 24): Retention time=1.424 min.
R$_f$-value: 0.45 (silica gel, petrole ether/ethylacetate 4:1)

Example LI

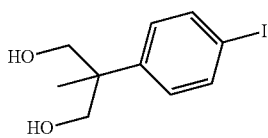

2-(4-iodophenyl)-2-methylpropane-1,3-diol 3.1 g Diethyl 2-(4-iodophenyl)-2-methylmalonate are dissolved in 50 ml dichloromethane and cooled to −78° C. 50 ml of a 1 M solution of diisobutylaluminium hydride in dichloromethane are added dropwise and the mixture is warmed to −10° C. during 5 hours. Then 0.9 ml water and 0.9 ml of a 4 M solution of sodium hydroxide in water are added successively under cooling. The mixture is stirred vigorously for 10 minutes and is then partitioned between 600 ml ethylacetate and 500 ml of a 0.5 M hydrochloric acid. The organic phase is washed with brine and dried with magnesium sulphate. The solvents are evaporated in vacuo and the residue is chromatographed on silica gel (petrole ether/ethylacetate 40:60 to 0:100).

Yield: 1.56 g (65% of theory)
Mass spectrometry (ESI$^+$): m/z=310 [M+NH$_4$]$^+$

Example LII

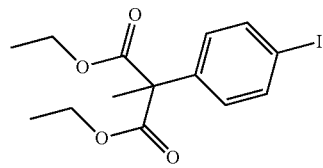 [SMILES: CCOC(=O)C(C)(C(=O)OCC)c1ccc(I)cc1]

Diethyl 2-(4-iodophenyl)-2-methylmalonate 3.7 g Diethyl 2-(4-aminophenyl)-2-methylmalonate are dissolved under cooling in an ethanol-icewater-bath in 5 ml concentrated hydrochloric acid. The mixture is diluted with 5 ml water and stirred for 10 minutes. The a solution of 970 mg sodium nitrite in water is added dropwise and stirring is continued for further 10 minutes. The so formed diazonium salt solution is added at −10° C. dropwise to a solution of 6 g potassium iodide in water. The mixture is stirred for 15 minutes at −10° C. and for 1 hour at room temperature. Afterwards it is diluted with diethylether and washed with a solution of sodium thiosulphate in water (10%). After drying with magnesium sulphate the solvents are evaporated in vacuo. The residue is chromatographed on silica gel (cyclohexane/ethylacetate 90:10 to 70:30).

Yield: 3.13 g (57% of theory)
Mass spectrometry (ESI$^+$): m/z=377 [M+NH$_4$]$^+$
HPLC (Method 7): Retention time=1.592 min.

Example LIII

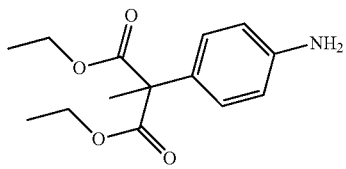 [SMILES: CCOC(=O)C(C)(C(=O)OCC)c1ccc(N)cc1]

Diethyl 2-(4-aminophenyl)-2-methylmalonate

To a solution of 4.98 g Diethyl 2-methyl-2-(4-nitrophenyl) malonate in 70 ml methanol are added 896 mg of 10% palladium on charcoal. The mixture is hydrogenated at 2 bar for 3 hours. After filtration the solvent is evaporated in vacuo and the residue is chromatographed on silica gel (cyclohexane/ethylacetate 90:10 to 50:50).

Yield: 4.34 g (97% of theory)
Mass spectrometry (ESI$^+$): m/z=266 [M+H]$^+$
HPLC (Method 7): Retention time=0.908 min.

Example LIV

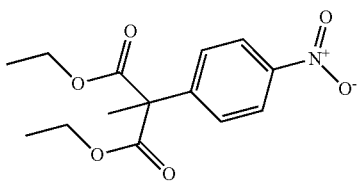 [SMILES: CCOC(=O)C(C)(C(=O)OCC)c1ccc([N+](=O)[O-])cc1]

Diethyl 2-methyl-2-(4-nitrophenyl)malonate 1.7 g sodium hydride (60% in mineral oil) are suspended in 10 ml dimethylsulfoxide at 0° C. The a solution of 6.4 ml diethyl 2-methylmalonate in 10 ml dimethylsulfoxide is added dropwise. The mixture is stirred for 30 minutes and then diluted with 20 ml dimethylsulfoxide. After stirring for further 2 hours a solution of 5 g 4-fluoronitrobenzene is added dropwise. The mixture is stirred for 12 hours while warming to room temperature. Then it is partitioned between icewater and ethylacetate. The aqueous phase is twice extracted with ethylacetate and the combined organic phases are washed with brine. After drying with magnesium sulphate the solvents are evaporated in vacuo. The residue is chromatographed on silica gel (cyclohexane/ethylacetate 90:10 to 50:50).

Yield: 5.14 g (50% of theory)

Mass spectrometry (ESI$^+$): m/z=296 [M+H]$^+$

HPLC (Method 2): Retention time=1.907 min.

Example LV

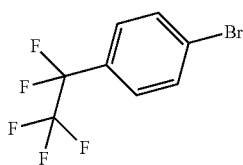 [SMILES: FC(F)(F)C(F)(F)c1ccc(Br)cc1]

1-Bromo-4-(perfluoroethyl)benzene

Under argon in a microwave vial 2 g 1-bromo-4-iodobenzene, 3.3 g trimethyl(perfluoroethyl)silane, 493 mg potassium fluoride and 2 g copper iodide are suspended in 10 ml N,N-dimethylformamide. The mixture is heated for 12 hours at 80° C. Further 3.3 g trimethyl(perfluoroethyl)silane are added and heating is continued for 48 hours. Then the mixture is partitioned between 2 M ammonia and diethylether. The aqueous phase is twice extracted with diethylether. The combined organic phases are washed three times with water and dried with magnesium sulphate. The solvent is evaporated in vacuo (300 mbar, temperature of water bath 50° C.). The residue is chromatographed on silica gel (dichloromethane).

Yield: 1.48 g (76% of theory)

HPLC (Method 25): Retention time=4.765 min.

Example LVI

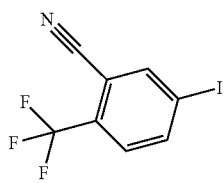 [SMILES: N#Cc1cc(I)ccc1C(F)(F)F]

5-Iodo-2-(trifluoromethyl)benzonitrile

In a microwave vial 2.24 g 5-bromo-2-(trifluoromethyl)benzonitrile are dissolved in 10 ml 1,4-dioxane. 90 mg copper-(I)-iodide and 2.7 g sodium iodide are added and the mixture is purged for 5 minutes with argon. 142 µl trans-N,N'-dimethylcyclohexane-1,2-diamine and 1.9 ml hexamethyldisilazane are added and the mixture is heated for 6 hours to 110° C. The mixture is diluted in 100 ml 4 M hydrochloric acid and stirred for 10 minutes. This aqueous phase is three times extracted with dichloromethane. The combined organic phases are washed with brine and dried with magnesium sulphate. The solvents are evaporated in vacuo and the residue is chromatographed on silica gel (cyclohexane/ethylacetate 85:15).

Yield: 2.35 g (88% of theory)

HPLC (Method 7): Retention time=1.288 min.

Example LVII

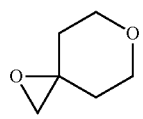

1,6-Dioxaspiro[2.5]octane

Under nitrogen 6.6 g sodiumhydride (60% in mineral oil) are suspended in 90 ml tetrahydrofurane and cooled to 0° C. 91.7 Trimethylsulfonium iodide are added in portions. To this mixture a solution of 15 g dihydro-2H-pyran-4(3H)-one in 300 ml dimethylsulfoxide and 60 ml tetrahydrofurane is added dropwise. Afterwards the mixture is warmed to room temperature and stirred for 18 hours. The mixture is then poured into 1.2 l icewater and extracted for three times with diethylether. The combined organic phases are washed with brine and dried with sodium sulphate. Evaporation of the solvents in vacuo gives the product.

Yield: 10.15 g (59% of theory)

R$_f$-value: 0.47 (silica gel, petrole ether/ethylacetate 1:1)

Example LVIII

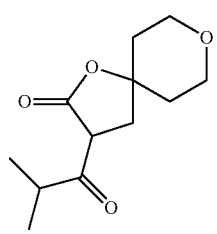 [SMILES: CC(C)C(=O)C1CC2(CCOCC2)OC1=O]

3-Isobutyryl-1,8-dioxaspiro[4.5]decan-2-one 6.6 g 1,6-Dioxaspiro[2.5]octane and 8.2 ml methyl 4-methyl-3-oxopentanoate are dissolved in 30 ml ethanol, cooled to 0° C. and treated in portions with 3.9 g sodium ethoxide. After completion of the addition the mixture is warmed to room temperature and stirred for 18 hours. Then the mixture is poured in 200 ml ice water, acidified to pH 3 by addition of 1 M hydrochloric acid and extracted for three times with ethylacetate. The combined organic phases are dried with sodium sulphate and the solvents are evaporated in vacuo. The residue is chromatographed on silica gel (petrole ether/ethylacetate 100:0 to 50:50).

Yield: 3.93 g (33% of theory)
Mass spectrometry (ESI$^+$): m/z=227 [M+H]$^+$
HPLC (Method 5): Retention time=0.952 min.

Analogously to example LVIII the following compounds are obtained:

(1) Ethyl 2-oxo-1,8-dioxaspiro[4.5]decane-3-carboxylate

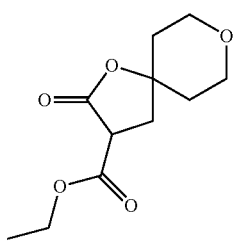 [SMILES: CCOC(=O)C1CC2(CCOCC2)OC1=O]

Obtained by starting from 1,6-dioxaspiro[2.5]octane and diethyl-malonate.
Mass spectrometry (ESI$^+$): m/z=229 [M+H]$^+$
R$_f$-value: 0.3 (silica gel, petrole ether/ethylacetate 1:1)

Example LIX

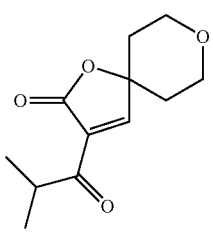 [SMILES: CC(C)C(=O)C1=CC2(CCOCC2)OC1=O]

3-Isobutyryl-1,8-dioxaspiro[4.5]dec-3-en-2-one 2.16 g 4-Methoxypyridine-1-oxide hydrate and 5.57 g 2-iodoxybenzoic acid (45 wt-%) are suspended in 20 ml dimethylsulfoxide and stirred for 20 minutes until all material has dissolved. Then 3.0 g 3-isobutyryl-1,8-dioxaspiro[4.5]decan-2-one are added and the mixture is stirred for 24 hours. The mixture is diluted with saturated solution of sodium bicarbonate in water and the formed precipitate is filtered off. The mother liquor is extracted for three times with ethylacetate. The combined organic phases are dried with sodium sulphate and the solvents are evaporated in vacuo. The residue is chromatographed on silica gel (petrole ether/ethylacetate 100:0 to 40:60).

Yield: 1.0 g (34% of theory)
Mass spectrometry (ESI$^+$): m/z=225 [M+H]$^+$
HPLC (Method 5): Retention time=0.899 min.

Analogously to example LIX the following compounds are obtained:

(1) Ethyl 2-oxo-1,8-dioxaspiro[4.5]dec-3-ene-3-carboxylate

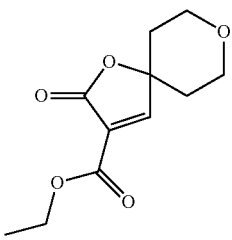 [SMILES: CCOC(=O)C1=CC2(CCOCC2)OC1=O]

Obtained by starting from ethyl 2-oxo-1,8-dioxaspiro[4.5]decane-3-carboxylate.
Mass spectrometry (ESI$^+$): m/z=227 [M+H]$^+$
R$_f$-value: 0.31 (silica gel, petrole ether/ethylacetate 1:1)

Example LX

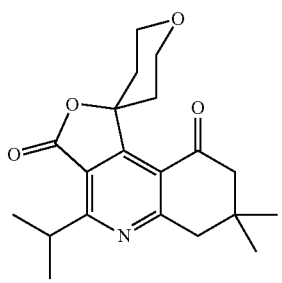 [SMILES: CC(C)c1nc2c(c3c1C(=O)OC31CCOCC1)C(=O)CC(C)(C)C2]

4-Isopropyl-7,7-dimethyl-2',3',5',6',7,8-hexahydro-3H-spiro[furo[3,4-c]quinoline-1,4'-pyran]-3,9(6H)-dione 3.12 g 3-Isobutyryl-1,8-dioxaspiro[4.5]dec-3-en-2-one and 2.13 g 3-amino-5,5-dimethylcyclohex-2-enone are mixed and heated to 200° C. for 10 minutes under a vacuo of 20 mbar. The mixture is cooled to room temperature, 15 ml ethylacetate are added and the mixture is stirred for 30 minutes. Then 15 ml petrole ether are added and the precipitate is isolated by filtration. The crude product is dissolved in 350 ml dichloromethane, treated with 2.46 g 2,3dichloro-5,6-dicyano-p-benzoquinone and stirred for 18 hours. 2 g Ascorbic acid are added and the mixture is stirred for 10 minutes. The it is washed for three times with water. The organic phase is dried with sodium sulphate and the solvents are evaporated in vacuo. The residue is chromatographed on silica gel (petrole ether/ethylacetate 100:0 to 50:50).

Yield: 2.55 g (53% of theory)
Mass spectrometry (ESI$^+$): m/z=344 [M+H]$^+$
HPLC (Method 5): Retention time=1.546 min.

Example LXI

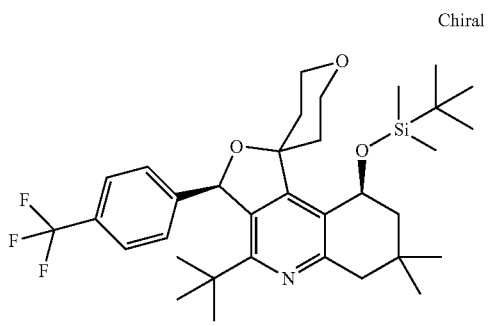 [SMILES: CC1(C)Cc2nc(C(C)(C)C)c3c(c2[C@@H](O[Si](C)(C)C(C)(C)C)C1)C1(CCOCC1)O[C@@H]3c1ccc(C(F)(F)F)cc1]

(3R,9S)-4-tert-Butyl-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]

30 mg (3R,9S)-9-(tert-butyldimethylsilyloxy)-7,7-dimethyl-4-(1-methylcyclopropyl)-3-(4-(trifluoromethyl)phenyl)-2',3',5',6,6',7,8,9-octahydro-3H-spiro[furo[3,4-c]quinoline-1,4'-pyran] are dissolved in 3 ml acetic acid and 1 ml acetic acid anhydride. 30 mg Platinum-(IV)-oxide are added and the mixture is hydrogenated for 2 hours at 60° C. and 3 bar. The catalyst is filtered off and washed with methanol. The liquid phases are combined and the solvents are evaporated in vacuo. The residue is chromatographed on silica gel (petrole ether/ethylacetate 100:0 to 90:10).

Yield: 10 mg (33% of theory)
Mass spectrometry (ESI$^+$): m/z=604 [M+H]$^+$
HPLC (Method 5): Retention time=2.022 min.

Example LXII

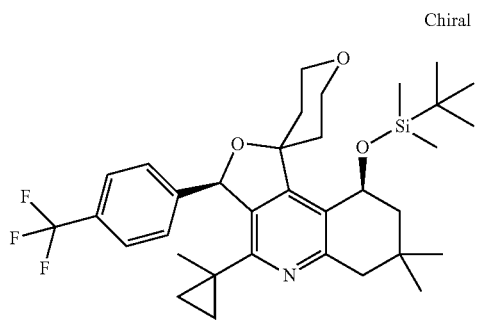 [SMILES: CC1(C)Cc2nc(C3(C)CC3)c3c(c2[C@@H](O[Si](C)(C)C(C)(C)C)C1)C1(CCOCC1)O[C@@H]3c1ccc(C(F)(F)F)cc1]

(3R,9S)-9-(tert-Butyldimethylsilyloxy)-7,7-dimethyl-4-(1-methylcyclopropyl)-3-(4-(trifluoromethyl)phenyl)-2',3',5',6,6',7,8,9-octahydro-3H-spiro[furo[3,4-c]quinoline-1,4'-pyran]

536 µl Diethylzinc (1 M in n-hexane) are dissolved in 5 ml dichloromethane, cooled to 0° C. and treated dropwise with a solution of 41 µl trifluoroacetic acid in 5 ml dichloromethane. The mixture is stirred for 20 minutes and then 41 µl diiodomethane in 2.5 ml dichloromethane are added dropwise. After stirring for further 20 minutes a solution of 150 mg (3R,9S)-9-(tert-butyldimethylsilyloxy)-7,7-dimethyl-4-(prop-1-en-2-yl)-3-(4-(trifluoromethyl)phenyl)-2',3',5',6,6',7,8,9-octahydro-3H-spiro[furo[3,4-c]quinoline-1,4'-pyran] in 2.5 ml dichloromethane are added dropwise. The mixture is then allowed to warm to room temperature and is stirred for 4 hours. Then it is partitioned between saturated solution of sodium bicarbonate in water and dichloromethane. The aqueous phase is twice extracted with dichloromethane. The combined organic phases are dried with sodium sulphate and the solvents are evaporated in vacuo. The residue is chromatographed on silica gel (petrole ether/ethylacetate 100:0 to 85:15).

Yield: 130 mg (85% of theory)
Mass spectrometry (ESI$^+$): m/z=602 [M+H]$^+$
HPLC (Method 5): Retention time=1.907 min.

Example LXIII

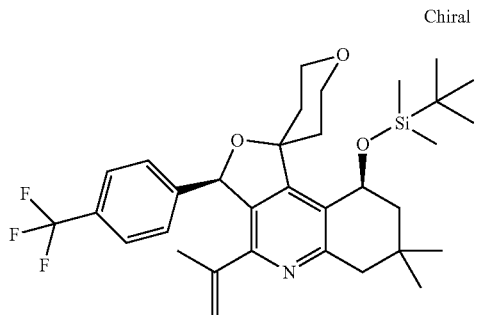 [SMILES: C=C(C)c1nc2c(c3c1[C@@H](c1ccc(C(F)(F)F)cc1)OC31CCOCC1)[C@@H](O[Si](C)(C)C(C)(C)C)CC(C)(C)C2]

(3R,9S)-9-(tert-Butyldimethylsilyloxy)-7,7-dimethyl-4-(prop-1-en-2-yl)-3-(4-(trifluoromethyl)phenyl)-2',3',5',6',7,8,9-octahydro-3H-spiro[furo[3,4-c]quinoline-1,4'-pyran]

500 mg (3R,9S)-9-(tert-butyldimethylsilyloxy)-4-chloro-7,7-dimethyl-3-(4-(trifluoromethyl)phenyl)-2',3',5',6,6',7,8,9-octahydro-3H-spiro[furo[3,4-c]quinoline-1,4'-pyran] and 254 mg potassium isopropenyltrifluoroborate are dissolved in 3 ml tetrahydrofurane, 0.5 ml toluene and 3 ml of a 2 M solution of caesium carbonate in water. The mixture is purged for 15 minutes with argon. Then 42 mg 1,1'-bis-(diphenylphosphino)-ferrocene-dichloro-palladium-(II) complex with dichloromethane are added and the mixture is stirred for 72 hours at 100° C. The mixture is partitioned between water and dichloromethane. The aqueous phase is twice extracted with dichloromethane. The combined organic phases are dried with sodium sulphate and the solvents are evaporated in vacuo. The residue is chromatographed on silica gel (petrole ether/ethylacetate 100:0 to 90:10).

Yield: 470 mg (93% of theory)
Mass spectrometry (ESI$^+$): m/z=588 [M+H]$^+$
HPLC (Method 5): Retention time=1.936 min.

Example LXIV

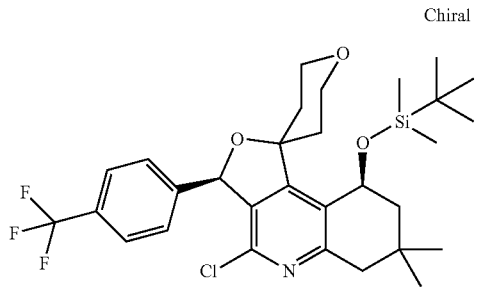 [SMILES: CC1(C)Cc2nc(Cl)c3c(c2[C@@H](O[Si](C)(C)C(C)(C)C)C1)C1(CCOCC1)O[C@@H]3c1ccc(C(F)(F)F)cc1]

(3R,9S)-9-(tert-Butyldimethylsilyloxy)-4-chloro-7,7-dimethyl-3-(4-(trifluoromethyl)phenyl)-2',3',5',6,6',7,8,9-octahydro-3H-spiro[furo[3,4-c]quinoline-1,4'-pyran]

and

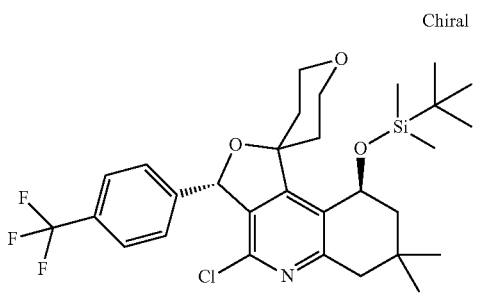 [SMILES: CC1(C)Cc2nc(Cl)c3c(c2[C@@H](O[Si](C)(C)C(C)(C)C)C1)C1(CCOCC1)O[C@H]3c1ccc(C(F)(F)F)cc1]

(3S,9S)-9-(tert-Butyldimethylsilyloxy)-4-chloro-7,7-dimethyl-3-(4-(trifluoromethyl)phenyl)-2',3',5',6,6',7,8,9-octahydro-3H-spiro[furo[3,4-c]quinoline-1,4'-pyran]

1.32 g (9S)-9-(tert-butyldimethylsilyloxy)-4-chloro-7,7-dimethyl-3-(4-(trifluoromethyl)phenyl)-2',3',5',6,6',7,8,9-octahydro-3H-spiro[furo[3,4-c]quinoline-1,4'-pyran]-3-ol and 2.9 ml triethylsilane are dissolved in 40 ml dichloromethane, cooled to −50° C. and treated dropwise with 4.4 ml of a 1 m solution of titanium-(IV)-chloride in dichloromethane. Then the mixture is allowed to warm to room temperature and stirred for 30 minutes. The mixture is partitioned between saturated solution of sodium bicarbonate in water and dichloromethane. The aqueous phase is twice extracted with dichloromethane. The combined organic phases are dried with sodium sulphate and the solvents are evaporated in vacuo. The residue is chromatographed on silica gel (petrole ether/ethylacetate 100:0 to 90:10).

(3R,9S)-9-(tert-butyldimethylsilyloxy)-4-chloro-7,7-dimethyl-3-(4-(trifluoromethyl)phenyl)-2',3',5',6,6',7,8,9-octahydro-3H-spiro[furo[3,4-c]quinoline-1,4'-pyran]:
Yield: 440 mg (34% of theory)
Mass spectrometry (ESI$^+$): m/z=582 [M+H]$^+$
HPLC (Method 5): Retention time=1.956 min.
R$_f$-value: 0.17 (silica gel, petrole ether/ethylacetate 9:1)
(3S,9S)-9-(tert-butyldimethylsilyloxy)-4-chloro-7,7-dimethyl-3-(4-(trifluoromethyl)phenyl)-2',3',5',6,6',7,8,9-octahydro-3H-spiro[furo[3,4-c]quinoline-1,4'-pyran]:
Yield: 660 mg (51% of theory)
Mass spectrometry (ESI$^+$): m/z=582 [M+H]$^+$
HPLC (Method 5): Retention time=1.956 min.

R$_f$-value: 0.33 (silica gel, petrole ether/ethylacetate 9:1)

Example LXV

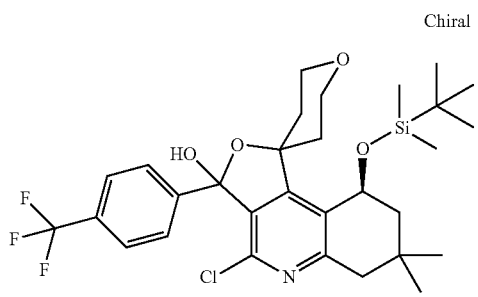 [SMILES: CC1(C)Cc2nc(Cl)c3c(c2[C@@H](O[Si](C)(C)C(C)(C)C)C1)C1(CCOCC1)OC3(O)c1ccc(C(F)(F)F)cc1]

(9S)-9-(tert-Butyldimethylsilyloxy)-4-chloro-7,7-dimethyl-3-(4-(trifluoromethyl)phenyl)-2',3',5',6,6',7,8,9-octahydro-3H-spiro[furo[3,4-c]quinoline-1,4'-pyran]-3-ol 2.31 g 1-Iodo-4-(trifluoromethyl)benzene are dissolved in 30 ml tetrahydrofurane, cooled to −65° C. and treated dropwise with 9.2 ml of a 1.6 M solution of tert.-butyllithium in n-pentan. The mixture is stirred for 30 minutes and then a solution of 1.9 g (S)-9-(tert-butyldimethylsilyloxy)-4-chloro-7,7-dimethyl-2',3',5',6,6',7,8,9-octahydro-3H-spiro[furo[3,4-c]quinoline-1,4'-pyran]-3-one in 30 ml tetrahydrofurane is added dropwise. The mixture is stirred for 30 minutes at −65° C. and for 30 minutes at −50° C. Then the reaction is quenched by addition of 0.5 ml methanol. The mixture is partitioned between 0.1 M hydrochloric acid and ethylacetate. The aqueous phase is twice extracted with ethylacetate. The combined organic phases are dried with sodium sulphate and the solvents are evaporated in vacuo. The residue is chromatographed on silica gel (petrole ether/ethylacetate 100:0 to 80:20).

Yield: 2.42 g (96% of theory)
Mass spectrometry (ESI$^+$): m/z=598 [M+H]$^+$
HPLC (Method 28): Retention time=1.526 and 1.563 min. (Diastereomers)

Analogously to example LXV the following compounds are obtained:

(1) (9S)-9-(tert-butyldimethylsilyloxy)-4-chloro-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]-3-ol

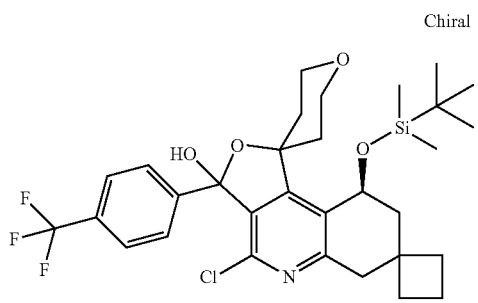 [SMILES: CC(C)(C)[Si](C)(C)O[C@H]1CC2(CCC2)Cc2nc(Cl)c3c(c21)C1(CCOCC1)OC3(O)c1ccc(C(F)(F)F)cc1]

Obtained by starting from (S)-9-(tert-butyldimethylsilyloxy)-4-chloro-7,7-(propan-1,3-diyl)-2',3',5',6,6',7,8,9-octahydro-3H-spiro[furo[3,4-c]quinoline-1,4'-pyran]-3-one.

Mass spectrometry (ESI$^+$): m/z=610 [M+H]$^+$
HPLC (Method 34): Retention time=1.57 min. and 1.58 min. (mixture of diastereomers)

Example LXVI

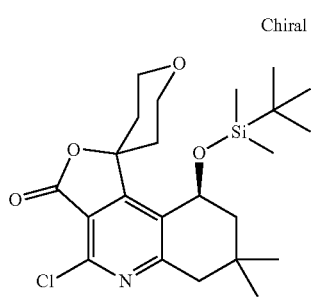 [SMILES: CC1(C)Cc2nc(Cl)c3c(c2[C@@H](O[Si](C)(C)C(C)(C)C)C1)C1(CCOCC1)OC3=O]

(S)-9-(tert-Butyldimethylsilyloxy)-4-chloro-7,7-dimethyl-2',3',5',6,6',7,8,9-octahydro-3H-spiro[furo[3,4-c]quinoline-1,4'-pyran]-3-one 1.69 g (S)-4-chloro-9-hydroxy-7,7-dimethyl-2',3',5',6,6',7,8,9-octahydro-3H-spiro[furo[3,4-c]quinoline-1,4'-pyran]-3-one are dissolved in 60 ml tetrahydrofurane and cooled to 0° C., 2.05 ml 2,6-lutidine and 3.71 ml trifluoromethanesulfonic acid-tert.-butyldimethylsilylester are added dropwise and the mixture is stirred for further 18 hours while warming to room temperature. Then the reaction is quenched by addition of 0.5 ml methanol. The mixture is partitioned between 0.1 M hydrochloric acid and ethylacetate. The aqueous phase is twice extracted with ethylacetate. The combined organic phases are dried with sodium sulphate and the solvents are evaporated in vacuo. The residue is chromatographed on silica gel (petrole ether/ethylacetate 100:0 to 70:30).

Yield: 1.9 g (84% of theory)
Mass spectrometry (ESI$^+$): m/z=452 [M+H]$^+$
HPLC (Method 28): Retention time=1.486 min.

Analogously to example LXVI the following compounds are obtained:

(1) (S)-9-(tert-butyldimethylsilyloxy)-4-chloro-7,7-(propan-1,3-diyl)-2',3',5',6,6',7,8,9-octahydro-3H-spiro[furo[3,4-c]quinoline-1,4'-pyran]-3-one

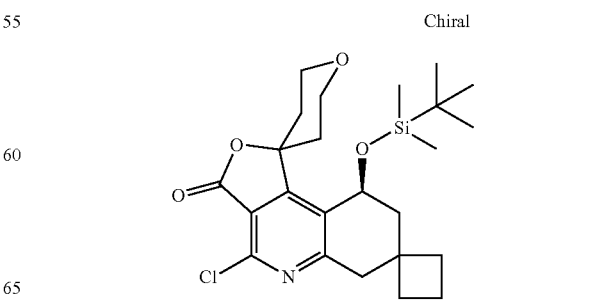

Obtained by starting from (S)-4-chloro-9-hydroxy-7,7-(propan-1,3-diyl)-2',3',5',6,6',7,8,9-octahydro-3H-spiro[furo[3,4-c]quinoline-1,4'-pyran]-3-one.

Mass spectrometry (ESI+): m/z=464 [M+H]+
HPLC (Method 34): Retention time=1.513 min.

Example LXVII

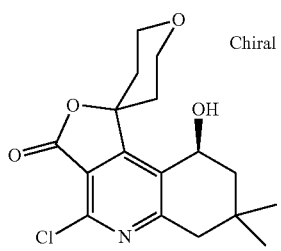 [SMILES: CC1(C)Cc2nc(Cl)c3c(c2[C@@H](O)C1)C1(CCOCC1)OC3=O]

Chiral (S)-4-Chloro-9-hydroxy-7,7-dimethyl-2',3',5',6,6',7,8,9-octahydro-3H-spiro[furo[3,4-c]quinoline-1,4'-pyran]-3-one 213 mg (1R,2S)-(+)-cis-1-Amino-2-indanol are dissolved in 250 ml tetrahydrofurane and to this solution are dropwise added 3.58 ml of a borane-diethylaniline-complex. After completion of gas evolution the solution is cooled to 0° C. and 3.17 g 4-chloro-7,7-dimethyl-2',3',5',6',7,8-hexahydro-3H-spiro[furo[3,4-c]quinoline-1,4'-pyran]-3,9(6H)-dione in 250 ml tetrahydrofurane are added dropwise. The temperature is raised during 2 hours to room temperature and the mixture is stirred for 18 hours, 213 mg (1R,2S)-(+)-cis-1-Amino-2-indanol are added and stirring is continued for further 7 hours. 20 ml methanol are added dropwise and the mixture is stirred for additional 10 minutes. The mixture is partitioned between 0.1 M hydrochloric acid and ethylacetate. The aqueous phase is twice extracted with ethylacetate. The combined organic phases are dried with sodium sulphate and the solvents are evaporated in vacuo. The residue is chromatographed on silica gel (petrole ether/ethylacetate 100:0 to 0:100).

Yield: 1.69 g (53% of theory)
Mass spectrometry (ESI+): m/z=338 [M+H]+
HPLC (Method 5): Retention time=1.224 min.

Analogously to example LXVII the following compounds are obtained:

(1) (S)-4-chloro-9-hydroxy-7,7-(propan-1,3-diyl)-2',3',5',6,6',7,8,9-octahydro-3H-spiro[furo[3,4-c]quinoline-1,4'-pyran]-3-one

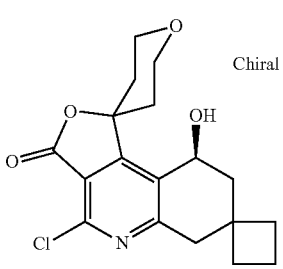 [SMILES: O=C1OC2(CCOCC2)c2c1c(Cl)nc1c2[C@@H](O)CC2(CCC2)C1]

Chiral

Obtained by starting from 4-chloro-7,7-(propan-1,3-diyl)-2',3',5',6',7,8-hexahydro-3H-spiro[furo[3,4-c]quinoline-1,4'-pyran]-3,9(6H)-dione.

Mass spectrometry (ESI+): m/z=350 [M+H]+

Example LXVIII

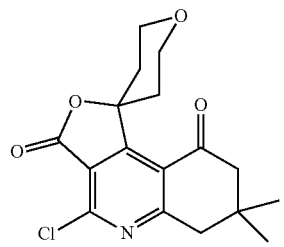 [SMILES: CC1(C)CC(=O)c2c(nc(Cl)c3c2C2(CCOCC2)OC3=O)C1]

4-Chloro-7,7-dimethyl-2',3',5',6',7,8-hexahydro-3H-spiro[furo[3,4-c]quinoline-1,4'-pyran]-3,9(6H)-dione 6.2 g 4-Hydroxy-7,7-dimethyl-2',3',5',6',7,8-hexahydro-3H-spiro[furo[3,4-c]quinoline-1,4'-pyran]-3,9(6H)-dione are suspended in 25 ml phosphoroxychloride, 1 drop of N,N-dimethylformamide is added and the mixture is heated for 18 hours to 65° C. Under vigorous stirring the mixture is added dropwise to 300 ml water while keeping the temperature below 35° C. After completion of the addition the mixture is stirred for 1 hour, the product is isolated by filtration, washed with water and dried in vacuo.

Yield: 5.8 g (88% of theory)
Mass spectrometry (ESI+): m/z=336 [M+H]+
HPLC (Method 28): Retention time=1.051 min.

Analogously to example LXVIII the following compounds are obtained:

(1) 4-chloro-7,7-(propan-1,3-diyl)-2',3',5',6',7,8-hexahydro-3H-spiro[furo[3,4-c]quinoline-1,4'-pyran]-3,9(6H)-dione

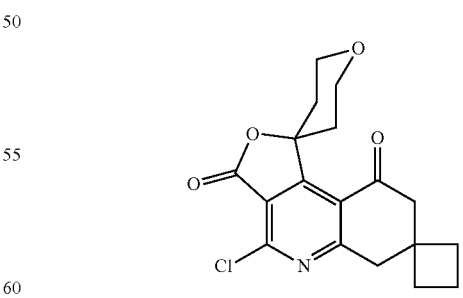

Obtained by starting from 4-hydroxy-7,7-dimethyl-2',3',5',6',7,8-hexahydro-3H-spiro[furo[3,4-c]quinoline-1,4'-pyran]-3,9(6H)-dione.

Mass spectrometry (ESI+): m/z=348 [M+H]+
HPLC (Method 35): Retention time=1.503 min.

Example LXIX

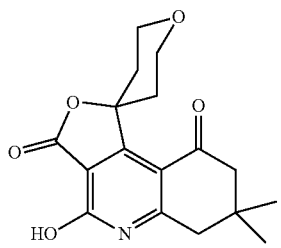

4-Hydroxy-7,7-dimethyl-2',3',5',6',7,8-hexahydro-3H-spiro[furo[3,4-c]quinoline-1,4'-pyran]-3,9(6H)-dione 10 g Ethyl 2-oxo-1,8-dioxaspiro[4.5]dec-3-ene-3-carboxylate and 6.15 g 3-amino-5,5-dimethylcyclohex-2-enone are mixed and heated to 200° C. for 20 minutes under a vacuo of 20 mbar. The mixture is cooled to room temperature and dissolved in 100 ml ethylacetate. 10 g 2,3-dichloro-5,6-dicyano-p-benzoquinone are added and the mixture is stirred for 4 hours at 50° C. and for 18 hours at room temperature. The product is isolated by filtration and washed with ethylacetate.

Yield: 8.9 g (63% of theory)

Mass spectrometry (ESI$^+$): m/z=318 [M+H]$^+$

HPLC (Method 28): Retention time=0.776 min.

Analogously to example LXIX the following compounds are obtained:

(1) 4-hydroxy-7,7-dimethyl-2',3',5',6',7,8-hexahydro-3H-spiro[furo[3,4-c]quinoline-1,4'-pyran]-3,9(6H)-dione

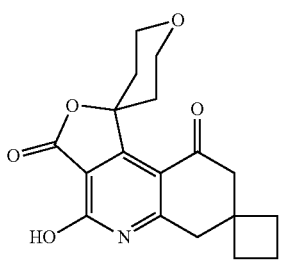 [SMILES: O=C1OC2(CCOCC2)c2c1c(Cl)nc1c2C(=O)CC2(CCC2)C1]

Obtained by starting from 2-oxo-1,8-dioxaspiro[4.5]dec-3-ene-3-carboxylate and 8-aminospiro[3.5]non-7-en-6-one.

Mass spectrometry (ESI$^+$): m/z=330 [M+H]$^+$

HPLC (Method 35): Retention time=1.177 min.

Example LXX

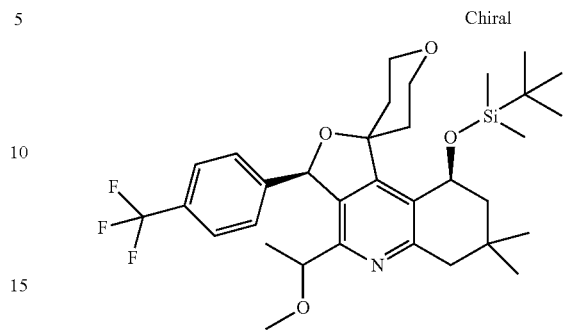

(3R,9S)-4-(1-Methoxyethyl)-7,7-dimethyl-3-(4-(trifluoromethyl)phenyl)-9-(2,3,3-trimethylbutan-2-yloxy)-2',3',5',6,6',7,8,9-octahydro-3H-spiro[furo[3,4-c]quinoline-1,4'-pyran]

70 mg 1-((3R,9S)-7,7-Dimethyl-3-(4-(trifluoromethyl)phenyl)-9-(2,3,3-trimethylbutan-2-yloxy)-2',3',5',6,6',7,8,9-octahydro-3H-spiro[furo[3,4-c]quinoline-1,4'-pyran]-4-yl)ethanol are dissolved in 1.5 ml tetrahydrofurane. 27 mg Potassium-tert.-butylate are added, the mixture is stirred for 5 minutes and the 11 µl methyliodide are added. The mixture is stirred for 20 minutes and then partitioned between 0.1 M hydrochloric acid and dichloromethane. The aqueous phase is extracted with dichloromethane and the combined organic phases are dried with sodium sulphate. The solvents are evaporated in vacuo and the residue is purified by preparative HPLC (Gemini C18, water/methanol/ammonia 90:10:0.1 to 0:100:0.1).

Yield: 36 mg (50% of theory)

Mass spectrometry (ESI$^+$): m/z=606 [M+H]$^+$

HPLC (Method 28): Retention time=1.560 min.

Example LXXI

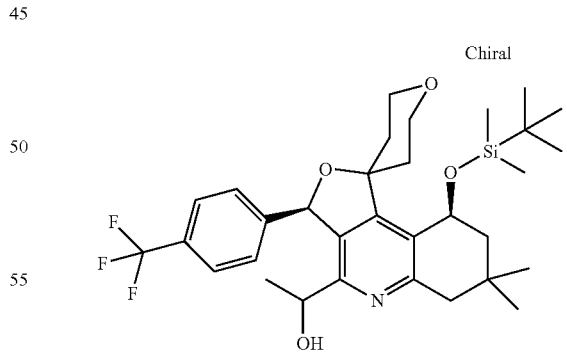

1-((3R,9S)-7,7-Dimethyl-3-(4-(trifluoromethyl)phenyl)-9-(2,3,3-trimethylbutan-2-yloxy)-2',3',5',6,6',7,8,9-octahydro-3H-spiro[furo[3,4-c]quinoline-1,4'-pyran]-4-yl)ethanol 200 mg (3R,9S)-7,7-dimethyl-4-(prop-1-en-2-yl)-3-(4-(trifluoromethyl)phenyl)-9-(2,3,3-trimethylbutan-2-yloxy)-

2',3',5',6,6',7,8,9-octahydro-3H-spiro[furo[3,4-c]quinoline-1,4'-pyran] are dissolved in 10 ml dichloromethane and cooled to −70° C. Ozone is bubbled through the solution until the solution gets a blue color. Then the mixture is purged for 10 minutes with oxygen. 5 ml Methanol and 14 mg sodium borohydride are added. The mixture is purged for 30 minutes with nitrogen, warmed to room temperature and stirred for 18 hours. The solvents are evaporated in vacuo and the residue is purified by preparative HPLC (Gemini C18, water/methanol/trifluoroacetic acid 50:50:0.1 to 0:100:0.1).

Yield: 100 mg (50% of theory)
Mass spectrometry (ESI⁺): m/z=592 [M+H]⁺
HPLC (Method 28): Retention time=1.486 min.

Example LXXII

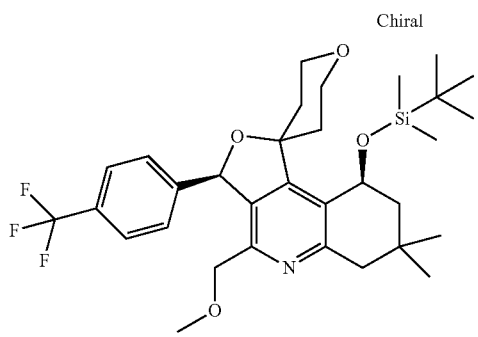 [SMILES: COCc1nc2c(c3c1[C@@H](c1ccc(C(F)(F)F)cc1)OC31CCOCC1)[C@@H](O[Si](C)(C)C(C)(C)C)CC(C)(C)C2]

(3R,9S)-9-(tert-butyldimethylsilyloxy)-4-(methoxymethyl)-7,7-dimethyl-3-(4-(trifluoromethyl)phenyl)-2',3',5',6,6',7,8,9-octahydro-3H-spiro[furo[3,4-c]quinoline-1,4'-pyran]

20 mg Sodium are dissolved in 3 ml methanol cooled to 0° C. and treated dropwise with a solution of 57 mg ((3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-yl)methyl methanesulfonate in 0.5 ml methanol. After stirring for 12 hours at room temperature the mixture is diluted with diethylether, washed with saturated aqueous ammonium chloride and dried with magnesium sulphate. The solvents are evaporated in vacuo. The product is directly used in the next step.

Mass spectrometry (ESI⁺): m/z=592 [M+H]⁺
HPLC (Method 29): Retention time=1.588 min.

Example LXXIII

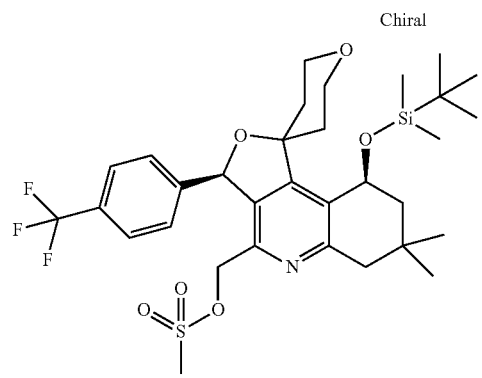 [SMILES: CC1(C)Cc2nc(COS(C)(=O)=O)c3c(c2[C@@H](O[Si](C)(C)C(C)(C)C)C1)C1(CCOCC1)O[C@@H]3c1ccc(C(F)(F)F)cc1]

((3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-yl)methyl methanesulfonate 50 mg ((3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-yl)methanol are dissolved in 1 ml dichloromethane, cooled to 0° C. and treated dropwise with 65 μl N,N-diisopropyl-N-ethylamine and 45 μl methanesulfonic anhydride. The mixture is stirred for 12 hours while warming to room temperature. Then it is diluted with diethylether, washed with saturated aqueous ammonium chloride and dried with magnesium sulphate. The solvents are evaporated in vacuo and the product is used directly in the next step.

Mass spectrometry (ESI⁺): m/z=656 [M+H]⁺
HPLC (Method 28): Retention time=1.586 min.

Example LXXIV

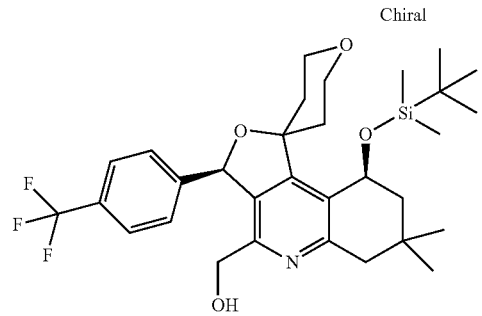 [SMILES: CC1(C)Cc2nc(CO)c3c(c2[C@@H](O[Si](C)(C)C(C)(C)C)C1)C1(CCOCC1)O[C@@H]3c1ccc(C(F)(F)F)cc1]

((3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-yl)methanol 1.28 g (3R,9S)-methyl 9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-carboxylate are dissolved in 10 ml tetrahydrofurane cooled to −10° C. and treated dropwise with 1.2 ml of a 1 M solution of lithiumaluminium hydride in tetrahydrofurane. The mixture is warmed to room temperature and stirred for 1 hour. Then it is diluted with diethylether and treated under vigorous stirring with 1 M hydrochloric acid. The organic phase is separated, dried with magnesium sulphate and evaporated in vacuo. The residue is chromatographed on silica gel (petrole ether/ethylacetate 70:30 to 40:60).

Yield: 375 mg (31% of theory)
Mass spectrometry (ESI$^+$): m/z=578 [M+H]$^+$
HPLC (Method 28): Retention time=1.515 min.

Example LXXV

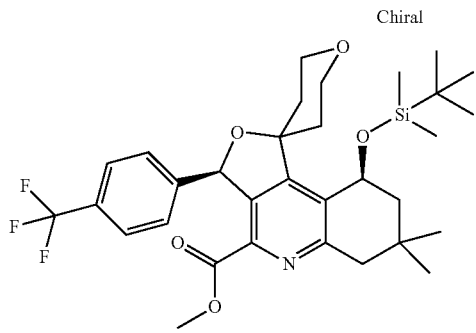 [SMILES: COC(=O)c1nc2c(c3c1[C@@H](c1ccc(C(F)(F)F)cc1)OC31CCOCC1)[C@@H](O[Si](C)(C)C(C)(C)C)CC(C)(C)C2]

(3R,9S)-Methyl 9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-carboxylate 1.5 g (3R,9S)-9-(tert-butyldimethylsilyloxy)-4-chloro-7,7-dimethyl-3-(4-(trifluoromethyl)phenyl)-2',3',5',6,6',7,8,9-octahydro-3H-spiro[furo[3,4-c]quinoline-1,4'-pyran] and 730 µl triethylamine are dissolved in 10 ml methanol and 5 ml N,N-dimethylformamide. The mixture is purged for 10 minutes with argon, treated with 150 mg 1,1'-bis-(diphenylphosphino)-ferrocene-dichloro-palladium-(II) and is heated for 18 hours to 100° C. under a carbonmonoxide atmosphere of 20 bar. The solvents are evaporated in vacuo and the residue is chromatographed on silica gel (petrole ether/ethylacetate 80:20 to 50:50).

Yield: 1.28 g (82% of theory)
Mass spectrometry (ESI$^+$): m/z=606 [M+H]$^+$
HPLC (Method 28): Retention time=1.611 min.

Example LXXVI

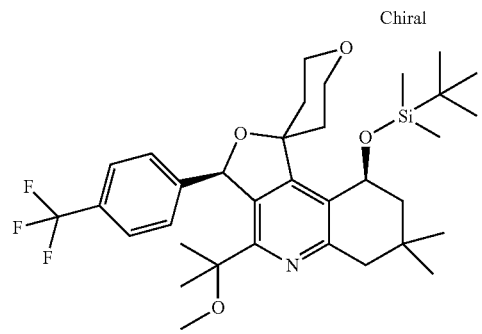 [SMILES: COC(C)(C)c1nc2c(c3c1[C@@H](c1ccc(C(F)(F)F)cc1)OC31CCOCC1)[C@@H](O[Si](C)(C)C(C)(C)C)CC(C)(C)C2]

(3R,9S)-9-(tert-butyldimethylsilyloxy)-4-(2-methoxypropan-2-yl)-7,7-dimethyl-3-(4-(trifluoromethyl)phenyl)-2',3',5',6,6',7,8,9-octahydro-3H-spiro[furo[3,4-c]quinoline-1,4'-pyran]

25 mg 2-((3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-yl)propan-2-ol are dissolved in 1 ml N,N-dimethylformamide, cooled to 0° C., treated with 3 mg sodium hydride (60% in mineral oil) and stirred for 1 minute. Then 5 µl methyliodide are added and the mixture is stirred for 4 hours at room temperature. The mixture is diluted with diethylether, washed with saturated aqueous ammonium chloride and dried with magnesium sulphate.

The solvents are evaporated in vacuo and the residue is chromatographed on silica gel (petrole ether/ethylacetate 95:5 to 50:50).

Yield: 13 mg (51% of theory)
Mass spectrometry (ESI$^+$): m/z=620 [M+H]$^+$
HPLC (Method 29): Retention time=1.652 min.

Example LXXVII

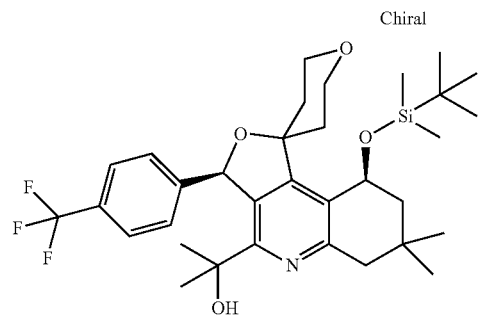 [SMILES: CC1(C)Cc2nc(C(C)(C)O)c3c(c2[C@@H](O[Si](C)(C)C(C)(C)C)C1)C1(CCOCC1)O[C@@H]3c1ccc(C(F)(F)F)cc1]

2-((3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-yl)propan-2-ol 26 mg 1-((3R,9S)-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran]-4-yl) ethanone are dissolved in 2 ml tetrahydrofurane cooled to −10° C. and treated with 110 µl of a 1.4 M solution of methylmagnesium bromide in toluene/tetrahydrofurane 75:25. The mixture is warmed to room temperature and stirred for 12 hours. The mixture is diluted with diethylether, washed with saturated aqueous ammonium chloride and dried with magnesium sulphate. The solvents are evaporated in vacuo and the residue is directly used in the next step.

Mass spectrometry (ESI⁺): m/z=606 [M+H]⁺

HPLC (Method 29): Retention time=1.598 min.

Analogously to example LXXVII the following compounds are obtained:

(1) 1-((3R,9S)-9-(tert-butyldimethylsilyloxy)-7,7-dimethyl-3-(4-(trifluoromethyl)phenyl)-2',3',5',6',7,8,9-octahydro-3H-spiro[furo[3,4-c]quinoline-1,4'-pyran]-4-yl)ethanol

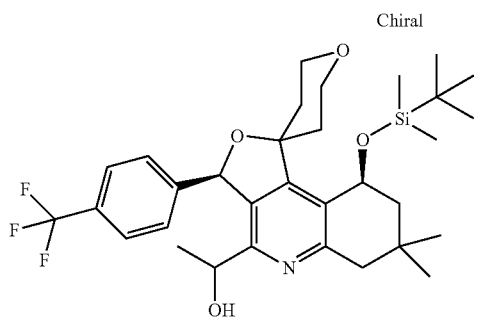 [SMILES: CC(O)c1nc2c(c3c1[C@@H](c1ccc(C(F)(F)F)cc1)OC31CCOCC1)[C@@H](O[Si](C)(C)C(C)(C)C)CC(C)(C)C2]

Obtained by starting from (3R,9S)-9-(tert-butyldimethylsilyloxy)-7,7-dimethyl-3-(4-(trifluoromethyl)phenyl)-2',3',5',6',7,8,9-octahydro-3H-spiro[furo[3,4-c]quinoline-1,4'-pyran]-4-carbaldehyde. The reaction is run for 2 hours at −40° C.

Mass spectrometry (ESI⁺): m/z=592 [M+H]⁺

HPLC (Method 29): Retention time=1.562 min.

Example LXXVIII

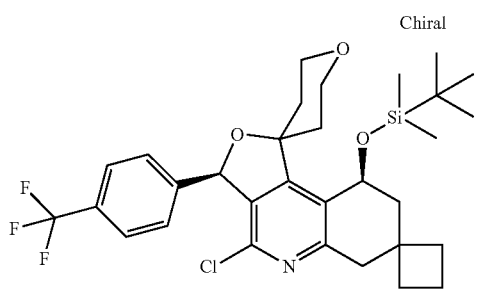 [SMILES: CC(C)(C)[Si](C)(C)O[C@H]1CC2(CCC2)Cc2nc(Cl)c3c(c21)C1(CCOCC1)O[C@@H]3c1ccc(C(F)(F)F)cc1]

(3R,9S)-9-(tert-butyldimethylsilyloxy)-4-chloro-7,7-(propan-1,3-diyl)-3-(4-(trifluoromethyl)phenyl)-2',3',5',6',7,8,9-octahydro-3H-spiro[furo[3,4-c]quinoline-1,4'-pyran]

and

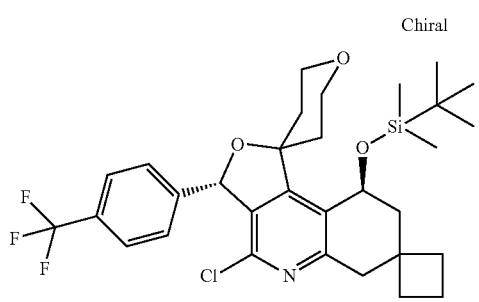 [SMILES: CC(C)(C)[Si](C)(C)O[C@H]1CC2(CCC2)Cc2nc(Cl)c3c(c21)C1(CCOCC1)O[C@H]3c1ccc(C(F)(F)F)cc1]

(3S,9S)-9-(tert-butyldimethylsilyloxy)-4-chloro-7,7-(propan-1,3-diyl)-3-(4-(trifluoromethyl)phenyl)-2',3',5',6',7,8,9-octahydro-3H-spiro[furo[3,4-c]quinoline-1,4'-pyran]

580 mg (9S)-9-(tert-butyldimethylsilyloxy)-4-chloro-7,7-(propan-1,3-diyl)-3-(4-(trifluoromethyl)phenyl)-2',3',5',6',7,8,9-octahydro-3H-spiro[furo[3,4-c]quinoline-1,4'-pyran]-3-01 are dissolved in 12 ml tetrahydrofurane, treated dropwise with 3.8 ml of a 1 M solution of titanium-(IV)-chloride in dichloromethane and stirred for 30 minutes. Then 1 g sodium triacetoxyborohydride is added and the mixture is stirred for 4 hours at room temperature. Afterwards the mixture is diluted with diethylether and washed with 1 M hydrochloric acid. The organic phase is dried with magnesium sulphate and the solvents are evaporated in vacuo. The residue is chromatographed on silica gel (petrole ether/ethylacetate 90:10 to 70:30).

(3R,9S)-9-(tert-butyldimethylsilyloxy)-4-chloro-7,7-(propan-1,3-diyl)-3-(4-(trifluoromethyl)phenyl)-2',3',5',6',7,8,9-octahydro-3H-spiro[furo[3,4-c]quinoline-1,4'-pyran]:

Yield: 370 mg (66% of theory)

Mass spectrometry (ESI⁺): m/z=594 [M+H]⁺

HPLC (Method 34): Retention time=1.653 min.

(3S,9S)-9-(tert-butyldimethylsilyloxy)-4-chloro-7,7-(propan-1,3-diyl)-3-(4-(trifluoromethyl)phenyl)-2',3',5',6',7,8,9-octahydro-3H-spiro[furo[3,4-c]quinoline-1,4'-pyran]:

Yield: 145 mg (26% of theory)

Mass spectrometry (ESI⁺): m/z=594 [M+H]⁺

HPLC (Method 34): Retention time=1.659 min.

Example LXXIX

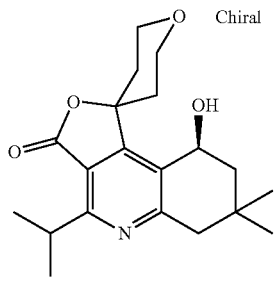 [SMILES: CC(C)c1nc2c(c3c1C(=O)OC31CCOCC1)[C@@H](O)CC(C)(C)C2]

(S)-9-hydroxy-4-isopropyl-7,7-dimethyl-2',3',5',6,6', 7,8,9-octahydro-3H-spiro[furo[3,4-c]quinoline-1,4'-pyran]-3-one 0.700 g (1R,2S)-(+)-cis-1-Amino-2-indanol are dissolved in 150 ml tetrahydrofurane and to this solution are dropwise added 6.12 ml of a borane-diethylaniline-complex. After completion of gas evolution the solution is cooled to 0° C. and 5.54 g 4-Isopropyl-7,7-dimethyl-2',3',5',6',7,8-hexahydro-3H-spiro[furo[3,4-c]quinoline-1,4'-pyran]-3,9(6H)-dione in 150 ml tetrahydrofurane are added dropwise. The temperature is raised during 2 hours to room temperature and the mixture is stirred for 24 hours. 10 ml Methanol are added dropwise and the solvents are evaporated in vacuo. The residue was dissolved in dichloromethane and is washed with 0.1 M hydrochloric acid and saturated aqueous sodium bicarbonate solution consecutively. The combined organic phases are dried with sodium sulphate and the solvents are evaporated in vacuo. The residue is chromatographed on silica gel (petrole ether/ethylacetate 100:0 to 3:2).

Yield: 3.65 g (65% of theory)
Mass spectrometry (ESI$^+$): m/z=346 [M+H]$^+$
HPLC (Method 28): Retention time=1.190 min.

Example LXXX

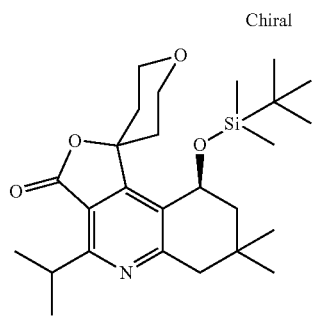 [SMILES: CC(C)c1nc2c(c3c1C(=O)OC31CCOCC1)[C@@H](O[Si](C)(C)C(C)(C)C)CC(C)(C)C2]

(S)-9-(tert-Butyldimethylsilyloxy)-4-isopropyl-7,7-dimethyl-2',3',5',6,6',7,8,9-octahydro-3H-spiro[furo[3,4-c]quinoline-1,4'-pyran]-3-one 1.2 g (S)-4-Isopropyl-9-hydroxy-7,7-dimethyl-2',3',5',6,6',7,8,9-octahydro-3H-spiro[furo[3,4-c]quinoline-1,4'-pyran]-3-one are dissolved in 15 ml tetrahydrofurane and 1.31 ml 2,6-lutidine and 2.44 ml trifluoromethanesulfonic acid- tert.-butyldimethylsilylester are added dropwise and the mixture is stirred for 4 hours at room temperature. Then the reaction is absorbed onto silica gel and chromatographed on silica gel (petrole ether/ethylacetate 100:0 to 50:50).

Yield: 1.55 g (97% of theory)
Mass spectrometry (ESI$^+$): m/z=460 [M+H]$^+$
HPLC (Method 5): Retention time=1.910 min.

Example LXXXI

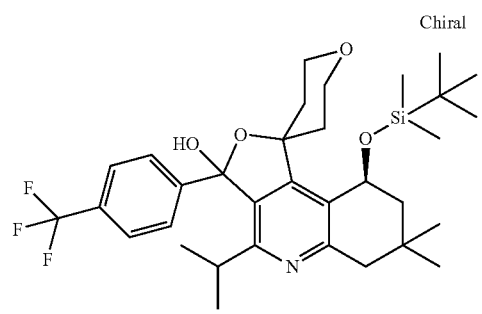 [SMILES: CC(C)c1nc2c(c3c1C(O)(c1ccc(C(F)(F)F)cc1)OC31CCOCC1)[C@@H](O[Si](C)(C)C(C)(C)C)CC(C)(C)C2]

(9S)-9-(tert-Butyldimethylsilyloxy)-4-isopropyl-7,7-dimethyl-3-(4-(trifluoromethyl)phenyl)-2',3',5',6,6',7, 8,9-octahydro-3H-spiro[furo[3,4-c]quinoline-1,4'-pyran]-3-ol 0.12 g 1-Iodo-4-(trifluoromethyl)benzene are dissolved in 3 ml tetrahydrofurane, cooled to −78° C. and treated dropwise with 0.54 ml of a 1.6 M solution of tert.-butyllithium in n-pentan. The mixture is stirred for 30 minutes and then a solution of 0.10 g (S)-9-(tert-butyldimethylsilyloxy)-4-isopropyl-7,7-dimethyl-2',3',5',6,6',7,8,9-octahydro-3H-spiro[furo[3,4-c]quinoline-1,4'-pyran]-3-one in 1 ml tetrahydrofurane is added dropwise. The mixture is stirred for 30 minutes at −78° C. and for 1 hour at −40° C. Then the reaction is quenched by addition of 0.5 ml methanol and purified via reversed phase chromatography (Varian Pursiut XRs C18 10μ, water/methanol/trifluoroacetic acid 90:10:0.1 to 0:100: 0.1; 180 mL/min; 18 min).

Yield: 0.1 g (75% of theory)
Mass spectrometry (ESI$^+$): m/z=606 [M+H]$^+$
HPLC (Method 5): Retention time=1.912 and 1.938 min. (Diastereomers)

Example LXXXII

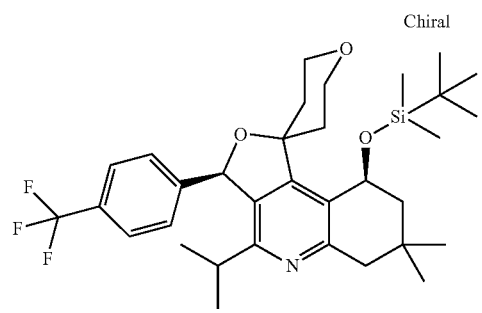 [SMILES: CC(C)c1nc2c(c3c1[C@@H](c1ccc(C(F)(F)F)cc1)OC31CCOCC1)[C@@H](O[Si](C)(C)C(C)(C)C)CC(C)(C)C2]

(3R,9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]

and

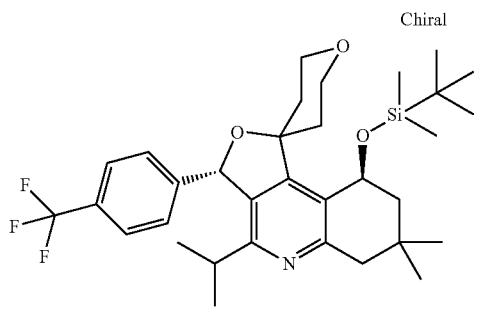 [SMILES: CC(C)c1nc2c(c3c1[C@H](c1ccc(C(F)(F)F)cc1)OC31CCOCC1)[C@@H](O[Si](C)(C)C(C)(C)C)CC(C)(C)C2]

(3S,9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]

180 mg (9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]-3-ol are dissolved in 5 ml tetrahydrofurane, treated dropwise with 1.19 ml titanium-(IV)-chloride (1 M in dichloromethane) and stirred for 30 minutes. Then 266 mg sodium triacetoxyborohydride is added and the mixture is stirred for 2 hours at room temperature. The mixture is added dropwise to saturated aqueous sodium bicarbonate solution, the phases are separated and the aqueous phase is extracted with ethylacetate. The organic phase is dried with magnesium sulphate and the solvents are evaporated in vacuo. The residue is chromatographed on silica gel (petrole ether/ethylacetate 90:10 to 70:30).

(3R,9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]:

Yield: 41 mg (23% of theory)

Mass spectrometry (ESI$^+$): m/z=696 [M+H]$^+$

R$_f$-value: 0.52 (silica gel, petrole ether/ethylacetate 4:1)

(3S,9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]:

Yield: 37 mg (12% of theory)

Mass spectrometry (ESI$^+$): m/z=696 [M+H]$^+$

R$_f$-value: 0.63 (silica gel, petrole ether/ethylacetate 4:1)

Preparation of the Final Compounds

Example 1

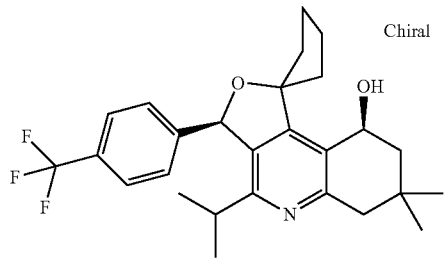 [SMILES: CC(C)c1nc2c(c3c1[C@@H](c1ccc(C(F)(F)F)cc1)OC31CCCC1)[C@@H](O)CC(C)(C)C2]

(3'R,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol To a solution of 30 mg (3'R,9'S)-9'-(tert-butyldimethylsilyloxy)-4'-isopropyl-,7',7'-dimethyl-3'-(4-(trifluoromethyl)phenyl)-6',7',8',9'-tetrahydro-3'H-spiro[cyclopentane-1,1'-furo[3,4-c]quinoline] in 2 ml tetrahydrofurane are added 150 µl of a 1 M solution of tetrabutylammonium fluoride in tetrahydrofurane. The solution is stirred for 12 hours at room temperature, then the solvent is evaporated in vacuo and the residue is chromatographed on silica gel (cyclohexane/ethylacetate 90:10 to 50:50).

Yield: 14 mg (58% of theory)

Mass spectrometry (ESI$^+$): m/z=460 [M+H]$^+$

HPLC (Method 1): Retention time=2.800 min.

R$_f$-value: 0.50 (silica gel, petrole ether/ethylacetate 4:1)

Analogously to example 1 the following compounds are obtained:

(1) (3'S,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

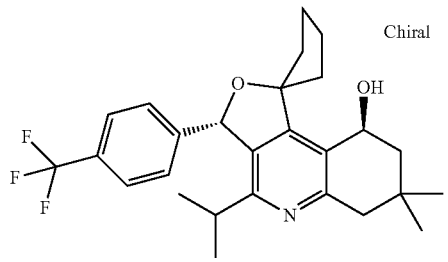 [SMILES: CC(C)c1nc2c(c3c1[C@H](c1ccc(C(F)(F)F)cc1)OC31CCCC1)[C@@H](O)CC(C)(C)C2]

Obtained by starting from (3'S,9'S)-9'-(tert-butyldimethylsilyloxy)-4'-isopropyl-,7',7'-dimethyl-3'-(4-(trifluoromethyl)phenyl)-6',7',8',9'-tetrahydro-3'H-spiro[cyclopentane-1,1'-furo[3,4-c]quinoline].

Mass spectrometry (ESI$^+$): m/z=460 [M+H]$^+$

HPLC (Method 1): Retention time=2.790 min.

R$_f$-value: 0.29 (silica gel, petrole ether/ethylacetate 4:1)

(2) (1R,3'S,9'S)-4'-isopropyl-7',7'-dimethyl-3'-(4-(trifluoromethyl)phenyl)-6',7',8',9'-tetrahydro-3'H-spiro[cyclopent[2]ene-1,1'-furo[3,4-c]quinolin]-9'-ol

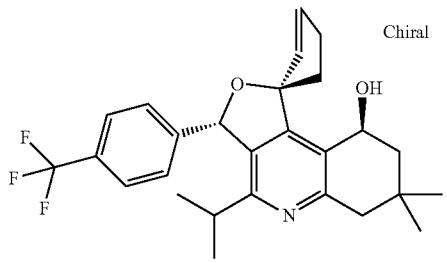

Obtained by starting from (1R,3'S,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopent[2]ene-1,1'-furo[3,4-c]quinoline].
Mass spectrometry (ESI⁺): m/z=458 [M+H]⁺
HPLC (Method 1): Retention time=2.596 min.
R$_f$-value: 0.25 (silica gel, petrole ether/ethylacetate 4:1)

(3) (3R,9S)-4-isopropyl-1,1,7,7-tetramethyl-3-(4-(trifluoromethyl)phenyl)-1,3,6,7,8,9-hexahydrofuro[3,4-c]quinolin-9-ol

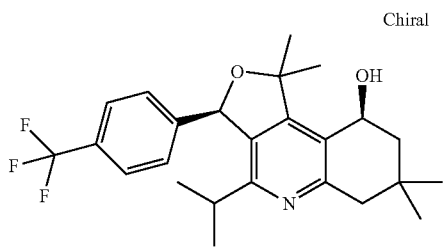 [SMILES: CC(C)c1nc2c(c3c1[C@@H](c1ccc(C(F)(F)F)cc1)OC3(C)C)[C@@H](O)CC(C)(C)C2]

Obtained by starting from (3R,9S)-9-(tert-butyldimethylsilyloxy)-4-isopropyl-1,1,7,7-tetramethyl-3-(4-(trifluoromethyl)phenyl)-1,3,6,7,8,9-hexahydrofuro[3,4-c]quinoline.
Mass spectrometry (ESI⁺): m/z=434 [M+H]⁺
HPLC (Method 1): Retention time=2.551 min.
R$_f$-value: 0.46 (silica gel, petrole ether/ethylacetate 4:1)

(4) (3'R,9'S)-4'-Isopropyl-7',7'-dimethyl-3'-(4-(trifluoromethyl)phenyl)-6',7',8',9'-tetrahydro-3'H-spiro[cyclohexane-1,1'-furo[3,4-c]quinolin]-9'-ol

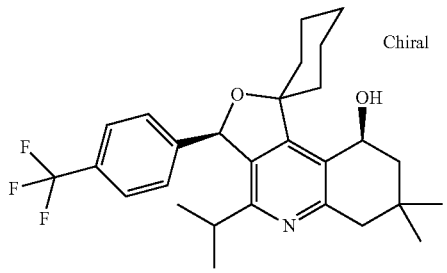 [SMILES: CC(C)c1nc2c(c3c1[C@@H](c1ccc(C(F)(F)F)cc1)OC31CCCCC1)[C@@H](O)CC(C)(C)C2]

Obtained by starting from (3'R,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclohexane-1,1'-furo[3,4-c]quinoline].
Mass spectrometry (ESI⁺): m/z=474 [M+H]⁺
HPLC (Method 1): Retention time=3.040 min.
R$_f$-value: 0.52 (silica gel, petrole ether/ethylacetate 4:1)

(5) (3'R,9'S)-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinolin]-9'-ol

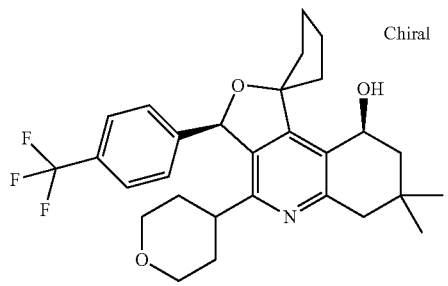 [SMILES: CC1(C)Cc2nc(C3CCOCC3)c3c(c2[C@@H](O)C1)C1(CCCC1)O[C@@H]3c1ccc(C(F)(F)F)cc1]

Obtained by starting from (3'R,9'S)-9'-(tert-butyldimethylsilyloxy)-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinoline].
Mass spectrometry (ESI⁺): m/z=502 [M+H]⁺
HPLC (Method 1): Retention time=2.891 min.
R$_f$-value: 0.25 (silica gel, petrole ether/ethylacetate 4:1)

(6) (3'R,9'S)-4'-cyclopentyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

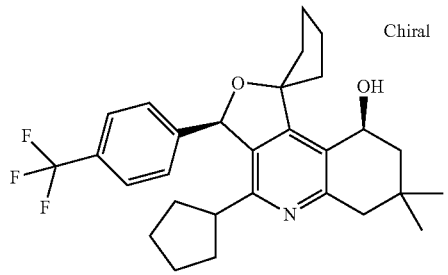 [SMILES: CC1(C)Cc2nc(C3CCCC3)c3c(c2[C@@H](O)C1)C1(CCCC1)O[C@@H]3c1ccc(C(F)(F)F)cc1]

Obtained by starting from (3'R,9'S)-9'-(tert-butyldimethylsilyloxy)-4'-cyclopentyl-7',7'-dimethyl-3'-(4-(trifluoromethyl)phenyl)-6',7',8',9'-tetrahydro-3'H-spiro[cyclopentane-1,1'-furo[3,4-c]quinoline].
Mass spectrometry (ESI⁺): m/z=486 [M+H]⁺
HPLC (Method 9): Retention time=1.22 min.

(7) (3'R,9'S)-4'-isopropyl-3'-(4-isopropylphenyl)-7',7'-dimethyl-6',7',8',9'-tetrahydro-3'H-spiro[cyclopentane-1,1'-furo[3,4-c]quinolin]-9'-ol

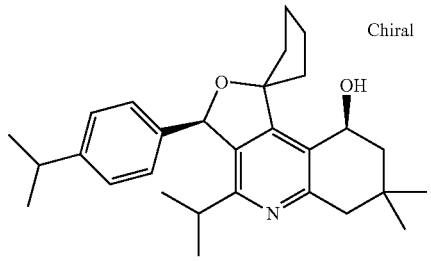 [SMILES: CC(C)c1ccc([C@H]2OC3(CCCC3)c3c2c(C(C)C)nc2c3[C@@H](O)CC(C)(C)C2)cc1]

Obtained by starting from (3'R,9'S)-9'-(tert-butyldimethylsilyloxy)-4'-isopropyl-3'-(4-isopropylphenyl)-7',7'-dimethyl-6',7',8',9'-tetrahydro-3'H-spiro[cyclopentane-1,1'-furo[3,4-c]quinoline].
Mass spectrometry (ESI$^+$): m/z=434 [M+H]$^+$
HPLC (Method 8): Retention time=0.82 min.

(8) (3'R,9'S)-3'-(4-fluorophenyl)-4'-isopropyl-7',7'-dimethyl-6',7',8',9'-tetrahydro-3'H-spiro[cyclopentane-1,1'-furo[3,4-c]quinolin]-9'-ol

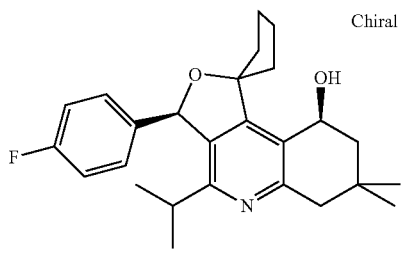 [SMILES: CC(C)c1nc2c(c3c1[C@@H](c1ccc(F)cc1)OC31CCCC1)[C@@H](O)CC(C)(C)C2]

Obtained by starting from (3'R,9'S)-9'-(tert-butyldimethylsilyloxy)-3'-(4-fluorophenyl)-4'-isopropyl-7',7'-dimethyl-6',7',8',9'-tetrahydro-3'H-spiro[cyclopentane-1,1'-furo[3,4-c]quinoline].
Mass spectrometry (ESI$^+$): m/z=410 [M+H]$^+$
HPLC (Method 19): Retention time=1.41 min.

(9) (3'R,9'S)-3'-(4-chlorophenyl)-4'-isopropyl-7',7'-dimethyl-6',7',8',9'-tetrahydro-3'H-spiro[cyclopentane-1,1'-furo[3,4-c]quinolin]-9'-ol

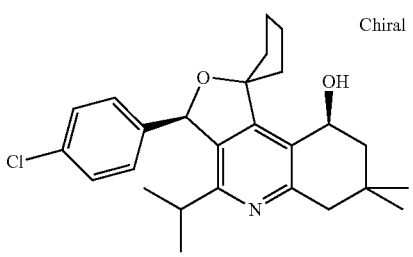 [SMILES: CC(C)c1nc2c(c3c1[C@@H](c1ccc(Cl)cc1)OC31CCCC1)[C@@H](O)CC(C)(C)C2]

Obtained by starting from (3'R,9'S)-9'-(tert-butyldimethylsilyloxy)-3'-(4-chlorophenyl)-4'-isopropyl-7',7'-dimethyl-6',7',8',9'-tetrahydro-3'H-spiro[cyclopentane-1,1'-furo[3,4-c]quinoline].
Mass spectrometry (ESI$^+$): m/z=426 [M+H]$^+$
HPLC (Method 20): Retention time=3.17 min.

(10) (3'R,9'S)-4'-cyclopentyl-3'-(4-fluorophenyl)-7',7'-dimethyl-6',7',8',9'-tetrahydro-3'H-spiro[cyclopentane-1,1'-furo[3,4-c]quinolin]-9'-ol

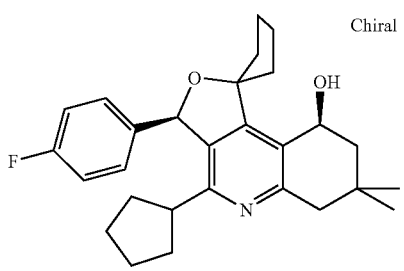 [SMILES: CC1(C)Cc2nc(C3CCCC3)c3c(c2[C@@H](O)C1)C1(CCCC1)O[C@@H]3c1ccc(F)cc1]

Obtained by starting from (3'R,9'S)-9'-(tert-butyldimethylsilyloxy)-4'-cyclopentyl-3'-(4-fluorophenyl)-7',7'-dimethyl-6',7',8',9'-tetrahydro-3'H-spiro[cyclopentane-1,1'-furo[3,4-c]quinoline].
Mass spectrometry (ESI$^+$): m/z=436 [M+H]$^+$
HPLC (Method 20): Retention time=3.14 min.

(11) (3'R,9'S)-3'-(4-tert-butylphenyl)-4'-isopropyl-7',7'-dimethyl-6',7',8',9'-tetrahydro-3'H-spiro[cyclopentane-1,1'-furo[3,4-c]quinolin]-9'-ol

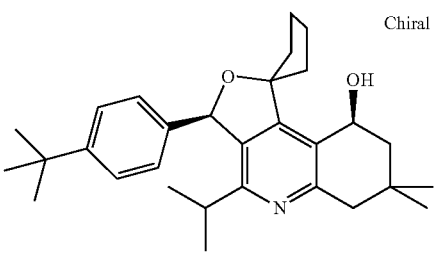 [SMILES: CC(C)c1nc2c(c3c1[C@@H](c1ccc(C(C)(C)C)cc1)OC31CCCC1)[C@@H](O)CC(C)(C)C2]

Obtained by starting from (3'R,9'S)-9'-(tert-butyldimethylsilyloxy)-3'-(4-tert-butylphenyl)-4'-isopropyl-7',7'-dimethyl-6',7',8',9'-tetrahydro-3'H-spiro[cyclopentane-1,1'-furo[3,4-c]quinoline].
Mass spectrometry (ESI$^+$): m/z=448 [M+H]$^+$
HPLC (Method 20): Retention time=3.45 min.

(12) (3'R,9'S)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinolin]-9'-ol

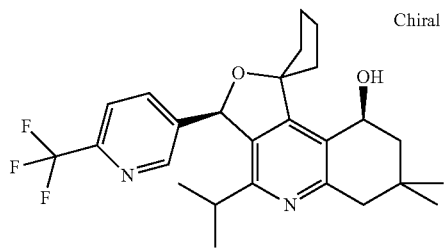 [SMILES: CC(C)c1nc2c(c3c1[C@@H](c1ccc(C(F)(F)F)nc1)OC31CCCC1)[C@@H](O)CC(C)(C)C2]

Obtained by starting from (3'R,9'S)-9'-(tert-butyldimethylsilyloxy)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline].

Mass spectrometry (ESI+): m/z=461 [M+H]+
HPLC (Method 14): Retention time=5.83 min.

(13) (3'S,9'S)-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinolin]-9'-ol

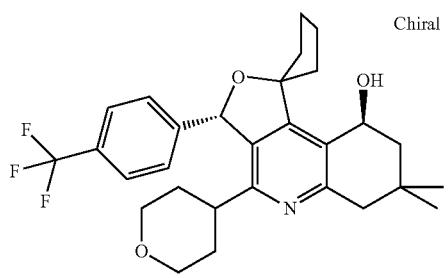 [SMILES: CC1(C)Cc2nc(C3CCOCC3)c3c(c2[C@@H](O)C1)C1(CCCC1)O[C@H]3c1ccc(C(F)(F)F)cc1]

Obtained by starting from (3'S,9'S)-9'-(tert-butyldimethylsilyloxy)-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinoline].

Mass spectrometry (ESI+): m/z=502 [M+H]+
HPLC (Method 1): Retention time=2.822 min.

(14) (3'R,9'S)-4'-isopropyl-7',7'-dimethyl-3'-p-tolyl-6',7',8',9'-tetrahydro-3'H-spiro[cyclopentane-1,1'-furo[3,4-c]quinolin]-9'-ol

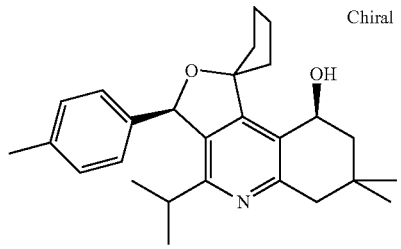

Obtained by starting from (3'R,9'S)-9'-(tert-butyldimethylsilyloxy)-4'-isopropyl-7',7'-dimethyl-3'-p-tolyl-6',7',8',9'-tetrahydro-3'H-spiro[cyclopentane-1,1'-furo[3,4-c]quinoline].

Mass spectrometry (ESI+): m/z=406 [M+H]+
HPLC (Method 20): Retention time=3.03 min.

(15) (3'R,9'S)-4'-isopropyl-7',7'-(propan-1,3-diyl)-3'-(4-(trifluoromethyl)phenyl)-6',7',8',9'-tetrahydro-3'H-spiro[cyclopentane-1,1'-furo[3,4-c]quinolin]-9'-ol

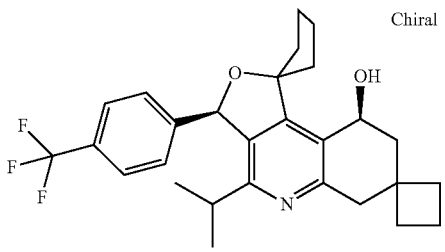 [SMILES: CC(C)c1nc2c(c3c1[C@@H](c1ccc(C(F)(F)F)cc1)OC31CCCC1)[C@@H](O)CC1(CCC1)C2]

Obtained by starting from (3'R,9'S)-9'-(tert-butyldimethylsilyloxy)-4'-isopropyl-,7',7'-(propan-1,3-diyl)-3'-(4-(trifluoromethyl)phenyl)-6',7',8',9'-tetrahydro-3'H-spiro[cyclopentane-1,1'-furo[3,4-c]quinoline].

Mass spectrometry (ESI+): m/z=472 [M+H]+
HPLC (Method 20): Retention time=3.16 min.

(16) (3'R,9'S)-3'-(3-fluoro-4-(trifluoromethyl)phenyl)-4'-isopropyl-7',7'-dimethyl-6',7',8',9'-tetrahydro-3'H-spiro[cyclopentane-1,1'-furo[3,4-c]quinolin]-9'-ol

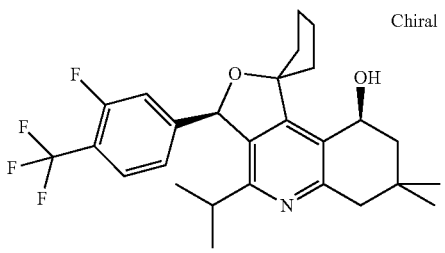 [SMILES: CC(C)c1nc2c(c3c1[C@@H](c1ccc(C(F)(F)F)c(F)c1)OC31CCCC1)[C@@H](O)CC(C)(C)C2]

Obtained by starting from (3'R,9'S)-9'-(tert-butyldimethyl-silyloxy)-3'-(3-fluoro-4-(trifluoromethyl)phenyl)-4'-isopropyl-7',7'-dimethyl-6',7',8',9'-tetrahydro-3'H-spiro[cyclopentane-1,1'-furo[3,4-c]quinoline].

Mass spectrometry (ESI⁺): m/z=478 [M+H]⁺

HPLC (Method 20): Retention time=3.21 min.

(17) (3'R,9'S)-4'-isopropyl-7',7'-dimethyl-3'-(4-(trifluoromethoxy)phenyl)-6',7',8',9'-tetrahydro-3'H-spiro[cyclopentane-1,1'-furo[3,4-c]quinolin]-9'-ol

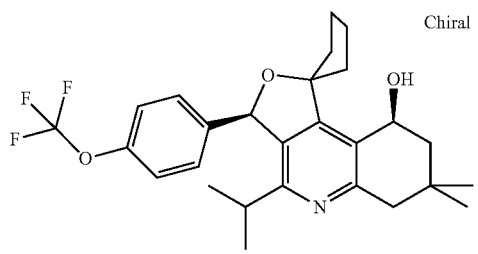 [SMILES: CC(C)c1nc2c(c3c1[C@@H](c1ccc(OC(F)(F)F)cc1)OC31CCCC1)[C@@H](O)CC(C)(C)C2]

Obtained by starting from (3'R,9'S)-9'-(tert-butyldimethyl-silyloxy)-4'-isopropyl-7',7'-dimethyl-3'-(4-(trifluoromethoxy)phenyl)-6',7',8',9'-tetrahydro-3'H-spiro[cyclopentane-1,1'-furo[3,4-c]quinoline].

Mass spectrometry (ESI⁺): m/z=476 [M+H]⁺

HPLC (Method 20): Retention time=3.18 min.

(18) (3R,9S)-3-(4-tert-butylphenyl)-4-isopropyl-1,1,7,7-tetramethyl-1,3,6,7,8,9-hexahydrofuro[3,4-c]quinolin-9-ol

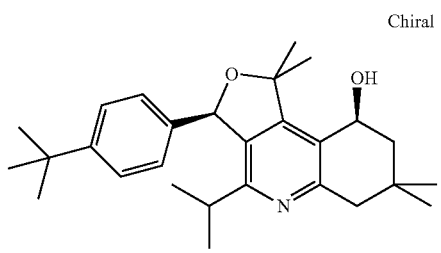 [SMILES: CC(C)c1nc2c(c3c1[C@@H](c1ccc(C(C)(C)C)cc1)OC3(C)C)[C@@H](O)CC(C)(C)C2]

Obtained by starting from (3R,9S)-9-(tert-butyldimethyl-silyloxy)-3-(4-tert-butylphenyl)-4-isopropyl-1,1,7,7-tetramethyl-1,3,6,7,8,9-hexahydrofuro[3,4-c]quinoline.

Mass spectrometry (ESI⁺): m/z=422 [M+H]⁺

HPLC (Method 22): Retention time=1.88 min.

(19) (3R,9S)-3-(4-tert-butylphenyl)-4-cyclopentyl-1,1,7,7-tetramethyl-1,3,6,7,8,9-hexahydrofuro[3,4-c]quinolin-9-ol

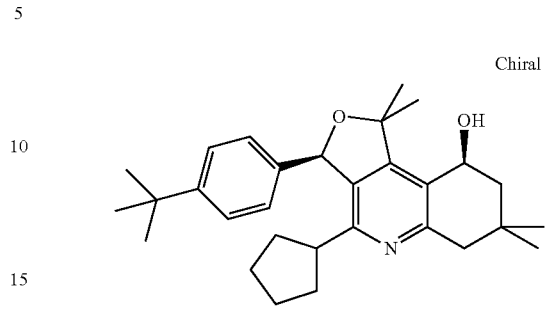

Obtained by starting from (3R,9S)-9-(tert-butyldimethyl-silyloxy)-3-(4-tert-butylphenyl)-4-cyclopentyl-1,1,7,7-tetramethyl-1,3,6,7,8,9-hexahydrofuro[3,4-c]quinoline.

Mass spectrometry (ESI⁺): m/z=448 [M+H]⁺

HPLC (Method 22): Retention time=2.00 min.

(20) 4-((3'R,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)benzonitrile

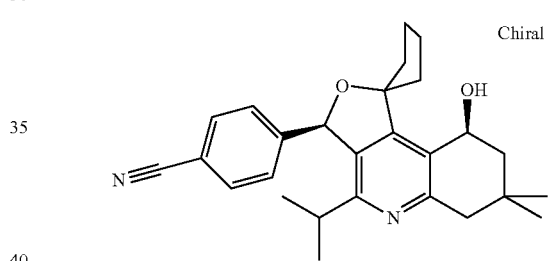

Obtained by starting from 4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)benzonitrile.

Mass spectrometry (ESI⁺): m/z=417 [M+H]⁺

HPLC (Method 9): Retention time=1.09 min.

(21) (3'S,9'S)-4'-isopropyl-7',7'-dimethyl-3'-(5-(trifluoromethyl)pyridin-2-yl)-6',7',8',9'-tetrahydro-3'H-spiro[cyclopentane-1,1'-furo[3,4-c]quinolin]-9'-ol

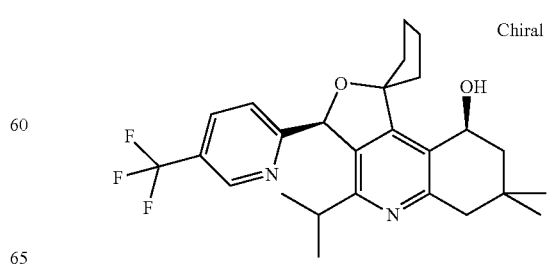

Obtained by starting from (3'S,9'S)-9'-(tert-butyldimethyl-silyloxy)-4'-isopropyl-7',7'-dimethyl-3'-(5-(trifluoromethyl)pyridin-2-yl)-6',7',8',9'-tetrahydro-3'H-spiro[cyclopentane-1,1'-furo[3,4-c]quinoline].

Mass spectrometry (ESI⁺): m/z=461 [M+H]⁺

HPLC (Method 15): Retention time=3.46 min.

(22) 2-(4-((3'R,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile

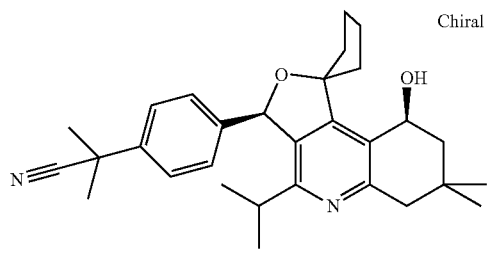 [SMILES: CC(C)c1nc2c(c3c1[C@@H](c1ccc(C(C)(C)C#N)cc1)OC31CCCC1)[C@@H](O)CC(C)(C)C2]

Obtained by starting from 2-(4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile.

Mass spectrometry (ESI⁺): m/z=459 [M+H]⁺

HPLC (Method 1): Retention time=2.440 min.

R$_f$-value: 0.47 (silica gel, petrole ether/ethylacetate 2:1)

(23) 2-(4-((3'S,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile

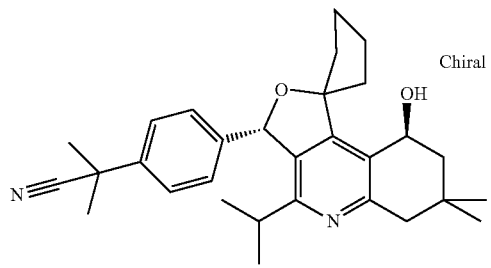 [SMILES: CC(C)c1nc2c(c3c1[C@H](c1ccc(C(C)(C)C#N)cc1)OC31CCCC1)[C@@H](O)CC(C)(C)C2]

Obtained by starting from 2-(4-((3'S,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile.

Mass spectrometry (ESI⁺): m/z=459 [M+H]⁺

HPLC (Method 1): Retention time=2.402 min.

R$_f$-value: 0.47 (silica gel, petrole ether/ethylacetate 2:1)

(24) (3'S,9'S)-4'-isopropyl-7',7'-dimethyl-3'-(5-(trifluoromethyl)thiophen-2-yl)-6',7',8',9'-tetrahydro-3'H-spiro[cyclopentane-1,1'-furo[3,4-c]quinolin]-9'-ol

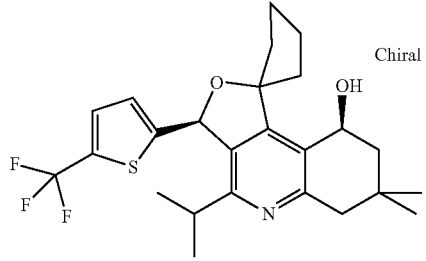 [SMILES: CC(C)c1nc2c(c3c1[C@@H](c1ccc(C(F)(F)F)s1)OC31CCCC1)[C@@H](O)CC(C)(C)C2]

Obtained by starting from (3'S,9'S)-9'-(tert-butyldimethylsilyloxy)-4'-isopropyl-7',7'-dimethyl-3'-(5-(trifluoromethyl)thiophen-2-yl)-6',7',8',9'-tetrahydro-3'H-spiro[cyclopentane-1,1'-furo[3,4-c]quinoline].

Mass spectrometry (ESI⁺): m/z=466 [M+H]⁺

HPLC (Method 11): Retention time=6.06 min.

(25) (3'R,9'S)-3'-(2-tert-butylpyrimidin-5-yl)-4'-isopropyl-7',7'-dimethyl-6',7',8',9'-tetrahydro-3'H-spiro[cyclopentane-1,1'-furo[3,4-c]quinolin]-9'-ol

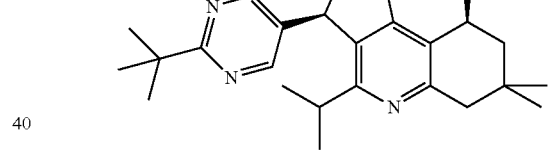

Obtained by starting from (3'R,9'S)-9'-(tert-butyldimethylsilyloxy)-3'-(2-tert-butylpyrimidin-5-yl)-4'-isopropyl-7',7'-dimethyl-6',7',8',9'-tetrahydro-3'H-spiro[cyclopentane-1,1'-furo[3,4-c]quinoline].

Mass spectrometry (ESI⁺): m/z=450 [M+H]⁺

HPLC (Method 16): Retention time=4.33 min.

(26) (3'R,9'S)-3'-(4-(2-hydroxypropan-2-yl)phenyl)-4'-isopropyl-7',7'-dimethyl-6',7',8',9'-tetrahydro-3'H-spiro[cyclopentane-1,1'-furo[3,4-c]quinolin]-9'-ol

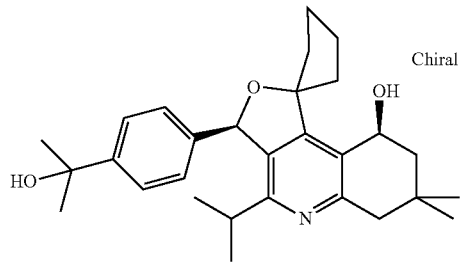 [SMILES: CC(C)c1nc2c(c3c1[C@@H](c1ccc(C(C)(C)O)cc1)OC31CCCC1)[C@@H](O)CC(C)(C)C2]

Obtained by starting from 2-(4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)propan-2-ol.

Mass spectrometry (ESI⁺): m/z=450 [M+H]⁺

HPLC (Method 1): Retention time=1.987 min.

$R_f$-value: 0.34 (silica gel, petrole ether/ethylacetate 2:1)

(27) (3'R,9'S)-3'-(4-isobutylphenyl)-4'-isopropyl-7',7'-dimethyl-6',7',8',9'-tetrahydro-3'H-spiro[cyclopentane-1,1'-furo[3,4-c]quinolin]-9'-ol

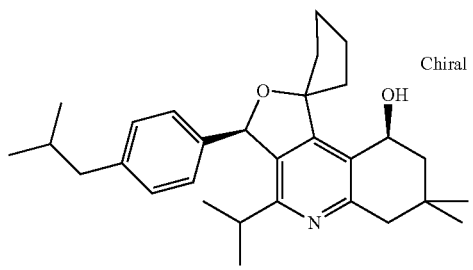 [SMILES: CC(C)Cc1ccc([C@H]2OC3(CCCC3)c3c2c(C(C)C)nc2c3[C@@H](O)CC(C)(C)C2)cc1]

Obtained by starting from (3'R,9'S)-9'-(tert-butyldimethylsilyloxy)-3'-(4-isobutylphenyl)-4'-isopropyl-7',7'-dimethyl-6',7',8',9'-tetrahydro-3'H-spiro[cyclopentane-1,1'-furo[3,4-c]quinoline].

Mass spectrometry (ESI⁺): m/z=448 [M+H]⁺

HPLC (Method 2): Retention time=1.775 min.

$R_f$-value: 0.20 (silica gel, cyclohexane/ethylacetate 9:1)

(28) (3'R,9'S)-4'-cyclobutyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

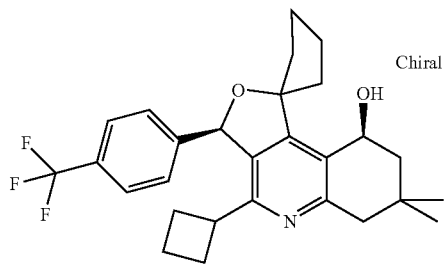 [SMILES: CC1(C)Cc2nc(C3CCC3)c3c(c2[C@@H](O)C1)C1(CCCC1)O[C@@H]3c1ccc(C(F)(F)F)cc1]

Obtained by starting from (3'R,9'S)-9'-(tert-butyldimethylsilyloxy)-4'-cyclobutyl-7',7'-dimethyl-3'-(4-(trifluoromethyl)phenyl)-6',7',8',9'-tetrahydro-3'H-spiro[cyclopentane-1,1'-furo[3,4-c]quinoline].

Mass spectrometry (ESI⁺): m/z=472 [M+H]⁺

HPLC (Method 2): Retention time=1.827 min.

$R_f$-value: 0.30 (silica gel, cyclohexane/ethylacetate 9:1)

(29) (3'R,9'S)-4'-cyclopentyl-3'-(4-isopropylphenyl)-7',7'-dimethyl-6',7',8',9'-tetrahydro-3'H-spiro[cyclopentane-1,1'-furo[3,4-c]quinolin]-9'-ol

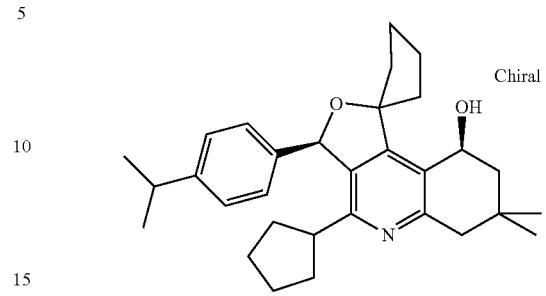

Obtained by starting from (3'R,9'S)-9'-(tert-butyldimethylsilyloxy)-4'-cyclopentyl-3'-(4-isopropylphenyl)-7',7'-dimethyl-6',7',8',9'-tetrahydro-3'H-spiro[cyclopentane-1,1'-furo[3,4-c]quinoline].

Mass spectrometry (ESI⁺): m/z=460 [M+H]⁺

HPLC (Method 4): Retention time=2.563 min.

(30) (3R,9S)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-9-ol

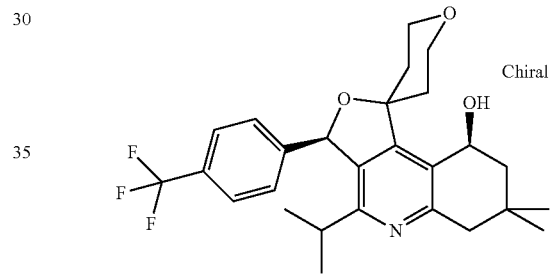

Obtained by starting from (3R,9S)-9-(tert-butyldimethylsilyloxy)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran].

Mass spectrometry (ESI⁺): m/z=476 [M+H]⁺

HPLC (Method 12): Retention time=4.96 min.

(31) (3'R,9'S)-3'-(3-tert-butylphenyl)-4'-cyclopentyl-7',7'-dimethyl-6',7',8',9'-tetrahydro-3'H-spiro[cyclopentane-1,1'-furo[3,4-c]quinolin]-9'-ol

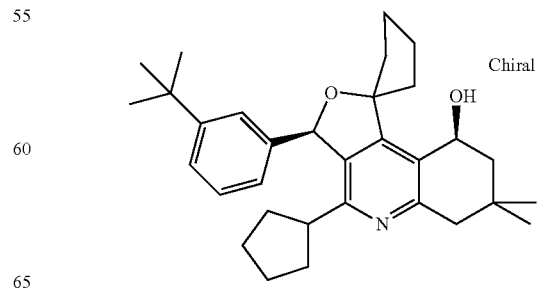

Obtained by starting from (3'R,9'S)-9'-(tert-butyldimethyl-silyloxy)-3'-(3-tert-butylphenyl)-4'-cyclopentyl-7',7'-dimethyl-6',7',8',9'-tetrahydro-3'H-spiro[cyclopentane-1,1'-furo[3,4-c]quinoline].

Mass spectrometry (ESI⁺): m/z=474 [M+H]⁺

HPLC (Method 4): Retention time=2.60 min.

(32) (3'R,9'S)-3'-(4-(1,1-difluoroethyl)phenyl)-4'-isopropyl-7',7'-dimethyl-6',7',8',9'-tetrahydro-3'H-spiro[cyclopentane-1,1'-furo[3,4-c]quinolin]-9'-ol

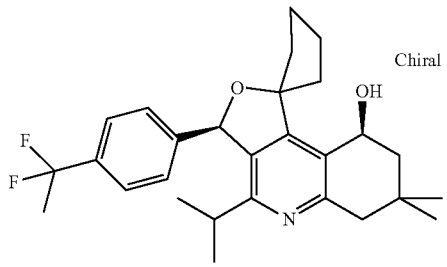 [SMILES: CC(C)c1nc2c(c3c1[C@@H](c1ccc(C(C)(F)F)cc1)OC31CCCC1)[C@@H](O)CC(C)(C)C2]

Obtained by starting from (3'R,9'S)-9'-(tert-butyldimethyl-silyloxy)-3'-(4-(1,1-difluoroethyl)phenyl)-4'-isopropyl-7',7'-dimethyl-6',7',8',9'-tetrahydro-3'H-spiro[cyclopentane-1,1'-furo[3,4-c]quinoline].

Mass spectrometry (ESI⁺): m/z=456 [M+H]⁺

HPLC (Method 4): Retention time=2.317 min.

(33) (3'R,6'R,9'S)-9'-hydroxy-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate

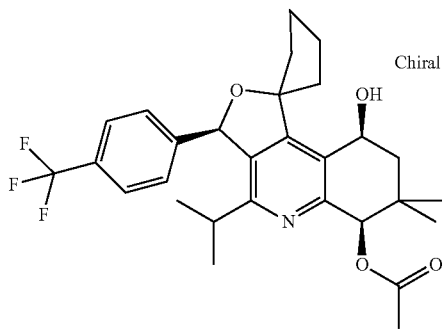 [SMILES: CC(=O)O[C@H]1c2nc(C(C)C)c3c(c2[C@@H](O)CC1(C)C)C1(CCCC1)O[C@@H]3c1ccc(C(F)(F)F)cc1]

Obtained by starting from (3'R,6'R,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate.

Mass spectrometry (ESI⁺): m/z=518 [M+H]⁺

HPLC (Method 16): Retention time=12.50 min.

(34) (3'R,6'S,9'S)-9'-hydroxy-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate

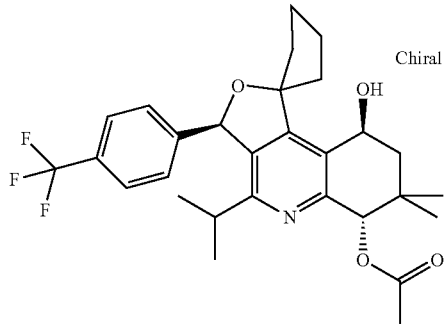 [SMILES: CC(=O)O[C@@H]1c2nc(C(C)C)c3c(c2[C@@H](O)CC1(C)C)C1(CCCC1)O[C@@H]3c1ccc(C(F)(F)F)cc1]

Obtained by starting from (3'R,6'S,9'S)-9'-(tert-butyldimethylsilyloxy)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate.

Mass spectrometry (ESI⁺): m/z=518 [M+H]⁺

HPLC (Method 16): Retention time=13.23 min.

(35) (3'R,9'S)-4'-isopropyl-7',7'-(propan-1,3-diyl)-3'-(4-(isopropyl)phenyl)-6',7',8',9'-tetrahydro-3'H-spiro[cyclopentane-1,1'-furo[3,4-c]quinolin]-9'-ol

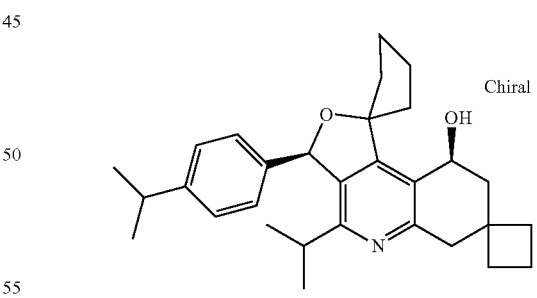

Obtained by starting from (3'R,9'S)-9'-(tert-butyldimethyl-silyloxy)-4'-isopropyl-,7',7'-(propan-1,3-diyl)-3'-(4-(isopropyl)phenyl)-6',7',8',9'-tetrahydro-3'H-spiro[cyclopentane-1,1'-furo[3,4-c]quinoline].

Mass spectrometry (ESI⁺): m/z=446 [M+H]⁺

HPLC (Method 23): Retention time=0.76 min.

389

(36) (3'R,9'S)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinolin]-9'-ol

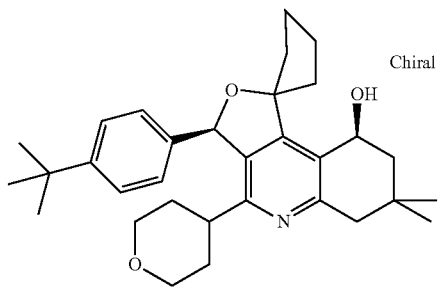 [SMILES: CC1(C)Cc2nc(C3CCOCC3)c3c(c2[C@@H](O)C1)C1(CCCC1)O[C@@H]3c1ccc(C(C)(C)C)cc1]

Obtained by starting from (3'R,9'S)-9'-(tert-butyldimethylsilyloxy)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline].

Mass spectrometry (ESI$^+$): m/z=490 [M+H]$^+$
HPLC (Method 2): Retention time=1.769 min.

(37) (3'R,9'S)-4'-ethyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

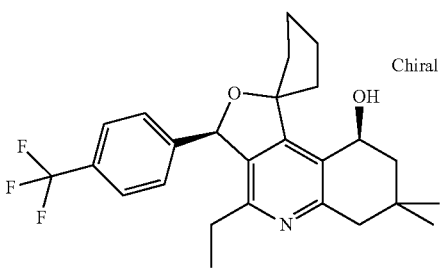 [SMILES: CCc1nc2c(c3c1[C@@H](c1ccc(C(F)(F)F)cc1)OC31CCCC1)[C@@H](O)CC(C)(C)C2]

Obtained by starting from (3'R,9'S)-9'-(tert-butyldimethylsilyloxy)-4'-ethyl-7',7'-dimethyl-3'-(4-(trifluoromethyl)phenyl)-6',7',8',9'-tetrahydro-3'H-spiro[cyclopentane-1,1'-furo[3,4-c]quinoline].

Mass spectrometry (ESI$^+$): m/z=446 [M+H]$^+$
HPLC (Method 19): Retention time=1.58 min.

390

(38) (3'R,9'S)-3'-(3,5-difluorophenyl)-4'-isopropyl-7',7'-dimethyl-6',7',8',9'-tetrahydro-3'H-spiro[cyclopentane-1,1'-furo[3,4-c]quinolin]-9'-ol

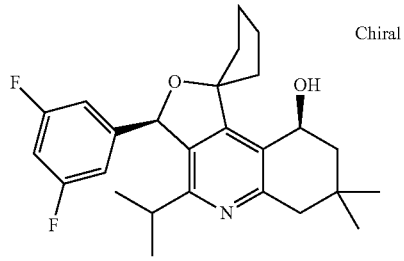 [SMILES: CC(C)c1nc2c(c3c1[C@@H](c1cc(F)cc(F)c1)OC31CCCC1)[C@@H](O)CC(C)(C)C2]

Obtained by starting from (3'R,9'S)-9'-(tert-butyldimethylsilyloxy)-3'-(3,5-difluoro-4-(trimethylsilyl)phenyl)-4'-isopropyl-7',7'-dimethyl-6',7',8',9'-tetrahydro-3'H-spiro[cyclopentane-1,1'-furo[3,4-c]quinoline]

Mass spectrometry (ESI$^+$): m/z=428 [M+H]$^+$
HPLC (Method 7): Retention time=1.395 min.

(39) (3R,9S)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-9-ol

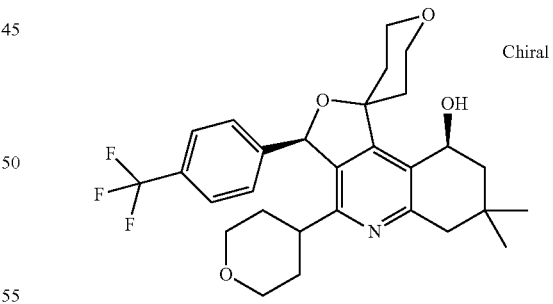

Obtained by starting from (3R,9S)-9-(tert-butyldimethylsilyloxy)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]

Mass spectrometry (ESI$^+$): m/z=518 [M+H]$^+$
HPLC (Method 7): Retention time=1.384 min.

391

(40) (3'R,9'S)-4'-isopropyl-7',7'-dimethyl-3'-(4-(1-methylcyclopropyl)phenyl)-6',7',8',9'-tetrahydro-3'H-spiro[cyclopentane-1,1'-furo[3,4-c]quinolin]-9'-ol

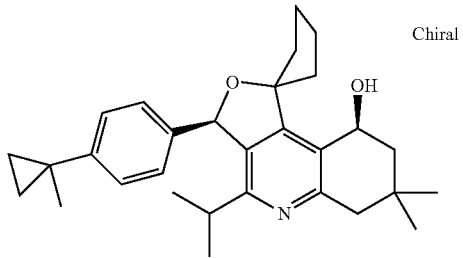 [SMILES: CC(C)c1nc2c(c3c1[C@@H](c1ccc(C4(C)CC4)cc1)OC31CCCC1)[C@@H](O)CC(C)(C)C2]

Obtained by starting from (3'R,9'S)-9'-(tert-butyldimethylsilyloxy)-4'-isopropyl-7',7'-dimethyl-3'-(4-(1-methylcyclopropyl)phenyl)-6',7',8',9'-tetrahydro-3'H-spiro[cyclopentane-1,1'-furo[3,4-c]quinoline].

Mass spectrometry (ESI$^+$): m/z=446 [M+H]$^+$

HPLC (Method 2): Retention time=1.684 min.

(41) (3'R,9'S)-4'-isopropyl-7',7'-dimethyl-3'-(3-(trifluoromethyl)phenyl)-6',7',8',9'-tetrahydro-3'H-spiro[cyclopentane-1,1'-furo[3,4-c]quinolin]-9'-ol

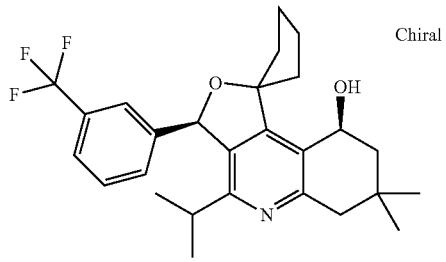 [SMILES: CC(C)c1nc2c(c3c1[C@@H](c1cccc(C(F)(F)F)c1)OC31CCCC1)[C@@H](O)CC(C)(C)C2]

Obtained by starting from (3'R,9'S)-9'-(tert-butyldimethylsilyloxy)-4'-isopropyl-7',7'-dimethyl-3'-(3-(trifluoromethyl)phenyl)-6',7',8',9'-tetrahydro-3'H-spiro[cyclopentane-1,1'-furo[3,4-c]quinoline].

Mass spectrometry (ESI$^+$): m/z=460 [M+H]$^+$

HPLC (Method 4): Retention time=2.46 min.

392

(42) (3R,9S)-3-(4-tert-butylphenyl)-4-isopropyl-7,7-dimethyl-2',3',5',6,6',7,8,9-octahydro-3H-spiro[furo[3,4-c]quinoline-1,4'-pyran]-9-ol

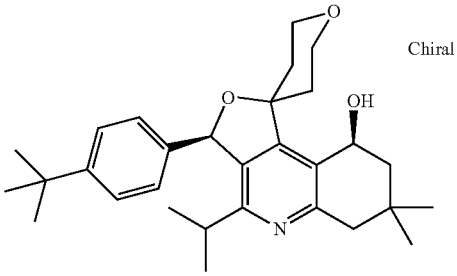 [SMILES: CC(C)c1nc2c(c3c1[C@@H](c1ccc(C(C)(C)C)cc1)OC31CCOCC1)[C@@H](O)CC(C)(C)C2]

Obtained by starting from (3R,9S)-9-(tert-butyldimethylsilyloxy)-3-(4-tert-butylphenyl)-4-isopropyl-7,7-dimethyl-2',3',5',6,6',7,8,9-octahydro-3H-spiro[furo[3,4-c]quinoline-1,4'-pyran].

Mass spectrometry (ESI$^+$): m/z=464 [M+H]$^+$

HPLC (Method 14): Retention time=9.81 min.

(43) (3'R,9'S)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinolin]-9'-ol

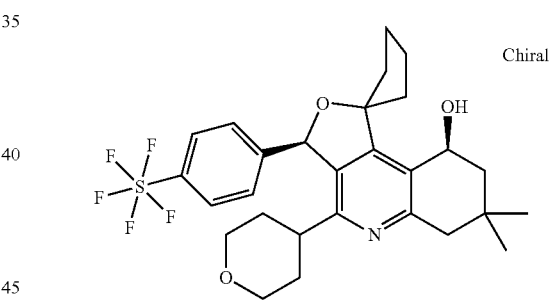

Obtained by starting from (3'R,9'S)-9'-(tert-butyldimethylsilyloxy)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline]

Mass spectrometry (ESI$^+$): m/z=560 [M+H]$^+$

HPLC (Method 7): Retention time=1.519 min.

(44) 1-(4-((3'R,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)phenyl)cyclopropanecarbonitrile

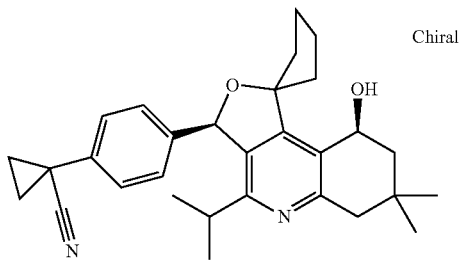 [SMILES: CC(C)c1nc2c(c3c1[C@@H](c1ccc(C4(C#N)CC4)cc1)OC31CCCC1)[C@@H](O)CC(C)(C)C2]

Obtained by starting from 1-(4-((3'R,9'S)-9'-(tert-butyldimethylsilyloxy)-4'-isopropyl-7',7'-dimethyl-6',7',8',9'-tetrahydro-3'H-spiro[cyclopentane-1,1'-furo[3,4-c]quinoline]-3'-yl)phenyl)cyclopropanecarbonitrile.

Mass spectrometry (ESI⁺): m/z=457 [M+H]⁺

HPLC (Method 7): Retention time=1.294 min.

R$_f$-value: 0.55 (silica gel, cyclohexane/ethylacetate 2:1)

(45) (3'R,9'S)-3'-(4-cyclopropylphenyl)-4'-isopropyl-7',7'-dimethyl-6',7',8',9'-tetrahydro-3'H-spiro[cyclopentane-1,1'-furo[3,4-c]quinolin]-9'-ol

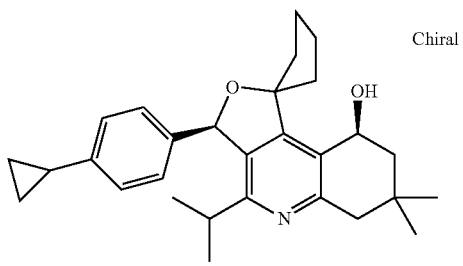 [SMILES: CC(C)c1nc2c(c3c1[C@@H](c1ccc(C4CC4)cc1)OC31CCCC1)[C@@H](O)CC(C)(C)C2]

Obtained by starting from (3'R,9'S)-9'-(tert-butyldimethylsilyloxy)-3'-(4-cyclopropylphenyl)-4'-isopropyl-7',7'-dimethyl-6',7',8',9'-tetrahydro-3'H-spiro[cyclopentane-1,1'-furo[3,4-c]quinoline].

Mass spectrometry (ESI⁺): m/z=432 [M+H]⁺

HPLC (Method 7): Retention time=1.465 min.

(46) (3'R,6'R,9'S)-9'-hydroxy-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]-6'-yl acetate

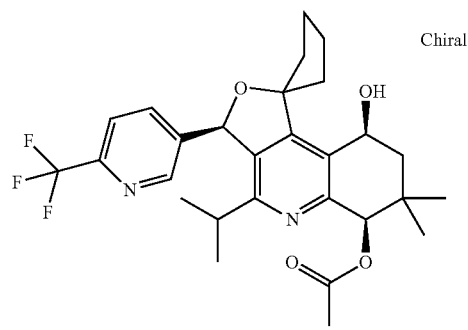 [SMILES: CC(=O)O[C@H]1c2nc(C(C)C)c3c(c2[C@@H](O)CC1(C)C)C1(CCCC1)O[C@@H]3c1ccc(C(F)(F)F)nc1]

Obtained by starting from (3'R,6'R,9'S)-9'-(tert-butyldimethylsilyloxy)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]-6'-yl acetate.

Mass spectrometry (ESI⁺): m/z=519 [M+H]⁺

HPLC (Method 12): Retention time=10.52 min.

(47) (3R,9S)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]-9-ol

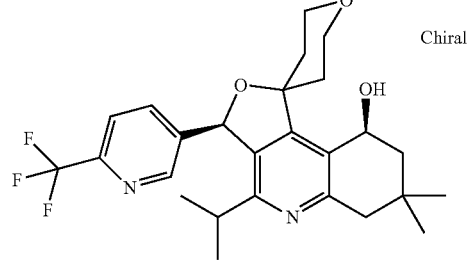

Obtained by starting from (3R,9S)-9-(tert-butyldimethylsilyloxy)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]

Mass spectrometry (ESI⁺): m/z=477 [M+H]⁺

HPLC (Method 14): Retention time=5.04 min.

(48) (3R,6R,9S)-9-hydroxy-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-6-yl acetate

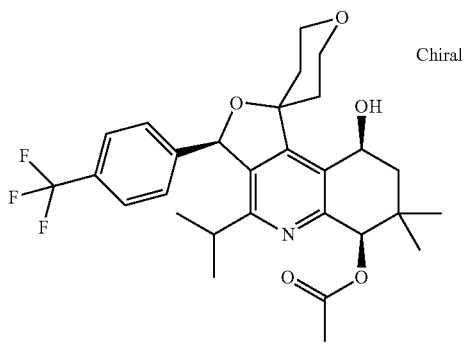 [SMILES: CC(=O)O[C@H]1c2nc(C(C)C)c3c(c2[C@@H](O)CC1(C)C)C1(CCOCC1)O[C@@H]3c1ccc(C(F)(F)F)cc1]

Obtained by starting from (3R,6R,9S)-9-(tert-butyldimethylsilyloxy)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-6-yl acetate.

Mass spectrometry (ESI$^+$): m/z=534 [M+H]$^+$

HPLC (Method 12): Retention time=10.10 min.

(49) (3S,9S)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]-9-ol

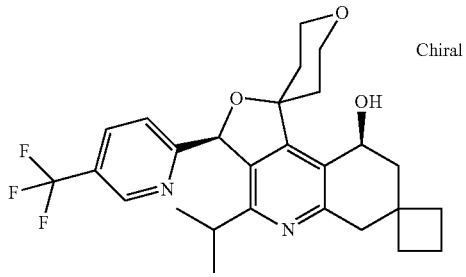 [SMILES: CC(C)c1nc2c(c3c1[C@@H](c1ccc(C(F)(F)F)cn1)OC31CCOCC1)[C@@H](O)CC1(CCC1)C2]

Obtained by starting from (3S,9S)-9-(tert-butyldimethylsilyloxy)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran].

Mass spectrometry (ESI$^+$): m/z=489 [M+H]$^+$

HPLC (Method 14): Retention time=9.34 min.

(50) (3R,9S)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]-9-ol

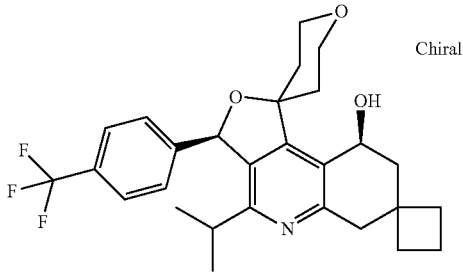 [SMILES: CC(C)c1nc2c(c3c1[C@@H](c1ccc(C(F)(F)F)cc1)OC31CCOCC1)[C@@H](O)CC1(CCC1)C2]

Obtained by starting from (3R,9S)-9-(tert-butyldimethylsilyloxy)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran].

Mass spectrometry (ESI$^+$): m/z=488 [M+H]$^+$

HPLC (Method 14): Retention time=10.49 min.

(51) (3S,9S)-3-(2-fluoro-4-(trifluoromethyl)phenyl)-4-isopropyl-7,7-(propan-1,3-diyl)-2',3',5',6,6',7,8,9-octahydro-3H-spiro[furo[3,4-c]quinoline-1,4'-pyran]-9-ol

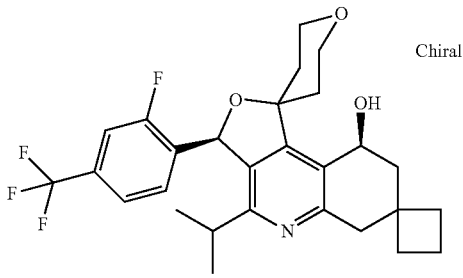 [SMILES: CC(C)c1nc2c(c3c1[C@@H](c1ccc(C(F)(F)F)cc1F)OC31CCOCC1)[C@@H](O)CC1(CCC1)C2]

Obtained by starting from (3S,9S)-9-(tert-butyldimethylsilyloxy)-3-(2-fluoro-4-(trifluoromethyl)phenyl)-4-isopropyl-7,7-(propan-1,3-diyl)-2',3',5',6,6',7,8,9-octahydro-3H-spiro[furo[3,4-c]quinoline-1,4'-pyran].

Mass spectrometry (ESI$^+$): m/z=506 [M+H]$^+$

HPLC (Method 14): Retention time=11.13 min.

(52) (3R,9S)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-9-ol

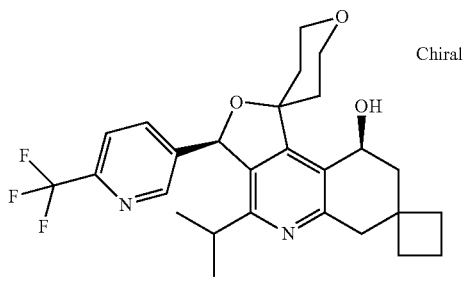 [SMILES: CC(C)c1nc2c(c3c1[C@@H](c1ccc(C(F)(F)F)nc1)OC31CCOCC1)[C@@H](O)CC1(CCC1)C2]

Obtained by starting from (3R,9S)-9-(tert-butyldimethylsilyloxy)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran].

Mass spectrometry (ESI+): m/z=489 [M+H]+
HPLC (Method 14): Retention time=9.78 min.

(53) (3R,9S)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-9-ol

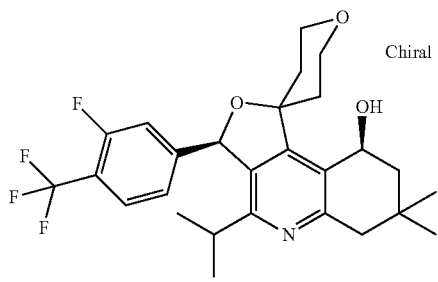 [SMILES: CC(C)c1nc2c(c3c1[C@@H](c1ccc(C(F)(F)F)c(F)c1)OC31CCOCC1)[C@@H](O)CC(C)(C)C2]

Obtained by starting from (3R,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran].

Mass spectrometry (ESI+): m/z=494 [M+H]+
HPLC (Method 14): Retention time=10.74 min.

(54) (3S,9S)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-9-ol

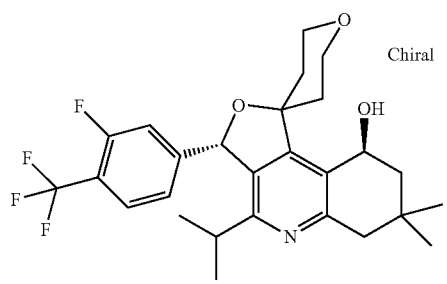 [SMILES: CC(C)c1nc2c(c3c1[C@H](c1ccc(C(F)(F)F)c(F)c1)OC31CCOCC1)[C@@H](O)CC(C)(C)C2]

Obtained by starting from (3S,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran].

Mass spectrometry (ESI+): m/z=494 [M+H]+
HPLC (Method 14): Retention time=10.56 min.

(55) (3S,9S)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-9-ol

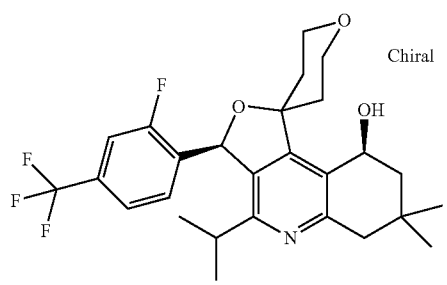 [SMILES: CC(C)c1nc2c(c3c1[C@@H](c1ccc(C(F)(F)F)cc1F)OC31CCOCC1)[C@@H](O)CC(C)(C)C2]

Obtained by starting from (3S,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran].

Mass spectrometry (ESI+): m/z=494 [M+H]+
HPLC (Method 14): Retention time=10.66 min.

(56) (3S,9S)-3-(5-tert-butyl-4-methylthiazol-2-yl)-4-isopropyl-7,7-dimethyl-2',3',5',6',7,8,9-octahydro-3H-spiro[furo[3,4-c]quinoline-1,4'-pyran]-9-ol

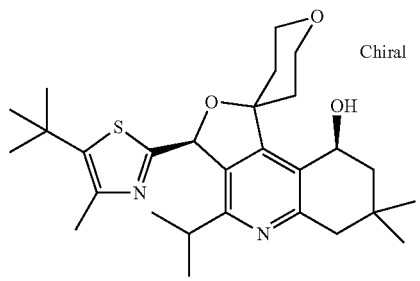 [SMILES: Cc1nc([C@H]2OC3(CCOCC3)c3c2c(C(C)C)nc2c3[C@@H](O)CC(C)(C)C2)sc1C(C)(C)C]

Obtained by starting from (3S,9S)-3-(5-tert-butyl-4-methylthiazol-2-yl)-9-(tert-butyldimethylsilyloxy)-4-isopropyl-7,7-dimethyl-2',3',5',6',7,8,9-octahydro-3H-spiro[furo[3,4-c]quinoline-1,4'-pyran].

Mass spectrometry (ESI$^+$): m/z=485 [M+H]$^+$
HPLC (Method 14): Retention time=10.12 min.

(57) (3R,9S)-4-isopropyl-7,7-(butan-1,4-diyl)-3-(4-(trifluoromethyl)phenyl)-2',3',5',6',7,8,9-octahydro-3H-spiro[furo[3,4-c]quinoline-1,4'-pyran]-9-ol

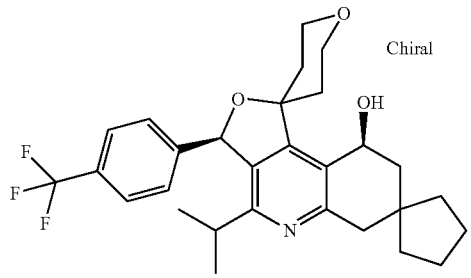 [SMILES: CC(C)c1nc2c(c3c1[C@@H](c1ccc(C(F)(F)F)cc1)OC31CCOCC1)[C@@H](O)CC1(CCCC1)C2]

Obtained by starting from (3R,9S)-9-(tert-butyldimethylsilyloxy)-4-isopropyl-7,7-(butan-1,4-diyl)-3-(4-(trifluoromethyl)phenyl)-2',3',5',6',7,8,9-octahydro-3H-spiro[furo[3,4-c]quinoline-1,4'-pyran].

Mass spectrometry (ESI$^+$): m/z=502 [M+H]$^+$
HPLC (Method 4): Retention time=2.62 min.

(58) (3R,9S)-3-(4-tert-butoxyphenyl)-4-isopropyl-7,7-dimethyl-2',3',5',6',7,8,9-octahydro-3H-spiro[furo[3,4-c]quinoline-1,4'-pyran]-9-ol

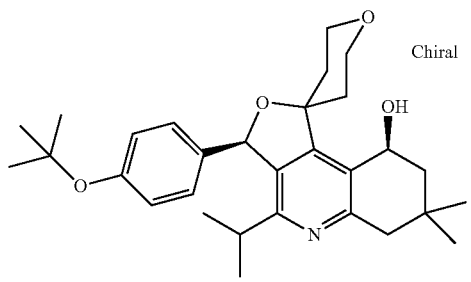 [SMILES: CC(C)c1nc2c(c3c1[C@@H](c1ccc(OC(C)(C)C)cc1)OC31CCOCC1)[C@@H](O)CC(C)(C)C2]

Obtained by starting from (3R,9S)-3-(4-tert-butoxyphenyl)-9-(tert-butyldimethylsilyloxy)-4-isopropyl-7,7-dimethyl-2',3',5',6',7,8,9-octahydro-3H-spiro[furo[3,4-c]quinoline-1,4'-pyran].

Mass spectrometry (ESI$^+$): m/z=480 [M+H]$^+$
HPLC (Method 4): Retention time=2.295 min.

(59) (3R,9S)-3-(4-isopropoxyphenyl)-4-isopropyl-7,7-dimethyl-2',3',5',6',7,8,9-octahydro-3H-spiro[furo[3,4-c]quinoline-1,4'-pyran]-9-ol

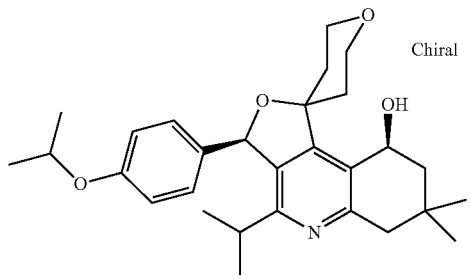 [SMILES: CC(C)Oc1ccc([C@H]2OC3(CCOCC3)c3c2c(C(C)C)nc2c3[C@@H](O)CC(C)(C)C2)cc1]

Obtained by starting from (3R,9S)-9-(tert-butyldimethylsilyloxy)-3-(4-isopropoxyphenyl)-4-isopropyl-7,7-dimethyl-2',3',5',6',7,8,9-octahydro-3H-spiro[furo[3,4-c]quinoline-1,4'-pyran].

Mass spectrometry (ESI$^+$): m/z=466 [M+H]$^+$
HPLC (Method 4): Retention time=2.37 min.

401

(60) (3'R,9'S)-4'-isopropyl-7',7'-dimethyl-3'-(4-(prop-1-en-2-yl)phenyl)-6',7',8',9'-tetrahydro-3'H-spiro[cyclopentane-1,1'-furo[3,4-c]quinolin]-9'-ol

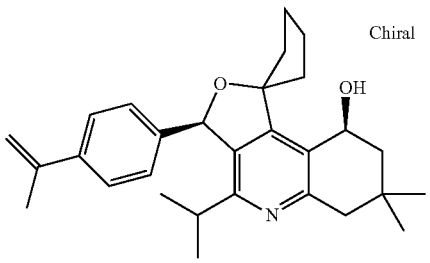 [SMILES: C=C(C)c1ccc([C@H]2OC3(CCCC3)c3c2c(C(C)C)nc2c3[C@@H](O)CC(C)(C)C2)cc1]

Obtained by starting from (3'R,9'S)-9'-(tert-butyldimethylsilyloxy)-3'-(4-(2-fluoropropan-2-yl)phenyl)-4'-isopropyl-7',7'-dimethyl-6',7',8',9'-tetrahydro-3'H-spiro[cyclopentane-1,1'-furo[3,4-c]quinoline].

Mass spectrometry (ESI$^+$): m/z=432 [M+H]$^+$

HPLC (Method 1): Retention time=2.676 min.

R$_f$-value: 0.47 (silica gel, petrole ether/ethylacetate 4:1)

(61) (3R,9S)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran]-9-ol

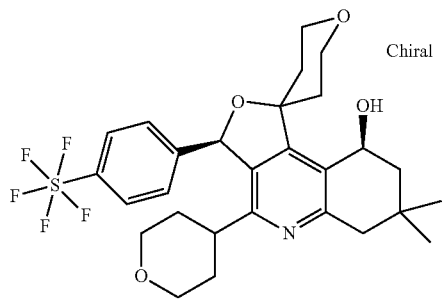 [SMILES: CC1(C)Cc2nc(C3CCOCC3)c3c(c2[C@@H](O)C1)C1(CCOCC1)O[C@@H]3c1ccc(S(F)(F)(F)(F)F)cc1]

Obtained by starting from (3R,9S)-9-(tert-butyldimethylsilyloxy)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran].

Mass spectrometry (ESI$^+$): m/z=576 [M+H]$^+$

HPLC (Method 24): Retention time=1.446 min.

R$_f$-value: 0.52 (silica gel, petrole ether/ethylacetate 1:1)

402

(62) (3'R,9'S)-3'-(4-tert-butylphenyl)-4'-isopropyl-7',7'-(propan-1,3-diyl)-6',7',8',9'-tetrahydro-3'H-spiro[cyclopentane-1,1'-furo[3,4-c]quinolin]-9'-ol

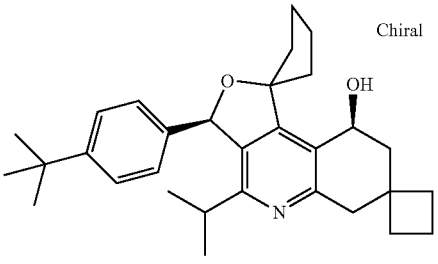 [SMILES: CC(C)c1nc2c(c3c1[C@@H](c1ccc(C(C)(C)C)cc1)OC31CCCC1)[C@@H](O)CC1(CCC1)C2]

Obtained by starting from (3'R,9'S)-9'-(tert-butyldimethylsilyloxy)-3'-(4-tert-butylphenyl)-4'-isopropyl-7',7'-(propan-1,3-diyl)-6',7',8',9'-tetrahydro-3'H-spiro[cyclopentane-1,1'-furo[3,4-c]quinoline].

Mass spectrometry (ESI$^+$): m/z=460 [M+H]$^+$

HPLC (Method 7): Retention time=1.574 min.

R$_f$-value: 0.3 (silica gel, cyclohexane/ethylacetate 9:1)

(63) (3R,9S)-3-(4-tert-butylphenyl)-4-isopropyl-7,7-(propan-1,3-diyl)-2',3',5',6,6',7,8,9-octahydro-3H-spiro[furo[3,4-c]quinoline-1,4'-pyran]-9-ol

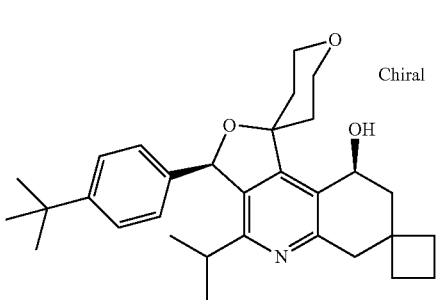 [SMILES: CC(C)c1nc2c(c3c1[C@@H](c1ccc(C(C)(C)C)cc1)OC31CCOCC1)[C@@H](O)CC1(CCC1)C2]

Obtained by starting from (3R,9S)-9-(tert-butyldimethylsilyloxy)-3-(4-tert-butylphenyl)-4-isopropyl-7,7-(propan-1,3-diyl)-2',3',5',6,6',7,8,9-octahydro-3H-spiro[furo[3,4-c]quinoline-1,4'-pyran].

Mass spectrometry (ESI$^+$): m/z=476 [M+H]$^+$

HPLC (Method 7): Retention time=1.519 min.

R$_f$-value: 0.4 (silica gel, cyclohexane/ethylacetate 3:1)

403

(64) (3R,9S)-4-isopropyl-7,7-dimethyl-3-(4-(3-methyloxetan-3-yl)phenyl)-2',3',5',6,6',7,8,9-octahydro-3H-spiro[furo[3,4-c]quinoline-1,4'-pyran]-9-ol

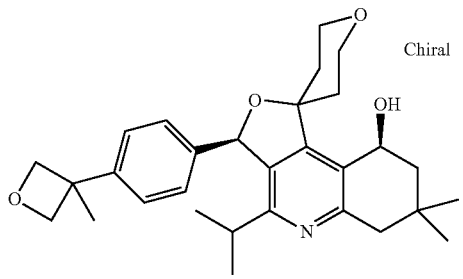 [SMILES: CC(C)c1nc2c(c3c1[C@@H](c1ccc(C4(C)COC4)cc1)OC31CCOCC1)[C@@H](O)CC(C)(C)C2]

Obtained by starting from (3R,9S)-9-(tert-butyldimethylsilyloxy)-4-isopropyl-7,7-dimethyl-3-(4-(3-methyloxetan-3-yl)phenyl)-2',3',5',6,6',7,8,9-octahydro-3H-spiro[furo[3,4-c]quinoline-1,4'-pyran].

Mass spectrometry (ESI$^+$): m/z=478 [M+H]$^+$

HPLC (Method 24): Retention time=1.226 min.

$R_f$-value: 0.25 (silica gel, petrole ether/ethylacetate 2:1)

(65) (3'R,9'S)-4'-isopropyl-7',7'-dimethyl-3'-(4-(perfluoroethyl)phenyl)-6',7',8',9'-tetrahydro-3'H-spiro[cyclopentane-1,1'-furo[3,4-c]quinolin]-9'-ol

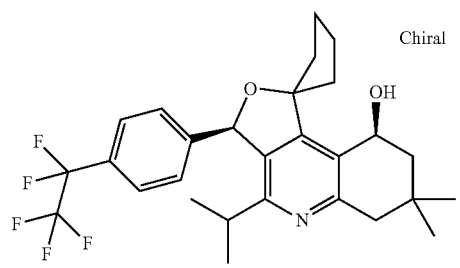 [SMILES: CC(C)c1nc2c(c3c1[C@@H](c1ccc(C(F)(F)C(F)(F)F)cc1)OC31CCCC1)[C@@H](O)CC(C)(C)C2]

Obtained by starting from (3'R,9'S)-9'-(tert-butyldimethylsilyloxy)-4'-isopropyl-7',7'-dimethyl-3'-(4-(perfluoroethyl)phenyl)-6',7',8',9'-tetrahydro-3'H-spiro[cyclopentane-1,1'-furo[3,4-c]quinoline].

Mass spectrometry (ESI$^+$): m/z=510 [M+H]$^+$

HPLC (Method 7): Retention time=1.531 min.

(66) 5-((3R,9S)-9-hydroxy-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile

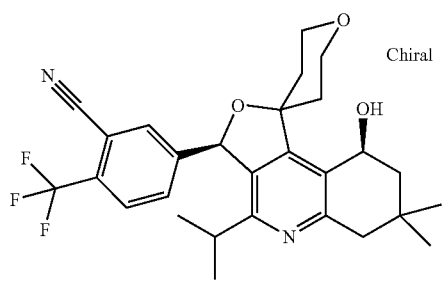 [SMILES: CC(C)c1nc2c(c3c1[C@@H](c1ccc(C(F)(F)F)c(C#N)c1)OC31CCOCC1)[C@@H](O)CC(C)(C)C2]

404

Obtained by starting from 5-((3R,9S)-9-(tert-butyldimethylsilyloxy)-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=501 [M+H]$^+$

HPLC (Method 26): Retention time=1.34 min.

(67) (3S,9S)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]-9-ol

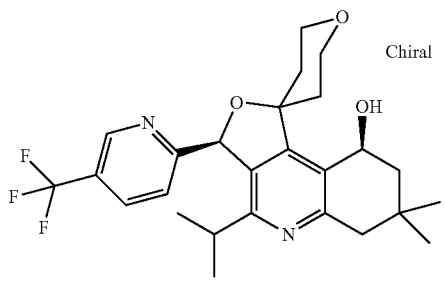 [SMILES: CC(C)c1nc2c(c3c1[C@@H](c1ccc(C(F)(F)F)cn1)OC31CCOCC1)[C@@H](O)CC(C)(C)C2]

Obtained by starting from (3S,9S)-9-(tert-butyldimethylsilyloxy)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran].

Mass spectrometry (ESI$^+$): m/z=477 [M+H]$^+$

HPLC (Method 7): Retention time=1.265 min.

$R_f$-value: 0.2 (silica gel, cyclohexane/ethylacetate 3:1)

(68) (3R,9S)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]-9-ol

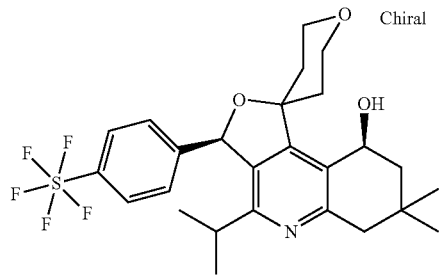 [SMILES: CC(C)c1nc2c(c3c1[C@@H](c1ccc(S(F)(F)(F)(F)F)cc1)OC31CCOCC1)[C@@H](O)CC(C)(C)C2]

Obtained by starting from (3R,9S)-9-(tert-butyldimethylsilyloxy)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran].

Mass spectrometry (ESI$^+$): m/z=534 [M+H]$^+$

HPLC (Method 24): Retention time=1.434 min.

$R_f$-value: 0.32 (silica gel, petrole ether/ethylacetate 2:1)

(69) (3R,9S)-4-isopropyl-7,7-(propan-1,3-diyl)-3-(4-(pentafluorosulfanyl)phenyl)-2',3',5',6,6',7,8,9-octahydro-3H-spiro[furo[3,4-c]quinoline-1,4'-pyran]-9-ol

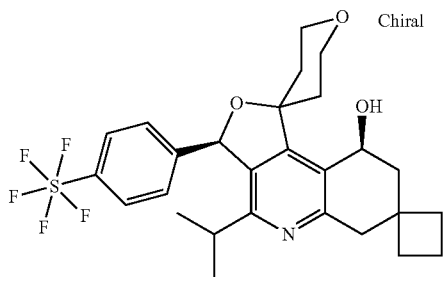 [SMILES: CC(C)c1nc2c(c3c1[C@@H](c1ccc(S(F)(F)(F)(F)F)cc1)OC31CCOCC1)[C@@H](O)CC1(CCC1)C2]

Obtained by starting from (3R,9S)-9-(tert-butyldimethylsilyloxy)-4-isopropyl-7,7-(propan-1,3-diyl)-3-(4-(pentafluorosulfanyl)phenyl)-2',3',5',6,6',7,8,9-octahydro-3H-spiro[furo[3,4-c]quinoline-1,4'-pyran].

Mass spectrometry (ESI$^+$): m/z=546 [M+H]$^+$
HPLC (Method 24): Retention time=1.442 min.

(70) (3R,9S)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran]-9-ol

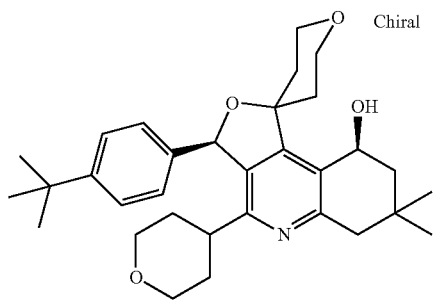 [SMILES: CC1(C)Cc2nc(C3CCOCC3)c3c(c2[C@@H](O)C1)C1(CCOCC1)O[C@@H]3c1ccc(C(C)(C)C)cc1]

Obtained by starting from (3R,9S)-9-(tert-butyldimethylsilyloxy)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran].

Mass spectrometry (ESI$^+$): m/z=506 [M+H]$^+$
HPLC (Method 24): Retention time=1.447 min.

(71) (3'R,9'S)-4'-isopropyl-7',7'-dimethyl-3'-(4-(pentafluorosulfanyl)phenyl)-6',7',8',9'-tetrahydro-3'H-spiro[cyclopentane-1,1'-furo[3,4-c]quinolin]-9'-ol

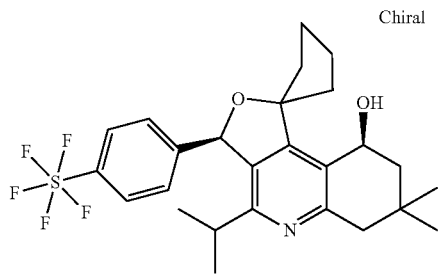 [SMILES: CC(C)c1nc2c(c3c1[C@@H](c1ccc(S(F)(F)(F)(F)F)cc1)OC31CCCC1)[C@@H](O)CC(C)(C)C2]

Obtained by starting from (3'R,9'S)-4'-isopropyl-7',7'-dimethyl-3'-(4-(pentafluorosulfanyl)phenyl)-9'-(2,3,3-trimethylbutan-2-yloxy)-6',7',8',9'-tetrahydro-3'H-spiro[cyclopentane-1,1'-furo[3,4-c]quinoline].

Mass spectrometry (ESI$^+$): m/z=518 [M+H]$^+$
HPLC (Method 5): Retention time=1.764 min.

(72) 5-((3R,9S)-9-hydroxy-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

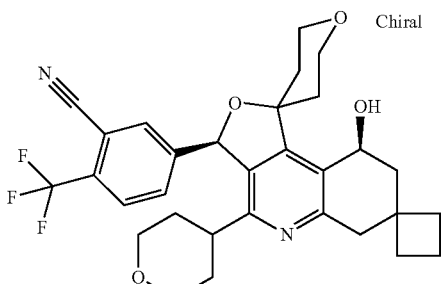

Obtained by starting from 5-((3R,9S)-9-(tert-butyldimethylsilyloxy)-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=555 [M+H]$^+$
HPLC (Method 7): Retention time=1.359 min.

407

(73) (3S,9S)-7,7-dimethyl-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]-9-ol

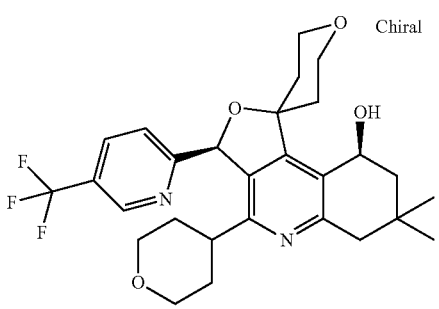 [SMILES: CC1(C)Cc2nc(C3CCOCC3)c3c(c2[C@@H](O)C1)C1(CCOCC1)O[C@@H]3c1ccc(C(F)(F)F)cn1]

Obtained by starting from (3S,9S)-9-(tert-butyldimethylsilyloxy)-7,7-dimethyl-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran].

Mass spectrometry (ESI$^+$): m/z=519 [M+H]$^+$

HPLC (Method 7): Retention time=1.267 min.

(74) 5-((3R,9S)-9-hydroxy-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

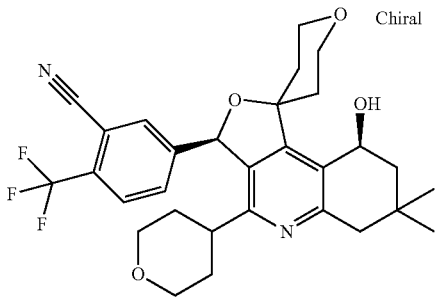 [SMILES: CC1(C)Cc2nc(C3CCOCC3)c3c(c2[C@@H](O)C1)C1(CCOCC1)O[C@@H]3c1ccc(C(F)(F)F)c(C#N)c1]

Obtained by starting from 5-((3R,9S)-9-(tert-butyldimethylsilyloxy)-4-cyclohexyl-7,7-dimethyl-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=543 [M+H]$^+$

HPLC (Method 26): Retention time=1.35 min.

408

(75) (3S,9S)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]-9-ol

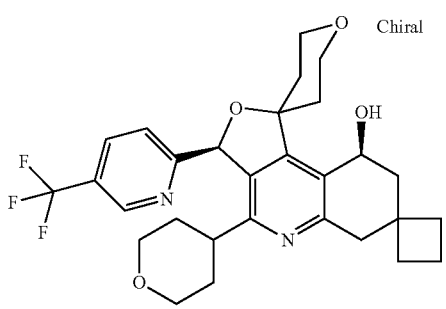 [SMILES: O[C@H]1CC2(CCC2)Cc2nc(C3CCOCC3)c3c(c21)C1(CCOCC1)O[C@@H]3c1ccc(C(F)(F)F)cn1]

Obtained by starting from (3S,9S)-9-(tert-butyldimethylsilyloxy)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran].

Mass spectrometry (ESI$^+$): m/z=531 [M+H]$^+$

HPLC (Method 7): Retention time=1.267 min.

(76) (3R,9S)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]-9-ol

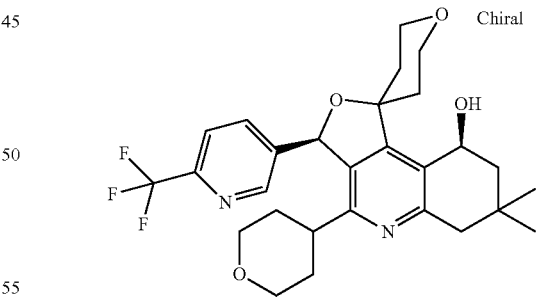

Obtained by starting from (3R,9S)-9-(tert-butyldimethylsilyloxy)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran].

Mass spectrometry (ESI$^+$): m/z=519 [M+H]$^+$

HPLC (Method 7): Retention time=1.186 min.

(77) (3R,9S)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-9-ol

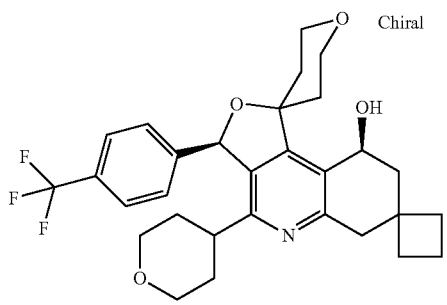 [SMILES: O[C@H]1CC2(CCC2)Cc2nc(C3CCOCC3)c3c(c21)C1(CCOCC1)O[C@@H]3c1ccc(C(F)(F)F)cc1]

Obtained by starting from (3R,9S)-9-(tert-butyldimethylsilyloxy)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran].

Mass spectrometry (ESI$^+$): m/z=530 [M+H]$^+$

HPLC (Method 7): Retention time=1.405 min.

(78) (3R,9S)-7,7-(propan-1,3-diyl)-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]-9-ol

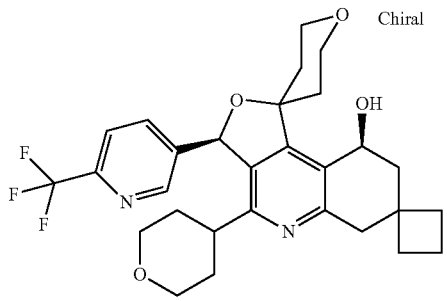 [SMILES: O[C@H]1CC2(CCC2)Cc2nc(C3CCOCC3)c3c(c21)C1(CCOCC1)O[C@@H]3c1ccc(C(F)(F)F)nc1]

Obtained by starting from (3R,9S)-9-(tert-butyldimethylsilyloxy)-7,7-(propan-1,3-diyl)-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran].

Mass spectrometry (ESI$^+$): m/z=531 [M+H]$^+$

HPLC (Method 7): Retention time=1.280 min.

(79) 5-((3R,9S)-9-hydroxy-4-isopropyl-7,7-(propan-1,3-diyl)-2',3',5',6,6',7,8,9-octahydro-3H-spiro[furo[3,4-c]quinoline-1,4'-pyran]-3-yl)-2-(trifluoromethyl)benzonitrile

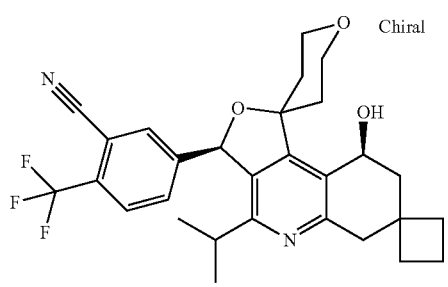 [SMILES: CC(C)c1nc2c(c3c1[C@@H](c1ccc(C(F)(F)F)c(C#N)c1)OC31CCOCC1)[C@@H](O)CC1(CCC1)C2]

Obtained by starting from 5-((3R,9S)-9-(tert-butyldimethylsilyloxy)-4-isopropyl-7,7-(propan-1,3-diyl)-2',3',5',6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=513 [M+H]$^+$

HPLC (Method 27): Retention time=1.32 min.

(80) (3R,9S)-4-tert-butyl-7,7-dimethyl-3-(4-(trifluoromethyl)phenyl)-2',3',5',6,6',7,8,9-octahydro-3H-spiro[furo[3,4-c]quinoline-1,4'-pyran]-9-ol

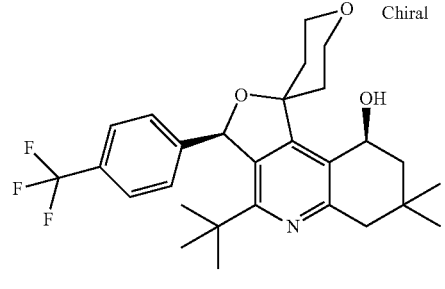 [SMILES: CC1(C)Cc2nc(C(C)(C)C)c3c(c2[C@@H](O)C1)C1(CCOCC1)O[C@@H]3c1ccc(C(F)(F)F)cc1]

Obtained by starting from (3R,9S)-4-tert-butyl-9-(tert-butyldimethylsilyloxy)-7,7-dimethyl-3-(4-(trifluoromethyl)phenyl)-2',3',5',6,6',7,8,9-octahydro-3H-spiro[furo[3,4-c]quinoline-1,4'-pyran].

Mass spectrometry (ESI$^+$): m/z=490 [M+H]$^+$

HPLC (Method 5): Retention time=1.765 min.

411

(81) (3R,9S)-4-(1-methoxyethyl)-7,7-dimethyl-3-(4-(trifluoromethyl)phenyl)-2',3',5',6,6',7,8,9-octahydro-3H-spiro[furo[3,4-c]quinoline-1,4'-pyran]-9-ol

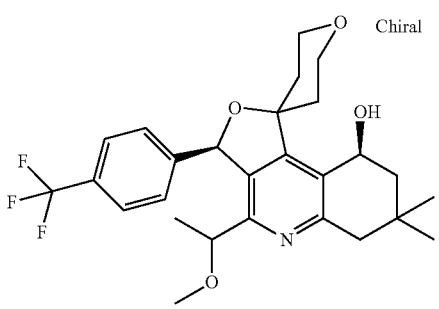 [SMILES: COC(C)c1nc2c(c3c1[C@@H](c1ccc(C(F)(F)F)cc1)OC31CCOCC1)[C@@H](O)CC(C)(C)C2]

Obtained by starting from (3R,9S)-4-(1-methoxyethyl)-7,7-dimethyl-3-(4-(trifluoromethyl)phenyl)-9-(2,3,3-trimethylbutan-2-yloxy)-2',3',5',6,6',7,8,9-octahydro-3H-spiro[furo[3,4-c]quinoline-1,4'-pyran].

Mass spectrometry (ESI⁺): m/z=492 [M+H]⁺

HPLC (Method 28): Retention time=1.193 min.

(82) (3R,9S)-4-(methoxymethyl)-7,7-dimethyl-3-(4-(trifluoromethyl)phenyl)-2',3',5',6,6',7,8,9-octahydro-3H-spiro[furo[3,4-c]quinoline-1,4'-pyran]-9-ol

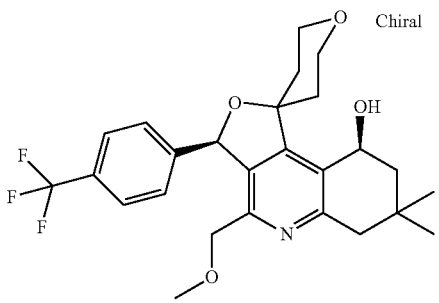 [SMILES: COCc1nc2c(c3c1[C@@H](c1ccc(C(F)(F)F)cc1)OC31CCOCC1)[C@@H](O)CC(C)(C)C2]

Obtained by starting from (3R,9S)-9-(tert-butyldimethylsilyloxy)-4-(methoxymethyl)-7,7-dimethyl-3-(4-(trifluoromethyl)phenyl)-2',3',5',6,6',7,8,9-octahydro-3H-spiro[furo[3,4-c]quinoline-1,4'-pyran].

Mass spectrometry (ESI⁺): m/z=478 [M+H]⁺

HPLC (Method 29): Retention time=1.296 min.

412

(83) (3R,9S)-4-(2-methoxypropan-2-yl)-7,7-dimethyl-3-(4-(trifluoromethyl)phenyl)-2',3',5',6,6',7,8,9-octahydro-3H-spiro[furo[3,4-c]quinoline-1,4'-pyran]-9-ol

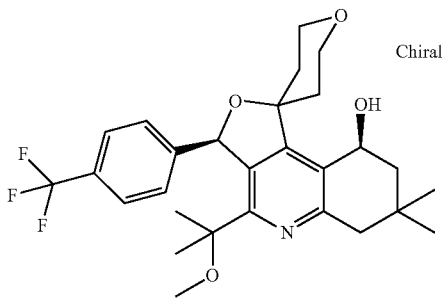 [SMILES: COC(C)(C)c1nc2c(c3c1[C@@H](c1ccc(C(F)(F)F)cc1)OC31CCOCC1)[C@@H](O)CC(C)(C)C2]

Obtained by starting from (3R,9S)-9-(tert-butyldimethylsilyloxy)-4-(2-methoxypropan-2-yl)-7,7-dimethyl-3-(4-(trifluoromethyl)phenyl)-2',3',5',6,6',7,8,9-octahydro-3H-spiro[furo[3,4-c]quinoline-1,4'-pyran].

Mass spectrometry (ESI⁺): m/z=506 [M+H]⁺

HPLC (Method 29): Retention time=1.451 min.

Example 2

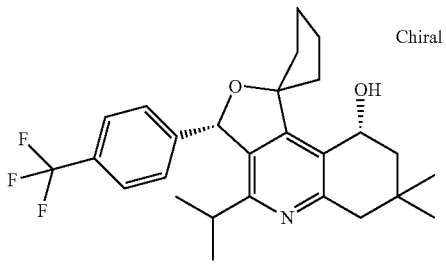 [SMILES: CC(C)c1nc2c(c3c1[C@H](c1ccc(C(F)(F)F)cc1)OC31CCCC1)[C@H](O)CC(C)(C)C2]

(3'S,9'R)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol and

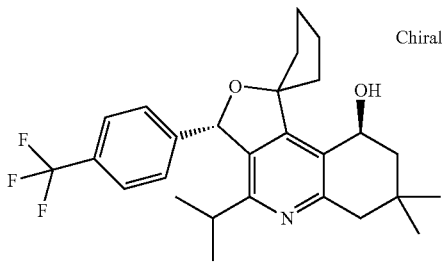 [SMILES: CC(C)c1nc2c(c3c1[C@H](c1ccc(C(F)(F)F)cc1)OC31CCCC1)[C@@H](O)CC(C)(C)C2]

(3'S,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol 120 µl of a 1 M solution of lithium aluminiumhydride in tetrahydrofurane are added dropwise to 55 mg (S)-4'-isopropyl-7',7'-dimethyl-3'-(4-(trifluoromethyl)phenyl)-7',8'-dihydro-3'H-spiro[cyclopentane-1,1'-furo[3,4-c]quinolin]-9'(6'H)-one in 2 ml tetrahydrofurane at room temperature. The mixture is stirred for 2 hours and then cooled to 0° C. 10 µl water and 10 µl 4 N solution of sodium hydroxide in water are added successively and the mixture is stirred for further 30 minutes. Then the mixture is diluted with ethylacetate and dried with magnesium sulphate. The solvents are evaporated in vacuo and the residue is chromatographed on silica gel (cyclohexane/ethylacetate 90:10 to 50:50).

Diastereomer 1:

Yield: 17 mg (31% of theory) (3'S,9'R)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol Mass spectrometry (ESI⁺): m/z=460 [M+H]⁺

R$_f$-value: 0.41 (silica gel, petrole ether/ethylacetate 4:1)

and

Diastereomer 2:

Yield: 29 mg (52% of theory) (3'S,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol Mass spectrometry (ESI⁺): m/z=460 [M+H]⁺

R$_f$-value: 0.30 (silica gel, petrole ether/ethylacetate 4:1

Example 3

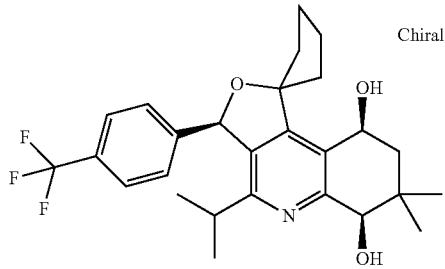

(3'R,6'R,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6',9'-diol 13 mg (3'R,6'R,9'S)-9'-hydroxy-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate are dissolved in 1 ml methanol and treated with 14 mg potassium carbonate. Three drops water are added and the mixture is stirred for 3 hours at room temperature. Then the solvent is evaporated in vacuo and the residue is partitioned between water and dichloromethane. The organic phase is dried with sodium sulphate and the solvent is evaporated in vacuo. The residue is chromatographed on silica gel (hexane/ethylacetate 4:1).

Yield: 8 mg (67% of theory)

Mass spectrometry (ESI⁺): m/z=476 [M+H]⁺

HPLC (Method 14): Retention time=13.14 min.

Analogously to example 3 the following compounds are obtained:

(1) (3'R,6'S,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6',9'-diol

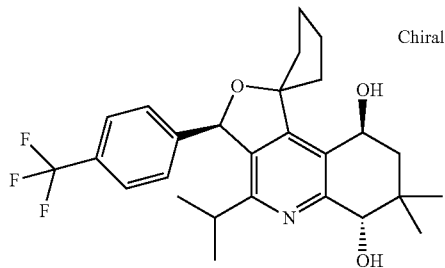

Obtained by starting from (3'R,6'S,9'S)-9'-hydroxy-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate.

Mass spectrometry (ESI⁺): m/z=476 [M+H]⁺

HPLC (Method 16): Retention time=12.59 min.

Example 4

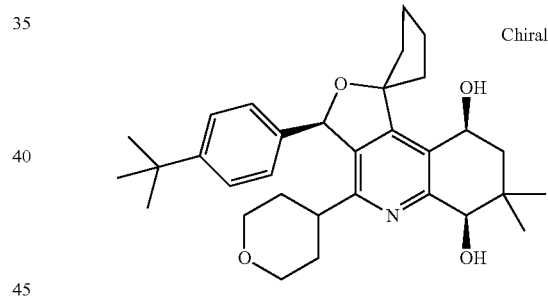

(3'R,6'R,9'S)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline]-6',9'-diol 17 mg (3'R,6'R,9'S)-9'-(tert-butyldimethylsilyloxy)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline]-6'-yl acetate are dissolved in 1 ml methanol and treated with 200 mg potassium carbonate. The mixture is stirred for 36 hours at room temperature, diluted with diethylether and washed with water and saturated aqueous sodium bicarbonate. The organic phase is dried with magnesium sulphate and the solvent is evaporated in vacuo. The residue is chromatographed on silica gel (petrole ether/ethylacetate 80:20 to 40:60).

Yield: 12 mg (92% of theory)

Mass spectrometry (ESI⁺): m/z=506 [M+H]⁺

HPLC (Method 3): Retention time=1.469 min.

Analogously to example 4 the following compounds are obtained:

(1) (3'R,6'R,9'S)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]-6',9'-diol

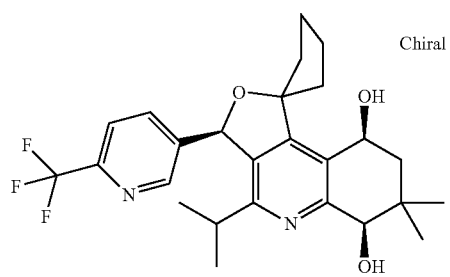 [SMILES: CC(C)c1nc2c(c3c1[C@@H](c1ccc(C(F)(F)F)nc1)OC31CCCC1)[C@@H](O)CC(C)(C)[C@H]2O]

Obtained by starting from (3'R,6'R,9'S)-9'-hydroxy-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]-6'-yl acetate.

Mass spectrometry (ESI⁺): m/z=477 [M+H]⁺

HPLC (Method 13): Retention time=0.57 min.

(2) (3R,6R,9S)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-6,9-diol

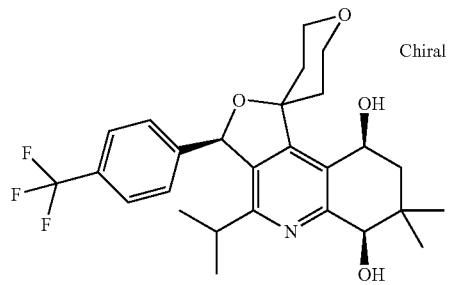 [SMILES: CC(C)c1nc2c(c3c1[C@@H](c1ccc(C(F)(F)F)cc1)OC31CCOCC1)[C@@H](O)CC(C)(C)[C@H]2O]

Obtained by starting from (3R,6R,9S)-9-(tert-butyldimethylsilyloxy)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-6-yl acetate.

Mass spectrometry (ESI⁺): m/z=492 [M+H]⁺

HPLC (Method 14): Retention time=12.31 min.

(3) (3'R,6'R,9'S)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6',9'-diol

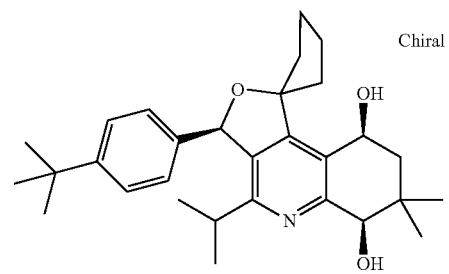 [SMILES: CC(C)c1nc2c(c3c1[C@@H](c1ccc(C(C)(C)C)cc1)OC31CCCC1)[C@@H](O)CC(C)(C)[C@H]2O]

Obtained by starting from (3'R,6'R,9'S)-3'-(4-tert-butylphenyl)-9'-hydroxy-4'-isopropyl-7',7'-dimethyl-6',7',8',9'-tetrahydro-3'H-spiro[cyclopentane-1,1'-furo[3,4-c]quinoline]-6'-yl acetate.

Mass spectrometry (ESI⁺): m/z=464 [M+H]⁺

HPLC (Method 12): Retention time=9.55 min.

(4) (3'R,6'S,9'S)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6',9'-diol

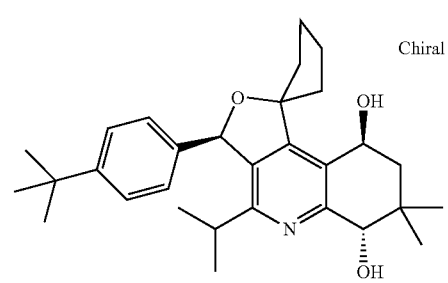 [SMILES: CC(C)c1nc2c(c3c1[C@@H](c1ccc(C(C)(C)C)cc1)OC31CCCC1)[C@@H](O)CC(C)(C)[C@@H]2O]

Obtained by starting from (3'R,6'S,9'S)-3'-(4-tert-butylphenyl)-9'-hydroxy-4'-isopropyl-7',7'-dimethyl-6',7',8',9'-tetrahydro-3'H-spiro[cyclopentane-1,1'-furo[3,4-c]quinoline]-6'-yl acetate.

Mass spectrometry (ESI⁺): m/z=464 [M+H]⁺

HPLC (Method 12): Retention time=9.85 min.

(5) (3S,6R,9S)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6,9-diol

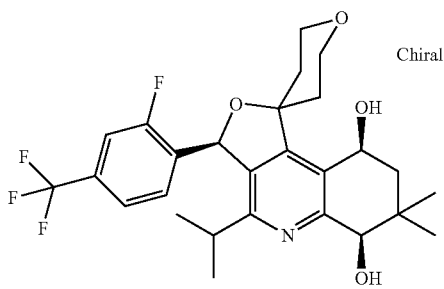 [SMILES: CC(C)c1nc2c(c3c1[C@@H](c1ccc(C(F)(F)F)cc1F)OC31CCOCC1)[C@@H](O)CC(C)(C)[C@H]2O]

Obtained by starting from (3S,6R,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate.

Mass spectrometry (ESI$^+$): m/z=510 [M+H]$^+$

HPLC (Method 14): Retention time=12.79 min.

(6) (3'R,6'R,9'S)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline]-6',9'-diol

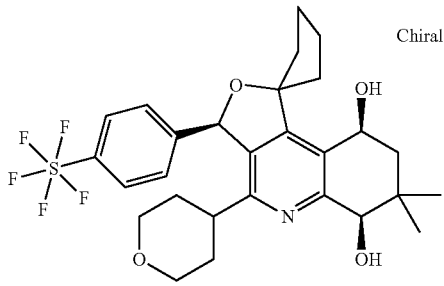 [SMILES: CC1(C)C[C@H](O)c2c(nc(C3CCOCC3)c3c2C2(CCCC2)O[C@@H]3c2ccc(S(F)(F)(F)(F)F)cc2)[C@@H]1O]

Obtained by starting from (3'R,6'R,9'S)-9'-(tert-butyldimethylsilyloxy)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline]-6'-yl acetate.

Mass spectrometry (ESI$^+$): m/z=576 [M+H]$^+$

HPLC (Method 24): Retention time=1.648 min.

R$_f$-value: 0.60 (silica gel, petrole ether/ethylacetate 1:1)

(7) (3R,6R,9S)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]-6,9-diol

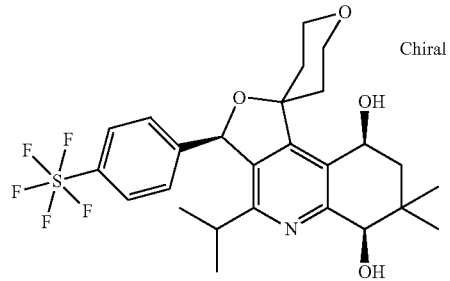 [SMILES: CC(C)c1nc2c(c3c1[C@@H](c1ccc(S(F)(F)(F)(F)F)cc1)OC31CCOCC1)[C@@H](O)CC(C)(C)[C@H]2O]

Obtained by starting from (3R,6R,9S)-9-(tert-butyldimethylsilyloxy)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]-6-yl acetate.

Mass spectrometry (ESI$^+$): m/z=550 [M+H]$^+$

HPLC (Method 24): Retention time=1.569 min.

R$_f$-value: 0.61 (silica gel, petrole ether/ethylacetate 1:1)

(8) (3R,6R,9S)-4-isopropyl-7,7-(propan-1,3-diyl)-3-(4-(pentafluorosulfanyl)phenyl)-2',3',5',6,6',7,8,9-octahydro-3H-spiro[furo[3,4-c]quinoline-1,4'-pyran]-6,9-diol

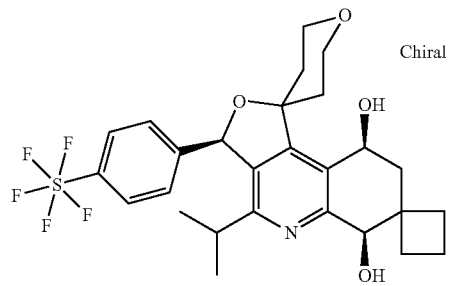 [SMILES: CC(C)c1nc2c(c3c1[C@@H](c1ccc(S(F)(F)(F)(F)F)cc1)OC31CCOCC1)[C@@H](O)CC1(CCC1)[C@H]2O]

Obtained by starting from (3R,6R,9S)-4-isopropyl-7,7-(propan-1,3-diyl)-3-(4-(pentafluorosulfanyl)phenyl)-9-(2,3,3-trimethylbutan-2-yloxy)-2',3',5',6,6',7,8,9-octahydro-3H-spiro[furo[3,4-c]quinoline-1,4'-pyran]-6-yl acetate.

Mass spectrometry (ESI$^+$): m/z=562 [M+H]$^+$

HPLC (Method 24): Retention time=1.431 min.

(9) 5-((3R,6R,9S)-6,9-dihydroxy-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

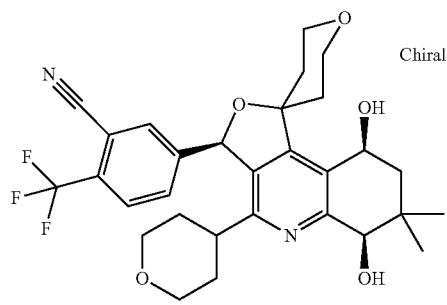 [SMILES: CC1(C)C[C@H](O)c2c(nc(C3CCOCC3)c3c2C2(CCOCC2)O[C@@H]3c2ccc(C(F)(F)F)c(C#N)c2)[C@@H]1O]

Obtained by starting from (3R,6R,9S)-9-(tert-butyldimethylsilyloxy)-3-(3-cyano-4-(trifluoromethyl)phenyl)-7,7-dimethyl-4-(tetrahydro-2H-pyran-4-yl)-2',3',5',6,6',7,8,9-octahydro-3H-spiro[furo[3,4-c]quinoline-1,4'-pyran]-6-yl acetate.

Mass spectrometry (ESI$^+$): m/z=559 [M+H]$^+$

HPLC (Method 2): Retention time=1.980 min.

(10) 5-((3R,6R,9S)-6,9-dihydroxy-4-isopropyl-7,7-(propan-1,3-diyl)-2',3',5',6,6',7,8,9-octahydro-3H-spiro[furo[3,4-c]quinoline-1,4'-pyran]-3-yl)-2-(trifluoromethyl)benzonitrile

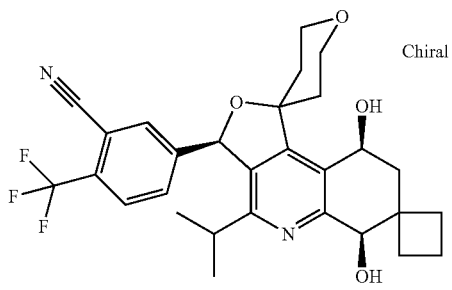 [SMILES: CC(C)c1nc2c(c3c1[C@@H](c1ccc(C(F)(F)F)c(C#N)c1)OC31CCOCC1)[C@@H](O)CC1(CCC1)[C@H]2O]

Obtained by starting from (3R,6R,9S)-9-(tert-butyldimethylsilyloxy)-3-(3-cyano-4-(trifluoromethyl)phenyl)-4-isopropyl-7,7-(propan-1,3-diyl)-2',3',5',6,6',7,8,9-octahydro-3H-spiro[furo[3,4-c]quinoline-1,4'-pyran]-6-yl acetate.

Mass spectrometry (ESI$^+$): m/z=529 [M+H]$^+$

HPLC (Method 28): Retention time=1.27 min.

(11) (3R,6R,9S)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-6,9-diol

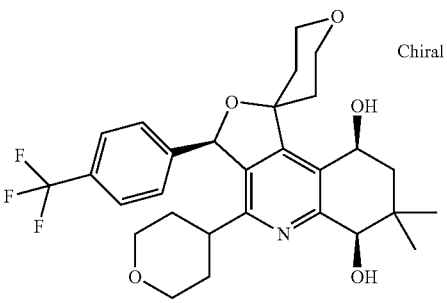 [SMILES: CC1(C)C[C@H](O)c2c(nc(C3CCOCC3)c3c2C2(CCOCC2)O[C@@H]3c2ccc(C(F)(F)F)cc2)[C@@H]1O]

Obtained by starting from (3R,6R,9S)-9-(tert-butyldimethylsilyloxy)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-6-yl acetate.

Mass spectrometry (ESI$^+$): m/z=534 [M+H]$^+$

HPLC (Method 28): Retention time=1.24 min.

(12) (3R,6R,9S)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran]-6,9-diol

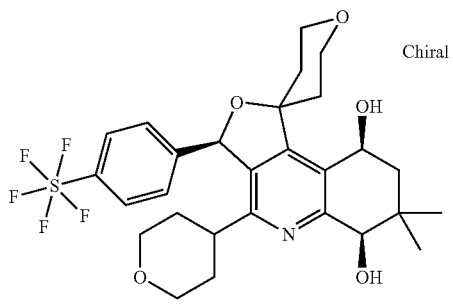 [SMILES: CC1(C)C[C@H](O)c2c(nc(C3CCOCC3)c3c2C2(CCOCC2)O[C@@H]3c2ccc(S(F)(F)(F)(F)F)cc2)[C@@H]1O]

Obtained by starting from (3R,6R,9S)-9-(tert-butyldimethylsilyloxy)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran]-6-yl acetate.

Mass spectrometry (ESI$^+$): m/z=592 [M+H]$^+$

HPLC (Method 24): Retention time=1.550 min.

(13) (3R,6R,9S)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran]-6,9-diol

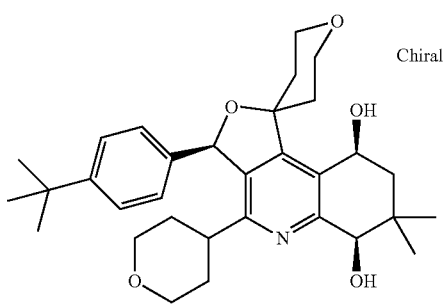 [SMILES: CC(C)(C)c1ccc([C@H]2OC3(CCOCC3)c3c2c(C2CCOCC2)nc2c3[C@@H](O)CC(C)(C)[C@H]2O)cc1]

Obtained by starting from (3R,6R,9S)-9-(tert-butyldimethylsilyloxy)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran]-6-yl acetate.

Mass spectrometry (ESI$^+$): m/z=522 [M+H]$^+$

HPLC (Method 24): Retention time=1.581 min.

(14) 5-((3R,6R,9S)-6,9-dihydroxy-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

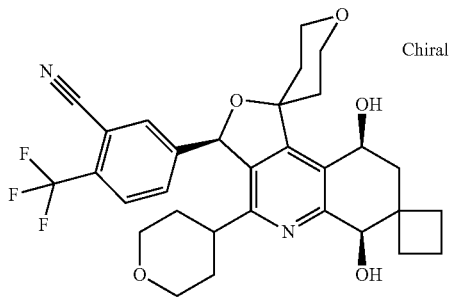 [SMILES: N#Cc1cc([C@H]2OC3(CCOCC3)c3c2c(C2CCOCC2)nc2c3[C@@H](O)CC3(CCC3)[C@H]2O)ccc1C(F)(F)F]

Obtained by starting from (3R,6R,9S)-9-(tert-butyldimethylsilyloxy)-3-(3-cyano-4-(trifluoromethyl)phenyl)-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-6-yl acetate.

Mass spectrometry (ESI$^+$): m/z=571 [M+H]$^+$

HPLC (Method 28): Retention time=1.19 min.

(15) 5-((3R,6R,9S)-6,9-dihydroxy-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile

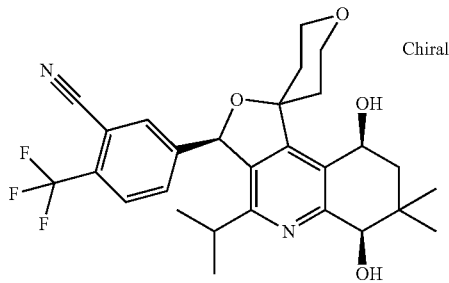 [SMILES: CC(C)c1nc2c(c3c1[C@@H](c1ccc(C(F)(F)F)c(C#N)c1)OC31CCOCC1)[C@@H](O)CC(C)(C)[C@H]2O]

Obtained by starting from (3R,6R,9S)-9-(tert-butyldimethylsilyloxy)-3-(3-cyano-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate.

Mass spectrometry (ESI$^+$): m/z=517 [M+H]$^+$

HPLC (Method 28): Retention time=1.24 min.

(16) (3R,6R,9S)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-6,9-diol

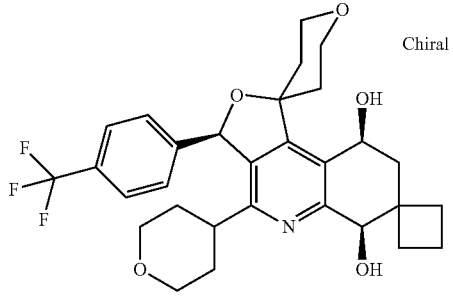 [SMILES: O[C@H]1CC2(CCC2)[C@@H](O)c2nc(C3CCOCC3)c3c(c21)C1(CCOCC1)O[C@@H]3c1ccc(C(F)(F)F)cc1]

Obtained by starting from (3R,6R,9S)-9-(tert-butyldimethylsilyloxy)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-6-yl acetate.

Mass spectrometry (ESI$^+$): m/z=546 [M+H]$^+$

HPLC (Method 32): Retention time=1.319 min.

Example 5

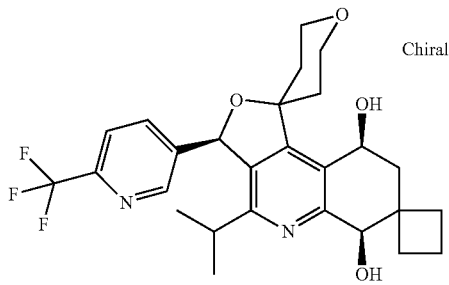 [SMILES: CC(C)c1nc2c(c3c1[C@@H](c1ccc(C(F)(F)F)nc1)OC31CCOCC1)[C@@H](O)CC1(CCC1)[C@H]2O]

(3R,6R,9S)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-6,9-diol 89 mg (3R,6R,9S)-9-(tert-butyldimethylsilyloxy)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-6-yl acetate are dissolved in 8 ml tetrahydrofurane, treated with 1.4 ml of 2 N hydrochloric acid and stirred for 16 hours at 40° C. After evaporation of tetrahydrofurane in vacuo the residue is partitioned between water and saturated aqueous sodium bicarbonate. The organic phase is dried with sodium sulphate. The solvents are evaporated in vacuo and the residue is purified by chromatography on silica gel (dichloromethane/ethylacetate 80:20).

Yield: 54 mg (79% of theory)
Mass spectrometry (ESI⁺): m/z=505 [M+H]⁺
HPLC (Method 31): Retention time=1.03 min.

Analogously to example 5 the following compounds are obtained:

(1) (3R,6R,9S)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]-6,9-diol

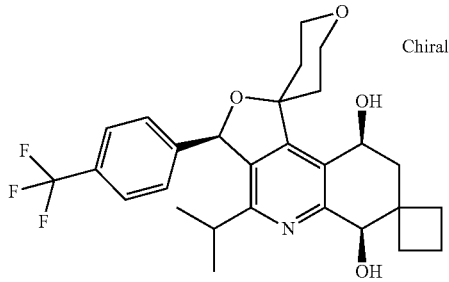 [SMILES: CC(C)c1nc2c(c3c1[C@@H](c1ccc(C(F)(F)F)cc1)OC31CCOCC1)[C@@H](O)CC1(CCC1)[C@H]2O]

Obtained by starting from (3R,6R,9S)-9-(tert-butyldimethylsilyloxy)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-6-yl acetate. The product is additionally purified by preparative HPLC (Sunfire C18, 5 μm, water (0.1% trifluoroacetic acid)/acetonitrile 70:30 to 5:95).

Mass spectrometry (ESI⁺): m/z=504 [M+H]⁺
HPLC (Method 14): Retention time=13.07 min.

(2) (3S,9S)-3-(3-fluoro-5-(trifluoromethyl)pyridin-2-yl)-4-isopropyl-7,7-dimethyl-2',3',5',6,6',7,8,9-octahydro-3H-spiro[furo[3,4-c]quinoline-1,4'-pyran]-9-ol

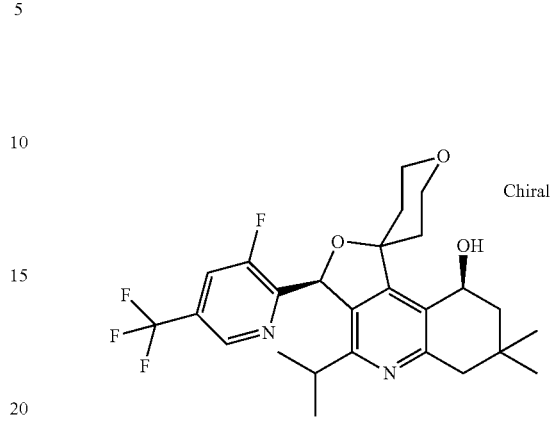

Obtained by starting from (3S,9S)-9-(tert-butyldimethylsilyloxy)-3-(3-fluoro-5-(trifluoromethyl)pyridin-2-yl)-4-isopropyl-7,7-dimethyl-2',3',5',6,6',7,8,9-octahydro-3H-spiro[furo[3,4-c]quinoline-1,4'-pyran].

Mass spectrometry (ESI⁺): m/z=495 [M+H]⁺
HPLC (Method 15): Retention time=3.09 min.

(3) (3S,6S,9S)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]-6,9-diol

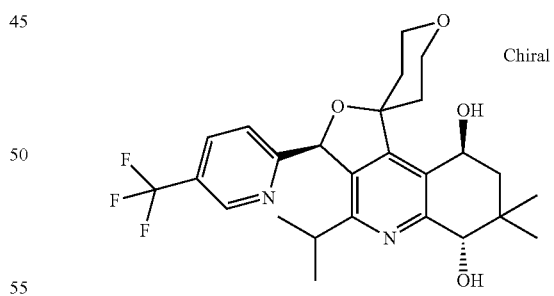

Obtained by starting from (3S,6S,9S)-9-(tert-butyldimethylsilyloxy)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]-6-yl acetate.

Mass spectrometry (ESI⁺): m/z=493 [M+H]⁺
HPLC (Method 14): Retention time=11.47 min.

(4) (3S,6R,9S)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]-6,9-diol

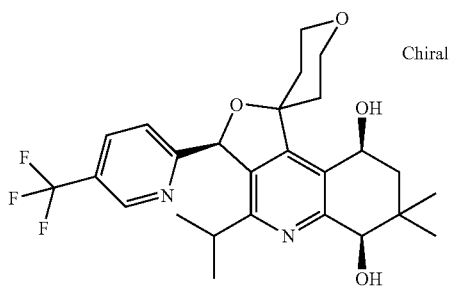 [SMILES: CC(C)c1nc2c(c3c1[C@@H](c1ccc(C(F)(F)F)cn1)OC31CCOCC1)[C@@H](O)CC(C)(C)[C@H]2O]

Obtained by starting from (3S,6R,9S)-9-(tert-butyldimethylsilyloxy)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]-6-yl acetate.

Mass spectrometry (ESI+): m/z=493 [M+H]+

HPLC (Method 14): Retention time=12.29 min.

(5) (3R,6R,9S)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]-6,9-diol

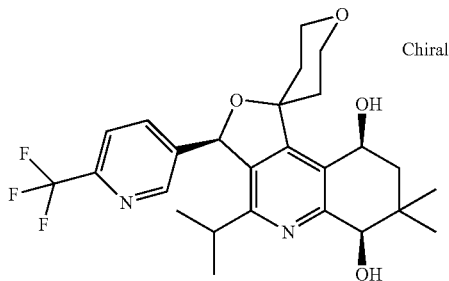 [SMILES: CC(C)c1nc2c(c3c1[C@@H](c1ccc(C(F)(F)F)nc1)OC31CCOCC1)[C@@H](O)CC(C)(C)[C@H]2O]

Obtained by starting from (3R,6R,9S)-9-(tert-butyldimethylsilyloxy)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]-6-yl acetate.

Mass spectrometry (ESI+): m/z=493 [M+H]+

HPLC (Method 15): Retention time=3.03 min.

(6) (3R,6R,9S)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6,9-diol

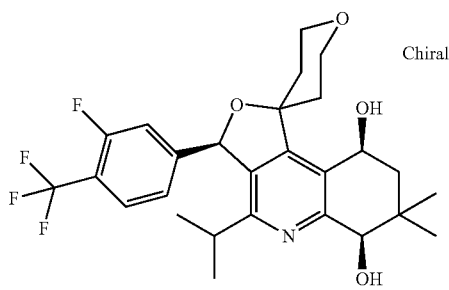 [SMILES: CC(C)c1nc2c(c3c1[C@@H](c1ccc(C(F)(F)F)c(F)c1)OC31CCOCC1)[C@@H](O)CC(C)(C)[C@H]2O]

Obtained by starting from (3R,6R,9S)-9-(tert-butyldimethylsilyloxy)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate.

Mass spectrometry (ESI+): m/z=510 [M+H]+

HPLC (Method 14): Retention time=12.64 min.

(7) (3R,6S,9S)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]-6,9-diol

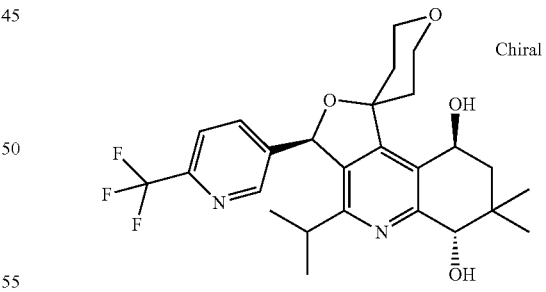

Obtained by starting from (3R,6S,9S)-9-(tert-butyldimethylsilyloxy)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]-6-yl acetate.

Mass spectrometry (ESI+): m/z=493 [M+H]+

HPLC (Method 15): Retention time=3.08 min.

(8) (3S,6R,9S)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]-6,9-diol

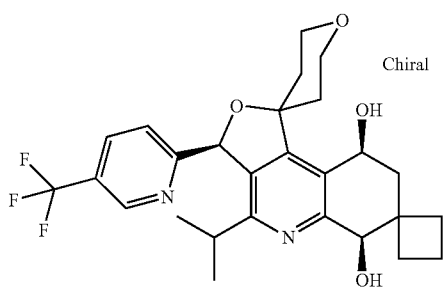 [SMILES: CC(C)c1nc2c(c3c1[C@@H](c1ccc(C(F)(F)F)cn1)OC31CCOCC1)[C@@H](O)CC1(CCC1)[C@H]2O]

Obtained by starting from (3S,6R,9S)-9-(tert-butyldimethylsilyloxy)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]-6-yl acetate.

Mass spectrometry (ESI⁺): m/z=505 [M+H]⁺

HPLC (Method 15): Retention time=3.19 min.

Example 6

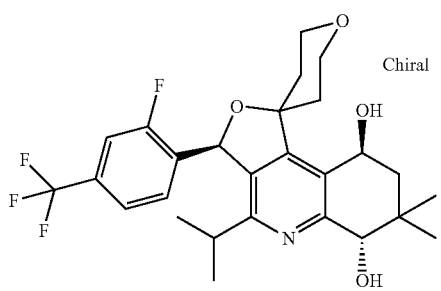 [SMILES: CC(C)c1nc2c(c3c1[C@@H](c1ccc(C(F)(F)F)cc1F)OC31CCOCC1)[C@@H](O)CC(C)(C)[C@@H]2O]

(3S,6S,9S)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6,9-diol 17 mg (3S,6S,9S)-9-(tert-butyldimethylsilyloxy)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6-yl acetate are dissolved in 2 ml methanol and treated with 70 mg potassium carbonate. The mixture is stirred for 36 hours. Then the solvent is evaporated in vacuo. The residue is partitioned between water and diethylether. The organic phase is separated and dried with magnesium sulphate. The solvent is evaporated in vacuo and the residue is taken up in 1 ml tetrahydrofurane. 50 µl Tetrabutylammonium fluoride are added and the mixture is stirred for 3 hours at room temperature. The solvent is evaporated in vacuo and the residue is chromatographed on silica gel (n-hexane/ethylacetate 80:20).

Yield: 7 mg (54% of theory)

Mass spectrometry (ESI⁺): m/z=510 [M+H]⁺

HPLC (Method 14): Retention time=12.79 min.

Analogously to example 6 the following compounds are obtained:

(1) (3S,6R,9S)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]-6,9-diol

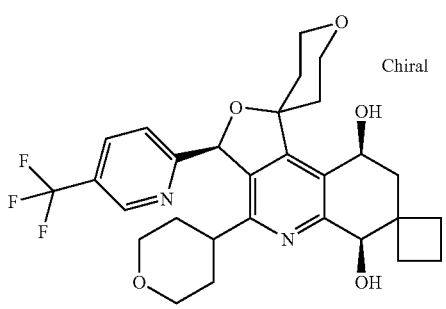 [SMILES: O[C@H]1CC2(CCC2)[C@@H](O)c2nc(C3CCOCC3)c3c(c21)C1(CCOCC1)O[C@@H]3c1ccc(C(F)(F)F)cn1]

Obtained by starting from (3S,6R,9S)-9-(tert-butyldimethylsilyloxy)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]-6-yl acetate.

Mass spectrometry (ESI⁺): m/z=547 [M+H]⁺

HPLC (Method 26): Retention time=1.45 min.

(2) (3R,6R,9S)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]-6,9-diol

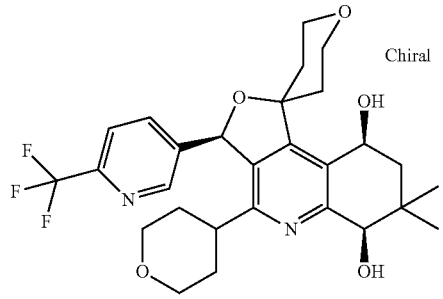 [SMILES: CC1(C)C[C@H](O)c2c(nc(C3CCOCC3)c3c2C2(CCOCC2)O[C@@H]3c2ccc(C(F)(F)F)nc2)[C@@H]1O]

Obtained by starting from (3R,6R,9S)-9-(tert-butyldimethylsilyloxy)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]-6-yl acetate.

Mass spectrometry (ESI⁺): m/z=535 [M+H]⁺

HPLC (Method 26): Retention time=1.38 min.

Example 7

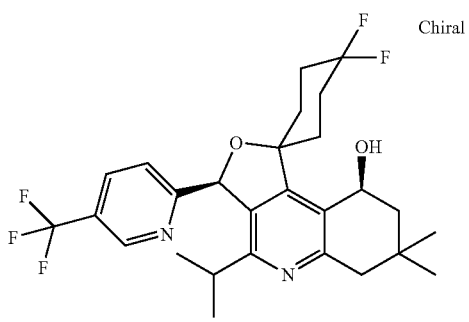 [SMILES: CC(C)c1nc2c(c3c1[C@@H](c1ccc(C(F)(F)F)cn1)OC31CCC(F)(F)CC1)[C@@H](O)CC(C)(C)C2]

(3'S,9'S)-4,4-difluoro-4'-isopropyl-7',7'-dimethyl-3'-
(5-(trifluoromethyl)pyridin-2-yl)-6',7',8',9'-tetrahydro-3'H-spiro[cyclohexane-1,1'-furo[3,4-c]quinolin]-
9'-ol (Diastereomer 1)

and (3'R,9'S)-4,4-difluoro-4'-isopropyl-7',7'-dimethyl-3'-
(5-(trifluoromethyl)pyridin-2-yl)-6',7',8',9'-tetrahydro-3'H-spiro[cyclohexane-1,1'-furo[3,4-c]quinolin]-
9'-ol (Diastereomer 2)

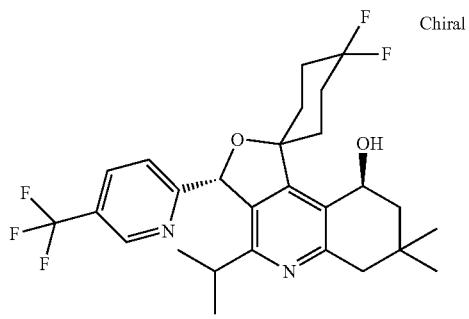 [SMILES: CC(C)c1nc2c(c3c1[C@H](c1ccc(C(F)(F)F)cn1)OC31CCC(F)(F)CC1)[C@@H](O)CC(C)(C)C2]

112 mg of (3'R,9'S)-9'-(tert-butyldimethylsilyloxy)-4,4-difluoro-4'-isopropyl-7',7'-dimethyl-3'-(5-(trifluoromethyl)pyridin-2-yl)-6',7',8',9'-tetrahydro-3'H-spiro[cyclohexane-1,1'-furo[3,4-c]quinoline] are dissolved in 5 ml tetrahydrofurane and treated with 535 μl 18-diazabicyclo[5.4.0]undec-7-ene with stirring for 16 hours. The solvents are evaporated in vacuo, the residue dissolved in dichloromethane, thoroughly washed with aqueous 0.5 M hydrochloric acid, water, and then with brine, dried with sodium sulphate and evaporated to dryness.

The material thus obtained is dissolved in tetrahydrofurane and treated with stirring with 3 ml aqueous 2 M hydrochloric acid, heating for 3 hours at 50° C. and then at 25° C. for 16 hours. Saturated aqueous NaHCO$_3$ solution is added, the mixture concentrated under vacuo to remove the bulk of the organic solvent and extracted with dichloromethane. The organic layer is collected, the solvents are evaporated in vacuo and the residue is submitted to Chiral semipreparative HPLC: (Column Daicel Chiralpak AD-H Semiprep, 250×20 mm; 5 μm; Hexane/2-propanol 95:5, 10 ml/min, room temperature).

(3'S,9'S)-4,4-difluoro-4'-isopropyl-7',7'-dimethyl-3'-(5-(trifluoromethyl)pyridin-2-yl)-6',7',8',9'-tetrahydro-3'H-spiro[cyclohexane-1,1'-furo[3,4-c]quinolin]-9'-ol:
Yield: 27 mg (30% of theory)
Mass spectrometry (ESI$^+$): m/z=511 [M+H]$^+$
HPLC (Method 9): Retention time=0.83 min.
Chiral HPLC (Column Daicel Chiralpak AD-H, 250×4.6 mm; 5 μm;
Hexane/2-propanol 95:5; 1 ml/min, 25° C.): Retention time=8.24 min (3'R,9'S)-4,4-difluoro-4'-isopropyl-7',7'-dimethyl-3-(5-(trifluoromethyl)pyridin-2-yl)-6',7',8',9'-tetrahydro-3'H-spiro[cyclohexane-1,1'-furo[3,4-c]quinolin]-9'-ol:
Yield: 40 mg (44% of theory)
Mass spectrometry (ESI$^+$): m/z=511 [M+H]$^+$
HPLC (Method 9): Retention time=0.85 min.
Chiral HPLC (Column Daicel Chiralpak AD-H, 250×4.6 mm; 5 μm;
Hexane/2-propanol 95:5; 1 ml/min, 25° C.): Retention time=6.35 min.

Some examples of formulations will now be described in which the term "active substance" denotes one or more compounds according to the invention, including the salts thereof. In the case of one of the combinations with one or more additional active substances as described previously, the term "active substance" also includes the additional active substances.

Example A

Tablets Containing 100 mg of Active Substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:
The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.
Weight of tablet: 220 mg
Diameter: 10 mm, biplanar, facetted on both sides and notched on one side.

Example B

Tablets Containing 150 mg of Active Substance

Composition:
1 tablet contains:

| | |
|---|---|
| active substance | 150.0 mg |
| powdered lactose | 89.0 mg |
| corn starch | 40.0 mg |
| colloidal silica | 10.0 mg |

431
-continued

| | |
|---|---|
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

Example C

Hard Gelatine Capsules Containing 150 mg of Active Substance

Composition:

1 Capsule Contains:

| | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

Example D

Suppositories Containing 150 mg of Active Substance

Composition:

1 Suppository Contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2000.0 mg |

Preparation:

After the suppository mass has been melted the active substance is homogeneously distributed therein and the melt is poured into chilled moulds.

Example E

Ampoules Containing 10 mg Active Substance

Composition:

| | | |
|---|---|---|
| active substance | | 10.0 mg |
| 0.01N hydrochloric acid q.s. | | |
| double-distilled waterad | ad | 2.0 ml |

Preparation:

The active substance is dissolved in the necessary amount of 0.01 N HCl, made isotonic with common salt, filtered sterile and transferred into 2 ml ampoules.

Example F

Ampoules Containing 50 mg of Active Substance

Composition:

| | | |
|---|---|---|
| active substance | | 50.0 mg |
| 0.01N hydrochloric acid q.s. | | |
| double-distilled water | ad | 10.0 ml |

Preparation:

The active substance is dissolved in the necessary amount of 0.01 N HCl, made isotonic with common salt, filtered sterile and transferred into 10 ml ampoules.

What is claimed is:

1. A compound of formula I

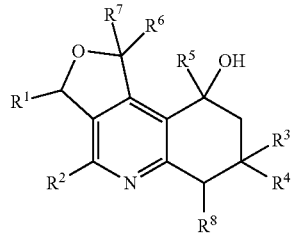

(I)

wherein $R^1$ is a mono- or bicyclic 5- to 10-membered aryl or heteroaryl group, which heteroaryl contains 1 to 4 heteroatoms selected from the group consisting of N, O and S, and which aryl or heteroaryl may optionally be substituted by $R^9$, $R^{10}$ and/or $R^{11}$, in which $R^9$ is hydrogen, halogen, cyano, 1-4C-alkyl, 2-4C-alkenyl, 3-6C-cycloalkyl, 1-4C-alkoxy, completely or partially fluorine-substituted 1-4C-alkyl, completely or partially fluorine-substituted 1-4C-alkoxy, pentafluorosulfanyl, cyano-1-4C-alkyl, 1-2C-alkyl-3-6C-cycloalkyl, cyano-3-6C-cycloalkyl, 1-2C-alkoxy-1-4C-alkyl, hydroxy-1-4C-alkyl or 3-(1-2C-alkyl)-oxetan-3-yl, $R^{10}$ is hydrogen, halogen, cyano, 1-4C-alkyl, 2-4C-alkenyl, 3-6C-cycloalkyl, 1-4C-alkoxy, completely or partially fluorine-substituted 1-4C-alkyl, completely or partially fluorine-substituted 1-4C-alkoxy, cyano-1-4C-alkyl, methyl-3-6C-cycloalkyl, cyano-3-6C-cycloalkyl, methoxy-1-4C-alkyl, hydroxy-1-4C-alkyl or 3-(1-2C-alkyl)-oxetan-3-yl, $R^{11}$ is hydrogen or halogen, or $R^9$ and $R^{10}$ together and with inclusion of the carbon atoms, to which they are attached, form a 5-6C-cycloalkane ring wherein one methylene group may optionally be replaced by oxygen,
which ring, for the case of 6-membered ring system, may optionally contain a double bond, and/or
which ring may optionally be mono- or disubstituted by methyl, wherein, for the case that both methyl groups are connected to the same carbon, the methyl groups together with the carbon to which they are connected, may optionally form a cyclopropyl ring, $R^2$ is 1-6C-alkyl, 1-3C-perfluoroalkyl, 1-4C-alkoxy-1-4C-alkyl, or 4-7C-cycloalkyl, which 4-7C-cycloalkyl may optionally be mono- or disubstituted by fluorine, hydroxy, methoxy and/or 1-2C-alkyl and in which, for the case of 5-7C-cycloalkyl systems, one methylene group may optionally be replaced by oxygen, $R^3$ is hydrogen or 1-4C-alkyl, $R^4$ is hydrogen or 1-4C-alkyl, or $R^3$ and $R^4$ together and with inclusion of the carbon atom, to which they are attached, form a 4-7C-cycloalkane ring, $R^5$ is hydrogen or 1-4C-alkyl, $R^6$ is 1-4C-alkyl, $R^7$ is hydrogen or 1-4C-alkyl, or $R^6$ and $R^7$ together and with inclusion of the carbon atom, to which they are attached, form a 5-7C-cycloalkane ring wherein one methylene group may optionally be replaced by oxygen,
which ring may optionally contain one double bond, and/or
which ring may optionally be mono- or disubstituted by fluorine, hydroxyl, 1-2C-alkoxy and/or 1-2C-alkyl, $R^8$ is hydrogen, acetoxy, propionyloxy, methoxy or hydroxy, or a tautomer thereof, a stereoisomer thereof, a mixture thereof or a salt thereof.

2. The compound of formula I according to claim 1, wherein $R^1$ denotes 2-($R^9$)-3-($R^{10}$)-thiophen-5-yl, 5-($R^9$)-4-($R^{10}$)-thiazol-2-yl, 1-($R^{10}$)-2-($R^9$)-3-($R^{11}$)-benzene-5-yl, 1-($R^{10}$)-2-($R^9$)-4-($R^{11}$)-benzene-5-yl, 5-($R^9$)-4-($R^{10}$)-pyridine-2-yl, 2-($R^9$)-3-($R^{10}$)-pyridine-5-yl, 5-($R^9$)-3-($R^{10}$)-pyridine-2-yl, 5-($R^9$)-4-($R^{10}$)-pyrimidine-2-yl, 2-($R^9$)-pyrimidine-5-yl, 3-($R^9$)-4-($R^{10}$)-pyridazine-6-yl, 2-($R^9$)-3-($R^{10}$)-pyrazine-5-yl, 1,1-dimethyl-1,3-dihydroisobenzofuran-5-yl, 3'H-spiro[cyclopropane-1,1'-isobenzofuran]-5'-yl, 3,3-dimethyl-2,3-dihydrobenzofuran-6-yl or 2H-spiro[benzofuran-3,1'-cyclopropane]-6-yl, in which $R^9$ is hydrogen, halogen, cyano, isopropyl, isobutyl, tert.-butyl, isopropenyl, cyclopropyl, cyclobutyl, methoxy, ethoxy, isopropoxy, tert.-butoxy, trifluoromethyl, pentafluoroethyl, difluoromethyl, 1,1-difluorethan-1-yl, trifluoromethoxy, difluoromethoxy, pentafluorosulfanyl, 2-cyano-propan-2-yl, 1-methyl-cyclopropan-1-yl, 1-methyl-cyclobutan-1-yl, 1-cyano-cyclopropan-1-yl, 1-cyano-cyclobutan-1-yl, 1-methoxy-ethan-1-yl, 2-methoxy-propan-2-yl, 1-hydroxy-ethan-1-yl, 2-hydroxy-propan-2-yl, or 3-(1-2C-alkyl)-oxetan-3-yl, $R^{10}$ is hydrogen, halogen, cyano, methyl, ethyl, isopropyl, tert.-butyl, methoxy, trifluoromethyl, trifluoromethoxy, or methoxymethyl, $R^{11}$ is hydrogen, fluorine or chlorine, $R^2$ denotes 1-5C-alkyl, trifluormethyl, pentafluorethyl, 1-3C-alkoxy-1-2C-alkyl, 1-3C-alkoxy-3C-alkyl or 4-7C-cycloalkyl, which 4-7C-cycloalkyl may optionally be mono- or disubstituted by fluorine, hydroxy, methoxy and/or methyl and in which, for the case of 5-7C-cycloalkyl systems, one methylene group may optionally be replaced by oxygen, $R^3$ and $R^4$ are independently selected from hydrogen and 1-3C-alkyl, or $R^3$ and $R^4$ together and with inclusion of the carbon atom, to which they are attached, form a 4-6C-cycloalkane ring, $R^5$ denotes hydrogen or methyl, $R^6$ denotes methyl, ethyl, propyl or isopropyl and $R^7$ denotes hydrogen, methyl or ethyl, or $R^6$ and $R^7$ together and with inclusion of the carbon atom, to which they are attached, form a 5-6C-cycloalkane ring wherein one methylene group may optionally be replaced by oxygen,
which ring may optionally contain one double bond, and/or
which ring may optionally be mono- or disubstituted by fluorine, hydroxyl, 1-2C-alkoxy and/or 1-2C-alkyl, $R^8$ denotes hydrogen, acetoxy or hydroxy, or a tautomer thereof, a stereoisomer thereof, a mixture thereof or a salt thereof.

3. The compound of formula I according to claim 1, wherein $R^1$ denotes 2-($R^9$)-thiophen-5-yl, 1-($R^9$)-2-($R^{10}$)-benzene-4-yl, 1-($R^9$)-3-($R^{10}$)-benzene-4-yl, 4-($R^9$)-benzene-1-yl, 3-tert.-butylphenyl, 3-trifluoromethylphenyl, 1,2,3-trifluoro-benzene-5-yl, 1,3-difluoro-benzene-5-yl, 5-($R^9$)-pyridine-2-yl, 2-($R^9$)-pyridine-5-yl, 5-($R^9$)-3-($R^{10}$)-pyridine-2-yl, 2-($R^9$)-pyrimidine-5-yl, 5-($R^9$)-4-($R^{10}$)-thiazol-2-yl, 1,1-dimethyl-1,3-dihydroisobenzofuran-5-yl or 3,3-dimethyl-2,3-dihydrobenzofuran-6-yl, in which $R^9$ is fluorine, chlorine, bromine, cyano, isopropyl, isobutyl, isopropenyl, tert.-butyl, cyclopropyl, cyclobutyl, methoxy, ethoxy, isopropoxy, tert.-butoxy, trifluoromethyl, pentafluoroethyl, difluoromethyl, 1,1-difluorethan-1-yl, trifluoromethoxy, difluoromethoxy, pentafluorosulfanyl, 2-cyano-propan-2-yl, 1-methyl-cyclopropan-1-yl, 1-methyl-cyclobutan-1-yl, 1-cyano-cyclopropan-1-yl, 1-cyano-cyclobutan-1-yl, 2-methoxy-propan-2-yl, 2-hydroxy-propan-2-yl, or 3-methyl-oxetan-3-yl, $R^{10}$ is hydrogen, methyl, cyano, fluorine or chlorine, $R^2$ denotes ethyl, isopropyl, 2-butyl, isobutyl, tert.-butyl, 3-pentyl, cyclobutyl, cyclopentyl, cyclohexyl, methoxymethyl, 1-methoxyethyl, 2-methoxy-propan-2-yl, tetrahydrofuran-2-yl, tetrahydrofuran-3-yl, tetrahydropyran-4-yl, tetrahydropyran-3-yl or tetrahydropyran-2-yl, $R^3$ and $R^4$ are independently selected from methyl and ethyl, or $R^3$ and $R^4$ together and with inclusion of the carbon atom, to which they are attached, form a cyclobutane or cyclopentane ring, $R^5$ denotes hydrogen, $R^6$ and $R^7$ independently denote methyl or ethyl, or $R^6$ and $R^7$ together and with inclusion of the carbon atom, to which they are attached, form a cyclopentane ring, cyclopent-2-ene-1,1-diyl ring, cyclohexane ring, 4,4-difluorocyclohexan-1,1-diyl ring or tetrahydropyrane-4,4-diyl ring, $R^8$ denotes hydrogen or hydroxy, or a tautomer thereof, a stereoisomer thereof, a mixture thereof or a salt thereof.

4. The compound of formula I according to claim 1, wherein $R^1$ denotes 4-trifluoromethylphenyl, 3-trifluoromethylphenyl, 4-(1,1-difluor-ethan-1-yl)-phenyl, 4-methylphenyl, 4-isopropylphenyl, 4-isobutylphenyl, 4-tert.-butylphenyl, 3-tert.-butylphenyl, 4-isopropenylphenyl, 4-cyanophenyl, 4-fluorphenyl, 3,5-difluorphenyl, 4-chlorphenyl, 4-methoxyphenyl, 4-isopropoxyphenyl, 4-tert.-butoxyphenyl, 4-trifluormethoxyphenyl, 4-pentafluorosulfanylphenyl, 4-perfluoroethyl-phenyl, 2-trifluormethyl-pyridin-5-yl, 5-trifluormethyl-pyridin-2-yl, 3-fluor-4-trifluormethyl-phenyl, 2-fluor-4-trifluormethyl-phenyl, 3-fluor-5-trifluormethyl-pyridin-2-yl, 3-cyano-4-trifluormethyl-phenyl, 4-(2-cyano-propan-2-yl)-phenyl, 4-(2-hydroxy-propan-2-yl)-phenyl, 4-cyclopropylphenyl, 4-(1-methylcyclopropyl-1-yl)-phenyl, 4-(1-cyanocyclopropyl-1-yl)-phenyl, 2-trifluormethyl-thiophen-5-yl, 5-tert.-butyl-4-methyl-thiazol-2-yl, or 2-tert.-butyl-pyrimidin-5-yl, $R^2$ denotes ethyl, isopropyl, tert.-butyl, methoxymethyl, 1-methoxyethyl, 2-methoxy-propan-2-yl, cyclobutyl, cyclopentyl or tetrahydropyran-4-yl, $R^3$ is methyl and $R^4$ is methyl, or $R^3$ and $R^4$ together and with inclusion of the carbon atom, to which they are attached, form a cyclobutane ring, $R^5$ denotes hydrogen, $R^6$ denotes methyl and $R^7$ denotes methyl, or $R^6$ and $R^7$ together and with inclusion of the carbon atom, to which they are attached, form a cyclopentane ring, cyclopent-2-ene-1,1-diyl ring, cyclohexane ring or tetrahydropyrane-4,4-diyl ring, $R^8$ denotes hydrogen, or a tautomer thereof, a stereoisomer thereof, a mixture thereof or a salt thereof.

5. The compound according to claim 1, which is of formula I*

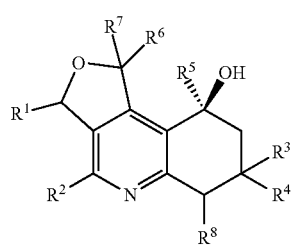

(I*)

wherein $R^1$ to $R^8$ are defined as in claim 1, or a tautomer thereof, a stereoisomer thereof, a mixture thereof or a salt thereof.

6. The compound according to claim 1, which is of formula I**

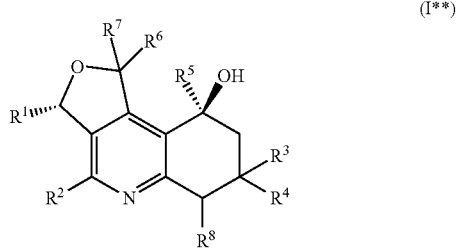

(I**)

wherein $R^1$ to $R^8$ are defined as in claim 1, or a tautomer thereof, a stereoisomer thereof, a mixture thereof or a salt thereof.

7. The compound according to claim 1, which is of formula I***

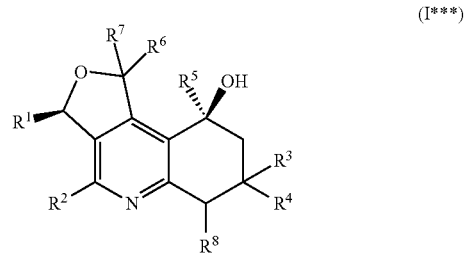

(I***)

wherein $R^1$ to $R^8$ are defined as in claim 1, or a tautomer thereof, a stereoisomer thereof, a mixture thereof or a salt thereof.

8. The compound according to claim 1, which is of formula I****

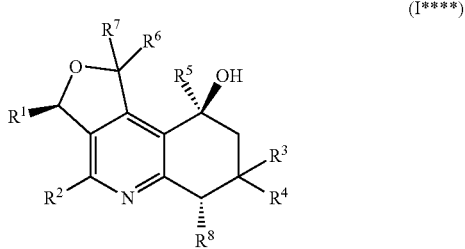

(I****)

wherein $R^1$ to $R^8$ are defined as in claim 1, or a tautomer thereof, a stereoisomer thereof, a mixture thereof or a salt thereof.

9. The compound according to claim 1, which is of formula I*****

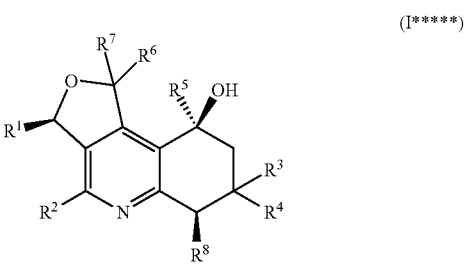

(I*****)

wherein R¹ to R⁸ are defined as in claim 1, or a tautomer thereof, a stereoisomer thereof, a mixture thereof or a salt thereof.

10. A compound selected from the group consisting of:

(3'R,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

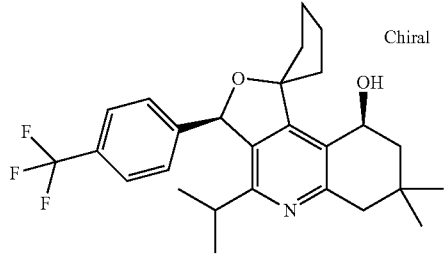 [SMILES: CC(C)c1nc2c(c3c1[C@@H](c1ccc(C(F)(F)F)cc1)OC31CCCC1)[C@@H](O)CC(C)(C)C2]

(3'S,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

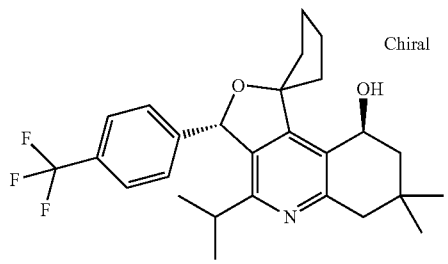 [SMILES: CC(C)c1nc2c(c3c1[C@H](c1ccc(C(F)(F)F)cc1)OC31CCCC1)[C@@H](O)CC(C)(C)C2]

(1R,3'S,9'S)-4'-isopropyl-7',7'-dimethyl-3'-(4-(trifluoromethyl)phenyl)-6',7',8',9'-tetrahydro-3'H-spiro[cyclopent[2]ene-1,1'-furo[3,4-c]quinolin]-9'

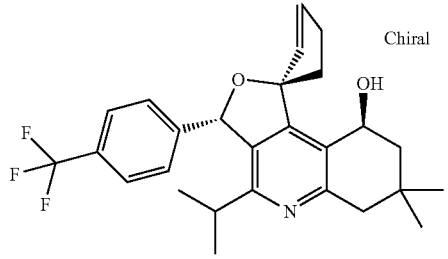

(3R,9S)-4-isopropyl-1,1,7,7-tetramethyl-3-(4-(trifluoromethyl)phenyl)-1,3,6,7,8,9-hexahydrofuro[3,4-c]quinolin-9-ol

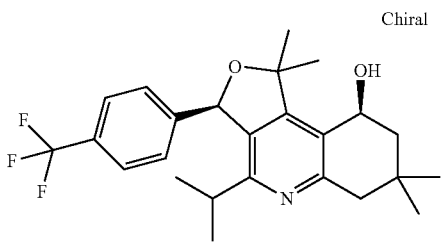 [SMILES: CC(C)c1nc2c(c3c1[C@@H](c1ccc(C(F)(F)F)cc1)OC3(C)C)[C@@H](O)CC(C)(C)C2]

(3'R,9'S)-4'-Isopropyl-7',7'-dimethyl-3'-(4-(trifluoromethyl)phenyl)-6',7',8',9'-tetrahydro-3'H-spiro[cyclohexane-1,1'-furo[3,4-c]quinolin]-9'-ol

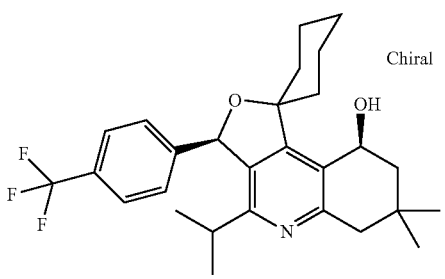 [SMILES: CC(C)c1nc2c(c3c1[C@@H](c1ccc(C(F)(F)F)cc1)OC31CCCCC1)[C@@H](O)CC(C)(C)C2]

(3'R,9'S)-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinolin]-9'-ol

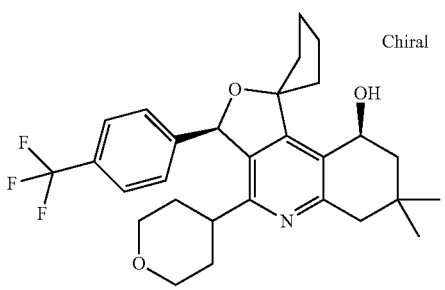 [SMILES: CC1(C)Cc2nc(C3CCOCC3)c3c(c2[C@@H](O)C1)C1(CCCC1)O[C@@H]3c1ccc(C(F)(F)F)cc1]

(3'R,9'S)-4'-cyclopentyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

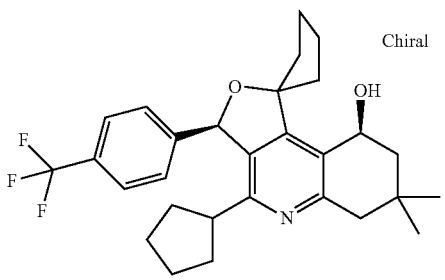 [SMILES: CC1(C)Cc2nc(C3CCCC3)c3c(c2[C@@H](O)C1)C1(CCCC1)O[C@@H]3c1ccc(C(F)(F)F)cc1]

439
(3'R,9'S)-4'-isopropyl-3'-(4-isopropylphenyl)-7',7'-dimethyl-6',7',8',9'-tetrahydro-3'H-spiro[cyclopentane-1,1'-furo[3,4-c]quinolin]-9'-ol

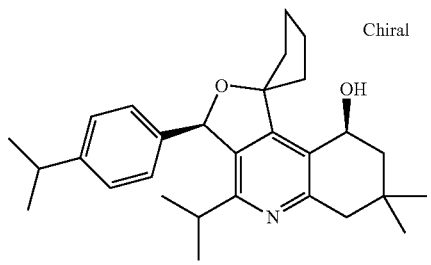 [SMILES: CC(C)c1ccc([C@H]2OC3(CCCC3)c3c2c(C(C)C)nc2c3[C@@H](O)CC(C)(C)C2)cc1]

440
(3'R,9'S)-3'-(4-tert-butylphenyl)-4'-isopropyl-7',7'-dimethyl-6',7',8',9'-tetrahydro-3'H-spiro[cyclopentane-1,1'-furo[3,4-c]quinolin]-9'-ol

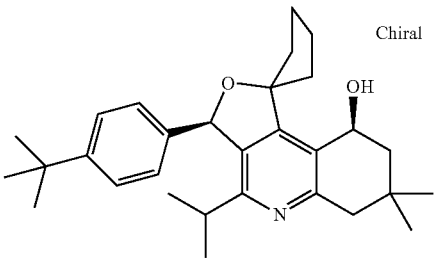

(3'R,9'S)-3'-(4-fluorophenyl)-4'-isopropyl-7',7'-dimethyl-6',7',8',9'-tetrahydro-3'H-spiro[cyclopentane-1,1'-furo[3,4-c]quinolin]-9'-ol

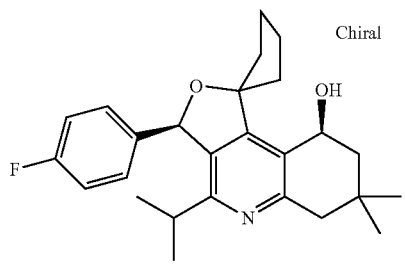 [SMILES: CC(C)c1nc2c(c3c1[C@@H](c1ccc(F)cc1)OC31CCCC1)[C@@H](O)CC(C)(C)C2]

(3'R,9'S)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinolin]-9'-ol

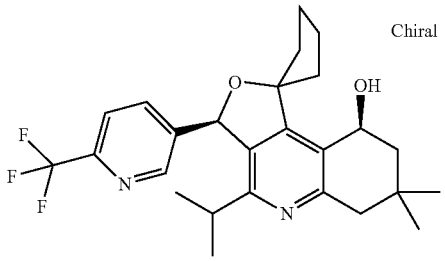

(3'R,9'S)-3'-(4-chlorophenyl)-4'-isopropyl-7',7'-dimethyl-6',7',8',9'-tetrahydro-3'H-spiro[cyclopentane-1,1'-furo[3,4-c]quinolin]-9'-ol

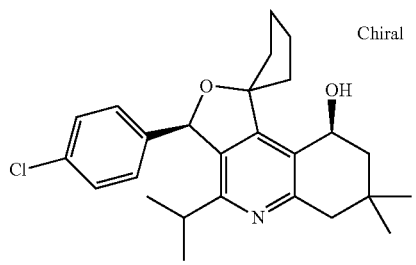 [SMILES: CC(C)c1nc2c(c3c1[C@@H](c1ccc(Cl)cc1)OC31CCCC1)[C@@H](O)CC(C)(C)C2]

(3'S,9'S)-7',7'-dimethyl-4'-(tetrahydro-2H-pyran-4-yl)-3'-(4-(trifluoromethyl)phenyl)-6',7',8',9'-tetrahydro-3'H-spiro[cyclopentane-1,1'-furo[3,4-c]quinolin]-9'-ol

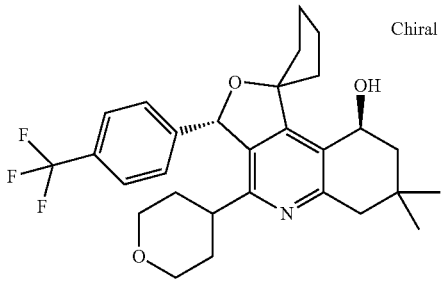

(3'R,9'S)-4'-cyclopentyl-3'-(4-fluorophenyl)-7',7'-dimethyl-6',7',8',9'-tetrahydro-3'H-spiro[cyclopentane-1,1'-furo[3,4-c]quinolin]-9'-ol

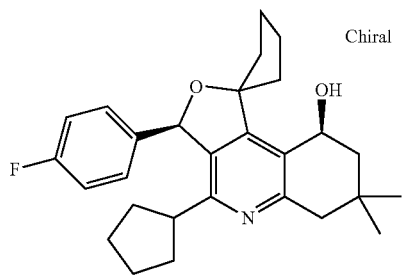 [SMILES: CC1(C)Cc2nc(C3CCCC3)c3c(c2[C@@H](O)C1)C1(CCCC1)O[C@@H]3c1ccc(F)cc1]

(3'R,9'S)-4'-isopropyl-7',7'-dimethyl-3'-p-tolyl-6',7',8',9'-tetrahydro-3'H-spiro[cyclopentane-1,1'-furo[3,4-c]quinolin]-9'-ol

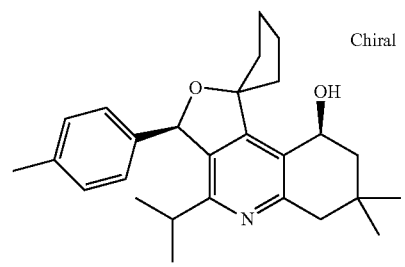

441

(3'R,9'S)-4'-isopropyl-7',7'-(propan-1,3-diyl)-3'-(4-(trifluoromethyl)phenyl)-6',7',8',9'-tetrahydro-3'H-spiro[cyclopentane-1,1'-furo[3,4-c]quinolin]-9'-ol

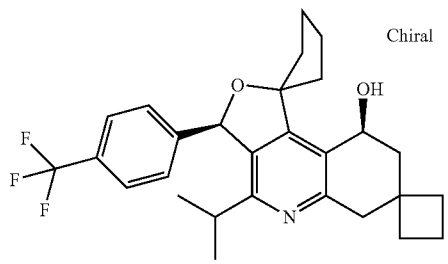 [SMILES: CC(C)c1nc2c(c3c1[C@@H](c1ccc(C(F)(F)F)cc1)OC31CCCC1)[C@@H](O)CC1(CCC1)C2]

(3'R,9'S)-3'-(3-fluoro-4-(trifluoromethyl)phenyl)-4'-isopropyl-7',7'-dimethyl-6',7',8',9'-tetrahydro-3'H-spiro[cyclopentane-1,1'-furo[3,4-c]quinolin]-9'-ol

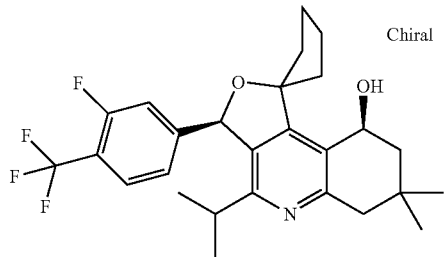 [SMILES: CC(C)c1nc2c(c3c1[C@@H](c1ccc(C(F)(F)F)c(F)c1)OC31CCCC1)[C@@H](O)CC(C)(C)C2]

(3'R,9'S)-4'-isopropyl-7',7'-dimethyl-3'-(4-(trifluoromethoxy)phenyl)-6',7',8',9'-tetrahydro-3'H-spiro[cyclopentane-1,1'-furo[3,4-c]quinolin]-9'-ol

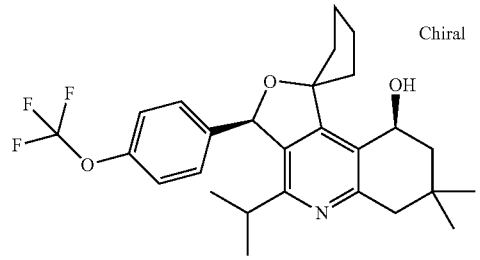 [SMILES: CC(C)c1nc2c(c3c1[C@@H](c1ccc(OC(F)(F)F)cc1)OC31CCCC1)[C@@H](O)CC(C)(C)C2]

(3R,9S)-3-(4-tert-butylphenyl)-4-isopropyl-1,1,7,7-tetramethyl-1,3,6,7,8,9-hexahydrofuro[3,4-c]quinolin-9-ol

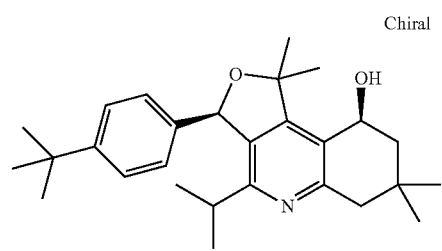 [SMILES: CC(C)c1nc2c(c3c1[C@@H](c1ccc(C(C)(C)C)cc1)OC3(C)C)[C@@H](O)CC(C)(C)C2]

442

(3R,9S)-3-(4-tert-butylphenyl)-4-cyclopentyl-1,1,7,7-tetramethyl-1,3,6,7,8,9-hexahydrofuro[3,4-c]quinolin-9-ol

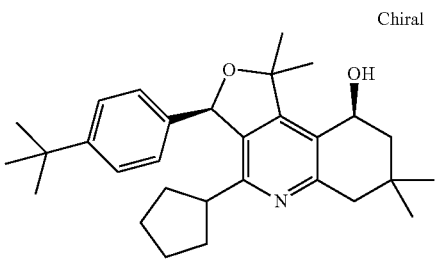 [SMILES: CC1(C)Cc2nc(C3CCCC3)c3c(c2[C@@H](O)C1)C(C)(C)O[C@@H]3c1ccc(C(C)(C)C)cc1]

4-((3'R,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)benzonitrile

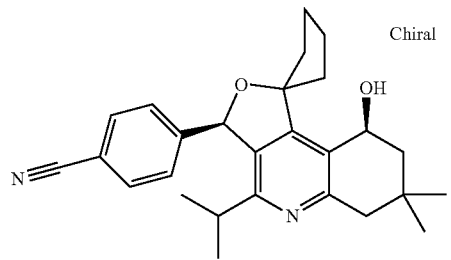 [SMILES: CC(C)c1nc2c(c3c1[C@@H](c1ccc(C#N)cc1)OC31CCCC1)[C@@H](O)CC(C)(C)C2]

(3'S,9'S)-4'-isopropyl-7',7'-dimethyl-3'-(5-(trifluoromethyl)pyridin-2-yl)-6',7',8',9'-tetrahydro-3'H-spiro[cyclopentane-1,1'-furo[3,4-c]quinolin]-9'-ol

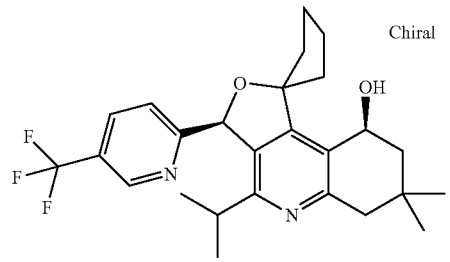 [SMILES: CC(C)c1nc2c(c3c1[C@@H](c1ccc(C(F)(F)F)cn1)OC31CCCC1)[C@@H](O)CC(C)(C)C2]

(3'S,9'R)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

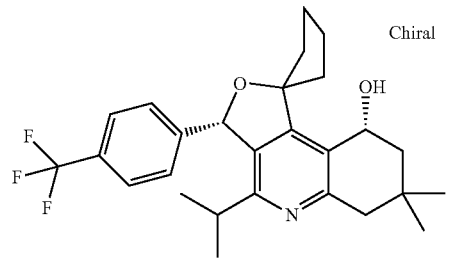 [SMILES: CC(C)c1nc2c(c3c1[C@H](c1ccc(C(F)(F)F)cc1)OC31CCCC1)[C@H](O)CC(C)(C)C2]

| 443 | 444 |
|---|---|
| 2-(4-((3'R,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile | (3'R,9'S)-3'-(4-(2-hydroxypropan-2-yl)phenyl)-4'-isopropyl-7',7'-dimethyl-6',7',8',9'-tetrahydro-3'H-spiro[cyclopentane-1,1'-furo[3,4-c]quinolin]-9'-ol |

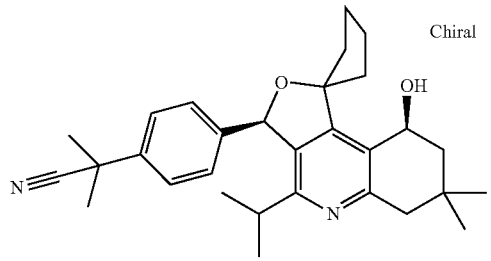 [SMILES: CC(C)c1nc2c(c3c1[C@@H](c1ccc(C(C)(C)C#N)cc1)OC31CCCC1)[C@@H](O)CC(C)(C)C2]

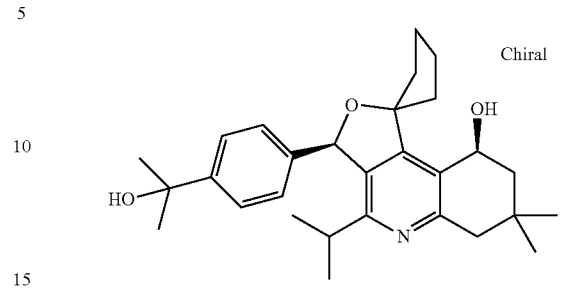

2-(4-((3'S,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)phenyl)-2-methylpropanenitrile (3'R,9'S)-3'-(4-isobutylphenyl)-4'-isopropyl-7',7'-dimethyl-6',7',8',9'-tetrahydro-3'H-spiro[cyclopentane-1,1'-furo[3,4-c]quinolin]-9'-ol

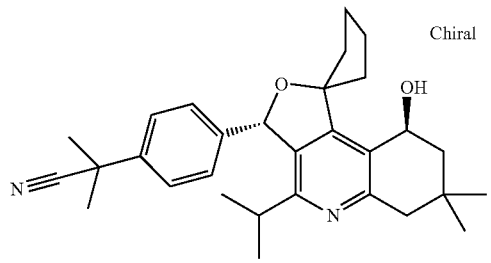 [SMILES: CC(C)c1nc2c(c3c1[C@H](c1ccc(C(C)(C)C#N)cc1)OC31CCCC1)[C@@H](O)CC(C)(C)C2]

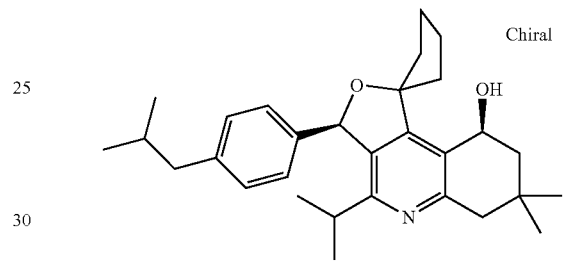

(3'S,9'S)-4'-isopropyl-7',7'-dimethyl-3'-(5-(trifluoromethyl)thiophen-2-yl)-6',7',8',9'-tetrahydro-3'H-spiro[cyclopentane-1,1'-furo[3,4-c]quinolin]-9'-ol (3'R,9'S)-4'-cyclobutyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

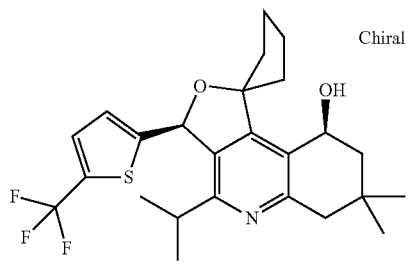 [SMILES: CC(C)c1nc2c(c3c1[C@@H](c1ccc(C(F)(F)F)s1)OC31CCCC1)[C@@H](O)CC(C)(C)C2]

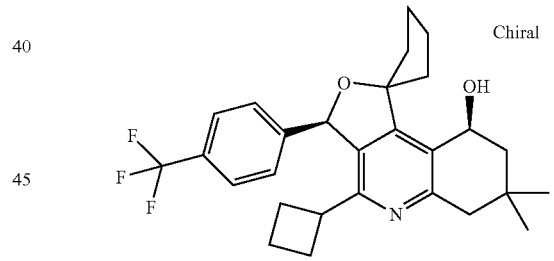

(3'R,9'S)-3'-(2-tert-butylpyrimidin-5-yl)-4'-isopropyl-7',7'-dimethyl-6',7',8',9'-tetrahydro-3'H-spiro[cyclopentane-1,1'-furo[3,4-c]quinolin]-9'-ol (3'R,9'S)-4'-cyclopentyl-3'-(4-isopropylphenyl)-7',7'-dimethyl-6',7',8',9'-tetrahydro-3'H-spiro[cyclopentane-1,1'-furo[3,4-c]quinolin]-9'-ol

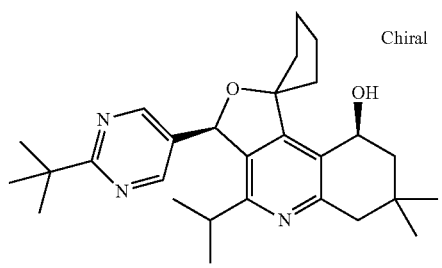 [SMILES: CC(C)c1nc2c(c3c1[C@@H](c1cnc(C(C)(C)C)nc1)OC31CCCC1)[C@@H](O)CC(C)(C)C2]

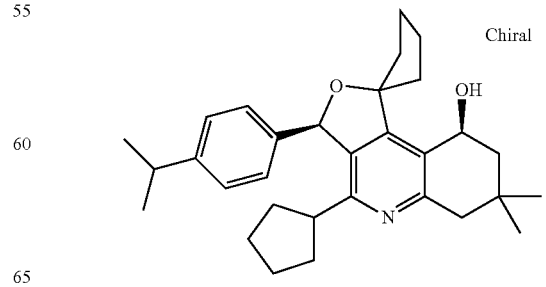

445

(3R,9S)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-9-ol

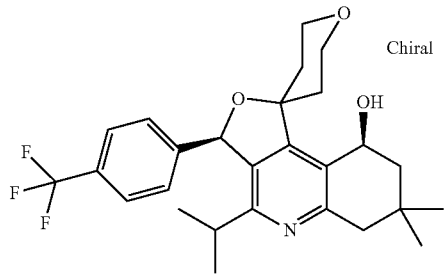 [SMILES: CC(C)c1nc2c(c3c1[C@@H](c1ccc(C(F)(F)F)cc1)OC31CCOCC1)[C@@H](O)CC(C)(C)C2]

(3'R,9'S)-3'-(3-tert-butylphenyl)-4'-cyclopentyl-7',7'-dimethyl-6',7',8',9'-tetrahydro-3'H-spiro[cyclopentane-1,1'-furo[3,4-c]quinolin]-9'-ol

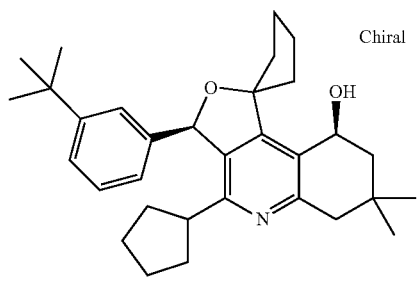 [SMILES: CC1(C)Cc2nc(C3CCCC3)c3c(c2[C@@H](O)C1)C1(CCCC1)O[C@@H]3c1cccc(C(C)(C)C)c1]

(3'R,9'S)-3'-(4-(1,1-difluoroethyl)phenyl)-4'-isopropyl-7',7'-dimethyl-6',7',8',9'-tetrahydro-3'H-spiro[cyclopentane-1,1'-furo[3,4-c]quinolin]-9'-ol

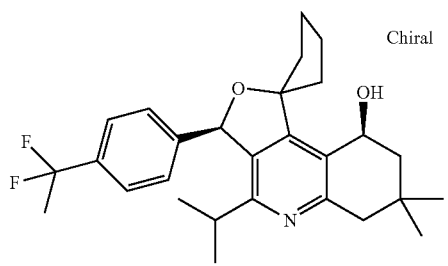

(3'R,6'R,9'S)-9'-hydroxy-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate

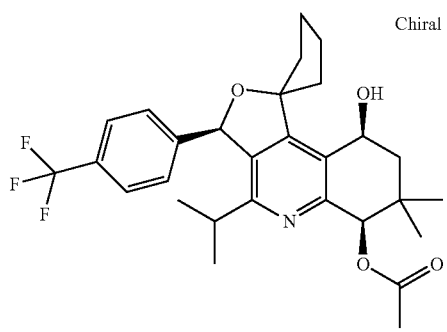 [SMILES: CC(=O)O[C@H]1c2nc(C(C)C)c3c(c2[C@@H](O)CC1(C)C)C1(CCCC1)O[C@@H]3c1ccc(C(F)(F)F)cc1]

446

(3'R,6'S,9'S)-9'-hydroxy-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6'-yl acetate

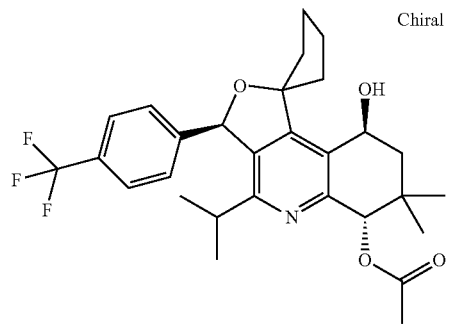 [SMILES: CC(=O)O[C@@H]1c2nc(C(C)C)c3c(c2[C@@H](O)CC1(C)C)C1(CCCC1)O[C@@H]3c1ccc(C(F)(F)F)cc1]

(3'R,6'R,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6',9'-diol

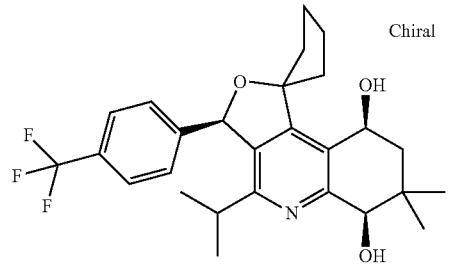 [SMILES: CC(C)c1nc2c(c3c1[C@@H](c1ccc(C(F)(F)F)cc1)OC31CCCC1)[C@@H](O)CC(C)(C)[C@H]2O]

(3'R,6'S,9'S)-4'-isopropyl-7',7'-dimethyl-3'-(4-(trifluoromethyl)phenyl)-6',7',8',9'-tetrahydro-3'H-spiro[cyclopentane-1,1'-furo[3,4-c]quinoline]-6',9'-diol

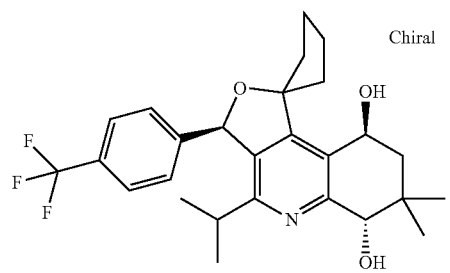 [SMILES: CC(C)c1nc2c(c3c1[C@@H](c1ccc(C(F)(F)F)cc1)OC31CCCC1)[C@@H](O)CC(C)(C)[C@@H]2O]

(3'R,9'S)-4'-isopropyl-7',7'-(propan-1,3-diyl)-3'-(4-(isopropyl)phenyl)-6',7',8',9'-tetrahydro-3'H-spiro[cyclopentane-1,1'-furo[3,4-c]quinolin]-9'-ol

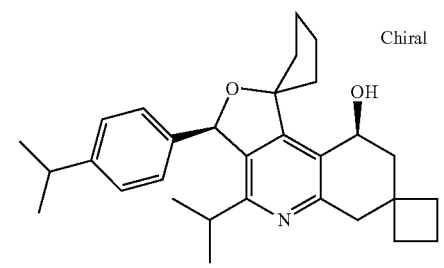 [SMILES: CC(C)c1ccc([C@H]2OC3(CCCC3)c3c2c(C(C)C)nc2c3[C@@H](O)CC3(CCC3)C2)cc1]

447

(3'R,9'S)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinolin]-9'

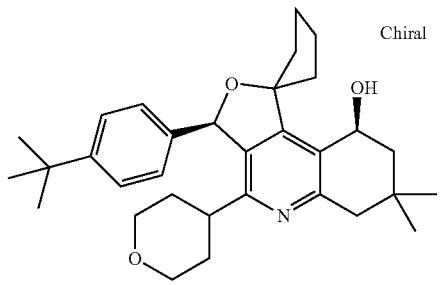 [SMILES: CC1(C)Cc2nc(C3CCOCC3)c3c(c2[C@@H](O)C1)C1(CCCC1)O[C@@H]3c1ccc(C(C)(C)C)cc1]

(3'R,9'S)-4'-ethyl-7',7'-dimethyl-3'-(4-(trifluoromethyl)phenyl)-6',7',8',9'-tetrahydro-3'H-spiro[cyclopentane-1,1'-furo[3,4-c]quinolin]-9'-ol

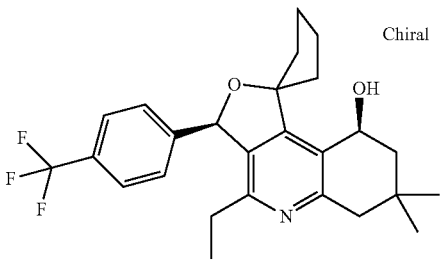 [SMILES: CCc1nc2c(c3c1[C@@H](c1ccc(C(F)(F)F)cc1)OC31CCCC1)[C@@H](O)CC(C)(C)C2]

(3'R,6'R,9'S)-3'-(4-tert-butylphenyl)-7',7'-dimethyl-4'-(tetrahydro-2H-pyran-4-yl)-6',7',8',9'-tetrahydro-3'H-spiro[cyclopentane-1,1'-furo[3,4-c]quinoline]-6',9'-diol

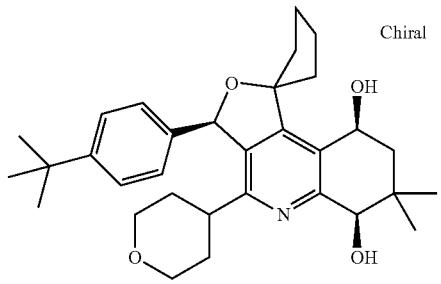 [SMILES: CC(C)(C)c1ccc([C@H]2OC3(CCCC3)c3c2c(C2CCOCC2)nc2c3[C@@H](O)CC(C)(C)[C@H]2O)cc1]

(3'R,9'S)-3'-(3,5-difluorophenyl)-4'-isopropyl-7',7'-dimethyl-6',7',8',9'-tetrahydro-3'H-spiro[cyclopentane-1,1'-furo[3,4-c]quinolin]-9'-ol

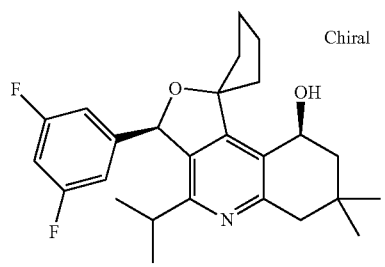 [SMILES: CC(C)c1nc2c(c3c1[C@@H](c1cc(F)cc(F)c1)OC31CCCC1)[C@@H](O)CC(C)(C)C2]

448

(3R,9S)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-9-ol

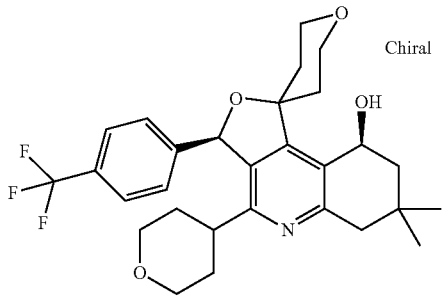 [SMILES: CC1(C)Cc2nc(C3CCOCC3)c3c(c2[C@@H](O)C1)C1(CCOCC1)O[C@@H]3c1ccc(C(F)(F)F)cc1]

(3'R,9'S)-4'-isopropyl-7',7'-dimethyl-3'-(4-(1-methylcyclopropyl)phenyl)-6',7',8',9'-tetrahydro-3'H-spiro[cyclopentane-1,1'-furo[3,4-c]quinolin]-9'-ol

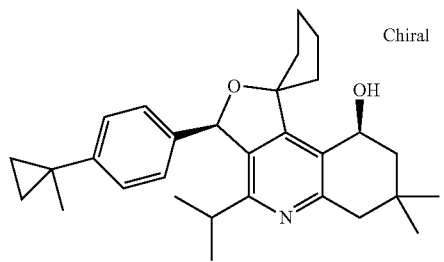 [SMILES: CC(C)c1nc2c(c3c1[C@@H](c1ccc(C4(C)CC4)cc1)OC31CCCC1)[C@@H](O)CC(C)(C)C2]

(3'R,9'S)-4'-isopropyl-7',7'-dimethyl-3'-(3-(trifluoromethyl)phenyl)-6',7',8',9'-tetrahydro-3'H-spiro[cyclopentane-1,1'-furo[3,4-c]quinolin]-9'-ol

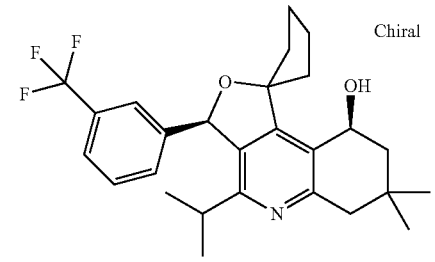 [SMILES: CC(C)c1nc2c(c3c1[C@@H](c1cccc(C(F)(F)F)c1)OC31CCCC1)[C@@H](O)CC(C)(C)C2]

(3R,9S)-3-(4-tert-butylphenyl)-4-isopropyl-7,7-dimethyl-2',3',5',6,6',7,8,9-octahydro-3H-spiro[furo[3,4-c]quinoline-1,4'-pyran]-9-ol

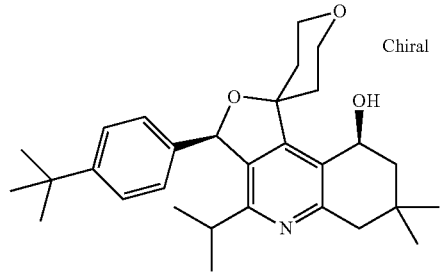 [SMILES: CC(C)c1nc2c(c3c1[C@@H](c1ccc(C(C)(C)C)cc1)OC31CCOCC1)[C@@H](O)CC(C)(C)C2]

(3'R,9'S)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinolin]-9'-ol

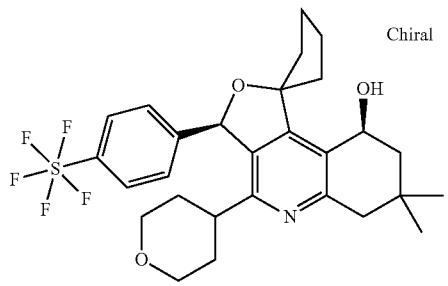 [SMILES: CC1(C)Cc2nc(C3CCOCC3)c3c(c2[C@@H](O)C1)C1(CCCC1)O[C@@H]3c1ccc(S(F)(F)(F)(F)F)cc1]

1-(4-((3'R,9'S)-9'-hydroxy-4'-isopropyl-7',7'-dimethyl-6',7',8',9'-tetrahydro-3'H-spiro[cyclopentane-1,1'-furo[3,4-c]quinoline]-3'-yl)phenyl)cyclopropanecarbonitrile

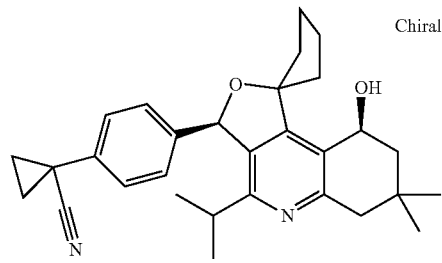 [SMILES: CC(C)c1nc2c(c3c1[C@@H](c1ccc(C4(C#N)CC4)cc1)OC31CCCC1)[C@@H](O)CC(C)(C)C2 ; "Chiral"]

(3'R,9'S)-3'-(4-cyclopropylphenyl)-4'-isopropyl-7',7'-dimethyl-6',7',8',9'-tetrahydro-3'H-spiro[cyclopentane-1,1'-furo[3,4-c]quinolin]-9'-ol

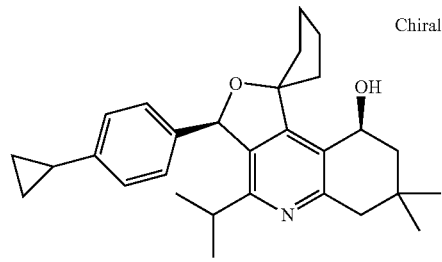 [SMILES: CC(C)c1nc2c(c3c1[C@@H](c1ccc(C4CC4)cc1)OC31CCCC1)[C@@H](O)CC(C)(C)C2 ; "Chiral"]

or a salt thereof.

11. A pharmaceutically acceptable salt of a compound according to claim 1 with an inorganic or organic acid or base.

12. A pharmaceutically acceptable salt of a compound according to claim 10 with an inorganic or organic acid or base.

13. A pharmaceutical composition comprising a compound according to claim 1, or a pharmaceutically acceptable salt thereof with an inorganic or organic acid or base, optionally together with one or more inert carriers and/or diluents.

14. A pharmaceutical composition comprising a compound according to claim 10, or a pharmaceutically acceptable salt thereof with an inorganic or organic acid or base, optionally together with one or more inert carriers and/or diluents.

15. A compound selected from the group consisting of:

(3'R,6'R,9'S)-9'-hydroxy-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]-6'-yl acetate

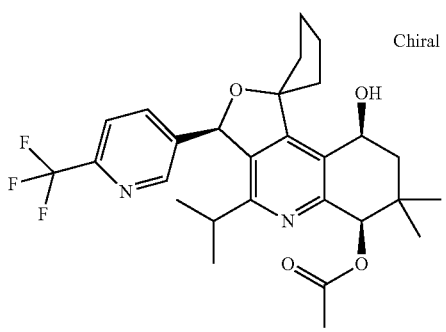 [SMILES: CC(=O)O[C@H]1c2nc(C(C)C)c3c(c2[C@@H](O)CC1(C)C)C1(CCCC1)O[C@@H]3c1ccc(C(F)(F)F)nc1]

(3R,9S)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]-9-ol

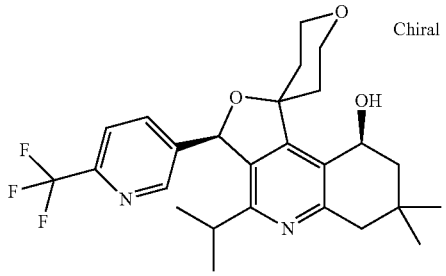 [SMILES: CC(C)c1nc2c(c3c1[C@@H](c1ccc(C(F)(F)F)nc1)OC31CCOCC1)[C@@H](O)CC(C)(C)C2]

(3'R,6'R,9'S)-4'-isopropyl-7',7'-dimethyl-3'-(6-(trifluoromethyl)pyridin-3-yl)-6',7',8',9'-tetrahydro-3'H-spiro[cyclopentane-1,1'-furo[3,4-c]quinoline]-6',9'-diol

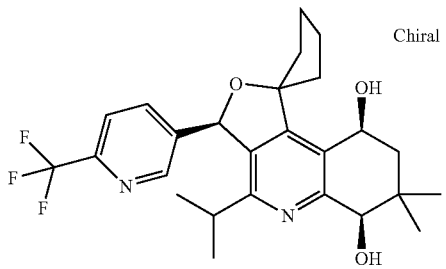 [SMILES: CC(C)c1nc2c(c3c1[C@@H](c1ccc(C(F)(F)F)nc1)OC31CCCC1)[C@@H](O)CC(C)(C)[C@H]2O]

451

(3R,6R,9S)-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-6,9-diol

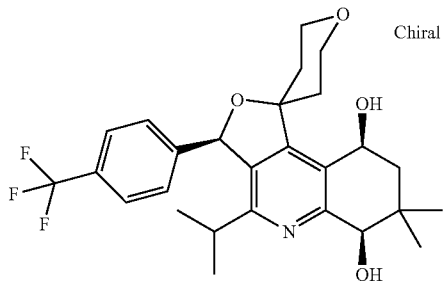 [SMILES: CC(C)c1nc2c(c3c1[C@@H](c1ccc(C(F)(F)F)cc1)OC31CCOCC1)[C@@H](O)CC(C)(C)[C@H]2O]

(3R,6R,9S)-9-hydroxy-4-isopropyl-7,7-dimethyl-3-(4-(trifluoromethyl)phenyl)-2',3',5',6,6',7,8,9-octahydro-3H-spiro[furo[3,4-c]quinoline-1,4'-pyran]-6-yl acetate

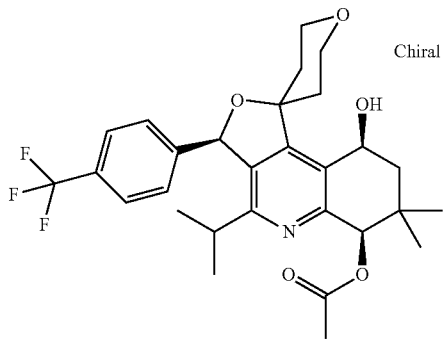 [SMILES: CC(=O)O[C@H]1c2nc(C(C)C)c3c(c2[C@@H](O)CC1(C)C)C1(CCOCC1)O[C@@H]3c1ccc(C(F)(F)F)cc1]

(3'R,6'R,9'S)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6',9'-diol

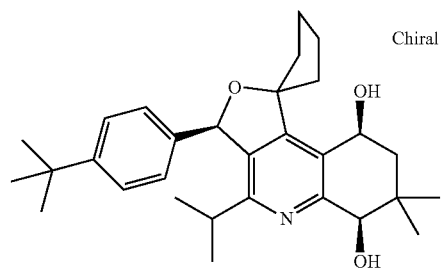 [SMILES: CC(C)c1nc2c(c3c1[C@@H](c1ccc(C(C)(C)C)cc1)OC31CCCC1)[C@@H](O)CC(C)(C)[C@H]2O]

(3'R,6'S,9'S)-3'-(4-tert-butylphenyl)-4'-isopropyl-7',7'-dimethyl-6',7',8',9'-tetrahydro-3'H-spiro[cyclopentane-1,1'-furo[3,4-c]quinoline]-6',9'-diol

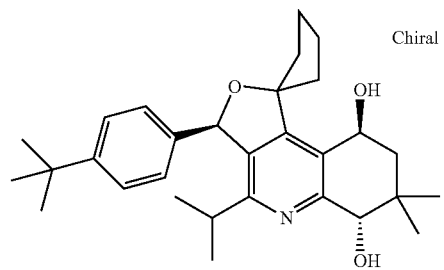 [SMILES: CC(C)c1nc2c(c3c1[C@@H](c1ccc(C(C)(C)C)cc1)OC31CCCC1)[C@@H](O)CC(C)(C)[C@@H]2O]

452

(3S,9S)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]-9-ol

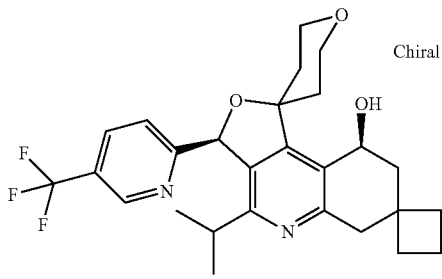 [SMILES: CC(C)c1nc2c(c3c1[C@@H](c1ccc(C(F)(F)F)cn1)OC31CCOCC1)[C@@H](O)CC1(CCC1)C2]

(3R,9S)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-9-ol

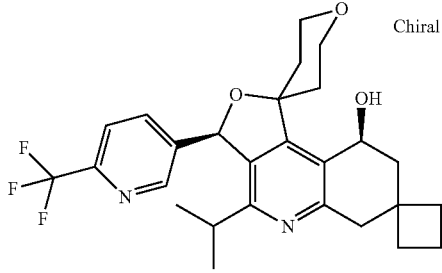 [SMILES: CC(C)c1nc2c(c3c1[C@@H](c1ccc(C(F)(F)F)nc1)OC31CCOCC1)[C@@H](O)CC1(CCC1)C2]

(3R,9S)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]-9-ol

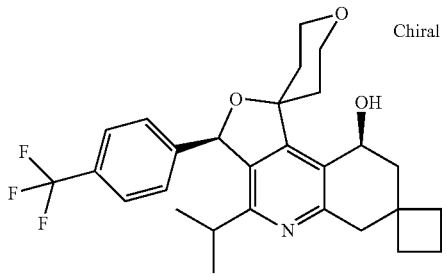 [SMILES: CC(C)c1nc2c(c3c1[C@@H](c1ccc(C(F)(F)F)cc1)OC31CCOCC1)[C@@H](O)CC1(CCC1)C2]

(3R,6R,9S)-4-isopropyl-7,7-(propan-1,3-diyl)-3-(4-(trifluoromethyl)phenyl)-2',3',5',6,6',7,8,9-octahydro-3H-spiro[furo[3,4-c]quinoline-1,4'-pyran]-6,9-diol

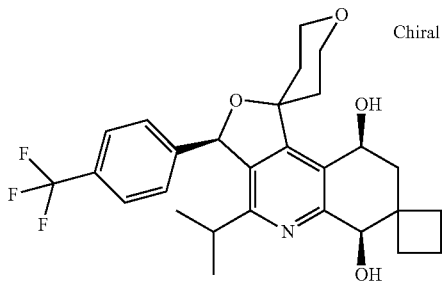 [SMILES: CC(C)c1nc2c(c3c1[C@@H](c1ccc(C(F)(F)F)cc1)OC31CCOCC1)[C@@H](O)CC1(CCC1)[C@H]2O]

453

(3S,9S)-3-(2-fluoro-4-(trifluoromethyl)phenyl)-4-isopropyl-7,7-(propan-1,3-diyl)-2',3',5',6,6',7,8,9-octahydro-3H-spiro[furo[3,4-c]quinoline-1,4'-pyran]-9-ol

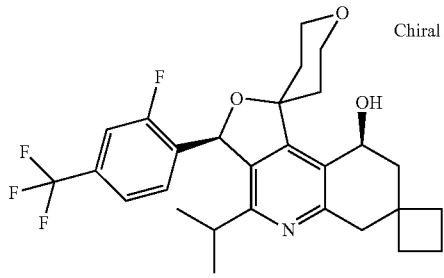 [SMILES: CC(C)c1nc2c(c3c1[C@@H](c1ccc(C(F)(F)F)cc1F)OC31CCOCC1)[C@@H](O)CC1(CCC1)C2]

(3R,6R,9S)-4-isopropyl-7,7-(propan-1,3-diyl)-3-(6-(trifluoromethyl)pyridin-3-yl)-2',3',5',6,6',7,8,9-octahydro-3H-spiro[furo[3,4-c]quinoline-1,4'-pyran]-6,9-diol

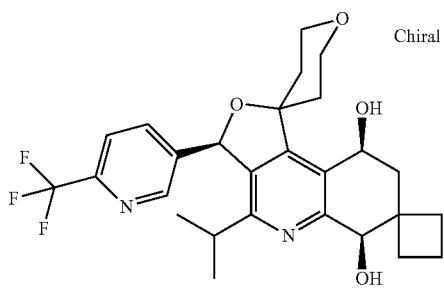 [SMILES: CC(C)c1nc2c(c3c1[C@@H](c1ccc(C(F)(F)F)nc1)OC31CCOCC1)[C@@H](O)CC1(CCC1)[C@H]2O]

(3S,9S)-3-(3-fluoro-5-(trifluoromethyl)pyridin-2-yl)-4-isopropyl-7,7-dimethyl-2',3',5',6,6',7,8,9-octahydro-3H-spiro[furo[3,4-c]quinoline-1,4'-pyran]-9-ol

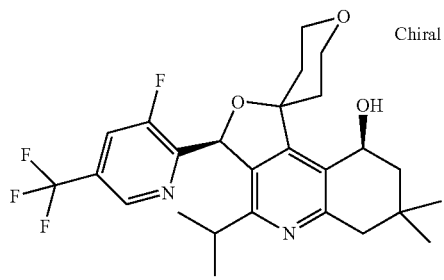

(3S,6S,9S)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]-6,9-diol

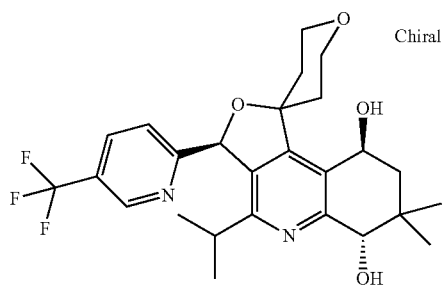

454

(3S,6R,9S)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]-6,9-diol

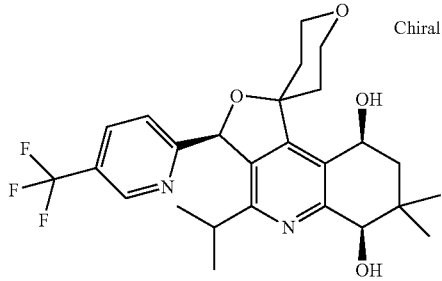 [SMILES: CC(C)c1nc2c(c3c1[C@@H](c1ccc(C(F)(F)F)cn1)OC31CCOCC1)[C@@H](O)CC(C)(C)[C@H]2O]

(3R,6S,9S)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]-6,9-diol

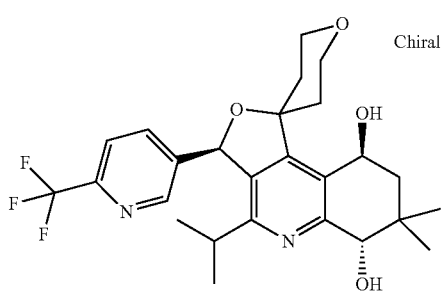 [SMILES: CC(C)c1nc2c(c3c1[C@@H](c1ccc(C(F)(F)F)nc1)OC31CCOCC1)[C@@H](O)CC(C)(C)[C@@H]2O]

(3R,6R,9S)-4-isopropyl-7,7-dimethyl-3-(6-(trifluoromethyl)pyridin-3-yl)-2',3',5',6,6',7,8,9-octahydro-3H-spiro[furo[3,4-c]quinoline-1,4'-pyran]-6,9-diol

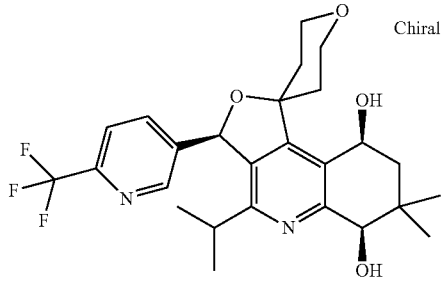 [SMILES: CC(C)c1nc2c(c3c1[C@@H](c1ccc(C(F)(F)F)nc1)OC31CCOCC1)[C@@H](O)CC(C)(C)[C@H]2O]

(3S,6R,9S)-4-isopropyl-7,7-(propan-1,3-diyl)-3-(5-(trifluoromethyl)pyridin-2-yl)-2',3',5',6,6',7,8,9-octahydro-3H-spiro[furo[3,4-c]quinoline-1,4'-pyran]-6,9-diol

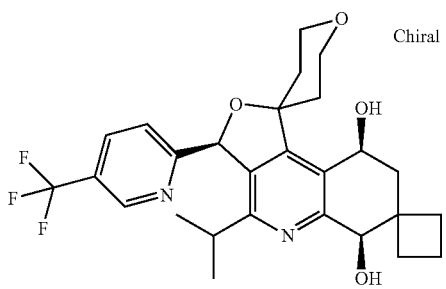 [SMILES: CC(C)c1nc2c(c3c1[C@@H](c1ccc(C(F)(F)F)cn1)OC31CCOCC1)[C@@H](O)CC1(CCC1)[C@H]2O]

455

(3R,9S)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-9-ol

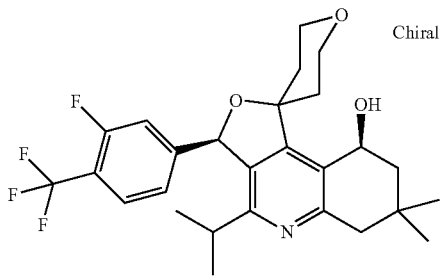 [SMILES: CC(C)c1nc2c(c3c1[C@@H](c1ccc(C(F)(F)F)c(F)c1)OC31CCOCC1)[C@@H](O)CC(C)(C)C2]

(3S,6R,9S)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6,9-diol

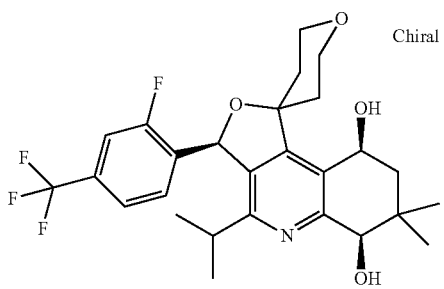

(3S,6S,9S)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6,9-diol

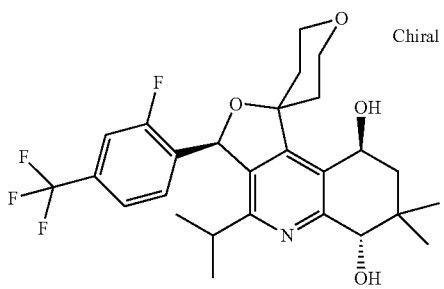 [SMILES: CC(C)c1nc2c(c3c1[C@@H](c1ccc(C(F)(F)F)cc1F)OC31CCOCC1)[C@@H](O)CC(C)(C)[C@@H]2O]

(3S,9S)-3-(2-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-9-ol

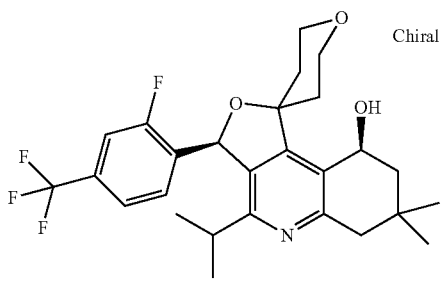 [SMILES: CC(C)c1nc2c(c3c1[C@@H](c1ccc(C(F)(F)F)cc1F)OC31CCOCC1)[C@@H](O)CC(C)(C)C2]

456

(3S,9S)-3-(5-tert-butyl-4-methylthiazol-2-yl)-4-isopropyl-7,7-dimethyl-2',3',5',6,6',7,8,9-octahydro-3H-spiro[furo[3,4-c]quinoline-1,4'-pyran]-9-ol

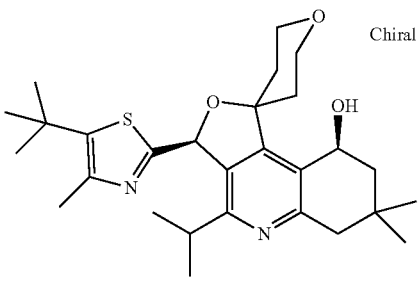 [SMILES: Cc1nc([C@H]2OC3(CCOCC3)c3c2c(C(C)C)nc2c3[C@@H](O)CC(C)(C)C2)sc1C(C)(C)C]

(3S,9S)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-9-ol

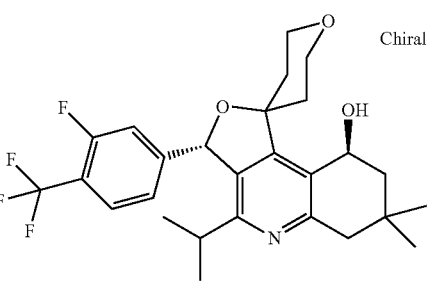

(3R,6R,9S)-3-(3-fluoro-4-(trifluoromethyl)phenyl)-4-isopropyl-7,7-dimethyl-2',3',5',6,6',7,8,9-octahydro-3H-spiro[furo[3,4-c]quinoline-1,4'-pyran]-6,9-diol

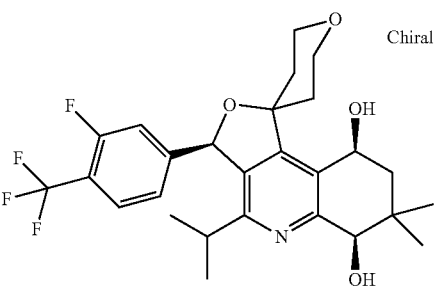 [SMILES: CC(C)c1nc2c(c3c1[C@@H](c1ccc(C(F)(F)F)c(F)c1)OC31CCOCC1)[C@@H](O)CC(C)(C)[C@H]2O]

(3R,9S)-4-isopropyl-7,7-(butan-1,4-diyl)-3-(4-(trifluoromethyl)phenyl)-2',3',5',6,6',7,8,9-octahydro-3H-spiro[furo[3,4-c]quinoline-1,4'-pyran]-9-ol

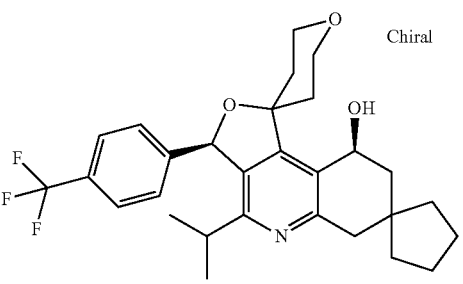 [SMILES: CC(C)c1nc2c(c3c1[C@@H](c1ccc(C(F)(F)F)cc1)OC31CCOCC1)[C@@H](O)CC1(CCCC1)C2]

457

(3R,9S)-3-(4-tert-butoxyphenyl)-4-isopropyl-7,7-dimethyl-2',3',5',6,6',7,8,9-octahydro-3H-spiro[furo[3,4-c]quinoline-1,4'-pyran]-9-ol

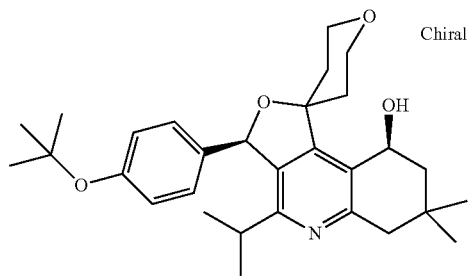 [SMILES: CC(C)c1nc2c(c3c1[C@@H](c1ccc(OC(C)(C)C)cc1)OC31CCOCC1)[C@@H](O)CC(C)(C)C2]

(3R,9S)-3-(4-isopropoxyphenyl)-4-isopropyl-7,7-dimethyl-2',3',5',6,6',7,8,9-octahydro-3H-spiro[furo[3,4-c]quinoline-1,4'-pyran]-9-ol

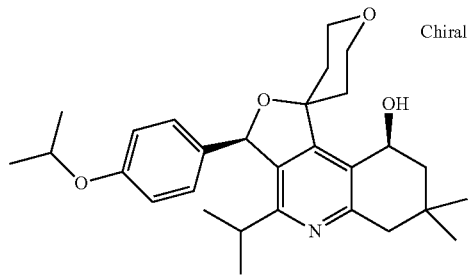 [SMILES: CC(C)Oc1ccc([C@H]2OC3(CCOCC3)c3c2c(C(C)C)nc2c3[C@@H](O)CC(C)(C)C2)cc1]

(3'R,9'S)-4'-isopropyl-7',7'-dimethyl-3'-(4-(prop-1-en-2-yl)phenyl)-6',7',8',9'-tetrahydro-3'H-spiro[cyclopentane-1,1'-furo[3,4-c]quinolin]-9'-ol

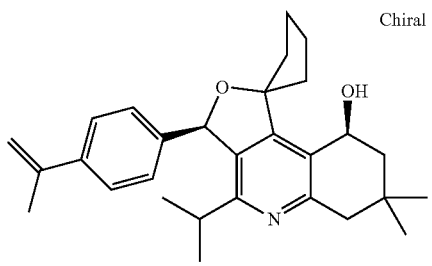 [SMILES: C=C(C)c1ccc([C@H]2OC3(CCCC3)c3c2c(C(C)C)nc2c3[C@@H](O)CC(C)(C)C2)cc1]

(3'R,6'R,9'S)-7',7'-dimethyl-4'-(tetrahydro-2H-pyran-4-yl)-3'-(4-(pentafluorosulfanyl)phenyl)-6',7',8',9'-tetrahydro-3'H-spiro[cyclopentane-1,1'-furo[3,4-c]quinoline]-6',9'-diol

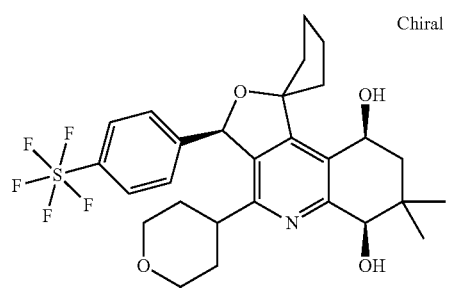 [SMILES: CC1(C)C[C@H](O)c2c(nc(C3CCOCC3)c3c2C2(CCCC2)O[C@@H]3c2ccc(S(F)(F)(F)(F)F)cc2)[C@@H]1O]

458

(3R,6R,9S)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]-6,9-diol

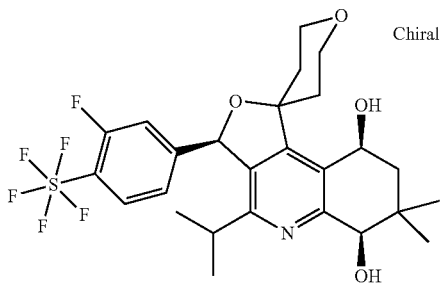 [SMILES: CC(C)c1nc2c(c3c1[C@@H](c1ccc(S(F)(F)(F)(F)F)c(F)c1)OC31CCOCC1)[C@@H](O)CC(C)(C)[C@H]2O]

(3R,9S)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran]-9-ol

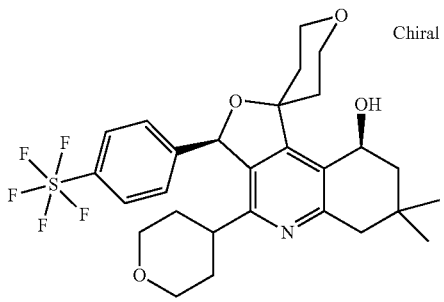 [SMILES: CC1(C)Cc2nc(C3CCOCC3)c3c(c2[C@@H](O)C1)C1(CCOCC1)O[C@@H]3c1ccc(S(F)(F)(F)(F)F)cc1]

(3'R,9'S)-3'-(4-tert-butylphenyl)-4'-isopropyl-7',7'-(propan-1,3-diyl)-6',7',8',9'-tetrahydro-3'H-spiro[cyclopentane-1,1'-furo[3,4-c]quinolin]-9'-ol

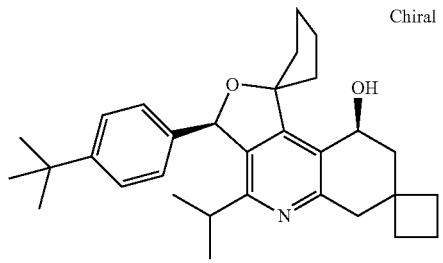 [SMILES: CC(C)c1nc2c(c3c1[C@@H](c1ccc(C(C)(C)C)cc1)OC31CCCC1)[C@@H](O)CC1(CCC1)C2]

(3R,9S)-3-(4-tert-butylphenyl)-4-isopropyl-7,7-(propan-1,3-diyl)-2',3',5',6,6',7,8,9-octahydro-3H-spiro[furo[3,4-c]quinoline-1,4'-pyran]-9-ol

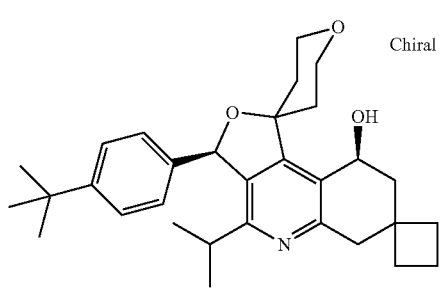 [SMILES: CC(C)c1nc2c(c3c1[C@@H](c1ccc(C(C)(C)C)cc1)OC31CCOCC1)[C@@H](O)CC1(CCC1)C2]

459

(3R,9S)-4-isopropyl-7,7-dimethyl-3-(4-(3-methyloxetan-3-yl)phenyl)-2',3',5',6,6',7,8,9-octahydro-3H-spiro[furo[3,4-c]quinoline-1,4'-pyran]-9-ol

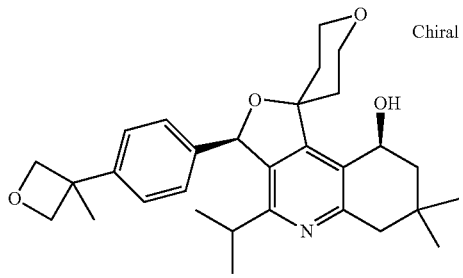 [SMILES: CC(C)c1nc2c(c3c1[C@@H](c1ccc(C4(C)COC4)cc1)OC31CCOCC1)[C@@H](O)CC(C)(C)C2]

(3'R,9'S)-4'-isopropyl-7',7'-dimethyl-3'-(4-(perfluoroethyl)phenyl)-6',7',8',9'-tetrahydro-3'H-spiro[cyclopentane-1,1'-furo[3,4-c]quinolin]-9'-ol

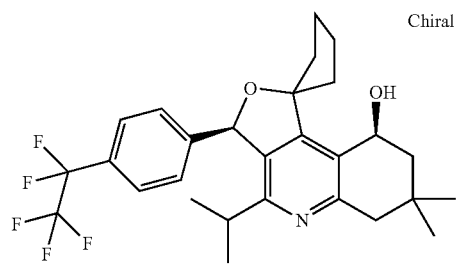 [SMILES: CC(C)c1nc2c(c3c1[C@@H](c1ccc(C(F)(F)C(F)(F)F)cc1)OC31CCCC1)[C@@H](O)CC(C)(C)C2]

5-((3R,9S)-9-hydroxy-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile

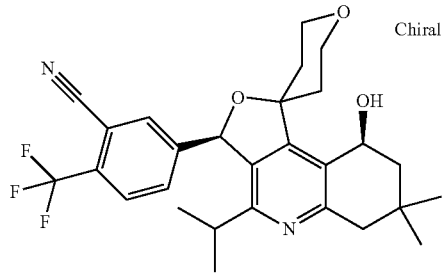 [SMILES: CC(C)c1nc2c(c3c1[C@@H](c1ccc(C(F)(F)F)c(C#N)c1)OC31CCOCC1)[C@@H](O)CC(C)(C)C2]

(3S,9S)-4-isopropyl-7,7-dimethyl-3-(5-(trifluoromethyl)pyridin-2-yl)-2',3',5',6,6',7,8,9-octahydro-3H-spiro[furo[3,4-c]quinoline-1,4'-pyran]-9-ol

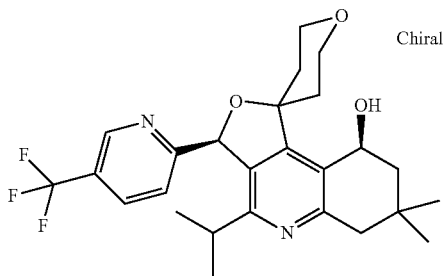 [SMILES: CC(C)c1nc2c(c3c1[C@@H](c1ccc(C(F)(F)F)cn1)OC31CCOCC1)[C@@H](O)CC(C)(C)C2]

460

(3R,9S)-4-isopropyl-7,7-dimethyl-3-(4-(pentafluorosulfanyl)phenyl)-2',3',5',6,6',7,8,9-octahydro-3H-spiro[furo[3,4-c]quinoline-1,4'-pyran]-9-ol

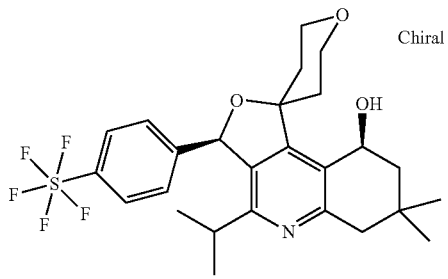 [SMILES: CC(C)c1nc2c(c3c1[C@@H](c1ccc(S(F)(F)(F)(F)F)cc1)OC31CCOCC1)[C@@H](O)CC(C)(C)C2]

(3R,9S)-4-isopropyl-7,7-(propan-1,3-diyl)-3-(4-(pentafluorosulfanyl)phenyl)-2',3',5',6,6',7,8,9-octahydro-3H-spiro[furo[3,4-c]quinoline-1,4'-pyran]-9-ol

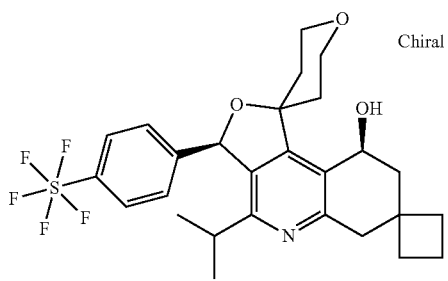 [SMILES: CC(C)c1nc2c(c3c1[C@@H](c1ccc(S(F)(F)(F)(F)F)cc1)OC31CCOCC1)[C@@H](O)CC1(CCC1)C2]

(3R,6R,9S)-4-isopropyl-7,7-(propan-1,3-diyl)-3-(4-(pentafluorosulfanyl)phenyl)-2',3',5',6,6',7,8,9-octahydro-3H-spiro[furo[3,4-c]quinoline-1,4'-pyran]-6,9-diol

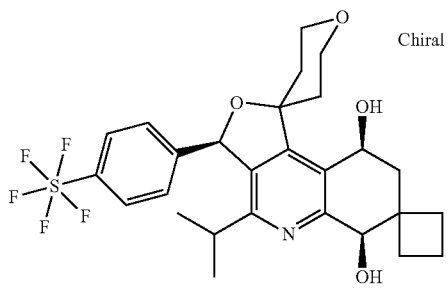 [SMILES: CC(C)c1nc2c(c3c1[C@@H](c1ccc(S(F)(F)(F)(F)F)cc1)OC31CCOCC1)[C@@H](O)CC1(CCC1)[C@H]2O]

(3R,9S)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran]-9-ol

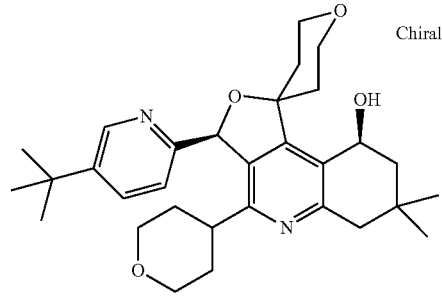 [SMILES: CC1(C)Cc2nc(C3CCOCC3)c3c(c2[C@@H](O)C1)C1(CCOCC1)O[C@@H]3c1ccc(C(C)(C)C)cn1]

461

(3'R,9'S)-4'-isopropyl-7',7'-dimethyl-3'-(4-(pentafluoro-sulfanyl)phenyl)-6',7',8',9'-tetrahydro-3'H-spiro[cyclo-pentane-1,1'-furo[3,4-c]quinolin]-9'-ol

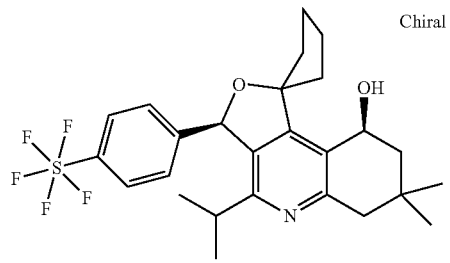 [SMILES: CC(C)c1nc2c(c3c1[C@@H](c1ccc(S(F)(F)(F)(F)F)cc1)OC31CCCC1)[C@@H](O)CC(C)(C)C2]

(3R,9S)-4-tert-butyl-7,7-dimethyl-3-(4-(trifluoromethyl)phenyl)-2',3',5',6,6',7,8,9-octahydro-3H-spiro[furo[3,4-c]quinoline-1,4'-pyran]-9-ol

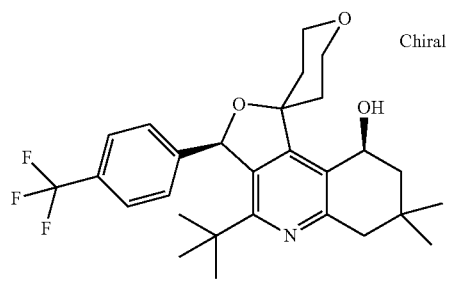 [SMILES: CC1(C)Cc2nc(C(C)(C)C)c3c(c2[C@@H](O)C1)C1(CCOCC1)O[C@@H]3c1ccc(C(F)(F)F)cc1]

(3R,9S)-4-(1-methoxyethyl)-7,7-dimethyl-3-(4-(trifluoromethyl)phenyl)-2',3',5',6,6',7,8,9-octahydro-3H-spiro[furo[3,4-c]quinoline-1,4'-pyran]-9-ol

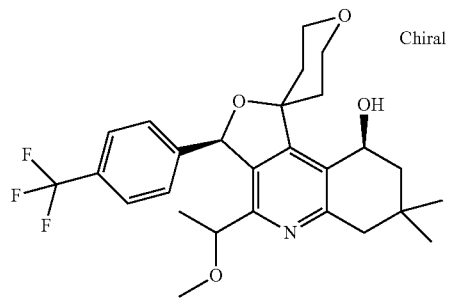 [SMILES: COC(C)c1nc2c(c3c1[C@@H](c1ccc(C(F)(F)F)cc1)OC31CCOCC1)[C@@H](O)CC(C)(C)C2]

5-((3R,9S)-9-hydroxy-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

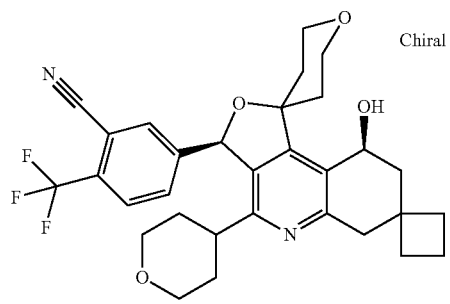 [SMILES: N#Cc1cc([C@H]2OC3(CCOCC3)c3c2c(C2CCOCC2)nc2c3[C@@H](O)CC3(CCC3)C2)ccc1C(F)(F)F]

462

5-((3R,6R,9S)-6,9-dihydroxy-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

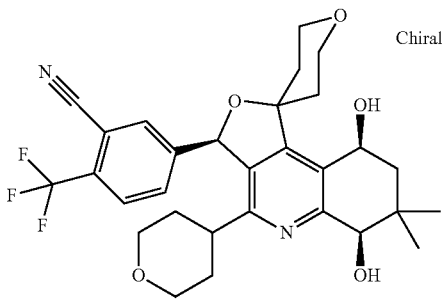 [SMILES: CC1(C)C[C@H](O)c2c(nc(C3CCOCC3)c3c2C2(CCOCC2)O[C@@H]3c2ccc(C(F)(F)F)c(C#N)c2)[C@@H]1O]

(3S,6R,9S)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'pyran]-6,9-diol

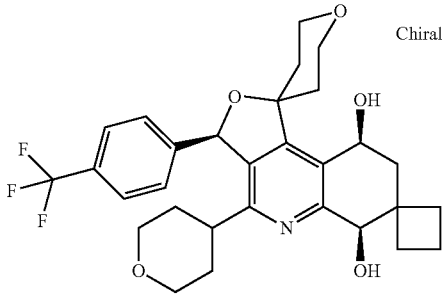 [SMILES: O[C@H]1CC2(CCC2)[C@@H](O)c2nc(C3CCOCC3)c3c(c21)C1(CCOCC1)O[C@@H]3c1ccc(C(F)(F)F)cc1]

(3S,9S)-7,7-dimethyl-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]-9-ol

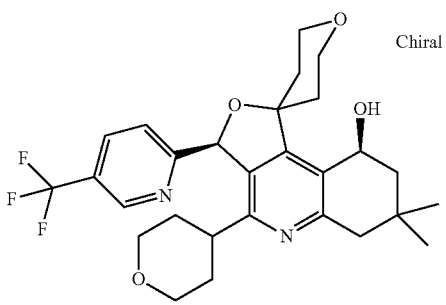 [SMILES: CC1(C)Cc2nc(C3CCOCC3)c3c(c2[C@@H](O)C1)C1(CCOCC1)O[C@@H]3c1ccc(C(F)(F)F)cn1]

| 463 | 464 |
|---|---|
| 5-((3R,9S)-9-hydroxy-7,7-dimethyl-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile | (3R,6R,9S)-7,7-dimethyl-4-(tetrahydro-2H-pyran-4-yl)-3-(4-(pentafluorosulfanyl)phenyl)-2',3',5',6,6',7,8,9-octahydro-3H-spiro[furo[3,4-c]quinoline-1,4'-pyran]-6,9-diol |

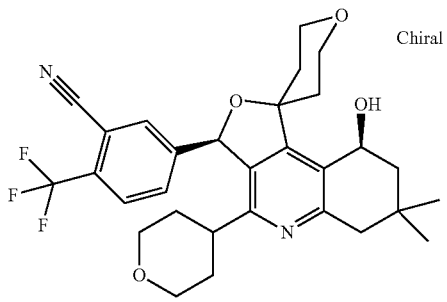 [SMILES: CC1(C)Cc2nc(C3CCOCC3)c3c(c2[C@@H](O)C1)C1(CCOCC1)O[C@@H]3c1ccc(C(F)(F)F)c(C#N)c1]
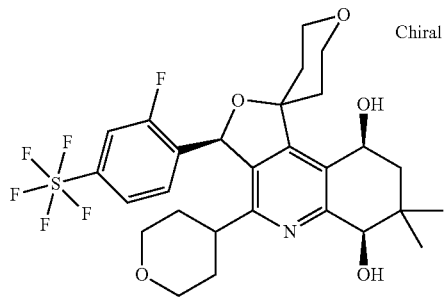

5-((3R,6R,9S)-6,9-dihydroxy-4-isopropyl-7,7-(propan-1,3-diyl)-2',3',5',6,6',7,8,9-octahydro-3H-spiro[furo[3,4-c]quinoline-1,4'pyran]-3-yl)-2-(trifluoromethyl)benzonitrile (3R,6R,9S)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]-6,9-diol

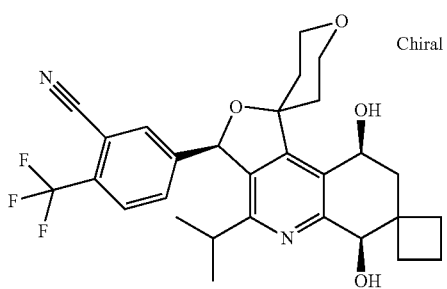 [SMILES: CC(C)c1nc2c(c3c1[C@@H](c1ccc(C(F)(F)F)c(C#N)c1)OC31CCOCC1)[C@@H](O)CC1(CCC1)[C@H]2O]

(3R,6R,9S)-7,7-dimethyl-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-6,9-diol (3R,9S)-4-(methoxymethyl)-7,7-dimethyl-3-(4-(trifluoromethyl)phenyl)-2',3',5',6,6',7,8,9-octahydro-3H-spiro[furo[3,4-c]quinoline-1,4'-pyran]-9-ol

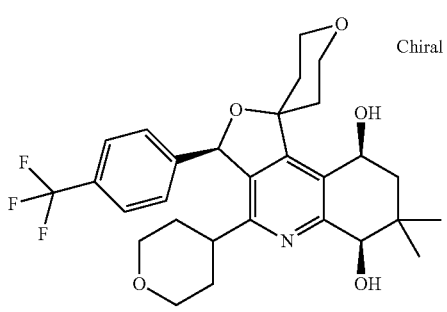 [SMILES: CC1(C)C[C@H](O)c2c(nc(C3CCOCC3)c3c2C2(CCOCC2)O[C@@H]3c2ccc(C(F)(F)F)cc2)[C@@H]1O]
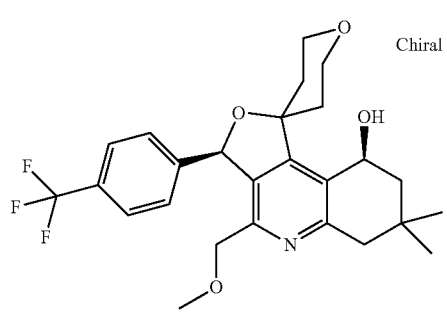 [SMILES: COCc1nc2c(c3c1[C@@H](c1ccc(C(F)(F)F)cc1)OC31CCOCC1)[C@@H](O)CC(C)(C)C2]

| 465 | 466 |
|---|---|
| (3R,6R,9S)-3-(4-tert-butylphenyl)-7,7-dimethyl-4-(tetrahydro-2H-pyran-4-yl)-2',3',5',6,6',7,8,9-octahydro-3H-spiro[furo[3,4-c]quinoline-1,4'-pyran]-6,9-diol | (3R,9S)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-9-ol |
| 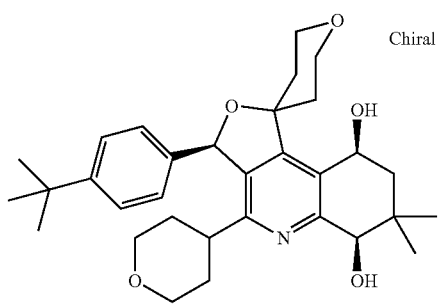 [SMILES: CC(C)(C)c1ccc([C@H]2OC3(CCOCC3)c3c2c(C2CCOCC2)nc2c3[C@@H](O)CC(C)(C)[C@H]2O)cc1] | 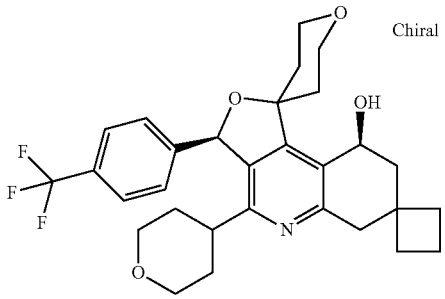 |
| (3S,9S)-7,7-(propan-1,3-diyl)-4-(tetrahydro-2H-pyran-4-yl)-3-(5-(trifluoromethyl)pyridin-2-yl)-2',3',5',6,6',7,8,9-octahydro-3H-spiro[furo[3,4-c]quinoline-1,4'-pyran]-9-ol | (3R,9S)-4-(2-methoxypropan-2-yl)-7,7-dimethyl-3-(4-(trifluoromethyl)phenyl)-2',3',5',6,6',7,8,9-octahydro-3H-spiro[furo[3,4-c]quinoline-1,4'-pyran]-9-ol |
| 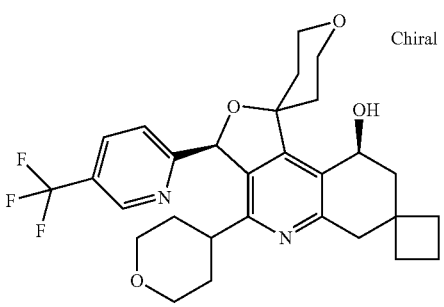 [SMILES: O[C@H]1CC2(CCC2)Cc2nc(C3CCOCC3)c3c(c21)C1(CCOCC1)O[C@@H]3c1ccc(C(F)(F)F)cn1] | 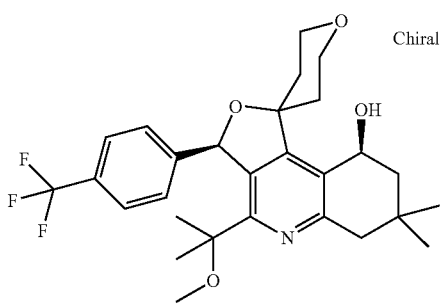 [SMILES: COC(C)(C)c1nc2c(c3c1[C@@H](c1ccc(C(F)(F)F)cc1)OC31CCOCC1)[C@@H](O)CC(C)(C)C2] |
| (3R,9S)-7,7-dimethyl-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4'-pyran]-9-ol | (3R,9S)-7,7-(propan-1,3-diyl)-4-(tetrahydro-2H-pyran-4-yl)-3-(6-(trifluoromethyl)pyridin-3-yl)-2',3',5',6,6',7,8,9-octahydro-3H-spiro[furo[3,4-c]quinoline-1,4]-pyran]-9-ol |
| 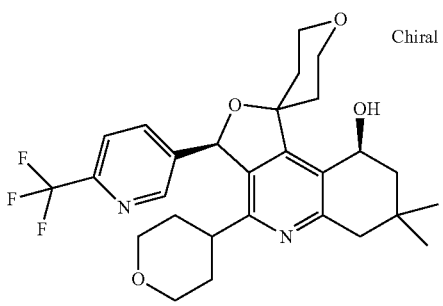 | 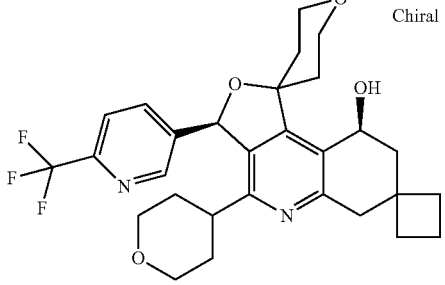 |

467

5-((3R,9S)-9-hydroxy-4-isopropyl-7,7-(propan-1,3-diyl)-2',3',5',6,6',7,8,9-octahydro-3H-spiro[furo[3,4-c]quinoline-1,4'pyran]-3-yl)-2-(trifluoromethyl)benzonitrile

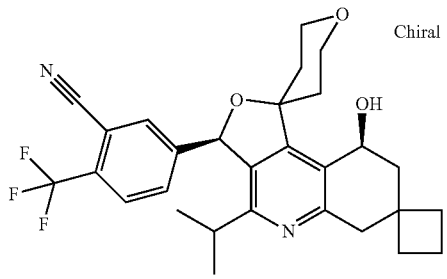 [SMILES: CC(C)c1nc2c(c3c1[C@@H](c1ccc(C(F)(F)F)c(C#N)c1)OC31CCOCC1)[C@@H](O)CC1(CCC1)C2]

5-((3R,6R,9S)-6,9-dihydroxy-7,7-(propan-1,3-diyl)-4-(tetrahydro-2H-pyran-4-yl)-2',3',5',6,6',7,8,9-octahydro-3H-spiro[furo[3,4-c]quinoline-1,4'-pyran]-3-yl)-2-(trifluoromethyl)benzonitrile

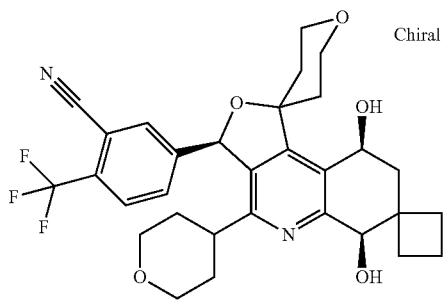 [SMILES: N#Cc1cc([C@H]2OC3(CCOCC3)c3c2c(C2CCOCC2)nc2c3[C@@H](O)CC3(CCC3)[C@H]2O)ccc1C(F)(F)F]

5-((3R,6R,9S)-6,9-dihydroxy-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile

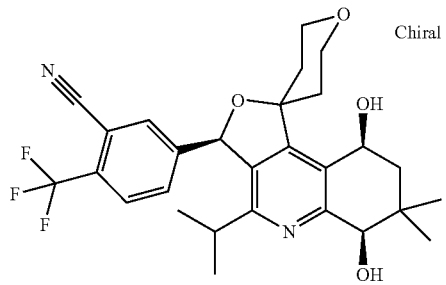 [SMILES: CC(C)c1nc2c(c3c1[C@@H](c1ccc(C(F)(F)F)c(C#N)c1)OC31CCOCC1)[C@@H](O)CC(C)(C)[C@H]2O]

468

(3R,6R,9S)-7,7-(propan-1,3-diyl)-4-(tetrahydro-2H-pyran-4-yl)-3-(4-(trifluoromethyl)phenyl)-2',3',5',6,6',7,8,9-octahydro-3H-spiro[furo[3,4-c]quinoline-1,4'-pyran]-6,9-diol

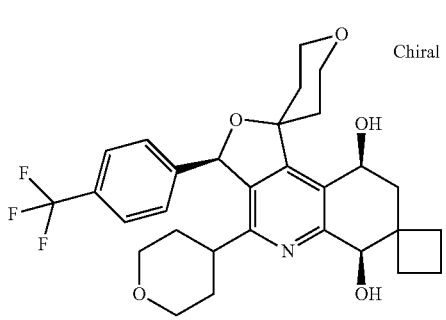 [SMILES: O[C@H]1CC2(CCC2)[C@@H](O)c2nc(C3CCOCC3)c3c(c21)C1(CCOCC1)O[C@@H]3c1ccc(C(F)(F)F)cc1]

(3'S,9'S)-4,4-difluoro-4'-isopropyl-7',7'-dimethyl-3'-(5-(trifluoromethyl)pyridin-2-yl)-6',7',8',9'-tetrahydro-3'H-spiro[cyclohexane-1,1'-furo[3,4-c]quinolin]-9'-ol

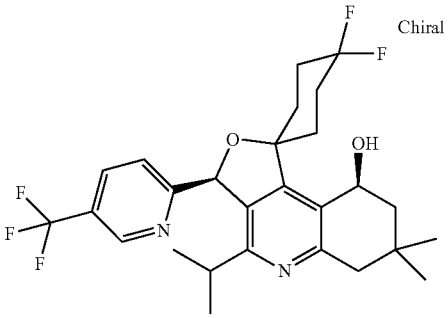 [SMILES: CC(C)c1nc2c(c3c1[C@@H](c1ccc(C(F)(F)F)cn1)OC31CCC(F)(F)CC1)[C@@H](O)CC(C)(C)C2]

and
(3'R,9'S)-4,4-difluoro-4'-isopropyl-7',7'-dimethyl-3'-(5-(trifluoromethyl)pyridin-2-yl)-6',7',8',9'-tetrahydro-3'H-spiro[cyclohexane-1,1'-furo[3,4-c)quinolin]-9'-ol

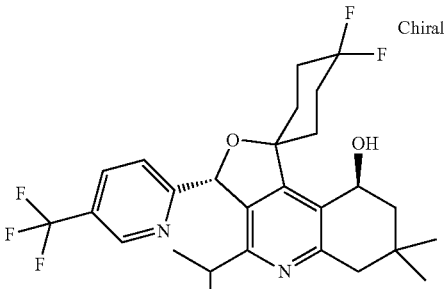

or a salt thereof.

* * * * *